US012588928B2

(12) United States Patent
Donnay et al.

(10) Patent No.: US 12,588,928 B2
(45) Date of Patent: Mar. 31, 2026

(54) MEDICAL DEVICE INSERTERS AND PROCESSES OF INSERTING AND USING MEDICAL DEVICES

(71) Applicant: ABBOTT DIABETES CARE INC., Alameda, CA (US)

(72) Inventors: Manuel Luis Donnay, San Francisco, CA (US); Tuan Nguyen, Dublin, CA (US); Louis G. Pace, San Carlos, CA (US); Peter G. Robinson, Alamo, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 497 days.

(21) Appl. No.: 16/002,847

(22) Filed: Jun. 7, 2018

(65) Prior Publication Data

US 2019/0076073 A1 Mar. 14, 2019

Related U.S. Application Data

(63) Continuation of application No. 13/436,768, filed on Mar. 30, 2012, now Pat. No. 10,010,280, which is a
(Continued)

(51) Int. Cl.
*A61B 5/15* (2006.01)
*A61B 5/00* (2006.01)
(Continued)

(52) U.S. Cl.
CPC ...... *A61B 17/3468* (2013.01); *A61B 5/14532* (2013.01); *A61B 5/14546* (2013.01);
(Continued)

(58) Field of Classification Search
CPC .......... A61B 5/15019; A61B 5/150022; A61B 5/150259; A61B 5/150282;
(Continued)

(56) References Cited

U.S. PATENT DOCUMENTS 2,402,306 A 6/1946 Turkel
2,752,918 A 7/1956 Uytenbogaart
(Continued)

FOREIGN PATENT DOCUMENTS

AU 2003259741 2/2004
CA 2291105 12/1998
(Continued)

OTHER PUBLICATIONS

EP, 20195922.8 Extended Search Report, dated Dec. 16, 2020.
(Continued)

*Primary Examiner* — Richard G Louis
(74) *Attorney, Agent, or Firm* — ONE LLP

(57) ABSTRACT

An apparatus for insertion of a medical device in the skin of a subject is provided, as well as methods of inserting medical devices. Embodiments include removing a substantially cylindrical cap from an inserter to expose a substantially cylindrical sleeve, removing a cover from a substantially cylindrical container holding sensor components, and fitting the sensor components into the inserter.

20 Claims, 99 Drawing Sheets

Related U.S. Application Data continuation of application No. 13/071,461, filed on Mar. 24, 2011, now Pat. No. 9,215,992.

(60) Provisional application No. 61/411,262, filed on Nov. 8, 2010, provisional application No. 61/361,374, filed on Jul. 2, 2010, provisional application No. 61/345,562, filed on May 17, 2010, provisional application No. 61/317,243, filed on Mar. 24, 2010.

(51) Int. Cl.

| | |
|---|---|
| *A61B 5/145* | (2006.01) |
| *A61B 5/151* | (2006.01) |
| *A61B 5/157* | (2006.01) |
| *A61B 17/34* | (2006.01) |
| *A61B 5/01* | (2006.01) |
| *A61B 17/00* | (2006.01) |
| *A61M 5/158* | (2006.01) |

(52) U.S. Cl.

CPC .............. *A61B 5/6848* (2013.01); *A61B 5/01* (2013.01); *A61B 2560/063* (2013.01); *A61M 2005/1585* (2013.01)

(58) Field of Classification Search

CPC ........ A61B 5/150419; A61B 5/150427; A61B 5/150511; A61B 5/15087; A61B 5/15107; A61B 5/15113; A61B 5/15117; A61B 5/1513; A61B 5/15186; A61B 5/1519; A61B 5/15194; A61B 5/157; A61B 5/15016; A61B 5/150732; A61B 5/1411; A61B 5/14503; A61B 5/14532; A61B 5/14535; A61B 5/14539; A61B 5/14542; A61B 5/14546

See application file for complete search history.

(56) References Cited

U.S. PATENT DOCUMENTS

| | | |
|---|---|---|
| 3,123,790 A | 3/1964 | Tyler |
| 3,132,123 A | 5/1964 | Harris, Jr. et al. |
| 3,173,200 A | 3/1965 | Dunmire et al. |
| 3,211,001 A | 10/1965 | Petit |
| 3,260,656 A | 7/1966 | Ross, Jr. |
| 3,517,670 A | 6/1970 | Speelman |
| 3,522,807 A | 8/1970 | Millenbach |
| 3,581,062 A | 5/1971 | Aston |
| 3,653,841 A | 4/1972 | Klein |
| 3,670,727 A | 6/1972 | Reiterman |
| 3,719,564 A | 3/1973 | Lilly, Jr. et al. |
| 3,776,832 A | 12/1973 | Oswin et al. |
| 3,837,339 A | 9/1974 | Aisenberg et al. |
| 3,926,760 A | 12/1975 | Allen et al. |
| 3,949,388 A | 4/1976 | Fuller |
| 3,960,497 A | 6/1976 | Acord et al. |
| 3,972,320 A | 8/1976 | Kalman |
| 3,979,274 A | 9/1976 | Newman |
| 4,008,717 A | 2/1977 | Kowarski |
| 4,016,866 A | 4/1977 | Lawton |
| 4,033,330 A | 7/1977 | Willis et al. |
| 4,036,749 A | 7/1977 | Anderson |
| 4,055,175 A | 10/1977 | Clemens et al. |
| 4,059,406 A | 11/1977 | Fleet |
| 4,076,596 A | 2/1978 | Connery et al. |
| 4,098,574 A | 7/1978 | Dappen |
| 4,100,048 A | 7/1978 | Pompei et al. |
| 4,120,292 A | 10/1978 | LeBlanc, Jr. et al. |
| 4,129,128 A | 12/1978 | McFarlane |
| 4,151,845 A | 5/1979 | Clemens |
| 4,168,205 A | 9/1979 | Danninger et al. |
| 4,172,770 A | 10/1979 | Semersky et al. |
| 4,178,916 A | 12/1979 | McNamara |
| 4,203,446 A | 5/1980 | Hofert et al. |
| 4,206,755 A | 6/1980 | Klein |
| 4,224,125 A | 9/1980 | Nakamura et al. |
| 4,240,438 A | 12/1980 | Updike et al. |
| 4,240,889 A | 12/1980 | Yoda et al. |
| 4,245,634 A | 1/1981 | Albisser et al. |
| 4,247,297 A | 1/1981 | Berti et al. |
| 4,294,258 A | 10/1981 | Bernard |
| 4,305,401 A | 12/1981 | Reissmueller et al. |
| 4,308,981 A | 1/1982 | Miura |
| 4,327,725 A | 5/1982 | Cortese et al. |
| 4,340,458 A | 7/1982 | Lerner et al. |
| 4,344,438 A | 8/1982 | Schultz |
| 4,349,728 A | 9/1982 | Phillips et al. |
| 4,352,960 A | 10/1982 | Dormer et al. |
| 4,353,888 A | 10/1982 | Sefton |
| 4,356,074 A | 10/1982 | Johnson |
| 4,365,637 A | 12/1982 | Johnson |
| 4,366,033 A | 12/1982 | Richter et al. |
| 4,373,527 A | 2/1983 | Fischell |
| 4,375,399 A | 3/1983 | Havas et al. |
| 4,384,586 A | 5/1983 | Christiansen |
| 4,390,621 A | 6/1983 | Bauer |
| 4,392,849 A | 7/1983 | Petre et al. |
| 4,401,122 A | 8/1983 | Clark, Jr. |
| 4,404,066 A | 9/1983 | Johnson |
| 4,418,148 A | 11/1983 | Oberhardt |
| 4,425,920 A | 1/1984 | Bourland et al. |
| 4,427,004 A | 1/1984 | Miller et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,441,968 A | 4/1984 | Emmer et al. |
| 4,450,842 A | 5/1984 | Zick et al. |
| 4,458,686 A | 7/1984 | Clark, Jr. |
| 4,461,691 A | 7/1984 | Frank |
| 4,464,170 A | 8/1984 | Clemens et al. |
| 4,469,110 A | 9/1984 | Slama |
| 4,477,314 A | 10/1984 | Richter et al. |
| 4,478,976 A | 10/1984 | Goertz et al. |
| 4,484,987 A | 11/1984 | Gough |
| 4,494,950 A | 1/1985 | Fischell |
| 4,509,531 A | 4/1985 | Ward |
| 4,522,690 A | 6/1985 | Venkatasetty |
| 4,524,114 A | 6/1985 | Samuels et al. |
| 4,526,661 A | 7/1985 | Steckhan et al. |
| 4,527,240 A | 7/1985 | Kvitash |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,553,541 A | 11/1985 | Burns |
| 4,560,534 A | 12/1985 | Kung et al. |
| 4,571,292 A | 2/1986 | Liu et al. |
| 4,573,994 A | 3/1986 | Fischell et al. |
| 4,581,336 A | 4/1986 | Malloy et al. |
| 4,592,745 A | 6/1986 | Rex et al. |
| 4,595,011 A | 6/1986 | Phillips |
| 4,619,754 A | 10/1986 | Niki et al. |
| 4,619,793 A | 10/1986 | Lee |
| 4,627,445 A | 12/1986 | Garcia et al. |
| 4,627,842 A | 12/1986 | Katz |
| 4,627,908 A | 12/1986 | Miller |
| 4,633,878 A | 1/1987 | Bombardieri |
| 4,637,403 A | 1/1987 | Garcia et al. |
| 4,639,062 A | 1/1987 | Taniguchi et al. |
| 4,650,547 A | 3/1987 | Gough |
| 4,654,197 A | 3/1987 | Lilja et al. |
| 4,655,880 A | 4/1987 | Liu |
| 4,655,885 A | 4/1987 | Hill et al. |
| 4,663,824 A | 5/1987 | Kenmochi |
| 4,671,288 A | 6/1987 | Gough |
| 4,675,346 A | 6/1987 | Lin et al. |
| 4,679,562 A | 7/1987 | Luksha |
| 4,680,268 A | 7/1987 | Clark, Jr. |
| 4,682,602 A | 7/1987 | Prohaska |
| 4,684,537 A | 8/1987 | Graetzel et al. |
| 4,685,463 A | 8/1987 | Williams |

(56)                   References Cited

U.S. PATENT DOCUMENTS

| | | |
|---|---|---|
| 4,685,466 A | 8/1987 | Rau |
| 4,690,675 A | 9/1987 | Katz |
| 4,698,057 A | 10/1987 | Joishy |
| 4,703,324 A | 10/1987 | White |
| 4,703,756 A | 11/1987 | Gough et al. |
| 4,711,245 A | 12/1987 | Higgins et al. |
| 4,711,247 A | 12/1987 | Fishman |
| 4,717,673 A | 1/1988 | Wrighton et al. |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,729,672 A | 3/1988 | Takagi |
| 4,731,726 A | 3/1988 | Allen, III |
| 4,749,985 A | 6/1988 | Corsberg |
| 4,755,173 A | 7/1988 | Konopka |
| 4,757,022 A | 7/1988 | Shults et al. |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |
| 4,777,953 A | 10/1988 | Ash et al. |
| 4,779,618 A | 10/1988 | Mund et al. |
| 4,781,683 A | 11/1988 | Wozniak et al. |
| 4,781,798 A | 11/1988 | Gough |
| 4,784,736 A | 11/1988 | Lonsdale et al. |
| 4,785,868 A | 11/1988 | Koenig, Jr. |
| 4,795,707 A | 1/1989 | Niiyama et al. |
| 4,796,634 A | 1/1989 | Huntsman et al. |
| 4,805,624 A | 2/1989 | Yao et al. |
| 4,813,424 A | 3/1989 | Wilkins |
| 4,815,469 A | 3/1989 | Cohen et al. |
| 4,817,603 A | 4/1989 | Turner et al. |
| 4,818,994 A | 4/1989 | Orth et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| RE32,947 E | 6/1989 | Dormer et al. |
| 4,840,893 A | 6/1989 | Hill et al. |
| 4,847,785 A | 7/1989 | Stephens |
| 4,848,351 A | 7/1989 | Finch |
| 4,852,025 A | 7/1989 | Herpichböhm |
| 4,854,322 A | 8/1989 | Ash et al. |
| 4,856,648 A | 8/1989 | Krueger |
| 4,865,038 A | 9/1989 | Rich et al. |
| 4,871,351 A | 10/1989 | Feingold |
| 4,871,440 A | 10/1989 | Nagata et al. |
| 4,874,500 A | 10/1989 | Madou et al. |
| 4,890,620 A | 1/1990 | Gough |
| 4,894,137 A | 1/1990 | Takizawa et al. |
| 4,895,147 A | 1/1990 | Bodicky et al. |
| 4,897,162 A | 1/1990 | Lewandowski et al. |
| 4,897,173 A | 1/1990 | Nankai et al. |
| 4,909,908 A | 3/1990 | Ross et al. |
| 4,911,794 A | 3/1990 | Parce et al. |
| 4,917,800 A | 4/1990 | Lonsdale et al. |
| 4,919,141 A | 4/1990 | Zier et al. |
| 4,919,767 A | 4/1990 | Vadgama et al. |
| 4,921,199 A | 5/1990 | Villaveces |
| 4,923,586 A | 5/1990 | Katayama et al. |
| 4,924,879 A | 5/1990 | O'Brien |
| 4,925,268 A | 5/1990 | Iyer et al. |
| 4,927,516 A | 5/1990 | Yamaguchi et al. |
| 4,934,369 A | 6/1990 | Maxwell |
| 4,935,105 A | 6/1990 | Churchouse |
| 4,935,345 A | 6/1990 | Guibeau et al. |
| 4,938,860 A | 7/1990 | Wogoman |
| 4,944,299 A | 7/1990 | Silvian |
| 4,950,378 A | 8/1990 | Nagara |
| 4,953,552 A | 9/1990 | DeMarzo |
| 4,954,129 A | 9/1990 | Giuliani et al. |
| 4,969,468 A | 11/1990 | Byers et al. |
| 4,970,145 A | 11/1990 | Bennetto et al. |
| 4,974,929 A | 12/1990 | Curry |
| 4,985,142 A | 1/1991 | Laycock et al. |
| 4,986,271 A | 1/1991 | Wilkins |
| 4,988,341 A | 1/1991 | Columbus et al. |
| 4,994,167 A | 2/1991 | Shults et al. |
| 4,995,402 A | 2/1991 | Smith et al. |
| 5,000,180 A | 3/1991 | Kuypers et al. |
| 5,001,054 A | 3/1991 | Wagner |
| 5,002,054 A | 3/1991 | Ash et al. |
| 5,006,110 A | 4/1991 | Garrison et al. |
| 5,013,161 A | 5/1991 | Zaragoza et al. |
| 5,019,974 A | 5/1991 | Beckers |
| 5,035,860 A | 7/1991 | Kleingeld et al. |
| 5,036,860 A | 8/1991 | Leigh et al. |
| 5,047,044 A | 9/1991 | Smith et al. |
| 5,050,612 A | 9/1991 | Matsumura |
| 5,051,688 A | 9/1991 | Murase et al. |
| 5,055,171 A | 10/1991 | Peck |
| 5,058,592 A | 10/1991 | Whisler |
| 5,068,536 A | 11/1991 | Rosenthal |
| 5,070,535 A | 12/1991 | Hochmair et al. |
| 5,082,550 A | 1/1992 | Rishpon et al. |
| 5,082,786 A | 1/1992 | Nakamoto |
| 5,086,246 A | 2/1992 | Dymond et al. |
| 5,089,112 A | 2/1992 | Skotheim et al. |
| 5,095,904 A | 3/1992 | Seligman et al. |
| 5,101,814 A | 4/1992 | Palti |
| 5,106,365 A | 4/1992 | Hernandez |
| 5,108,564 A | 4/1992 | Szuminsky et al. |
| 5,108,889 A | 4/1992 | Smith et al. |
| 5,109,850 A | 5/1992 | Blanco et al. |
| 5,120,420 A | 6/1992 | Nankai et al. |
| 5,122,925 A | 6/1992 | Inpyn |
| 5,124,661 A | 6/1992 | Zelin et al. |
| 5,126,034 A | 6/1992 | Carter et al. |
| 5,133,856 A | 7/1992 | Yamaguchi et al. |
| 5,135,003 A | 8/1992 | Souma |
| 5,135,004 A | 8/1992 | Adams et al. |
| 5,140,985 A | 8/1992 | Schroeder et al. |
| 5,141,868 A | 8/1992 | Shanks et al. |
| 5,161,532 A | 11/1992 | Joseph |
| 5,162,407 A | 11/1992 | Turner |
| 5,165,407 A | 11/1992 | Wilson et al. |
| 5,173,165 A | 12/1992 | Schmid et al. |
| 5,174,291 A | 12/1992 | Schoonen et al. |
| 5,190,041 A | 3/1993 | Palti |
| 5,192,416 A | 3/1993 | Wang et al. |
| 5,193,545 A | 3/1993 | Marsoner et al. |
| 5,198,367 A | 3/1993 | Aizawa et al. |
| 5,202,261 A | 4/1993 | Musho et al. |
| 5,204,264 A | 4/1993 | Kaminer et al. |
| 5,205,297 A | 4/1993 | Montecalvo et al. |
| 5,205,920 A | 4/1993 | Oyama et al. |
| 5,208,154 A | 5/1993 | Weaver et al. |
| 5,209,229 A | 5/1993 | Gilli |
| 5,217,595 A | 6/1993 | Smith et al. |
| 5,228,449 A | 7/1993 | Christ et al. |
| 5,229,282 A | 7/1993 | Yoshioka et al. |
| 5,231,988 A | 8/1993 | Wernicke et al. |
| 5,234,835 A | 8/1993 | Nestor et al. |
| 5,238,729 A | 8/1993 | Debe |
| 5,243,696 A | 9/1993 | Carr et al. |
| 5,245,314 A | 9/1993 | Kah et al. |
| 5,246,867 A | 9/1993 | Lakowicz et al. |
| 5,250,439 A | 10/1993 | Musho et al. |
| 5,251,126 A | 10/1993 | Kahn et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,105 A | 11/1993 | Gregg et al. |
| 5,264,106 A | 11/1993 | McAleer et al. |
| 5,267,963 A | 12/1993 | Bachynsky |
| 5,271,815 A | 12/1993 | Wong |
| 5,279,294 A | 1/1994 | Anderson |
| 5,284,156 A | 2/1994 | Schramm et al. |
| 5,285,792 A | 2/1994 | Sjoquist et al. |
| 5,286,362 A | 2/1994 | Hoenes et al. |
| 5,286,364 A | 2/1994 | Yacynych et al. |

(56)                References Cited

U.S. PATENT DOCUMENTS

| | | |
|---|---|---|
| 5,288,636 A | 2/1994 | Pollmann et al. |
| 5,289,497 A | 2/1994 | Jackobson et al. |
| 5,293,546 A | 3/1994 | Tadros et al. |
| 5,293,877 A | 3/1994 | O'Hara et al. |
| 5,299,571 A | 4/1994 | Mastrototaro |
| 5,305,008 A | 4/1994 | Turner et al. |
| 5,318,583 A | 6/1994 | Rabenau et al. |
| 5,320,098 A | 6/1994 | Davidson |
| 5,320,715 A | 6/1994 | Berg |
| 5,320,725 A | 6/1994 | Gregg et al. |
| 5,322,063 A | 6/1994 | Allen et al. |
| 5,333,615 A | 8/1994 | Craelius et al. |
| 5,337,747 A | 8/1994 | Neftel |
| 5,340,722 A | 8/1994 | Wolfbeis et al. |
| 5,342,789 A | 8/1994 | Chick et al. |
| 5,352,348 A | 10/1994 | Young et al. |
| 5,356,420 A | 10/1994 | Czernecki et al. |
| 5,356,786 A | 10/1994 | Heller et al. |
| 5,360,404 A | 11/1994 | Novacek et al. |
| 5,368,028 A | 11/1994 | Palti |
| 5,372,133 A | 12/1994 | Hogen Esch |
| 5,372,427 A | 12/1994 | Padovani et al. |
| 5,376,251 A | 12/1994 | Kaneko et al. |
| 5,378,628 A | 1/1995 | Gratzel et al. |
| 5,379,238 A | 1/1995 | Stark |
| 5,384,547 A | 1/1995 | Lynk et al. |
| 5,387,327 A | 2/1995 | Khan |
| 5,390,670 A | 2/1995 | Centa et al. |
| 5,390,671 A | 2/1995 | Lord et al. |
| 5,391,250 A | 2/1995 | Cheney, II et al. |
| 5,394,877 A | 3/1995 | Orr et al. |
| 5,395,504 A | 3/1995 | Saurer et al. |
| 5,400,782 A | 3/1995 | Beaubiah |
| 5,400,794 A | 3/1995 | Gorman |
| 5,402,780 A | 4/1995 | Faasse, Jr. |
| 5,407,431 A | 4/1995 | Botich et al. |
| 5,408,999 A | 4/1995 | Singh et al. |
| 5,410,326 A | 4/1995 | Goldstein |
| 5,411,647 A | 5/1995 | Johnson et al. |
| 5,425,361 A | 6/1995 | Fenzlein et al. |
| 5,431,160 A | 7/1995 | Wilkins |
| 5,431,921 A | 7/1995 | Thombre |
| 5,437,999 A | 8/1995 | Diebold et al. |
| 5,438,983 A | 8/1995 | Falcone |
| 5,462,051 A | 10/1995 | Oka et al. |
| 5,462,645 A | 10/1995 | Albery et al. |
| 5,469,846 A | 11/1995 | Khan |
| 5,472,317 A | 12/1995 | Field et al. |
| 5,482,473 A | 1/1996 | Lord et al. |
| 5,484,403 A | 1/1996 | Yoakum et al. |
| 5,489,414 A | 2/1996 | Schreiber et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,499,243 A | 3/1996 | Hall |
| 5,507,288 A | 4/1996 | Bocker et al. |
| 5,509,410 A | 4/1996 | Hill et al. |
| 5,514,718 A | 5/1996 | Lewis et al. |
| 5,516,832 A | 5/1996 | Kennan et al. |
| 5,527,288 A | 6/1996 | Gross et al. |
| 5,531,878 A | 7/1996 | Vadgama et al. |
| 5,532,686 A | 7/1996 | Urbas et al. |
| 5,533,977 A | 7/1996 | Metcalf et al. |
| 5,536,259 A | 7/1996 | Utterberg |
| 5,543,326 A | 8/1996 | Heller et al. |
| 5,544,196 A | 8/1996 | Tiedmann, Jr. et al. |
| 5,545,191 A | 8/1996 | Mann et al. |
| 5,549,568 A | 8/1996 | Sheilds |
| 5,551,427 A | 9/1996 | Altman |
| 5,555,190 A | 9/1996 | Derby et al. |
| 5,558,638 A | 9/1996 | Evers et al. |
| 5,560,357 A | 10/1996 | Faupei et al. |
| 5,562,713 A | 10/1996 | Silvian |
| 5,564,434 A | 10/1996 | Halperin et al. |
| 5,565,085 A | 10/1996 | Ikeda et al. |
| 5,567,302 A | 10/1996 | Song et al. |
| 5,568,806 A | 10/1996 | Cheney, II et al. |
| 5,569,186 A | 10/1996 | Lord et al. |
| 5,571,022 A | 11/1996 | Schaarschmidt |
| 5,575,563 A | 11/1996 | Chiu et al. |
| 5,581,206 A | 12/1996 | Chevallier et al. |
| 5,582,184 A | 12/1996 | Erickson et al. |
| 5,582,697 A | 12/1996 | Ikeda et al. |
| 5,582,698 A | 12/1996 | Flaherty et al. |
| 5,584,813 A | 12/1996 | Livingston et al. |
| 5,586,553 A | 12/1996 | Halli et al. |
| 5,589,326 A | 12/1996 | Deng et al. |
| 5,593,852 A | 1/1997 | Heller et al. |
| 5,596,150 A | 1/1997 | Arndt et al. |
| 5,600,301 A | 2/1997 | Robinson, III |
| 5,601,435 A | 2/1997 | Quy |
| 5,609,575 A | 3/1997 | Larson et al. |
| 5,613,978 A | 3/1997 | Harding |
| 5,617,851 A | 4/1997 | Lipkovker |
| 5,623,933 A | 4/1997 | Amano et al. |
| 5,626,566 A | 5/1997 | Petersen et al. |
| 5,628,310 A | 5/1997 | Rao et al. |
| 5,628,324 A | 5/1997 | Sarbach |
| 5,628,890 A | 5/1997 | Carter et al. |
| 5,632,557 A | 5/1997 | Simons |
| 5,634,468 A | 6/1997 | Platt et al. |
| 5,636,640 A | 6/1997 | Staehlin |
| 5,638,832 A | 6/1997 | Singer et al. |
| 5,640,954 A | 6/1997 | Pfeiffer et al. |
| 5,651,869 A | 7/1997 | Yoshioka et al. |
| 5,653,239 A | 8/1997 | Pompei et al. |
| 5,659,454 A | 8/1997 | Vermesse |
| 5,660,163 A | 8/1997 | Schulman et al. |
| 5,665,071 A | 9/1997 | Wyrick |
| 5,665,222 A | 9/1997 | Heller et al. |
| 5,669,543 A | 9/1997 | Ueno |
| 5,669,890 A | 9/1997 | Grimm |
| 5,670,031 A | 9/1997 | Hintsche et al. |
| 5,673,322 A | 9/1997 | Pepe et al. |
| 5,680,858 A | 10/1997 | Hansen et al. |
| 5,682,233 A | 10/1997 | Brinda |
| 5,695,623 A | 12/1997 | Michel et al. |
| 5,707,502 A | 1/1998 | McCaffrey et al. |
| 5,708,247 A | 1/1998 | McAleer et al. |
| 5,711,001 A | 1/1998 | Bussan et al. |
| 5,711,297 A | 1/1998 | Iliff et al. |
| 5,711,861 A | 1/1998 | Ward et al. |
| 5,711,862 A | 1/1998 | Sakoda et al. |
| 5,724,030 A | 3/1998 | Urbas et al. |
| 5,726,646 A | 3/1998 | Bane et al. |
| 5,733,044 A | 3/1998 | Rose et al. |
| 5,733,259 A | 3/1998 | Valcke et al. |
| 5,733,262 A | 3/1998 | Paul |
| 5,733,313 A | 3/1998 | Barreras, Sr. et al. |
| 5,735,285 A | 4/1998 | Albert et al. |
| 5,738,220 A | 4/1998 | Geszler |
| 5,741,211 A | 4/1998 | Renirie et al. |
| 5,743,262 A | 4/1998 | Lepper, Jr. et al. |
| 5,746,217 A | 5/1998 | Erickson et al. |
| 5,746,697 A | 5/1998 | Swedlow et al. |
| 5,748,103 A | 5/1998 | Flach et al. |
| 5,749,656 A | 5/1998 | Boehm et al. |
| 5,749,907 A | 5/1998 | Mann |
| 5,758,290 A | 5/1998 | Nealon et al. |
| 5,766,131 A | 6/1998 | Kondo et al. |
| 5,770,028 A | 6/1998 | Maley et al. |
| 5,771,001 A | 6/1998 | Cobb |
| 5,771,891 A | 6/1998 | Gozani |
| 5,772,586 A | 6/1998 | Heinonen et al. |
| 5,778,879 A | 7/1998 | Ota et al. |
| 5,779,665 A | 7/1998 | Mastrototaro et al. |
| 5,786,439 A | 7/1998 | Van Antwerp et al. |
| 5,791,344 A | 8/1998 | Schulman et al. |
| 5,798,961 A | 8/1998 | Heyden et al. |
| 5,800,420 A | 9/1998 | Gross et al. |
| 5,804,047 A | 9/1998 | Karube et al. |
| 5,807,375 A | 9/1998 | Gross et al. |
| 5,814,020 A | 9/1998 | Gross |

(56)           References Cited

U.S. PATENT DOCUMENTS

| | | | | | | |
|---|---|---|---|---|---|---|
| 5,820,551 | A | 10/1998 | Hill et al. | 6,091,975 | A | 7/2000 | Daddona et al. |
| 5,820,570 | A | 10/1998 | Erickson et al. | 6,091,976 | A | 7/2000 | Pfeiffer et al. |
| 5,820,622 | A | 10/1998 | Gross et al. | 6,091,987 | A | 7/2000 | Thompson |
| 5,822,715 | A | 10/1998 | Worthington et al. | 6,093,172 | A | 7/2000 | Funderburk et al. |
| 5,823,802 | A | 10/1998 | Bartley | 6,096,364 | A | 8/2000 | Bok et al. |
| 5,827,184 | A | 10/1998 | Netherly et al. | 6,097,480 | A | 8/2000 | Kaplan |
| 5,830,064 | A | 11/1998 | Bradish et al. | 6,099,484 | A | 8/2000 | Douglas et al. |
| 5,833,603 | A | 11/1998 | Kovacs et al. | 6,102,896 | A | 8/2000 | Roser |
| 5,840,020 | A | 11/1998 | Heinonen et al. | 6,103,033 | A | 8/2000 | Say et al. |
| 5,842,983 | A | 12/1998 | Abel et al. | 6,106,484 | A | 8/2000 | Terwilliger |
| 5,851,197 | A | 12/1998 | Marano et al. | 6,117,290 | A | 9/2000 | Say et al. |
| 5,856,758 | A | 1/1999 | Joffe et al. | 6,119,028 | A | 9/2000 | Schulman et al. |
| 5,858,001 | A | 1/1999 | Tsals et al. | 6,120,676 | A | 9/2000 | Heller et al. |
| 5,865,804 | A | 2/1999 | Bachynsky | 6,121,009 | A | 9/2000 | Heller et al. |
| 5,871,494 | A | 2/1999 | Simons et al. | 6,121,611 | A | 9/2000 | Lindsay et al. |
| 5,875,186 | A | 2/1999 | Belanger et al. | 6,122,351 | A | 9/2000 | Schlueter, Jr. et al. |
| 5,879,311 | A | 3/1999 | Duchon et al. | 6,129,666 | A | 10/2000 | DeLuca et al. |
| 5,885,211 | A | 3/1999 | Eppstein et al. | 6,130,623 | A | 10/2000 | MacLellan et al. |
| 5,891,049 | A | 4/1999 | Cyrus et al. | 6,132,449 | A | 10/2000 | Lum et al. |
| 5,899,855 | A | 5/1999 | Brown | 6,134,461 | A | 10/2000 | Say et al. |
| 5,899,856 | A | 5/1999 | Schoendorfer et al. | 6,141,573 | A | 10/2000 | Kurnik et al. |
| 5,914,026 | A | 6/1999 | Blubaugh, Jr. et al. | 6,143,164 | A | 11/2000 | Heller et al. |
| 5,918,603 | A | 7/1999 | Brown | 6,144,837 | A | 11/2000 | Quy |
| 5,919,141 | A | 7/1999 | Money et al. | 6,144,871 | A | 11/2000 | Saito et al. |
| 5,921,963 | A | 7/1999 | Erez et al. | 6,144,922 | A | 11/2000 | Douglas et al. |
| 5,924,979 | A | 7/1999 | Sedlow et al. | 6,149,626 | A | 11/2000 | Bachynsky et al. |
| 5,925,021 | A | 7/1999 | Castellano et al. | 6,157,850 | A | 12/2000 | Diab et al. |
| 5,931,814 | A | 8/1999 | Alex et al. | 6,159,147 | A | 12/2000 | Lichter et al. |
| 5,931,868 | A | 8/1999 | Gross | 6,159,181 | A | 12/2000 | Crossman et al. |
| 5,935,224 | A | 8/1999 | Svancarek et al. | 6,161,095 | A | 12/2000 | Brown |
| 5,938,679 | A | 8/1999 | Freeman et al. | 6,162,611 | A | 12/2000 | Heller et al. |
| 5,942,979 | A | 8/1999 | Luppino | 6,168,606 | B1 | 1/2001 | Levin et al. |
| 5,948,006 | A | 9/1999 | Mann | 6,175,752 | B1 | 1/2001 | Say et al. |
| 5,951,485 | A | 9/1999 | Cyrus et al. | 6,186,982 | B1 | 2/2001 | Gross et al. |
| 5,951,492 | A | 9/1999 | Douglas et al. | 6,192,891 | B1 | 2/2001 | Gravel et al. |
| 5,951,521 | A | 9/1999 | Mastrototaro et al. | 6,197,040 | B1 | 3/2001 | LeVaughn et al. |
| 5,951,582 | A | 9/1999 | Thorne et al. | 6,198,946 | B1 | 3/2001 | Shin et al. |
| 5,954,643 | A | 9/1999 | Van Antwerp | 6,200,265 | B1 | 3/2001 | Walsh et al. |
| 5,954,685 | A | 9/1999 | Tierny | 6,203,495 | B1 | 3/2001 | Bardy et al. |
| 5,957,854 | A | 9/1999 | Besson et al. | 6,212,416 | B1 | 4/2001 | Ward et al. |
| 5,961,451 | A | 10/1999 | Reber et al. | 6,213,972 | B1 | 4/2001 | Butterfield et al. |
| 5,964,718 | A | 10/1999 | Duchon et al. | 6,219,574 | B1 | 4/2001 | Cormier et al. |
| 5,964,993 | A | 10/1999 | Blubaugh, Jr. et al. | 6,223,283 | B1 | 4/2001 | Chaiken et al. |
| 5,965,380 | A | 10/1999 | Heller et al. | 6,231,531 | B1 | 5/2001 | Lum et al. |
| 5,971,922 | A | 10/1999 | Arita et al. | 6,233,471 | B1 | 5/2001 | Berner et al. |
| 5,971,941 | A | 10/1999 | Simons et al. | 6,237,394 | B1 | 5/2001 | Harris et al. |
| 5,972,199 | A | 10/1999 | Heller et al. | 6,248,067 | B1 | 6/2001 | Causey, III et al. |
| 5,987,353 | A | 11/1999 | Khatchatrian et al. | 6,254,536 | B1 | 7/2001 | DeVito |
| 5,993,411 | A | 11/1999 | Choi | 6,254,586 | B1 | 7/2001 | Mann et al. |
| 5,995,860 | A | 11/1999 | Sun et al. | 6,264,810 | B1 | 7/2001 | Stol et al. |
| 5,997,501 | A | 12/1999 | Gross et al. | 6,270,455 | B1 | 8/2001 | Brown |
| 6,001,067 | A | 12/1999 | Shults et al. | 6,275,717 | B1 | 8/2001 | Gross et al. |
| 6,004,278 | A | 12/1999 | Botich et al. | 6,283,761 | B1 | 9/2001 | Joao |
| 6,017,335 | A | 1/2000 | Burnham | 6,283,982 | B1 | 9/2001 | Levaughn et al. |
| 6,022,315 | A | 2/2000 | Iliff | 6,284,478 | B1 | 9/2001 | Heller et al. |
| 6,022,368 | A | 2/2000 | Gavronsky et al. | 6,291,200 | B1 | 9/2001 | LeJeune et al. |
| 6,024,699 | A | 2/2000 | Surwit et al. | 6,293,925 | B1 | 9/2001 | Safabash et al. |
| 6,026,321 | A | 2/2000 | Miyata et al. | 6,294,997 | B1 | 9/2001 | Paratore et al. |
| 6,027,459 | A | 2/2000 | Shain et al. | 6,295,506 | B1 | 9/2001 | Heinonen et al. |
| 6,028,413 | A | 2/2000 | Brockmann | 6,298,255 | B1 | 10/2001 | Cordero et al. |
| 6,032,064 | A | 2/2000 | Devlin et al. | 6,299,347 | B1 | 10/2001 | Pompei |
| 6,036,924 | A | 3/2000 | Simons et al. | 6,299,757 | B1 | 10/2001 | Feldman et al. |
| 6,048,352 | A | 4/2000 | Douglas et al. | 6,302,866 | B1 | 10/2001 | Marggi |
| 6,049,727 | A | 4/2000 | Crothall | 6,304,766 | B1 | 10/2001 | Colvin, Jr. |
| 6,052,565 | A | 4/2000 | Ishikura et al. | 6,306,104 | B1 | 10/2001 | Cunningham et al. |
| 6,056,718 | A | 5/2000 | Funderburk et al. | 6,309,884 | B1 | 10/2001 | Cooper et al. |
| 6,059,946 | A | 5/2000 | Yukawa et al. | 6,314,317 | B1 | 11/2001 | Willis |
| 6,066,243 | A | 5/2000 | Anderson et al. | 6,329,161 | B1 | 12/2001 | Heller et al. |
| 6,068,399 | A | 5/2000 | Tseng | 6,331,244 | B1 | 12/2001 | Lewis et al. |
| 6,071,294 | A | 6/2000 | Simons et al. | 6,336,269 | B1 | 1/2002 | Eldridge et al. |
| 6,071,391 | A | 6/2000 | Gotoh et al. | 6,338,790 | B1 | 1/2002 | Feldman et al. |
| 6,083,710 | A | 7/2000 | Heller et al. | 6,341,232 | B1 | 1/2002 | Conn et al. |
| 6,085,342 | A | 7/2000 | Marholev et al. | 6,348,640 | B1 | 2/2002 | Navot et al. |
| 6,088,605 | A | 7/2000 | Griffith et al. | 6,359,270 | B1 | 3/2002 | Bridson |
| 6,088,608 | A | 7/2000 | Schulman et al. | 6,359,444 | B1 | 3/2002 | Grimes |
| | | | | 6,360,888 | B1 | 3/2002 | McIvor et al. |
| | | | | 6,364,890 | B1 | 4/2002 | Lum et al. |
| | | | | 6,366,794 | B1 | 4/2002 | Moussy et al. |
| | | | | 6,368,141 | B1 | 4/2002 | Van Antwerp et al. |

(56) References Cited

U.S. PATENT DOCUMENTS

| | | | |
|---|---|---|---|
| 6,368,274 | B1 | 4/2002 | Van Antwerp et al. |
| 6,377,828 | B1 | 4/2002 | Chaiken et al. |
| 6,377,829 | B1 | 4/2002 | Al-Ali |
| 6,377,894 | B1 | 4/2002 | Deweese et al. |
| 6,379,301 | B1 | 4/2002 | Worthington et al. |
| 6,387,048 | B1 | 5/2002 | Schulman et al. |
| 6,400,974 | B1 | 6/2002 | Lesho |
| 6,405,066 | B1 | 6/2002 | Essenpreis et al. |
| 6,409,740 | B1 | 6/2002 | Kuhr et al. |
| 6,413,393 | B1 | 7/2002 | Van Antwerp et al. |
| 6,416,471 | B1 | 7/2002 | Kumar et al. |
| 6,418,332 | B1 | 7/2002 | Mastrototaro et al. |
| 6,418,346 | B1 | 7/2002 | Nelson et al. |
| 6,424,847 | B1 | 7/2002 | Mastrototaro et al. |
| 6,427,088 | B1 | 7/2002 | Bowman, IV et al. |
| 6,433,743 | B1 | 8/2002 | Massy et al. |
| 6,435,017 | B1 | 8/2002 | Nowicki, Jr. et al. |
| 6,437,679 | B1 | 8/2002 | Roques |
| 6,438,414 | B1 | 8/2002 | Conn et al. |
| 6,440,068 | B1 | 8/2002 | Brown et al. |
| 6,442,413 | B1 | 8/2002 | Silver |
| 6,445,374 | B2 | 9/2002 | Albert et al. |
| 6,458,109 | B1 | 10/2002 | Henley et al. |
| 6,461,496 | B1 | 10/2002 | Feldman et al. |
| 6,471,689 | B1 | 10/2002 | Joseph et al. |
| 6,472,220 | B1 | 10/2002 | Simons et al. |
| 6,478,736 | B1 | 11/2002 | Mault |
| 6,482,176 | B1 | 11/2002 | Wich |
| 6,484,045 | B1 | 11/2002 | Holker et al. |
| 6,484,046 | B1 | 11/2002 | Say et al. |
| 6,493,069 | B1 | 12/2002 | Nagashimada et al. |
| 6,494,830 | B1 | 12/2002 | Wessel |
| 6,496,729 | B2 | 12/2002 | Thompson |
| 6,497,655 | B1 | 12/2002 | Linberg et al. |
| 6,503,381 | B1 | 1/2003 | Gotoh et al. |
| 6,510,344 | B1 | 1/2003 | Halpern |
| 6,514,460 | B1 | 2/2003 | Fendrock |
| 6,514,689 | B2 | 2/2003 | Han et al. |
| 6,514,718 | B2 | 2/2003 | Heller et al. |
| 6,520,326 | B2 | 2/2003 | McIvor et al. |
| 6,522,927 | B1 | 2/2003 | Bishay et al. |
| 6,537,242 | B1 | 3/2003 | Palmer |
| 6,540,891 | B1 | 4/2003 | Stewart et al. |
| 6,544,212 | B2 | 4/2003 | Galley et al. |
| 6,546,268 | B1 | 4/2003 | Ishikawa et al. |
| 6,549,796 | B2 | 4/2003 | Sohrab |
| 6,551,494 | B1 | 4/2003 | Heller et al. |
| 6,551,496 | B1 | 4/2003 | Moles et al. |
| 6,554,795 | B2 | 4/2003 | Bagaoisan et al. |
| 6,554,798 | B1 | 4/2003 | Mann et al. |
| 6,558,320 | B1 | 5/2003 | Causey, III et al. |
| 6,558,321 | B1 | 5/2003 | Burd et al. |
| 6,558,351 | B1 | 5/2003 | Steil et al. |
| 6,560,471 | B1 | 5/2003 | Heller et al. |
| 6,561,975 | B1 | 5/2003 | Pool et al. |
| 6,561,978 | B1 | 5/2003 | Conn et al. |
| 6,562,001 | B2 | 5/2003 | Lebel et al. |
| 6,564,105 | B2 | 5/2003 | Starkweather et al. |
| 6,565,509 | B1 | 5/2003 | Say et al. |
| 6,571,128 | B2 | 5/2003 | Lebel et al. |
| 6,572,542 | B1 | 6/2003 | Houben et al. |
| 6,572,566 | B2 | 6/2003 | Effenhauser |
| 6,574,490 | B2 | 6/2003 | Abbink et al. |
| 6,574,510 | B2 | 6/2003 | Von Arx et al. |
| 6,575,895 | B1 | 6/2003 | Blair |
| 6,576,101 | B1 | 6/2003 | Heller et al. |
| 6,577,899 | B2 | 6/2003 | Lebel et al. |
| 6,579,231 | B1 | 6/2003 | Phipps |
| 6,579,690 | B1 | 6/2003 | Bonnecaze et al. |
| 6,584,335 | B1 | 6/2003 | Haar et al. |
| 6,585,644 | B2 | 7/2003 | Lebel et al. |
| 6,589,229 | B1 | 7/2003 | Connelly et al. |
| 6,591,125 | B1 | 7/2003 | Buse et al. |
| 6,592,745 | B1 | 7/2003 | Feldman et al. |
| 6,595,919 | B2 | 7/2003 | Berner et al. |
| 6,600,997 | B2 | 7/2003 | Deweese et al. |
| 6,602,268 | B2 | 8/2003 | Kuhr et al. |
| 6,603,995 | B1 | 8/2003 | Carter |
| 6,604,050 | B2 | 8/2003 | Trippel et al. |
| 6,605,200 | B1 | 8/2003 | Mao et al. |
| 6,605,201 | B1 | 8/2003 | Mao et al. |
| 6,607,509 | B2 | 8/2003 | Bobroff et al. |
| 6,607,543 | B2 | 8/2003 | Purcell et al. |
| 6,608,562 | B1 | 8/2003 | Kimura et al. |
| 6,610,012 | B2 | 8/2003 | Mault |
| 6,611,206 | B2 | 8/2003 | Eshelman et al. |
| 6,613,015 | B2 | 9/2003 | Sandstrom et al. |
| 6,616,819 | B1 | 9/2003 | Liamos et al. |
| 6,618,934 | B1 | 9/2003 | Feldman et al. |
| 6,627,154 | B1 | 9/2003 | Goodman et al. |
| 6,631,281 | B1 | 10/2003 | Kastle |
| 6,633,772 | B2 | 10/2003 | Ford et al. |
| 6,635,014 | B2 | 10/2003 | Starkweather et al. |
| 6,635,167 | B1 | 10/2003 | Batman et al. |
| 6,637,611 | B2 | 10/2003 | Luch |
| 6,641,533 | B2 | 11/2003 | Causey, III et al. |
| 6,645,359 | B1 | 11/2003 | Bhullar et al. |
| 6,648,821 | B2 | 11/2003 | Lebel et al. |
| 6,650,471 | B2 | 11/2003 | Doi |
| 6,654,625 | B1 | 11/2003 | Say et al. |
| 6,656,114 | B1 | 12/2003 | Poulson et al. |
| 6,658,396 | B1 | 12/2003 | Tang et al. |
| 6,659,948 | B2 | 12/2003 | Lebel et al. |
| 6,662,439 | B1 | 12/2003 | Bhullar |
| 6,666,849 | B2 | 12/2003 | Marshall et al. |
| 6,668,196 | B1 | 12/2003 | Villegas et al. |
| 6,671,534 | B2 | 12/2003 | Putz |
| 6,675,030 | B2 | 1/2004 | Ciurczak et al. |
| 6,676,290 | B1 | 1/2004 | Lu |
| 6,676,816 | B2 | 1/2004 | Mao et al. |
| 6,687,546 | B2 | 2/2004 | Lebel et al. |
| 6,689,056 | B1 | 2/2004 | Kilcoyne et al. |
| 6,694,191 | B2 | 2/2004 | Starkweather et al. |
| 6,695,860 | B1 | 2/2004 | Ward et al. |
| 6,698,269 | B2 | 3/2004 | Baber et al. |
| 6,699,188 | B2 | 3/2004 | Wessel |
| 6,702,857 | B2 | 3/2004 | Brauker et al. |
| 6,706,159 | B2 | 3/2004 | Moerman et al. |
| 6,721,582 | B2 | 4/2004 | Trepagnier et al. |
| 6,730,025 | B1 | 5/2004 | Platt |
| 6,730,072 | B2 | 5/2004 | Shawgo et al. |
| 6,730,200 | B1 | 5/2004 | Stewart et al. |
| 6,731,976 | B2 | 5/2004 | Penn et al. |
| 6,733,446 | B2 | 5/2004 | Lebel et al. |
| 6,735,183 | B2 | 5/2004 | O'Toole et al. |
| 6,735,479 | B2 | 5/2004 | Fabian et al. |
| 6,736,957 | B1 | 5/2004 | Forrow et al. |
| 6,740,075 | B2 | 5/2004 | Lebel et al. |
| 6,741,877 | B1 | 5/2004 | Shults et al. |
| 6,743,635 | B2 | 6/2004 | Neel et al. |
| 6,746,582 | B2 | 6/2004 | Heller et al. |
| 6,748,445 | B1 | 6/2004 | Darcey et al. |
| 6,749,740 | B2 | 6/2004 | Liamos et al. |
| 6,758,810 | B2 | 7/2004 | Lebel et al. |
| 6,758,835 | B2 | 7/2004 | Close et al. |
| 6,764,581 | B1 | 7/2004 | Forrow et al. |
| 6,767,440 | B1 | 7/2004 | Bhullar et al. |
| 6,770,030 | B1 | 8/2004 | Schaupp et al. |
| 6,773,671 | B1 | 8/2004 | Lewis et al. |
| 6,781,522 | B2 | 8/2004 | Sleva et al. |
| 6,790,178 | B1 | 9/2004 | Mault et al. |
| 6,804,558 | B2 | 10/2004 | Haller et al. |
| 6,804,561 | B2 | 10/2004 | Stover |
| 6,809,653 | B1 | 10/2004 | Mann et al. |
| 6,810,290 | B2 | 10/2004 | Lebel et al. |
| 6,811,533 | B2 | 11/2004 | Lebel et al. |
| 6,811,534 | B2 | 11/2004 | Bowman, IV et al. |
| 6,813,519 | B2 | 11/2004 | Lebel et al. |
| 6,814,844 | B2 | 11/2004 | Bhullar et al. |
| 6,830,551 | B1 | 12/2004 | Uchigaki et al. |
| 6,837,858 | B2 | 1/2005 | Cunningham et al. |
| 6,837,885 | B2 | 1/2005 | Koblish et al. |
| 6,837,988 | B2 | 1/2005 | Leong et al. |
| 6,849,052 | B2 | 2/2005 | Ughigaki et al. |

(56)                 References Cited

U.S. PATENT DOCUMENTS

| | | | |
|---|---|---|---|
| 6,850,790 B2 | 2/2005 | Berner et al. |
| 6,850,859 B1 | 2/2005 | Schuh |
| 6,854,882 B2 | 2/2005 | Chen |
| 6,862,465 B2 | 3/2005 | Shults et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,895,265 B2 | 5/2005 | Silver |
| 6,923,763 B1 | 8/2005 | Kovatchev et al. |
| 6,923,764 B2 | 8/2005 | Aceti et al. |
| 6,925,393 B1 | 8/2005 | Kalatz et al. |
| 6,931,327 B2 | 8/2005 | Goode, Jr. et al. |
| 6,932,892 B2 | 8/2005 | Chen |
| 6,932,894 B2 | 8/2005 | Mao et al. |
| 6,936,006 B2 | 8/2005 | Sabra |
| 6,937,222 B2 | 8/2005 | Numao |
| 6,940,403 B2 | 9/2005 | Kail, IV |
| 6,941,163 B2 | 9/2005 | Ford et al. |
| 6,942,518 B2 | 9/2005 | Liamos et al. |
| 6,950,708 B2 | 9/2005 | Bowman, IV et al. |
| 6,954,662 B2 | 10/2005 | Freger et al. |
| 6,958,705 B2 | 10/2005 | Lebel et al. |
| 6,959,211 B2 | 10/2005 | Rule et al. |
| 6,960,192 B1 | 11/2005 | Flaherty et al. |
| 6,968,294 B2 | 11/2005 | Gutta et al. |
| 6,971,274 B2 | 12/2005 | Olin |
| 6,971,999 B2 | 12/2005 | Py et al. |
| 6,973,706 B2 | 12/2005 | Say et al. |
| 6,974,437 B2 | 12/2005 | Lebel et al. |
| 6,975,893 B2 | 12/2005 | Say et al. |
| 6,983,867 B1 | 1/2006 | Fugere |
| 6,990,366 B2 | 1/2006 | Say et al. |
| 6,997,907 B2 | 2/2006 | Safabash et al. |
| 6,998,247 B2 | 2/2006 | Monfre et al. |
| 6,999,854 B2 | 2/2006 | Roth |
| 7,003,336 B2 | 2/2006 | Holker et al. |
| 7,003,340 B2 | 2/2006 | Say et al. |
| 7,003,341 B2 | 2/2006 | Say et al. |
| 7,005,857 B2 | 2/2006 | Stiene et al. |
| 7,009,511 B2 | 3/2006 | Mazar et al. |
| 7,010,356 B2 | 3/2006 | Jog et al. |
| 7,015,817 B2 | 3/2006 | Copley et al. |
| 7,016,713 B2 | 3/2006 | Gardner et al. |
| 7,020,508 B2 | 3/2006 | Stivoric et al. |
| 7,022,072 B2 | 4/2006 | Fox et al. |
| 7,022,219 B2 | 4/2006 | Mansouri et al. |
| 7,024,236 B2 | 4/2006 | Ford et al. |
| 7,024,245 B2 | 4/2006 | Lebel et al. |
| 7,025,743 B2 | 4/2006 | Mann et al. |
| 7,025,774 B2 | 4/2006 | Freeman et al. |
| 7,027,848 B2 | 4/2006 | Robinson et al. |
| 7,027,859 B1 | 4/2006 | McNichols et al. |
| 7,027,931 B1 | 4/2006 | Jones et al. |
| 7,029,444 B2 | 4/2006 | Shin et al. |
| 7,041,057 B1 | 5/2006 | Faupel et al. |
| 7,041,068 B2 | 5/2006 | Freeman et al. |
| 7,041,468 B2 | 5/2006 | Drucker et al. |
| 7,043,305 B2 | 5/2006 | Kenknight et al. |
| 7,046,153 B2 | 5/2006 | Oja et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,073,246 B2 | 7/2006 | Bhullar et al. |
| 7,074,307 B2 | 7/2006 | Simpson et al. |
| 7,081,195 B2 | 7/2006 | Simpson et al. |
| 7,082,334 B2 | 7/2006 | Boute et al. |
| 7,097,637 B2 | 8/2006 | Triplett et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,120,483 B2 | 10/2006 | Russel et al. |
| 7,123,950 B2 | 10/2006 | Mannheimer |
| 7,124,027 B1 | 10/2006 | Ernst et al. |
| 7,125,382 B2 | 10/2006 | Zhou et al. |
| 7,131,984 B2 | 11/2006 | Sato et al. |
| 7,134,999 B2 | 11/2006 | Brauker et al. |
| 7,136,689 B2 | 11/2006 | Shults et al. |
| 7,144,384 B2 | 12/2006 | Gorman et al. |
| 7,146,202 B2 | 12/2006 | Ward et al. |
| 7,154,398 B2 | 12/2006 | Chen et al. |
| 7,155,290 B2 | 12/2006 | Von Arx et al. |
| 7,167,818 B2 | 1/2007 | Brown |
| 7,169,600 B2 | 1/2007 | Hoss et al. |
| 7,171,274 B2 | 1/2007 | Starkweather et al. |
| 7,174,199 B2 | 2/2007 | Berner et al. |
| 7,179,226 B2 | 2/2007 | Crothall et al. |
| 7,183,102 B2 | 2/2007 | Monfre et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,203,549 B2 | 4/2007 | Schommer et al. |
| 7,207,974 B2 | 4/2007 | Safabash et al. |
| 7,220,387 B2 | 5/2007 | Flaherty et al. |
| 7,223,276 B2 | 5/2007 | List et al. |
| 7,225,535 B2 | 6/2007 | Feldman et al. |
| 7,226,442 B2 | 6/2007 | Sheppard et al. |
| 7,226,978 B2 | 6/2007 | Tapsak et al. |
| 7,228,162 B2 | 6/2007 | Ward et al. |
| 7,228,182 B2 | 6/2007 | Healy et al. |
| 7,237,712 B2 | 7/2007 | DeRocco et al. |
| 7,267,665 B2 | 9/2007 | Steil et al. |
| 7,276,029 B2 | 10/2007 | Goode, Jr. et al. |
| 7,276,146 B2 | 10/2007 | Wilsey |
| 7,276,147 B2 | 10/2007 | Wilsey |
| 7,278,983 B2 | 10/2007 | Ireland et al. |
| 7,286,894 B1 | 10/2007 | Grant et al. |
| 7,287,318 B2 | 10/2007 | Bhullar et al. |
| 7,291,497 B2 | 11/2007 | Holmes et al. |
| 7,295,867 B2 | 11/2007 | Berner et al. |
| 7,297,151 B2 | 11/2007 | Boecker et al. |
| 7,299,082 B2 | 11/2007 | Feldman et al. |
| 7,310,544 B2 | 12/2007 | Brister et al. |
| 7,318,816 B2 | 1/2008 | Bobroff et al. |
| 7,324,012 B2 | 1/2008 | Mann et al. |
| 7,324,850 B2 | 1/2008 | Persen et al. |
| 7,329,239 B2 | 2/2008 | Safabash et al. |
| 7,335,294 B2 | 2/2008 | Heller et al. |
| 7,340,287 B2 | 3/2008 | Mason et al. |
| 7,340,309 B2 | 3/2008 | Miazga et al. |
| 7,344,500 B2 | 3/2008 | Talbot et al. |
| 7,347,819 B2 | 3/2008 | Lebel et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,381,184 B2 | 6/2008 | Funderburk et al. |
| 7,384,397 B2 | 6/2008 | Zhang et al. |
| 7,386,937 B2 | 6/2008 | Bhullar et al. |
| 7,387,010 B2 | 6/2008 | Sunshine et al. |
| 7,399,277 B2 | 7/2008 | Saidara et al. |
| 7,400,111 B2 | 7/2008 | Batman et al. |
| 7,401,111 B1 | 7/2008 | Batman et al. |
| 7,402,153 B2 | 7/2008 | Steil et al. |
| 7,404,796 B2 | 7/2008 | Ginsberg |
| 7,407,493 B2 | 8/2008 | Cane |
| 7,408,132 B2 | 8/2008 | Wambsganss et al. |
| 7,416,541 B2 | 8/2008 | Yuzhakov et al. |
| 7,419,573 B2 | 9/2008 | Gundel |
| 7,424,318 B2 | 9/2008 | Brister et al. |
| 7,429,255 B2 | 9/2008 | Thompson |
| 7,433,727 B2 | 10/2008 | Ward |
| 7,448,996 B2 | 11/2008 | Khanuja et al. |
| 7,455,663 B2 | 11/2008 | Bikovsky |
| 7,460,898 B2 | 12/2008 | Brister et al. |
| 7,462,264 B2 | 12/2008 | Heller et al. |
| 7,467,003 B2 | 12/2008 | Brister et al. |
| 7,468,125 B2 | 12/2008 | Kraft et al. |
| 7,471,972 B2 | 12/2008 | Rhodes et al. |

(56)        References Cited

U.S. PATENT DOCUMENTS

| | | | |
|---|---|---|---|
| 7,476,827 B1 | 1/2009 | Bhullar et al. |
| 7,481,819 B2 | 1/2009 | Koeppel et al. |
| 7,492,254 B2 | 2/2009 | Bandy et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,519,408 B2 | 4/2009 | Rasdal et al. |
| 7,545,272 B2 | 6/2009 | Goodnow et al. |
| 7,547,281 B2 | 6/2009 | Hayes et al. |
| 7,565,197 B2 | 7/2009 | Haubrich et al. |
| 7,568,619 B2 | 8/2009 | Todd et al. |
| 7,569,030 B2 | 8/2009 | Lebel et al. |
| 7,574,266 B2 | 8/2009 | Dudding et al. |
| 7,582,059 B2 | 9/2009 | Funderburk et al. |
| 7,583,990 B2 | 9/2009 | Goode, Jr. et al. |
| 7,585,287 B2 | 9/2009 | Bresina et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,604,178 B2 | 10/2009 | Stewart |
| 7,604,592 B2 | 10/2009 | Freeman et al. |
| 7,613,491 B2 | 11/2009 | Boock et al. |
| 7,615,007 B2 | 11/2009 | Shults et al. |
| 7,618,369 B2 | 11/2009 | Hayter et al. |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbies et al. |
| 7,643,798 B2 | 1/2010 | Ljung |
| 7,651,596 B2 | 1/2010 | Petisce et al. |
| 7,651,845 B2 | 1/2010 | Doyle, III et al. |
| 7,653,425 B2 | 1/2010 | Hayter et al. |
| 7,654,956 B2 | 2/2010 | Brister et al. |
| 7,657,297 B2 | 2/2010 | Simpson et al. |
| 7,659,823 B1 | 2/2010 | Killian et al. |
| 7,660,615 B2 | 2/2010 | VanAntwerp et al. |
| 7,666,149 B2 | 2/2010 | Simons et al. |
| 7,668,596 B2 | 2/2010 | Von Arx et al. |
| 7,682,338 B2 | 3/2010 | Griffin |
| 7,697,967 B2 | 4/2010 | Stafford |
| 7,699,775 B2 | 4/2010 | Desai et al. |
| 7,699,807 B2 | 4/2010 | Faust et al. |
| 7,701,052 B2 | 4/2010 | Borland et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,727,147 B1 | 6/2010 | Osorio et al. |
| 7,729,737 B2 | 6/2010 | Ward |
| 7,731,657 B2 | 6/2010 | Stafford |
| 7,731,691 B2 | 6/2010 | Cote et al. |
| 7,736,310 B2 | 6/2010 | Taub et al. |
| 7,736,344 B2 | 6/2010 | Moberg et al. |
| 7,741,734 B2 | 6/2010 | Joannopoulos et al. |
| 7,763,042 B2 | 7/2010 | Iio et al. |
| 7,766,829 B2 | 8/2010 | Sloan et al. |
| 7,768,387 B2 | 8/2010 | Fennell et al. |
| 7,771,352 B2 | 8/2010 | Shults et al. |
| 7,774,145 B2 | 8/2010 | Brauker et al. |
| 7,775,444 B2 | 8/2010 | DeRocco et al. |
| 7,778,680 B2 | 8/2010 | Goode, Jr. et al. |
| 7,779,332 B2 | 8/2010 | Karr et al. |
| 7,780,827 B1 | 8/2010 | Bhullar et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,811,231 B2 | 10/2010 | Jin et al. |
| 7,813,809 B2 | 10/2010 | Strother et al. |
| 7,822,454 B1 | 10/2010 | Alden et al. |
| 7,826,981 B2 | 11/2010 | Goode, Jr. et al. |
| 7,831,310 B2 | 11/2010 | Lebel et al. |
| 7,833,151 B2 | 11/2010 | Khait et al. |
| 7,833,170 B2 | 11/2010 | Matsumoto et al. |
| 7,837,633 B2 | 11/2010 | Conway et al. |
| 7,846,132 B2 | 12/2010 | Gravesen et al. |
| 7,850,652 B2 | 12/2010 | Liniger et al. |
| 7,860,574 B2 | 12/2010 | Von Arx et al. |
| 7,866,026 B1 | 1/2011 | Wang et al. |
| 7,867,244 B2 | 1/2011 | Lathrop et al. |
| 7,873,299 B2 | 1/2011 | Berner et al. |
| 7,882,611 B2 | 2/2011 | Shah et al. |
| 7,883,464 B2 | 2/2011 | Stafford |
| 7,883,473 B2 | 2/2011 | LeVaughn et al. |
| 7,885,697 B2 | 2/2011 | Brister et al. |
| 7,889,069 B2 | 2/2011 | Fifolt et al. |
| 7,896,844 B2 | 3/2011 | Thalmann et al. |
| 7,899,511 B2 | 3/2011 | Shults et al. |
| 7,899,545 B2 | 3/2011 | John |
| 7,905,833 B2 | 3/2011 | Brister et al. |
| 7,912,655 B2 | 3/2011 | Power et al. |
| 7,912,674 B2 | 3/2011 | Killoren Clark et al. |
| 7,914,450 B2 | 3/2011 | Goode, Jr. et al. |
| 7,914,460 B2 | 3/2011 | Melker et al. |
| 7,916,013 B2 | 3/2011 | Stevenson |
| 7,920,906 B2 | 4/2011 | Goode, Jr. et al. |
| 7,920,907 B2 | 4/2011 | McGarraugh et al. |
| 7,938,797 B2 | 5/2011 | Estes |
| 7,941,200 B2 | 5/2011 | Weinart et al. |
| 7,946,984 B2 | 5/2011 | Brister et al. |
| 7,946,985 B2 | 5/2011 | Mastrototaro et al. |
| 7,955,258 B2 | 6/2011 | Goscha et al. |
| 7,955,297 B2 | 6/2011 | Radmer et al. |
| 7,970,448 B2 | 6/2011 | Shults et al. |
| 7,970,449 B2 | 6/2011 | Ward |
| 7,972,296 B2 | 7/2011 | Braig et al. |
| 7,974,672 B2 | 7/2011 | Shults et al. |
| 7,976,467 B2 | 7/2011 | Young et al. |
| 7,978,063 B2 | 7/2011 | Baldus et al. |
| 7,985,203 B2 | 7/2011 | Haueter et al. |
| 7,996,158 B2 | 8/2011 | Hayter et al. |
| 7,999,674 B2 | 8/2011 | Kamen |
| 8,000,918 B2 | 8/2011 | Fjield et al. |
| 8,005,524 B2 | 8/2011 | Brauker et al. |
| 8,010,174 B2 | 8/2011 | Goode, Jr. et al. |
| 8,010,256 B2 | 8/2011 | Oowada |
| 8,016,774 B2 | 9/2011 | Freeman et al. |
| 8,028,837 B2 | 10/2011 | Gerstle et al. |
| 8,029,441 B2 | 10/2011 | Mazza et al. |
| 8,029,442 B2 | 10/2011 | Funderburk et al. |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B2 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,103,471 B2 | 1/2012 | Hayter |
| 8,111,042 B2 | 2/2012 | Bennett |
| 8,112,240 B2 | 2/2012 | Fennell |
| 8,115,488 B2 | 2/2012 | McDowell |
| 8,116,681 B2 | 2/2012 | Baarman |
| 8,116,683 B2 | 2/2012 | Baarman |
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,565 B2 | 3/2012 | Docks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |

(56)        References Cited

U.S. PATENT DOCUMENTS

| | | |
|---|---|---|
| 8,140,312 B2 | 3/2012 | Hayter et al. |
| 8,150,321 B2 | 4/2012 | Winter et al. |
| 8,150,516 B2 | 4/2012 | Levine et al. |
| 8,160,670 B2 | 4/2012 | Quyang et al. |
| 8,160,900 B2 | 4/2012 | Taub et al. |
| 8,172,805 B2 | 5/2012 | Mogensen et al. |
| 8,175,673 B2 | 5/2012 | Say et al. |
| 8,179,266 B2 | 5/2012 | Hermle |
| 8,180,423 B2 | 5/2012 | Mang et al. |
| 8,192,394 B2 | 6/2012 | Estes et al. |
| 8,216,138 B1 | 7/2012 | McGaraugh et al. |
| 8,221,332 B2 | 7/2012 | Robbins et al. |
| 8,224,410 B2 | 7/2012 | Hadvary et al. |
| 8,239,166 B2 | 8/2012 | Hayter et al. |
| 8,255,026 B1 | 8/2012 | Al-Ali |
| 8,260,558 B2 | 9/2012 | Hayter et al. |
| 8,262,618 B2 | 9/2012 | Scheurer |
| 8,282,549 B2 | 10/2012 | Brauker et al. |
| 8,333,714 B2 | 12/2012 | Stafford |
| 8,346,335 B2 | 1/2013 | Harper et al. |
| 8,346,337 B2 | 1/2013 | Heller et al. |
| 8,373,544 B2 | 2/2013 | Pitt-Plady |
| 8,374,668 B1 | 2/2013 | Hayter et al. |
| 8,376,945 B2 | 2/2013 | Hayter et al. |
| 8,377,271 B2 | 2/2013 | Mao et al. |
| 8,382,671 B2 | 2/2013 | Anthony et al. |
| 8,398,664 B2 | 3/2013 | Lamps et al. |
| 8,409,093 B2 | 4/2013 | Bugler |
| 8,409,145 B2 | 4/2013 | Raymond et al. |
| 8,439,838 B2 | 5/2013 | Mogensen et al. |
| 8,444,560 B2 | 5/2013 | Hayter et al. |
| 8,461,985 B2 | 6/2013 | Fennell et al. |
| 8,469,986 B2 | 6/2013 | Schraga |
| 8,512,243 B2 | 8/2013 | Stafford |
| 8,515,518 B2 | 8/2013 | Ouyang et al. |
| 8,515,519 B2 | 8/2013 | Brister et al. |
| 8,538,512 B1 | 9/2013 | Bibian et al. |
| 8,545,403 B2 | 10/2013 | Peyser et al. |
| 8,560,038 B2 | 10/2013 | Hayter et al. |
| 8,562,567 B2 | 10/2013 | Gundberg |
| 8,571,808 B2 | 10/2013 | Hayter |
| 8,583,205 B2 | 11/2013 | Budiman et al. |
| 8,585,591 B2 | 11/2013 | Sloan et al. |
| 8,597,570 B2 | 12/2013 | Terashima et al. |
| 8,600,681 B2 | 12/2013 | Hayter et al. |
| 8,602,991 B2 | 12/2013 | Stafford |
| 8,612,163 B2 | 12/2013 | Hayter et al. |
| 8,615,282 B2 | 12/2013 | Brister et al. |
| 8,617,069 B2 | 12/2013 | Bernstein et al. |
| 8,617,071 B2 | 12/2013 | Say et al. |
| 8,622,903 B2 | 1/2014 | Jin et al. |
| 8,628,498 B2 | 1/2014 | Safabach et al. |
| 8,641,674 B2 | 2/2014 | Bobroff et al. |
| 8,652,043 B2 | 2/2014 | Drucker et al. |
| 8,682,408 B2 | 3/2014 | Boock et al. |
| 8,682,615 B2 | 3/2014 | Hayter et al. |
| 8,684,930 B2 | 4/2014 | Feldman et al. |
| 8,692,655 B2 | 4/2014 | Zimman et al. |
| 8,710,993 B2 | 4/2014 | Hayter et al. |
| 8,747,363 B2 | 6/2014 | Nielsen et al. |
| 8,750,955 B2 | 6/2014 | Brister et al. |
| 8,771,183 B2 | 7/2014 | Sloan |
| 8,797,163 B2 | 8/2014 | Finkenzeller |
| 8,808,515 B2 | 8/2014 | Feldman et al. |
| 8,834,366 B2 | 9/2014 | Hayter et al. |
| 8,845,536 B2 | 9/2014 | Brauker et al. |
| 8,870,822 B2 | 10/2014 | Thalmann et al. |
| 8,880,138 B2 | 11/2014 | Cho |
| 8,945,056 B2 | 2/2015 | Iio et al. |
| 8,961,413 B2 | 2/2015 | Teller et al. |
| 9,007,781 B2 | 4/2015 | Moein et al. |
| 9,014,774 B2 | 4/2015 | Mao et al. |
| 9,031,630 B2 | 5/2015 | Hoss et al. |
| 9,060,719 B2 | 6/2015 | Hayter et al. |
| 9,060,805 B2 | 6/2015 | Goodnow et al. |
| 9,066,697 B2 | 6/2015 | Peyser et al. |
| 9,101,302 B2 | 8/2015 | Mace et al. |
| 9,186,098 B2 | 11/2015 | Lee et al. |
| 9,215,992 B2 * | 12/2015 | Donnay ............ A61B 5/15186 |
| 9,241,631 B2 | 1/2016 | Valdes et al. |
| 9,259,175 B2 | 2/2016 | Stafford |
| 9,289,179 B2 | 3/2016 | Hayter et al. |
| 9,295,786 B2 | 3/2016 | Gottlieb et al. |
| 9,357,951 B2 | 6/2016 | Simpson et al. |
| 9,398,872 B2 | 7/2016 | Hayter et al. |
| 9,402,544 B2 | 8/2016 | Yee et al. |
| 9,402,570 B2 | 8/2016 | Pace et al. |
| 9,439,586 B2 | 9/2016 | Bugler |
| 9,451,910 B2 | 9/2016 | Brister et al. |
| 9,474,479 B2 | 10/2016 | Pusey et al. |
| 9,480,421 B2 | 11/2016 | Stafford |
| 9,483,608 B2 | 11/2016 | Hayter et al. |
| 9,504,471 B2 | 11/2016 | Vaitekunas et al. |
| 9,558,325 B2 | 1/2017 | Hayter et al. |
| 9,566,384 B2 | 2/2017 | Gyrn et al. |
| 9,636,068 B2 | 5/2017 | Yee et al. |
| 9,668,682 B2 | 6/2017 | Brister et al. |
| 9,743,876 B2 | 8/2017 | Gelfand et al. |
| 9,808,574 B2 | 11/2017 | Yodfat et al. |
| 9,814,414 B2 | 11/2017 | Brister et al. |
| 10,213,139 B2 | 2/2019 | Rao et al. |
| 10,292,632 B2 | 5/2019 | Lee et al. |
| 10,342,489 B2 | 7/2019 | Stafford |
| 10,772,547 B1 | 9/2020 | Lee et al. |
| 10,820,842 B2 | 11/2020 | Harper |
| 10,827,954 B2 | 11/2020 | Hoss et al. |
| 10,874,338 B2 | 12/2020 | Stafford |
| 10,881,340 B2 | 1/2021 | Curry et al. |
| 10,881,341 B1 | 1/2021 | Curry et al. |
| 10,945,647 B2 | 3/2021 | Mazza et al. |
| 10,945,649 B2 | 3/2021 | Lee et al. |
| 10,952,653 B2 | 3/2021 | Harper |
| 10,959,654 B2 | 3/2021 | Curry et al. |
| 10,966,644 B2 | 4/2021 | Stafford |
| 10,973,443 B2 | 4/2021 | Funderburk et al. |
| 10,980,461 B2 | 4/2021 | Bohm et al. |
| 11,000,213 B2 | 5/2021 | Kamath et al. |
| 11,000,216 B2 | 5/2021 | Curry et al. |
| 11,006,870 B2 | 5/2021 | Yee et al. |
| 11,006,871 B2 | 5/2021 | Yee et al. |
| 11,013,440 B2 | 5/2021 | Lee et al. |
| 11,051,724 B2 | 7/2021 | Pace et al. |
| 11,064,917 B2 | 7/2021 | Simpson et al. |
| 11,116,430 B2 | 9/2021 | Funderburk et al. |
| 11,141,084 B2 | 10/2021 | Funderburk et al. |
| 11,166,656 B2 | 11/2021 | Yee et al. |
| 11,179,068 B2 | 11/2021 | Pace et al. |
| 11,197,625 B1 | 12/2021 | Schleicher et al. |
| 11,202,591 B2 | 12/2021 | Yee et al. |
| 11,213,229 B2 | 1/2022 | Yee et al. |
| 11,246,519 B2 | 2/2022 | Donnay et al. |
| 11,266,335 B2 | 3/2022 | Donnay et al. |
| 11,298,056 B2 | 4/2022 | Harper |
| 11,298,058 B2 | 4/2022 | Stafford |
| 11,510,625 B2 | 11/2022 | Gray et al. |
| 2001/0016682 A1 | 8/2001 | Berner et al. |
| 2001/0034479 A1 | 10/2001 | Ring et al. |
| 2001/0037060 A1 | 11/2001 | Thompson et al. |
| 2001/0037366 A1 | 11/2001 | Webb et al. |
| 2001/0039387 A1 | 11/2001 | Rutynowski et al. |
| 2001/0044608 A1 | 11/2001 | Odell et al. |
| 2001/0047127 A1 | 11/2001 | New et al. |
| 2001/0056262 A1 | 12/2001 | Cabiri et al. |
| 2002/0002344 A1 | 1/2002 | Douglas et al. |
| 2002/0010390 A1 | 1/2002 | Guice et al. |
| 2002/0013522 A1 | 1/2002 | Lav et al. |
| 2002/0013538 A1 | 1/2002 | Teller |
| 2002/0016534 A1 | 2/2002 | Trepagnier et al. |
| 2002/0016568 A1 | 2/2002 | Lebel et al. |
| 2002/0019022 A1 | 2/2002 | Dunn et al. |
| 2002/0019584 A1 | 2/2002 | Schulze et al. |
| 2002/0019586 A1 | 2/2002 | Teller et al. |
| 2002/0019606 A1 | 2/2002 | Lebel et al. |
| 2002/0022855 A1 | 2/2002 | Bobroff et al. |

(56)　　References Cited

U.S. PATENT DOCUMENTS

| | | |
|---|---|---|
| 2002/0023852 A1 | 2/2002 | McIvor et al. |
| 2002/0029058 A1 | 3/2002 | LeVaughn et al. |
| 2002/0032386 A1 | 3/2002 | Sackner et al. |
| 2002/0039026 A1 | 4/2002 | Stroth et al. |
| 2002/0042090 A1 | 4/2002 | Heller et al. |
| 2002/0045808 A1 | 4/2002 | Ford et al. |
| 2002/0049482 A1 | 4/2002 | Fabian et al. |
| 2002/0050250 A1 | 5/2002 | Peterson et al. |
| 2002/0055711 A1 | 5/2002 | Lavi et al. |
| 2002/0057993 A1 | 5/2002 | Maisey et al. |
| 2002/0065454 A1 | 5/2002 | Lebel et al. |
| 2002/0066764 A1 | 6/2002 | Peny et al. |
| 2002/0072720 A1 | 6/2002 | Hague et al. |
| 2002/0072784 A1 | 6/2002 | Sheppard et al. |
| 2002/0074162 A1 | 6/2002 | Su et al. |
| 2002/0076966 A1 | 6/2002 | Carron et al. |
| 2002/0077599 A1 | 6/2002 | Wojcik |
| 2002/0082487 A1 | 6/2002 | Kollias et al. |
| 2002/0084196 A1 | 7/2002 | Liamos et al. |
| 2002/0091796 A1 | 7/2002 | Higginson et al. |
| 2002/0093969 A1 | 7/2002 | Lin et al. |
| 2002/0095076 A1 | 7/2002 | Krausman et al. |
| 2002/0103499 A1 | 8/2002 | Perez et al. |
| 2002/0106709 A1 | 8/2002 | Potts et al. |
| 2002/0111832 A1 | 8/2002 | Judge |
| 2002/0117639 A1 | 8/2002 | Paolini et al. |
| 2002/0118528 A1 | 8/2002 | Su et al. |
| 2002/0119711 A1 | 8/2002 | VanAntwerp et al. |
| 2002/0120186 A1 | 8/2002 | Keimel |
| 2002/0124017 A1 | 9/2002 | Mault |
| 2002/0128594 A1 | 9/2002 | Das et al. |
| 2002/0130042 A1 | 9/2002 | Moerman et al. |
| 2002/0133066 A1 | 9/2002 | Miller et al. |
| 2002/0147135 A1 | 10/2002 | Schnell |
| 2002/0150959 A1 | 10/2002 | Lejeune et al. |
| 2002/0151770 A1 | 10/2002 | Noll et al. |
| 2002/0151796 A1 | 10/2002 | Koulik |
| 2002/0151816 A1 | 10/2002 | Rich et al. |
| 2002/0154050 A1 | 10/2002 | Krupp et al. |
| 2002/0161288 A1 | 10/2002 | Shin et al. |
| 2002/0161290 A1 | 10/2002 | Chance |
| 2002/0161338 A1 | 10/2002 | Peterson |
| 2002/0164836 A1 | 11/2002 | Ho |
| 2002/0165462 A1 | 11/2002 | Westbrook et al. |
| 2002/0169369 A1 | 11/2002 | Ward et al. |
| 2002/0169439 A1 | 11/2002 | Flaherty et al. |
| 2002/0169635 A1 | 11/2002 | Shillingburg |
| 2002/0183604 A1 | 12/2002 | Gowda et al. |
| 2002/0185128 A1 | 12/2002 | Theobald |
| 2002/0185130 A1 | 12/2002 | Wright et al. |
| 2002/0188748 A1 | 12/2002 | Blackwell et al. |
| 2002/0197522 A1 | 12/2002 | Lawrence et al. |
| 2002/0198444 A1 | 12/2002 | Ughigaki et al. |
| 2003/0002682 A1 | 1/2003 | Smith et al. |
| 2003/0004403 A1 | 1/2003 | Drinan et al. |
| 2003/0020477 A1 | 1/2003 | Goldstein |
| 2003/0023189 A1 | 1/2003 | Kuo |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0028184 A1 | 2/2003 | Lebel et al. |
| 2003/0032077 A1 | 2/2003 | Itoh et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0050546 A1 | 3/2003 | Desai et al. |
| 2003/0054428 A1 | 3/2003 | Monfre et al. |
| 2003/0055380 A1 | 3/2003 | Flaherty |
| 2003/0060692 A1 | 3/2003 | Ruchti et al. |
| 2003/0060753 A1 | 3/2003 | Starkweather et al. |
| 2003/0065308 A1 | 4/2003 | Lebel et al. |
| 2003/0069509 A1 | 4/2003 | Matzinger et al. |
| 2003/0069510 A1 | 4/2003 | Semler |
| 2003/0076792 A1 | 4/2003 | Theimer |
| 2003/0077642 A1 | 4/2003 | Fritsch et al. |
| 2003/0078481 A1 | 4/2003 | McIvor et al. |
| 2003/0078560 A1 | 4/2003 | Miller et al. |
| 2003/0083686 A1 | 5/2003 | Freeman et al. |
| 2003/0088166 A1 | 5/2003 | Say et al. |
| 2003/0097092 A1 | 5/2003 | Flaherty |
| 2003/0100040 A1 | 5/2003 | Bonnecaze et al. |
| 2003/0100821 A1 | 5/2003 | Heller et al. |
| 2003/0109775 A1 | 6/2003 | O'Neil et al. |
| 2003/0114897 A1 | 6/2003 | Von Arx et al. |
| 2003/0114898 A1 | 6/2003 | Von Arx et al. |
| 2003/0119457 A1 | 6/2003 | Standke |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0135127 A1 | 7/2003 | Sackner et al. |
| 2003/0135333 A1 | 7/2003 | Aceti et al. |
| 2003/0144579 A1 | 7/2003 | Buss |
| 2003/0144581 A1 | 7/2003 | Conn et al. |
| 2003/0144608 A1 | 7/2003 | Kojima et al. |
| 2003/0153900 A1 | 8/2003 | Aceti et al. |
| 2003/0155656 A1 | 8/2003 | Chiu et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0188427 A1 | 10/2003 | Say et al. |
| 2003/0199744 A1 | 10/2003 | Buse et al. |
| 2003/0199790 A1 | 10/2003 | Boecker et al. |
| 2003/0199910 A1 | 10/2003 | Boecker et al. |
| 2003/0204290 A1 | 10/2003 | Sadler et al. |
| 2003/0208113 A1 | 11/2003 | Mault et al. |
| 2003/0208114 A1 | 11/2003 | Ackerman |
| 2003/0212317 A1 | 11/2003 | Kovatchev et al. |
| 2003/0212379 A1 | 11/2003 | Bylund et al. |
| 2003/0212579 A1 | 11/2003 | Brown et al. |
| 2003/0216621 A1 | 11/2003 | Alpert et al. |
| 2003/0216630 A1 | 11/2003 | Jersey-Willuhn et al. |
| 2003/0217966 A1 | 11/2003 | Tapsak et al. |
| 2003/0225361 A1 | 12/2003 | Sabra |
| 2003/0225373 A1 | 12/2003 | Bobroff et al. |
| 2003/0236489 A1 | 12/2003 | Jacobson et al. |
| 2004/0010207 A1 | 1/2004 | Flaherty et al. |
| 2004/0011671 A1 | 1/2004 | Shults et al. |
| 2004/0015131 A1 | 1/2004 | Flaherty et al. |
| 2004/0017300 A1 | 1/2004 | Kotzin et al. |
| 2004/0030226 A1 | 2/2004 | Quy |
| 2004/0030531 A1 | 2/2004 | Miller et al. |
| 2004/0030581 A1 | 2/2004 | Levin et al. |
| 2004/0034289 A1 | 2/2004 | Teller et al. |
| 2004/0039255 A1 | 2/2004 | Simonsen et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0060818 A1 | 4/2004 | Feldman et al. |
| 2004/0061232 A1 | 4/2004 | Shah et al. |
| 2004/0063435 A1 | 4/2004 | Sakamoto et al. |
| 2004/0064068 A1 | 4/2004 | DeNuzzio et al. |
| 2004/0064133 A1 | 4/2004 | Miller et al. |
| 2004/0072357 A1 | 4/2004 | Steine et al. |
| 2004/0073266 A1 | 4/2004 | Haefner et al. |
| 2004/0078215 A1 | 4/2004 | Dahlin et al. |
| 2004/0096959 A1 | 5/2004 | Steine et al. |
| 2004/0100376 A1 | 5/2004 | Lye et al. |
| 2004/0105411 A1 | 6/2004 | Boatwright et al. |
| 2004/0106858 A1 | 6/2004 | Say et al. |
| 2004/0106859 A1 | 6/2004 | Say et al. |
| 2004/0106860 A1 | 6/2004 | Say et al. |
| 2004/0111017 A1 | 6/2004 | Say et al. |
| 2004/0116847 A1 | 6/2004 | Wall |
| 2004/0116865 A1 | 6/2004 | Bengtsson |
| 2004/0116866 A1 | 6/2004 | Gorman et al. |
| 2004/0117204 A1 | 6/2004 | Mazar et al. |
| 2004/0119169 A1 | 6/2004 | Hanawa |
| 2004/0122353 A1 | 6/2004 | Shahmirian et al. |
| 2004/0122489 A1 | 6/2004 | Mazar et al. |
| 2004/0133089 A1 | 7/2004 | Kilcoyne et al. |
| 2004/0133164 A1 | 7/2004 | Funderburk et al. |
| 2004/0133390 A1 | 7/2004 | Osorio et al. |
| 2004/0135571 A1 | 7/2004 | Uutela et al. |

(56) References Cited

U.S. PATENT DOCUMENTS

| | | |
|---|---|---|
| 2004/0135684 A1 | 7/2004 | Steinthal et al. |
| 2004/0138544 A1 | 7/2004 | Ward et al. |
| 2004/0138588 A1 | 7/2004 | Saikley et al. |
| 2004/0138688 A1 | 7/2004 | Giraud |
| 2004/0140211 A1 | 7/2004 | Broy et al. |
| 2004/0142403 A1 | 7/2004 | Hetzel et al. |
| 2004/0146909 A1 | 7/2004 | Duong et al. |
| 2004/0147872 A1 | 7/2004 | Thompson |
| 2004/0147996 A1 | 7/2004 | Miazga et al. |
| 2004/0152366 A1 | 8/2004 | Schultz et al. |
| 2004/0152622 A1 | 8/2004 | Keith et al. |
| 2004/0158207 A1 | 8/2004 | Hunn et al. |
| 2004/0162521 A1 | 8/2004 | Bengtsson et al. |
| 2004/0162678 A1 | 8/2004 | Hetzel et al. |
| 2004/0167801 A1 | 8/2004 | Say et al. |
| 2004/0171910 A1 | 9/2004 | Moore-Steele |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193020 A1 | 9/2004 | Chiba et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0204673 A1 | 10/2004 | Flaherty |
| 2004/0204687 A1 | 10/2004 | Mogensen et al. |
| 2004/0204744 A1 | 10/2004 | Penner et al. |
| 2004/0204868 A1 | 10/2004 | Maynard et al. |
| 2004/0206625 A1 | 10/2004 | Bhullar et al. |
| 2004/0206916 A1 | 10/2004 | Colvin, Jr. et al. |
| 2004/0210122 A1 | 10/2004 | Sieburg |
| 2004/0221057 A1 | 11/2004 | Darcey et al. |
| 2004/0223876 A1 | 11/2004 | Kirollos et al. |
| 2004/0223985 A1 | 11/2004 | Dunfield et al. |
| 2004/0225199 A1 | 11/2004 | Evanyk et al. |
| 2004/0225262 A1 | 11/2004 | Fathallah et al. |
| 2004/0225338 A1 | 11/2004 | Lebel et al. |
| 2004/0236200 A1 | 11/2004 | Say et al. |
| 2004/0236251 A1 | 11/2004 | Roe et al. |
| 2004/0240426 A1 | 12/2004 | Wu et al. |
| 2004/0249253 A1 | 12/2004 | Racchini et al. |
| 2004/0249999 A1 | 12/2004 | Connolly et al. |
| 2004/0254433 A1 | 12/2004 | Bandis et al. |
| 2004/0254434 A1 | 12/2004 | Goodnow et al. |
| 2004/0258564 A1 | 12/2004 | Charlton |
| 2004/0260224 A1 | 12/2004 | Binder et al. |
| 2004/0267300 A1 | 12/2004 | Mace |
| 2005/0001024 A1 | 1/2005 | Kusaka et al. |
| 2005/0003470 A1 | 1/2005 | Nelson et al. |
| 2005/0004439 A1 | 1/2005 | Shin et al. |
| 2005/0004494 A1 | 1/2005 | Perez et al. |
| 2005/0006122 A1 | 1/2005 | Burnette |
| 2005/0010269 A1 | 1/2005 | Lebel et al. |
| 2005/0017864 A1 | 1/2005 | Tsoukalis |
| 2005/0027177 A1 | 2/2005 | Shin et al. |
| 2005/0027180 A1 | 2/2005 | Goode, Jr. et al. |
| 2005/0027181 A1 | 2/2005 | Goode et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0033132 A1 | 2/2005 | Shults et al. |
| 2005/0038332 A1 | 2/2005 | Saidara et al. |
| 2005/0038465 A1 | 2/2005 | Shraga |
| 2005/0038680 A1 | 2/2005 | McMahon |
| 2005/0043598 A1 | 2/2005 | Goode, Jr. et al. |
| 2005/0049179 A1 | 3/2005 | Davidson et al. |
| 2005/0051427 A1 | 3/2005 | Brauker et al. |
| 2005/0051440 A1 | 3/2005 | Simpson et al. |
| 2005/0056552 A1 | 3/2005 | Simpson et al. |
| 2005/0065464 A1 | 3/2005 | Talbot et al. |
| 2005/0070774 A1 | 3/2005 | Addison et al. |
| 2005/0070819 A1 | 3/2005 | Poux et al. |
| 2005/0085872 A1 | 4/2005 | Yanagihara et al. |
| 2005/0090607 A1 | 4/2005 | Tapsak et al. |
| 2005/0090850 A1 | 4/2005 | Thoes et al. |
| 2005/0096511 A1 | 5/2005 | Fox et al. |
| 2005/0096512 A1 | 5/2005 | Fox et al. |
| 2005/0096516 A1 | 5/2005 | Soykan et al. |
| 2005/0096520 A1 | 5/2005 | Maekawa et al. |
| 2005/0096587 A1 | 5/2005 | Santini, Jr. et al. |
| 2005/0101912 A1 | 5/2005 | Faust et al. |
| 2005/0101932 A1 | 5/2005 | Cote et al. |
| 2005/0103624 A1 | 5/2005 | Bhullar et al. |
| 2005/0104457 A1 | 5/2005 | Jordan et al. |
| 2005/0106713 A1 | 5/2005 | Phan et al. |
| 2005/0112169 A1 | 5/2005 | Brauker et al. |
| 2005/0112544 A1 | 5/2005 | Xu et al. |
| 2005/0113648 A1 | 5/2005 | Yang et al. |
| 2005/0113653 A1 | 5/2005 | Fox et al. |
| 2005/0113886 A1 | 5/2005 | Fischell et al. |
| 2005/0114068 A1 | 5/2005 | Chey et al. |
| 2005/0115832 A1 | 6/2005 | Simpson et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0131347 A1 | 6/2005 | Marano-Ford et al. |
| 2005/0134731 A1 | 6/2005 | Lee et al. |
| 2005/0137488 A1 | 6/2005 | Henry et al. |
| 2005/0137530 A1 | 6/2005 | Campbell et al. |
| 2005/0143635 A1 | 6/2005 | Kamath et al. |
| 2005/0151976 A1 | 7/2005 | Toma |
| 2005/0154271 A1 | 7/2005 | Rasdal et al. |
| 2005/0154410 A1 | 7/2005 | Conway et al. |
| 2005/0159678 A1 | 7/2005 | Taniike et al. |
| 2005/0161346 A1 | 7/2005 | Simpson et al. |
| 2005/0165404 A1 | 7/2005 | Miller |
| 2005/0171442 A1 | 8/2005 | Shirasaki et al. |
| 2005/0173245 A1 | 8/2005 | Feldman et al. |
| 2005/0176136 A1 | 8/2005 | Burd et al. |
| 2005/0177398 A1 | 8/2005 | Watanabe et al. |
| 2005/0181010 A1 | 8/2005 | Hunter et al. |
| 2005/0182306 A1 | 8/2005 | Sloan |
| 2005/0182358 A1 | 8/2005 | Heit et al. |
| 2005/0187442 A1 | 8/2005 | Cho et al. |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0197554 A1 | 9/2005 | Polcha |
| 2005/0197793 A1 | 9/2005 | Baker, Jr. |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0214892 A1 | 9/2005 | Kovatchev et al. |
| 2005/0215871 A1 | 9/2005 | Feldman et al. |
| 2005/0221504 A1 | 10/2005 | Petruno et al. |
| 2005/0222518 A1 | 10/2005 | Dib |
| 2005/0222599 A1 | 10/2005 | Czernecki et al. |
| 2005/0236277 A9 | 10/2005 | Imran et al. |
| 2005/0236361 A1 | 10/2005 | Ufer et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245844 A1 | 11/2005 | Mace et al. |
| 2005/0245904 A1 | 11/2005 | Estes et al. |
| 2005/0247319 A1 | 11/2005 | Berger |
| 2005/0251033 A1 | 11/2005 | Scarantino et al. |
| 2005/0261563 A1 | 11/2005 | Zhou et al. |
| 2005/0267325 A1 | 12/2005 | Bouchier et al. |
| 2005/0267327 A1 | 12/2005 | Lizuka et al. |
| 2005/0269214 A1 | 12/2005 | Lee |
| 2005/0277164 A1 | 12/2005 | Drucker et al. |
| 2005/0277912 A1 | 12/2005 | John |
| 2005/0281234 A1 | 12/2005 | Kawamura et al. |
| 2005/0283114 A1 | 12/2005 | Bresina et al. |
| 2005/0283208 A1 | 12/2005 | Von Arx et al. |
| 2005/0283209 A1 | 12/2005 | Katoozi et al. |
| 2005/0284758 A1 | 12/2005 | Funke et al. |
| 2005/0287620 A1 | 12/2005 | Heller et al. |

(56) References Cited

U.S. PATENT DOCUMENTS

| | | |
|---|---|---|
| 2006/0001538 A1 | 1/2006 | Kraft et al. |
| 2006/0001551 A1 | 1/2006 | Kraft et al. |
| 2006/0004270 A1 | 1/2006 | Bedard et al. |
| 2006/0004272 A1 | 1/2006 | Shah et al. |
| 2006/0004303 A1 | 1/2006 | Weidenhaupt et al. |
| 2006/0006141 A1 | 1/2006 | Ufer et al. |
| 2006/0009727 A1 | 1/2006 | O'Mahony et al. |
| 2006/0010098 A1 | 1/2006 | Goodnow et al. |
| 2006/0012464 A1 | 1/2006 | Nitzan et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025662 A1 | 2/2006 | Buse et al. |
| 2006/0025663 A1 | 2/2006 | Talbot et al. |
| 2006/0029177 A1 | 2/2006 | Cranford et al. |
| 2006/0030789 A1 | 2/2006 | Allen |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0040402 A1 | 2/2006 | Brauker et al. |
| 2006/0040793 A1 | 2/2006 | Martens et al. |
| 2006/0041276 A1 | 2/2006 | Chan |
| 2006/0042080 A1 | 3/2006 | Say et al. |
| 2006/0047220 A1 | 3/2006 | Sakata et al. |
| 2006/0049359 A1 | 3/2006 | Busta et al. |
| 2006/0058588 A1 | 3/2006 | Zdeblick |
| 2006/0064035 A1 | 3/2006 | Wang et al. |
| 2006/0068208 A1 | 3/2006 | Tapsak et al. |
| 2006/0079740 A1 | 4/2006 | Silver et al. |
| 2006/0081469 A1 | 4/2006 | Lee |
| 2006/0086624 A1 | 4/2006 | Tapsak et al. |
| 2006/0091006 A1 | 5/2006 | Wang et al. |
| 2006/0094944 A1 | 5/2006 | Chuang |
| 2006/0095014 A1 | 5/2006 | Ethelfeld |
| 2006/0116607 A1 | 6/2006 | Nakamura et al. |
| 2006/0129173 A1 | 6/2006 | Wilkinson |
| 2006/0129733 A1 | 6/2006 | Solbelman |
| 2006/0135908 A1 | 6/2006 | Liniger et al. |
| 2006/0142651 A1 | 6/2006 | Brister et al. |
| 2006/0154642 A1 | 7/2006 | Scannell |
| 2006/0155180 A1 | 7/2006 | Brister et al. |
| 2006/0155210 A1 | 7/2006 | Beckman et al. |
| 2006/0155317 A1 | 7/2006 | List |
| 2006/0161194 A1 | 7/2006 | Freeman et al. |
| 2006/0161664 A1 | 7/2006 | Motoyama |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0181695 A1 | 8/2006 | Sage, Jr. |
| 2006/0183984 A1 | 8/2006 | Dobbles et al. |
| 2006/0183985 A1 | 8/2006 | Brister et al. |
| 2006/0189851 A1 | 8/2006 | Tvig et al. |
| 2006/0189863 A1 | 8/2006 | Peyser et al. |
| 2006/0189939 A1 | 8/2006 | Gonnelli et al. |
| 2006/0193375 A1 | 8/2006 | Lee et al. |
| 2006/0195029 A1 | 8/2006 | Shults et al. |
| 2006/0195133 A1 | 8/2006 | Freeman et al. |
| 2006/0200020 A1 | 9/2006 | Brister et al. |
| 2006/0200022 A1 | 9/2006 | Brauker et al. |
| 2006/0200181 A1 | 9/2006 | Fukuzawa et al. |
| 2006/0200970 A1 | 9/2006 | Brister et al. |
| 2006/0200981 A1 | 9/2006 | Bhullar et al. |
| 2006/0200982 A1 | 9/2006 | Bhullar et al. |
| 2006/0202805 A1 | 9/2006 | Schulman et al. |
| 2006/0202859 A1 | 9/2006 | Mastrototaro et al. |
| 2006/0211921 A1 | 9/2006 | Brauker et al. |
| 2006/0220839 A1 | 10/2006 | Fifolt et al. |
| 2006/0222566 A1 | 10/2006 | Brauker et al. |
| 2006/0222866 A1 | 10/2006 | Nakamura et al. |
| 2006/0224108 A1 | 10/2006 | Brauker et al. |
| 2006/0224109 A1 | 10/2006 | Steil et al. |
| 2006/0224141 A1 | 10/2006 | Rush et al. |
| 2006/0224171 A1 | 10/2006 | Sakata et al. |
| 2006/0226985 A1 | 10/2006 | Goodnow et al. |
| 2006/0229512 A1 | 10/2006 | Petisce et al. |
| 2006/0233839 A1 | 10/2006 | Jacquet |
| 2006/0247508 A1 | 11/2006 | Fennell |
| 2006/0247710 A1 | 11/2006 | Goetz et al. |
| 2006/0247895 A1 | 11/2006 | Liamos et al. |
| 2006/0248398 A1 | 11/2006 | Neel et al. |
| 2006/0253085 A1 | 11/2006 | Geismar et al. |
| 2006/0253086 A1 | 11/2006 | Moberg et al. |
| 2006/0258929 A1 | 11/2006 | Goode, Jr. et al. |
| 2006/0258939 A1 | 11/2006 | Pesach et al. |
| 2006/0258959 A1 | 11/2006 | Sode |
| 2006/0264785 A1 | 11/2006 | Dring et al. |
| 2006/0264888 A1 | 11/2006 | Moberg et al. |
| 2006/0270922 A1 | 11/2006 | Brauker et al. |
| 2006/0270923 A1 | 11/2006 | Brauker et al. |
| 2006/0271013 A1 | 11/2006 | Triplett et al. |
| 2006/0272652 A1 | 12/2006 | Stocker et al. |
| 2006/0273759 A1 | 12/2006 | Reggiardo |
| 2006/0276714 A1 | 12/2006 | Holt et al. |
| 2006/0276724 A1 | 12/2006 | Freeman et al. |
| 2006/0276771 A1 | 12/2006 | Galley et al. |
| 2006/0281985 A1 | 12/2006 | Ward et al. |
| 2006/0282042 A1 | 12/2006 | Walters et al. |
| 2006/0287591 A1 | 12/2006 | Ocvirk et al. |
| 2006/0287691 A1 | 12/2006 | Drew |
| 2006/0290496 A1 | 12/2006 | Peeters et al. |
| 2006/0293607 A1 | 12/2006 | Alt et al. |
| 2007/0007133 A1 | 1/2007 | Mang et al. |
| 2007/0010950 A1 | 1/2007 | Abensour et al. |
| 2007/0016129 A1 | 1/2007 | Liniger et al. |
| 2007/0016381 A1 | 1/2007 | Kamath et al. |
| 2007/0017983 A1 | 1/2007 | Frank et al. |
| 2007/0027381 A1 | 2/2007 | Stafford |
| 2007/0027384 A1 | 2/2007 | Brister et al. |
| 2007/0027385 A1 | 2/2007 | Brister et al. |
| 2007/0027507 A1 | 2/2007 | Burdett et al. |
| 2007/0030154 A1 | 2/2007 | Aiki et al. |
| 2007/0032706 A1 | 2/2007 | Kamath et al. |
| 2007/0032717 A1 | 2/2007 | Brister et al. |
| 2007/0032718 A1 | 2/2007 | Shults et al. |
| 2007/0033074 A1 | 2/2007 | Nitzan et al. |
| 2007/0038044 A1 | 2/2007 | Dobbies et al. |
| 2007/0045902 A1 | 3/2007 | Brauker et al. |
| 2007/0049865 A1 | 3/2007 | Radmer et al. |
| 2007/0055799 A1 | 3/2007 | Koehler et al. |
| 2007/0056858 A1 | 3/2007 | Chen et al. |
| 2007/0059196 A1 | 3/2007 | Brister et al. |
| 2007/0060801 A1 | 3/2007 | Neinast |
| 2007/0060814 A1 | 3/2007 | Stafford |
| 2007/0060869 A1 | 3/2007 | Tolle et al. |
| 2007/0066873 A1 | 3/2007 | Kamath et al. |
| 2007/0068807 A1 | 3/2007 | Feldman et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0088377 A1 | 4/2007 | Levaughn et al. |
| 2007/0090511 A1 | 4/2007 | Borland et al. |
| 2007/0093704 A1 | 4/2007 | Brister et al. |
| 2007/0093754 A1 | 4/2007 | Mogensen et al. |
| 2007/0093786 A1 | 4/2007 | Goldsmith et al. |
| 2007/0095661 A1 | 5/2007 | Wang et al. |
| 2007/0100218 A1 | 5/2007 | Sweitzer et al. |

(56) References Cited

U.S. PATENT DOCUMENTS

| | | |
|---|---|---|
| 2007/0100222 A1 | 5/2007 | Mastrototaro et al. |
| 2007/0106133 A1 | 5/2007 | Satchwell et al. |
| 2007/0106135 A1 | 5/2007 | Sloan et al. |
| 2007/0108048 A1 | 5/2007 | Wang et al. |
| 2007/0110124 A1 | 5/2007 | Shiraki et al. |
| 2007/0111196 A1 | 5/2007 | Alarcon et al. |
| 2007/0123819 A1 | 5/2007 | Mernoe et al. |
| 2007/0124002 A1 | 5/2007 | Estes et al. |
| 2007/0129621 A1 | 6/2007 | Kellogg et al. |
| 2007/0135696 A1 | 6/2007 | Ward |
| 2007/0149873 A1 | 6/2007 | Say et al. |
| 2007/0149875 A1 | 6/2007 | Ouyang et al. |
| 2007/0153705 A1 | 7/2007 | Rosar et al. |
| 2007/0156033 A1 | 7/2007 | Causey, III et al. |
| 2007/0156094 A1 | 7/2007 | Safabash et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173711 A1 | 7/2007 | Shah et al. |
| 2007/0173741 A1 | 7/2007 | Deshmukh et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0179406 A1 | 8/2007 | DeNuzzio et al. |
| 2007/0191701 A1 | 8/2007 | Feldman et al. |
| 2007/0191702 A1 | 8/2007 | Yodfat et al. |
| 2007/0197889 A1 | 8/2007 | Brister et al. |
| 2007/0199818 A1 | 8/2007 | Petyt et al. |
| 2007/0202562 A1 | 8/2007 | Curry et al. |
| 2007/0203407 A1 | 8/2007 | Hoss et al. |
| 2007/0203539 A1 | 8/2007 | Stone et al. |
| 2007/0203966 A1 | 8/2007 | Brauker et al. |
| 2007/0208244 A1 | 9/2007 | Brauker et al. |
| 2007/0208245 A1 | 9/2007 | Brauker et al. |
| 2007/0208246 A1 | 9/2007 | Brauker et al. |
| 2007/0213611 A1 | 9/2007 | Simpson et al. |
| 2007/0219480 A1 | 9/2007 | Kamen et al. |
| 2007/0219496 A1 | 9/2007 | Kamen et al. |
| 2007/0222609 A1 | 9/2007 | Duron et al. |
| 2007/0227911 A1 | 10/2007 | Wang et al. |
| 2007/0228071 A1 | 10/2007 | Kamen et al. |
| 2007/0231846 A1 | 10/2007 | Cosentino et al. |
| 2007/0232877 A1 | 10/2007 | He |
| 2007/0232878 A1 | 10/2007 | Kovatchev et al. |
| 2007/0232879 A1 | 10/2007 | Brister et al. |
| 2007/0232880 A1 | 10/2007 | Siddiqui et al. |
| 2007/0233013 A1 | 10/2007 | Schoenberg et al. |
| 2007/0235331 A1 | 10/2007 | Simpson et al. |
| 2007/0244368 A1 | 10/2007 | Bayloff et al. |
| 2007/0244379 A1 | 10/2007 | Boock et al. |
| 2007/0244383 A1 | 10/2007 | Talbot et al. |
| 2007/0244398 A1 | 10/2007 | Lo et al. |
| 2007/0249922 A1 | 10/2007 | Peyser et al. |
| 2007/0253021 A1 | 11/2007 | Mehta et al. |
| 2007/0255116 A1 | 11/2007 | Mehta et al. |
| 2007/0255125 A1 | 11/2007 | Moberg et al. |
| 2007/0255302 A1 | 11/2007 | Koeppel et al. |
| 2007/0255321 A1 | 11/2007 | Gerber et al. |
| 2007/0255348 A1 | 11/2007 | Holtzclaw |
| 2007/0255531 A1 | 11/2007 | Drew |
| 2007/0258395 A1 | 11/2007 | Jollota et al. |
| 2007/0270672 A1 | 11/2007 | Hayter |
| 2007/0282299 A1 | 12/2007 | Hellwig |
| 2007/0285238 A1 | 12/2007 | Batra |
| 2008/0004512 A1 | 1/2008 | Funderbunk et al. |
| 2008/0004515 A1 | 1/2008 | Jennewine et al. |
| 2008/0004573 A1 | 1/2008 | Kaufmann et al. |
| 2008/0004601 A1 | 1/2008 | Jennewine et al. |
| 2008/0004904 A1 | 1/2008 | Tran |
| 2008/0009304 A1 | 1/2008 | Fry |
| 2008/0009692 A1 | 1/2008 | Stafford |
| 2008/0009805 A1 | 1/2008 | Ethelfeld |
| 2008/0017522 A1 | 1/2008 | Heller et al. |
| 2008/0018433 A1 | 1/2008 | Pitt-Pladdy |
| 2008/0021666 A1 | 1/2008 | Goode, Jr. et al. |
| 2008/0027296 A1 | 1/2008 | Hadvary et al. |
| 2008/0027474 A1 | 1/2008 | Curry et al. |
| 2008/0029391 A1 | 2/2008 | Mao et al. |
| 2008/0030369 A1 | 2/2008 | Mann et al. |
| 2008/0031941 A1 | 2/2008 | Pettersson |
| 2008/0033254 A1 | 2/2008 | Kamath et al. |
| 2008/0033268 A1 | 2/2008 | Stafford |
| 2008/0033273 A1 | 2/2008 | Zhou et al. |
| 2008/0033318 A1 | 2/2008 | Mace et al. |
| 2008/0039702 A1 | 2/2008 | Hayter et al. |
| 2008/0045824 A1 | 2/2008 | Tapsak et al. |
| 2008/0046038 A1 | 2/2008 | Hill et al. |
| 2008/0055070 A1 | 3/2008 | Bange et al. |
| 2008/0057484 A1 | 3/2008 | Miyata et al. |
| 2008/0058625 A1 | 3/2008 | McGarraugh et al. |
| 2008/0058626 A1 | 3/2008 | Miyata et al. |
| 2008/0058678 A1 | 3/2008 | Miyata et al. |
| 2008/0058773 A1 | 3/2008 | John |
| 2008/0058830 A1 | 3/2008 | Cole et al. |
| 2008/0059227 A1 | 3/2008 | Clapp |
| 2008/0060955 A1 | 3/2008 | Goodnow |
| 2008/0061961 A1 | 3/2008 | John |
| 2008/0062055 A1 | 3/2008 | Cunningham et al. |
| 2008/0064437 A1 | 3/2008 | Chambers et al. |
| 2008/0064937 A1 | 3/2008 | McGarraugh et al. |
| 2008/0064941 A1 | 3/2008 | Funderbunk et al. |
| 2008/0064943 A1 | 3/2008 | Talbot et al. |
| 2008/0064944 A1 | 3/2008 | Van Antwerp et al. |
| 2008/0065646 A1 | 3/2008 | Zhang et al. |
| 2008/0066305 A1 | 3/2008 | Wang et al. |
| 2008/0067627 A1 | 3/2008 | Boeck et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0071580 A1 | 3/2008 | Marcus |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0092911 A1 | 4/2008 | Schulman et al. |
| 2008/0097246 A1 | 4/2008 | Stafford |
| 2008/0097289 A1 | 4/2008 | Steil et al. |
| 2008/0097908 A1 | 4/2008 | Dicks et al. |
| 2008/0099332 A1 | 5/2008 | Scott et al. |
| 2008/0102441 A1 | 5/2008 | Chen et al. |
| 2008/0108942 A1 | 5/2008 | Brister et al. |
| 2008/0112848 A1 | 5/2008 | Huffstodt et al. |
| 2008/0114228 A1 | 5/2008 | Mccluskey et al. |
| 2008/0114280 A1 | 5/2008 | Stafford |
| 2008/0119705 A1 | 5/2008 | Patel et al. |
| 2008/0119707 A1 | 5/2008 | Stafford |
| 2008/0119710 A1 | 5/2008 | Reggiardo et al. |
| 2008/0125636 A1 | 5/2008 | Ward et al. |
| 2008/0127052 A1 | 5/2008 | Rostoker |
| 2008/0129486 A1 | 6/2008 | Jeckelmann et al. |
| 2008/0133059 A1 | 6/2008 | Trippel et al. |
| 2008/0133702 A1 | 6/2008 | Sharma et al. |
| 2008/0139910 A1 | 6/2008 | Mastrototaro et al. |
| 2008/0148873 A1 | 6/2008 | Wang |
| 2008/0154205 A1 | 6/2008 | Wojcik |
| 2008/0154513 A1 | 6/2008 | Kovatchev et al. |
| 2008/0161664 A1 | 7/2008 | Mastrototaro et al. |
| 2008/0161666 A1 | 7/2008 | Feldman et al. |
| 2008/0167543 A1 | 7/2008 | Say et al. |
| 2008/0167572 A1 | 7/2008 | Stivoric et al. |
| 2008/0167578 A1 | 7/2008 | Bryer et al. |
| 2008/0172205 A1 | 7/2008 | Breton et al. |
| 2008/0177149 A1 | 7/2008 | Weinart et al. |
| 2008/0177165 A1 | 7/2008 | Blomquist et al. |
| 2008/0179187 A1 | 7/2008 | Ouyang |
| 2008/0182537 A1 | 7/2008 | Manku et al. |
| 2008/0183060 A1 | 7/2008 | Steil et al. |
| 2008/0183061 A1 | 7/2008 | Goode, Jr. et al. |
| 2008/0183399 A1 | 7/2008 | Goode, Jr. et al. |

(56) References Cited

U.S. PATENT DOCUMENTS

| | | |
|---|---|---|
| 2008/0188731 A1 | 8/2008 | Brister et al. |
| 2008/0188796 A1 | 8/2008 | Steil et al. |
| 2008/0189051 A1 | 8/2008 | Goode, Jr. et al. |
| 2008/0194926 A1 | 8/2008 | Goh et al. |
| 2008/0194934 A1 | 8/2008 | Ray et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195049 A1 | 8/2008 | Thalmann et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200897 A1 | 8/2008 | Hoss et al. |
| 2008/0201325 A1 | 8/2008 | Doniger et al. |
| 2008/0208025 A1 | 8/2008 | Shults et al. |
| 2008/0208026 A1 | 8/2008 | Noujaim et al. |
| 2008/0208113 A1 | 8/2008 | Daminao et al. |
| 2008/0214481 A1 | 9/2008 | Challoner et al. |
| 2008/0214900 A1 | 9/2008 | Fennell et al. |
| 2008/0214910 A1 | 9/2008 | Buck |
| 2008/0214915 A1 | 9/2008 | Brister et al. |
| 2008/0214918 A1 | 9/2008 | Brister et al. |
| 2008/0215035 A1 | 9/2008 | Yodfat et al. |
| 2008/0228051 A1 | 9/2008 | Shults et al. |
| 2008/0228054 A1 | 9/2008 | Shults et al. |
| 2008/0234561 A1 | 9/2008 | Roesicke et al. |
| 2008/0234992 A1 | 9/2008 | Ray et al. |
| 2008/0235469 A1 | 9/2008 | Drew |
| 2008/0242961 A1 | 10/2008 | Brister et al. |
| 2008/0242962 A1 | 10/2008 | Roesicke et al. |
| 2008/0242963 A1 | 10/2008 | Essenpreis et al. |
| 2008/0243051 A1 | 10/2008 | DeStefano |
| 2008/0252459 A1 | 10/2008 | Butler et al. |
| 2008/0254544 A1 | 10/2008 | Modzelewski et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255440 A1 | 10/2008 | Eilerson et al. |
| 2008/0255808 A1 | 10/2008 | Hayter |
| 2008/0256048 A1 | 10/2008 | Hayter |
| 2008/0262300 A1 | 10/2008 | Reynolds et al. |
| 2008/0262469 A1 | 10/2008 | Brister et al. |
| 2008/0267823 A1 | 10/2008 | Wang et al. |
| 2008/0269584 A1 | 10/2008 | Shekalim |
| 2008/0269673 A1 | 10/2008 | Butoi et al. |
| 2008/0269683 A1 | 10/2008 | Bikovsky |
| 2008/0269687 A1 | 10/2008 | Chong et al. |
| 2008/0269714 A1 | 10/2008 | Mastrototaro et al. |
| 2008/0275313 A1 | 11/2008 | Brister et al. |
| 2008/0275327 A1 | 11/2008 | Faarbaek et al. |
| 2008/0278333 A1 | 11/2008 | Fennell et al. |
| 2008/0281178 A1 | 11/2008 | Chuang et al. |
| 2008/0281179 A1 | 11/2008 | Fennell et al. |
| 2008/0283396 A1 | 11/2008 | Wang et al. |
| 2008/0287755 A1 | 11/2008 | Sass et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0294024 A1 | 11/2008 | Cosentino et al. |
| 2008/0294096 A1 | 11/2008 | Uber et al. |
| 2008/0296155 A1 | 12/2008 | Shults et al. |
| 2008/0300476 A1 | 12/2008 | Stafford |
| 2008/0300572 A1 | 12/2008 | Rankers et al. |
| 2008/0306368 A1 | 12/2008 | Goode, Jr. et al. |
| 2008/0306434 A1 | 12/2008 | Dobbies et al. |
| 2008/0306435 A1 | 12/2008 | Kamath et al. |
| 2008/0306444 A1 | 12/2008 | Brister et al. |
| 2008/0308523 A1 | 12/2008 | Krulevitch et al. |
| 2008/0312518 A1 | 12/2008 | Jina et al. |
| 2008/0312601 A1 | 12/2008 | Cane |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0312859 A1 | 12/2008 | Skyggebjerg et al. |
| 2008/0319085 A1 | 12/2008 | Wright et al. |
| 2008/0319295 A1 | 12/2008 | Bernstein et al. |
| 2008/0319296 A1 | 12/2008 | Bernstein et al. |
| 2008/0319414 A1 | 12/2008 | Yodfat et al. |
| 2008/0319416 A1 | 12/2008 | Yodfat et al. |
| 2009/0005659 A1 | 1/2009 | Kollias et al. |
| 2009/0005665 A1 | 1/2009 | Hayter et al. |
| 2009/0005666 A1 | 1/2009 | Shin et al. |
| 2009/0005729 A1 | 1/2009 | Hendrixson et al. |
| 2009/0006034 A1 | 1/2009 | Hayter et al. |
| 2009/0006061 A1 | 1/2009 | Thukral et al. |
| 2009/0006133 A1 | 1/2009 | Weinart et al. |
| 2009/0012376 A1 | 1/2009 | Agus |
| 2009/0012377 A1 | 1/2009 | Jennewine et al. |
| 2009/0012379 A1 | 1/2009 | Goode, Jr. et al. |
| 2009/0018424 A1 | 1/2009 | Kamath et al. |
| 2009/0018425 A1 | 1/2009 | Ouyang et al. |
| 2009/0020502 A1 | 1/2009 | Bhullar et al. |
| 2009/0028824 A1 | 1/2009 | Chiang et al. |
| 2009/0030293 A1 | 1/2009 | Cooper et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0036915 A1 | 2/2009 | Karbowniczek et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048499 A1 | 2/2009 | Glejbol |
| 2009/0048503 A1 | 2/2009 | Dalal et al. |
| 2009/0048563 A1 | 2/2009 | Ethelfeld et al. |
| 2009/0054737 A1 | 2/2009 | Magar et al. |
| 2009/0054745 A1 | 2/2009 | Jennewine et al. |
| 2009/0054747 A1 | 2/2009 | Fennell |
| 2009/0054748 A1 | 2/2009 | Feldman et al. |
| 2009/0054753 A1 | 2/2009 | Robinson et al. |
| 2009/0054866 A1 | 2/2009 | Teisen-Simony et al. |
| 2009/0055149 A1 | 2/2009 | Hayter et al. |
| 2009/0058635 A1 | 3/2009 | LaLonde et al. |
| 2009/0062633 A1 | 3/2009 | Brauker et al. |
| 2009/0062635 A1 | 3/2009 | Brauker et al. |
| 2009/0062767 A1 | 3/2009 | Van Antwerp et al. |
| 2009/0063187 A1 | 3/2009 | Johnson et al. |
| 2009/0063402 A1 | 3/2009 | Hayter |
| 2009/0069658 A1 | 3/2009 | Say et al. |
| 2009/0069750 A1 | 3/2009 | Schraga |
| 2009/0076356 A1 | 3/2009 | Simpson et al. |
| 2009/0076359 A1 | 3/2009 | Peyser |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0085873 A1 | 4/2009 | Betts et al. |
| 2009/0088614 A1 | 4/2009 | Taub |
| 2009/0088787 A1 | 4/2009 | Koike et al. |
| 2009/0093687 A1 | 4/2009 | Telfort et al. |
| 2009/0099436 A1 | 4/2009 | Brister et al. |
| 2009/0099521 A1 | 4/2009 | Gravesen et al. |
| 2009/0102678 A1 | 4/2009 | Mazza et al. |
| 2009/0105554 A1 | 4/2009 | Stahmann et al. |
| 2009/0105560 A1 | 4/2009 | Solomon |
| 2009/0105568 A1 | 4/2009 | Bugler |
| 2009/0105569 A1 | 4/2009 | Stafford |
| 2009/0105570 A1 | 4/2009 | Sloan et al. |

(56) References Cited

U.S. PATENT DOCUMENTS

| | | |
|---|---|---|
| 2009/0105571 A1 | 4/2009 | Fennell et al. |
| 2009/0105636 A1 | 4/2009 | Hayter et al. |
| 2009/0108992 A1 | 4/2009 | Shafer |
| 2009/0112123 A1 | 4/2009 | Freeman et al. |
| 2009/0112478 A1 | 4/2009 | Mueller, Jr. et al. |
| 2009/0118592 A1 | 5/2009 | Klitgaard |
| 2009/0124877 A1 | 5/2009 | Shariati et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0124979 A1 | 5/2009 | Raymond et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0131860 A1 | 5/2009 | Nielsen |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0149728 A1 | 6/2009 | Van Antwerp et al. |
| 2009/0150186 A1 | 6/2009 | Cohen et al. |
| 2009/0150454 A1 | 6/2009 | Gejdos et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0163855 A1 | 6/2009 | Shin et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0171182 A1 | 7/2009 | Stafford |
| 2009/0177068 A1 | 7/2009 | Stivoric et al. |
| 2009/0178459 A1 | 7/2009 | Li et al. |
| 2009/0182217 A1 | 7/2009 | Li et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0198186 A1 | 8/2009 | Mernoe et al. |
| 2009/0198215 A1 | 8/2009 | Chong et al. |
| 2009/0203981 A1 | 8/2009 | Brauker et al. |
| 2009/0204340 A1 | 8/2009 | Feldman et al. |
| 2009/0204341 A1 | 8/2009 | Brauker et al. |
| 2009/0210249 A1 | 8/2009 | Rasch-Menges et al. |
| 2009/0212766 A1 | 8/2009 | Olson et al. |
| 2009/0216100 A1 | 8/2009 | Ebner et al. |
| 2009/0216103 A1 | 8/2009 | Brister et al. |
| 2009/0216215 A1 | 8/2009 | Thalmann et al. |
| 2009/0234200 A1 | 9/2009 | Husheer |
| 2009/0240120 A1 | 9/2009 | Mensinger et al. |
| 2009/0240121 A1 | 9/2009 | Bickoff |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0247931 A1 | 10/2009 | Damgaard-Sorenson |
| 2009/0253973 A1 | 10/2009 | Bashan et al. |
| 2009/0259118 A1 | 10/2009 | Feldman et al. |
| 2009/0259201 A1 | 10/2009 | Hwang et al. |
| 2009/0259202 A1 | 10/2009 | Leeflang et al. |
| 2009/0267765 A1 | 10/2009 | Greene et al. |
| 2009/0270765 A1 | 10/2009 | Ghesquire et al. |
| 2009/0277242 A1 | 11/2009 | Crane et al. |
| 2009/0281406 A1 | 11/2009 | McGarraugh et al. |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0292184 A1 | 11/2009 | Funderburk et al. |
| 2009/0292185 A1 | 11/2009 | Funderburk et al. |
| 2009/0294277 A1 | 12/2009 | Thomas et al. |
| 2009/0298182 A1 | 12/2009 | Schulat et al. |
| 2009/0299152 A1 | 12/2009 | Taub et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299167 A1 | 12/2009 | Seymour |
| 2009/0299276 A1 | 12/2009 | Brauker et al. |
| 2009/0299301 A1 | 12/2009 | Gottlieb et al. |
| 2010/0004597 A1 | 1/2010 | Gryn et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0014626 A1 | 1/2010 | Fennell et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0022863 A1 | 1/2010 | Mogensen et al. |
| 2010/0022988 A1 | 1/2010 | Wochner et al. |
| 2010/0025238 A1 | 2/2010 | Gottlieb et al. |
| 2010/0030038 A1 | 2/2010 | Brauker et al. |
| 2010/0030053 A1 | 2/2010 | Goode, Jr. et al. |
| 2010/0030111 A1 | 2/2010 | Perriere |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0036281 A1 | 2/2010 | Doi |
| 2010/0041971 A1 | 2/2010 | Goode, Jr. et al. |
| 2010/0045465 A1 | 2/2010 | Brauker et al. |
| 2010/0049014 A1 | 2/2010 | Funderburk et al. |
| 2010/0049024 A1 | 2/2010 | Saint et al. |
| 2010/0049129 A1 | 2/2010 | Yokoi et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0069728 A1 | 3/2010 | Funderburk et al. |
| 2010/0076283 A1 | 3/2010 | Simpson et al. |
| 2010/0081905 A1 | 4/2010 | Bommakanti et al. |
| 2010/0081906 A1 | 4/2010 | Hayter et al. |
| 2010/0081908 A1 | 4/2010 | Dobbies et al. |
| 2010/0081910 A1 | 4/2010 | Brister et al. |
| 2010/0081953 A1 | 4/2010 | Syeda-Mahmood et al. |
| 2010/0087724 A1 | 4/2010 | Brauker et al. |
| 2010/0094251 A1 | 4/2010 | Estes et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0100113 A1 | 4/2010 | Iio et al. |
| 2010/0105999 A1 | 4/2010 | Dixon et al. |
| 2010/0106088 A1 | 4/2010 | Yodfat et al. |
| 2010/0113897 A1 | 5/2010 | Brenneman et al. |
| 2010/0119693 A1 | 5/2010 | Tapsak et al. |
| 2010/0119881 A1 | 5/2010 | Patel et al. |
| 2010/0121167 A1 | 5/2010 | McGarraugh et al. |
| 2010/0121169 A1 | 5/2010 | Petisce et al. |
| 2010/0137695 A1 | 6/2010 | Yodfat et al. |
| 2010/0141656 A1 | 6/2010 | Krieftewirth |
| 2010/0145229 A1 | 6/2010 | Perez et al. |
| 2010/0145377 A1 | 6/2010 | Lai et al. |
| 2010/0146300 A1 | 6/2010 | Brown |
| 2010/0152548 A1 | 6/2010 | Koski |
| 2010/0152554 A1 | 6/2010 | Steine et al. |
| 2010/0152674 A1 | 6/2010 | Kavazov et al. |
| 2010/0160757 A1 | 6/2010 | Weinart et al. |
| 2010/0160759 A1 | 6/2010 | Celentano et al. |
| 2010/0160760 A1 | 6/2010 | Shults et al. |
| 2010/0161269 A1 | 6/2010 | Kamath et al. |
| 2010/0168538 A1 | 7/2010 | Keenan et al. |
| 2010/0168540 A1 | 7/2010 | Kamath et al. |

(56) References Cited

U.S. PATENT DOCUMENTS

| | | | |
|---|---|---|---|
| 2010/0168541 | A1 | 7/2010 | Kamath et al. |
| 2010/0168542 | A1 | 7/2010 | Kamath et al. |
| 2010/0168543 | A1 | 7/2010 | Kamath et al. |
| 2010/0168544 | A1 | 7/2010 | Kamath et al. |
| 2010/0168545 | A1 | 7/2010 | Kamath et al. |
| 2010/0168546 | A1 | 7/2010 | Kamath et al. |
| 2010/0168547 | A1 | 7/2010 | Kamath et al. |
| 2010/0168660 | A1 | 7/2010 | Galley et al. |
| 2010/0168677 | A1 | 7/2010 | Gabriel et al. |
| 2010/0174157 | A1 | 7/2010 | Brister et al. |
| 2010/0174158 | A1 | 7/2010 | Kamath et al. |
| 2010/0174163 | A1 | 7/2010 | Brister et al. |
| 2010/0174164 | A1 | 7/2010 | Brister et al. |
| 2010/0174165 | A1 | 7/2010 | Brister et al. |
| 2010/0174166 | A1 | 7/2010 | Brister et al. |
| 2010/0174167 | A1 | 7/2010 | Kamath et al. |
| 2010/0174168 | A1 | 7/2010 | Goode, Jr. et al. |
| 2010/0174266 | A1 | 7/2010 | Estes |
| 2010/0179399 | A1 | 7/2010 | Goode, Jr. et al. |
| 2010/0179400 | A1 | 7/2010 | Brauker et al. |
| 2010/0179401 | A1 | 7/2010 | Rasdal et al. |
| 2010/0179402 | A1 | 7/2010 | Goode, Jr. et al. |
| 2010/0179404 | A1 | 7/2010 | Kamath et al. |
| 2010/0179405 | A1 | 7/2010 | Goode, Jr. et al. |
| 2010/0179407 | A1 | 7/2010 | Goode, Jr. et al. |
| 2010/0179408 | A1 | 7/2010 | Kamath et al. |
| 2010/0179409 | A1 | 7/2010 | Kamath et al. |
| 2010/0185065 | A1 | 7/2010 | Goode, Jr. et al. |
| 2010/0185069 | A1 | 7/2010 | Brister et al. |
| 2010/0185070 | A1 | 7/2010 | Brister et al. |
| 2010/0185071 | A1 | 7/2010 | Simpson et al. |
| 2010/0185072 | A1 | 7/2010 | Goode, Jr. et al. |
| 2010/0185073 | A1 | 7/2010 | Goode, Jr. et al. |
| 2010/0185074 | A1 | 7/2010 | Goode, Jr. et al. |
| 2010/0185075 | A1 | 7/2010 | Brister et al. |
| 2010/0185175 | A1 | 7/2010 | Kamen et al. |
| 2010/0190435 | A1 | 7/2010 | Cook et al. |
| 2010/0191082 | A1 | 7/2010 | Brister et al. |
| 2010/0191087 | A1 | 7/2010 | Talbot et al. |
| 2010/0191472 | A1 | 7/2010 | Doniger et al. |
| 2010/0198033 | A1 | 8/2010 | Krulevitch et al. |
| 2010/0198034 | A1 | 8/2010 | Thomas et al. |
| 2010/0198035 | A1 | 8/2010 | Kamath et al. |
| 2010/0198036 | A1 | 8/2010 | Kamath et al. |
| 2010/0198042 | A1 | 8/2010 | Sloan et al. |
| 2010/0198142 | A1 | 8/2010 | Sloan et al. |
| 2010/0198314 | A1 | 8/2010 | Wei |
| 2010/0204557 | A1 | 8/2010 | Kiaie et al. |
| 2010/0204653 | A1 | 8/2010 | Gryn et al. |
| 2010/0212583 | A1 | 8/2010 | Brister et al. |
| 2010/0213057 | A1 | 8/2010 | Feldman et al. |
| 2010/0213080 | A1 | 8/2010 | Celentano et al. |
| 2010/0214104 | A1 | 8/2010 | Goode, Jr. et al. |
| 2010/0217105 | A1 | 8/2010 | Yodfat et al. |
| 2010/0217557 | A1 | 8/2010 | Kamath et al. |
| 2010/0223013 | A1 | 9/2010 | Kamath et al. |
| 2010/0223022 | A1 | 9/2010 | Kamath et al. |
| 2010/0223023 | A1 | 9/2010 | Kamath et al. |
| 2010/0228109 | A1 | 9/2010 | Kamath et al. |
| 2010/0228111 | A1 | 9/2010 | Friman et al. |
| 2010/0228497 | A1 | 9/2010 | Kamath et al. |
| 2010/0230285 | A1 | 9/2010 | Hoss et al. |
| 2010/0235439 | A1 | 9/2010 | Goodnow et al. |
| 2010/0240975 | A1 | 9/2010 | Goode, Jr. et al. |
| 2010/0240976 | A1 | 9/2010 | Goode, Jr. et al. |
| 2010/0256471 | A1 | 10/2010 | Say et al. |
| 2010/0259543 | A1 | 10/2010 | Tarassenko et al. |
| 2010/0261987 | A1 | 10/2010 | Kamath et al. |
| 2010/0262201 | A1 | 10/2010 | He et al. |
| 2010/0267161 | A1 | 10/2010 | Wu et al. |
| 2010/0274107 | A1 | 10/2010 | Boock et al. |
| 2010/0274111 | A1 | 10/2010 | Say et al. |
| 2010/0274515 | A1 | 10/2010 | Hoss et al. |
| 2010/0275108 | A1 | 10/2010 | Sloan et al. |
| 2010/0280341 | A1 | 11/2010 | Boock et al. |
| 2010/0286496 | A1 | 11/2010 | Simpson et al. |
| 2010/0298684 | A1 | 11/2010 | Leach et al. |
| 2010/0312176 | A1 | 12/2010 | Lauer et al. |
| 2010/0313105 | A1 | 12/2010 | Nekoomaram et al. |
| 2010/0317952 | A1 | 12/2010 | Budiman et al. |
| 2010/0324392 | A1 | 12/2010 | Yee et al. |
| 2010/0324403 | A1 | 12/2010 | Brister et al. |
| 2010/0325868 | A1 | 12/2010 | Wang et al. |
| 2010/0326842 | A1 | 12/2010 | Mazza et al. |
| 2010/0331642 | A1 | 12/2010 | Bruce et al. |
| 2010/0331644 | A1 | 12/2010 | Neale et al. |
| 2010/0331647 | A1 | 12/2010 | Shah et al. |
| 2010/0331648 | A1 | 12/2010 | Kamath et al. |
| 2010/0331651 | A1 | 12/2010 | Groll |
| 2010/0331653 | A1 | 12/2010 | Stafford |
| 2010/0331656 | A1 | 12/2010 | Mensinger et al. |
| 2010/0331657 | A1 | 12/2010 | Mensinger et al. |
| 2011/0004085 | A1 | 1/2011 | Mensinger et al. |
| 2011/0004276 | A1 | 1/2011 | Blair et al. |
| 2011/0009727 | A1 | 1/2011 | Mensinger et al. |
| 2011/0015509 | A1 | 1/2011 | Peyser |
| 2011/0016691 | A1 | 1/2011 | Alden et al. |
| 2011/0021889 | A1 | 1/2011 | Hoss et al. |
| 2011/0022411 | A1 | 1/2011 | Hjelm et al. |
| 2011/0024043 | A1 | 2/2011 | Boock et al. |
| 2011/0024307 | A1 | 2/2011 | Simpson et al. |
| 2011/0027127 | A1 | 2/2011 | Simpson et al. |
| 2011/0027453 | A1 | 2/2011 | Boock et al. |
| 2011/0027458 | A1 | 2/2011 | Boock et al. |
| 2011/0028815 | A1 | 2/2011 | Simpson et al. |
| 2011/0028816 | A1 | 2/2011 | Simpson et al. |
| 2011/0031986 | A1 | 2/2011 | Bhat et al. |
| 2011/0040163 | A1 | 2/2011 | Telson et al. |
| 2011/0040256 | A1 | 2/2011 | Bobroff et al. |
| 2011/0040263 | A1 | 2/2011 | Hordum et al. |
| 2011/0046456 | A1 | 2/2011 | Hordum et al. |
| 2011/0046467 | A1 | 2/2011 | Simpson et al. |
| 2011/0046977 | A1 | 2/2011 | Goodnow et al. |
| 2011/0054275 | A1 | 3/2011 | Stafford |
| 2011/0054282 | A1 | 3/2011 | Nekoomaram et al. |
| 2011/0060196 | A1 | 3/2011 | Stafford |
| 2011/0060530 | A1 | 3/2011 | Fennell |
| 2011/0070633 | A1 | 3/2011 | Matsumoto et al. |
| 2011/0073475 | A1 | 3/2011 | Kastanos et al. |
| 2011/0077469 | A1 | 3/2011 | Blocker et al. |
| 2011/0077490 | A1 | 3/2011 | Simpson et al. |
| 2011/0077494 | A1 | 3/2011 | Doniger et al. |
| 2011/0077659 | A1 | 3/2011 | Mandecki et al. |
| 2011/0081726 | A1 | 4/2011 | Berman et al. |
| 2011/0082484 | A1 | 4/2011 | Saravia et al. |
| 2011/0087196 | A1 | 4/2011 | Hunn et al. |
| 2011/0097090 | A1 | 4/2011 | Cao |
| 2011/0106126 | A1 | 5/2011 | Love et al. |
| 2011/0112696 | A1 | 5/2011 | Yodfat et al. |
| 2011/0118579 | A1 | 5/2011 | Goode, Jr. et al. |
| 2011/0118580 | A1 | 5/2011 | Goode, Jr. et al. |
| 2011/0123971 | A1 | 5/2011 | Berkowitz et al. |
| 2011/0124992 | A1 | 5/2011 | Brauker et al. |
| 2011/0124997 | A1 | 5/2011 | Goode, Jr. et al. |
| 2011/0125040 | A1 | 5/2011 | Crawford et al. |
| 2011/0125410 | A1 | 5/2011 | Goode, Jr. et al. |
| 2011/0130970 | A1 | 6/2011 | Goode, Jr. et al. |
| 2011/0130971 | A1 | 6/2011 | Goode, Jr. et al. |
| 2011/0130998 | A1 | 6/2011 | Goode, Jr. et al. |
| 2011/0137257 | A1 | 6/2011 | Gyrn et al. |
| 2011/0137571 | A1 | 6/2011 | Power et al. |
| 2011/0144465 | A1 | 6/2011 | Shults et al. |
| 2011/0148905 | A1 | 6/2011 | Simmons et al. |
| 2011/0152637 | A1 | 6/2011 | Kateraas et al. |
| 2011/0172510 | A1 | 7/2011 | Chickering, III et al. |
| 2011/0178378 | A1 | 7/2011 | Brister et al. |
| 2011/0178461 | A1 | 7/2011 | Chong et al. |
| 2011/0184258 | A1 | 7/2011 | Stafford |
| 2011/0184482 | A1 | 7/2011 | Eberman et al. |
| 2011/0184752 | A1 | 7/2011 | Ray et al. |
| 2011/0190603 | A1 | 8/2011 | Stafford |
| 2011/0190614 | A1 | 8/2011 | Brister et al. |
| 2011/0191044 | A1 | 8/2011 | Stafford |
| 2011/0193704 | A1 | 8/2011 | Harper et al. |

(56)     References Cited

U.S. PATENT DOCUMENTS

| | | |
|---|---|---|
| 2011/0201910 A1 | 8/2011 | Rasdal et al. |
| 2011/0201911 A1 | 8/2011 | Johnson et al. |
| 2011/0208027 A1 | 8/2011 | Wagner et al. |
| 2011/0213225 A1 | 9/2011 | Bernstein et al. |
| 2011/0218414 A1 | 9/2011 | Kamath et al. |
| 2011/0218490 A1 | 9/2011 | Ocvirk et al. |
| 2011/0230741 A1 | 9/2011 | Liang et al. |
| 2011/0231107 A1 | 9/2011 | Brauker et al. |
| 2011/0231140 A1 | 9/2011 | Goode, Jr. et al. |
| 2011/0231141 A1 | 9/2011 | Goode, Jr. et al. |
| 2011/0231142 A1 | 9/2011 | Goode, Jr. et al. |
| 2011/0253533 A1 | 10/2011 | Shults et al. |
| 2011/0257495 A1 | 10/2011 | Hoss et al. |
| 2011/0257521 A1 | 10/2011 | Fraden |
| 2011/0257895 A1 | 10/2011 | Brauker et al. |
| 2011/0263958 A1 | 10/2011 | Brauker et al. |
| 2011/0263959 A1 | 10/2011 | Young et al. |
| 2011/0264378 A1 | 10/2011 | Breton et al. |
| 2011/0270062 A1 | 11/2011 | Goode, Jr. et al. |
| 2011/0270158 A1 | 11/2011 | Brauker et al. |
| 2011/0275919 A1 | 11/2011 | Petisce et al. |
| 2011/0282327 A1 | 11/2011 | Kellogg et al. |
| 2011/0287528 A1 | 11/2011 | Fern et al. |
| 2011/0288574 A1 | 11/2011 | Cuny et al. |
| 2011/0289497 A1 | 11/2011 | Kiaie et al. |
| 2011/0290645 A1 | 12/2011 | Brister et al. |
| 2011/0313543 A1 | 12/2011 | Brauker et al. |
| 2011/0319729 A1 | 12/2011 | Donnay et al. |
| 2011/0319733 A1 | 12/2011 | Stafford |
| 2011/0319738 A1 | 12/2011 | Woodruff et al. |
| 2011/0319739 A1 | 12/2011 | Kamath et al. |
| 2011/0320130 A1 | 12/2011 | Valdes et al. |
| 2012/0010642 A1 | 1/2012 | Lee et al. |
| 2012/0035445 A1 | 2/2012 | Boock et al. |
| 2012/0040101 A1 | 2/2012 | Tapsak et al. |
| 2012/0046534 A1 | 2/2012 | Simpson et al. |
| 2012/0078071 A1 | 3/2012 | Bohm et al. |
| 2012/0088995 A1 | 4/2012 | Fennell et al. |
| 2012/0095406 A1 | 4/2012 | Gyrn et al. |
| 2012/0108934 A1 | 5/2012 | Valdes et al. |
| 2012/0108983 A1 | 5/2012 | Banet et al. |
| 2012/0116322 A1 | 5/2012 | Brink et al. |
| 2012/0123385 A1 | 5/2012 | Edwards et al. |
| 2012/0143135 A1 | 6/2012 | Cole et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0179113 A1 | 7/2012 | Yokota et al. |
| 2012/0184909 A1 | 7/2012 | Gym et al. |
| 2012/0190989 A1 | 7/2012 | Kaiser et al. |
| 2012/0197098 A1 | 8/2012 | Donnay et al. |
| 2012/0197222 A1 | 8/2012 | Donnay et al. |
| 2012/0245447 A1 | 9/2012 | Karan et al. |
| 2012/0265042 A1 | 10/2012 | Neinast et al. |
| 2012/0296327 A1 | 11/2012 | Hutchins et al. |
| 2012/0303043 A1 | 11/2012 | Donnay et al. |
| 2013/0035575 A1 | 2/2013 | Mayou et al. |
| 2013/0047981 A1 | 2/2013 | Bacon |
| 2013/0109940 A1 | 5/2013 | Yang et al. |
| 2013/0111248 A1 | 5/2013 | Ghesquiere et al. |
| 2013/0150691 A1 | 6/2013 | Pace et al. |
| 2013/0184547 A1 | 7/2013 | Taub et al. |
| 2013/0199312 A1 | 8/2013 | Wilmer et al. |
| 2013/0225959 A1 | 8/2013 | Bugler |
| 2013/0235166 A1 | 9/2013 | Jones et al. |
| 2013/0253289 A1 | 9/2013 | Hadvary et al. |
| 2013/0267811 A1 | 10/2013 | Pryor et al. |
| 2013/0317323 A1 | 11/2013 | Fujiwara et al. |
| 2014/0031655 A1 | 1/2014 | Stafford |
| 2014/0121480 A1 | 5/2014 | Budiman et al. |
| 2014/0148667 A1 | 5/2014 | Boock et al. |
| 2014/0171771 A1 | 6/2014 | Feldman et al. |
| 2014/0188053 A1 | 7/2014 | Lundquist |
| 2014/0228760 A1 | 8/2014 | Ethelfeld |
| 2014/0275907 A1 | 9/2014 | Feldman et al. |
| 2015/0005601 A1 | 1/2015 | Hoss et al. |
| 2015/0018643 A1 | 1/2015 | Cole et al. |
| 2015/0025338 A1 | 1/2015 | Lee et al. |
| 2015/0073238 A1 | 3/2015 | Matsumoto et al. |
| 2015/0105644 A1 | 4/2015 | Yang et al. |
| 2015/0141776 A1 | 5/2015 | Hadvary et al. |
| 2015/0164545 A1 | 6/2015 | Gyrn |
| 2015/0173661 A1 | 6/2015 | Myles |
| 2015/0241407 A1 | 8/2015 | Ou et al. |
| 2015/0326072 A1 | 11/2015 | Petras et al. |
| 2016/0058342 A1 | 3/2016 | Maiz-Aguinaga et al. |
| 2016/0058470 A1 | 3/2016 | Peterson et al. |
| 2016/0058474 A1 | 3/2016 | Peterson et al. |
| 2016/0128615 A1 | 5/2016 | Curry et al. |
| 2016/0157759 A1 | 6/2016 | Yang |
| 2016/0256106 A1 | 9/2016 | Krasnow et al. |
| 2016/0331283 A1 | 11/2016 | Rao et al. |
| 2016/0331284 A1 | 11/2016 | Pace |
| 2016/0338733 A1 | 11/2016 | Shah et al. |
| 2016/0338734 A1 | 11/2016 | Shah et al. |
| 2016/0354555 A1 | 12/2016 | Gibson et al. |
| 2017/0112531 A1 | 4/2017 | Schoonmaker et al. |
| 2017/0112533 A1 | 4/2017 | Schoonmaker et al. |
| 2017/0112534 A1 | 4/2017 | Schoonmaker et al. |
| 2017/0127985 A1 | 5/2017 | Thompson et al. |
| 2017/0128011 A1 | 5/2017 | Frey et al. |
| 2017/0165451 A1 | 6/2017 | Frey et al. |
| 2017/0188908 A1 | 7/2017 | Hoss et al. |
| 2017/0188910 A1 | 7/2017 | Halac et al. |
| 2017/0188912 A1 | 7/2017 | Halac et al. |
| 2017/0216536 A1 | 8/2017 | Scott |
| 2017/0265791 A1 | 9/2017 | Pace et al. |
| 2017/0290533 A1 | 10/2017 | Antonio et al. |
| 2017/0290534 A1 | 10/2017 | Antonio et al. |
| 2017/0290535 A1 | 10/2017 | Rao et al. |
| 2017/0290546 A1 | 10/2017 | Antonio et al. |
| 2017/0319137 A1 | 11/2017 | Tsubouchi et al. |
| 2017/0367630 A1 | 12/2017 | Arita et al. |
| 2017/0368268 A1 | 12/2017 | Chopra |
| 2018/0116572 A1 | 5/2018 | Simpson et al. |
| 2018/0125464 A1 | 5/2018 | Kolb et al. |
| 2018/0235520 A1 | 8/2018 | Rao et al. |
| 2018/0360493 A1 | 12/2018 | Baker et al. |
| 2018/0368771 A1 | 12/2018 | Gray et al. |
| 2019/0133501 A1 | 5/2019 | Rao et al. |
| 2019/0133638 A1 | 5/2019 | Il et al. |
| 2019/0298240 A1 | 10/2019 | Lee et al. |
| 2020/0077928 A1 | 3/2020 | Brister et al. |
| 2020/0100712 A1 | 4/2020 | Stafford |
| 2020/0113494 A1 | 4/2020 | Akiyama |
| 2020/0178899 A1 | 6/2020 | Chae et al. |
| 2020/0196919 A1 | 6/2020 | Rao et al. |
| 2020/0397356 A1 | 12/2020 | Yee et al. |
| 2021/0030969 A1 | 2/2021 | Huang et al. |
| 2021/0113124 A1 | 4/2021 | Yee et al. |
| 2021/0161437 A1 | 6/2021 | Thomas et al. |
| 2021/0177315 A1 | 6/2021 | Thomas et al. |
| 2021/0204841 A1 | 7/2021 | Thomas et al. |
| 2021/0204843 A1 | 7/2021 | Mazza et al. |
| 2021/0378592 A1 | 12/2021 | Rodriguez et al. |
| 2022/0007973 A1 | 1/2022 | Rao et al. |
| 2022/0079475 A1 | 3/2022 | Cole et al. |
| 2022/0125480 A1 | 4/2022 | Rao et al. |
| 2023/0108476 A1 | 4/2023 | Rao |
| 2024/0293615 A1 | 9/2024 | Lanigan |

FOREIGN PATENT DOCUMENTS

| | | |
|---|---|---|
| CA | 2468577 | 6/2003 |
| CA | 2495648 | 2/2004 |
| CA | 2143172 | 7/2005 |
| CA | 2498682 | 9/2005 |
| CA | 2555749 | 9/2005 |
| CA | 2632709 | 6/2007 |
| CA | 2396613 | 3/2008 |
| CA | 2678336 | 5/2008 |
| CA | 2615575 | 6/2008 |
| CA | 2626349 | 9/2008 |
| CA | 2701374 | 4/2009 |

(56) References Cited

FOREIGN PATENT DOCUMENTS

| | | |
|---|---|---|
| CA | 2413148 | 8/2010 |
| CA | 2728831 | 7/2011 |
| CA | 2766693 A1 | 9/2011 |
| CA | 2617965 | 10/2011 |
| CA | 2766685 A1 | 12/2011 |
| CA | 3050721 | 7/2018 |
| CN | 1202872 | 5/2005 |
| CN | 101163440 | 4/2008 |
| CN | 101268932 | 9/2008 |
| CN | 101296650 | 10/2008 |
| CN | 201370857 | 12/2009 |
| DE | 4401400 | 7/1995 |
| DE | 201 10 059 | 8/2002 |
| DE | 101 17 285 | 11/2002 |
| EP | 0 010 375 | 4/1980 |
| EP | 0 026 995 | 4/1981 |
| EP | 0 048 090 | 3/1982 |
| EP | 0 078 636 | 5/1983 |
| EP | 0 096 288 | 12/1983 |
| EP | 0 098 592 | 1/1984 |
| EP | 0 125 139 | 11/1984 |
| EP | 0 127 958 | 12/1984 |
| EP | 0 136 362 | 4/1985 |
| EP | 0 170 375 | 2/1986 |
| EP | 0 177 743 | 4/1986 |
| EP | 0 080 304 | 5/1986 |
| EP | 0 184 909 | 6/1986 |
| EP | 0 206 218 | 12/1986 |
| EP | 0 230 472 | 8/1987 |
| EP | 0 241 309 | 10/1987 |
| EP | 0 245 073 | 11/1987 |
| EP | 0 255 291 | 2/1988 |
| EP | 0 278 647 | 8/1988 |
| EP | 0 319 277 A1 | 6/1989 |
| EP | 0320109 | 6/1989 |
| EP | 0353328 | 2/1990 |
| EP | 0 359 831 | 3/1990 |
| EP | 0 368 209 | 5/1990 |
| EP | 0390390 | 10/1990 |
| EP | 0396788 | 11/1990 |
| EP | 0 400 918 | 12/1990 |
| EP | 0 453 283 | 10/1991 |
| EP | 0 470 290 | 2/1992 |
| EP | 0 567 725 | 11/1993 |
| EP | 0286118 | 1/1995 |
| EP | 0 680 727 | 11/1995 |
| EP | 0 724 859 | 8/1996 |
| EP | 0 805 574 | 11/1997 |
| EP | 1 897 488 | 12/1999 |
| EP | 0 973 289 | 1/2000 |
| EP | 0 678 308 | 5/2000 |
| EP | 1048264 | 11/2000 |
| EP | 1177802 | 2/2002 |
| EP | 0 729 366 | 7/2002 |
| EP | 1 292 218 | 3/2003 |
| EP | 1 077 634 | 7/2003 |
| EP | 1 092 390 | 7/2004 |
| EP | 1 568 309 | 8/2005 |
| EP | 1 630 898 | 3/2006 |
| EP | 1 666 091 | 6/2006 |
| EP | 1 669 020 | 6/2006 |
| EP | 1 703 697 | 9/2006 |
| EP | 1 704 893 | 9/2006 |
| EP | 1704889 A1 | 9/2006 |
| EP | 1 729 128 | 12/2006 |
| EP | 0 987 982 | 1/2007 |
| EP | 1 956 371 | 8/2008 |
| EP | 1 972 270 | 9/2008 |
| EP | 2 031 534 | 3/2009 |
| EP | 2060284 | 5/2009 |
| EP | 1 897 487 | 11/2009 |
| EP | 1 897 492 | 11/2009 |
| EP | 2 113 864 | 11/2009 |
| EP | 1 681 992 | 4/2010 |
| EP | 2201969 | 6/2010 |
| EP | 1 448 489 | 8/2010 |
| EP | 1 971 396 | 8/2010 |
| EP | 1 725 163 | 12/2010 |
| EP | 2 260 757 | 12/2010 |
| EP | 1 413 245 | 6/2011 |
| EP | 2 327 362 | 6/2011 |
| EP | 2 327 984 | 6/2011 |
| EP | 2 335 587 | 6/2011 |
| EP | 2 153 382 | 2/2012 |
| EP | 2 284 773 | 2/2012 |
| EP | 1 789 116 B1 | 5/2013 |
| EP | 3 251 597 B1 | 11/2019 |
| EP | 3 632 314 | 4/2020 |
| EP | 3 632 315 A1 | 4/2020 |
| EP | 3 851 045 A1 | 7/2021 |
| EP | 3 730 044 B1 | 12/2021 |
| EP | 3 730 045 B1 | 3/2022 |
| EP | 3 766 408 B1 | 4/2022 |
| EP | 3 928 688 B1 | 6/2022 |
| EP | 4 111 949 B1 | 7/2023 |
| EP | 4 344 633 | 4/2024 |
| EP | 4 203 819 | 7/2024 |
| GB | 1 394 171 | 5/1975 |
| GB | 1 599 241 | 9/1981 |
| GB | 2 073 891 | 10/1981 |
| GB | 2 067 764 | 1/1984 |
| GB | 2 154 003 | 8/1985 |
| GB | 2 204 408 | 11/1988 |
| GB | 2 254 436 | 10/1992 |
| GB | 2 409 951 | 7/2005 |
| JP | 54-041191 | 4/1979 |
| JP | 55-010581 | 1/1980 |
| JP | 55-010583 | 1/1980 |
| JP | 55-010584 | 1/1980 |
| JP | 55-012406 | 1/1980 |
| JP | 56-163447 | 2/1981 |
| JP | 57-070448 | 4/1982 |
| JP | 60-173457 | 9/1985 |
| JP | 60-173458 | 9/1985 |
| JP | 60-173459 | 9/1985 |
| JP | 62-085855 | 4/1987 |
| JP | 62-114747 | 5/1987 |
| JP | 63-058149 | 3/1988 |
| JP | 63-128252 | 5/1988 |
| JP | 63-139246 | 6/1988 |
| JP | 63-294799 | 12/1988 |
| JP | 63-317757 | 12/1988 |
| JP | 63-317758 | 12/1988 |
| JP | 01-114746 | 5/1989 |
| JP | 01-114747 | 5/1989 |
| JP | 01-124060 | 5/1989 |
| JP | 01-134244 | 5/1989 |
| JP | 01-156658 | 6/1989 |
| JP | 02-062958 | 3/1990 |
| JP | 02-120655 | 5/1990 |
| JP | 02-287145 | 11/1990 |
| JP | 02-310457 | 12/1990 |
| JP | 03-020752 | 1/1991 |
| JP | 03-026956 | 2/1991 |
| JP | 03-028752 | 2/1991 |
| JP | 03-500940 | 2/1991 |
| JP | 03-194458 | 8/1991 |
| JP | 03-202764 | 9/1991 |
| JP | 05-072171 | 3/1993 |
| JP | 05-196595 | 8/1993 |
| JP | 06-190050 | 7/1994 |
| JP | 07-055757 | 3/1995 |
| JP | 07-072585 | 3/1995 |
| JP | 07-182462 | 7/1995 |
| JP | 07-311196 | 11/1995 |
| JP | 08-285814 | 11/1996 |
| JP | 08-285815 | 11/1996 |
| JP | 09-021778 | 1/1997 |
| JP | 09-101280 | 4/1997 |
| JP | 09-285459 | 4/1997 |
| JP | 10-170471 | 6/1998 |
| JP | 10-305016 | 11/1998 |
| JP | 11-506629 | 6/1999 |
| JP | 11-225359 | 8/1999 |

(56)  References Cited

FOREIGN PATENT DOCUMENTS

| | | |
|----|----|----|
| JP | 2003-144417 | 5/2003 |
| JP | 2004-033438 | 2/2004 |
| JP | 2004-214014 | 7/2004 |
| JP | 2004-520103 | 7/2004 |
| JP | 2004-520898 | 7/2004 |
| JP | 2004-358016 | 12/2004 |
| JP | 2006-021031 | 1/2006 |
| JP | 2006-280464 | 10/2006 |
| JP | 2006-527036 | 11/2006 |
| JP | 2007-510499 | 4/2007 |
| JP | 2007-152037 | 6/2007 |
| JP | 2008-506468 | 3/2008 |
| KR | 10-2017-0068694 | 6/2017 |
| SU | 1281988 | 1/1987 |
| WO | WO 89/05119 | 6/1989 |
| WO | WO 89/08713 | 9/1989 |
| WO | WO 90/05300 | 5/1990 |
| WO | WO 90/05910 | 5/1990 |
| WO | WO 91/01680 | 2/1991 |
| WO | WO 91/04704 | 4/1991 |
| WO | WO-1991/015993 | 10/1991 |
| WO | WO-1992/013271 | 8/1992 |
| WO | WO-1994/020602 | 9/1994 |
| WO | WO 95/28878 | 2/1995 |
| WO | WO-1996/039977 | 5/1996 |
| WO | WO-1996/025089 | 8/1996 |
| WO | WO 96/35370 | 11/1996 |
| WO | WO 97/02847 | 1/1997 |
| WO | WO 97/19344 | 5/1997 |
| WO | WO 97/21457 | 6/1997 |
| WO | WO 97/33513 | 9/1997 |
| WO | WO 97/42882 | 11/1997 |
| WO | WO 97/42883 | 11/1997 |
| WO | WO 97/42886 | 11/1997 |
| WO | WO 97/42888 | 11/1997 |
| WO | WO 97/43962 | 11/1997 |
| WO | WO 98/04902 | 2/1998 |
| WO | WO-1998/035053 | 8/1998 |
| WO | WO-1998/056293 | 12/1998 |
| WO | WO 99/27849 | 6/1999 |
| WO | WO 99/28736 | 6/1999 |
| WO | WO-1999/033504 | 7/1999 |
| WO | WO-1999/056613 | 11/1999 |
| WO | WO 00/40159 | 7/2000 |
| WO | WO-2000/049940 | 8/2000 |
| WO | WO 00/60350 | 10/2000 |
| WO | WO-2000/059370 | 10/2000 |
| WO | WO 00/74753 | 12/2000 |
| WO | WO-2000/078992 | 12/2000 |
| WO | WO 01/52727 A1 | 7/2001 |
| WO | WO-2001/052935 | 7/2001 |
| WO | WO 01/58348 | 8/2001 |
| WO | WO-2001/054753 | 8/2001 |
| WO | WO 02/15778 | 2/2002 |
| WO | WO-2002/016905 | 2/2002 |
| WO | WO-2002/050534 | 6/2002 |
| WO | WO-2002/058537 | 8/2002 |
| WO | WO 02/100457 | 12/2002 |
| WO | WO 03/026728 | 4/2003 |
| WO | WO-2003/028784 | 4/2003 |
| WO | WO 03/056319 | 7/2003 |
| WO | WO 03/057027 | 7/2003 |
| WO | WO 03/072164 | 9/2003 |
| WO | WO 03/073936 | 9/2003 |
| WO | WO-2003/076893 | 9/2003 |
| WO | WO 03/085372 | 10/2003 |
| WO | WO-2003/082091 | 10/2003 |
| WO | WO 2004/015539 | 2/2004 |
| WO | WO-2004/028337 | 4/2004 |
| WO | WO 2004/030726 | 4/2004 |
| WO | WO 2004/034024 | 4/2004 |
| WO | WO 2004/047445 | 6/2004 |
| WO | WO 2004/049237 | 6/2004 |
| WO | WO 2004/054445 | 7/2004 |
| WO | WO-2004/060436 | 7/2004 |
| WO | WO-2004/061420 | 7/2004 |
| WO | WO 2004/090503 | 10/2004 |
| WO | WO 2004/098405 | 11/2004 |
| WO | WO 2004/098682 A2 | 11/2004 |
| WO | WO 2004/098683 | 11/2004 |
| WO | WO-2004/098684 | 11/2004 |
| WO | WO 2004/098685 | 11/2004 |
| WO | WO 2004/107971 | 12/2004 |
| WO | WO-2004/112602 | 12/2004 |
| WO | WO 2005/011779 A1 | 2/2005 |
| WO | WO 2005/018450 | 3/2005 |
| WO | WO 2005/037184 | 4/2005 |
| WO | WO 2005/041766 | 5/2005 |
| WO | WO 2005/044116 | 5/2005 |
| WO | WO 2005/045744 | 5/2005 |
| WO | WO 2005/046780 | 5/2005 |
| WO | WO 2005/051170 | 6/2005 |
| WO | WO 2005/057175 | 6/2005 |
| WO | WO 2005/065538 | 7/2005 |
| WO | WO-2005/084534 | 9/2005 |
| WO | WO-2005/089103 | 9/2005 |
| WO | WO 2005/092177 | 10/2005 |
| WO | WO 2005/121785 | 12/2005 |
| WO | WO 2005/123186 | 12/2005 |
| WO | WO 2006/001024 | 1/2006 |
| WO | WO 2006/015922 | 2/2006 |
| WO | WO 2006/017358 | 2/2006 |
| WO | WO 2006/020212 | 2/2006 |
| WO | WO-2006/024671 | 3/2006 |
| WO | WO 2006/026741 | 3/2006 |
| WO | WO 2006/036145 | 4/2006 |
| WO | WO 2006/040083 | 4/2006 |
| WO | WO-2006/042811 | 4/2006 |
| WO | WO 2006/061354 | 6/2006 |
| WO | WO 2006/064397 | 6/2006 |
| WO | WO 2006/072035 | 7/2006 |
| WO | WO 2006/079114 | 7/2006 |
| WO | WO 2006/086423 | 8/2006 |
| WO | WO 2006/094513 | 9/2006 |
| WO | WO-2006/108809 | 10/2006 |
| WO | WO 2006/110742 | 10/2006 |
| WO | WO 2006/114297 | 11/2006 |
| WO | WO 2006/118947 | 11/2006 |
| WO | WO 2006/121921 | 11/2006 |
| WO | WO 2006/124099 | 11/2006 |
| WO | WO 2007/002189 | 1/2007 |
| WO | WO 2007/007459 | 1/2007 |
| WO | WO 2007/016399 | 2/2007 |
| WO | WO 2007/019289 | 2/2007 |
| WO | WO 2007/027788 | 3/2007 |
| WO | WO 2007/041069 | 4/2007 |
| WO | WO 2007/041070 | 4/2007 |
| WO | WO 2007/041248 | 4/2007 |
| WO | WO 2007/053832 | 5/2007 |
| WO | WO 2007/056638 | 5/2007 |
| WO | WO 2007/065285 | 6/2007 |
| WO | WO 2007/089738 | 8/2007 |
| WO | WO 2007/092618 | 8/2007 |
| WO | WO 2007/097754 | 8/2007 |
| WO | WO 2007/101223 | 9/2007 |
| WO | WO 2007/120363 | 10/2007 |
| WO | WO 2007/126444 | 11/2007 |
| WO | WO 2007/140783 | 12/2007 |
| WO | WO 2007/143225 | 12/2007 |
| WO | WO 2007/149319 | 12/2007 |
| WO | WO 2008/001366 | 1/2008 |
| WO | WO 2008/014792 | 2/2008 |
| WO | WO 2008/021913 | 2/2008 |
| WO | WO 2008/031106 | 3/2008 |
| WO | WO 2008/031110 | 3/2008 |
| WO | WO 2008/039944 | 4/2008 |
| WO | WO 2008/042760 | 4/2008 |
| WO | WO 2008/048452 | 4/2008 |
| WO | WO 2008/051920 | 5/2008 |
| WO | WO 2008/051924 | 5/2008 |
| WO | WO 2008/052374 | 5/2008 |
| WO | WO 2008/061552 | 5/2008 |
| WO | WO 2008/062099 | 5/2008 |
| WO | WO 2008/065646 | 6/2008 |

US 12,588,928 B2

Page 20

(56)	References Cited

FOREIGN PATENT DOCUMENTS

| WO | WO 2008/073813 | 6/2008 |
| WO | WO 2008/086541 | 7/2008 |
| WO | WO 2008/103620 | 8/2008 |
| WO | WO 2008/114223 | 9/2008 |
| WO | WO 2008/115409 | 9/2008 |
| WO | WO 2008/128210 | 10/2008 |
| WO | WO 2008/129532 | 10/2008 |
| WO | WO 2008/130896 | 10/2008 |
| WO | WO 2008/130897 | 10/2008 |
| WO | WO 2008/130898 | 10/2008 |
| WO | WO 2008/133702 | 11/2008 |
| WO | WO 2008/138006 | 11/2008 |
| WO | WO 2008/143943 | 11/2008 |
| WO | WO 2008/144445 | 11/2008 |
| WO | WO 2008/147921 | 12/2008 |
| WO | WO 2008/147921 A1 | 12/2008 |
| WO | WO 2008/150917 | 12/2008 |
| WO | WO 2008/153693 | 12/2008 |
| WO | WO 2008/155377 | 12/2008 |
| WO | WO 2008/157821 | 12/2008 |
| WO | WO 2009/007287 | 1/2009 |
| WO | WO 2009/010396 | 1/2009 |
| WO | WO 2009/016635 | 2/2009 |
| WO | WO 2009/016638 A1 | 2/2009 |
| WO | WO 2009/018058 | 2/2009 |
| WO | WO 2006/032653 | 3/2009 |
| WO | WO 2009/035773 | 3/2009 |
| WO | WO 2009/039013 | 3/2009 |
| WO | WO 2009/062674 | 5/2009 |
| WO | WO-2009/062675 | 5/2009 |
| WO | WO 2009/066288 A1 | 5/2009 |
| WO | WO 2009/068661 | 6/2009 |
| WO | WO 2009/086216 | 7/2009 |
| WO | WO 2009/097594 | 8/2009 |
| WO | WO 2010/062898 | 6/2010 |
| WO | WO 2010/077329 | 7/2010 |
| WO | WO 2010/091005 | 8/2010 |
| WO | WO 2010/099507 | 9/2010 |
| WO | WO-2010/112521 | 10/2010 |
| WO | WO 2010/141922 | 12/2010 |
| WO | WO 2011/000528 | 1/2011 |
| WO | WO-2011/002815 | 1/2011 |
| WO | WO 2011/015659 | 2/2011 |
| WO | WO 2011/022418 | 2/2011 |
| WO | WO 2011/025549 | 3/2011 |
| WO | WO 2011/104616 | 9/2011 |
| WO | WO 2011/119896 | 9/2011 |
| WO | WO 2011/119898 A1 | 9/2011 |
| WO | WO 2012/103429 | 8/2012 |
| WO | WO 2013/090215 | 6/2013 |
| WO | WO 2016/183493 | 11/2016 |
| WO | WO 2017/027749 | 2/2017 |
| WO | WO 2017/116915 | 7/2017 |
| WO | WO 2017/134227 | 8/2017 |
| WO | WO 2018/136898 | 7/2018 |
| WO | WO 2018/166963 | 9/2018 |
| WO | WO 2019/005627 A1 | 1/2019 |
| WO | WO 2019/236850 | 12/2019 |
| WO | WO 2019/236859 | 12/2019 |
| WO | WO 2019/236876 | 12/2019 |
| WO | WO 01/17875 A1 | 3/2021 |
| WO | WO 2022/046416 | 3/2022 |
| WO | WO 2022/060677 | 3/2022 |

OTHER PUBLICATIONS

Aussedat, B., et al., "A User-Friendly Method for Calibrating a Subcutaneous Glucose Sensor-Based Hypoglycemic Alarm", Biosensors & Bioelectronics, vol. 12, No. 11, 1997, pp. 1061-1071.
Australian Patent Application No. 2011230596, Examination Report dated Feb. 28, 2014.
Australian Patent Application No. 2011269796, Examination Report dated Apr. 3, 2014.

Bennion, N., et al., "Alternate Site Glucose Testing: A Crossover Design", Diabetes Technology & Therapeutics, vol. 4, No. 1, 2002, pp. 25-33.
Chinese Patent Application No. 201180002616.7, Original Language and English Translation of Office Action dated Apr. 24, 2014.
Chinese Patent Application No. 201180002617.1, Original Language and English Translation of Office Action dated Jul. 3, 2014.
Claremont, D. J., et al., "Biosensors for Continuous In Vivo Glucose Monitoring", Proceedings of the Annual International Conference of the IEEE Engineering in Medicine and Biology Society, vol. 10, 1988.
Clark Jr., L. C., et al., "Electrode Systems for Continuous Monitoring in Cardiovascular Surgery", Annals New York Academy of Sciences, 1962, pp. 29-45.
Clark Jr., L. C., et al., "Long-term Stability of Electroenzymatic Glucose Sensors Implanted in Mice", American Society of Artificial Internal Organs Transactions, vol. XXXIV, 1988, pp. 259-265.
Csoregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.
Csoregi, E., et al., "Design, Characterization, and One-Point in Vivo Calibration of a Subcutaneously Implanted Glucose Electrode", Analytical Chemistry, vol. 66 No. 19, 1994, pp. 3131-3138.
European Patent Application No. EP 11760268.0, Extended European Search Report dated Apr. 14, 2014.
Feldman, B., et al., "A Continuous Glucose Sensor Based on Wired Enzyme™ Technology—Results from a 3-Day Trial in Patients with Type 1 Diabetes", Diabetes Technology & Therapeutics, vol. 5, No. 5, 2003, pp. 769-779.
Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.
Isermann, R., "Supervision, Fault-Detection and Fault-Diagnosis Methods—An Introduction", Control Engineering Practice, vol. 5, No. 5, 1997, pp. 639-652.
Isermann, R., et al., "Trends in the Application of Model-Based Fault Detection and Diagnosis of Technical Processes", Control Engineering Practice, vol. 5, No. 5, 1997, pp. 709-719.
Johnson, P. C., "Peripheral Circulation", John Wiley & Sons, 1978, pp. 198.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm", Diabetes Care, vol. 24, No. 7, 2001, pp. 1303-1304.
Koudelka, M., et al., "In-Vivo Behaviour of Hypodermically Implanted Microfabricated Glucose Sensors", Biosensors & Bioelectronics, vol. 6, 1991, pp. 31-36.
Lager, W., et al., "Implantable Electrocatalytic Glucose Sensor", Hormone Metabolic Research, vol. 26, 1994, pp. 526-530.
Moatti-Sirat, D., et al., "Evaluating In Vitro and In Vivo the Interference of Ascorbate and Acetaminophen on Glucose Detection by a Needle-Type Glucose Sensor", Biosensors & Bioelectronics, vol. 7, 1992, pp. 345-352.
Moatti-Sirat, D., et al., "Reduction of Acetaminophen Interference in Glucose Sensors by a Composite Nafion Membrane: Demonstration in Rats and Man", Diabetologia, vol. 37, 1994, pp. 610-616.
Olievier, C. N., et al., "In Vivo Measurement of Carbon Dioxide Tension with a Miniature Electrodes", Pflugers Archiv: European Journal of Physiology, vol. 373, 1978, pp. 269-272.
Pickup, J., "Developing Glucose Sensors for In Vivo Use", Tibtech, vol. 11, 1993, pp. 285-291.
Pickup, J., et al., "Implantable Glucose Sensors: Choosing the Appropriate Sensing Strategy", Biosensors, vol. 3, 1987/88, pp. 335-346.
Pickup, J., et al., "Potentially-Implantable, Amperometric Glucose Sensors with Mediated Electron Transfer: Improving the Operating Stability", Biosensors, vol. 4, 1989, pp. 109-119.
Poitout, V., et al., "A Glucose Monitoring System for On Line Estimation in Man of Blood Glucose Concentration Using a Min-

(56)            References Cited

OTHER PUBLICATIONS iaturized Glucose Sensor Implanted in the Subcutaneous Tissue and a Wearable Control Unit", Diabetolgia, vol. 36, 1993, pp. 658-663.

Poitout, V., et al., "Calibration in Dogs of a Subcutaneous Miniaturized Glucose Sensor Using a Glucose Meter for Blood Glucose Determination", Biosensors & Bioelectronics, vol. 7, 1992, pp. 587-592.

Quinn, C. P., et al., "Kinetics of Glucose Delivery to Subcutaneous Tissue in Rats Measured with 0.3-mm Amperometric Microsensors", The American Physiological Society, 1995, E155-E161.

Roe, J. N., et al., "Bloodless Glucose Measurements", Critical Review in Therapeutic Drug Carrier Systems, vol. 15, Issue 3, 1998, pp. 199-241.

Salehi, C., et al., "A Telemetry-Instrumentation System for Long-Term Implantable Glucose and Oxygen Sensors", Analytical Letters, vol. 29, No. 13, 1996, pp. 2289-2308.

Scheller, F., et al., "Enzyme Electrodes and Their Application", Philosophical Transactions of The Royal Society of London B, vol. 316, 1987, pp. 85-94.

Schmidt, F. J., et al., "Calibration of a Wearable Glucose Sensor", The International Journal of Artificial Organs, vol. 15, No. 1, 1992, pp. 55-61.

Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294-299.

Shaw, G. W., et al., "In Vitro Testing of a Simply Constructed, Highly Stable Glucose Sensor Suitable for Implantation in Diabetic Patients", Biosensors & Bioelectronics, vol. 6, 1991, pp. 401-406.

Shichiri, M., et al., "Membrane Design for Extending the Long-Life of an Implantable Glucose Sensor", Diabetes Nutrition and Metabolism, vol. 2, 1989, pp. 309-313.

Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.

Thompson, M., et al., "In Vivo Probes: Problems and Perspectives", Clinical Biochemistry, vol. 19, 1986, pp. 255-261.

Velho, G., et al., "In Vitro and In Vivo Stability of Electrode Potentials in Needle-Type Glucose Sensors", Diabetes, vol. 38, No. 2, 1989, pp. 164-171.

Von Woedtke, T., et al., "In Situ Calibration of Implanted Electrochemical Glucose Sensors", Biomedica Biochimica Acta, vol. 48, 1989, pp. 943-952.

PCT Application No. PCT/US2011/029881, International Search Report and Written Opinion of the International Searching Authority dated May 20, 2011.

PCT Application No. PCT/US2011/029883, International Search Report and Written Opinion of the International Searching Authority dated Jun. 2, 2011.

PCT Application No. PCT/US2011/029884, International Search Report and Written Opinion of the International Searching Authority dated Jun. 1, 2011.

PCT Application No. PCT/US2010/022860, International Preliminary Report on Patentability and Written Opinion of the International Searching Authority dated Aug. 18, 2011.

PCT Application No. PCT/US2010/047381, International Preliminary Report on Patentability and Written Opinion of the International Searching Authority dated Mar. 15, 2012.

PCT Application No. PCT/US2010/050772, International Preliminary Report on Patentability and Written Opinion of the International Searching Authority dated Apr. 12, 2012.

PCT Application No. PCT/US2010/050888, International Preliminary Report on Patentability and Written Opinion of the International Searching Authority dated Apr. 12, 2012.

PCT Application No. PCT/US2010/051861, International Preliminary Report on Patentability and Written Opinion of the International Searching Authority dated Apr. 19, 2012.

Alcock, S.J., et al., "Continuous analyte monitoring to aid clinical practice," IEEE Engineering in Medicine & Biology Magazine, 13:319-25 (1994).

Armour, J.C., et al., "Application of Chronic Intravascular Blood Glucose Sensor in Dogs," Diabetes, vol. 39, pp. 1519-1526, Dec. 1990.

Bindra, D.S. et al., "Design and in Vitro Studies of a Needle-Type Glucose Sensor for Subcutaneous Monitoring," Anal. Chem., 63(17):1692-1696 (Sep. 1, 1991).

Bobbioni-Harsch, E. et al., "Lifespan of subcutaneous glucose sensors and their performances during dynamic glycaemia changes in rats," J. Biomed. Eng. 15:457-463 (1993).

Cass, A.E.G. et al., "Ferrocene-Mediated Enzyme Electrode for Amperometric Determination of Glucose," Anal. Chem., 56(4):667-671 (Apr. 1984).

Gregg, B. A. et al., "Cross-Linked Redox Gels Containing Glucose Oxidase for Amperometric Biosensor Applications," Analytical Chemistry, 62(3):258-263 (Feb. 1, 1990).

Harrison, DJ. et al., "Characterization of Perfluorosulfonic Acid Polymer Coated Enzyme Electrodes and a Miniaturized Integrated Potentiostat for Glucose Analysis in Whole Blood," Anal. Chem., 60 (19):2002-2007 (Oct. 1, 1988).

Heller, A., "Electrical Connection of Enzyme Redox Centers to Electrodes," J. Phys. Chern., 96 (9):3579-3587 (1992).

Heller, A., "Electrical Wiring of Redox Enzymes," Acc. Chem. Res., 23(5):129-134 (1990).

Johnson, K., et al., "In vivo evaluation of an electroenzymatic glucose sensor implanted in subcutaneous tissue," Biosensors and Bioelectronics. 1992, vol. 7, pp. 709-714.

Maidan, R. et al., "Elimination of Electrooxidizable Interferant-Produced Currents in Amperometric Biosensors," Analytical Chemistry, 64(23):2889-2896 (Dec. 1, 1992).

Mastrototaro, J.J., et al., "An Electroenzymatic Glucose Sensor Fabricated on a Flexible Substrate," Sensors and Biosensors B Chemical, B5: 139-144 (1991).

McKean, B., et al., "A Telemetry-Instrumentation System for Chronically Implanted Glucose and Oxygen Sensors," IEEE Transactions on Biomedical Engineering, vol. 35, No. 7, (Jul. 1988), pp. 526-532.

Moatti-Sirat, D., et al., "Towards continuous glucose monitoring: in vivo evaluation of a miniaturized glucose sensor implanted for several days in rat subcutaneous tissue," Diabetologia, 35(3) (1 page—Abstract only) (Mar. 1992).

Ohara, T. J., et al., "Glucose Electrodes Based on Cross-Linked [Os(bpy)$_2$Cl]$^{+/2+}$ Complexed Poly(1-vinylimadazole) Films," Analytical Chemistry, 65(23):3512-3516 (Dec. 1, 1993).

Opinion of the Court, Supreme Court of the United States, No. 04-1350, KSR International co., Petitioner v. Teleflex Inc. et al., Apr. 30, 2007.

Pickup, J. C., et al., "In vivo molecular sensing in diabetes mellitus: an implantable glucose sensor with direct electron transfer," Diabetologia, 32(3):213-217 (1989).

Pishko, M. V., et al., "Amperometric Glucose Microelectrodes Prepared Through Immobilization of Glucose Oxidase in Redox Hydrogels," Anal. Chem., 63(20):2268-2272 (Oct. 15, 1991).

Poitout, V., et al., "In vitro and in vivo evaluation in dogs of a miniaturized glucose sensor," ASAIO Transactions, 37(3) (1 page—Abstract only) (Jul.-Sep. 1991).

Reach, G., et al., "Can Continuous Glucose Monitoring Be Used for the Treatment of Diabetes?," Analytical Chemistry, 64(6):381-386 (Mar. 15, 1992).

Rebrin, K., et al., "Automated Feedback Control of Subcutaneous Glucose Concentration in Diabetic Dogs," Diabetologia, 32(8):573-576 (Aug. 1989).

Sakakida, M., et al., "Ferrocene-mediate needle-type glucose sensor covered with newly designed biocompatible membrane," Sensors and Actuators B, 13-14:319-322 (1993).

Sakakida, M., et al., "Development of ferrocene-mediated needle-type glucose sensor as a measure of true subcutaneous tissue glucose concentrations", Artif Organs Today. 1992, vol. 2, No. 2, pp. 145-458.

Shichiri, M., et al., "Glycaemic Control in Pancreatectomized Dogs with a Wearable Artificial Endocrine Pancreas," Diabetologia, 24(3):179-184 (Mar. 1983).

(56)         References Cited

OTHER PUBLICATIONS

Shichiri, M., et al., "Telemetry Glucose Monitoring Device with Needle-type Glucose Sensor: A Useful Tool for Blood Glucose Monitoring in Diabetic Individuals," Diabetes Care, vol. 9, No. 3 (May-Jun. 1986), pp. 298-301.

Shichiri, M., et al., "In vivo characteristics of needle-type glucose sensor—Measurement of subcutaneous glucose concentrations in human volunteers," Horm Metab Res Suppl. 1988, vol. 20, pp. 17-20.

Shichiri, M., et al., "Wearable artificial endocrine pancreas with needle-type glucose sensor," The Lancet, 1982, vol. 2, No. 8308, pp. 1129-1131.

Shults, M., "A Telemetry-Instrumentation System for Monitoring Multiple Subcutaneously Implanted Glucose Sensors," IEEE Transactions on Biomedical Engineering, vol. 41, No. 10 (Oct. 1994), pp. 937-942.

Sternberg, R., et al., "Study and Development of Multilayer Needle-type Enzyme-based Glucose Microsensors," Biosensors, 4:27-40 (1988).

Turner, A.P.F., et al., "Diabetes Mellitus: Biosensors for Research and Management", Biosensors, 1:85-115 (1985).

Updike, S. et al., "Principles of Long-term Fully Implanted Sensors with Emphasis on Radiotelemetric Monitoring of Blood Glucose from Inside a Subcutaneous Foreign Body Capsule (FBC)" in "Biosensors in the Body: Continuous in vivo Monitoring" (John Wiley & Sons, Ltd., 1997) Chapter 4, pp. 117-137.

Velho, G. et al., "Strategies for calibrating a subcutaneous glucose sensor," Biomed. Biochim. Acta, 48 (11112):957-964 (1989).

Wilson, G. S. et al., "Progress toward the Development of an Implantable Sensor for Glucose," Clinical Chemistry, 38(9):1613-1617 (1992).

Ye, L. et al., "High Current Density "Wired" Quinoprotein Glucose Dehydrogenase Electroade," Anal. Chem., 65(3):238-241 (Feb. 1, 1993).

U.S. Patent Reexamination Application No. 90/008,172, Request for Reexamination of U.S. Pat. No. 6,990,366, filed Aug. 16, 2006.

U.S. Patent Reexamination Application No. 90/008,457, Notice of Intent to Issue Reexamination Certificate dated Mar. 13, 2008.

U.S. Patent Reexamination Application No. 90/008,457, Order Granting Request for Reexamination dated Feb. 23, 2007.

U.S. Patent Reexamination Application No. 90/008,457, Request for Reexamination of U.S. Pat. No. 6,990,366 filed Jan. 23, 2007.

U.S. Patent Reexamination Application Nos. 90/009,328 & 90/009,328, Notice of Intent to Issue Reexamination Certificate dated Nov. 20, 2009.

U.S. Patent Reexamination Application Nos. 90/009,328 & 90/009,328, Office Action dated Aug. 4, 2009.

U.S. Patent Reexamination Application Nos. 90/009,328 & 90/009,328, Office Action dated Sep. 30, 2009.

U.S. Patent Reexamination Application No. 90/009,104, Office Action dated Oct. 16, 2008.

U.S. Patent Reexamination Application No. 90/009,104, Order Granting Request for Reexamination dated Jun. 5, 2008.

U.S. Patent Reexamination Application No. 90/009,104, Request for Reexamination of U.S. Pat. No. 6,990,366 filed Apr. 8, 2008.

U.S. Patent Reexamination Application No. 90/009,328, Order Granting Request for Reexamination dated Dec. 9, 2008.

U.S. Patent Reexamination Application No. 90/009,328, Request for Reexamination of U.S. Pat. No. 6,990,366 filed Nov. 10, 2008.

U.S. Patent Reexamination Application No. 90/010,791, Notice of Intent to Issue Reexamination Certificate dated May 17, 2011.

U.S. Patent Reexamination Application No. 90/010,791, Office Action dated Dec. 17, 2010.

U.S. Patent Reexamination Application No. 90/010,791, Office Action dated May 28, 2010.

U.S. Patent Reexamination Application No. 90/010,791, Order Granting Request for Reexamination dated Feb. 22, 2010.

U.S. Patent Reexamination Application No. 90/010,791, Request for Reexamination of U.S. Pat. No. 6,990,366 filed Dec. 22, 2009.

U.S. Patent Reexamination Application No. 90/011,730, Notice of Intent to Issue Reexam Certificate for U.S. Pat. No. 6,990,366 dated Apr. 5, 2012.

U.S. Patent Reexamination Application No. 90/011,730, Office Action dated Jan. 11, 2012.

U.S. Patent Reexamination Application No. 90/011,730, Order Granting Request for Reexamination of U.S. Pat. No. 6,990,366 dated Aug. 24, 2011.

U.S. Patent Reexamination Application No. 90/011,730, Request for Reexamination of U.S. Pat. No. 6,990,366 filed Jun. 3, 2011.

EP, 16176370.1 Extended Search Report, dated Dec. 7, 2016.

JP, 2016-44196 Office Action, dated Apr. 11, 2017.

AU, 2007309066 Examiner's Report, Jul. 12, 2012.

AU, 2007309066 Examiner's Report, Aug. 16, 2013.

AU, 2008265541 Examiner's Report, Oct. 15, 2012.

AU, 2008265541 Examiner's Report, Nov. 29, 2013.

AU, 2016201703 Examiner's Report, Mar. 22, 2017.

AU, 2017254903 Examiner's Report, Dec. 11, 2018.

AU, 2018200899 Examiner's Report, Dec. 6, 2018.

CA, 2,765,712 Examiner's Report, Apr. 10, 2017.

CA, 2,765,712 Examiner's Report, Mar. 27, 2018.

CN, 200780045373.9 Notice of Allowance, May 18, 2011.

CN, 200780045373.9 Office Action, Apr. 14, 2010.

CN, 20180027344.1 Office Action, Jun. 5, 2014.

CN, 20180027344.1 Office Action, Feb. 6, 2015.

CN, 201080006480.2 Office Action, May 6, 2013.

CN, 201080006480.2 Office Action, Dec. 11, 2013.

CN, 201080006481.7 Office Action, Dec. 2, 2014.

CN, 20160144860.1 Office Action, Mar. 23, 2018.

CN, 20160144860.1 Office Action, Dec. 10, 2018.

CN, 20160144860.1 Office Action, May 23, 2019.

EP, 068041227 Decision to Refuse the Application, Feb. 25, 2013.

EP, 06804122.7 Examination Report, Nov. 30, 2011.

EP, 06804122.7 Examination Report, Jan. 25, 2011.

EP, 06815715.5 Extended Search Report, Oct. 30, 2009.

EP, 07842173.2 Examination Report, Mar. 21, 2013.

EP, 07842173.2 Extended Search Report, Dec. 29, 2010.

EP, 07842180.7 Examination Report, Oct. 23, 2012.

EP, 07842180.7 Examination Report, Dec. 14, 2011.

EP, 07842180.7 Examination Report, Feb. 23, 2011.

EP, 07842180.7 Extended Search Report, Sep. 28, 2009.

EP, 10739015.5 Extended Search Report, May 10, 2013.

EP, 10739031.2 Extended Search Report, May 7, 2013.

EP, 10739031.2 Examination Report, Oct. 28, 2016.

EP, 10739031.2 Notice of Opposition, Dec. 20, 2018.

EP, 10739031.2 Reply to Notice of Opposition, May 21, 2019.

EP, 10739031.2 Reply to Notice of Opposition Reply, Aug. 8, 2019.

EP, 10739031.2 Summons to Attend Oral Proceedings, Sep. 17, 2019.

EP, 10739031.2 Written Submissions, Dec. 3, 2019.

EP, 10739031.2 Response to Written Submissions, Jan. 24, 2020.

EP, 10739031.2 Summons to Attend Oral Proceedings, May 20, 2020.

EP, 10739031.2 Written Submissions, Nov. 20, 2020.

EP, 10739031.2 Response to Written Submissions, Jan. 7, 2021.

EP, 10739031.2 Decision and Grounds for Revoking Patent, Jun. 9, 2021.

EP, 10739031.2 Grounds of Appeal, Oct. 19, 2021.

EP, 10739031.2 Response to Grounds of Appeal, Mar. 1, 2022.

EP, 10812438.9 Extended European Search Report, Dec. 10, 2013.

EP, 11760268.0 Communication from Board of Appeals, Mar. 31, 2022.

EP, 11760268.0 Response to Written Submissions, Jan. 14, 2020.

EP 11760268.0 Response to Notice of Appeal, Sep. 15, 2019.

EP 11760268.0 Statement of Grounds of Appeal, Apr. 23, 2019.

EP 11760268.0 Grounds of Appeal, Apr. 18, 2019.

EP 11760268.0 Notice of Appeal ADC, Feb. 25, 2019.

EP 11760268.0 Notice of Appeal Dexcom, Feb. 22, 2019.

EP 11760268.0 Interlocutory Decision, Dec. 13, 2018.

EP 11760268.0 Response to Summons to Attend Oral Proceedings, Sep. 13, 2018.

EP 11760268.0 Letter Regarding the Opposition Procedure, Sep. 12, 2018.

(56)         References Cited

OTHER PUBLICATIONS

EP 11760268.0 Summons to Attend Oral Proceedings, Mar. 22, 2018.
EP 11760268.0 Comments on Reply to Notice of Opposition, Dec. 27, 2017.
EP 11760268.0 Reply to Notice of Opposition, Sep. 4, 2017.
EP 11760268.0 Notice of Opposition, Mar. 29, 2017.
EP 13000105.0 Examination Report, Oct. 18, 2016.
EP 13000105.0 Minutes of the Oral Proceedings, Oct. 18, 2016.
EP 13000105.0 Opposition, Jan. 4, 2019.
EP 15184320.8 Examination Report, Apr. 18, 2017.
EP 16793637.6 Extended Search Report, Oct. 9, 2018.
EP 17182379.2 Extended Search Report, Feb. 21, 2018.
EP 17201183.5 Extended Search Report, May 7, 2018.
EP 17201183.5 Examination Report, May 7, 2019.
EP 18192278.2 Extended Search Report, Mar. 13, 2019.
EP 18208224.8 Extended Search Report, Oct. 11, 2019.
EP 18741791.0 Extended Search Report, Sep. 23, 2020.
EP 19151577.4 Extended Search Report, Aug. 16, 2019.
EP 19184881.1 Extended Search Report, Nov. 21, 2019.
EP 20177703.4 Extended Search Report, Sep. 25, 2020.
EP 20177712.5 Extended Search Report, Sep. 30, 2020.
EP 21152231.3 Extended Search Report, May 11, 2011.
EP 21192910.4 Extended Search Report, Mar. 31, 2022.
IL 198329 Office Action, Mar. 5, 2012.
JP 2009-534798 Office Action, Sep. 25, 2012.
JP 2012-526736 Office Action, Apr. 15, 2014.
JP 2012-526736 Office Action, Dec. 16, 2014.
JP 2013-501503 Office Action, Mar. 3, 2015.
JP 2015-159805 Office Action, Aug. 9, 2016.
MX MX/a/2009/004398 Office Action, Sep. 24, 2012.
NL 2009963 Search Report, Aug. 12, 2013.
US Petition For Inter Partes Review Of U.S. Pat. No. 10,945,649, IPR No. 2022-00605, Feb. 15, 2022.
US Petition For Inter Partes Review Of U.S. Pat. No. 11,013,440, IPR No. 2022-00637, Feb. 8, 2022.
US Reexamination U.S. Appl. No. 95/002,162 Request to Review Order Denying Request for Reexamination, Dec. 13, 2012.
US Reexamination U.S. Appl. No. 95/002,162 Order Denying Request for Reexamination, Nov. 13, 2012.
US Request for Reexamination U.S. Appl. No. 95/002,162 of U.S. Pat. No. 8,175,673, Sep. 7, 2012.
US Reexamination U.S. Appl. No. 95/002,113 Request to Review Order Denying Request for Reexamination, Dec. 13, 2012.
US Reexamination U.S. Appl. No. 95/002,113 Order Denying Request for Reexamination, Nov. 13, 2012.
US Request for Reexamination U.S. Appl. No. 95/002,113 of U.S. Pat. No. 6,990,366, Aug. 30, 2012.
US Reexamination U.S. Appl. No. 90/007,910 Patent Board Decision, May 17, 2013.
US Reexamination U.S. Appl. No. 90/007,910 Decision on Appeal, Jan. 18, 2011.
US Reexamination U.S. Appl. No. 90/007,910 Advisory Action, Jul. 30, 2009.
US Reexamination U.S. Appl. No. 90/007,910 Advisory Action, Feb. 6, 2009.
US Reexamination U.S. Appl. No. 90/007,910 Examiner's Answer to Appeal Brief, Nov. 19, 2009.
US Reexamination U.S. Appl. No. 90/007,910 Office Action, Oct. 2, 2008.
US Reexamination U.S. Appl. No. 90/007,910 Office Action, Feb. 13, 2008.
US Reexamination U.S. Appl. No. 90/007,910 Order Granting Request for Reexamination, Mar. 27, 2006.
US Request for Reexamination U.S. Appl. No. 90/007,910 of U.S. Pat. No. 6,175,752, Feb. 1, 2006.
US Reexamination U.S. Appl. No. 90/009,270 Order Denying Request for Reexamination, Dec. 1, 2008.
US Request for Reexamination U.S. Appl. No. 90/009,270 of U.S. Pat. No. 6,175,752, Sep. 8, 2008.

US Reexamination U.S. Appl. No. 90/009,497 Notice of Intent to Issue Reexamination Certificate, Aug. 23, 2010.
US Reexamination U.S. Appl. No. 90/009,497 Order Granting Request, Jul. 30, 2009.
US Request for Reexamination U.S. Appl. No. 90/009,497 of U.S. Pat. No. 6,175,752, Jun. 17, 2009.
WO PCT/US2006/037928 ISR and Written Opinion, Jul. 11, 2008.
WO PCT/US2007/078065 ISR and Written Opinion, Apr. 11, 2008.
WO PCT/US2007/078073 ISR and Written Opinion, Apr. 11, 2008.
WO PCT/US2007/082114 ISR and Written Opinion, May 9, 2008.
WO PCT/US2010/002401 ISR and Written Opinion, Nov. 12, 2010.
WO PCT/US2010/022928 ISR and Written Opinion, Mar. 21, 2010.
WO PCT/US2012/068839 ISR and Written Opinion, Feb. 22, 2013.
WO PCT/US2016/032485 ISR and Written Opinion, Sep. 12, 2016.
WO PCT/US2018/014745 ISR and Written Opinion, Jun. 4,2018.
WO PCT/US2019/035843 ISR and Written Opinion, Sep. 18, 2019.
WO PCT/US2021/040541 ISR and Written Opinion, Dec. 20, 2021.
WO PCT/US2021/045576 ISR and Written Opinion, Jan. 27, 2022.
WO PCT/US2021/048086 ISR and Written Opinion, Feb. 28, 2022.
WO PCT/US2021/0500672 ISR and Written Opinion, Jan. 5, 2022.
Abruna, H. D., et al., "Rectifying Interfaces Using Two-Layer Films of Electrochemically Polymerized Vinylpyridine and Vinylbipyridine Complexes of Ruthenium and Iron on Electrodes", Journal of the American Chemical Society, 1981, vol. 103, No. 1, pp. 1-5.
Ahson, S., et al., "RFID Handbook: Applications, Technology, Security, and Privacy", 2008, Chapter 4, Far-Field Tag Antenna Design Methodology, and Chapter 13, RFID Tags for Metallic Object Identification, pp. 71 and 253-254.
Albery, W.J., et al., "Amperometric Enzyme Electrodes Part II: Conducting Salts as Electrode Materials for the Oxidation of Glucose Oxidase", Journal of ElectroAnalytical Chemistry, 1985, vol. 194, pp. 223-235.
Albery, W.J., et al., "Amperometric Enzyme Electrodes", Philosophical Transactions of the Royal Society of London, 1987, vol. 316, pp. 107-119.
Ambade, V. N., et al., "Methods for Estimation of Blood Glucose: A Comparative Evaluation", Medical Journal Armed Forces India, 1998, vol. 54, No. 2, pp. 131-133.
Anderson, L. B., et al., "Thin-Layer Electrochemistry: Steady-State Methods of Studying Rate Processes", Journal of ElectroAnalytical Chemistry, 1965, vol. 10, pp. 295-305.
Application Note AN048, Antenna Part No. FR05-S1-N-0-102, Company Reach Xtend™, Bluetooth®, 802.11b/g WLAN Chip Antenna, 2008, pp. 1-13.
Application Note AVR2023 - AT86RF231 Pcb reference design for antenna diversity, Atmel Corporation, 2008, pp. 1-15.
Application Note nRF9E5 RF and antenna layout, Nordic Semiconductor, 2006, pp. 1-13.
ASTM International, Designation D2240-05, 2010, pp. 1-13.
Bartlett, P. N., et al., "Covalent Binding of Electron Relays to Glucose Oxidase", Journal of the Chemical Society, Chemical Communications, 1987, pp. 1603-1604.
Bartlett, P. N., et al., "Modification of Glucose Oxidase by Tetrathiafulvalene", Journal of the Chemical Society, Chemical Communications, 1990, pp. 1135-1136.
Benki, K., et al., "Using RSSI value for distance estimation in Wireless sensor networks based on ZigBee", 15th International Conference on Systems, Signals and Image Processing, Bratislava, Slovakia, 2008, pp. 1-4.
Biosensors: Fundamentals and Applications, Turner et al., Eds., 1987, pp. 1-786.
Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE, 2002, vol. 4624, pp. 1-10.
"Bluetooth Antenna Design", National Semiconductor Application Note, 2005, pp. 1-16.
Bluetooth Core Specification 4.0, Jun. 30, 2010, Master Table of Contents & Compliance Requirements, pp. 1-89.
Bonnett, A. H., et al., "Squirrel-Cage Rotor Options for AC Induction Motors", IEEE Transactions on Industry Applications, 2001, vol. 37, No. 4, pp. 1197-1209.

(56) References Cited

OTHER PUBLICATIONS

Brandt, J., et al., "Covalent Attachment of Proteins to Polysaccharide Carriers by Means of Benzoquinone", Biochimica et Biophysica Acta, 1975, vol. 386, pp. 196-202.

Brooks, S. L., et al., "Development of an On-Line Glucose Sensor for Fermentation Monitoring", Biosensors, 1987/88, vol. 3, pp. 45-56.

Brownlee, M., et al., "A Glucose-Controlled Insulin-Delivery System: Semisynthetic Insulin Bound to Lectin", Science, 1979, vol. 206, pp. 1190-1191.

Bühling, K. J., et al., "Optimal timing for postprandial glucose measurement in pregnant women with diabetes and a non-diabetic pregnant population evaluated by the Continuous Glucose Monitoring System (CGMS®)", Journal of Perinatal Medicine, 2005, vol. 33, No. 2, pp. 125-131.

Callaway, Jr., E. H., "Wireless Sensor Networks: Architectures and Protocols", 2004, Chapter 8, Antennas and the Definition of RF Performance, pp. 201-202.

Cass, A.E.G et al., "Ferricinium Ion as an Electron Acceptor for Oxido-Reductases", Journal of ElectroAnalytical Chemistry, 1985, vol. 190, pp. 117-127.

Castner, J. F., et al., "Mass Transport and Reaction Kinetic Parameters Determined Electrochemically for Immobilized Glucose Oxidase", Biochemistry, 1984, vol. 23, No. 10, pp. 2203-2210.

Cheyne, E.H., et al., "Performance of a Continuous Glucose Monitoring System During Controlled Hypoglycaemia in Healthy Volunteers", Diabetes Technology & Therapeutics, 2002, vol. 4, No. 5, pp. 607-613.

Clark Jr., L. C., et al., "Differential Anodic Enzyme Polarography for the Measurement of Glucose", Oxygen Transport to Tissue: Instrumentation, Methods, and Physiology, 1973, pp. 127-133.

Clarke, W. L., et al., "Evaluating Clinical Accuracy of Systems for Self-Monitoring of Blood Glucose", Diabetes Care, 1987, vol. 10, No. 5, pp. 622-628.

Clarke, W., et al., "Statistical Tools to Analyze Continuous Glucose Monitor Data", Diabetes Technology & Therapeutics, 2009, vol. 11, Suppl. 1, pp. S-45 - S-54.

Complaint *Abbott Diabetes Care Inc.* v. *Dexcom, Inc.* U.S. District Court Delaware C.A. No. 05-590 filed Aug. 11, 2005.

Complaint, Amended, *Abbott Diabetes Care Inc.* v. *Dexcom, Inc.* U.S. District Court Delaware C.A. No. 05-590 filed Jun. 27, 2006.

Complaint *Abbott Diabetes Care Inc.* v. *Dexcom, Inc.* U.S. District Court Delaware C.A. No. 06-514 filed Aug. 17, 2006.

Csoregi, E., et al., "On-Line Glucose Monitoring by Using Microdialysis Sampling and Amperometric Detection Based on 'Wired' Glucose Oxidase in Carbon Paste", Mikrochimica Acta, 1995, vol. 121, pp. 31-40.

Cullen, M.T., et al., "The Changing Presentations of Diabetic Ketoacidosis During Pregnancy", Amer. J. Perinatol, 1996, vol. 13, No. 7, pp. 449-451 (abstract only).

In Vivo Glucose Sensing, Cunningham et al., Eds., 2010, Chemical Analysis, vol. 174, pp. 1-466.

Davis, G., "Electromechanical Techniques for the Development of Amperometric Biosensors", Biosensors, 1985, vol. 1, pp. 161-178.

IPR2022-00605 (Ex. 1003) Declaration of Gary D. Fletcher, Ph.D dated Feb. 15, 2022, pp. 1-122.

IPR2022-00605 (Ex. 1003) Corrected Declaration of Gary D. Fletcher, Ph.D dated Feb. 18, 2022, pp. 1-124.

IPR2022-00637 (Ex. 1035) Second Declaration of Gary D. Fletcher, Ph.D dated Feb. 28, 2022, pp. 1-136.

Decuir, J., "Bluetooth 4.0: Low Energy", IEEE Scv Consultants' Network of Silicon Valley, 2012, pp. 1-68.

Degani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", The Journal of Physical Chemistry, 1987, vol. 91, No. 6, pp. 1285-1289.

Degani, Y., et al., "Direct Electrical Communication Between Chemically Modified Enzymes and Metal Electrodes. 2. Methods for Bonding Electron-Transfer Relays to Glucose Oxidase and D-Amino-Acid Oxidase", Journal of the American Chemical Society, 1988, vol. 110, No. 8, pp. 2615-2620.

Degani, Y., et al., "Electrical Communication Between Redox Centers of Glucose Oxidase and Electrodes via Electrostatically and Covalently Bound Redox Polymers", Journal of the American Chemical Society, 1989, vol. 111, pp. 2357-2358.

Dehez, B., et al., "Development of a Spherical Induction Motor With Two Degrees of Freedom", IEEE Transactions on Magnetics, 2006, vol. 42, No. 8, pp. 2077-2089.

Dementyev, A., et al., "Power Consumption Analysis of Bluetooth Low Energy, ZigBee and ANT Sensor Nodes in a Cyclic Sleep Scenario", IEEE International Wireless Symposium (IWS), 2013, Beijing, China, pp. 1-4.

Denisevich, P., et al., "Unidirectional Current Flow and Charge State Trapping at Redox Polymer Interfaces on Bilayer Electrodes: Principles, Experimental Demonstration, and Theory", Journal of the American Chemical Society, 1981, vol. 103, pp. 4727-4737.

DexCom™ STS™M Continuous Glucose Monitoring System User's Guide, 2006, pp. 1-57.

Dicks, J.M., et al., "Ferrocene Modified Polypyrrole with Immobilised Glucose Oxidase and its Application in Amperometric Glucose Microbiosensors", Annales de Biologie Clinique, 1989, vol. 47, pp. 607-619.

Diem, P., et al., "Clinical Performance of a Continuous Viscometric Affinity Sensor for Glucose", Diabetes Technology & Therapeutics, 2004, vol. 6, pp. 790-799.

ECMA International Standard ECMA-340, Near Field Communication Interface and Protocol (NFCIP-1), 2nd Edition, 2004, pp. 1-65.

El-Khatib, F. H, et al., "Adaptive Closed-Loop Control Provides Blood-Glucose Regulation Using Subcutaneous Insulin and Glucagon Infusion in Diabetic Swine", Journal of Diabetes Science and Technology, 2007, vol. 1, No. 2, pp. 181-192.

Ellis, C. D., et al., "Selectivity and Directed Charge Transfer through an Electroactive Metallopolymer Film", Journal of the American Chemical Society, 1981, vol. 103, No. 25, pp. 7480-7483.

Engstrom, R. C., "Electrochemical Pretreatment of Glassy Carbon Electrodes", Analytical Chemistry, 1982, vol. 54, No. 13, pp. 2310-2314.

Engstrom, R. C., et al., "Characterization of Electrochemically Pretreated Glassy Carbon Electrodes", Analytical Chemistry, 1984, vol. 56, No. 2, pp. 136-141.

Facchinetti, A., et al., "A New Index to Optimally Design and Compare Continuous Glucose Monitoring Glucose Prediction Algorithms", Diabetes Technology & Therapeutics, 2011, vol. 13, No. 2, pp. 111-119.

Feldman, B., et al., "Electron Transfer Kinetics at Redox Polymer/Solution Interfaces Using Microelectrodes and Twin Electrode Thin Layer Cells", Journal of ElectroAnalytical Chemistry, 1985, vol. 194, pp. 63-81.

Fischer, H., et al., "Intramolecular Electron Transfer Medicated by 4,4'-Bypyridine and Related Bridging Groups", Journal of the American Chemical Society, 1976, vol. 98, No. 18, pp. 5512-5517.

Foulds, N. C., et al., "Enzyme Entrapment in Electrically Conducting Polymers: Immobilisation of Glucose Oxidase in Polypyrrole and its Application in Amperometric Glucose Sensors", Journal of the Chemical Society, Faraday Transactions 1, 1986, vol. 82, pp. 1259-1264.

Foulds, N. C., et al., "Immobilization of Glucose Oxidase in Ferrocene-Modified Pyrrole Polymers", Analytical Chemistry, 1988, vol. 60, No. 22, pp. 2473-2478.

Freedman, D., et al., Statistics: Second Edition, 1991, Chapter 5, p. 74.

Frenzel, L. E., "Printed-Circuit-Board Antennas", retrieved from https://www.electronicdesign.com/technologies/boards/article/21751417/printedcircuitboard-antennasprint/3266, Electronic Design, 2005, pp. 1-4.

Frew, J. E., et al., "Electron-Transfer Biosensors", Philosophical Transactions of the Royal Society of London, 1987, vol. 316, pp. 95-106.

Fujipoly Silver ZEBRA® Connector Data Sheet FSDS 01-34, Version 5, 2006, pp. 1-7.

(56) References Cited

OTHER PUBLICATIONS

Garg, S., et al., "Improvement in Glycemic Excursions with a Transcutaneous, Real-Time Continuous Glucose Sensor", Diabetes Care, 2006, vol. 29, No. 1, pp. 44-50.

Gilligan, B. J., et al., "Evaluation of a Subcutaneous Glucose Sensor out to 3 Months in a Dog Model", Diabetes Care, 1994, vol. 17, No. 8, pp. 882-887.

Gonzalez, O. L., et al., "Low-Cost Wireless Sensors—Designer Reference Manual", Freescale Semiconductor, 2007, pp. 1-146.

Gorton, L., et al., "Selective Detection in Flow Analysis Based on the Combination of Immobilized Enzymes and Chemically Modified Electrodes", Analytica Chimica Acta, 1991, vol. 250, pp. 203-248.

Gregg, B. A., et al., "Redox Polymer Films Containing Enzymes. 1. A Redox-Conducting Epoxy Cement: Synthesis, Characterization, and Electrocatalytic Oxidation of Hydroquinone", Journal of Physical Chemistry, 1991, vol. 95, No. 15, pp. 5970-5975.

Guerra, S., et al., "A Dynamic Risk Measure from Continuous Glucose Monitoring Data", Diabetes Technology & Therapeutics, 2011, vol. 13, No. 8, pp. 843-852.

Güler, N. F., et al., "Theory and Applications of Biotelemetry", Journal of Medical Systems, 2002, vol. 26, No. 2, pp. 159-178.

Gunasingham, et al., "Electrochemically Modulated Optrode for Glucose", Biosensors & Bioelectronics, 1992, vol. 7, pp. 353-359.

Hale, P. D., et al., "A New Class of Amperometric Biosensor Incorporating a Polymeric Electron-Transfer Mediator", Journal of the American Chemical Society, 1989, vol. 111, No. 9, pp. 3482-3484.

Hao, Y., "Wireless body sensor networks for health-monitoring applications", Physiol. Meas., 2008, vol. 29, R27-R56.

Hawkridge, F. M., et al., "Indirect Coulometric Titration of Biological Electron Transport Components", Analytical Chemistry, 1973, vol. 45, No. 7, pp. 1021-1027.

Heftman, G., "Chip Antenna Reduces Cell-Phone Dimensions", Microwaves & RF, 1999, p. 182.

Heise, T., et al., "Hypoglycemia Warning Signal and Glucose Sensors: Requirements and Concepts", Diabetes Technology & Therapeutics, 2003, vol. 5, No. 4, pp. 563-571.

Heller, A., et al., "Amperometric Biosensors Based on Three-Dimensional Hydrogel- Forming Epoxy Networks", Sensors and Actuators B, 1993, vol. 13-14, pp. 180-183.

Heller, A., "Implanted Electrochemical Glucose Sensors for the Management of Diabetes", Annnu. Rev. Biomed. Eng., 1999, vol. 1, pp. 153-175.

Hoel, P. G., Elementary Statistics: Fourth Edition, 1976, Chapter 5, pp. 113-114.

Huang, Y., et al., "Antennas from Theory to Practice", 2008, Chapter 8, Antenna Diversity, pp. 322-325.

Ianniello, R. M., et al., "Immobilized Enzyme Chemically Modified Electrode as an Amperometric Sensor", Analytical Chemistry, 1981, vol. 53, No. 13, pp. 2090-2095.

Ianniello, R. M., et al., "Differential Pulse Voltammetric Study of Direct Electron Transfer in Glucose Oxidase Chemically Modified Graphite Electrodes", Analytical Chemistry, 1982, vol. 54, No. 7, pp. 1098-1101.

Ikeda, T., et al., "Kinetics of Outer-Sphere Electron Transfers Between Metal Complexes in Solutions and Polymeric Films on Modified Electrodes", Journal of the American Chemical Society, 1981, vol. 103, No. 25, pp. 7422-7425.

Ikeda, T., et al., "Glucose Oxidase- Immobilized Benzoquinone-Carbon Paste Electrode as a Glucose Sensor", Agricultural and Biological Chemistry, 1985, vol. 49, No. 2, pp. 541-543.

Ikeda, T., et al., "Artificial Pancreas—Investigation of the Stability of Glucose Sensors Using a Telemetry System" (English language translation of abstract), Jpn. J. Artif. Organs, 1990, vol. 19, No. 2, pp. 889-892.

"In Vitro Diagnostic Products for Human Use", Federal Register, 1974, vol. 39, No. 126, pp. 24136-24147.

Jain, A.K., et al., "Wound Rotor Induction Generator With Sensorless Control and Integrated Active Filter for Feeding Nonlinear Loads in a Stand-Alone Grid", IEEE Transactions on Industrial Electronics, 2008, vol. 55, No. 1, pp. 218-228.

James, Jr., et al., "Handbook of Microstrip Antennas", 1969, pp. 1038-1047.

Johnson, J. M., et al., "Potential-Dependent Enzymatic Activity in an Enzyme Thin-Layer Cell", Analytical Chemistry, 1982, vol. 54, No. 8, pp. 1377-1383.

Johnson, K. W., "Reproducible Electrodeposition of Biomolecules for the Fabrication of Miniature Electroenzymatic Biosensors", Sensors and Actuators B, 1991, vol. 5, pp. 85-89.

Jonsson, G., et al., "An Amperometric Glucose Sensor Made by Modification of a Graphite Electrode Surface With Immobilized Glucose Oxidase and Adsorbed Mediator", Biosensors, 1985, vol. 1, pp. 355-368.

Josowicz, M., et al., "Electrochemical Pretreatment of Thin Film Platinum Electrodes", Journal of the Electrochemical Society, 1988, vol. 135, No. 1, pp. 112-115.

Jovanovic, L., "The Role of Continuous Glucose Monitoring in Gestational Diabetes Mellitus", Diabetes Technology & Therapeutics, 2000, vol. 2, Supplement 1, pp. S-67-S-71.

Kaplan, S. M., "Wiley Electrical and Electronics Engineering Dictionary", IEEE Press, 2004, pp. 141, 142, 548, 549.

Katakis, I., et al., "L-ß-Glycerophosphate and $_L$-Lactate Electrodes Based on the Electrochemical 'Wiring' of Oxidases", Analytical Chemistry, 1992, vol. 64, No. 9, pp. 1008-1013.

Katakis, I., et al., "Electrostatic Control of the Electron Transfer Enabling Binding of Recombinant Glucose Oxidase and Redox Polyelectrolytes", Journal of the American Chemical Society, 1994, vol. 116, No. 8, pp. 3617-3618.

Kenausis, G., et al., "Wiring' of Glucose Oxidase and Lactate Oxidase Within a Hydrogel Made with Poly(vinyl pyridine) complexed with [Os(4,4'-dimethoxy-2,2'-bipyridine) 2Cl] +/2+", Journal of the Chemical Society, Faraday Transactions, 1996, vol. 92, No. 20, pp. 4131-4136.

Klonoff, D. C., "A Review of Continuous Glucose Monitoring Technology", Diabetes Technology & Therapeutics, 2005, vol. 7, No. 5, pp. 770-775.

Kondepati, V., et al., "Recent Progress in Analytical Instrumentation for Glycemic Control in Diabetic and Critically Ill Patients", Analytical Bioanalytical Chemistry, 2007, vol. 388, pp. 545-563.

Kulys, J., et al., "Mediatorless Peroxidase Electrode and Preparation of Bienzyme Sensors", Bioelectrochemistry and Bioenergetics, 1990, vol. 24, pp. 305-311.

Leon, L. P., et al., "Continuous-Flow Analysis for Glucose in Serum, with Use of Hexokinase and Glucose-6-Phosphate Dehydrogenase Co-Immobilized in Tubular Form", Clinical Chemistry, 1980, vol. 26, No. 1, pp. 123-129.

Lindner, E., et al., "Flexible (Kapton-Based) Microsensor Arrays of High Stability for Cardiovascular Applications", Journal of the Chemical Society, Faraday Transactions, 1993, vol. 89, No. 2, pp. 361-367.

Lo, B., et al., "Key Technical Challenges and Current Implementations of Body Sensor Networks", Body Sensor Networks, 2005, pp. 1-5.

Lodwig, V., et al., "Continuous Glucose Monitoring with Glucose Sensors: Calibration and Assessment Criteria", Diabetes Technology & Therapeutics, 2003, vol. 5, No. 4, pp. 573-587.

Lortz, J., et al., "What is Bluetooth? We Explain The Newest Short-Range Connectivity Technology", Smart Computing Learning Series, Wireless Computing, 2002, vol. 8, Issue 5, pp. 72-74.

Loy, M., et al., "ISM—Band and Short Range Device Antennas", Texas Instruments Application Report, 2005, pp. 1-38.

Malin, S. F., et al., "Noninvasive Prediction of Glucose by Near-Infrared Diffuse Reflectance Spectoscopy", Clinical Chemistry, 1999, vol. 45, No. 9, pp. 1651-1658.

McGarraugh, G., et al., "Glucose Measurements Using Blood Extracted from the Forearm and the Finger", TheraSense, Inc., 2001, 16 Pages.

McGarraugh, G., et al., "Physiological Influences on Off-Finger Glucose Testing", Diabetes Technology & Therapeutics, 2001, vol. 3, No. 3, pp. 367-376.

(56) References Cited

OTHER PUBLICATIONS

McNeil, C. J., et al., "Thermostable Reduced Nicotinamide Adenine Dinucleotide Oxidase: Application to Amperometric Enzyme Assay", Analytical Chemistry, 1989, vol. 61, No. 1, pp. 25-29.

IPR2022-00605 (Ex. 1027) The Merriam-Webster Dictionary, Merriam Webster, Incorporated (2005), pp. 66, 403, and 415.

Microchip Technology Inc., MRF24J40MA Data Sheet, 2008, pp. 1-30.

Minimed Technologies, "Tape Tips and Other Infusion Site Information", 1995.

Miyawaki, O., et al., "Electrochemical and Glucose Oxidase Coenzyme Activity of Flavin Adenine Dinucleotide Covalently Attached to Glassy Carbon at the Adenine Amino Group", Biochimica et Biophysica Acta, 1985, vol. 838, pp. 60-68.

Moore, B., "The Potential Use of Radio Frequency Identification Devices for Active Monitoring of Blood Glucose Levels", Journal of Diabetes Science and Technology, 2009, vol. 3, No. 1, pp. 180-183.

Morak, J., et al., "Design and Evaluation of a Telemonitoring Concept Based on NFC- Enabled Mobile Phones and Sensor Devices", IEEE Transactions on Information Technology in Biomedicine, 2012, vol. 16, No. 1, pp. 17-23.

Morbiducci, U., et al., "Improved Usability of the Minimal Model of Insulin Sensitivity Based on an Automated Approach and Genetic algorithms for Parameter Estimation", Clinical Science, vol. 112, 2007, pp. 257-263.

Mougiakakou, S. G., et al., "A Real Time Simulation Model of Glucose-Insulin Metabolism For Type 1 Diabetes Patients", Proceedings of the 2005 IEEE, 2005, pp. 298-301.

Movassaghi, S., et al., "Wireless Technologies for Body Area Networks: Characteristics and Challenges", 2012 International Symposium on Communications and Information Technologies (ISCIT), 2012, Gold Coast, QLD, Australia, pp. 42-47.

"Murata Puts Antenna on a Chip", Passives, 1999, vol. 44, 1 page.

Nagy, G., et al., "A New Type of Enzyme Electrode: The Ascorbic Acid Eliminator Electrode", Life Sciences, 1982, vol. 31, No. 23, pp. 2611-2616.

Nakamura, S., et al., "Effect of Periodate Oxidation on the Structure and Properties of Glucose Oxidase", Biochimica et Biophysica Acta., 1976, vol. 445, pp. 294-308.

Narasimham, K., et al., "ρ-Benzoquinone Activation of Metal Oxide Electrodes for Attachment of Enzymes", Enzyme and Microbial Technology, 1985, vol. 7, pp. 283-286.

Ohara, T. J., et al., "Wired' Enzyme Electrodes for Amperometric Determination of Glucose or Lactate in the Presence of Interfering Substances", Analytical Chemistry, 1994, vol. 66, No. 15, pp. 2451-2457.

Ohara, T. J., "Osmium Bipyridyl Redox Polymers Used in Enzyme Electrodes", Platinum Metals Review, 1995, vol. 39, No. 2, pp. 54-62.

Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", Journal of ElectroAnalytical Chemistry, 1989, vol. 260, pp. 487-494.

Palleschi, G., et al., "A Study of Interferences in Glucose Measurements in Blood by Hydrogen Peroxide Based Glucose Probes", Analytical Biochemistry, 1986, vol. 159, pp. 114-121.

Pankratov, I., et al., "Sol-Gel Derived Renewable-Surface Biosensors", Journal of ElectroAnalytical Chemistry, 1995, vol. 393, pp. 35-41.

Parker, R., et al., "Robust Ho Glucose Control in Diabetes Using a Physiological Model", AIChE Journal, 2000, vol. 46, No. 12, 2000, pp. 2537-2549.

Passey, R. B., et al., "Evaluation and Comparison of 10 Glucose Methods and the Reference Method Recommendation in the Proposed Product Class Standard (1974)", Clinical Chemistry, 1977, vol. 23, No. 1, pp. 131-139.

Pathak, C., et al., "Rapid Photopolymerization of Immunoprotective Gels in Contact with Cells and Tissue", Journal of the American Chemical Society, 1992, vol. 114, No. 21, pp. 8311-8312.

Pollak, A., et al., "Enzyme Immobilization by Condensation Copolymerization into Cross- Linked Polyacrylamide Gels", Journal of the American Chemical Society, 1980, vol. 102, No.

Ratner, B. D., "Reducing Capsular Thickness and Enhancing Angeiogenesis Around Implant Drug Release Systems", Journal of Controlled Release, 2002, vol. 78, pp. 211-218.

Rodriguez, N., et al., "Flexible Communication and Control Protocol for Injectable Neuromuscular Interfaces", IEEE Transactions on Biomedical Circuits and Systems, 2007, vol. 1, No. 1, pp. 19-27.

IPR2022-00605 (Ex. 1024) "Rotor," Dictionary of Mechanical Engineering, Fourth Ed., G.H.F. Nayler, Society of Automotive Engineers, Inc., 1996, p. 328.

IPR2022-00605 (Ex. 1025) "Rotor," Random House Kernerman Webster's College Dictionary, K Dictionaries Ltd. (2010), available at https://www.thefreedictionary.com/rotor.

IPR2022-00605 (Ex. 1026) "Rotate," Random House Kernerman Webster's College Dictionary, K Dictionaries Ltd. (2010), available at https://www.thefreedictionary.com/rotate.

Salditt, P., "Trends in Medical Device Design and Manufacturing", SMTA News and Journal of Surface Mount Technology, 2004, vol. 17, pp. 19-24.

Samuels, G. J., et al., "An Electrode-Supported Oxidation Catalyst Based on Ruthenium (IV). pH "Encapsulation" in a Polymer Film", Journal of the American Chemical Society, 1981, vol. 103, No. 2, pp. 307-312.

Sandham, W., et al., "Blood Glucose Prediction for Diabetes Therapy Using a Recurrent Artificial Neural Network", 9th European Signal Processing Conference, 1998, Rhodes, Greece, pp. 1-4.

Sasso, S. V., et al., "Electropolymerized 1,2-Diaminobenzene as a Means to Prevent Interferences and Fouling and to Stabilize Immobilized Enzyme in Electrochemical Biosensors", Analytical Chemistry, 1990, vol. 62, No. 11, pp. 1111-1117.

IPR2022-00605 (Ex. 1013) Scheduling Order in *Abbott Diabetes Care Inc., et al.* v. *Dexcom, Inc.*, 1:21-cv-00977 (D. Del.), dated Dec. 2, 2021.

Schmehl, R. H., et al., "The Effect of Redox Site Concentration on the Rate of Mediated Oxidation of Solution Substrates by a Redox Copolymer Film", Journal of ElectroAnalytical Chemistry, 1983, vol. 152, pp. 97-109.

Schoepke, E., "Chip Antenna Layout Considerations for 802.11 Applications", Johanson Technology, 2006, retrieved from https://www.johansontechnology.com/chip-antenna-layout-considerations-for-802-11-applications, pp. 1-7.

Sharawi, M. S., "Use of low-cost patch antennas in modern wireless technology", IEEE Potentials, 2006, pp. 35-38 and 47.

Sittampalam, G., et al., "Surface-Modified Electrochemical Detector for Liquid Chromatography", Analytical Chemistry, 1983, vol. 55, No. 9, pp. 1608-1610.

Soegijoko, S., et al., "External Artificial Pancreas: A New Control Unit Using Microprocessor", Hormone and Metabolic Research Supplement Series, 1982, vol. 12, pp. 165-169.

Sparacino, G., et al., "Glucose Concentration Can Be Predicted Ahead in Time from Continuous Glucose Monitoring Sensor Time-Series", IEEE Transactions on Biomedical Engineering, 2007, vol. 54, No. 5, pp. 931-937.

Sprules, S. D., et al., "Evaluation of a New Disposable Screen-Printed Sensor Strip for the Measurement of NADH and Its Modification to Produce a Lactate Biosensor Employing Microliter Volumes", Electroanalysis, 1996, vol. 8, No. 6, pp. 539-543.

Sternberg, F., et al., "Calibration Problems of Subcutaneous Glucosensors when Applied "In-Situ" in Man", Hormone and Metabolic Research, 1994, vol. 26, pp. 523-526.

Sternberg, R., et al., "Covalent Enzyme Coupling on Cellulose Acetate Membranes for Glucose Sensor Development", Analytical Chemistry, 1988, vol. 60, No. 24, pp. 2781-2786.

Suekane, M., et al., "Immobilization of Glucose Isomerase", Zettschrift fur Allgemeine Mikrobiologie, 1982, vol. 22, No. 8, pp. 565-576.

Tajima, S., et al., "Simultaneous Determination of Glucose and 1,5-Anydroglucitol", Chemical Abstracts, 1989, vol. 111, No. 25, p. 394.

(56) References Cited

OTHER PUBLICATIONS

Tarasevich, M. R., "Bioelectrocatalysis", Comprehensive Treatise of Electrochemistry, 1985, vol. 10, pp. 231-295.

Tatsuma, T., et al., "Enzyme Monolayer- and Bilayer-Modified Tin Oxide Electrodes for the Determination of Hydrogen Peroxide and Glucose", Analytical Chemistry, 1989, vol. 61, No. 21, pp. 2352-2355.

Taylor, C., et al., ""Wiring" of Glucose Oxidase Within a Hydrogel Made with Polyvinyl Imidazole Complexed with [(Os-4,4'-dimethoxy-2,2'-bipyridine)Cl]$^{+/2+}$", Journal of ElectroAnalytical Chemistry, 1995, vol. 396, pp. 511-515.

Townsend, K., et al., "Getting Started with Bluetooth Low Energy—Chapter 1", 2014, pp. 1-26.

Trojanowicz, M., et al., "Enzyme Entrapped Polypyrrole Modified Electrode for Flow-Injection Determination of Glucose", Biosensors & Bioelectronics, 1990, vol. 5, pp. 149-156.

Tung, S., "Layers of Security for Active RFID Tags", RFID Handbook: Applications, Technology, Security, and Privacy, Edited by Ehson, et al., Chapter 33, 2008, pp. 1-28.

Turner, R.F.B., et al., "A Biocompatible Enzyme Electrode for Continuous in vivo Glucose Monitoring in Whole Blood", Sensors and Actuators B, 1990, vol. 1, pp. 561-564.

Tuzhi, P., et al., "Constant Potential Pretreatment of Carbon Fiber Electrodes for in Vivo Electrochemistry", Analytical Letters, 1991, vol. 24, No. 6, pp. 935-945.

Umana, M., "Protein-Modified Electrochemically Active Biomaterial Surface", U.S. Army Research Office, Analytical and Chemical Sciences Research Triangle Institute, 1988, pp. 1-9.

United States Court of Appeals for the Federal Circuit, No. 06-1402, *Leapfrog Enterprises, Inc.* v. *Fisher-Price, Inc. and Mattel, Inc.*, May 9, 2007.

Updike, S. J., et al., "A Subcutaneous Glucose Sensor With Improved Longevity, Dynamic Range, and Stability of Calibration", Diabetes Care, 2000, vol. 23, pp. 208-214.

Urban, G., et al., "Miniaturized Thin-Film Biosensors Using Covalently Immobilized Glucose Oxidase", Biosensors & Bioelectronics, 1991, vol. 6, pp. 555-562.

Vreeke, M. S., et al., "Hydrogen Peroxide Electrodes Based on Electrical Connection of Redox Centers of Various Peroxidases to Electrodes through a Three-Dimensional Electron- Relaying Polymer Network", Diagnostic Biosensors Polymers, Chapter 15, 1993, pp. 180-193.

Vreeke, M., et al., "Hydrogen Peroxide and B-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", Analytical Chemistry, 1992, vol. 64, No. 24, pp. 3084-3090.

Wang, D. L., et al., "Miniaturized Flexible Amperometric Lactate Probe", Analytical Chemistry, 1993, vol. 65, No. 8, pp. 1069-1073.

Wang, J., et al., "Activation of Glassy Carbon Electrodes by Alternating Current Electrochemical Treatment", Analytica Chimica Acta, 1985, vol. 167, pp. 325-334.

Wang, J., et al., "Amperometric Biosensing of Organic Peroxides with Peroxidase-Modified Electrodes", Analytica Chimica Acta, 1991, vol. 254, pp. 81-88.

Wang, J., et al., "Screen-Printable Sol-Gel Enzyme-Containing Carbon Inks", Analytical Chemistry, 1996, vol. 68, No. 15, pp. 2705-2708.

Wang, J., et al., "Sol-Gel-Derived Metal-Dispersed Carbon Composite Amperometric Biosensors", Electroanalysis, 1997, vol. 9, No. 1, pp. 52-55.

Wang, X.H., et al., "Bluetooth: Opening a blue sky for healthcare", Mobile Information Systems, 2006, vol. 2, pp. 151-167.

Waterhouse, R., "Printed Antennas for Wireless Communications," 2007, pp. 116-129 and 284-289.

Williams, D. L., et al., "Electrochemical-Enzymatic Analysis of Blood Glucose and Lactate", Analytical Chemistry, 1970, vol. 42, No. 1, pp. 118-121.

Wong, KL, "Planar Antennas for Wireless Communications," 2003, Chapter 1, Introduction and Overview, pp. 4-17, 38-45, and 218-221.

Yabuki, S., et al., "Electro-Conductive Enzyme Membrane", Journal of the Chemical Society, Chemical Communications, 1989, pp. 945-946.

Yang, L., et al., "Determination of Oxidase Enzyme Substrates Using Cross-Flow Thin-Layer Amperometry", Electroanalysis, 1996, vol. 8, No. 8-9, pp. 716-721.

Yao, S. J., et al., "The Interference of Ascorbate and Urea in Low-Potential Electrochemical Glucose Sensing", Proceedings of the Twelfth Annual International Conference of the IEEE Engineering in Medicine and Biology Society, 1990, vol. 12, Part 2, pp. 487-489.

Yao, T., "A Chemically-Modified Enzyme Membrane Electrode as an Amperometric Glucose Sensor", Analytica Chimica Acta, 1983, vol. 148, pp. 27-33.

Yildiz, A., et al., "Evaluation of an Improved Thin-Layer Electrode", Analytical Chemistry, 1968, vol. 40, No. 7, pp. 1018-1024.

Zamzow, K., et al., "New Wearable Continuous Blood Glucose Monitor (BGM) and Artificial Pancreas (AP)", Diabetes, 1990, vol. 39, pp. 5A-20.

Z-Carbon Connector, retrieved from http://www.zaxisconnector.com/SS_zc.shtml, 2004, 2 pages.

Zhang, Y., et al., "Application of Cell Culture Toxicity Tests to the Development of Implantable Biosensors", Biosensors & Bioelectronics, 1991, vol. 6, pp. 653-661.

Zhang, Y., et al., "Elimination of the Acetaminophen Interference in an Implantable Glucose Sensor", Analytical Chemistry, 1994, vol. 66, No. 7, pp. 1183-1188.

Zhu, J., et al., "Fabrication and Characterization of Glucose Sensors Based on a Microarray $H_2O_2$ electrode", Biosensors & Bioelectronics, 1994, vol. 9, pp. 295-300.

Z-Silver Connector, retrieved from http://www.zaxisconnector.com/SS_zs.shtml, 2004, 2 pages.

EP 10739031.2 Response to Response to Grounds of Appeal, Jul. 29, 2022.

EP 11760268.0 Minutes of Oral Proceedings, Aug. 11, 2022.

EP 19151577.4 Examination Report, May 27, 2022.

GB Claim No. HP-2021-000025 Amended Reply and Defence to Counterclaim, Apr. 19, 2022.

GB Claim No. HP-2021-000025 Amended Defence and Counterclaim, Mar. 28, 2022.

GB Claim No. HP-2021-000025 Amended Grounds of Invalidity, Mar. 28, 2022.

US Institution Decision, IPR No. 2022-00605, Jul. 27, 2022.

US Patent Owner's Preliminary Sur-Reply, IPR No. 2022-00605, Jun. 28, 2022.

US Petitioner's Preliminary Reply to Patent Owner's Preliminary Response, IPR No. 2022-00605, Jun. 21, 2022.

US Patent Owner's Preliminary Response, IPR No. 2022-00605, May 24, 2022.

US Institution Decision, IPR No. 2022-00637, Jul. 27, 2022.

US Patent Owner's Preliminary Sur-Reply, IPR No. 2022-00637, Jun. 28, 2022.

US Petitioner's Preliminary Reply to Patent Owner's Preliminary Response, IPR No. 2022-00637, Jun. 21, 2022.

US Patent Owner's Preliminary Response, IPR No. 2022-00637, Jun. 9, 2022.

US Exhibit 216-1 from DexCom, Inc.'s Preliminary Invalidity Contentions, Case No. 21-CV-977-KAJ (D. Delaware), May 6, 2022.

US Exhibit 216-2 from DexCom, Inc.'s Preliminary Invalidity Contentions, Case No. 21-CV-977-KAJ, (D. Delaware), May 6, 2022.

US Exhibit 216-3 from DexCom, Inc.'s Preliminary Invalidity Contentions, Case No. 21-CV-977-KAJ (D. Delaware), May 6, 2022.

US Exhibit 216-4 from DexCom, Inc.'s Preliminary Invalidity Contentions, Case No. 21-CV-977-KAJ (D. Delaware), May 6, 2022.

(56) References Cited

OTHER PUBLICATIONS

US Exhibit 216-5 from DexCom, Inc.'s Preliminary Invalidity Contentions, Case No. 21-CV-977-KAJ (D. Delaware), May 6, 2022.

US Exhibit 216-6 from DexCom, Inc.'s Preliminary Invalidity Contentions, Case No. 21-CV-977-KAJ (D. Delaware), May 6, 2022.

US Exhibit 216-7 from DexCom, Inc.'s Preliminary Invalidity Contentions, Case No. 21-CV-977-KAJ (D. Delaware), May 6, 2022.

US Exhibit 216-8 from DexCom, Inc.'s Preliminary Invalidity Contentions, Case No. 21-CV-977-KAJ (D. Delaware), May 6, 2022.

US Exhibit 216-9 from DexCom, Inc.'s Preliminary Invalidity Contentions, Case No. 21-CV-977-KAJ (D. Delaware), May 6, 2022.

US Exhibit 216-10 from DexCom, Inc.'s Preliminary Invalidity Contentions, Case No. 21-CV-977-KAJ (D. Delaware), May 6, 2022.

US Exhibit 216-11 from DexCom, Inc.'s Preliminary Invalidity Contentions, Case No. 21-CV-977-KAJ (D. Delaware), May 6, 2022.

US Exhibit 216-12 from DexCom, Inc.'s Preliminary Invalidity Contentions, Case No. 21-CV-977-KAJ (D. Delaware), May 6, 2022.

US Exhibit 216-13 from DexCom, Inc.'s Preliminary Invalidity Contentions, Case No. 21-CV-977-KAJ (D. Delaware), May 6, 2022.

US Exhibit 440-1 from DexCom, Inc.'s Preliminary Invalidity Contentions, Case No. 21-CV-977-KAJ, (D. Delaware), May 6, 2022.

US Exhibit 440-2 from DexCom, Inc.'s Preliminary Invalidity Contentions, Case No. 21-CV-977-KAJ (D. Delaware), May 6, 2022.

US Exhibit 440-3 from DexCom, Inc.'s Preliminary Invalidity Contentions, Case No. 21-CV-977-KAJ (D. Delaware), May 6, 2022.

US Exhibit 440-4 from DexCom, Inc.'s Preliminary Invalidity Contentions, Case No. 21-CV-977-KAJ (D. Delaware), May 6, 2022.

US Exhibit 440-5 from DexCom, Inc.'s Preliminary Invalidity Contentions, Case No. 21-CV-977-KAJ (D. Delaware), May 6, 2022.

US Exhibit 440-6 from DexCom, Inc.'s Preliminary Invalidity Contentions, Case No. 21-CV-977-KAJ (D. Delaware), May 6, 2022.

US Exhibit 440-7 from DexCom, Inc.'s Preliminary Invalidity Contentions, Case No. 21-CV-977-KAJ (D. Delaware), May 6, 2022.

US Exhibit 440-8 from DexCom, Inc.'s Preliminary Invalidity Contentions, Case No. 21-CV-977-KAJ (D. Delaware), May 6, 2022.

US Exhibit 440-9 from DexCom, Inc.'s Preliminary Invalidity Contentions, Case No. 21-CV-977-KAJ (D. Delaware), May 6, 2022.

US Exhibit 440-10 from DexCom, Inc.'s Preliminary Invalidity Contentions, Case No. 21-CV-977-KAJ (D. Delaware), May 6, 2022.

US Exhibit 440-11 from DexCom, Inc.'s Preliminary Invalidity Contentions, Case No. 21-CV-977-KAJ (D. Delaware), May 6, 2022.

US Exhibit 440-12 from DexCom, Inc.'s Preliminary Invalidity Contentions, Case No. 21-CV-977-KAJ (D. Delaware), May 6, 2022.

US Exhibit 440-13 from DexCom, Inc.'s Preliminary Invalidity Contentions, Case No. 21-CV-977-KAJ (D.Delaware), May 6, 2022.

US Exhibit 649-1 from DexCom, Inc.'s Preliminary Invalidity Contentions, Case No. 21-CV-977-KAJ (D. Delaware), May 6, 2022.

US Exhibit 649-2 from DexCom, Inc.'s Preliminary Invalidity Contentions, Case No. 21-CV-977-KAJ (D. Delaware), May 6, 2022.

US Exhibit 649-3 from DexCom, Inc.'s Preliminary Invalidity Contentions, Case No. 21-CV-977-KAJ (D. Delaware), May 6, 2022.

US Exhibit 649-4 from DexCom, Inc.'s Preliminary Invalidity Contentions, Case No. 21-CV-977-KAJ (D. Delaware), May 6, 2022.

US Exhibit 649-5 from DexCom, Inc.'s Preliminary Invalidity Contentions, Case No. 21-CV-977-KAJ (D. Delaware), May 6, 2022.

US Exhibit 649-6 from DexCom, Inc.'s Preliminary Invalidity Contentions, Case No. 21-CV-977-KAJ (D. Delaware), May 6, 2022.

US Exhibit 649-7 from DexCom, Inc.'s Preliminary Invalidity Contentions, Case No. 21-CV-977-KAJ (D. Delaware), May 6, 2022.

US Exhibit 649-8 from DexCom, Inc.'s Preliminary Invalidity Contentions, Case No. 21-CV-977-KAJ (D. Delaware), May 6, 2022.

US Exhibit 649-9 from DexCom, Inc.'s Preliminary Invalidity Contentions, Case No. 21-CV-977-KAJ (D. Delaware), May 6, 2022.

US Exhibit 649-10 from DexCom, Inc.'s Preliminary Invalidity Contentions, Case No. 21-CV-977-KAJ (D. Delaware), May 6, 2022.

US Exhibit 649-11 from DexCom, Inc.'s Preliminary Invalidity Contentions, Case No. 21-CV-977-KAJ (D. Delaware), May 6, 2022.

US Exhibit 649-12 from DexCom, Inc.'s Preliminary Invalidity Contentions, Case No. 21-CV-977-KAJ (D. Delaware), May 6, 2022.

US Exhibit 649-13 from DexCom, Inc.'s Preliminary Invalidity Contentions, Case No. 21-CV-977-KAJ (D. Delaware), May 6, 2022.

US Exhibit 654-1 from DexCom, Inc.'s Preliminary Invalidity Contentions, Case No. 21-CV-977-KAJ (D. Delaware), May 6, 2022.

US Exhibit 654-2 from DexCom, Inc.'s Preliminary Invalidity Contentions, Case No. 21-CV-977-KAJ (D. Delaware), May 6, 2022.

US Exhibit 654-3 from DexCom, Inc.'s Preliminary Invalidity Contentions, Case No. 21-CV-977-KAJ (D. Delaware), May 6, 2022.

US Exhibit 654-4 from DexCom, Inc.'s Preliminary Invalidity Contentions, Case No. 21-CV-977-KAJ (D. Delaware), May 6, 2022.

US Exhibit 654-5 from DexCom, Inc.'s Preliminary Invalidity Contentions, Case No. 21-CV-977-KAJ (D. Delaware), May 6, 2022.

US Exhibit 654-6 from DexCom, Inc.'s Preliminary Invalidity Contentions, Case No. 21-CV-977-KAJ (D. Delaware), May 6, 2022.

US Exhibit 654-7 from DexCom, Inc.'s Preliminary Invalidity Contentions, Case No. 21-CV-977-KAJ (D. Delaware), May 6, 2022.

US Exhibit 654-8 from DexCom, Inc.'s Preliminary Invalidity Contentions, Case No. 21-CV-977-KAJ (D. Delaware), May 6, 2022.

US Exhibit 654-9 from DexCom, Inc.'s Preliminary Invalidity Contentions, Case No. 21-CV-977-KAJ (D. Delaware), May 6, 2022.

US Exhibit 654-10 from DexCom, Inc.'s Preliminary Invalidity Contentions, Case No. 21-CV-977-KAJ (D. Delaware), May 6, 2022.

US Exhibit 654-11 from DexCom, Inc.'s Preliminary Invalidity Contentions, Case No. 21-CV-977-KAJ (D. Delaware), May 6, 2022.

US Exhibit 654-12 from DexCom, Inc.'s Preliminary Invalidity Contentions, Case No. 21-CV-977-KAJ (D. Delaware), May 6, 2022.

(56) References Cited

OTHER PUBLICATIONS

US Exhibit 654-13 from DexCom, Inc.'s Preliminary Invalidity Contentions, Case No. 21-CV-977-KAJ (D. Delaware), May 6, 2022.

US Defendant Dexcom, Inc.'s Corrected First Supplemental Response to Plaintiffs' Interrogatories 3 and 4, Case 21-CV-977-KAJ, Mar. 31, 2022.

US Dexcom, Inc.'s Answer to First Amended Complaint and Affirmative Defenses to Plaintiffs' First Amended Complaint, Case 21-CV-977-KAJ, Feb. 22, 2022.

US Transcript of Oral Arguments, Case 21-CV-977-KAJ, Feb. 11, 2022.

US Order Denying Dexcom, Inc.'s Motion to Dismiss, Case 21-CV-977-KAJ, Feb. 8, 2022.

US Defendant Dexcom, Inc.'s Response to Plaintiff's First Set of Interrogatories, Case 21-CV-977-KAJ, Dec. 10, 2021.

US Defendant Dexcom, Inc.'s Reply Brief in Support of its Motion to Dismiss Pursuant to Federal Rule of Civil Procedure 12(b)(6), Case 21-CV-977-KAJ, Nov. 22, 2021.

US Plaintiff's Answering Brief in Opposition to Defendant Motion to Dismiss Under Rule 12(b)(6), Case 21-CV-977-KAJ, Nov. 15, 2021.

US Defendant Dexcom, Inc.'s Appendix to Opening Brief in Support of its Motion to Dismiss Pursuant to Federal Rule of Civil Procedure 12(b)(6), Case 21-CV-977-KAJ, Nov. 1, 2021.

US Defendant Dexcom, Inc.'s Opening Brief in Support of its Motion to Dismiss Pursuant to Federal Rule of Civil Procedure 12(b)(6), Case 21-CV-977-KAJ, Nov. 1, 2021.

US Defendant Dexcom, Inc.'s Motion to Dismiss Under Rule 12(b)(6), Case 21-CV-977-KAJ, Nov. 1, 2021.

US First Amended Complaint filed by Abbott Diabetes Care Inc. and Abbott Diabetes Care Limited against Dexcom, Inc., Case 21-CV-977-KAJ, Oct. 4, 2021.

US Complaint filed by Abbott Diabetes Care Inc. and Abbott Diabetes Care Limited against Dexcom, Inc., Case 21-CV-977-KAJ, Jul. 1, 2021.

ACCU-CHEK Compact Plus Owner's Booklet, 2008, pp. 1-100.

ACCU-CHEK Softclix Plus Lancet Device retrieved from https://web.archive.org/web/20061018055737/http://www.accu-check.com/US/rewrite/content/en_US/2.1.7.1:10/article/ACCM_general_article_3303.htm, 2006, pp. 1-2.

Bindra, D.S., et al., "Pulsed Amperometric Detection of Glucose in Biological Fluids at a Surface-Modified Gold Electrode", American Chemical Society, 1989, vol. 61, No. 22, pp. 2566-2570.

Cleo™ 90 Infusion Set, 510(k) Summary of Safety and Effectiveness, pp. 1-618.

Cleo® 90 Infusion Set Training Guide, 1 page.

Compact Plus Blood Glucose Meter retrieved from https://web.archive.org/web/20090316065810/http://www.accu-check.com/US/rewrite/content/en_US/2.1.9:0/article/ACCM_general_article_5136.htm, 2009, pp. 1-3.

Cox, M., "An Overview of Continuous Glucose Monitoring Systems", Journal of Pediatric Health Care, 2009, vol. 23, No. 5, pp. 344-347.

Darley, J., "Is your user experience as good as your technology?", 2019, retrieved from https://www.massdevice.com/is-your-user-experience-as-good-as-your-technology/, pp. 1-16.

IPR2022-00605 (Ex. 2001) Declaration of Michael Cima, Ph.D dated May 24, 2022, pp. 1-70.

IPR2022-00637 (Ex. 2001) Declaration of Michael Cima, Ph.D dated Jun. 9, 2022, pp. 1-79.

"Dexcom CEO tells investors not to fear new competition from Abbott's Freestyle Libre", 2017, retrieved from https://www.mobihealthnews.com/content/dexcom-ceo-tells-investors-not-fear-new-competition-abbotts-freestyle-libre, pp. 1-3.

Dexcom G5 Mobile System User Guide, 2020, pp. 1-410.

Dexcom G6, Winner Health & Wellness Award, Core77 Design Awards, 2019, retrieved from https://designawards.core77.com/health-wellness/85111/Dexcom-G6, pp. 1-8.

Freestyle Navigator Continuous Glucose Monitor FDA Premarket Approval (PMA), May 2022, pp. 1-6.

Freestyle Navigator Summary of Safety and Effectiveness Data, 2008, pp. 1-27.

Freestyle Navigator User's Guide, 2008, pp. 1-195.

Gonzales, W. V., et al., "The Progress of Glucose Monitoring-A Review of Invasive to Minimally and Non-Invasive Techniques, Devices and Sensors", Sensors, 2019, vol. 19, No. 800, pp. 1-45.

Gregg, T. H., "How Continuous Glucose Monitoring is Transforming Diabetes Treatment", Qualcomm Life Connect, 2013, pp. 1-33.

Guardian® RT Continuous Glucose Monitoring System Ref MMT-7900 User Guide, 2005, pp. 1-128.

Hirsch, I. B., "Introduction: History of Glucose Monitoring", Clinical Compendia, 2018, vol. 2018, No. 1, 1 page.

Howe, D., "Comparing the Dexcom G6 To the G5", 2018, retrieved from https://beyondtype1.org/comparing-the-dexcom-g6-to-the-g5/, pp. 1-10.

Medtronic Guardian® REAL-Time Continuous Glucose Monitoring System User Guide, 2006, pp. 1-184.

IPR2022-00605 (Ex. 2008) MiniMed® Glucose Sensor, Ref MMT-7002, Instructions for Use, pp. 1-4.

IPR2022-00605 (Ex. 2003) "Monitoring Your Blood Sugar", retrieved from https://www.cdc.gov/diabetes/managing/managing-blood-sugar/bloodglucosemonitoring.html, pp. 1-3.

OmniPod Insulet UST400 User Manual, 2011, pp. 1-190.

Patton, S. R., et al., "Continuous Glucose Monitoring Versus Self-monitoring of Blood Glucose in Children with Type 1 Diabetes—Are there Pros and Cons for Both?", US Endocrinol., 2012, vol. 8, No. 1, pp. 27-29.

Zisser, H. C., "The OmniPod Insulin Management System: the Latest Innovation in Insulin Pump Therapy", Diabetes Ther, 2010, vol. 1, No. 1, pp. 10-24.

Delve Talks: Jake Leach, Dexcom, retrieved from https://www.delve.com/podcasts/delve-talks-jake-leach-dexcom, 2019, pp. 1-9.

MINIMED Quick-set™ retrieved from https://web.archive.org/web/20010412224824/http://www.minimed.com/patientfam/pf_ipt_pum pinfusion_quickset.shtml, Apr. 12, 2001, pp. 1-2.

MINIMED Sof-set Micro QR® Sof-set Ultimate QR® retrieved from https://web.archive.org/web/20010412225617/http://www.minimed.com/patientfam/pf_ipt_pum pinfusion_sofset.shtml, Apr. 12, 2001, pp. 1-2.

Osmonics, Poretics® Polycarbonate Membrane; Product Leaflet; Engineering Purity, 2002, pp. 1-2.

Repas, R., "Sensor Sense: RFID for smart position sensing", retrieved from https://www.machinedesign/com/automation-iiot/article/21818777/sensor-sense-rfid-for-smart-position-sensing, 2010, pp. 1-2.

EP 11760268.0 Decision of the Oral Proceedings, Sep. 27, 2022.

EP 20177703.4 Grounds of Opposition, Sep. 26, 2022.

EP 20177703.4 Notice of Opposition, Sep. 28, 2022.

EP 20177703.4 Examination Report, Jun. 25, 2021.

EP 22168031.7 Extended Search Report, Aug. 17, 2022.

EP 22169853.3 Extended Search Report, Sep. 2, 2022.

MY PI2021004760 Examination Report, Mar. 30, 2022.

MY PI2021005830 Examination Report, Sep. 30, 2022.

MY PI2021005830 Examination Report, Aug. 29, 2022.

US Plaintiffs' Comments on Defendant's Technology Tutorial, Case 21-CV-977-KAJ (D. Delaware), Sep. 9, 2022.

US Plaintiffs' Second Supplemental Response to Defendant's First Set of Interrogatories, Nos. 1-10, Interrogatory No. 5, Case 21-CV-977-KAJ (D. Delaware), Sep. 8, 2022.

US Plaintiffs' First Updated Identification of Asserted Claims, Case 21-CV-977-KAJ (D. Delaware), Sep. 7, 2022.

US Second Declaration of Dr. Jeffrey Vaitekunas, PH.D, Case 21-CV-977-KAJ (D. Delaware), Aug. 31, 2022.

US Defendant's Sur-Reply Claim Construction Brief, Case 21-CV-977-KAJ (D. Delaware), Aug. 31, 2022.

US Second Declaration of Karl R. Leinsing, MSME, PE, Case 21-CV-977-KAJ (D. Delaware), Aug. 17, 2022.

US Plaintiffs' Reply Brief Regarding Claim Construction, Case 21-CV-977-KAJ (D. Delaware), Aug. 17, 2022.

US Plaintiffs' Response to Defendant's Second Set of Interrogatories, No. 11, Case 21-CV-977-KAJ (D. Delaware), Aug. 8, 2022.

(56)  References Cited

OTHER PUBLICATIONS

US Declaration of Dr. Jeffrey Vaitekunas, PH.D, re Claim Construction for U.S. Pat. Nos. 10,881,341; 10,959,654; 11,000,216; 10,973,443; 10,945,649; 11,013,440; 10,945,647, Case 21-CV-977-KAJ (D. Delaware).
US Defendant's Answering Claim Construction Brief, Case 21-CV-977-KAJ (D. Delaware), Aug. 3, 2022.
US Declaration of Karl R. Leinsing, MSME, PE, Case 21-CV-977-KAJ (D. Delaware), Jul. 13, 2022.
US Plaintiffs' Opening Claim Construction Brief, Case 21-CV-977-KAJ (D. Delaware), Jul. 13, 2022.
US Dexcom, Inc.'s Answer to Second Amended Complaint, Case 21-CV-977-KAJ (D. Delaware), Jun. 30, 2022.
US Joint Claim Construction Chart, Case 21-CV-977-KAJ (D. Delaware), Jun. 22, 2022.
US Plaintiffs' Second Amended Complaint, Case 21-CV-977-KAJ (D. Delaware), May 20, 2022.
US Exhibit 216-2S from DexCom, Inc.'s Supplemental Preliminary Invalidity Contentions, Case No. 21-CV-977-KAJ (D. Delaware), May 6, 2022.
US Exhibit 216-3S from DexCom, Inc.'s Supplemental Preliminary Invalidity Contentions, Case No. 21-CV-977-KAJ (D. Delaware), May 6, 2022.
US Exhibit 216-4S from DexCom, Inc.'s Supplemental Preliminary Invalidity Contentions, Case No. 21-CV-977-KAJ (D. Delaware), May 6, 2022.
US Exhibit 216-5S from DexCom, Inc.'s Supplemental Preliminary Invalidity Contentions, Case No. 21-CV-977-KAJ (D. Delaware), May 6, 2022.
US Exhibit 216-6S from DexCom, Inc.'s Supplemental Preliminary Invalidity Contentions, Case No. 21-CV-977-KAJ (D. Delaware), May 6, 2022.
US Exhibit 216-7S from DexCom, Inc.'s Supplemental Preliminary Invalidity Contentions, Case No. 21-CV-977-KAJ (D. Delaware), May 6, 2022.
US Exhibit 216-9S from DexCom, Inc.'s Supplemental Preliminary Invalidity Contentions, Case No. 21-CV-977-KAJ (D. Delaware), May 6, 2022.
US Exhibit 216-10S from DexCom, Inc.'s Supplemental Preliminary Invalidity Contentions, Case No. 21-CV-977-KAJ (D. Delaware), May 6, 2022.
US Exhibit 216-11S from DexCom, Inc.'s Supplemental Preliminary Invalidity Contentions, Case No. 21-CV-977-KAJ (D. Delaware), May 6, 2022.
US Exhibit 216-12S from DexCom, Inc.'s Supplemental Preliminary Invalidity Contentions, Case No. 21-CV-977-KAJ (D. Delaware), May 6, 2022.
US Exhibit 341-1 from DexCom, Inc.'s Preliminary Invalidity Contentions, Case No. 21-CV-977-KAJ (D. Delaware), May 6, 2022.
US Exhibit 341-2 from DexCom, Inc.'s Preliminary Invalidity Contentions, Case No. 21-CV-977-KAJ (D. Delaware), May 6, 2022.
US Exhibit 341-2S from DexCom, Inc.'s Supplemental Preliminary Invalidity Contentions, Case No. 21-CV-977-KAJ (D. Delaware), May 6, 2022.
US Exhibit 341-3 from DexCom, Inc.'s Preliminary Invalidity Contentions, Case No. 21-CV-977-KAJ (D. Delaware), May 6, 2022.
US Exhibit 341-3S from DexCom, Inc.'s Supplemental Preliminary Invalidity Contentions, Case No. 21-CV-977-KAJ (D. Delaware), May 6, 2022.
US Exhibit 341-4 from DexCom, Inc.'s Preliminary Invalidity Contentions, Case No. 21-CV-977-KAJ (D. Delaware), May 6, 2022.
US Exhibit 341-4S from DexCom, Inc.'s Supplemental Preliminary Invalidity Contentions, Case No. 21-CV-977-KAJ (D. Delaware), May 6, 2022.

US Exhibit 341-5 from DexCom, Inc.'s Preliminary Invalidity Contentions, Case No. 21-CV-977-KAJ (D. Delaware), May 6, 2022.
US Exhibit 341-5S from DexCom, Inc.'s Supplemental Preliminary Invalidity Contentions, Case No. 21-CV-977-KAJ (D. Delaware), May 6, 2022.
US Exhibit 341-6 from DexCom, Inc.'s Preliminary Invalidity Contentions, Case No. 21-CV-977-KAJ (D. Delaware), May 6, 2022.
US Exhibit 341-6S from DexCom, Inc.'s Supplemental Preliminary Invalidity Contentions, Case No. 21-CV-977-KAJ (D. Delaware), May 6, 2022.
US Exhibit 341-7 from DexCom, Inc.'s Preliminary Invalidity Contentions, Case No. 21-CV-977-KAJ (D. Delaware), May 6, 2022.
US Exhibit 341-7S from DexCom, Inc.'s Supplemental Preliminary Invalidity Contentions, Case No. 21-CV-977-KAJ (D. Delaware), May 6, 2022.
US Exhibit 341-8 from DexCom, Inc.'s Preliminary Invalidity Contentions, Case No. 21-CV-977-KAJ (D. Delaware), May 6, 2022.
US Exhibit 341-9 from DexCom, Inc.'s Preliminary Invalidity Contentions, Case No. 21-CV-977-KAJ (D. Delaware), May 6, 2022.
US Exhibit 341-9S from DexCom, Inc.'s Supplemental Preliminary Invalidity Contentions, Case No. 21-CV-977-KAJ (D. Delaware), May 6, 2022.
US Exhibit 341-10 from DexCom, Inc.'s Preliminary Invalidity Contentions, Case No. 21-CV-977-KAJ (D. Delaware), May 6, 2022.
US Exhibit 341-10S from DexCom, Inc.'s Supplemental Preliminary Invalidity Contentions, Case No. 21-CV-977-KAJ (D. Delaware), May 6, 2022.
US Exhibit 341-11 from DexCom, Inc.'s Preliminary Invalidity Contentions, Case No. 21-CV-977-KAJ (D. Delaware), May 6, 2022.
US Exhibit 341-11S from DexCom, Inc.'s Supplemental Preliminary Invalidity Contentions, Case No. 21-CV-977-KAJ (D. Delaware), May 6, 2022.
US Exhibit 341-12 from DexCom, Inc.'s Preliminary Invalidity Contentions, Case No. 21-CV-977-KAJ (D. Delaware), May 6, 2022.
US Exhibit 341-12S from DexCom, Inc.'s Supplemental Preliminary Invalidity Contentions, Case No. 21-CV-977-KAJ (D. Delaware), May 6, 2022.
US Exhibit 341-13 from DexCom, Inc.'s Preliminary Invalidity Contentions, Case No. 21-CV-977-KAJ (D. Delaware), May 6, 2022.
US Exhibit 440-1S from DexCom, Inc.'s Supplemental Preliminary Invalidity Contentions, Case No. 21-CV-977-KAJ (D. Delaware), May 6, 2022.
US Exhibit 440-2S from DexCom, Inc.'s Supplemental Preliminary Invalidity Contentions, Case No. 21-CV-977-KAJ (D. Delaware), May 6, 2022.
US Exhibit 440-4S from DexCom, Inc.'s Supplemental Preliminary Invalidity Contentions, Case No. 21-CV-977-KAJ (D. Delaware), May 6, 2022.
US Exhibit 440-5S from DexCom, Inc.'s Supplemental Preliminary Invalidity Contentions, Case No. 21-CV-977-KAJ (D. Delaware), May 6, 2022.
US Exhibit 440-7S from DexCom, Inc.'s Supplemental Preliminary Invalidity Contentions, Case No. 21-CV-977-KAJ (D. Delaware), May 6, 2022.
US Exhibit 440-8S from DexCom, Inc.'s Supplemental Preliminary Invalidity Contentions, Case No. 21-CV-977-KAJ (D. Delaware), May 6, 2022.
US Exhibit 440-12S from DexCom, Inc.'s Supplemental Preliminary Invalidity Contentions, Case No. 21-CV-977-KAJ (D. Delaware), May 6, 2022.
US Exhibit 440-13S from DexCom, Inc.'s Supplemental Preliminary Invalidity Contentions, Case No. 21-CV-977-KAJ (D. Delaware), May 6, 2022.

(56)        References Cited

OTHER PUBLICATIONS

US Exhibit 649-1S from DexCom, Inc.'s Supplemental Preliminary Invalidity Contentions, Case No. 21-CV-977-KAJ (D. Delaware), May 6, 2022.
US Exhibit 649-2S from DexCom, Inc.'s Supplemental Preliminary Invalidity Contentions, Case No. 21-CV-977-KAJ (D. Delaware), May 6, 2022.
US Exhibit 649-3S from DexCom, Inc.'s Supplemental Preliminary Invalidity Contentions, Case No. 21-CV-977-KAJ (D. Delaware), May 6, 2022.
US Exhibit 649-4S from DexCom, Inc.'s Supplemental Preliminary Invalidity Contentions, Case No. 21-CV-977-KAJ (D. Delaware), May 6, 2022.
US Exhibit 649-5S from DexCom, Inc.'s Supplemental Preliminary Invalidity Contentions, Case No. 21-CV-977-KAJ (D. Delaware), May 6, 2022.
US Exhibit 649-6S from DexCom, Inc.'s Supplemental Preliminary Invalidity Contentions, Case No. 21-CV-977-KAJ (D. Delaware), May 6, 2022.
US Exhibit 649-8S from DexCom, Inc.'s Supplemental Preliminary Invalidity Contentions, Case No. 21-CV-977-KAJ (D. Delaware), May 6, 2022.
US Exhibit 649-13S from DexCom, Inc.'s Supplemental Preliminary Invalidity Contentions, Case No. 21-CV-977-KAJ (D. Delaware), May 6, 2022.
US Exhibit 654-2S from DexCom, Inc.'s Supplemental Preliminary Invalidity Contentions, Case No. 21-CV-977-KAJ (D. Delaware), May 6, 2022.
US Exhibit 654-3S from DexCom, Inc.'s Supplemental Preliminary Invalidity Contentions, Case No. 21-CV-977-KAJ (D. Delaware), May 6, 2022.
US Exhibit 654-4S from DexCom, Inc.'s Supplemental Preliminary Invalidity Contentions, Case No. 21-CV-977-KAJ (D. Delaware), May 6, 2022.
US Exhibit 654-5S from DexCom, Inc.'s Supplemental Preliminary Invalidity Contentions, Case No. 21-CV-977-KAJ (D. Delaware), May 6, 2022.
US Exhibit 654-6S from DexCom, Inc.'s Supplemental Preliminary Invalidity Contentions, Case No. 21-CV-977-KAJ (D. Delaware), May 6, 2022.
US Exhibit 654-7S from DexCom, Inc.'s Supplemental Preliminary Invalidity Contentions, Case No. 21-CV-977-KAJ (D. Delaware), May 6, 2022.
US Exhibit 654-9S from DexCom, Inc.'s Supplemental Preliminary Invalidity Contentions, Case No. 21-CV-977-KAJ (D. Delaware), May 6, 2022.
US Exhibit 654-10S from DexCom, Inc.'s Supplemental Preliminary Invalidity Contentions, Case No. 21-CV-977-KAJ (D. Delaware), May 6, 2022.
US Exhibit 654-11S from DexCom, Inc.'s Supplemental Preliminary Invalidity Contentions, Case No. 21-CV-977-KAJ (D. Delaware), May 6, 2022.
US Exhibit 654-12S from DexCom, Inc.'s Supplemental Preliminary Invalidity Contentions, Case No. 21-CV-977-KAJ (D. Delaware), May 6, 2022.
US Defendant Dexcom, Inc.'s First Supplemental Preliminary Invalidity Contentions, Case 21-CV- 977-KAJ, May 6, 2022.
US Defendant Dexcom, Inc.'s Preliminary Invalidity Contentions, Case 21-CV-977-KAJ, May 6, 2022.
WO PCT/US2022/037291 ISR and Written Opinion, Nov. 22, 2022.
WO PCT/US2022/037291 Invitation to Pay Additional Fees, Sep. 29, 2022.
Affidavit of Richard Paragas signed on May 18, 2016, pp. 1-4.
Affidavit of Paul Neale signed on May 18, 2016, pp. 1-2.
Certified U.S. Appl. No. 60/424,099, filed Nov. 5, 2002.
Choleau, C., et al., "Calibration of a Subcutaneous Amperometric Glucose Sensor Implanted for 7 Days in Diabetic Patients Part 2. Superiority of the One-Point Calibration Method", Biosensor & Bioelectronics, 2002, vol. 17, No. 8, pp. 647-654.

Choleau, C., et al., "Calibration of a Subcutaneous Amperometric Glucose Sensor Part 1. Effect of Measurement Uncertainties on the Determination of Sensor Sensitivity and Background Current", Biosensor & Bioelectronics, 2002, vol. 17, No. 8, pp. 641-646.
De Block, C., et al., "Minimally-Invasive and Non-Invasive Continuous Glucose Monitoring Systems: Indications, Advantages, Limitations and Clinical Aspects", Current Diabetes Reviews, 2008, vol. 4, No. 3, pp. 159-168.
U.S. Appl. No. 10/633,367.
Guerci, B., et al., "Clinical Performance of CGMS in Type 1 Diabetic Patients Treated by Continuous Subcutaneous Insulin Infusion Using Insulin Analogs", Diabetes Care, 2003, vol. 26, No. 3, pp. 582-589.
Kovatchev, B. P., et al., "Evaluating the Accuracy of Continuous Glucose-Monitoring Sensors", Diabetes Care, 2004, vol. 27, No. 8, pp. 1922-1928.
Mauras, N., et al., "Lack of Accuracy of Continuous Sensors in Healthy, Nondiabetic Children: Results of the Diabetes Research in Children Network (DirecNet) Accuracy Study", Journal of Pediatrics, 2004, pp. 770-775.
Medtronic MiniMed Sen-Serter® User Guide, 2006, pp. 1-96.
Schmidtke, D. W., et al., "Accuracy of the One-Point In Vivo Calibration of "Wired" Glucose Oxidase Electrodes Implanted in Jugular Veins of Rats in Periods of Rapid Rise and Decline of the Glucose Concentration", Analytical Chemistry, 1998, vol. 70, No. 10, pp. 2149-2155.
Tierney, M. J., et al., "Effect of Acetaminophen on the Accuracy of Glucose Measurements Obtained with the GlucoWatch Biographer", Diabetes Technology & Therapeutics, 2000, vol. 2, No. 2, pp. 199-207.
Tsalikian, e., et al., "Accuracy of the GlucoWatch G2® Biographer and the Continuous Glucose Monintoring System During Hypoglycemia: Experience of the Diabetes Research in Children Network", Diabetes Care, 2004, vol. 27, No. 3, pp. 722-726.
Ward, W. K., et al., "Rise in Background Current Over Time in a Subcutaneous Glucose Sensor in the Rabbit: Relevance to Calibration and Accuracy", Biosensors & Bioelectronics, 2000, vol. 15, pp. 53-61.
CA 2,872,576 Examiner's Report, Feb. 17, 2015.
CA 2,872,576 Examiner's Report, Feb. 19, 2015.
CA 3,182,961 Examiner's Report, Mar. 29, 2023.
CN 3,182,961 First Office Action, Jan. 10, 2023.
EP 06851063.5 Extended Search Report, Sep. 21, 2009.
EP 07843396.8 Extended Search Report, Dec. 22, 2010.
EP 10739031.2 Response to Response to Response to Grounds of Appeal, Jan. 18, 2023.
EP 13000104.3 Extended Search Report, Mar. 12, 2023.
EP 14179905.6 Summons to Attend Oral Proceedings, Apr. 10, 2017.
EP 14179905.6 Notice of Opposition, May 19, 2016.
EP 14179905.6 Extended Search Report, Dec. 26, 2014.
EP 15002441.2 Extended Search Report, Dec. 18, 2015.
EP 20177703.4 Reply to Opposition, Feb. 22, 2023.
EP 20177712.5 Grounds of Opposition Guife & Partner Patent, Dec. 22, 2022.
EP 20177712.5 Grounds of Opposition Dexcom, Dec. 22, 2022.
EP 20177712.5 Notice of Opposition Guide & Partner Patent, Dec. 22, 2022.
EP 20177712.5 Notice of Opposition Dexcom, Dec. 22, 2022.
EP 20195922.8 Grounds of Opposition Dexcom, Jan. 26, 2023.
EP 20195922.8 Notice of Opposition Dexcom, Jan. 26, 2023.
GB Claim No. HP-2021-000025 Re-Re-Re-Amended Grounds of Invalidity, Mar. 14, 2023.
GB Claim No. HP-2021-000025 Sealed Order, Jan. 12, 2023.
GB Claim No. HP-2021-000025 Statement of Grounds of Amendment of Ep (UK) 2,549,918, Dec. 23, 2022
GB Claim No. HP-2021-000025 Application Notice, Dec. 23, 2022.
GB Claim No. HP-2021-000026 Sealed Order, Jan. 12, 2023.
GB Claim No. HP-2021-000026 Statement of Grounds of Amendment of EP (UK) 2,549,918, Dec. 23, 2022.
JP 2021-531135 Office Action, Feb. 22, 2023.

(56)                    References Cited

OTHER PUBLICATIONS

US Complaint, Case 21-CV-977-KAJ (D. Delaware), Mar. 3, 2023
US Exhibit 216-1F from DexCom, Inc.'s Final Invalidity Contentions, Case No. 21-CV-977-KAJ (D. Delaware), Feb. 9, 2023.
US Exhibit 216-2F from DexCom, Inc.'s Final Invalidity Contentions, Case No. 21-CV-977-KAJ (D. Delaware), Feb. 9, 2023.
US Exhibit 216-3F from DexCom, Inc.'s Final Invalidity Contentions, Case No. 21-CV-977-KAJ (D. Delaware), Feb. 9, 2023.
US Exhibit 216-4F from DexCom, Inc.'s Final Invalidity Contentions, Case No. 21-CV-977-KAJ (D. Delaware), Feb. 9, 2023.
US Exhibit 216-5F from DexCom, Inc.'s Final Invalidity Contentions, Case No. 21-CV-977-KAJ (D. Delaware), Feb. 9, 2023.
US Exhibit 216-6F from DexCom, Inc.'s Final Invalidity Contentions, Case No. 21-CV-977-KAJ (D. Delaware), Feb. 9, 2023.
US Exhibit 216-7F from DexCom, Inc.'s Final Invalidity Contentions, Case No. 21-CV-977-KAJ (D. Delaware), Feb. 9, 2023.
US Exhibit 216-8F from DexCom, Inc.'s Final Invalidity Contentions, Case No. 21-CV-977-KAJ (D. Delaware), Feb. 9, 2023.
US Exhibit 216-10F from DexCom, Inc.'s Final Invalidity Contentions, Case No. 21-CV-977-KAJ (D. Delaware), Feb. 9, 2023.
US Exhibit 216-11F from DexCom, Inc.'s Final Invalidity Contentions, Case No. 21-CV-977-KAJ (D. Delaware), Feb. 9, 2023.
US Exhibit 216-12F from DexCom, Inc.'s Final Invalidity Contentions, Case No. 21-CV-977-KAJ (D. Delaware), Feb. 9, 2023.
US Exhibit 216-13F from DexCom, Inc.'s Final Invalidity Contentions, Case No. 21-CV-977-KAJ (D. Delaware), Feb. 9, 2023.
US Exhibit 341-1F from DexCom, Inc.'s Final Invalidity Contentions, Case No. 21-CV-977-KAJ (D. Delaware), Feb. 9, 2023.
US Exhibit 341-2F from DexCom, Inc.'s Final Invalidity Contentions, Case No. 21-CV-977-KAJ (D. Delaware), Feb. 9, 2023.
US Exhibit 341-3F from DexCom, Inc.'s Final Invalidity Contentions, Case No. 21-CV-977-KAJ (D. Delaware), Feb. 9, 2023.
US Exhibit 341-4F from DexCom, Inc.'s Final Invalidity Contentions, Case No. 21-CV-977-KAJ (D. Delaware), Feb. 9, 2023.
US Exhibit 341-5F from DexCom, Inc.'s Final Invalidity Contentions, Case No. 21-CV-977-KAJ (D. Delaware), Feb. 9, 2023.
US Exhibit 341-6F from DexCom, Inc.'s Final Invalidity Contentions, Case No. 21-CV-977-KAJ (D. Delaware), Feb. 9, 2023.
US Exhibit 341-7F from DexCom, Inc.'s Final Invalidity Contentions, Case No. 21-CV-977-KAJ (D. Delaware), Feb. 9, 2023.
US Exhibit 341-8F from DexCom, Inc.'s Final Invalidity Contentions, Case No. 21-CV-977-KAJ (D. Delaware), Feb. 9, 2023.
US Exhibit 341-10F from DexCom, Inc.'s Final Invalidity Contentions, Case No. 21-CV-977-KAJ (D. Delaware), Feb. 9, 2023.
US Exhibit 341-11F from DexCom, Inc.'s Final Invalidity Contentions, Case No. 21-CV-977-KAJ (D. Delaware), Feb. 9, 2023.
US Exhibit 341-12F from DexCom, Inc.'s Final Invalidity Contentions, Case No. 21-CV-977-KAJ (D. Delaware), Feb. 9, 2023.
US Exhibit 341-13F from DexCom, Inc.'s Final Invalidity Contentions, Case No. 21-CV-977-KAJ (D. Delaware), Feb. 9, 2023.
US Exhibit 440-1F from DexCom, Inc.'s Final Invalidity Contentions, Case No. 21-CV-977-KAJ (D. Delaware), Feb. 9, 2023.
US Exhibit 440-2F from DexCom, Inc.'s Final Invalidity Contentions, Case No. 21-CV-977-KAJ (D. Delaware), Feb. 9, 2023.
US Exhibit 440-3F from DexCom, Inc.'s Final Invalidity Contentions, Case No. 21-CV-977-KAJ (D. Delaware), Feb. 9, 2023.
US Exhibit 440-4F from DexCom, Inc.'s Final Invalidity Contentions, Case No. 21-CV-977-KAJ (D. Delaware), Feb. 9, 2023.
US Exhibit 440-5F from DexCom, Inc.'s Final Invalidity Contentions, Case No. 21-CV-977-KAJ (D. Delaware), Feb. 9, 2023.
US Exhibit 440-6F from DexCom, Inc.'s Final Invalidity Contentions, Case No. 21-CV-977-KAJ (D. Delaware), Feb. 9, 2023.
US Exhibit 440-8F from DexCom, Inc.'s Final Invalidity Contentions, Case No. 21-CV-977-KAJ (D. Delaware), Feb. 9, 2023.
US Exhibit 440-9F from DexCom, Inc.'s Final Invalidity Contentions, Case No. 21-CV-977-KAJ (D. Delaware), Feb. 9, 2023.
US Exhibit 440-10F from DexCom, Inc.'s Final Invalidity Contentions, Case No. 21-CV-977-KAJ (D. Delaware), Feb. 9, 2023.
US Exhibit 440-11F from DexCom, Inc.'s Final Invalidity Contentions, Case No. 21-CV-977-KAJ (D. Delaware), Feb. 9, 2023.
US Exhibit 440-12F from DexCom, Inc.'s Final Invalidity Contentions, Case No. 21-CV-977-KAJ (D. Delaware), Feb. 9, 2023.
US Exhibit 440-13F from DexCom, Inc.'s Final Invalidity Contentions, Case No. 21-CV-977-KAJ (D. Delaware), Feb. 9, 2023.
US Exhibit 649-1F from DexCom, Inc.'s Final Invalidity Contentions, Case No. 21-CV-977-KAJ (D. Delaware), Feb. 9, 2023.
US Exhibit 649-2F from DexCom, Inc.'s Final Invalidity Contentions, Case No. 21-CV-977-KAJ (D. Delaware), Feb. 9, 2023.
US Exhibit 649-3F from DexCom, Inc.'s Final Invalidity Contentions, Case No. 21-CV-977-KAJ (D. Delaware), Feb. 9, 2023.
US Exhibit 649-4F from DexCom, Inc.'s Final Invalidity Contentions, Case No. 21-CV-977-KAJ (D. Delaware), Feb. 9, 2023.
US Exhibit 649-5F from DexCom, Inc.'s Final Invalidity Contentions, Case No. 21-CV-977-KAJ (D. Delaware), Feb. 9, 2023.
US Exhibit 649-6F from DexCom, Inc.'s Final Invalidity Contentions, Case No. 21-CV-977-KAJ (D. Delaware), Feb. 9, 2023.
US Exhibit 649-7F from DexCom, Inc.'s Final Invalidity Contentions, Case No. 21-CV-977-KAJ (D. Delaware), Feb. 9, 2023.
US Exhibit 649-9F from DexCom, Inc.'s Final Invalidity Contentions, Case No. 21-CV-977-KAJ (D. Delaware), Feb. 9, 2023.
US Exhibit 649-10F from DexCom, Inc.'s Final Invalidity Contentions, Case No. 21-CV-977-KAJ (D. Delaware), Feb. 9, 2023.
US Exhibit 649-11F from DexCom, Inc.'s Final Invalidity Contentions, Case No. 21-CV-977-KAJ (D. Delaware), Feb. 9, 2023.
US Exhibit 649-12F from DexCom, Inc.'s Final Invalidity Contentions, Case No. 21-CV-977-KAJ (D. Delaware), Feb. 9, 2023.
US Exhibit 649-13F from DexCom, Inc.'s Final Invalidity Contentions, Case No. 21-CV-977-KAJ (D. Delaware), Feb. 9, 2023.
US Exhibit 654-1F from DexCom, Inc.'s Final Invalidity Contentions, Case No. 21-CV-977-KAJ (D. Delaware), Feb. 9, 2023.
US Exhibit 654-2F from DexCom, Inc.'s Final Invalidity Contentions, Case No. 21-CV-977-KAJ (D. Delaware), Feb. 9, 2023.
US Exhibit 654-3F from DexCom, Inc.'s Final Invalidity Contentions, Case No. 21-CV-977-KAJ (D. Delaware), Feb. 9, 2023.
US Exhibit 654-4F from DexCom, Inc.'s Final Invalidity Contentions, Case No. 21-CV-977-KAJ (D. Delaware), Feb. 9, 2023.
US Exhibit 654-5F from DexCom, Inc.'s Final Invalidity Contentions, Case No. 21-CV-977-KAJ (D. Delaware), Feb. 9, 2023.
US Exhibit 654-6F from DexCom, Inc.'s Final Invalidity Contentions, Case No. 21-CV-977-KAJ (D. Delaware), Feb. 9, 2023.
US Exhibit 654-7F from DexCom, Inc.'s Final Invalidity Contentions, Case No. 21-CV-977-KAJ (D. Delaware), Feb. 9, 2023.
US Exhibit 654-8F from DexCom, Inc.'s Final Invalidity Contentions, Case No. 21-CV-977-KAJ (D. Delaware), Feb. 9, 2023.
US Exhibit 654-10F from DexCom, Inc.'s Final Invalidity Contentions, Case No. 21-CV-977-KAJ (D. Delaware), Feb. 9, 2023.
US Exhibit 654-11F from DexCom, Inc.'s Final Invalidity Contentions, Case No. 21-CV-977-KAJ (D. Delaware), Feb. 9, 2023.
US Exhibit 654-12F from DexCom, Inc.'s Final Invalidity Contentions, Case No. 21-CV-977-KAJ (D. Delaware), Feb. 9, 2023.
US Exhibit 654-13F from DexCom, Inc.'s Final Invalidity Contentions, Case No. 21-CV-977-KAJ (D. Delaware), Feb. 9, 2023.
US Defendant Dexcom, Inc.'s Second Supplemental Preliminary Invalidity Contentions, Case 21-CV-977-KAJ (D. Delaware), Oct. 4, 2022.
US Defendant's Comments on Plaintiffs' Technology Tutorial, Case 21-CV-977-KAJ (D. Delaware), Sep. 16, 2022.
US Plaintiffs' Response to Defendant's Third Set of Interrogatories (Nos. 12-15), Case 21-CV-977-KAJ (D. Delaware), Sep. 14, 2022.
WO PCT/US2006/062690 ISR and Written Opinion, Jan. 2, 2008.
WO PCT/US2007/079774 ISR and Written Opinion, Apr. 1, 2008.
WO PCT/US2023/010054 Invitation to Pay Additional Fees, Mar. 24, 2023.
DE Infringement Action of EP 3 766 408 B1, Feb. 20, 2023.
EP 20177703.4 Response to Notice of Opposition, Jun. 29, 2023.
EP 20177703.4 Notice of Intervention, Jun. 23, 2023.
EP 20177712.5 Notice of Intervention, Jun. 23, 2023.
EP 20177712.5 Reply to Opposition, May 23, 2023.
EP 20195922.8 Reply to Opposition, Jun. 23, 2023.
EP 20195922.8 Notice of Intervention, Jun. 13, 2023.
GB Particulars of Claim, May 15, 2023.
GB Claimant's Initial List of Disclosure Documents, May 15, 2023.
GB Grounds of Invalidity, May 15, 2023.

(56)          References Cited

OTHER PUBLICATIONS

GB Claim No. HP-2021-000025 Re-Re-Amended Reply and Defence to Counterclaim, Apr. 28, 2023.
GB Claim No. HP-2021-000025 Defendants' Response to the Claimant's Reply to Issues of Fact Raised in Defendants' Grounds of Opposition—EP918, Apr. 25, 2023.
GB Claim No. HP-2021-000025 Re-Re-Re-Re- Amended Grounds of Invalidity, Apr. 24, 2023.
GB Claim No. HP-2021-000025 Claimants' Notice to Admit Facts, Apr. 6, 2023.
GB Claim No. HP-2021-000025 Re-Amended Reply and Defence to Counterclaim, Mar. 28, 2023.
GB Claim No. HP-2021-000025 Reply to Issues of Fact Raised in Defendants' Grounds of Opposition—EP918, Mar. 17, 2023.
GB Claim No. HP-2021-000025 Consent Order, Mar. 14, 2023.
MY PI2022007295 Examination Report, Jul. 11, 2023.
US Final Written Decision, IPR No. 2022-00605, Jul. 10, 2023.
US Dexcom, Inc.'s Answer, Affirmative Defenses, and Counterclaims, Case No. 23-CV-239-UNA (D. Delaware), May 12, 2023.
US Complaint, Case No. 23-CV-239-UNA (D. Delaware), Mar. 3, 2023.
US Defendant Dexcom, Inc.'s Objections and Responses to Plaintiffs' Second Set of Interrogatories, Case No. 21-CV-977-KAJ (D. Delaware)—Public Version, Oct. 11, 2022.
WO PCT/US2012/062551 ISR and Written Opinion, Jan. 2, 2023.
WO PCT/US2023/010054 ISR and Written Opinion, May 15, 2023.
Anderson, A. J., "Foundations of Computer Technology", 1994, pp. 55-57.
Kal, S., "Basic Electronics—Devices, Circuits and IT Fundamentals", 2006, Chapter 13, Microcomputers and Microprocessors, p. 412.
"Abbott Receives CE Mark for Freestyle® Libre, A Revolutionary Glucose Monitoring System for People With Diabetes", 2014, 7 pages.
"Alcove", Webster's New College Dictionary, 2001, p. 26.
Boise, M., "Dexcom CEO Kevin Sayer Explains G6", 2018, retrieved from https://beyondtype1.org/dexcom-ceo-kevin-sayer-explains-g6/, 9 pages.
Certified True Preliminary Amendment filed on Apr. 20, 2018 for U.S. Pat. No. 10,827,954, 7 pages.
Certified True Excerpts of the File History of U.S. Pat. No. 10,973,443, 22 pages.
CGMs Changing Diabetes Management: Kevin Sayer, DIC Interview Transcript, 2019, retrieved from https://www.diabetesincontrol.com/cgms-changing-diabetes-management-kevin-sayer-dic-interview-transcript/, 10 pages.
"Deciding When to Submit a 510(k) for a Change to an Existing Device, Guidance for Industry and Food and Drug Administration Staff", 2017, pp. 1-77.
"Deciding When to Submit a 510(k) for a Software Change to an Existing Device, Guidance for Industry and Food and Drug Administration Staff", 2017, pp. 1-31.
Dexcom CEO—Prime Position in Our Market—Mad Money—CNBC.mp4, Transcript 2023 by Sonix, 2 pages.
DexCom (DXCM) 2017 Q4 Earnings Call Transcript, 2017, retrieved from https://docoh.com/transcript/1093557/2017Q4/DXCM, 11 pages.
DexCom (DXCM) Q1 2018 Results—Earnings Call Transcript, 2018, retrieved from https://seekingalpha.com/article/4168949-dexcom-dxcm-q1-2018-results-earnings-call-transcript, 4 pages.
Dexcom, Inc. NasdaqGS:DXCM Company Conference Presentation, 2019, 10 pages.
Dexcom, Inc. NasdaqGS:DXCM Company Conference Presentation, 2020, 9 pages.
Dexcom, Inc. NasdaqGS:DXCM Company Conference Presentation, 2021, 16 pages.
Dexcom G6 Continuous Glucose Monitoring System User Guide, pp. 1-22.
Dexcom G6 Start Here Set up Guide, pp. 1-8.
Dexcom G6 Using Your G6 Guide, Mar. 2020, pp. 1-7.

Dexcom Seven® Plus Continuous Glucose Monitoring System User's Guide, 2011, pp. 1-144.
DexCom™ STS™ Continuous Glucose Monitoring System FDA Premarket Approval (PMA), 2006, pp. 1-7.
DexCom™ STS™ Continuous Glucose Monitoring System Summary of Safety and Effectiveness Data, 2006, 20 pages.
DexCom™ STS™ Sensor Instructions for Use, 2006, pp. 1-6.
Dexcom STS-7 Continuous Glucose Monitoring System FDA Premarket Approval (PMA), 2007, pp. 1-7.
Dexcom STS®-7 Continuous Glucose Monitoring System Summary of Safety and Effectiveness Data, 2007, 14 pages.
Dexcom STS®-7 Continuous Glucose Monitoring System User's Guide, 2007, pp. 1-74.
Diglas, J., et al., "Reduced pain perception with Pen Mate™, an automatic needle insertion device for use with an insulin pen", Practical Diabetes International, 1999, vol. 16, No. 2, pp. 39-41.
"Does Dexcom Really Have a Future If It Can't Match Abbott's Scale", 2019, retrieved from https://www.sprucepointcap.com/reports/dxcm_research_thesis_3-21-2019.pdf, p. 46.
Email from John Shaw of Shaw & Keller dated May 16, 2023, 2 pages.
Email chain from Sophie Hood, oldest email dated Jan. 24, 2023, 5 pages.
European Standard, ISO 11607-1, Packaging for terminally sterilized medical devices—Part 1: Requirements for materials, sterile barrier systems and packaging systems, 2006, 32 pages.
European Standard, ISO 13485, Medical devices—Quality management systems—Requirement for regulatory purposes, 2003, 69 pages.
European Standard, ISO 15197, In vitro diagnostic test systems—Requirements for blood glucose monitoring systems for self-testing in managing diabetes mellitus, 2003, 43 pages.
Explore The Monroe Street Market Community, Retrieved from https://www.monroestreetmarket.com/floor-plans/apartment/B-231, 2 pages.
"FDA authorizes first fully interoperable continuous glucose monitoring system, streamlines review pathway for similar devices", FDA News Release, 2018, retrieved from https://www.fda.gov/news-events/press-announcements/fda-authorizes-first-fully-interoperable-continuous-glucose-monitoring-system-streamlines-review, 3 pages.
Food and Drug Administration, HHS, 2009, Code of Federal Regulation § 820.30, Subpart C—Design Controls, pp. 147-148.
Freestyle Libre Pro Flash Glucose Monitoring System Summary of Safety and Effectiveness Data, 2016, 31 pages.
FreeStyle Lite Blood Glucose Monitoring System Owner's Booklet, 2006, 15 pages.
FreeStyle Navigator Continuous Glucose Monitoring System FDA Premarket Approval (PMA), 2008, pp. 1-7.
Hemmerich, K. J., et al., "Sterilization Methods Stand the Test of Time", 2004, retrieved from https://www.mddionline.com/sterilization/sterilization-methods-stand-test-time, pp. 1-8.
Hirsch, I. B., "Realistic Expectations and Practical Use of Continuous Glucose Monitoring for the Endocrinologist", The Journal of Clinical Endocrinology & Metabolism, 2009, VI. 94, No. 7, pp. 2232-2238.
Hoss, U., et al., "Continuous glucose monitoring in the tissue: Do we really need to calibrate in-vivo?", pp. 1-21.
Hoss, U., et al., "Continuous Glucose Monitoring in Subcutaneous Tissue Using Factory-Calibrated Sensors: A Pilot Study", Diabetes Technology & Therapeutics, 2010, vol. 12, No. 8, pp. 591-597.
Hoss, U., et al., "Feasibility of Factory Calibration for Subcutaneous Glucose Sensors in Subjects With Diabetes", Journal of Diabetes Science and Technology, 2014, vol. 8, No. 1, pp. 89-94.
"Housing", "recess", "release", and "retain", Merriam-Webster's Collegiate Dictionary, Tenth Edition, 1999, pp. 563, 975, 987, and 999.
"Housing" and "recess", The New Penguin English Dictionary, 2000, pp. 678 and 1167.
Hughes, M. D., "The Business of Self-Monitoring of Blood Glucose: A Market Profile", Journal of Diabetes Science and Technology, 2009, vol. 3, No. 5, pp. 1219-1223.
IEEE 100 The Authoritative Dictionary of IEEE Standards Terms, Seventh Edition, 2000, 3 pages.

(56) References Cited

OTHER PUBLICATIONS

International Standard, ISO 14971, Medical devices—Application of risk management to medical devices, 2007, 90 pages.

"An Interview with Kevin Sayer, President and CEO of Dexcom, About The New G6", 2021, 5 pages.

Klueh, U., et al., "Inflammation and Glucose Sensors: Use of Dexamethasone to Extend Glucose Sensor Function and Life Span in Vivo", Journal of Diabetes Science and Technology, 2007, vol. 1, No. 4, pp. 496-504.

Klueh, U., et al., "Blood-Induced Interference of Glucose Sensor Function in Vitro: Implications for in Vivo Sensor Function", Journal of Diabetes Science and Technology, 2007, vol. 1, No. 6, pp. 842-849.

Medtronic Guardian® REAL-Time Continuous Glucose Monitoring System User Guide, 2006, pp. 1-181.

Medtronic MiniMed Guardian RT FDA Premarket Approval (PMA), 2005, pp. 1-6.

Medtronic MiniMed Guardian RT Summary of Safety and Effectiveness Data, 2005, 13 pages.

Medtronic MiniMed Paradigm® REAL-Time 522 and 722 Insulin Pumps User Guide, 2008, pp. 1-262.

Occupational Safety and Health Admin., Labor, 2003, 29 CFR § 1910.1030 Bloodborne pathogens, pp. 260-273.

Omnipod image, Exhibit 182 of ADC Reply Brief SJ, Daubert, Sep. 22, 2022, 2 pages.

OneTouch® Ultra™ Blood Glucose Monitoring System Owner's Booklet, 2000, 23 pages.

One Touch Ultra2 Blood Glucose Monitoring System Owner's Booklet, 2005, 34 pages.

Order, Federal Communications Commission, 2006, pp. 1-8.

Program, 2nd International Conference on Advanced Technologies & Treatments for Diabetes, Athens, Greece, 2009, 3 pages.

"Recess", Cambridge Dictionary of American English, 2000, pp. 710-711.

"Retract", The Chambers Dictionary, 1998, p. 1410.

"Retract", The New Oxford American Dictionary, 2001, p. 1455.

"Retract", Webster's Third New International Dictionary, 1993, pp. 1939-1940.

"Submission and Review of Sterility Information in Premarket Notification (510(k)) Submissions for Devices Labeled as Sterile, Guidance for Industry and Food and Drug Administration Staff", 2016, pp. 1-11.

Tegnestedt, C., et al., "Levels and sources of sound in the intensive care unit—an observational study of three room types", Acta Anaesthiesiologica Scandinavica, 2013, pp. 1-10.

Watkin, J., "An Introduction to Flash Glucose Monitoring", 14 pages.

CN 201980082748.1 Second Office Action, Jul. 10, 2023.

EP 20177712.5 Reply to Reply to Notice of Opposition Dexcom, Sep. 27, 2023.

EP 20177712.5 Reply to Reply to Notice of Opposition Gulde & Partner Patent, Aug. 30, 2023.

EP 20195922.8 Summons to Attend Oral Proceedings, Sep. 21, 2023.

EP 20195922.8 Reply to Notice of Intervention, Aug. 29, 2023.

EP 20195922.8 Reply to Reply to Notice of Opposition, Aug. 21, 2023.

GB Claim No. HP-2021-000025 Annex 4 to Abbott's Closing Submissions, Jul. 18, 2023.

GB Claim No. HP-2021-000025 Annex 3 to Abbott's Closing Submissions, Jul. 18, 2023.

GB Claim No. HP-2021-000025 Annex 2 to Abbott's Closing Submissions, Jul. 18, 2023.

GB Claim No. HP-2021-000025 Annex 1 to Abbott's Closing Submissions—Claim Integers, Jul. 18, 2023.

GB Claim No. HP-2021-000025 Abbott's Closing Submissions Trial C, Jul. 18, 2023.

GB Claim No. HP-2021-000025 Annex CA2 of Dexcom's Closing Skeleton Argument Trial C, Jul. 18, 2023.

GB Claim No. HP-2021-000025 of Dexcom's Closing Skeleton Argument Trial C, Jul. 18, 2023.

GB Claim No. HP-2021-000025 Abbott's Supplementary Skeleton Argument Trial C, Jul. 7, 2023.

GB Claim No. HP-2021-000025 Annex 2 to Abbott's Opening Skeleton Argument—Commercial devices and their key features, Jul. 5, 2023.

GB Claim No. HP-2021-000025 Annex 1 to Abbott's Opening Skeleton Argument—Claim Integers, Jul. 5, 2023.

GB Claim No. HP-2021-000025 Abbott's Opening Skeleton Argument Trial C, Jul. 5, 2023.

GB Claim No. HP-2021-000025 Annex 3 of Dexcom's Opening Skeleton Argument—Trial C, Jul. 5, 2023.

GB Claim No. HP-2021-000025 Annex 2 of Dexcom's Opening Skeleton Argument—Trial C, Jul. 5, 2023.

GB Claim No. HP-2021-000025 Annex 1 of Dexcom's Opening Skeleton Argument—Trial C, Jul. 5, 2023.

GB Claim No. HP-2021-000025 of Dexcom's Opening Skeleton Argument—Trial C, Jul. 5, 2023.

GB Claim No. HP-2021-000025 and Claim No. HP-2021-000026 Fifth Expert Report of Andrew Varde, Jun. 23, 2023.

GB Claim No. HP-2021-000025 PTR Order, Jun. 20, 2023.

GB Claim No. HP-2021-000025 Second Expert Report of Douglas Jennings, Jun. 9, 2023.

GB Claim No. HP-2021-000025 and Claim No. HP-2021-000026 Fourth Expert Report of Andrew Varde, Jun. 9, 2023.

GB Claim No. HP-2021-000025 Third Expert Report of Dr. Michael Schoemaker, Jun. 2, 2023.

GB Claim No. HP-2021-000025 Claim Integer (Exhibit DJ-9), May 12, 2023.

GB Claim No. HP-2021-000025 Trial B—Joint CGK Statement (Exhibit DJ-2), May 12, 2023.

GB Claim No. HP-2021-000025 First Expert Report of Douglas Jennings, May 12, 2023.

GB Claim No. HP-2021-000025 and Claim No. HP-2021-000026 Third Expert Report of Andrew Varde, May 11, 2023.

GB Claim No. HP-2021-000025 and Claim No. HP-2021-000026 Third Letter (Exhibit PG-12), May 10, 2023.

GB Claim No. HP-2021-000025 and Claim No. HP-2021-000026 Third Expert Report of Pantelis Georgiou, May 10, 2023.

GB Claim No. HP-2023-000012 and Claim No. HP-2023-000016 Order for Directions—Trial D, Jul. 24, 2023.

GB Claim No. HP-2023-000012 Reply and Defence to Counterclaim, Jul. 5, 2023.

GB Claim No. HP-2023-000012 Application Notice, Jun. 19, 2023.

GB Claim No. HP-2023-000012 Defence and Counterclaim, Jun. 14, 2023.

JP 2021-531135 Office Action, Aug. 9, 2023.

US Petition For Inter Partes Review Of U.S. Pat. No. 11,202,591, IPR No. 2023-01409, Oct. 11, 2023.

US Petition For Inter Partes Review Of U.S. Pat. No. 11,266,335, IPR No. 2023-01397, Oct. 6, 2023.

US Petition For Inter Partes Review Of U.S. Pat. No. 11,266,335, IPR No. 2023-01396, Oct. 6, 2023.

US Record of Oral Hearing, IPR No. 2022-00605, Apr. 26, 2023.

US Petitioner's Reply to Patent Owner's Response to Petition, IPR No. 2022-00605, Jan. 11, 2023.

US Supplemental Declaration of Gary D. Fletcher, Ph.D, IPR No. 2022-00605, Jan. 11, 2023.

US Second Declaration by Dr. Michael Cima in Support of Patent Owner's Response, IPR No. 2022-00605, Oct. 19, 2022.

US Patent Owner's Response, IPR No. 2022-00605, Oct. 19, 2023.

US Amended [Proposed] Final Pretrial Order, Case No. 21-CV-977-KAJ (D. Delaware), Sep. 20, 2023.

US Exhibit 3P to the Proposed Pretrial Order Abbott's Statement of Issues of Law Which Remain to be Litigated, Case No. 21-CV-977-KAJ (D. Delaware), Sep. 20, 2023.

US Exhibit 3D to the Proposed Pretrial Order Dexcom's Statement of Issues of Law Which Remain to be Litigated, Case No. 21-CV-977-KAJ (D. Delaware), Sep. 20, 2023.

US Exhibit 2P to the Proposed Pretrial Order Abbott's Statement of Issues of Fact Which Remain to be Litigated, Case No. 21-CV-977-KAJ (D. Delaware), Sep. 20, 2023.

(56)                    References Cited

OTHER PUBLICATIONS

US Exhibit 2D to Proposed Pretrial Order Dexcom's Statement of Contested Facts, Case No. 21-CV-977-KAJ (D. Delaware), Sep. 20, 2023.

US Exhibit 1 to the Proposed Pretrial Order Parties' Joint Statement of Uncontroverted Facts, Case No. 21-CV-977-KAJ (D. Delaware), Sep. 20, 2023.

US Memorandum Opinion, Case No. 21-CV-977-KAJ (D. Delaware)—Public Version, Aug. 15, 2023.

US Order, Case No. 21-CV-977-KAJ (D. Delaware), Aug. 15, 2023.

US Appendix of Attachments and Exhibits for Plaintiffs' Opening Letter Brief in Support of Plaintiffs' Motion to Strike Defendant's New Claim Constructions, Case No. 21-CV-977-KAJ (D. Delaware)—Public Version, Aug. 10, 2023.

US Opening Letter Brief in Support of Plaintiffs' Motion to Strike Defendant's New Claim Constructions, Case No. 21-CV-977-KAJ (D. Delaware)—Public Version, Aug. 10, 2023.

US Dexcom's Letter Brief in Opposition to Abbott's Motion to Strike, Case No. 21-CV-977-KAJ (D. Delaware)—Public Version, Aug. 9, 2023.

US Plaintiffs' Motion to Strike Defendant's New Claim Constructions, Case No. 21-CV-977-KAJ (D. Delaware), Aug. 3, 2023.

US Plaintiffs' Letter Response to the Court's Questions Regarding the IPR Final Written Decision Relating to U.S. Pat. No. 10,945,649, Case No. 21-CV-977-KAJ (D. Delaware)—Public Version, Jul. 26, 2023.

US Letter to Hon. Kent Jordan re Impact of Final Written Decision, Case No. 21-CV-977-KAJ (D. Delaware), Jul. 19, 2023.

US *Abbott* v *Dexcom* —Trial C—Construction Schedule, Case No. 21-CV-977-KAJ (D. Delaware), Jul. 18, 2023.

US Notice of Final Written Decision Re Inter Partes Review of the '649 Patent, Case No. 21-CV-977-KAJ (D. Delaware), Jul. 13, 2023.

US Transcript of Motion Hearing, Case No. 21-CV-977-KAJ (D. Delaware), Jun. 30, 2023.

US Defendant Dexcom, Inc.'s Reply Brief in Support of its Motion to Strike Abbott's Late-Disclosed Supplemental Declarations, Case No. 21-CV-977-KAJ (D. Delaware)—Public Version, Jun. 26, 2023.

US Appendix of Exhibits in Support of Dexcom, Inc.'s Opposition to Plaintiffs' Motion for Summary Judgement and Daubert Challenges—vol. 2, Case No. 21-CV-977-KAJ (D. Delaware)—Public Version, Jun. 23, 2023.

US Appendix of Exhibits in Support of Dexcom, Inc.'s Opposition to Plaintiffs' Motion for Summary Judgement and Daubert Challenges—vol. 1, Case No. 21-CV-977-KAJ (D. Delaware)—Public Version, Jun. 23, 2023.

US Defendant Dexcom, Inc.'s Appendix to Brief in Support of its Reply to Abbott Diabetes Care Inc. and Abbott Diabetes Care Limited's Opposition to Dexcom Inc.'s Motions for Summary Judgement, Case No. 21-CV-977-KAJ (D. Delaware)—Public Version, Jun. 23, 2023.

US Appendix of Exhibits and Attachments for Plaintiffs' Responsive Letter Brief In Opposition to Dexcom's Motion to Strike Expert Declarations (D.I. 408), Case No. 21-CV-977-KAJ (D. Delaware)—Public Version, Jun. 23, 2023.

US Plaintiffs' Responsive Letter Brief in Opposition to Defendant's Motion to Strike Expert Declarations, Case No. 21-CV-977-KAJ (D. Delaware)—Public Version, Jun. 23, 2023.

US Defendant Dexcom, Inc.'s Appendix to Brief in Support of its Reply to Abbott Diabetes Care Inc. and Abbott Diabetes Care Limited's Opposition to Dexcom Inc.'s Motions to Exclude Expert Reports and Testimony, Case No. 21-CV-977-KAJ (D. Delaware)—Public Version, Jun. 16, 2023.

US Defendant Dexcom, Inc.'s Opening Brief in Support of its Motion to Strike Abbott's Late-Disclosed Supplemental Declarations, Case No. 21-CV-977-KAJ (D. Delaware)—Public Version, Jun. 16, 2023.

US Dexcom, Inc.'s Motion to Strike Plaintiffs' Untimely Expert Opinions, Case No. 21-CV-977-KAJ (D. Delaware), Jun. 16, 2023.

US Appendix of Exhibits (vol. 3 of 3, Exhibits 151-171) for Plaintiffs' Answering Briefs In Opposition to Dexcom's Motions for Summary Judgement (D.I. 331) and to Exclude Expert Reports and Testimony (D.I. 337), Case No. 21-CV-977-KAJ (D. Delaware)—Public Version, Jun. 7, 2023.

US Appendix of Exhibits (vol. 2 of 3, Exhibits 138-150) for Plaintiffs' Answering Briefs In Opposition to Dexcom's Motions for Summary Judgement (D.I. 331) and to Exclude Expert Reports and Testimony (D.I. 337), Case No. 21-CV-977-KAJ (D. Delaware)—Public Version, Jun. 7, 2023.

US Appendix of Exhibits (vol. 1 of 3, Exhibits 98-137) for Plaintiffs' Answering Briefs In Opposition to Dexcom's Motions for Summary Judgement (D.I. 331) and to Exclude Expert Reports and Testimony (D.I. 337), Case No. 21-CV-977-KAJ (D. Delaware)—Public Version, Jun. 7, 2023.

US Supplemental Declaration of Karl R. Leinsing, MSME, PE, Regarding Validity, Case No. 21-CV-977-KAJ (D. Delaware)—Public Version, Jun. 7, 2023.

US Declaration of John L. Smith, PH.D., on Validity, in Support of Plaintiffs' Answering Brief in Opposition to Dexcom's Motions for Summary Judgement and Plaintiffs' Answering Brief in Opposition to Dexcom's Motions to Exclude Expert Reports and Testimony, Case No. 21-CV-977-KAJ (D. Delaware)—Public Version, Jun. 7, 2023.

US Declaration of John L. Smith, PH.D., Regarding Infringement, in Support of Plaintiffs' Answering Brief in Opposition to Dexcom's Motions for Summary Judgement and Plaintiffs' Answering Brief in Opposition to Dexcom's Motions to Exclude Expert Reports and Testimony, Case No. 21-CV-977-KAJ (D. Delaware)—Public Version, Jun. 7, 2023.

US Declaration of Dr. John E. Anderson in Opposition to Defendant Dexcom, Inc.'s Motions to Exclude Expert Reports and Testimony, Case No. 21-CV-977-KAJ (D. Delaware)—Public Version, Jun. 7, 2023.

US Declaration of Dr. Eden M. Miller in Opposition to Defendant Dexcom, Inc.'s Motions to Exclude Expert Reports and Testimony, Case No. 21-CV-977-KAJ (D. Delaware)—Public Version, Jun. 7, 2023.

US Declaration of Catherine M. Lawton in Opposition to Defendant Dexcom, Inc.'s Motions to Exclude Expert Reports and Testimony, Case No. 21-CV-977-KAJ (D. Delaware)—Public Version, Jun. 7, 2023.

US Declaration of Eric B. Hanson in Support of Dexcom's Opposition to Plaintiffs' Motion for Summary Judgement and Daubert Challenges, Case No. 21-CV-977-KAJ (D. Delaware), Jun. 6, 2023.

US Defendant Dexcom, Inc.'s Opening Brief in Support of Its Motions to Exclude Expert Reports and Testimony, Case No. 21-CV-977-KAJ (D. Delaware)—Public Version, May 19, 2023.

US Declaration of Karl R. Leinsing, MSME, PE, in Support of Abbott's Motion for Summary Judgement, Case No. 21-CV-977-KAJ (D. Delaware)—Public Version, May 19, 2023.

US Video-Recorded Deposition of Neil Sheehan, Ph.D, Case No. 21-CV-977-KAJ (D. Delaware), May 4, 2023.

US Video Deposition of Karl R. Leinsing, MSME, PE, vol. I, Case No. 21-CV-977-KAJ (D. Delaware), May 3, 2023.

US Videotaped Deposition of John Mastrototaro, Ph.D, Case No. 21-CV-977-KAJ (D. Delaware), Apr. 26, 2023.

US Video-Recorded Deposition of John Smith, Ph.D, Case No. 21-CV-977-KAJ (D. Delaware), Apr. 21, 2023.

US Expert Report of John L. Smith, Ph.D., on Infringement of the Asserted Claims of U.S. Pat. No. 10,827,954, Case No. 21-CV-977-KAJ (D. Delaware), Mar. 14, 2023.

US Oral Argument Hearing Before Hon. Kent A. Jordan, U.S. Circuit Court Judge, Case No. 21-CV-977-KAJ (D. Delaware), Mar. 9, 2023.

US Defendant Dexcom, Inc.'s Supplemental Responses to Plaintiffs Abbott Diabetes Care Inc's. and Abbott Diabetes Care Limited's Notice of Rule 30(b)(6) Deposition, Case No. 21-CV-977-KAJ (D. Delaware), Feb. 8, 2023.

US Telephone Conference Before Kent A. Jordan, U.S. Circuit Court Judge, Case No. 21-CV-977-KAJ (D. Delaware), Jan. 3, 2023.

US Letter to the Honorable Kent A. Jordan Regarding Discovery Disputes, Case No. 21-CV-977-KAJ (D. Delaware), Dec. 28, 2022.

(56)　　　　　References Cited

OTHER PUBLICATIONS

US Order Denying Evenflo's Motion for Summary Judgement of Non-Infringement and Granting in Part and Denying in Part Wonderland's Motion for Partial Summary Judgement, Case 20-CV-727-JPM (D. Delaware), Dec. 6, 2022.
US Defendant Dexcom, Inc.'s Notice of Deposition to Plaintiff Abbott Diabetes Care Limited, Case No. 21-CV-977-KAJ (D. Delaware), Aug. 19, 2022.
US Defendant Dexcom, Inc.'s Notice of Deposition to Plaintiff Abbott Diabetes Care Inc., Case No. 21-CV-977-KAJ (D. Delaware), Aug. 19, 2022.
US Plaintiffs' Proposed Claim Constructions, Case 21-CV- 977-KAJ, May 27, 2022.
US Plaintiffs' Identification of Claim Terms For Construction, Case 21-CV-977-KAJ (D. Delaware), May 13, 2022.
US Joint Claim Construction Brief, Case 20-1679-RGA-JLH (D. Delaware), Feb. 11, 2022.
US Plaintiff Dexcom, Inc.'s Amended Preliminary Disclosure of Asserted Claims and Infringement Contentions to Abbott Diabetes Care Inc. and Abbott Diabetes Care Sales Corp., Case 21-CV-690-ADA ((D. Texas), Jan. 5, 2022.
US Findings of Fact and Conclusions of Law Regrading Subject Matter Eligibility of U.S. Pat. No. 6,975,308 Under 35 U.S.C. §101, Case 20-CV-101-ADA (D. Texas), Dec. 7, 2021.
US Non-Final Office Action issued in U.S. Appl. No. 17/030,030, Dec. 17, 2020.
US Non-Final Office Action issued in U.S. Appl. No. 17/017,590.
US Notice of Allowance issued in U.S. Appl. No. 15/963,828, Mar. 3, 2021.
US Response to Non-Final Office Action filed in U.S. Appl. No. 15/963,828, Dec. 8, 2020.
US Request Under 37 CRR 1.48(a) to Correct Inventorship filed in U.S. Appl. No. 15/963,828, Dec. 8, 2020.
US Joint Declaration Under 37 C.F.R. 1.131 filed in U.S. Appl. No. 15/963,828, Nov. 30, 2020.
US Non-Final Office Action issued in U.S. Appl. No. 14/884,622, Jun. 13, 2018.
US Response to Restriction Requirement, and Acknowledgement Receipt, filed in U.S. Appl. No. 14/884,622, Apr. 5, 2018.
Breton, M. D., et al., "Optimum Subcutaneous Glucose Sampling and Fourier Analysis of Continuous Glucose Monitors", Journal of Diabetes Science and Technology, 2008, vol. 2, No. 3, pp. 495-500.
Dexcom G6 Continuous Glucose Monitoring System User Guide, 2019, pp. 1-27.
Dexcom G7 Inserting Sensor Instructions for Use, 2021, pp. 1-2.
Dexcom G7, Start Here, Operational Manual, 2022, pp. 1-9 (English Abstract).
Dexcom G7, User Guide, 2022, p. 1-179 (English Abstract).
Panteleon, A. E., et al., "The Role of the Independent Variable to Glucose Sensor Calibration", Diabetes Technology & Therapeutics, 2003, vol. 5, No. 3, pp. 401-410.
Parker, S. P., ed., McGraw-Hill Dictionary of Mechanical and Design Engineering, 1984 (excerpted), pp. 1-4.
Shenoi, B. A., ed., Introduction to Digital Signal Processing and Filter Design, 2006, "Introduction", Chapter 1, pp. 1-30.
Smith, S. S., ed., The Scientist and Engineer's Guide to Digital Signal Processing, Second Edition, 1997-1999, "Digital Signal Processors", Chapter 28, pp. 503-534.
CA 2,617,192 Examiner's Report, Oct. 22, 2012.
CA 2,984,939 Examiner's Report, Nov. 15, 2023.
CA 3,182,961 Examiner's Report, Dec. 6, 2023.
CN 200780039416.2 Second Office Action, Apr. 25, 2012.
CN 200780039416.2 First Office Action, Mar. 30, 2011.
CN 200880005388.7 Second Office Action, May 16, 2012.
CN 200880005388.7 First Office Action, Jul. 25, 2011.
CN 201980082748.1 Final Office Action, Nov. 27, 2023.
EP 06788869.3 Examination Report, Sep. 25, 2012.
EP 06788869.3 Extended Search Report, Mar. 18, 2010.
EP 06813967.4 Extended Search Report, Mar. 4, 2010.
EP 07854298.2 Extended Search Report, Mar. 29, 2010.

EP 08730066.1 Extended Search Report, Oct. 5, 2012.
EP 10739031.2 Communication from Board of Appeals, Feb. 21, 2024.
EP 10739031.2 Summons to Attend Oral Proceedings, Oct. 26, 2023.
EP 18741791.0 Examination Report, Dec. 15, 2023.
EP 20177703.4 Reply to Reply to Reply to Notice of Oppositon ADC, Dec. 18, 2023.
EP 20177703.4 Reply to Notice of Intervention, Nov. 17, 2023.
EP 20177712.5 Response to Written Submissions Dexcom, Feb. 26, 2024.
EP 20177712.5 Written Submissions ADC, Jan. 26, 2024.
EP 20177712.5 Reply to Reply to Reply to Notice of Opposition ADC, Dec. 18, 2023.
EP 20177712.5 Reply to Notice of Intervention, Nov. 17, 2023.
EP 20195922.8 Written Submissions Dexcom, Mar. 15, 2024.
EP 20195922.8 Response to Summons to Attend Oral Proceedings, Feb. 15, 2024.
EP 20195922.8 Written Submissions Dexcom, Dec. 12, 2023.
EP 20195922.8 Written Submissions ADC, Oct. 23, 2023.
EP 23166498.8 Extended Search Report, Nov. 17, 2023.
EP 23190032.5 Extended Search Report, Nov. 17, 2023.
JP 2009-534799 Final Office Action, Feb. 19, 2013.
JP 2009-534799 Office Action, Sep. 27, 2011.
MX MX/a/2009/004322 Office Action, Mar. 11, 2013.
MX MX/a/2009/004322 Office Action, Sep. 19, 2012.
MY PI2023005466 Examination Report, Dec. 28, 2023.
RU 2009135048 Office Action, Dec. 20, 2011.
RU 2009119430 Office Action, Jun. 5, 2011.
US Third Declaration of Gary Fletcher, Ph.D., IPR No. 2024-00520, Jan. 31, 2024.
US Petition For Inter Partes Review of U.S. Pat. No. 11,266,335, IPR. 2024-00520, Jan. 31, 2024.
US Patent Owner's Preliminary Response, IPR No. 2023-01409, Jan. 18, 2024.
US Notice of Filing Date Accorded to Petition and Time for Filing Patent Owner Preliminary Resonse, IPR No. 2023-01409, Oct. 18, 2023.
US Patent Owner's Response to Petitioner's Explanation of Material Differences Between Petitions, IPR Nos. 2023-01396 and 2023-01397, Jan. 18, 2024.
US Petitioner's Explanation of Material Differences Between Petitions, IPR No. 2023-01397, Oct. 6, 2023.
US Declaration of Gary D. Fletcher, Ph.D, IPR No. 2023-01396 and IPR No. 2023-01397, Oct. 6, 2023.
US Patent Owner's Preliminary Response, IPR No. 2023-01396, Jan. 18, 2024.
US Notice of Filing Date Accorded to Petition and Time for Filing Patent Owner Preliminary Response, IPR No. 2023-01396, Oct. 18, 2023.
US Petitioner's Explanation of Material Differences Between Petitions, IPR No. 2023-01396, Oct. 6, 2023.
US Notice of Final Written Decision re Inter Partes Review of the '649 Patent, IPR No. 2022-00605, Jul. 13, 2023.
US Reexamination U.S. Appl. No. 90/019,329 Order Granting Request for Reexamination of U.S. Pat. No. 11,013,440, Jan. 23, 2024.
US Request for Ex Parte Reexamination Under 35.U.S.C. §§ 302-307 and 37 C.F.R. § 1.510 of U.S. Pat. No. 11,013,440, Dec. 11, 2023.
US Reexamination U.S. Appl. No. 90/019,331 Order Granting Request for Reexamination of U.S. Pat. No. 11,000,216, Jan. 23, 2024.
US Request for Ex Parte Reexamination Under 35.U.S.C. §§ 302-307 and 37 C.F.R. § 1.510 of U.S. Pat. No. 11,000,216, Dec. 11, 2023.
US Reexamination U.S. Appl. No. 90/019,307 Order Granting Request for Reexamination of U.S. Pat. No. 10,973,443, Dec. 22, 2023.
US Request for Ex Parte Reexamination Under 35.U.S.C. §§ 302-307 and 37 C.F.R. § 1.510 of U.S. Pat. No. 10,973,443, Nov. 27, 2023.

(56) References Cited

OTHER PUBLICATIONS

US Reexamination U.S. Appl. No. 90/019,330 Order Granting Request for Reexamination of U.S. Pat. No. 10,959,654, Jan. 23, 2024.
US Request for Ex Parte Reexamination Under 35.U.S.C. §§ 302-307 and 37 C.F.R. § 1.510 of U.S. Pat. No. 10,959,654, Dec. 11, 2023.
US Scheduling Order, Case No. 23-239-KAJ, Sep. 19, 2023.
US Dexcom, Inc.'s Answer, Affirmative Defenses, and Counterclaims, Case No. 23-CV-239-UNA (D. Delaware), May 12, 2023, May 12, 2023.
US Complaint, Case 23-CV-239-UNA (D. Delaware), Mar. 3, 2023.
US Dexcom's Motions In Limine, Abbott Exhibit 11, Case No. 21-CV-977-KAJ (D. Delaware), Jan. 12, 2024.
US Dexcom's Motions In Limine, Abbott Exhibit 9, Case No. 21-CV-977-KAJ (D. Delaware), Jan. 12, 2024.
US Dexcom's Motions In Limine, Abbott Exhibit 8, Case No. 21-CV-977-KAJ (D. Delaware), Jan. 12, 2024.
US Dexcom's Motions In Limine, Abbott Exhibit 3, Case No. 21-CV-977-KAJ (D. Delaware), Jan. 12, 2024.
US Abbott's Motions In Limine, Dexcom Exhibit B, Case No. 21-CV-977-KAJ (D. Delaware), Jan. 12, 2024.
US [Proposed] Final Pretrial Order, vol. 3, Case No. 21-CV-977-KAJ (D. Delaware)—Public Version, Jan. 12, 2024.
US [Proposed] Final Pretrial Order, vol. 2, Case No. 21-CV-977-KAJ (D. Delaware)—Public Version, Jan. 12, 2024.
US Exhibit 7P to the Proposed Pretrial Order Abbott's Brief Summary of Opinion Testimony, Case No. 21-CV-977-KAJ (D. Delaware), Jan. 4, 2024.
US Exhibit 6P to the Proposed Pretrial Order Abbott's Deposition Designations, Case No. 21-CV-977-KAJ (D. Delaware), Jan. 4, 2024.
US Exhibit 6D to the Proposed Pretrial Order Dexcom's Deposition Designations, Case No. 21-CV-977-KAJ (D. Delaware), Jan. 4, 2024.
US Exhibit 5P to the Proposed Pretrial Order Abbott's List of Trial Exhibits, Case No. 21-CV-977-KAJ (D. Delaware), Jan. 4, 2024.
US Exhibit 5D to the Proposed Pretrial Order Dexcom's List of Trial Exhibits, Case No. 21-CV-977-KAJ (D. Delaware), Jan. 4, 2024.
US Exhibit 4 to the Proposed Pretrial Order Joint List of Trial Exhibits, Case No. 21-CV-977-KAJ (D. Delaware), Jan. 4, 2024.
US Exhibit 3P to the Proposed Pretrial Order Abbott's Statement of Issues of Law Which Remain to be Litigated, Case No. 21-CV-977-KAJ (D. Delaware), Jan. 4, 2024.
US Exhibit 3D to the Proposed Pretrial Order Dexcom's Statement of Issues of Law Which Remain to be Litigated, Case No. 21-CV-977-KAJ (D. Delaware), Jan. 4, 2024.
US Exhibit 2P to the Proposed Pretrial Order Abbott's Statement of Issues of Fact Which Remain to be Litigated, Case No. 21-CV-977-KAJ (D. Delaware), Jan. 4, 2024.
US Exhibit 2D to Proposed Pretrial Order Dexcom's Statement of Contested Facts, Case No. 21-CV-977-KAJ (D. Delaware), Jan. 4, 2024.
US Exhibit 1 to the Proposed Pretrial Order Parties' Joint Statement of Uncontroverted Facts, Case No. 21-CV-977-KAJ (D. Delaware), Jan. 4, 2024.
US [Proposed] Final Pretrial Order, Case No. 21-CV-977-KAJ (D. Delaware), Jan. 4, 2024.
US Joint Letter to the Honorable Kent A. Jordan Regarding Additional Issues Related to the Upcoming Trial, Case No. 21-CV-977-KAJ (D. Delaware)—Public Version, Oct. 6, 2023.
US Defendant Dexcom, Inc.'s Reply in Support of its Motions to Exclude Expert Reports and Testimony, Case No. 21-CV-977-KAJ (D. Delaware)—Public Version, May 16, 2023.
US Plaintiffs' Answering Briefs In Opposition to Dexcom's Motions to Exclude Expert Reports and Testimony, Case No. 21-CV-977-KAJ (D. Delaware)—Public Version, Jun. 7, 2023.

US Dexcom, Inc.'s Amended Answer to Second Amended Complaint, Case 21-CV-977-KAJ (D. Delaware)—Public Version, Mar. 17, 2023.
US Defendant Dexcom, Inc.'s Supplemental Objections and Responses to Plaintiffs' Second Set of Interrogatories, Nos. 11, 14, 15, 21-25, Corrected, Case No. 21-CV-977-KAJ (D. Delaware)—Public Version, Dec. 20, 2022.
US Defendant Dexcom, Inc.'s Supplemental Objections and Responses to Plaintiffs' Second Set of Interrogatories, Nos. 11, 14, 15, 21-25, Case No. 21-CV-977-KAJ (D. Delaware)—Public Version, Dec. 6, 2022.
US Defendant Dexcom, Inc.'s Objections and Responses to Plaintiffs' Second Set of Interrogatories, Case No. 21-CV-977-KAJ (D. Delaware)—Public Version, Dec. 6, 2022.
WO PCT/US2006/029541 ISR and Written Opinion, Apr. 24, 2007.
WO PCT/US2006/033885 ISR and Written Opinion, Aug. 3, 2007.
WO PCT/US2007/082121 ISR and Written Opinion, May 9, 2008.
WO PCT/US2008/054186 ISR and Written Opinion, Aug. 8, 2008.
WO PCT/US2008/065154 ISR and Written Opinion, Sep. 3, 2008.
WO PCT/US2010/047065 ISR and Written Opinion, Dec. 21, 2010.
WO PCT/US2010/047414 ISR and Written Opinion, Dec. 27, 2010.
WO PCT/US2010/047415 ISR and Written Opinion, Oct. 25, 2010.
CA 2,984,939 Examiner's Report, Aug. 7, 2024.
CA 3,120,335 Examiner's Report, May 27, 2024.
CA 3,120,335 Examiner's Report, Mar. 31, 2023.
CN 200880005149.1 Notice of Allowance, Jun. 21, 2013.
CN 200880005149.1 Fourth Office Action, Dec. 3, 2012.
CN 200880005149.1 Third Office Action, Feb. 16, 2012.
CN 200880005149.1 Second Office Action, Aug. 17, 2011.
CN 200880005149.1 First Office Action, Jul. 29, 2010.
DE Complaint in Litigation of EP 3300658, Mar. 20, 2024.
DE Statement of Defense (Counterclaim), Case No. 21 O 6562/23, Sep. 1, 2023.
EP 10739031.2 Decision of Oral Proceedings, Jun. 11, 2024.
EP 10739031.2 Minutes of Oral Proceedings, May 10, 2024.
EP 17182379.2 Grounds of Opposition, Jul. 12, 2024.
EP 17182379.2 Notice of Opposition, Jul. 12, 2024.
EP 17182379.2 Reply to Examination Report, Apr. 9, 2021.
EP 17182379.2 Reply to Search Report, Oct. 3, 2018.
EP 19900891.3 Extended Search Report, Sep. 26, 2022.
EP 20177703.4 Summons to Attend Oral Proceedings, Apr. 29, 2024.
EP 20177712.5 Response to Summons to Attend Oral Proceedings, Aug. 30, 2024.
EP 20177712.5 Summons to Attend Oral Proceedings, Jul. 2, 2024.
EP 20195922.8 Grounds of Appeal, Sep. 6, 2024.
EP 20195922.8 Notice of Appeal, Jul. 4, 2024.
EP 20195922.8 Written Submissions Dexcom, May 9, 2024.
EP 20195922.8 Decision Revoking the European Patent, May 8, 2024.
EP 20195922.8 Minutes of the Oral Proceedings, May 8, 2024.
EP 21211041.5 Reply to Notice of Opposition, Jul. 17, 2024.
EP 21211041.5 Grounds of Opposition Dexcom, Mar. 28, 2024.
EP 21211041.5 Notice of Opposition Dexcom, Mar. 28, 2024.
EP 23166498.8 Examination Report, Sep. 2, 2024.
EP 24152079.0 Extended Search Report, Sep. 4, 2024.
EP 25152079.0 Partial Search Report, Jun. 14, 2024.
GB Claim No. HP-2023-000012 Amended Grounds of Invalidity, Mar. 15, 2024.
GB Claim No. HP-2023-000012 Order Mar. 7, 2024.
GB Claim No. HP-2023-000012 Dexcom's Statement of Case on Validity, Feb. 8, 2024.
GB Claim No. HP-2023-000025 Approved Judgement, Oct. 18, 2023.
MX MX/a/2021/007294 Office Action, Aug. 20, 2024.
RU 2009134334 Office Action, Feb. 7, 2012.
UP First Expoert Opinion of Dr. Michael Schoemaker of Litigation of EP 3977921, Jun. 11, 2024.
US Notice of Filing Date Accorded to Petition and Time for Filing Patent Owner Preliminary Response, IPR No. 2024-00860, May 23, 2024.
US Declaration of Dr. Cameron Riviere, Ph.D., IPR No. 2024-00860, May 9, 2024.

(56) References Cited

OTHER PUBLICATIONS

US Petition For Inter Partes Review Of U.S. Pat. No. 11,510,625, IPR No. 2024-00860, May 9, 2024.

US Decision Denying Institution of Inter Partes Review, IPR No. 2024-00520, Aug. 8, 2024.

US Patent Owner's Authorized Sur-Reply to Petitioner's Reply to Patent Owner's Preliminary Response, IPR No. 2024-00520, Jun. 11, 2024.

US Petitioner's Authorized Reply to Patent Owner's Preliminary Response, IPR No. 2024-00520, May 31, 2024.

US Patent Owner's Preliminary Response, IPR No. 2024-00520, May 8, 2024.

US Patent Owner's Exhibit List, IPR No. 2024-00520, Mar. 25, 2024.

US Telephonic Hearing, IPR No. 2024-00520, Mar. 13, 2024.

US Petitioner's Explanation of Material Differences Between the Petition in IPR2024-00520 and Previously Filed Petitions in IPR2023-01396 and IPR2023-01397, IPR No. 2024-00520, Jan. 31, 2024.

US Order, IPR No. 2023-01409, May 30, 2024.

US Notice of Stipulation, IPR No. 2023-01409, May 29, 2024.

US Patent Owner's Objections to Petitioner's Exhibits to the Petition, IPR No. 2023-01409, Apr. 29, 2024.

US Patent Owner's Request for Rehearing by the Director, IPR 2023-01409, Apr. 29, 2024.

US Email of Peter McAndrews, IPR 2023-01409, Apr. 29, 2024.

US Decision Granting Institution of Inter Partes Review, IPR No. 2023-01409, Apr. 15, 2024.

US Scheduling Order, IPR 2023-01409, Apr. 15, 2024.

US Order Conduct of the Proceeding 37 C.F.R. § 42.5, IPR No. 2023-01409, Feb. 6, 2024.

US Petitioner's Updated Exhibit List, IPR No. 2023-01409, Feb. 6, 2024.

US Telephonic Conference Call, IPR No. 2023-01409, Feb. 2, 2024.

US Patent Owner's Updated Mandatory Notices, IPR No. 2023-01409, Feb. 2, 2024.

US Email of Andrew M. Mason, IPR 2023-01409, Jan. 30, 2024.

US Decision Denying Institution of Inter Partes Review, IPR No. 2023-01397, Apr. 16, 2024.

US Patent Owner's Updated Exhibit List, IPR No. 2023-01397, Mar. 25, 2024.

US Telephonic Hearing, IPR No. 2023-01397, Mar. 13, 2024.

US Petitioner's Updated Mandatory Notices Pursuant to 37 C.F.R. § 42.8(a)(3), IPR No. 2023-01397, Feb. 19, 2024.

US Patent Owner's Updated Mandatory Notices, IPR No. 2023-01397, Feb. 2, 2024.

US Patent Owner's Preliminary Response, IPR No. 2023-01397, Jan. 18, 2024.

US Petitioner's Request for Rehearing of Decision Denying Institution, IPR No. 2023-01396, May 16, 2024.

US Decision Denying Institution of Inter Partes Review, IPR No. 2023-01396, Apr. 16, 2024.

US Patent Owner's Updated Exhibit List, IPR No. 2023-01396, Mar. 25, 2024.

US Telephonic Hearing, IPR No. 2023-01396, Mar. 13, 2024.

US Petitioner's Updated Mandatory Notices Pursuant to 37 C.F.R. § 42.8(a)(3), IPR No. 2023-01396, Feb. 19, 2024.

US Reexamination U.S. Appl. No. 90/019,331 Notification of Concurrent Proceedings, May 15, 2024.

US Petition Under 37 CFR § 1.181 and/or § 1.182 to Terminate Reexamination No. U.S. Appl. No. 90/019,329, Apr. 26, 2024.

US Reexamination U.S. Appl. No. 90/019,331 Order Granting Request for Reexamination of U.S. Pat. No. 11,013,440, Jan. 30, 2024.

US Reexamination U.S. Appl. No. 90/019,331 Declaration of Gary D. Fletcher, Ph.D., Dec. 11, 2023.

US Reexamination U.S. Appl. No. 90/019,331 Decision Granting Petition, Aug. 26, 2024.

US Reexamination U.S. Appl. No. 90/019,331 Petition to Withdraw From Issue and Reopen the Proceeding, Jul. 26, 2024.

US Reexamination U.S. Appl. No. 90/019,331 Notice of Intent to Issue Ex Parte Reexamination Certificate, Jul. 10, 2024.

US Reexamination U.S. Appl. No. 90/019,330 Decision Granting Petition and Vacating a Reexamination Certificate, Aug. 26, 2024.

US Ex Parte Reexamination Certificate of U.S. Pat. No. 10,959,654, Aug. 5, 2024.

US Reexamination U.S. Appl. No. 90/019,330 Petition to Withdraw From Issue and Reopen the Proceeding, Jul. 26, 2024.

US Reexamination U.S. Appl. No. 90/019,330 Notice of Intent to Issue Ex Parte Reexamination Certificate of U.S. Pat. No. 10,959,654, Jul. 1, 2024.

US Reexamination U.S. Appl. No. 90/019,330 Notification of Concurrent Proceedings, May 15, 2024.

US Reexamination U.S. Appl. No. 90/019,330 Declaration of John Mastrototaro, Ph.D., Dec. 11, 2023.

US Abbott's Initial Claim Charts, Case No. 23-239-KAJ, Dec. 20, 2023.

Reference PTX-0619 of Dexcom's Reply in Support of Its Renewed Motion for Judgment as a Matter of Law and Motion for a New Trial, Case No. 21-CV-977-KAJ, Jul. 12, 2024.

US Dexcom's Reply in Support of Its Renewed Motion for Judgment as a Matter of Law and Motion for a New Trial, Case No. 21-CV-977-KAJ, Jul. 12, 2024.

US Plaintiffs' Reply Brief in Support of Their Motion for Judgment as a Matter of Law Under Federal Rule of Civil Procedure 50 and for a New Trial Under Federal Rule of Civil Procedure 59, Case No. 21-CV-977-KAJ (D. Delaware), Jul. 12, 2024.

US Reference DX4961 of Defendant Dexcom, Inc.'s Memorandum in Opposition to Plaintiffs' Motion for Judgment as a Matter of Law or, Alternatively, for a New Trial, Case No. 21-CV-977-KAJ (D. Delaware), Jun. 21, 2024.

US Reference DX4756 of Defendant Dexcom, Inc.'s Memorandum in Opposition to Plaintiffs' Motion for Judgment as a Matter of Law or, Alternatively, for a New Trial, Case No. 21-CV-977-KAJ (D. Delaware), Jun. 21, 2024.

US Reference DX4720 of Defendant Dexcom, Inc.'s Memorandum in Opposition to Plaintiffs' Motion for Judgment as a Matter of Law or, Alternatively, for a New Trial, Case No. 21-CV-977-KAJ (D. Delaware), Jun. 21, 2024.

US Reference DX1550 of Defendant Dexcom, Inc.'s Memorandum in Opposition to Plaintiffs' Motion for Judgment as a Matter of Law or, Alternatively, for a New Trial, Case No. 21-CV-977-KAJ (D. Delaware), Jun. 21, 2024.

US Reference DX0179 of Defendant Dexcom, Inc.'s Memorandum in Opposition to Plaintiffs' Motion for Judgment as a Matter of Law or, Alternatively, for a New Trial, Case No. 21-CV-977-KAJ (D. Delaware), Jun. 21, 2024.

US Reference DDX-8 of Defendant Dexcom, Inc.'s Memorandum in Opposition to Plaintiffs' Motion for Judgment as a Matter of Law or, Alternatively, for a New Trial, Case No. 21-CV-977-KAJ (D. Delaware), Jun. 21, 2024.

US Defendant Dexcom, Inc.'s Memorandum in Opposition to Plaintiffs' Motion for Judgment as a Matter of Law or, Alternatively, for a New Trial, Case No. 21-CV-977-KAJ (D. Delaware), Jun. 21, 2024.

US Plaintiffs' Opening Brief in Support of Their Motion for Judgment as a Matter of Law Under Federal Rule of Civil Procedure 50 and for a New Trial Under Federal Rule of Civil Procedure 59, Case No. 21-CV-977-KAJ (D. Delaware), May 24, 2024.

US Defendant Dexcom, Inc.'s Opening Brief in Support of Its Renewed Motion for Judgment as a Matter of Law and Motion for New Trial, Case No. 21-CV-977-KAJ (D. Delaware), May 24, 2024.

US Reference Exhibit B of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.

US Reference Exhibit A of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.

(56)        References Cited

OTHER PUBLICATIONS

US Reference DDX-4 of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.
US Reference DX4726 of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.
US Reference DX4721 of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.
US Reference DX4719 of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.
US Reference DX0381 of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.
US Reference DX0189 of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.
US Reference DX0183 of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.
US Reference DX0012 of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.
US Reference PDX07 of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.
US Reference PTX-3026 of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.
US Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.
US Joint Status Report, Case No. 21-CV-977-KAJ (D. Delaware), May 7, 2024.
US Plaintiffs' Renewed Motion for Judgment as a Matter of Law, Case No. 21-CV-977-KAJ (D. Delaware), Apr. 19, 2024.
US Dexcom, Inc's Renewed Motion for Judgment as a Matter of Law and Motion for New Trial, Case No. 21-CV-977-KAJ (D. Delaware), Apr. 19, 2024.
US Joint Status Report, Case No. 21-CV-977-KAJ (D. Delaware), Apr. 5, 2024.
US Transcript of Jury Trial, vol. X, Case No. 21-CV-977-KAJ (D. Delaware), Mar. 22, 2024.
US Transcript of Jury Trial, vol. IX, Case No. 21-CV-977-KAJ (D. Delaware), Mar. 21, 2024.
US Transcript of Jury Trial, vol. VIII, Case No. 21-CV-977-KAJ (D. Delaware), Mar. 20, 2024.
US Transcript of Jury Trial, Case No. 21-CV-977-KAJ (D. Delaware), Mar. 19, 2024.
US Transcript of Jury Trial, vol. VI, Case No. 21-CV-977- Kaj (D. Delaware), Mar. 18, 2024.
US [Joint Proposed] Final Jury Instructions, Case No. 21-CV-977-KAJ (D. Delaware), Mar. 17, 2024.
US Transcript of Jury Trial, vol. V, Case No. 21-CV-977-KAJ (D. Delaware), Mar. 15, 2024.
US Transcript of Jury Trial, vol. IV, Case No. 21-CV-977-KAJ (D. Delaware), Mar. 14, 2024.

US Transcript of Jury Trial, vol. III, Case No. 21-CV-977-KAJ (D. Delaware), Mar. 13, 2024.
US Transcript of Jury Trial, vol. II, Case No. 21-CV-977-KAJ (D. Delaware), Mar. 12, 2024.
US Transcript of Jury Trial, vol. I, Case No. 21-CV-977-KAJ (D. Delaware), Mar. 11, 2024.
US [Joint Proposed] Final Jury Instructions, Case No. 21-CV-977-KAJ (D. Delaware), Mar. 7, 2024.
US [Proposed] Final Pretrial Order, vol. 2, Case No. 21-CV-977-KAJ (D. Delaware), Mar. 7, 2024.
US Exhibit 7P to the Proposed Pretrial Order Abbott's Brief Summary of Opinion Testimony, Case No. 21-CV-977-KAJ (D. Delaware), Mar. 7, 2024.
US Exhibit 7D to the Proposed Pretrial Order Dexcom's Brief Summary of Opinion Testimony, Case No. 21-CV-977-KAJ (D. Delaware), Mar. 7, 2024.
US Exhibit 6D to the Proposed Pretrial Order Dexcom's Deposition Designations, Case No. 21-CV-977-KAJ (D. Delaware), Mar. 7, 2024.
US Exhibit 5P to the Proposed Pretrial Order Abbott's List of Trial Exhibits, Case No. 21-CV-977-KAJ (D. Delaware), Mar. 7, 2024.
US Exhibit 5D to the Proposed Pretrial Order Dexcom's List of Trial Exhibits, Case No. 21-CV-977-KAJ (D. Delaware), Mar. 7, 2024.
US Exhibit 3P to the Proposed Pretrial Order Abbott's Statement of Issues of Law Which Remain to be Litigated, Case No. 21-CV-977-KAJ (D. Delaware), Mar. 7, 2024.
US Exhibit 3D to the Proposed Pretrial Order Dexcom's Statement of Issues of Law Which Remain to be Litigated, Case No. 21-CV-977-KAJ (D. Delaware), Mar. 7, 2024.
US Exhibit 2P to the Proposed Pretrial Order Abbott's Statement of Issues of Fact Which Remain to be Litigated, Case No. 21-CV-977-KAJ (D. Delaware), Mar. 7, 2024.
US Exhibit 2D to Proposed Pretrial Order Dexcom's Statement of Contested Facts, Case No. 21-CV-977-KAJ (D. Delaware), Mar. 7, 2024.
US Exhibit 1 to the Proposed Pretrial Order Parties' Joint Statement of Uncontroverted Facts, Case No. 21-CV-977-KAJ (D. Delaware), Mar. 7, 2024.
US [Proposed] Final Pretrial Order, Case No. 21-CV-977- Kaj (D. Delaware), Mar. 7, 2024.
US Joint Stipulation and [Proposed] Order Regarding Dismissal of Certain Asserted Patent Claims, Case No. 21-CV-977-KAJ (D. Delaware), Mar. 1, 2024.
US Defendant Dexcom, Inc.'s Notice Pursuant to 35 U.S.C. § 282, Case No. 21-CV-977-KAJ (D. Delaware), Feb. 9, 2024.
US Letter to the Honorable Kent A. Jordan Regarding Pretrial Order, Case No. 21-CV-977-KAJ (D. Delaware), Feb. 2, 2024.
US Letter to the Honorable Kent A. Jordan From Nathan R. Hoeschen Regarding Pretrial Order, Case No. 21-CV-977-KAJ (D. Delaware)—Public Version, Feb. 1, 2024.
US [Joint Proposed] Final Jury Instructions, Case No. 21-CV-977-KAJ (D. Delaware), Jan. 31, 2024.
US Plaintiffs' Opening Brief in Support of Its Motions for Summary Judgement and Daubert Challenges, Case No. 21-CV-977-KAJ (D. Delaware)—Public Version, May 19, 2023.
US Order, Case No. 21-CV-977-KAJ (D. Delaware), Mar. 22, 2023.
US Memorandum Opinion, Case No. 21-CV-977-KAJ (D. Delaware), Mar. 22, 2023.
US Plaintiffs' Second Set of Interrogatories (Nos. 10-33) to Defendant, Case 21-CV-977-KAJ (D. Delaware), Sep. 8, 2022.
US Memorandum Opinion and Order, Case No. 21-209-WCB (D. Delaware), Mar. 3, 2023.
WO PCT/US2008/054165 ISR and Written Opinion, Jun. 5, 2008.
WO PCT/US2008/067791 ISR and Written Opinion, Sep. 30, 2008.
WO PCT/US24/11756 ISR and Written Opinion, Jun. 28, 2024.
WO PCT/US24/11756 Invitation to Pay Additional Fees, May 7, 2024.
WO PCT/US24/16127 Invitation to Pay Additional Fees, Jun. 4, 2024.
WO PCT/US24/18665 ISR and Written Opinion, Jun. 21, 2024.

(56) References Cited

OTHER PUBLICATIONS

"27 Winners Announced at the 19th Annual Medical Design Excellence Awards (MDEA) Award Ceremony", UBM Americas, 2017, 4 pages.

"55 Chosen as Winners in Annual BIG Innovation Awards", 2018, retrieved from https://www.bintelligence.com/posts/55-chosen-as-winners-in-annual-big-innovation-awards, 2 pages.

2017 Good Design Award, retrieved from https://www.g-mark.org/gallery/winners/9dda01a3-803d-11ed-af7e-0242ac130002, 9 pages.

"2019 Top 10 Innovations", The Scientist, retrieved from https://www.the-scientist.com/2019-top-10-innovations-66738, 7 pages.

Abbott 2023 Annual Report, retrieved from https://www.abbottinvestor.com/static-files/6cb09c09-2422-40e0-a24b-6545ffcf5267, pp. 1-82.

Abbott Clinical Trials Competitor and Ecosystem Players, 2020, 28 pages.

"Abbott's Freestyle Libre® Is Named Best Medical Technology In Last 50 Years By The Galien Foundation", 2022, PRNewswire, 1 page.

"Abbott's Freestyle® Libre 2 ICGM Cleared in U.S. for Adults and Children With Diabetes, Achieving Highest Level of Accuracy and Performance Standards", retrieved from https://abbott.mediaroom.com/2020-06-15-Abbotts-FreeStyle-R-Libre-2-iCGM-Cleared-in-U-S-for-Adults-and-Children-with-Diabetes-Achieving-Highest-Level-of-Accuracy-and-Performance-tandards# :~:text=FDA%20clears%20Abbott's%20FreeStyle%20Libre,high%20or%20low%20without%20scanning, on Jul. 7, 2024, 3 pages.

"Abbott's Freestyle Libre® 3 Receives U.S. FDA Clearance—Features World's Smallest, Thinnest and Most Accurate 14-Day Glucose Sensor", 2022, PRNewswire, 3 pages.

"Abbott's Freestyle Libre Flash Glucose Monitoring System Wins the IMSTA Most Innovative Product Multi-National Award 2017", retrieved from https://www.ie.abbott/media-center/news/abbotts-freestyle-libre-flash-glucose-monitoring-system-wins-the-imsta-award-2017.html, 2 pages.

"Abbott's Freestyle® Libre 14 Day Flash Glucose Monitoring System Now Approved in U.S.", 2018, PRNewswire, 2 pages.

About the Edison Awards retrieved from https://edisonawards.com/about/, 2024, 3 pages.

Ahn, D., "Abbott's Euro approved wearable glucose monitor is different than anything on the market", 2014, retrieved from https://www.imedicalapps.com/2014/09/abbotts-wearable-glucose-monitor/, 6 pages.

"BinaxNOW, FreeStyle Libre 2 win BIG innovation honors", 2021, retrieved from https://www.abbott.com/corpnewsroom/strategy-and-strength/binaxnow-freestyle-libre-win-big-innovation-honors.html, 6 pages.

Blum, A., "Freestyle Libre Glucose Monitoring System", Clinical Pharmacology Update, 2018, vol. 36, No. 2, pp. 203-204.

Cather, D. E., "CGM Frustrations Survey", 2020, 36 pages.

Certified U.S. Appl. No. 61/149,639, filed Feb. 3, 2009.

CES 2022 Innovation Award Honorees, retrieved from https://www.ces.tech/innovation-awards/honorees/2022/best-of/f/freestyle-libre-3-system.aspx, 1 page.

2019 Chicago Innovation Award Winner Abbott Laboratories, retrieved from https://chicagoinnovation.com/winners/abbott-laboratories/, 4 pages.

Design Concepts Project Status Update, Glucose Sensor Applicator Dexcom (project #2554), 2014, 5 pages.

Dexcom G5 Quick Start Guide, 2020, pp. 1-31.

Dexcom G6 Start Here Set up Guide, 2022, pp. 18 pages.

Dexcom G6 Continuous Glucose Monitoring (CGM) System Section 510(k) Approval, 2022, 7 pages.

"The Dexcom G7. The most accurate CGM system.1" retrieved from https://www.dexcom.com/g7-cgm-system on Jun. 27, 2024, 20 pages.

Dexcom G7 Continuous Glucose Monitoring (CGM) System Section 510(k) Approval, 2022, 10 pages.

Dexcom G7 User Guide, 2024, p. i-186.

Edison Awards Announces 2016 Gold, Silver, and Bronze Awards Winners, Edison Awards, 9 pages.

Edison Best New Product Awards™ 2021 Winners retrieved from https://edisonawards.com/2021-winners/, 19 pages.

Edison Best New Product Awards™ 2022 Winners retrieved from https://edisonawards.com/2022-winners/, 52 pages.

Email from Christopher M Dougherty dated Dec. 17, 2019, 68 pages.

U.S. Appl. No. 62/524,247.

Freestyle Libre FAQ, 2024, retrieved from https://www.freestyle.abbott/uk-en/support/faq/question-answer.html?q=UKFaqquestion-55#, 2 pages.

"FreeStyle Libre Honored by Prix Galien", 2019, 4 pages.

FreeStyle Libre In-Service Guide, 2021, 28 pages.

FreeStyle Libre 2 Get Started Guide, 2023, pp. 1-28.

Freestyle Libre 2 HCP Pulse Report, 2021, 13 pages.

"FreeStyle Libre 2—Zucker messen ohne stechen per Sensor und App", German Innovation Awards Gold Winner, 2020, retrieved from https://www.german-innovation-award.de/preistraeger/preis/gewinner/freestyle-libre-2-zucker-messen-ohne-stechen-per-sensor-und-app/# :~:text=Beschreibung%20Die%20kontinuierliche%20Glukosemessung%20mit, um%20die%20Glukosewerte%20kontinuierlich%20aufzuzeichnen, 1 page.

FreeStyle Libre 3 Get Started Guide, 2023, pp. 1-20.

FreeStyle Libre 3 User's Manual, 2022-2023, pp. iv-241.

The Galien Foundation is proud to announce the laureates of the best-of-the-best from the half century 1970-2020, The 2022 Galien Golden Jubilee Winners, retrieved from https://www.galienfoundation.org/galien-golden-jubilee, 3 pages.

Gough, D. A., et al., "Development of the Implantable Glucose Sensor: What Are the Prospects and Why Is It Taking So Long?", Diabetes, 1995, vol. 44, pp. 1005-1009.

Hermanides, J., et al., "Current Application of Continuous Glucose Monitoring in the Treatment of Diabetes", Diabetes Care, 2011, vol. 34, Suppl. 2, pp. S197-S201.

Hovorka, R., "Continuous glucose monitoring and closed-loop systems", Diabetic Medicine, 2005, vol. 23, pp. 1-12.

Insert Molding, 1996, retrieved from https://www.mddionline.com/equipment/insert-molding, 4 pages.

International Diabetes Device 2022 Blue Book, Seagrove Partners, 142 pages.

Joseph, J. I., et al., "Glucose Sensing in the Subcutaneous Tissue: Attempting to Correlate the Immune Response with Continuous Glucose Monitoring Accuracy", Diabetes Technology & Therapeutics, 2018, vol. 20, No. 5, pp. 321-324.

Lomas, P., "Dexcom G7 Release: The Most Exciting New Features", 2024, retrieved from https://notjustapatch.com/dexcom-g7-features/, 13 pages.

Lovett, L., "What's next for Dexcom? Ceo, Cto talk G6 for inpatient use, expanding CGMs for patients without diabetes", 2020, retrieved from https://www.mobihealthnews.com/news/whats-next-dexcom-ceo-cto-talk-g6-inpatient-use-expanding-cgms-patients-without-diabetes, 6 pages.

Medtronic Enlite Serter User Guide, 2014, 26 pages.

Meltsner, M A, et al., "Observations on rotating needle insertions using a brachytherapy robot", Phys. Med. Biol., 2007, vol. 52, pp. 6027-6037.

Ólafsdóttir, A. F., et al., "A Clinical Trial of the Accuracy and Treatment Experience of the Flash Glucose Monitor FreeStyle Libre in Adults with Type 1 Diabetes", Diabetes Technology & Therapeutics, 2017, vol. 19, No. 3, pp. 164-172.

"Periphery", Cambridge Dictionary of American English, 2000, p. 631.

"Product Review: Abbott FreeStyle Libre Flash Glucose Monitor", DiabetesMine Team, 2021, retrieved from https://www.healthline.com/diabetesmine/abbott-freestyle-libre-review#bottom-line, 6 pages.

"Real-World Data Show Abbott's Freestyle Libre® Systems And GLP-1 Medicines Work Better Together For People With Type 2 Diabetes", 2024, PRNewswire, 2 pages.

Sclater, N., et al., eds., Mechanisms and Mechanical Devices Sourcebook, Fourth Edition, 2007, Chapter 12—Shaft Couplings and Connections, pp. 290-307.

Tsumura, R., et al., "Histological Evaluation of Tissue Damage Caused by Rotational Needle Insertion", Proceedings of the Annual

(56)     References Cited

OTHER PUBLICATIONS

International Conference of the IEEE Engineering in Medicine and Biology Society, 2016, pp. 5120-5123.

Van Den Boom, L., et al., "Changes in the utilization of blood glucose test strips among patients using intermittent-scanning continuous glucose monitoring in Germany", Diabetes, Obesity and Metabolism, 2020, vol. 22, pp. 922-928.

CA 3,050,721 Examiner's Report, Nov. 8, 2024.

EP 20177703.4 Written Submissions Dexcom, Nov. 22, 2024.

EP 20177712.5 Summons to Attend Oral Proceedings, Oct. 1, 2024.

EP 21211041.5 Response to Summons to Attend Oral Proceedings Dexcom, Nov. 12, 2024.

EP 21211041.5 Response to Summons to Attend Oral Proceedings, Nov. 12, 2024.

EP 21211041.5 Summons to Attend Oral Proceedings, Sep. 23, 2024.

EP 24152079.0 Examination Report, Dec. 2, 2024.

EP 24183336.7 Extended Search Report, Oct. 11, 2024.

EP 24187206.8 Extended Search Report, Oct. 9, 2024.

EP 24194029.5 Extended Search Report, Nov. 18, 2024.

GB Claim No. HP-2023-000012 and Claim No. HP-2023-000016 Dexcom's Written Closing for Trial D, Redacted, Nov. 27, 2024.

GB Claim No. HP-2023-000012 and Claim No. HP-2023-000016 Abbott's Closing Skeleton Argument—Trial D, Redacted, Nov. 27, 2024.

GB Claim No. HP-2023-000012 and Claim No. HP-2023-000016 Annex 1 to Dexcom's Opening Skeleton Argument for Trial D, Nov. 13, 2024.

GB Claim No. HP-2023-000012 and Claim No. HP-2023-000016 Annex 2 to Dexcom's Opening Skeleton Argument for Trial D, Nov. 13, 2024.

GB Claim No. HP-2023-000012 and Claim No. HP-2023-000016 Annex 3 to Dexcom's Opening Skeleton Argument for Trial D, Nov. 13, 2024.

GB Claim No. HP-2023-000012 and Claim No. HP-2023-000016 Dexcom's Opening Skeleton Argument for Trial D, Redacted, Nov. 13, 2024.

GB Claim No. HP-2023-000012 and Claim No. HP-2023-000016 Abbott's Opening Skeleton Argument Trial D: commencing Nov. 18, 2024, Redacted, Nov. 13, 2024.

GB Claim No. HP-2023-000012 and Claim No. HP-2023-000016 Trial D—Joint CGK Statement, Nov. 11, 2024.

GB Claim No. HP-2023-000012 and Claim No. HP-2023-000016 Second Expert Report of Colin Anthony Chong, Oct. 1, 2024.

GB Claim No. HP-2023-000012 Second Expert Report of Eugene Randal Prais, Oct. 1, 2024.

GB Claim No. HP-2023-000012 and Claim No. HP-2023-000016 Exhibit CC-8 to the First Expert Report of Colin Anthony Chong, Aug. 13, 2024.

GB Claim No. HP-2023-000012 and Claim No. HP-2023-000016 First Expert Report of Colin Anthony Chong, Aug. 13, 2024.

GB Claim No. HP-2023-000012 Exhibit ERP-20 to the Expert Report of Eugene Randal Prais, Aug. 13, 2024.

GB Claim No. HP-2023-000012 Expert Report of Eugene Randal Prais, Aug. 13, 2024.

JP 2024-31538 Office Action, Oct. 16, 2024.

US Decision Denying Institution of Inter Partes Review, IPR No. 2024-00860, Nov. 20, 2024.

US Patent Owner's Response To Petitioner's Explanation Of Parallel Petitions Challenging U.S. Pat. No. 11,510,325, IPR No. 2024-00860, Aug. 23, 2024.

US Patent Owner Preliminary Response Pursuant to 37 C.F.R. § 42.107, IPR No. 2024-00860, Aug. 23, 2024.

US Declaration of Julia Castellano, IPR No. 2024-00860, Aug. 21, 2024.

US Declaration of Scott E. Davis, IPR No. 2024-00860, Jun. 5, 2024.

US Petitioner's Explanation Of Parallel Petitions Challenging U.S. Pat. No. 11,510,325, IPR No. 2024-00860, May 9, 2024.

US Patent Owner's Request For Oral Argument, IPR No. 2023-01409, Dec. 3, 2024.

US Petitioner's Request For Oral Argument, IPR No. 2023-01409, Dec. 3, 2024.

US Patent Owner's Objections to Petitioner's Exhibits Submitted With Its Reply, IPR No. 2023-01409, Nov. 1, 2024.

US Petitioner's Updated Exhibit List, IPR No. 2023-01409, Oct. 25, 2024.

US Second Declaration of Gary Fletcher, Ph.D., IPR No. 2023-01409, Oct. 25, 2025

US Petitioner's Reply to Patent Owner's Response, IPR No. 2023-01409, Oct. 25, 2024.

US Deposition of Karl R. Leinsing, MSME, PE, IPR No. 2023-01409, Oct. 17, 2024.

US Conference Call Before The Patent Trial And Appeal Board · Before Judge Cynthia Hardman, IPR No. 2023-01409, Oct. 17, 2024.

US Notice of Joint Stipulation to Modify Schedule, IPR No. 2023-01409, Sep. 26, 2024.

US Declaration of Karl R. Leinsing, MSME, PE, IPR No. 2023-01409, Jul. 19, 2024.

US Patent Owner's Response, IPR No. 2023-01409, Jul. 19, 2024.

US Deposition of Gary Fletcher, Ph.D., IPR No. 2023-01409, Jun. 26, 2024.

US Decision Denying Patent Owner's Request on Rehearing of Decision Denying Institution, IPR No. 2023-01396, Aug. 9, 2024.

US Ex Parte Reexamination Certificate of U.S. Pat. No. 11,013,440, Oct. 30, 2024.

US Reexamination U.S. Appl. No. 90/019,329 Notice of Intent to Issue Ex Parte Reexamination Certificate, Oct. 8, 2024.

US Reexamination U.S. Appl. No. 90/019,329 Decision on Petition Under 37 C.F.R. § 1.59, Sep. 16, 2024.

US Reexamination U.S. Appl. No. 90/019,329 Statutory disclaimer per Manual of Patent Examining Procedure (MPEP) 1490, Sep. 3, 2024.

US Reexamination U.S. Appl. No. 90/019,329 Petition Under 37 C.F.R. § 1.182 to Seal Document Versions Filed via IDS and Substitute Redacted Document Versions Therfor, Aug. 1, 2024.

US Reexamination U.S. Appl. No. 90/019,329 Petition Under 37 CFR § 1.59 to Expunge Application Papers, Aug. 1, 2024.

US Reexamination U.S. Appl. No. 90/019,329 Ex Parte Reexamination Interview Summary, Jul. 25, 2024.

US Reexamination U.S. Appl. No. 90/019,329 Decision on Petition Under 37 C.F.R. § 1.59, Jul. 22, 2024.

US Reexamination U.S. Appl. No. 90/019,329 Decision Sua Sponte Vacating Notice of Intent to Issue Ex Parte Reexamination Certificate, Jul. 3, 2024.

US Reexamination U.S. Appl. No. 90/019,329 Petition Under 37 CFR § 1.59 to Expunge Application Papers, Jun. 12, 2024.

US Ex Parte Reexamination Certificate of U.S. Pat. No. 11,000,216, Nov. 14, 2024.

US Reexamination U.S. Appl. No. 90/019,331 Notice of Intent to Issue Ex Parte Reexamination Certificate, Oct. 15, 2024.

US Reexamination U.S. Appl. No. 90/019,331 Decision on Petition Under 37 C.F.R. § 1.59, Sep. 16, 2024.

US Reexamination U.S. Appl. No. 90/019,331 Petition Under 37 C.F.R. § 1.182 to Seal Document Versions Filed via IDS and Substitute Redacted Document Versions Therfor, Aug. 1, 2024.

US Reexamination U.S. Appl. No. 90/019,331 Petition Under 37 CFR § 1.59 to Expunge Application Papers, Aug. 1, 2024.

US Reexamination U.S. Appl. No. 90/019,331 Decision on Petition Under 37 C.F.R. § 1.59, Jul. 16, 2024.

US Reexamination U.S. Appl. No. 90/019,331 Petition Under 37 CFR § 1.59 to Expunge Application Papers, Jun. 12, 2024.

US Reexamination U.S. Appl. No. 90/019,307 Petition Under 37 CFR § 1.181 to Terminate, Aug. 15, 2024.

US Reexamination U.S. Appl. No. 90/019,307 Decision on Petitions, Aug. 7, 2024.

US Reexamination U.S. Appl. No. 90/019,307 Petition Under 37 CFR § 1.59 to Expunge Application Papers, Aug. 1, 2024.

US Reexamination U.S. Appl. No. 90/019,307 Petition Under 37 CFR § 1.59 to Expunge Application Papers, Jun. 12, 2024.

(56)                    References Cited

OTHER PUBLICATIONS

US Reexamination U.S. Appl. No. 90/019,307 Notification of Concurrent Proceedings, May 15, 2024.
US Reexamination U.S. Appl. No. 90/019,307 Petition Under 37 CFR §§ 1.182 and/or § 1.183 to Allow Filing and Consideration of Response to Patent Owner's Extraordinary Petition to Suspend, Mar. 19, 2024.
US Reexamination U.S. Appl. No. 90/019,307 Petition Under 37 CFR § 1.181 and/or § 1.183 to Suspend, Mar. 1, 2024.
US Ex Parte Reexamination Certificate of U.S. Pat. No. 10,959,654, Nov. 5, 2024.
US Reexamination U.S. Appl. No. 90/019,330 Notice of Intent to Issue Ex Parte Reexamination Certificate, Oct. 7, 2024.
US Reexamination U.S. Appl. No. 90/019,330 Decision on Petition Under 37 C.F.R. § 1.59, Sep. 16, 2024.
US Reexamination U.S. Appl. No. 90/019,330 Petition Under 37 C.F.R. § 1.182 to Seal Document Versions Filed via IDS and Substitute Redacted Document Versions Therfor, Aug. 1, 2024.
US Reexamination U.S. Appl. No. 90/019,330 Petition Under 37 CFR § 1.59 to Expunge Application Papers, Aug. 1, 2024.
US Reexamination U.S. Appl. No. 90/019,330 Decision on Petition Under 37 C.F.R. § 1.59, Jul. 16, 2024.
US Reexamination U.S. Appl. No. 90/019,330 Petition Under 37 CFR § 1.59 to Expunge Application Papers, Jun. 12, 2024.
US Dexcom's Notice of Appeal, Case No. 21-CV-977-KAJ, Nov. 26, 2024.
US Order, Case No. 21-CV-977-KAJ, Nov. 21, 2024.
US Order, Case No. 21-CV-977-KAJ, Nov. 13, 2024.
US Memorandum Opinion, Case No. 21-CV-977-KAJ, Nov. 13, 2024.
WO PCT/US24/16127 ISR and Written Opinion, Sep. 11, 2024.
Abbott Patent Marking Diabetes, 2024, retrieved from https://www.abbott.com/patents/diabetes-patents.html, 6 pages.
ACCU-CHEK® Softclix Lancet Device retrieved from file:///C:/Users/afredericks/Downloads/softclix-user-manual.pdf, 2007, 2 pages.
Using your ACCU-CHEK® Multiclix Lancet Device, 2005, retrieved from https://www.northcoastmed.com/wp-content/uploads/2023/03/multiclix_userguide.pdf, 2 pages.
"The Advantages of the Cleo® 90 Infusion Set Are Clear", 2019, retrieved from https://web.archive.org/web/20220816002119/https://smiths-medical.com/-/media/M/Smiths-medical_com//Files/Import-Files/Product-Literature/IN193873GB-092019_LR.pdf, 2 pages.
American National Standard, ANSI/AAMI HE75:2009, Human factors engineering—Design of medical devices, 2010, 465 pages.
Automated Retractable VanishPoint Syringe 510(k) Safety and Effectiveness Summary, 1998, 5 pages.
"Bluetooth rival unveiled by Nokia", 2006, retrieved from news.bbc.co.uk/1/hi/technology/5403564.stm, 2 pages.
Breton, M., et al., "Fully Integrated Artificial Pancreas in Type 1 Diabetes: Modular Closed-Loop Glucose Control Maintains Near Normoglycemia", Diabetes, 2012, vol. 61, No. 9, pp. 2230-2237.
Burge, M. R., et al., "Continuous Glucose Monitoring: The Future of Diabetes Management", Diabetes Spectrum, 2008, vol. 21, No. 2, pp. 112-119.
Clancy, N. T., et al., "A new device for assessing changes in skin viscoelasticity using indentation and optical measurement", Skin Research and Technology, 2010, vol. 16, pp. 210-228.
Cleo® 90 Infusion Set 510(k) Premarket Notification, 2004, 1 page.
Dexcom G5 Mobile System User Guide, 2015, pp. 1-260.
Dexcom STS Continuous Monitors FDA Premarket Approval (PMA), 2006, 2 pages.
U.S. Appl. No. 61/569,287.
Freestyle Navigator Answers to Frequently Asked Questions, 2007, retrieved from https://web.archive.org/web/20080917183534/http://www.freestylenavigator.com/ab_nav/url/content/en_US/3 0.10.10:1 O/general_content/General_ContenL0000004.htm, 2 pages.
"The Future is Bright for Veteran-centric Rehabilitation Research Publications", Journal of Rehabilitation Research & Development (JRRD), 2013, retrieved from https://www.rehab.research.va.gov/jrrd/index.html, 2 pages.

International Standard, IEC 62366, Medical devices—Application of usability engineering to medical devices, 2007, 214 pages.
Kaye, R., et al., "Medical Device Use-Safety: Incorporating Human Factors Engineering into Risk Management", 2000, retrieved from https://www.qualysinnova.com/download/files/MD-Use-Safety.pdf, pp. 1-33.
Mazze, R. S., et al., "Evaluating the Accuracy, Reliability, and Clinical Applicability of Continuous Glucose Monitoring (CGM): Is CGM Ready for Real Time?", Diabetes Technology & Therapeutics, 2009, vol. 11, No. 1., pp. 11-18.
Medtronic MiniMed Guardian® REAL-Time Components, 2007, retrieved from https://web.archive.org/20071013095335/http:/www.medtronicdiabetes.com/products/guardian/components.html, 2 pages.
Medtronic MiniMed Guardian® REAL-Time Features, 2007, retrieved from https://web.archive.org/20071013095335/http:/www.medtronicdiabetes.com/products/guardian/features.html, 2 pages.
Medtronic MiniMed One-press Serter User Guide, 2015, 26 pages.
Medtronic MiniMed Paradigm® 512 and 712 Insulin Pumps User Guide, 2005, pp. 1-136.
Microlet® 2 Lancing Device, 2008, retrieved from https://image.tigermedical.com/Manuals/BAY6606-20141216010820833.pdf, 1 page.
Piper, H. G., et al., "Real-Time Continuous Glucose Monitoring in Pediatric Patients During and After Cardiac Surgery", Pediatrics, 2006, vol. 118, No. 3, pp. 1176-1184.
Rabiee, A., et al., "Numerical and Clinical Accuracy of a Continuous Glucose Monitoring System during Intravenous Insulin Therapy in the Surgical and Burn Intensive Care Units", Journal of Diabetes Science and Technology, 2009, vol. 3, No. 4, pp. 951-959.
Sacks, A. H., et al., "Skin blood flow changes and tissue deformations produced by cylindrical indentors", Journal of Rehabilitation Research and Development, 1985, vol. 22, No. 3, pp. 1-6.
Schneider, M., et al., "Evaluating the use of the Cleo® 90 infusion set for patients on a palliative care unit", International Journal of Palliative Nursing, 2009, vol. 15,. No. 8, pp. 372-376.
AU 2019404908 Examiner's Report, Feb. 17, 2025.
CA 3,228,738 Examiner's Report, May 8, 2025.
CN 202211091194.1 Notification of Filing Divisional Application, Mar. 27, 2025.
EP 17182379.2 Reply to Opposition, Feb. 27, 2025.
EP 19151577.4 Examination Report, Oct. 7, 2024.
EP 19900891.3 Examination Report, May 8, 2025.
EP 20177703.4 Response to Withdrawals, Jan. 7, 2025.
EP 20177703.4 Withdrawal of Intervention, Dec. 27, 2024.
EP 20177703.4 Withdrawal of Opposition, Dec. 27, 2024.
EP 20195922.8 Withdrawal of Intervention, Dec. 27, 2024.
EP 20195922.8 Withdrawal of Opposition, Dec. 27, 2024.
EP 21211041.5 Grounds of Appeal, Apr. 23, 2025.
EP 21211041.5 Withdrawal of Opposition, Dec. 27, 2024.
EP 21211041.5 Notice of Appeal, Dec. 17, 2024.
EP 21211041.5 Minutes of Oral Proceedings, Dec. 13, 2024.
EP 24201435.5 Extended Search Report, Jan. 27, 2025.
JP 2023-516522 Office Action, Mar. 5, 2025.
MX MX/a/2021/007294 Second Office Action, Feb. 19, 2025.
MY PI2021003022 Examination Report, Mar. 5, 2025.
MY PI2022002786 Examination Report, Jan. 8, 2025.
UP Second Expert Opinion of Dr Michael Schoemaker in Litigation of EP 3977921, Nov. 8, 2024.
US Termination Due to Settlement After Institution of Trial, IPR No. 2023-01409, Jan. 7, 2025.
US Joint Motion to Treat Settlement Agreement as Business Confidential Information. IPR No. 2023-01409, Jan. 3, 2025.
US Joint Motion to Terminate Proceeding Under 35 U.S.C. § 317(a), IPR No. 2023-01409, Jan. 3, 2025.
US Order Setting Oral Argument, IPR No. 2023-01409, Dec. 11, 2024.
US Patent Owner's Sur-Reply, IPR No. 2023-01409, Dec. 10, 2024.
US Deposition of Gary D. Fletcher, Ph.D., IPR No. 2023-01409, Dec. 4, 2024.
US Reexamination U.S. Appl. No. 90/019,307 Office Action, Mar. 18, 2025.
US Reexamination U.S. Appl. No. 90/019,307 Decision on Petition, Feb. 13, 2025.

(56) References Cited

OTHER PUBLICATIONS

US Reexamination U.S. Appl. No. 90/019,329 Decision on Petition Under 37 C.F.R. § 1.181, Mar. 18, 2025.
WO PCT/US25/13698 Invitation to Pay Additional Fees, Apr. 15, 2025.
CN 202180063087.5 First Office Action, Aug. 14, 2025.
EP 17182379.2 Written Submissions, Aug. 6, 2025.
EP 17182379.2 Summons to Attend Oral Proceedings, Jul. 4, 2025.
EP 17182379.2 Reply to Reply to Opposition, May 16, 2025.
EP 19151577.4 Examination Report, Sep. 3, 2025.
EP 20177712.5 Written Submissions Gulde, Aug. 21, 2025.
EP 20177712.5 Response to Summons to Attend Oral Proceedings, Aug. 21, 2025.
EP 23190032.5 Examination Report, May 19, 2025.
EP 24218309.3 Extended Search Report, Jul. 9, 2025.
EP 24194029.5 Examination Report, Aug. 26, 2025.
EP 24220160.6 Extended Search Report, Jun. 17, 2025.
JP 2023-514023 Final Office Action, Aug. 20, 2025.
JP 2023-514023 Office Action, Apr. 16, 2025.
JP 2023-514024 Office Action, Apr. 30, 2025.
JP 2023-532327 Office Action, Jul. 23, 2025.
JP 2025-026588 Office Action, Aug. 27, 2025.
US Reexamination U.S. Appl. No. 90/019,307 Final Office Action, Jul. 8, 2025.
WO PCT/US25/13698 ISR and Written Opinion, Jun. 5, 2025.
WO PCT/US25/27260 Invitation to Pay Additional Fees, Jul. 24, 2025.
EP 18741791.0 Examination Report, Sep. 12, 2025.
EP 21192910.4 Notice of Opposition Stolmar, Sep. 10, 2025.
EP 21192910.4 Notice of Opposition Strawman, Sep. 10, 2025.

* cited by examiner

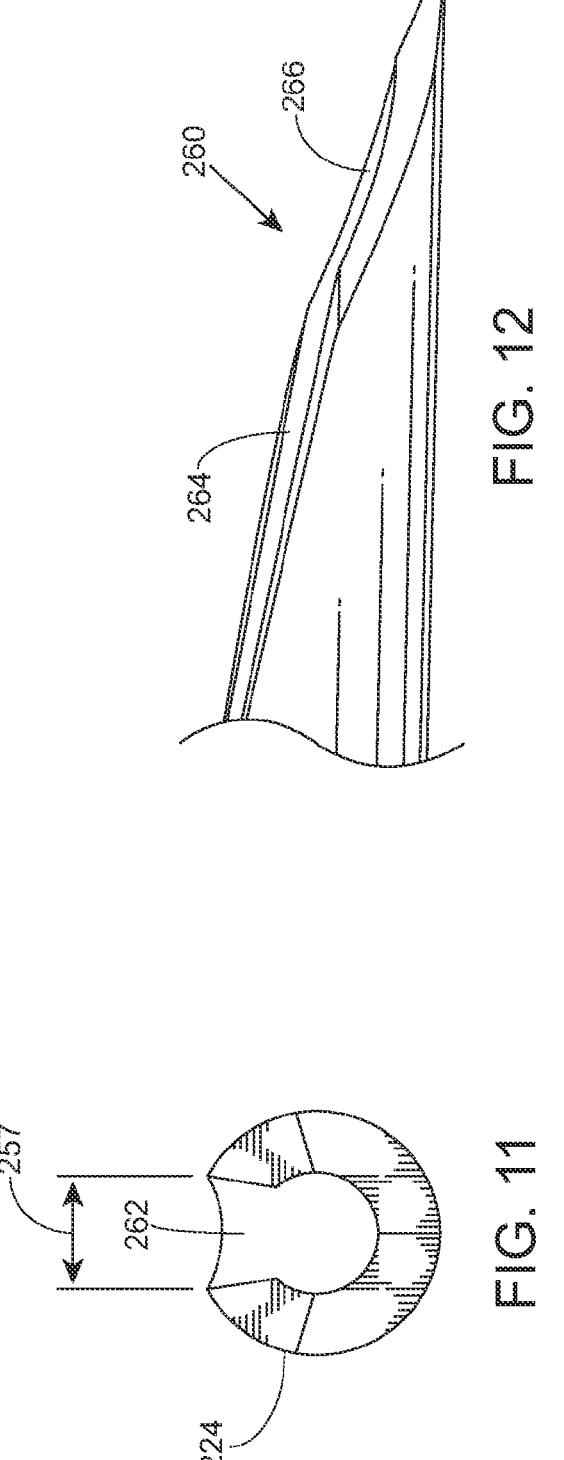
FIG. 12
FIG. 11
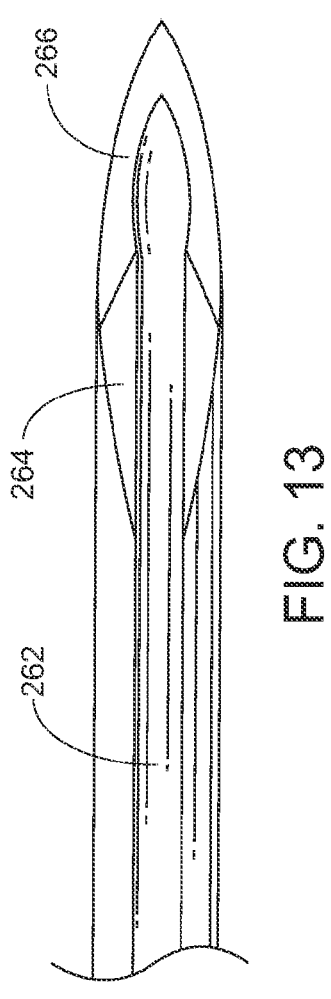
FIG. 13

224

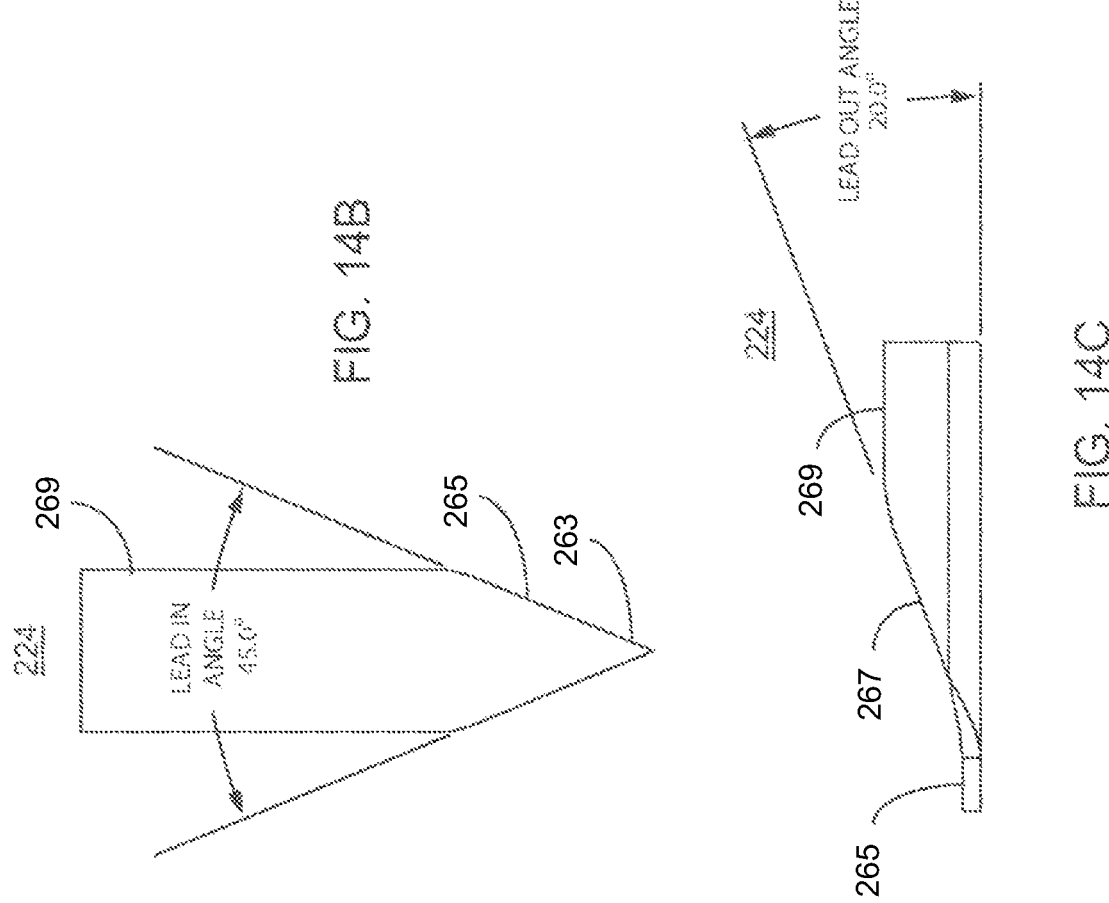
FIG. 14B
FIG. 14C
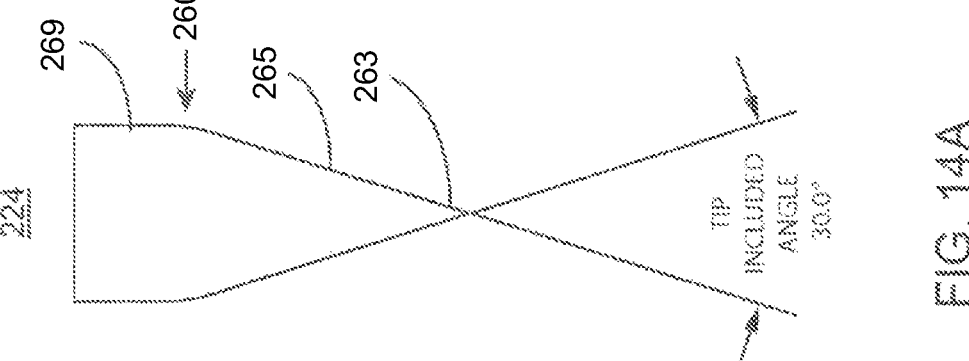
FIG. 14A

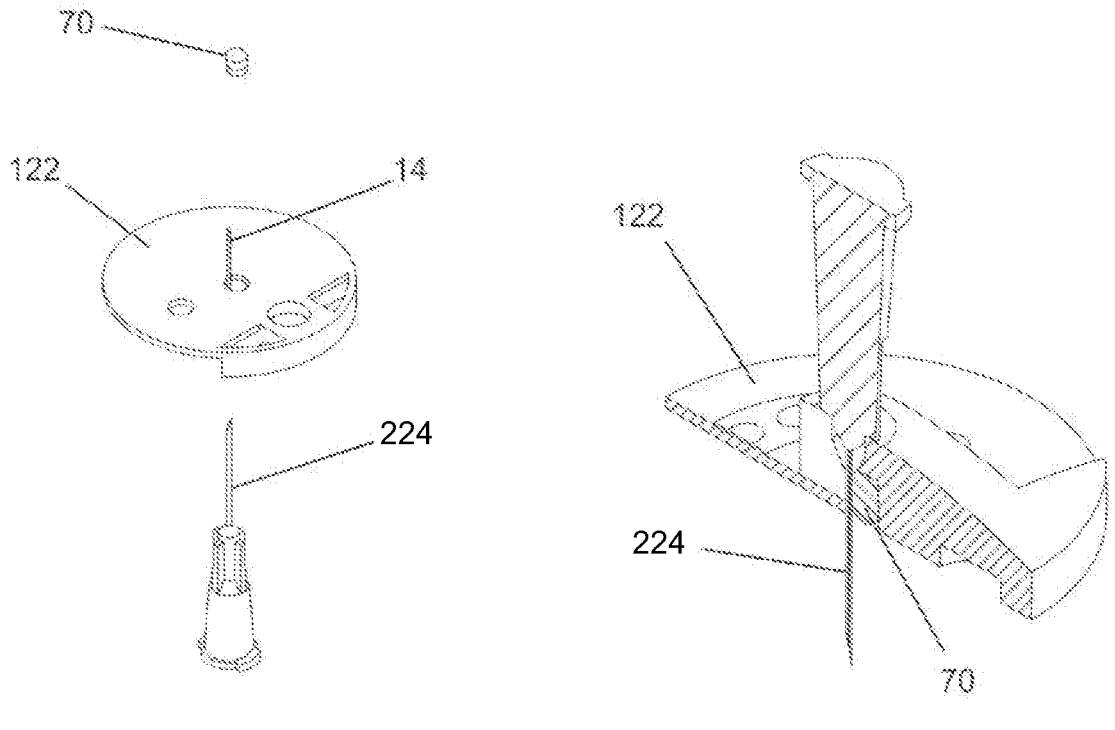
FIG. 19                                    FIG. 20
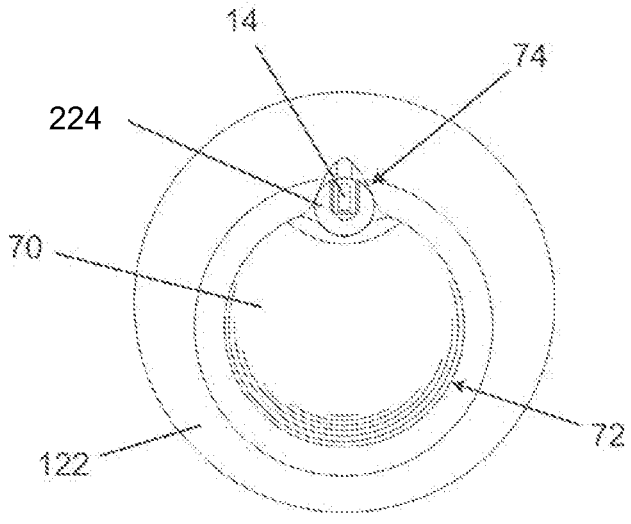
FIG. 21

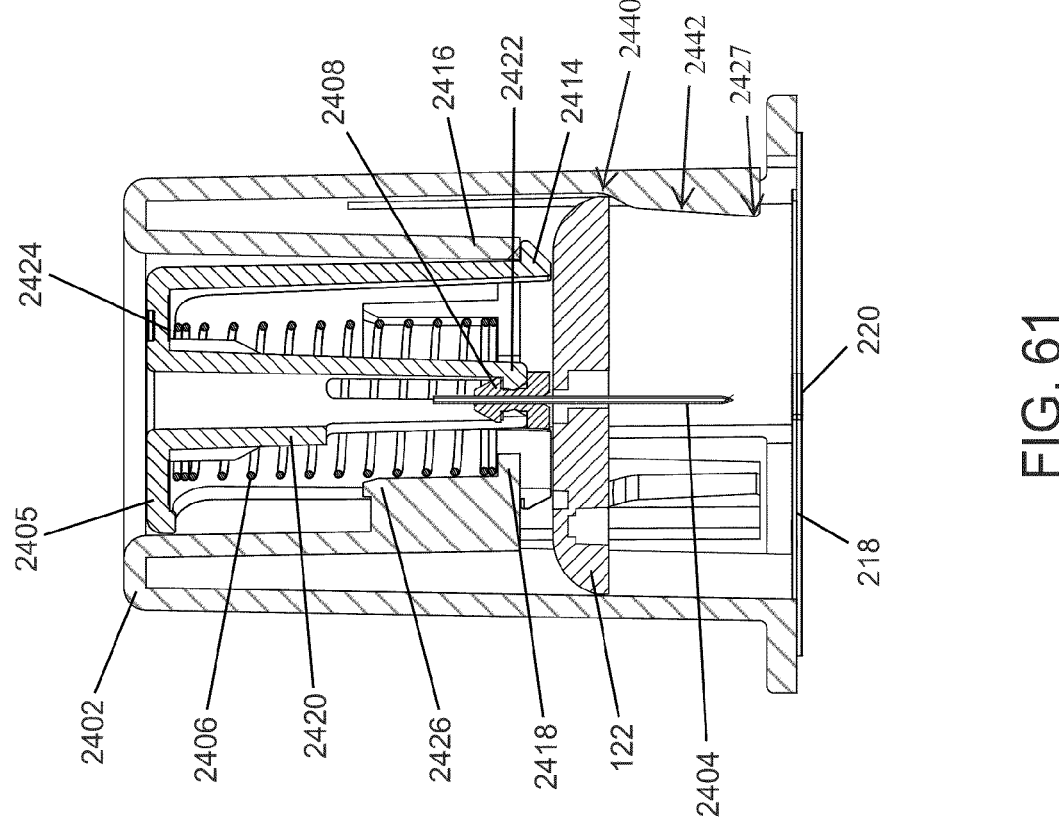
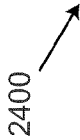
FIG. 61

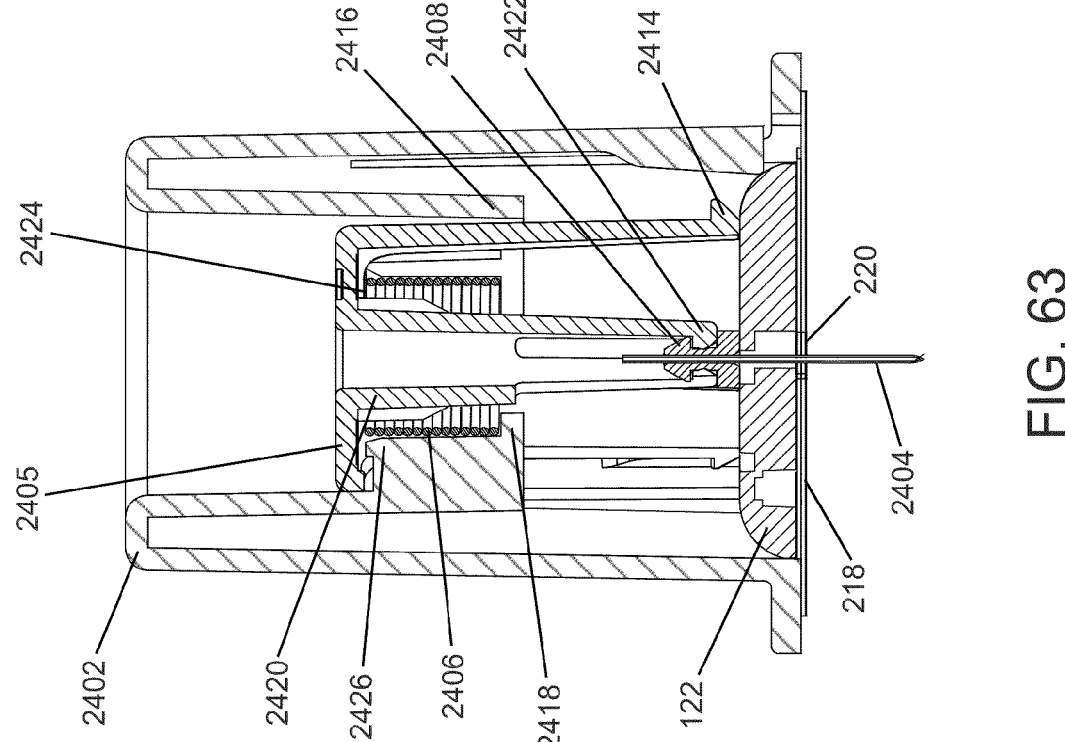
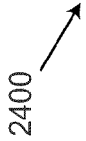
FIG. 63

2400

2480

2400

2400

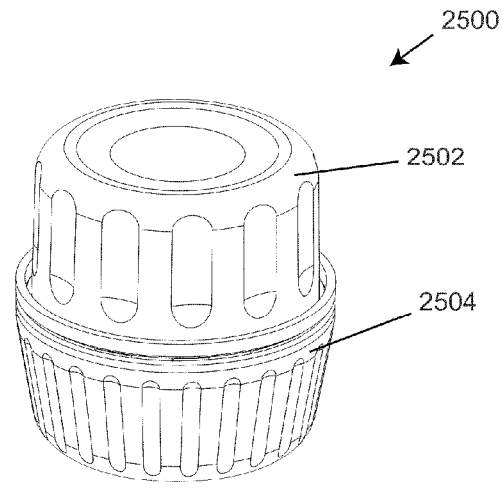
FIG. 73
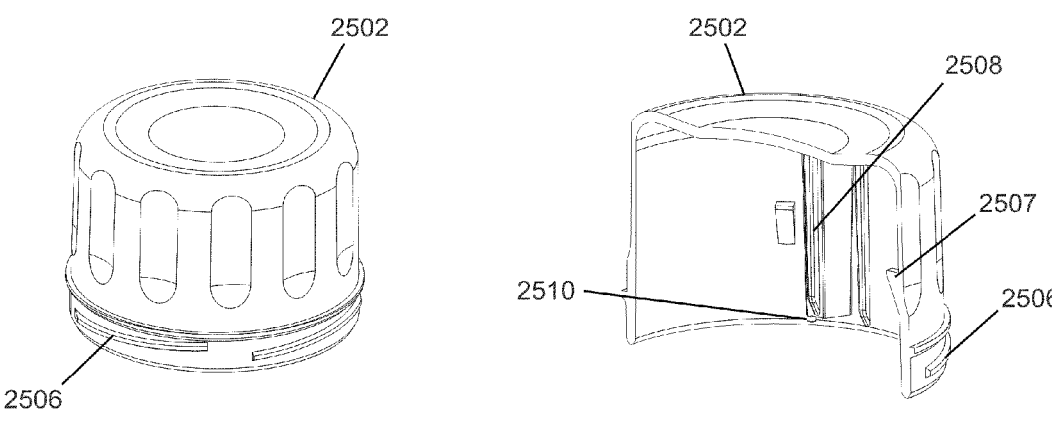
FIG. 74                           FIG. 75

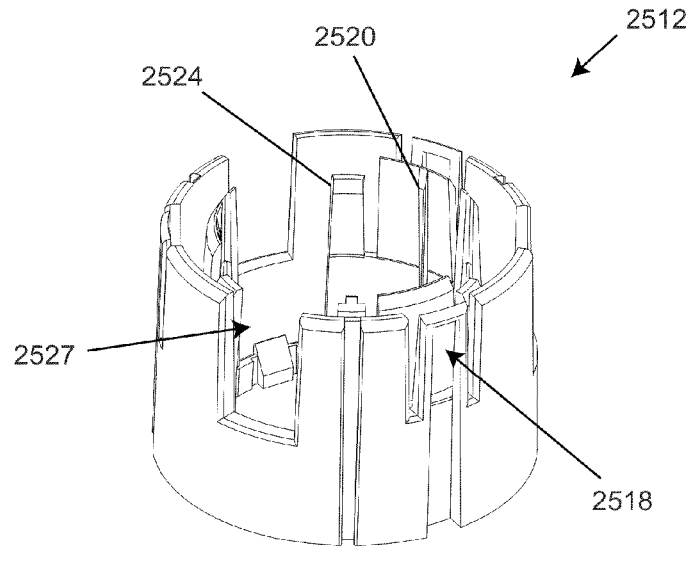
FIG. 76
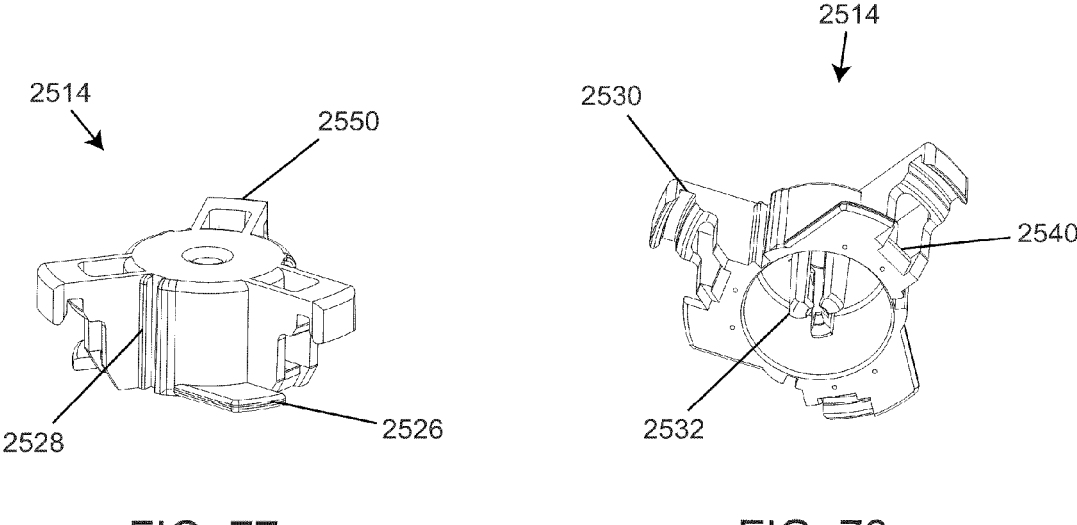
FIG. 77                     FIG. 78

2516

2536

2538

2516

2542

2522

2502

2504

2502

2512

2502

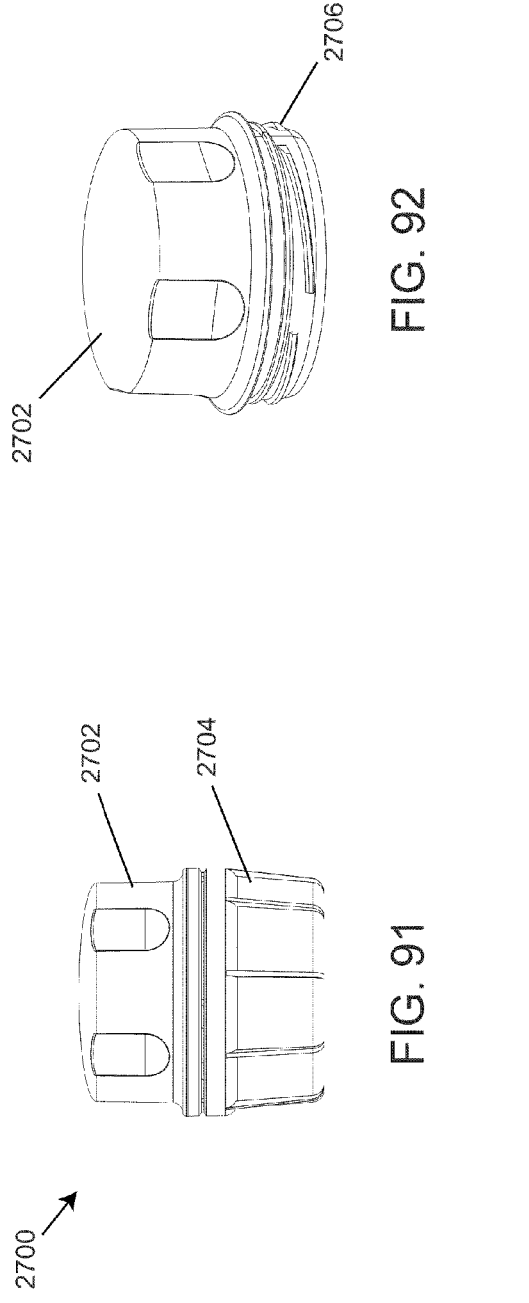
FIG. 91
FIG. 92
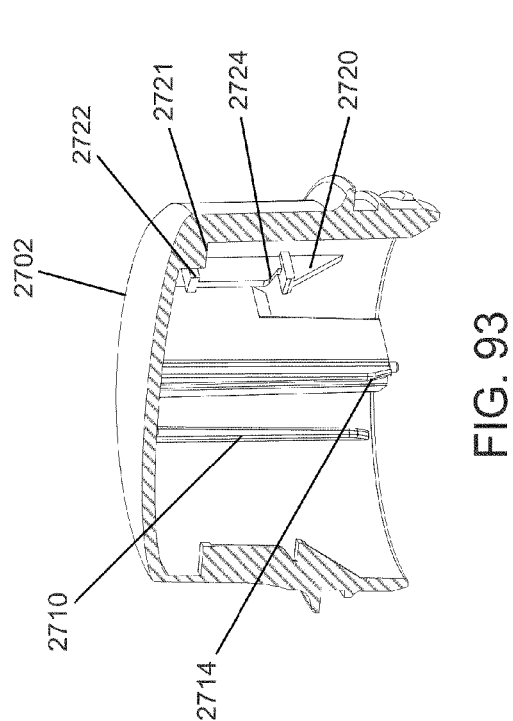
FIG. 93

2730
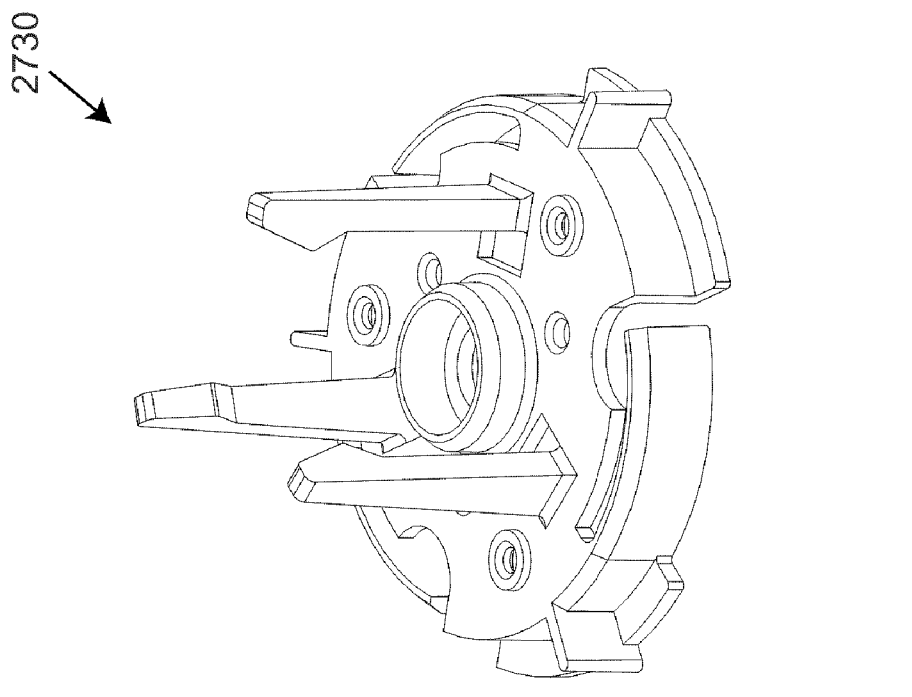
FIG. 108
2730
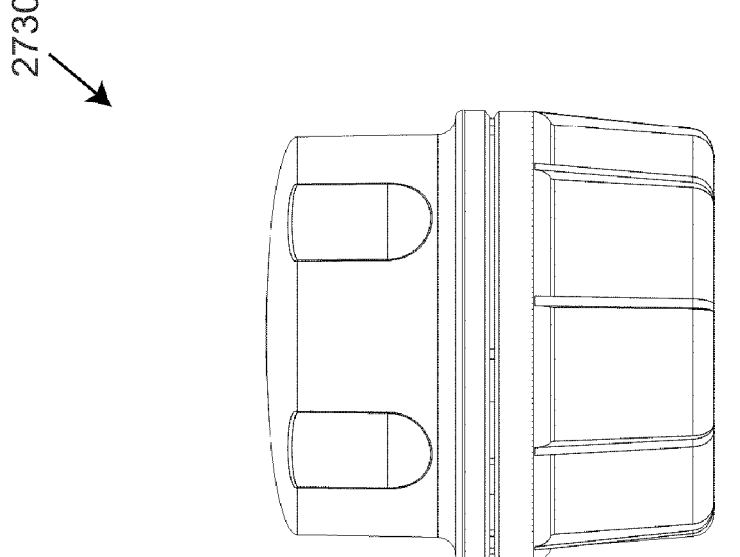
FIG. 107

3700

3702

3704

3702

3706

3708

3702

3706

3702

3706

3708

322

318

3704
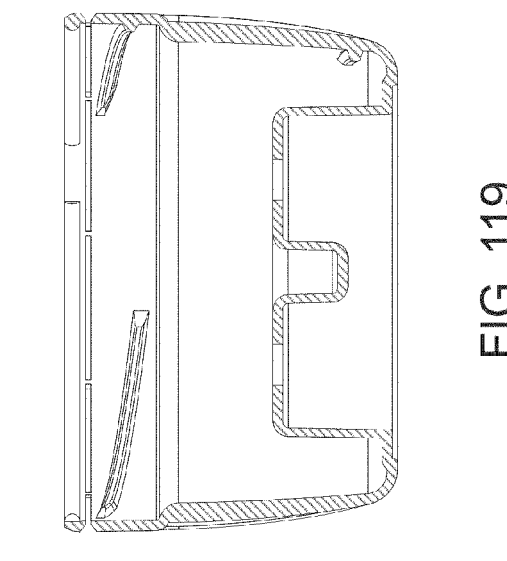
FIG. 119
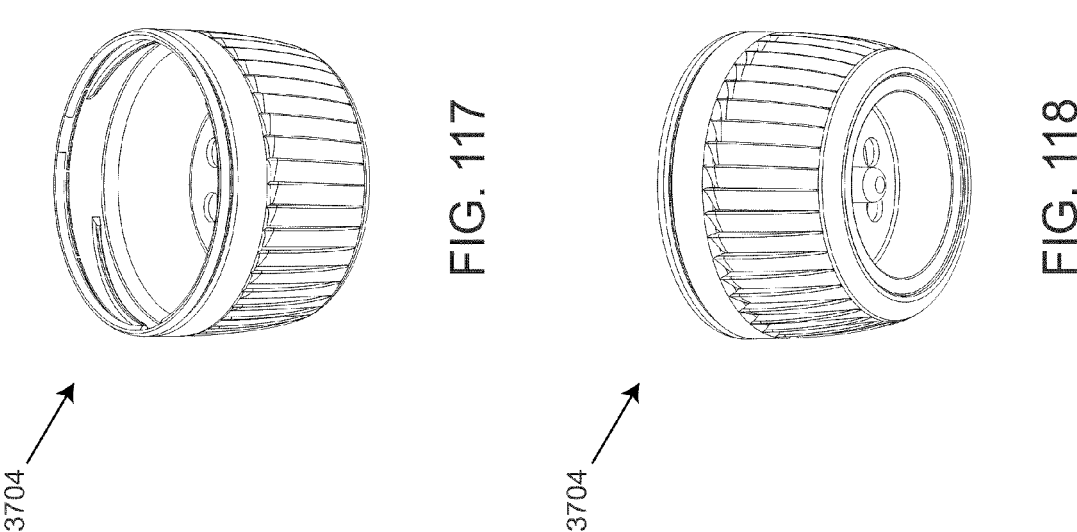
3704
FIG. 117
3704
FIG. 118

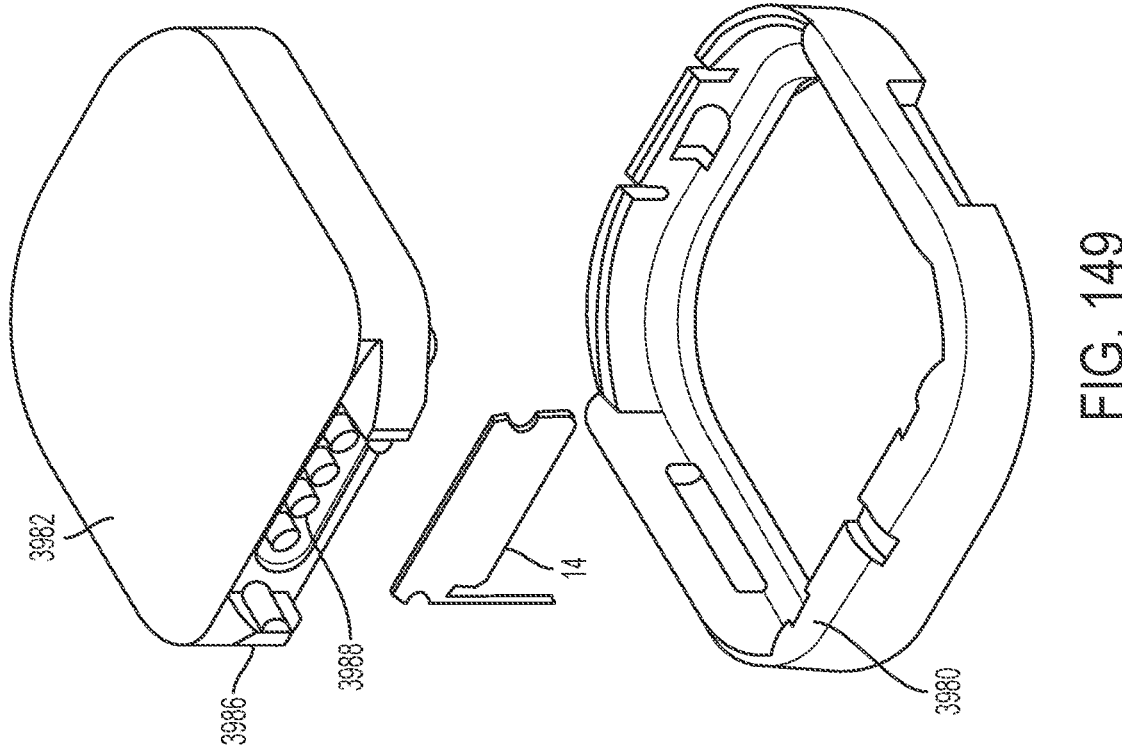
FIG. 149

4700

4722

4720

MEDICAL DEVICE INSERTERS AND PROCESSES OF INSERTING AND USING MEDICAL DEVICES

CROSS-REFERENCE TO RELATED APPLICATIONS

The present application is a continuation of U.S. patent application Ser. No. 13/436,768, filed Mar. 30, 2012, which is a continuation of U.S. patent application Ser. No. 13/071, 461, filed Mar. 24, 2011, now U.S. Pat. No. 9,215,992, which claims the benefit of U.S. Provisional Application Nos. 61/317,243, filed Mar. 24, 2010; 61/345,562, filed May 17, 2010; 61/361,374, filed Jul. 2, 2010; and 61/411,262, filed Nov. 8, 2010, all of which are incorporated herein by reference in their entireties and for all purposes.

INCORPORATION BY REFERENCE

Patents, applications and/or publications described herein, including the following patents, applications and/or publications are incorporated herein by reference for all purposes: U.S. Pat. Nos. 4,545,382; 4,711,245; 5,262,035; 5,262,305; 5,264,104; 5,320,715; 5,356,786; 5,509,410; 5,543,326; 5,593,852; 5,601,435; 5,628,890; 5,820,551; 5,822,715; 5,899,855; 5,918,603; 6,071,391; 6,103,033; 6,120,676; 6,121,009; 6,134,461; 6,143,164; 6,144,837; 6,161,095; 6,175,752; 6,270,455; 6,284,478; 6,299,757; 6,338,790; 6,377,894; 6,461,496; 6,503,381; 6,514,460; 6,514,718; 6,540,891; 6,560,471; 6,579,690; 6,591,125; 6,592,745; 6,600,997; 6,605,200; 6,605,201; 6,616,819; 6,618,934; 6,650,471; 6,654,625; 6,676,816; 6,730,200; 6,736,957; 6,746,582; 6,749,740; 6,764,581; 6,773,671; 6,881,551; 6,893,545; 6,932,892; 6,932,894; 6,942,518; 7,041,468; 7,167,818; and 7,299,082; 7,381,184; 7,740,581; 7,811,231; U.S. Published Application Nos. 2005/0182306, now U.S. Pat. No. 8,771,183; 2006/0091006; 2007/0056858, now U.S. Pat. No. 8,298,389; 2007/0068807, now U.S. Pat. No. 7,846,311; 2007/0095661; 2007/0108048, now U.S. Pat. No. 7,918,975; 2007/0149873, now U.S. Pat. No. 9,014,773; 2007/0149875, now U.S. Pat. No. 8,515,518; 2007/ 0199818, now U.S. Pat. No. 7,811,430; 2007/0227911, now U.S. Pat. No. 7,887,682; 2007/0233013; 2008/0058625, now U.S. Pat. No. 7,920,907; 2008/0064937; 2008/ 0066305, now U.S. Pat. No. 7,895,740; 2008/0071157; 2008/0071158; 2008/0081977, now U.S. Pat. No. 7,618, 369; 2008/0102441, now U.S. Pat. No. 7,822,557; 2008/ 0148873, now U.S. Pat. No. 7,802,467; 2008/0161666; 2008/0179187, now U.S. Pat. No. 8,808,515; 2008/ 0267823; 2008/0319295, now U.S. Pat. No. 8,597,188; 2008/0319296, now U.S. Pat. No. 8,617,069; 2009/ 0018425, now U.S. Pat. No. 8,160,670; 2009/0247857, now U.S. Pat. No. 8,346,335; 2009/0257911, now U.S. Pat. No. 8,252,229, 2009/0281406; 2009/0294277; 2009/0054748, now U.S. Pat. No. 7,885,698; 2009/0054749; 2010/ 0030052; 2010/0065441, now U.S. Pat. No. 8,636,884; 2010/0081905, now U.S. Pat. No. 8,983,568; 2010/ 0081909, now U.S. Pat. No. 8,219,173; 2010/0213057; 2010/0325868, now U.S. Pat. No. 7,866,026; 2010/ 0326842; 2010/0326843, now U.S. Pat. No. 8,437,827; 2010/0331643; 2011/0046466; U.S. patent application Ser. No. 12/624,767, now U.S. Patent Publ. No. 2011/0124993; Ser. No. 12/625,185, now U.S. Pat. No. 8,354,013; Ser. No. 12/625,208, now U.S. Pat. No. 9,042,954; Ser. No. 12/625, 524, now U.S. Pat. No. 8,390,455; Ser. No. 12/625,525, now U.S. Pat. No. 8,358,210; Ser. No. 12/625,528, now U.S. Pat. No. 8,115,635; Ser. No. 12/628,177, now U.S. Patent Publ.

No. 2010/0076289; Ser. No. 12/628,198, now U.S. Patent Publ. No. 2010/0076291; Ser. No. 12/628,201, now U.S. Patent Publ. No. 2010/0076280; Ser. No. 12/628,203, now U.S. Patent Publ. No. 2010/0076292; Ser. No. 12/628,210, now U.S. Patent Publ. No. 2010/0076293; Ser. No. 12/698, 124, now U.S. Patent Publ. No. 2010/0198034; Ser. No. 12/698,129, now U.S. Patent Publ. No. 2010/03243925; Ser. No. 12/699,653, now U.S. Patent Publ. No. 2010/0198142; Ser. No. 12/699,844, now U.S. Pat. No. 8,930,203; Ser. No. 12/714,439, now U.S. Patent Publ. No. 2010/0230285; Ser. Nos. 12/730,193; 12/794,721, now U.S. Pat. No. 8,595,607; Ser. No. 12/807,278, now U.S. Patent Publ. No. 2011/ 0213225; Ser. No. 12/842,013, now U.S. Patent Publ. No. 2011/0021889; Ser. No. 12/870,818, now U.S. Patent Publ. No. 2011/0073475; Ser. No. 12/871,901, now U.S. Pat. No. 8,514,086; Ser. No. 12/873,301, now U.S. Patent Publ. No. 2011/0054275; Ser. No. 12/873,302, now U.S. Patent Publ. No. 2011/0060196; Ser. No. 13/011,897, now U.S. Patent Publ. No. 2011/0184265; and U.S. Provisional Application Nos. 61/238,646; 61/246,825; 61/247,516; 61/249,535; 61/317,243; 61/325,155; 61/345,562; and 61/359,265.

BACKGROUND

The detection and/or monitoring of glucose levels or other analytes, such as lactate, oxygen, A1C, or the like, in certain individuals is vitally important to their health. For example, the monitoring of glucose is particularly important to individuals with diabetes. Diabetics generally monitor glucose levels to determine if their glucose levels are being maintained within a clinically safe range, and may also use this information to determine if and/or when insulin is needed to reduce glucose levels in their bodies or when additional glucose is needed to raise the level of glucose in their bodies.

Growing clinical data demonstrates a strong correlation between the frequency of glucose monitoring and glycemic control. Despite such correlation, many individuals diagnosed with a diabetic condition do not monitor their glucose levels as frequently as they should due to a combination of factors including convenience, testing discretion, pain associated with glucose testing, and cost.

Devices have been developed for the automatic monitoring of analyte(s), such as glucose, in bodily fluid such as in the blood stream or in interstitial fluid ("ISF"), or other biological fluid. Some of these analyte measuring devices are configured so that at least a portion of the devices are positioned below a skin surface of a user, e.g., in a blood vessel or in the subcutaneous tissue of a user, so that the monitoring is accomplished in vivo.

With the continued development of analyte monitoring devices and systems, there is a need for such analyte monitoring devices, systems, and methods, as well as for processes for manufacturing analyte monitoring devices and systems that are cost effective, convenient, and with reduced pain, provide discreet monitoring to encourage frequent analyte monitoring to improve glycemic control.

SUMMARY

In certain embodiments, an apparatus for inserting a medical device into the skin of a subject is provided, which includes a sheath defining a distal surface for placement on the skin of the subject; a device support movable between a proximal and distal position, and adapted to support the medical device; a sharp support movable between a proximal and a distal position and adapted to support a sharp for inserting the medical device into the skin of the subject and extending through a portion of said device support, the device support comprising a first engagement member for releasably coupling the sharp support to the device support and a second engagement member for engaging the medical device; a handle movable between a proximal position and a distal position relative to the sheath and adapted to urge the device support and the sharp support from a proximal to a distal position to insert the sharp into the skin of the subject; and a driver for advancing the sharp support towards the proximal position when the sharp support reaches the distal position.

In some embodiments, the handle and sheath define an interlocking configuration which prevents relative movement of the handle with respect to the sheath which is overcome by a force applied to the handle. In some embodiment, the second engagement member includes one or more movable arms for engaging the device. The one or more movable arms are normally biased in a position spaced apart from the medical device in some embodiments. The one or more movable arms may be maintained in engagement with the medical device when the device support is in the proximal position. In some embodiments, the one or more movable arms return to the configuration space apart from the medical device when the device support is in the distal position.

In some embodiments, the engagement member is released from the sharp support when the device support reaches a distal position. In some embodiments, the engagement member is maintained in engagement with the device support by a portion of the sheath.

In some embodiments, a stop is provided to maintain the device support in the proximal position.

In some embodiments, the handle includes a button disposed within an outer housing. The handle may be flush with the top of the outer housing in an initial configuration when the medical device is supported in the device support, and the handle may protrude above the outer housing after the medical device is released from the device support.

In some embodiments, the medical device is an analyte sensor.

A method for using a medical device is provided which includes providing an apparatus comprising a sheath defining a distal surface, a device support adapted to support the medical device, a sharp support adapted to support a sharp extending through a portion of said device support, a handle movable relative to the sheath, and a driver for displacing the sharp support; disposing the distal surface of the sheath on the skin of the subject; and displacing the handle in a first longitudinal direction; displacing the sharp support in the first longitudinal direction, the sharp support displacing the sharp and the medical device. The method further includes inserting the sharp into the skin of the subject; delivering the medical device to the subject; releasing the driver; and displacing the sharp in the second longitudinal direction by the driver.

In some embodiments, the method further includes locking at least a portion of the sheath to the handle.

These and other features, objects, and advantages of the disclosed subject matter will become apparent to those persons skilled in the art upon reading the detailed description as more fully described below.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

FIG. 11 is a distal end view of a sharp in accordance with one embodiment of the disclosed subject matter;

FIG. 12 is a side view of a sharp in accordance with one embodiment of the disclosed subject matter;

FIG. 13 is a side view of a sharp in accordance with one embodiment of the disclosed subject matter;

FIGS. 14A-B are top views of a sharp in accordance with one embodiment of the disclosed subject matter;

FIG. 14C is a side view of a sharp in accordance with one embodiment of the disclosed subject matter;

FIGS. 19-21 depict an alternative method for retaining a sharp and sensor within the on body housing;

FIGS. 61-65 are cross-sectional views of the inserter of FIG. 51 in accordance with the disclosed subject matter;

FIG. 73 is a perspective view of another inserter in accordance with the disclosed subject matter;

FIG. 74 is a perspective view of a component of the inserter of FIG. 73 in accordance with the disclosed subject matter;

FIG. 75 is a cross-sectional view of a component of the inserter of FIG. 73 in accordance with the disclosed subject matter;

FIGS. 76-80 are perspective views of components of the inserter of FIG. 73 in accordance with the disclosed subject matter;

FIG. 91 is a perspective view of another inserter in accordance with the disclosed subject matter;

FIGS. 92-99 are additional views of the components of the inserter of FIG. 91 in accordance with the disclosed subject matter;

FIGS. 107-108 are views of an alternate embodiment of the inserter of FIG. 91 in accordance with the disclosed subject matter; and FIGS. 109-134 are views of an alternate embodiment of the inserter of FIG. 73 in accordance with the disclosed subject matter.

FIGS. 145*a*-147*b* illustrate the attachment of a two piece on body housing in accordance with the disclosed subject matter.

FIG. 149 illustrates another two-piece on body housing in accordance with the disclosed subject matter.

DETAILED DESCRIPTION OF THE EMBODIMENTS

Figure 1:
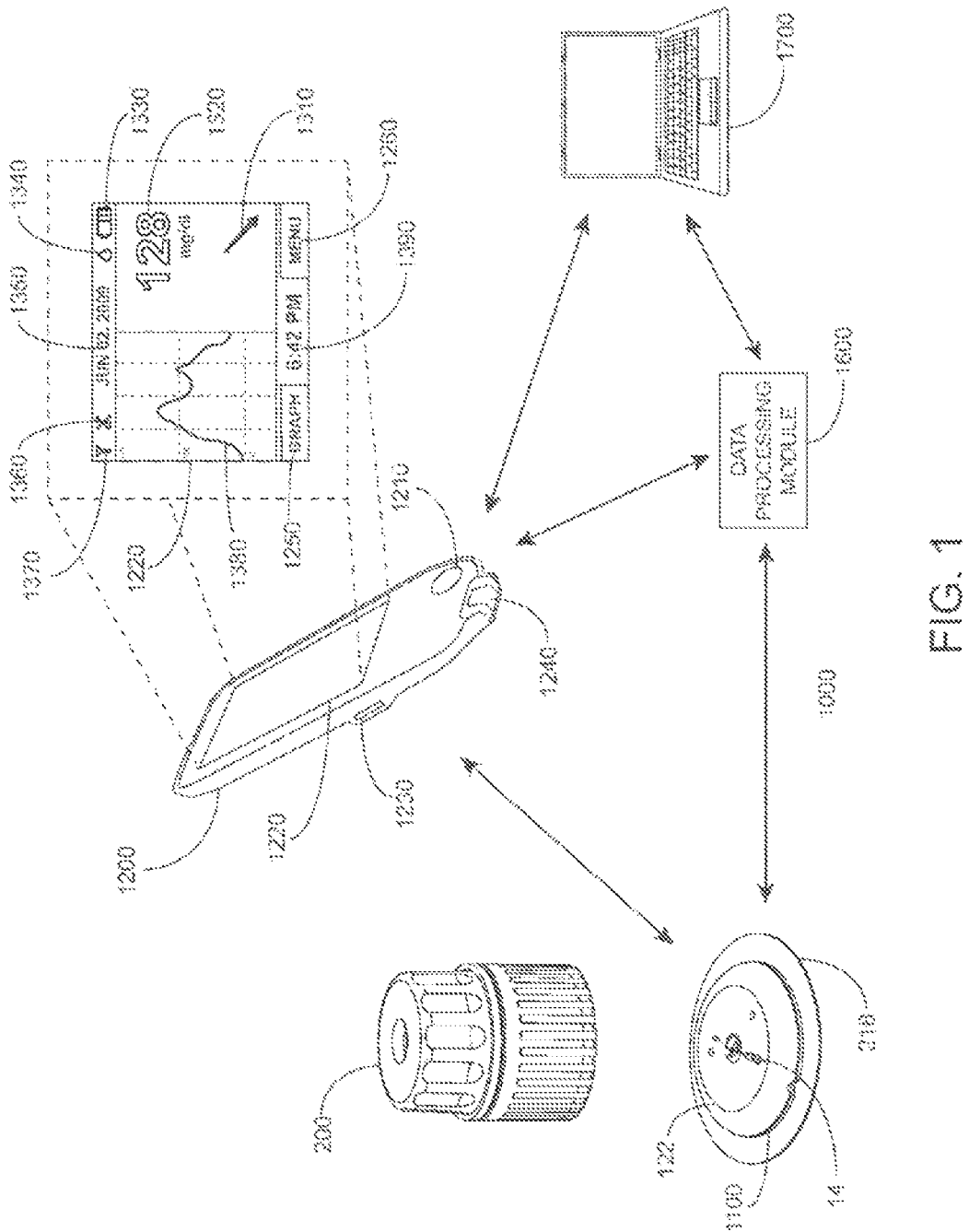
FIG. 1 illustrates an analyte monitoring system for real time analyte (e.g., glucose) measurement, data acquisition and/or processing in certain embodiments.

A detailed description of the disclosure is provided herein. It should be understood, in connection with the following description, that the subject matter is not limited to particular embodiments described, as the particular embodiments of the subject matter may, of course, vary. It is also to be understood that the terminology used herein is for the purpose of describing particular embodiments only, and is not intended to be limiting, since the scope of the disclosed subject matter will be limited only by the appended claims.

Where a range of values is provided, it is understood that each intervening value between the upper and lower limit of that range, and any other stated or intervening value in that stated range, is encompassed within the disclosed subject matter. Every range stated is also intended to specifically disclose each and every "subrange" of the stated range. That is, each and every range smaller than the outside range specified by the outside upper and outside lower limits given for a range, whose upper and lower limits are within the range from said outside lower limit to said outside upper limit (unless the context clearly dictates otherwise), is also to be understood as encompassed within the disclosed subject matter, subject to any specifically excluded range or limit within the stated range. Where a range is stated by specifying one or both of an upper and lower limit, ranges excluding either or both of those stated limits, or including one or both of them, are also encompassed within the disclosed subject matter, regardless of whether or not words such as "from," "to," "through," or "including" are or are not used in describing the range.

Unless defined otherwise, all technical and scientific terms used herein have the same meaning as commonly understood by one of ordinary skill in the art to which this disclosed subject matter belongs. Although any methods and materials similar or equivalent to those described herein can also be used in the practice or testing of the present disclosed subject matter, this disclosure may specifically mention certain exemplary methods and materials.

All publications mentioned in this disclosure are, unless otherwise specified, incorporated by reference herein for all purposes, including without limitation to disclose and describe the methods and/or materials in connection with which the publications are cited.

The publications discussed herein are provided solely for their disclosure prior to the filing date of the present application. Nothing herein is to be construed as an admission that the present disclosed subject matter is not entitled to antedate such publication by virtue of prior invention. Further, the dates of publication provided may be different from the actual publication dates, which may need to be independently confirmed.

As used herein and in the appended claims, the singular forms "a," "an," and "the" include plural referents unless the context clearly dictates otherwise.

Nothing contained in the Abstract or the Summary should be understood as limiting the scope of the disclosure. The Abstract and the Summary are provided for bibliographic and convenience purposes and due to their formats and purposes should not be considered comprehensive.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosed subject matter. Any recited method can be carried out in the order of events recited, or in any other order which is logically possible.

Reference to a singular item includes the possibility that there are plural of the same item present. When two or more items (for example, elements or processes) are referenced by an alternative "or," this indicates that either could be present separately or any combination of them could be present together except where the presence of one necessarily excludes the other or others.

Generally, embodiments of the present disclosure relate to an apparatus for inserting a medical device at least partially into the skin of the patient. Some embodiments relate to in vivo methods and devices for detecting at least one analyte such as glucose in body fluid. Accordingly, embodiments include in vivo analyte sensors configured so that at least a portion of the sensor is positioned in the body of a user (e.g., within the ISF), to obtain information about at least one analyte of the body, e.g., transcutaneously positioned in user's body. In certain embodiments, an in vivo analyte sensor is coupled to an electronics unit that is maintained on the body of the user to process information obtained from the sensor.

In certain embodiments, analyte information is communicated from a first device such as an on body electronics unit to a second device which may include user interface features, including a display, and/or the like. Information may be communicated from the first device to the second device automatically and/or continuously when the analyte information is available, or may not be communicated automatically and/or continuously, but rather stored or logged in a memory of the first device. Accordingly, in many embodiments of the system, analyte information derived by the sensor/on body electronics (for example, on body electronics) is made available in a user-usable or viewable form only when queried by the user such that the timing of data communication is selected by the user. In some embodiments, the display of information is selected by the user, while the timing of data communication is not.

In this manner, analyte information is only provided or evident to a user (provided at a user interface device) in some embodiments when desired by the user even though an in vivo analyte sensor automatically and/or continuously monitors the analyte level in vivo, i.e., the sensor automatically monitors analyte such as glucose on a pre-defined time interval over its usage life. For example, an analyte sensor may be positioned in vivo and coupled to on body electronics for a given sensing period, e.g., about 14 days. In certain embodiments, the sensor-derived analyte information is automatically communicated from the sensor electronics assembly to a remote monitor device or display device for output to a user throughout the 14 day period according to a schedule programmed at the on body electronics (e.g., about every 1 minute or about every 5 minutes or about every 10 minutes, or the like). In certain embodiments, sensor-derived analyte information is only communicated from the sensor electronics assembly to a remote monitor device or display device at user-determined times, e.g., whenever a user decides to check analyte information. At such times, a communications system is activated, and sensor-derived information is then sent from the on body electronics to the remote device or display device.

In still other embodiments, the information may be communicated from the first device to the second device automatically and/or continuously when the analyte information is available, and the second device stores or logs the received information without presenting or outputting the information to the user. In such embodiments, the information is received by the second device from the first device when the information becomes available (e.g., when the sensor detects the analyte level according to a time schedule). However, the received information is initially stored in the second device and only output to a user interface or an output component of the second device (e.g., display) upon detection of a request for the information on the second device.

Accordingly, in certain embodiments an inserter as described herein is used to place a sensor electronics assembly on the body so that at least a portion of the in vivo sensor is in contact with bodily fluid such as ISF. Once the sensor is electrically coupled to the electronics unit, sensor derived analyte information may be communicated from the on body electronics to a display device on-demand by powering on the display device (or it may be continually powered), and executing a software algorithm stored in and accessed from a memory of the display device, to generate one or more request commands, control signal or data packet to send to the on body electronics. The software algorithm executed under, for example, the control of the microprocessor or application specific integrated circuit (ASIC) of the display device may include routines to detect the position of the on body electronics relative to the display device to initiate the transmission of the generated request command, control signal and/or data packet.

Display devices may also include programming stored in memory for execution by one or more microprocessors and/or ASICs to generate and transmit the one or more request command, control signal or data packet to send to the on body electronics in response to a user activation of an input mechanism on the display device such as depressing a button on the display device, triggering a soft button associated with the data communication function, and so on. The input mechanism may be alternatively or additionally provided on or in the on body electronics which may be configured for user activation. In certain embodiments, voice commands or audible signals may be used to prompt or instruct the microprocessor or ASIC to execute the software routine(s) stored in the memory to generate and transmit the one or more request command, control signal or data packet to the on body device. In the embodiments that are voice activated or responsive to voice commands or audible signals, on body electronics and/or display device includes a microphone, a speaker, and processing routines stored in the respective memories of the on body electronics and/or the display device to process the voice commands and/or audible signals. In certain embodiments, positioning the on body electronics and the display device within a predetermined distance (e.g., close proximity) relative to each other initiates one or more software routines stored in the memory of the display device to generate and transmit a request command, control signal or data packet.

Different types and/or forms and/or amounts of information may be sent for each on demand reading, including but not limited to one or more of current analyte level information (i.e., real time or the most recently obtained analyte level information temporally corresponding to the time the reading is initiated), rate of change of an analyte over a predetermined time period, rate of the rate of change of an analyte (acceleration in the rate of change), historical analyte information corresponding to analyte information obtained prior to a given reading and stored in memory of the assembly. Some or all of real time, historical, rate of change, rate of rate of change (such as acceleration or deceleration) information may be sent to a display device for a given reading. In certain embodiments, the type and/or form and/or amount of information sent to a display device may be preprogrammed and/or unchangeable (e.g., preset at manufacturing), or may not be preprogrammed and/or unchangeable so that it may be selectable and/or changeable in the field one or more times (e.g., by activating a switch of the system, etc.). Accordingly, in certain embodiments, for each on demand reading, a display device will output a current (real time) sensor-derived analyte value (e.g., in numerical format), a current rate of analyte change (e.g., in the form of an analyte rate indicator such as an arrow pointing in a direction to indicate the current rate), and analyte trend history data based on sensor readings acquired by and stored in memory of on body electronics (e.g., in the form of a graphical trace). Additionally, the on skin or sensor temperature reading or measurement associated with each on demand reading may be communicated from the on body electronics to the display device. The temperature reading or measurement, however, may not be output or displayed on the display device, but rather, used in conjunction with a software routine executed by the display device to correct or compensate the analyte measurement output to the user on the display device.

As described, embodiments include inserters for in vivo analyte sensors and on body electronics that together provide body wearable sensor electronics assemblies. In certain embodiments, in vivo analyte sensors are fully integrated with on body electronics (fixedly connected during manufacture), while in other embodiments they are separate but connectable post manufacture (e.g., before, during or after sensor insertion into a body). On body electronics may include an in vivo glucose sensor, electronics, battery, and antenna encased (except for the sensor portion that is for in vivo positioning) in a waterproof housing that includes or is attachable to an adhesive pad. In certain embodiments, the housing withstands immersion in about one meter of water for up to at least 30 minutes. In certain embodiments, the housing withstands continuous underwater contact, e.g., for longer than about 30 minutes, and continues to function properly according to its intended use, e.g., without water damage to the housing electronics where the housing is suitable for water submersion.

Embodiments include sensor insertion devices, which also may be referred to herein as sensor delivery units, or the like. Insertion devices may retain on body electronics assemblies completely in an interior compartment, i.e., an insertion device may be "pre-loaded" with on body electronics assemblies during the manufacturing process (e.g., on body electronics may be packaged in a sterile interior compartment of an insertion device). In such embodiments, insertion devices may form sensor assembly packages (including sterile packages) for pre-use or new on body electronics assemblies, and insertion devices configured to apply on body electronics assemblies to recipient bodies.

Embodiments include portable handheld display devices, as separate devices and spaced apart from an on body electronics assembly, that collect information from the assemblies and provide sensor derived analyte readings to users. Such devices may also be referred to as meters, readers, monitors, receivers, human interface devices, companions, or the like. Certain embodiments may include an integrated in vitro analyte meter. In certain embodiments, display devices include one or more wired or wireless communications ports such as USB, serial, parallel, or the like, configured to establish communication between a display device and another unit (e.g., on body electronics, power unit to recharge a battery, a PC, etc.). For example, a display device communication port may enable charging a display device battery with a respective charging cable and/or data exchange between a display device and its compatible informatics software.

Compatible informatics software in certain embodiments include, for example, but not limited to stand alone or network connection enabled data management software program, resident or running on a display device, personal computer, a server terminal, for example, to perform data analysis, charting, data storage, data archiving and data communication as well as data synchronization. Informatics software in certain embodiments may also include software for executing field upgradable functions to upgrade firmware of a display device and/or on body electronics unit to upgrade the resident software on the display device and/or the on body electronics unit, e.g., with versions of firmware that include additional features and/or include software bugs or errors fixed, etc. Embodiments may include a haptic feedback feature such as a vibration motor or the like, configured so that corresponding notifications (e.g., a successful on-demand reading received at a display device), may be delivered in the form of haptic feedback.

Embodiments include programming embedded on a computer readable medium, i.e., computer-based application software (may also be referred to herein as informatics software or programming or the like) that processes analyte information obtained from the system and/or user self-reported data. Application software may be installed on a host computer such as a mobile telephone, PC, an Internet-enabled human interface device such as an Internet-enabled phone, personal digital assistant, or the like, by a display device or an on body electronics unit. Informatics programming may transform data acquired and stored on a display device or on body unit for use by a user.

Embodiments of the subject disclosure are described primarily with respect to glucose monitoring devices and systems, and methods of glucose monitoring, for convenience only and such description is in no way intended to limit the scope of the disclosure. It is to be understood that the analyte monitoring system may be configured to monitor a variety of analytes at the same time or at different times.

As described in detail below, embodiments include devices, systems, kits and/or methods to monitor one or more physiological parameters such as, for example, but not limited to, analyte levels, temperature levels, heart rate, user activity level, over a predetermined monitoring time period. Also provided are methods of manufacturing. Predetermined monitoring time periods may be less than about 1 hour, or may include about 1 hour or more, e.g., about a few hours or more, e.g., about a few days of more, e.g., about 3 or more days, e.g., about 5 days or more, e.g., about 7 days or more, e.g., about 10 days or more, e.g., about 14 days or more, e.g., about several weeks, e.g., about 1 month or more. In certain embodiments, after the expiration of the predetermined monitoring time period, one or more features of the system may be automatically deactivated or disabled at the on body electronics assembly and/or display device.

For example, a predetermined monitoring time period may begin with positioning the sensor in vivo and in contact with a body fluid such as ISF, and/or with the initiation (or powering on to full operational mode) of the on body electronics. Initialization of on body electronics may be implemented with a command generated and transmitted by a display device in response to the activation of a switch and/or by placing the display device within a predetermined distance (e.g., close proximity) to the on body electronics, or by user manual activation of a switch on the on body electronics unit, e.g., depressing a button, or such activation may be caused by the insertion device, e.g., as described in U.S. patent application Ser. No. 12/698,129, filed on Feb. 1, 2010, and U.S. Provisional Application Nos. 61/238,646, 61/246,825, 61/247,516, 61/249,535, 61/317,243, 61/345, 562, and 61/361,374, the disclosures of each of which are incorporated herein by reference for all purposes.

When initialized in response to a received command from a display device, the on body electronics retrieves and executes from its memory software routine to fully power on the components of the on body electronics, effectively placing the on body electronics in full operational mode in response to receiving the activation command from the display device. For example, prior to the receipt of the command from the display device, a portion of the components in the on body electronics may be powered by its internal power supply such as a battery while another portion of the components in the on body electronics may be in powered down or maintained in a low power state including no power state, inactive mode, or all components may be in an inactive, powered down mode. Upon receipt of the command, the remaining portion (or all) of the components of the on body electronics is switched to active, fully operational mode.

Embodiments of on body electronics may include one or more printed circuit boards with electronics including control logic implemented in ASIC, microprocessors, memory, and the like, and transcutaneously positionable analyte sensors forming a single assembly. On body electronics may be configured to provide one or more signals or data packets associated with a monitored analyte level upon detection of a display device of the analyte monitoring system within a predetermined proximity for a period of time (for example, about 2 minutes, e.g., 1 minute or less, e.g., about 30 seconds or less, e.g., about 10 seconds or less, e.g., about 5 seconds or less, e.g., about 2 seconds or less) and/or until a confirmation, such as an audible and/or visual and/or tactile (e.g., vibratory) notification, is output on the display device indicating successful acquisition of the analyte related signal from the on body electronics. A distinguishing notification may also be output for unsuccessful acquisition in certain embodiments.

In certain embodiments, the monitored analyte level may be correlated and/or converted to glucose levels in blood or other fluids such as ISF. Such conversion may be accomplished with the on body electronics, but in many embodiments will be accomplished with display device electronics. In certain embodiments, glucose level is derived from the monitored analyte level in the ISF.

Analyte sensors may be insertable into a vein, artery, or other portion of the body containing analyte. In certain embodiments, analyte sensors may be positioned in contact with ISF to detect the level of analyte, where the detected analyte level may be used to infer the user's glucose level in blood or interstitial tissue.

Embodiments include transcutaneous sensors and also wholly implantable sensors and wholly implantable assemblies in which a single assembly including the analyte sensor and electronics are provided in a sealed housing (e.g., hermetically sealed biocompatible housing) for implantation in a user's body for monitoring one or more physiological parameters.

Embodiments include analyte monitors that are provided in small, lightweight, battery-powered and electronically-controlled systems. Such systems may be configured to detect physical parameters of subjects, such as signals indicative of in vivo analyte levels using an electrochemical sensor, and collect such signals, with or without processing. Any suitable measurement technique may be used to obtain signals from the sensors, e.g., may detect current, may employ potentiometry, etc. Techniques may include, but are not limited to amperometry, coulometry, and voltammetry. In some embodiments, sensing systems may be optical, colorimetric, and the like. In some embodiments, the portion of the system that performs this initial processing may be configured to provide the raw or at least initially processed data to another unit for further collection and/or processing. Such provision of data may be affected, for example, by a wired connection, such as an electrical, or by a wireless connection, such as an IR or RF connection.

In certain systems, the analyte sensor is in communication with on body electronics. The on-body unit may include a housing in which the on body electronics and at least a portion of the sensor are received.

Certain embodiments are modular. The on-body unit may be separately provided as a physically distinct assembly from a monitor unit, e.g., which displays or otherwise indicates analyte levels to a user. The on-body unit may be configured to provide the analyte levels detected by the sensor and/or other information (such as temperature, sensor life, etc.) over a communication link to the monitor unit. The monitor unit, in some embodiments, may include, e.g., a mobile telephone device, an in vitro glucose meter, a personal digital assistant, or other consumer electronics such as MP3 device, camera, radio, personal computer, etc., or other communication-enabled data-processing device.

The display unit may perform a variety of functions such as but not limited to data storage and/or processing and/or analysis and/or communication, etc., on the received analyte data to generate information pertaining to the monitored analyte levels and/or process the other information. The monitor unit may incorporate a display screen, which can be used, for example, to display measured analyte levels, and/or an audio component such as a speaker to audibly provide information to a user, and/or a vibration device to provide tactile feedback to a user. It is also useful for a user of an analyte-monitoring system to be able to see trend indications (including the magnitude and direction of any ongoing trend, e.g., the rate of change of an analyte or other parameter, and the amount of time a subject is above and/or below a threshold, such as a hypoglycemic and/or hyperglycemic threshold, etc.); such data may be displayed either numerically, or by a visual indicator such as an arrow that may vary in visual attributes, like size, shape, color, animation, or direction. The monitor unit may further be adapted to receive information from or about an in vitro analyte test strip, which may be manually or automatically entered into the monitor unit. In some embodiments a monitor unit may incorporate an in vitro analyte test strip port and related electronics in order to be able to make discrete (e.g., blood glucose) measurements using an in vitro test strip (see, e.g., U.S. Pat. No. 6,175,752, the disclosure of which is incorporated by reference herein for all purposes).

The modularity of these systems may vary where one or more components may be constructed to be single use and one or more may be constructed to be re-useable. In some embodiments the sensor is designed to be attachable and detachable from the on body electronics (and the on-body unit may be reusable), e.g., so that one or more of the components may be reused one or more times, while in other embodiments, the sensor and on body electronics may be provided as an integrated, undetachable package, which may be designed to be disposable after use, i.e., not re-used.

Embodiments of In Vivo Monitoring Systems

For purpose of illustration, and not limitation, the inserters described herein may be used in connection with an exemplary analyte monitoring system as depicted in FIG. 1. It is understood that the inserters described herein may be used with any medical device on its own or in connection with a system. FIG. 1 shows an exemplary in vivo-based analyte monitoring system 100 in accordance with embodiments of the present disclosure. As shown, in certain embodiments, analyte monitoring system 100 includes on body electronics 1100 electrically coupled to in vivo analyte sensor 14 (a proximal portion of which is shown in FIG. 1, and attached to adhesive layer 218 for attachment on a skin surface on the body of a user. On body electronics 1100 includes on body housing 122 that defines an interior compartment.

Also shown in FIG. 1 is insertion device 200 (or insertion devices 300, 400, 2400, 2500, 2700, 3700 described herein) that, when operated, transcutaneously positions a portion of analyte sensor 14 through a skin surface and in fluid contact with ISF, and positions on body electronics 1100 and adhesive layer 218 on a skin surface, as will be described in greater detail herein. In certain embodiments, on body electronics 1100, analyte sensor 14 and adhesive layer 218 are sealed within the housing of insertion device 200 before use, and in certain embodiments, adhesive layer 218 is also sealed within the housing or the adhesive layer can provide a seal for preserving the sterility of the apparatus. Additional details regarding insertion devices are discussed, e.g., in U.S. patent application Ser. No. 12/698,129 and U.S. Provisional Application Nos. 61/238,646, 61/246,825, 61/247, 516, 61/249,535, and 61/345,562, the disclosures of each of which are incorporated herein by reference for all purposes.

Referring back to the FIG. 1, analyte monitoring system 100 includes display device 1200 which includes a display 1220 to output information to the user, an input component 1210 such as a button, actuator, a touch sensitive switch, a capacitive switch, pressure sensitive switch, jog wheel or the like, to input data or command to display device 1200 or otherwise control the operation of display device 1200. It is noted that some embodiments may include display-less devices or devices without any user interface components. These devices may be functionalized to store data as a data logger and/or provide a conduit to transfer data from on body electronics and/or a display-less device to another device and/or location. Embodiments will be described herein as display devices for exemplary purposes which are in no way intended to limit the embodiments of the present disclosure. It will be apparent that display-less devices may also be used in certain embodiments.

In certain embodiments, on body electronics 1100 may be configured to store some or all of the monitored analyte related data received from analyte sensor 14 in a memory during the monitoring time period, and maintain it in memory until the usage period ends. In such embodiments, stored data is retrieved from on body electronics 1100 at the conclusion of the monitoring time period, for example, after removing analyte sensor 14 from the user by detaching on body electronics 1100 from the skin surface where it was positioned during the monitoring time period. In such data logging configurations, real time monitored analyte level is not communicated to display device 1200 during the monitoring period or otherwise transmitted from on body electronics 1100, but rather, retrieved from on body electronics 1100 after the monitoring time period.

In certain embodiments, input component 1210 of display device 1200 may include a microphone and display device 1200 may include software configured to analyze audio input received from the microphone, such that functions and operation of the display device 1200 may be controlled by voice commands. In certain embodiments, an output component of display device 1200 includes a speaker for outputting information as audible signals. Similar voice responsive components such as a speaker, microphone and software routines to generate, process and store voice driven signals may be provided to on body electronics 1100.

In certain embodiments, display 1220 and input component 1210 may be integrated into a single component, for example a display that can detect the presence and location of a physical contact touch upon the display such as a touch screen user interface. In such embodiments, the user may control the operation of display device 1200 by utilizing a set of pre-programmed motion commands, including, but not limited to, single or double tapping the display, dragging a finger or instrument across the display, motioning multiple fingers or instruments toward one another, motioning multiple fingers or instruments away from one another, etc. In certain embodiments, a display includes a touch screen having areas of pixels with single or dual function capacitive elements that serve as LCD elements and touch sensors.

Display device 1200 also includes data communication port 1230 for wired data communication with external devices such as remote terminal (personal computer) 1700, for example. Example embodiments of the data communication port 1230 include USB port, mini USB port, RS-232 port, Ethernet port, Firewire port, or other similar data communication ports configured to connect to the compatible data cables. Display device 1200 may also include an integrated in vitro glucose meter, including in vitro test strip port 1240 to receive an in vitro glucose test strip for performing in vitro blood glucose measurements.

Referring still to FIG. 1, display 1220 in certain embodiments is configured to display a variety of information—some or all of which may be displayed at the same or different time on display 1220. In certain embodiments the displayed information is user-selectable so that a user can customize the information shown on a given display screen. Display 1220 may include but is not limited to graphical display 1380, for example, providing a graphical output of glucose values over a monitored time period (which may show important markers such as meals, exercise, sleep, heart rate, blood pressure, etc., numerical display 1320, for example, providing monitored glucose values (acquired or received in response to the request for the information), and trend or directional arrow display 1310 that indicates a rate of analyte change and/or a rate of the rate of analyte change, e.g., by moving locations on display 1220.

As further shown in FIG. 1, display 1220 may also include date display 1350 providing for example, date information for the user, time of day information display 1390 providing time of day information to the user, battery level indicator display 1330 which graphically shows the condition of the battery (rechargeable or disposable) of the display device 1200, sensor calibration status icon display 1340 for example, in monitoring systems that require periodic, routine or a predetermined number of user calibration events, notifying the user that the analyte sensor calibration is necessary, audio/vibratory settings icon display 1360 for displaying the status of the audio/vibratory output or alarm state, and wireless connectivity status icon display 1370 that provides indication of wireless communication connection with other devices such as on body electronics, data processing module 1600, and/or remote terminal 1700. As additionally shown in FIG. 1, display 1220 may further include simulated touch screen button 1250, 1260 for accessing menus, changing display graph output configurations or otherwise for controlling the operation of display device 1200.

Referring back to FIG. 1, in certain embodiments, display 1220 of display device 1200 may be additionally, or instead of visual display, configured to output alarms notifications such as alarm and/or alert notifications, glucose values etc., which may be audible, tactile, or any combination thereof. In one aspect, the display device 1200 may include other output components such as a speaker, vibratory output component and the like to provide audible and/or vibratory output indication to the user in addition to the visual output indication provided on display 1220. Further details and other display embodiments can be found in, e.g., U.S. patent application Ser. No. 12/871,901, U.S. Provisional Application Nos. 61/238,672, 61/247,541, 61/297,625, the disclosures of each of which are incorporated herein by reference for all purposes.

After the positioning of on body electronics 1100 on the skin surface and analyte sensor 14 in vivo to establish fluid contact with ISF (or other appropriate body fluid), on body electronics 1100 in certain embodiments is configured to wirelessly communicate analyte related data (such as, for example, data corresponding to monitored analyte level and/or monitored temperature data, and/or stored historical analyte related data) when on body electronics 1100 receives a command or request signal from display device 1200. In certain embodiments, on body electronics 1100 may be configured to at least periodically broadcast real time data associated with monitored analyte level which is received by display device 1200 when display device 1200 is within communication range of the data broadcast from on body electronics 1100, i.e., it does not need a command or request from a display device to send information.

For example, display device 1200 may be configured to transmit one or more commands to on body electronics 1100 to initiate data transfer, and in response, on body electronics

1100 may be configured to wirelessly transmit stored analyte related data collected during the monitoring time period to display device 1200. Display device 1200 may in turn be connected to a remote terminal 1700 such as a personal computer and functions as a data conduit to transfer the stored analyte level information from the on body electronics 1100 to remote terminal 1700. In certain embodiments, the received data from the on body electronics 1100 may be stored (permanently or temporarily) in one or more memory of the display device 1200. In certain other embodiments, display device 1200 is configured as a data conduit to pass the data received from on body electronics 1100 to remote terminal 1700 that is connected to display device 1200.

Referring still to FIG. 1, also shown in analyte monitoring system 1000 are data processing module 1600 and remote terminal 1700. Remote terminal 1700 may include a personal computer, a server terminal a laptop computer or other suitable data processing devices including software for data management and analysis and communication with the components in the analyte monitoring system 1000. For example, remote terminal 1700 may be connected to a local area network (LAN), a wide area network (WAN), or other data network for uni-directional or bi-directional data communication between remote terminal 1700 and display device 1200 and/or data processing module 1600.

Remote terminal 1700 in certain embodiments may include one or more computer terminals located at a physician's office or a hospital. For example, remote terminal 1700 may be located at a location other than the location of display device 1200. Remote terminal 1700 and display device 1200 could be in different rooms or different buildings. Remote terminal 1700 and display device 1200 could be at least about one mile apart, e.g., at least about 100 miles apart, e.g., at least about 1000 miles apart. For example, remote terminal 1700 could be in the same city as display device 1200, remote terminal 1700 could be in a different city than display device 1200, remote terminal 1700 could be in the same state as display device 1200, remote terminal 1700 could be in a different state than display device 1200, remote terminal 1700 could be in the same country as display device 1200, or remote terminal 1700 could be in a different country than display device 1200, for example.

In certain embodiments, a separate, optional data communication/processing device such as data processing module 1600 may be provided in analyte monitoring system 1000. Data processing module 1600 may include components to communicate using one or more wireless communication protocols such as, for example, but not limited to, infrared (IR) protocol, Bluetooth® protocol, Zigbee protocol, and 802.11 wireless LAN protocol. Additional description of communication protocols including those based on Bluetooth® protocol and/or Zigbee protocol can be found in U.S. Patent Publication No. 2006/0193375, incorporated herein by reference for all purposes. Data processing module 1600 may further include communication ports, drivers or connectors to establish wired communication with one or more of display device 1200, on body electronics 1100, or remote terminal 1700 including, for example, but not limited to USB connector and/or USB port, Ethernet connector and/or port, FireWire connector and/or port, or RS-232 port and/or connector.

In certain embodiments, data processing module 1600 is programmed to transmit a polling or query signal to on body electronics 1100 at a predetermined time interval (e.g., once every minute, once every five minutes, or the like), and in response, receive the monitored analyte level information from on body electronics 1100. Data processing module

1600 stores in its memory the received analyte level information, and/or relays or retransmits the received information to another device such as display device 1200. More specifically in certain embodiments, data processing module 1600 may be configured as a data relay device to retransmit or pass through the received analyte level data from on body electronics 1100 to display device 1200 or a remote terminal (for example, over a data network such as a cellular or WiFi data network) or both.

In certain embodiments, on body electronics 1100 and data processing module 1600 may be positioned on the skin surface of the user within a predetermined distance of each other (for example, about 1-12 inches, or about 1-10 inches, or about 1-7 inches, or about 1-5 inches) such that periodic communication between on body electronics 1100 and data processing module 1600 is maintained. Alternatively, data processing module 1600 may be worn on a belt or clothing item of the user, such that the desired distance for communication between the on body electronics 1100 and data processing module 1600 for data communication is maintained. In a further aspect, the housing of data processing module 1600 may be configured to couple to or engage with on body electronics 1100 such that the two devices are combined or integrated as a single assembly and positioned on the skin surface. In further embodiments, data processing module 1600 is detachably engaged or connected to on body electronics 1100 providing additional modularity such that data processing module 1600 may be optionally removed or reattached as desired.

Referring again to FIG. 1, in certain embodiments, data processing module 1600 is programmed to transmit a command or signal to on body electronics 1100 at a predetermined time interval such as once every minute, or once every 5 minutes or once every 30 minutes or any other suitable or desired programmable time interval to request analyte related data from on body electronics 1100. When data processing module 1600 receives the requested analyte related data, it stores the received data. In this manner, analyte monitoring system 1000 may be configured to receive the continuously monitored analyte related information at the programmed or programmable time interval, which is stored and/or displayed to the user. The stored data in data processing module 1600 may be subsequently provided or transmitted to display device 1200, remote terminal 1700 or the like for subsequent data analysis such as identifying frequency of periods of glycemic level excursions over the monitored time period, or the frequency of the alarm event occurrence during the monitored time period, for example, to improve therapy related decisions. Using this information, the doctor, healthcare provider or the user may adjust or recommend modification to the diet, daily habits and routines such as exercise, and the like.

In another embodiment, data processing module 1600 transmits a command or signal to on body electronics 1100 to receive the analyte related data in response to a user activation of a switch provided on data processing module 1600 or a user initiated command received from display device 1200. In further embodiments, data processing module 1600 is configured to transmit a command or signal to on body electronics 1100 in response to receiving a user initiated command only after a predetermined time interval has elapsed. For example, in certain embodiments, if the user does not initiate communication within a programmed time period, such as, for example about 5 hours from last communication (or 10 hours from the last communication, or 24 hours from the last communication), the data processing module 1600 may be programmed to automatically transmit a request command or signal to on body electronics 1100. Alternatively, data processing module 1600 may be programmed to activate an alarm to notify the user that a predetermined time period of time has elapsed since the last communication between the data processing module 1600 and on body electronics 1100. In this manner, users or healthcare providers may program or configure data processing module 1600 to provide certain compliance with analyte monitoring regimen, so that frequent determination of analyte levels is maintained or performed by the user.

In certain embodiments, when a programmed or programmable alarm condition is detected (for example, a detected glucose level monitored by analyte sensor 14 that is outside a predetermined acceptable range indicating a physiological condition) which requires attention or intervention for medical treatment or analysis (for example, a hypoglycemic condition, a hyperglycemic condition, an impending hyperglycemic condition or an impending hypoglycemic condition), the one or more output indications may be generated by the control logic or processor of the on body electronics 1100 and output to the user on a user interface of on body electronics 1100 so that corrective action may be timely taken. In addition to or alternatively, if display device 1200 is within communication range, the output indications or alarm data may be communicated to display device 1200 whose processor, upon detection of the alarm data reception, controls the display 1220 to output one or more notification.

In certain embodiments, control logic or microprocessors of on body electronics 1100 include software programs to determine future or anticipated analyte levels based on information obtained from analyte sensor 14, e.g., the current analyte level, the rate of change of the analyte level, the acceleration of the analyte level change, and/or analyte trend information determined based on stored monitored analyte data providing a historical trend or direction of analyte level fluctuation as function time during monitored time period. Predictive alarm parameters may be programmed or programmable in display device 1200, or the on body electronics 1100, or both, and output to the user in advance of anticipating the user's analyte level reaching the future level. This provides the user an opportunity to take timely corrective action.

Information, such as variation or fluctuation of the monitored analyte level as a function of time over the monitored time period providing analyte trend information, for example, may be determined by one or more control logic or microprocessors of display device 1200, data processing module 1600, and/or remote terminal 1700, and/or on body electronics 1100. Such information may be displayed as, for example, a graph (such as a line graph) to indicate to the user the current and/or historical and/or and predicted future analyte levels as measured and predicted by the analyte monitoring system 1000. Such information may also be displayed as directional arrows (for example, see trend or directional arrow display 1310) or other icon(s), e.g., the position of which on the screen relative to a reference point indicated whether the analyte level is increasing or decreasing as well as the acceleration or deceleration of the increase or decrease in analyte level. This information may be utilized by the user to determine any necessary corrective actions to ensure the analyte level remains within an acceptable and/or clinically safe range. Other visual indicators, including colors, flashing, fading, etc., as well as audio indicators including a change in pitch, volume, or tone of an audio output and/or vibratory or other tactile indicators may also be incorporated into the display of trend data as means of notifying the user of the current level and/or direction and/or rate of change of the monitored analyte level. For example, based on a determined rate of glucose change, programmed clinically significant glucose threshold levels (e.g., hyperglycemic and/or hypoglycemic levels), and current analyte level derived by an in vivo analyte sensor, the system 1000 may include an algorithm stored on computer readable medium to determine the time it will take to reach a clinically significant level and will output notification in advance of reaching the clinically significant level, e.g., 30 minutes before a clinically significant level is anticipated, and/or 20 minutes, and/or 10 minutes, and/or 5 minutes, and/or 3 minutes, and/or 1 minute, and so on, with outputs increasing in intensity or the like.

Referring again back to FIG. 1, in certain embodiments, software algorithm(s) for execution by data processing module 1600 may be stored in an external memory device such as an SD card, microSD card, compact flash card, XD card, Memory Stick card, Memory Stick Duo card, or USB memory stick/device including executable programs stored in such devices for execution upon connection to the respective one or more of the on body electronics 1100, remote terminal 1700 or display device 1200. In a further aspect, software algorithms for execution by data processing module 1600 may be provided to a communication device such as a mobile telephone including, for example, WiFi or Internet enabled smart phones or personal digital assistants (PDAs) as a downloadable application for execution by the downloading communication device.

Examples of smart phones include Windows®, Android™, iPhone® operating system, Palm® WebOS™, Blackberry® operating system, or Symbian® operating system based mobile telephones with data network connectivity functionality for data communication over an internet connection and/or a local area network (LAN). PDAs as described above include, for example, portable electronic devices including one or more microprocessors and data communication capability with a user interface (e.g., display/output unit and/or input unit, and configured for performing data processing, data upload/download over the internet, for example. In such embodiments, remote terminal 1700 may be configured to provide the executable application software to the one or more of the communication devices described above when communication between the remote terminal 1700 and the devices are established.

In still further embodiments, executable software applications may be provided over-the-air (OTA) as an OTA download such that wired connection to remote terminal 1700 is not necessary. For example, executable applications may be automatically downloaded as software download to the communication device, and depending upon the configuration of the communication device, installed on the device for use automatically, or based on user confirmation or acknowledgement on the communication device to execute the installation of the application. The OTA download and installation of software may include software applications and/or routines that are updates or upgrades to the existing functions or features of data processing module 1600 and/or display device 1200.

Referring back to remote terminal 1700 of FIG. 1, in certain embodiments, new software and/or software updates such as software patches or fixes, firmware updates or software driver upgrades, among others, for display device 1200 and/or on body electronics 1100 and/or data processing module 1600 may be provided by remote terminal 1700 when communication between the remote terminal 1700 and display device 1200 and/or data processing module 1600 is established. For example, software upgrades, executable programming changes or modification for on body electronics 1100 may be received from remote terminal 1700 by one or more of display device 1200 or data processing module 1600, and thereafter, provided to on body electronics 1100 to update its software or programmable functions. For example, in certain embodiments, software received and installed in on body electronics 1100 may include software bug fixes, modification to the previously stalled software parameters (modification to analyte related data storage time interval, resetting or adjusting time base or information of on body electronics 1100, modification to the transmitted data type, data transmission sequence, or data storage time period, among others). Additional details describing field upgradability of software of portable electronic devices, and data processing are provided in U.S. application Ser. Nos. 12/698,124, 12/794,721, 12/699,653, and 12/699,844, and U.S. Provisional Application Nos. 61/359,265, and 61/325, 155 the disclosures of which are incorporated by reference herein for all purposes.

The Sensor

The analyte sensor 14 of the analyte measurement system 100 may be used to monitor levels of a wide variety of analytes. Analytes that may be monitored include, for example, acetylcholine, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid-stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. One or more analyte may be monitored by a given sensor. In those embodiments that monitor more than one analyte, the analytes may be monitored at the same or different times, which may use the same on body electronics (e.g., simultaneously) or with different on body electronics.

In one embodiment of the present disclosure, sensor 14 is physically positioned in or on the body of a user whose analyte level is being monitored. Sensor 14 may be configured to continuously sample the analyte level of the user and convert the sampled analyte level, e.g., glucose concentration into a corresponding data signal, e.g., a current or voltage, for input into on body electronics. Alternatively, sensor 14 may be configured to sample analyte levels on demand. The on body electronics may amplify, filter, average, and/or otherwise process signal provided by the sensor.

Figure 2:
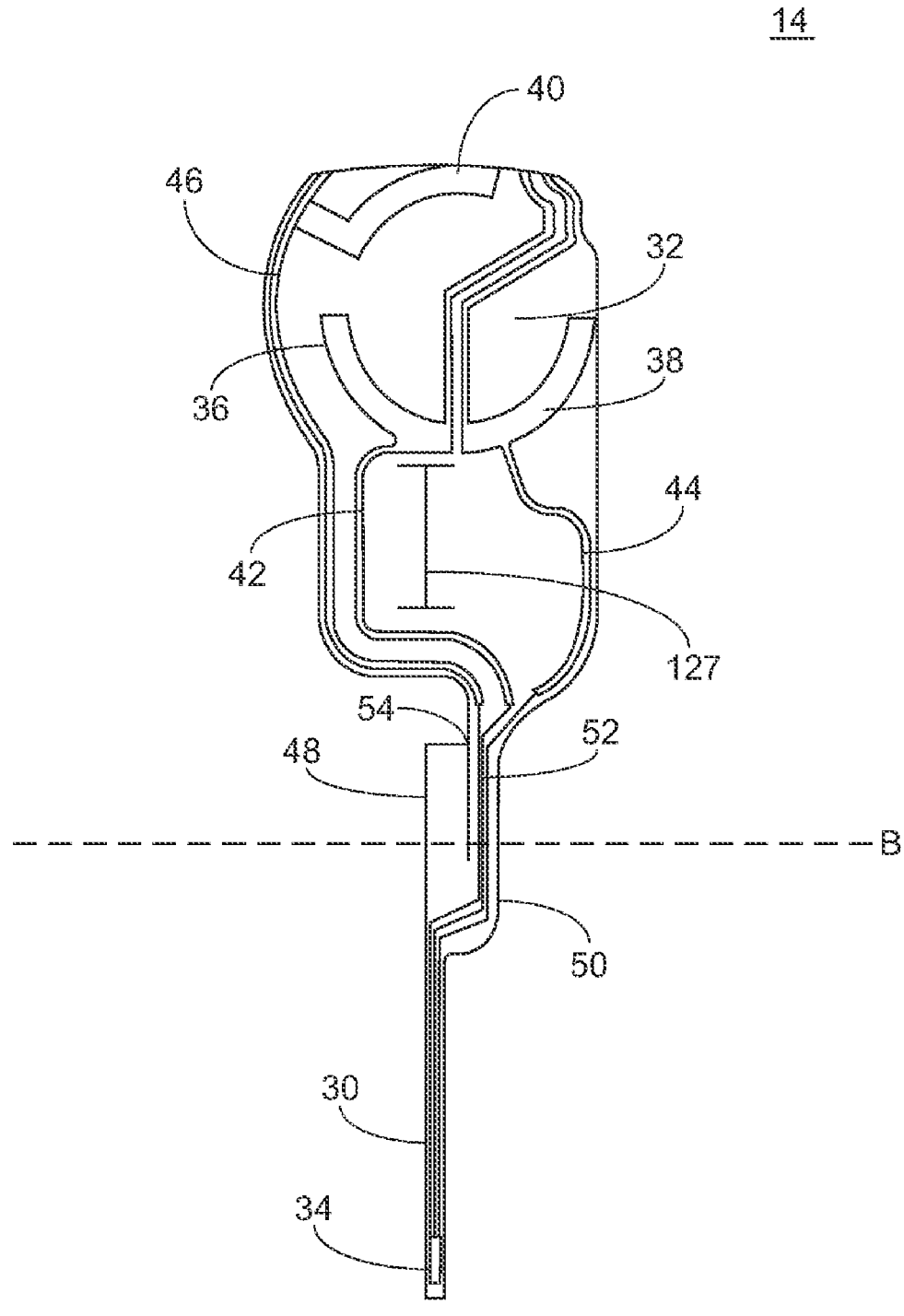
FIG. 2 is a view of an electrochemical sensor in accordance with an embodiment of the disclosed subject matter.

An embodiment of the sensor 14 is illustrated in FIG. 2. It is understood that the inserters described herein can be used with other medical devices. The shape(s) described herein are exemplary only. Other sensor shapes are contemplated. In some embodiments, sensor 14 includes a substrate which is a dielectric, e.g., a polymer or plastic material, such as polyester or polyamide. In this embodiment, the sensor is constructed so that a portion is positionable beneath skin and a portion is above skin. Accordingly, sensor 14 includes an insertion or internal portion 30 and an external or electrical contact portion 32. In some embodiments, the contact portion 32 includes several conductive contacts 36, 38, and 40 (herein shown as three contacts) for connection to other electronics, e.g., at the on body electronics 1100. (See FIG. 1.) The contacts provided in this embodiment are for a working electrode, a reference electrode, and a counter electrode. In some embodiments, two or more working electrodes are provided. The operative portions of these electrodes, that is, working electrode, reference electrode, and counter electrode (not individually shown), are provided at the insertion portion, e.g., at the distal end of insertion portion 30, e.g., portion 34. In some embodiments, one or more electrodes may be external to the body, e.g., an external counter electrode. The contact and operative portions of the electrodes are connected by circuit traces 42, 44, and 46 running on the surface of the substrate. In some embodiments, the traces are provided in channels, or may be embedded within the substrate, or may traverse different sides of the substrate. The conductive contacts, conductive traces, and electrodes are fabricated from conductive material, such as platinum, palladium, gold, carbon, or the like. More than one material may be used for a given sensor. Further details of sensors are described, e.g., in U.S. Pat. Nos. 6,175,572 and 6,103,033, which are incorporated by reference herein for all purposes.

Sensor 14 may include a proximal retention portion 48. The insertion portion 30 and the proximal retention portion 48 are sized and configured to be positioned with a sharp for installation into the skin of a subject, as described herein. In use, the sensor 14 may be configured to bend (e.g., along the line B) and therefore be positioned in two substantially perpendicular, intersecting planes. Such bending may occur prior to or during coupling to the on body electronics as described below. (See FIG. 17).

Figure 3:
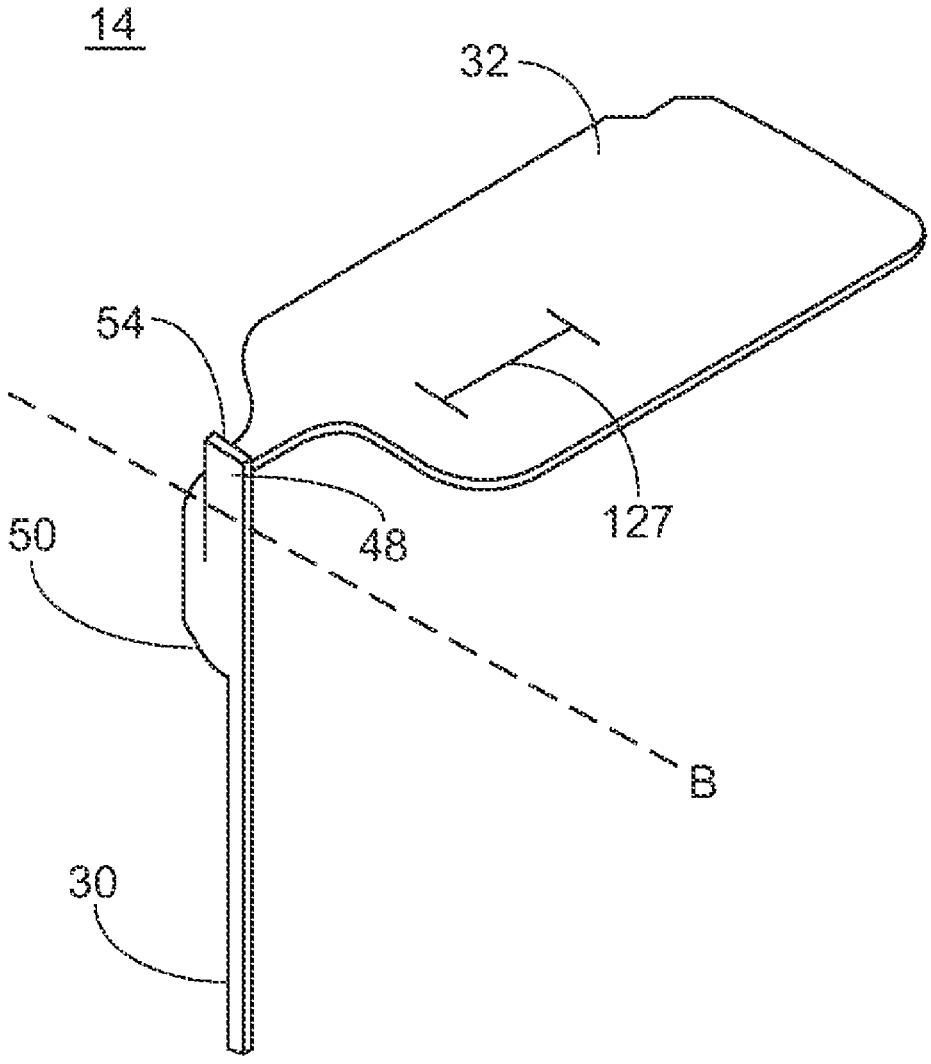
FIG. 3 is a view of the electrochemical sensor of FIG. 2 in a folded configuration in accordance with the disclosed subject matter.

Portions 48 and 52 provide a path for electrical connections, e.g., the conductive traces, between the proximal and distal portions of the sensor. Sensor 14 is further provided with a notch or cut-out 54. Such configuration facilitates the sensor 14 to bend (e.g., along the line indicated by line B) such that retention portion 48 remains upright and therefore be positioned in two substantially perpendicular, intersecting planes, as illustrated in FIG. 3. As will be described below, the sensor tab 50 can be encased in the on body housing 122 to aid in securing and positioning the sensor 14. Proximal retention portion 48 maintains its longitudinal alignment with insertion portion 30 for positioning within an insertion sharp.

Embodiments of analyte sensors have been described herein to operate electrochemically, through an arrangement of electrodes having chemical sensing layers applied thereto, by generating an electrical current proportional to the volume of a redox reaction of the analyte (and indicative of analyte concentration), catalyzed by an analyte-specific oxidizing enzyme. Embodiments exist in which the number of electrodes provided to bring about and detect the level of these reactions is two, three, or a greater number. However, other types of sensors may be employed as described herein.

A portion of sensor 14 may be situated above the surface of the skin, with a distal portion 30 penetrating through the skin and into the subcutaneous space in contact with the user's biofluid, such as ISF. Further details regarding the electrochemistry of sensor 14 is provided in U.S. Pat. Nos. 5,264,104; 5,356,786; 5,262,035; 5,320,725; and 6,990,366, each of which is incorporated by reference herein for all purposes.

In some embodiments, the sensor is implantable into a subject's body for a usage period (e.g., a minute or more, at least one day or more, about one to about 30 days or even longer, about three to about fourteen days, about three to about seven days, or in some embodiments, longer periods of up to several weeks) to contact and monitor an analyte present in a biological fluid. In this regard, the sensor can be disposed in a subject at a variety of sites (e.g., abdomen, upper arm, thigh, etc.), including intramuscularly, transcutaneously, intravascularly, or in a body cavity.

In some embodiments, sensor 14 is employed by insertion and/or implantation into a user's body for some usage period. In such embodiments, the substrate may be formed from a relatively flexible material.

While the embodiments illustrated in FIGS. 2-3 have three electrodes, other embodiments can include a fewer or greater number of electrodes. For example, a two-electrode sensor can be utilized. The sensor 14 may be externally-powered and allow a current to pass which is proportional to the amount of analyte present. Alternatively, the sensor 14 itself may act as a current source in some embodiments. In some two-electrode embodiments, the sensor may be self-biasing and there may be no need for a reference electrode. An exemplary self-powered, two-electrode sensor is described in U.S. patent application Ser. No. 12/393,921, filed Feb. 26, 2009, and entitled "Self-Powered Analyte Sensor," which is hereby incorporated by reference herein for all purposes. The level of current provided by a self-powered sensor may be low, for example, on the order of nanoamperes, in certain embodiments.

Insertion Assembly

Insertion assemblies are provided, which are used to install a medical device to the subject. In some embodiments, an insertion assembly includes an inserter and the medical device itself. The inserter can be configured to insert various medical devices into the subject, such as for example, an analyte sensor, an infusion set, or a cannula. In some embodiments, the inserter can be configured to install a combination of such devices, e.g., a combined sensor/infusion set, etc., at the same or different times or locations. For example, in certain embodiments a given inserter can be configured to install a first device and a second device at different times. In this regard, the inserter can be reusable. For example, an inserter may be modifiable to be used with more than one medical device, to include more than one type of medical device, e.g., by attaching an adapter and/or removing detaching a portion of an inserter. The inserter can install the medical device in, under, or through the skin of the subject, or place the medical device on the surface of the skin. The medical device can include features or structures, e.g., barbs, tabs, adhesive, etc., to maintain the device in position with respect to the skin after insertion. The inserter device may also be used as a lancet, e.g., to pierce the skin without inserting or installing a medical device.

In some embodiments, an insertion assembly includes an inserter, an analyte sensor, and a power supply. The power supply may be applied to the patient, e.g., to the surface of the skin, simultaneously with the analyte sensor by the inserter. In other embodiments, the battery is installed after or before installation of the analyte sensor. In such case the power supply may be applied by the inserter or separately. The power supply may be used to provide a current or a potential to the sensor and/or to provide power for communication of one or more signals to the monitor unit.

In some embodiments, an insertion assembly includes an inserter, a medical device such as an analyte sensor, and on body electronics. The on body electronics may be deployed and/or installed simultaneously with the analyte sensor by the inserter. In other embodiments, the on body electronics are installed after or before installation of the analyte sensor. For example, the analyte sensor may be installed by the inserter, and the on body electronics may be subsequently installed.

In some embodiments, the on body electronics provide a voltage or current to the analyte sensor. In some embodiments, the on body electronics process signals provided by the analyte sensor. In further embodiments, the on body electronics may include communications functionality for providing signal relating to signal provided by the analyte sensor to a further component, such as, e.g., a monitor unit, a computer, or other component. In some embodiments, communications circuitry, such as an RFID antenna, is provided. The power supply may be used to power some or all of these functions. In some embodiments, power is provided from the monitor unit, e.g., via inductive coupling.

An inserter can include a plurality of different components. For example, an inserter may include one or more components for advancing a sharp towards the skin of the subject. The sensor and on body electronics may be supported by a support structure, such as a carriage. A driver may be provided for advancing the sharp and/or the analyte sensor/support structure towards the skin of the patient. In some embodiments, the actuator is directly or indirectly coupled to the sharp and/or support structure, such that manual force applied by the user to the actuator is transferred to the sharp and/or support structure. In some embodiments, the applied force drives the sharp and/or support structure between a retracted position (disposed within the insertion device) and an advanced position (disposed towards the skin of the patient). In some embodiments, the sensor and on body electronics is maintained in a retracted position prior to installation by contacting projections extending inwardly from a recess in the inserter. In accordance with this embodiment, the sensor and on body electronics are temporarily maintained operatively between the support structure and the projections disposed on the interior wall of the sheath.

An inserter can also include one or more components for retracting the sharp, while allowing the analyte sensor and optional on body electronics to remain on the subject. The components for retracting the sharp can include a retractor. It is understood that the retractor and the actuator may be the same structure or include some common components. In some embodiments, the retractor is directly or indirectly coupled to the sharp such that the manual force applied by the user is transferred from the retractor to the sharp to retract the sharp from the skin. In other embodiments, a drive assembly may be provided to retract the sharp. For example, the drive assembly may include a spring, motor, hydraulic piston, etc., to retract the sharp away from the skin of the subject. The drive assembly may also include a linear drive component.

In some embodiments, the retractor withdraws the sharp upon actuation by the user. In such cases, the user actuates the retractor when it is desired to withdraw the sharp. For example, the retractor may include a release switch. Upon activation of the release switch, the drive assembly, e.g., the spring or other driver, retracts the sharp from the skin. In other embodiments, the retractor and the actuator include common components. After activating the actuator to advance the sharp and the analyte sensor, the user releases the actuator, which allows the drive assembly to withdraw the sharp from the skin.

In some embodiments, the retractor withdraws the sharp without further user interaction after actuation of insertion. For example, the inserter may include features or components which automatically retract the sharp upon advancement of the sharp and support structure by a predetermined amount. Inserter devices, in which no further action by the user is required to initiate withdrawal of the sharp after insertion, are referred to herein as having "automatic" withdrawal of the sharp.

Inserter Devices

Figure 4:
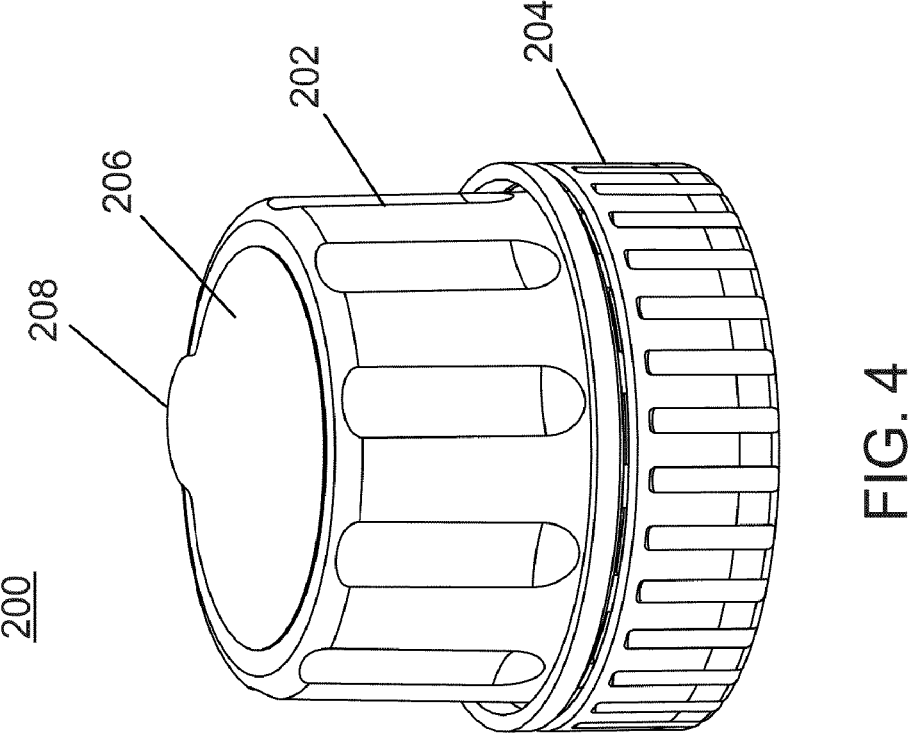
FIG. 4 is a perspective view of an embodiment of an inserter in accordance with one embodiment of the disclosed subject matter.

An inserter 200 in accordance with an exemplary embodiment is illustrated in FIG. 4. Inserter 200 includes a housing 202 and a removable distal cap 204 for maintaining a sterile environment for the medical device and sharp housed therein. In some embodiments, inserter 200 has a maximum diameter, of about 30 mm to about 60 mm, e.g., about 40 mm, about 43 mm, about 43.5 mm, about 50.5 mm, about 54.5 mm, etc. In some embodiments, inserter 200 has a maximum height of about 40 mm to about 80 mm, e.g., about 44 mm, about 46 mm, about 50 mm, about 53 mm, about 67 mm, about 71 mm, etc. In some embodiments, inserter 200 has a volume of about 35 cm$^3$ to about 110 cm$^3$, e.g., about 40 cm$^3$, about 41 cm$^3$, about 50 cm$^3$, about 60 cm$^3$, about 61 cm$^3$, about 62 cm$^3$, about 69 cm$^3$, about 70 cm$^3$, about 79 cm$^3$, about 90 cm$^3$, about 106 cm$^3$, etc. In the case of inserter 200, the dimensions are defined with respect to the housing 202.

Housing 202 and distal cap 204 may be fabricated from any suitable materials such as metal, plastic, etc. In some embodiments cap 204 may be fabricated from a polymer or plastic material. Also provided is a removable proximal cover 206, which, among other things, prevents accidental deployment of the inserter 200 and maintains a sterile environment. In some embodiments, proximal cover 206 is a sheet of material such as a foil sheet or the like secured to the upper surface of housing 202 using an adhesive, and may include a tab 208 to assist removal of the cover 206. Proximal cover 206 may also be a plastic sheet or member that forms a seal with housing 202. In some embodiments, proximal cover 206 may include a pull tab or a perforated section for easy removal.

Figure 5:
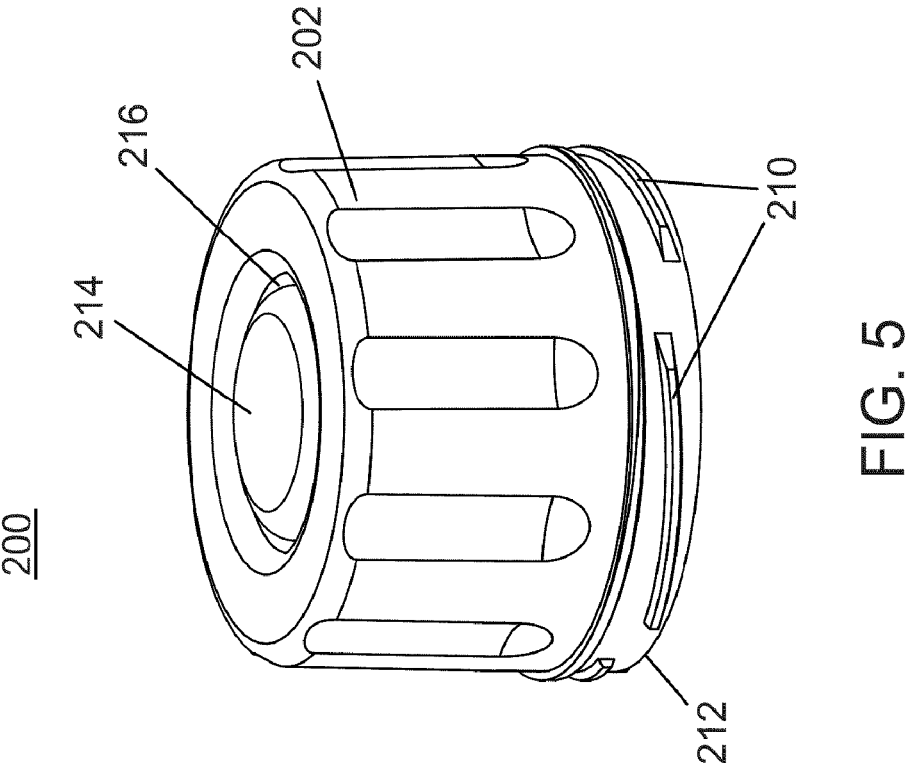
FIGS. 5-6 are perspective views of the inserter of FIG. 4 in accordance with the disclosed subject matter.

As illustrated in FIG. 5, proximal cover 206 and distal cap 204 are shown removed from inserter 200. Distal cap 204 is secured to housing 202, e.g., by use of threads 210. In some embodiments, distal cap 204 is secured by a friction fit, snap fit, a bayonet mount, an adhesive, etc. The distal portion of cap 204 may include a recess for retaining a desiccant therein. In some embodiments, a silica gel or molecular sieves may be used. Such material can be in granular form (pellets) or pressed into tablets, or otherwise. In some embodiments, silica gel tablets are used. Embodiments may include desiccant and/or packaging as described in U.S. patent application Ser. No. 12/714,439, which is incorporated by reference herein for all purposes. Cap 204 may be provided with one or more apertures, which allows for passage of air to the desiccant to remove moisture from the interior of the inserter 200.

Housing 202 includes a distal portion 212 for placement on the skin of a subject. Inserter 200 includes an actuator 214 to advance a medical device into the skin of the subject. In some embodiments, actuator 214 is disposed within an opening 216 in housing 202 and can be longitudinally moveable within housing 202.

Figure 6:
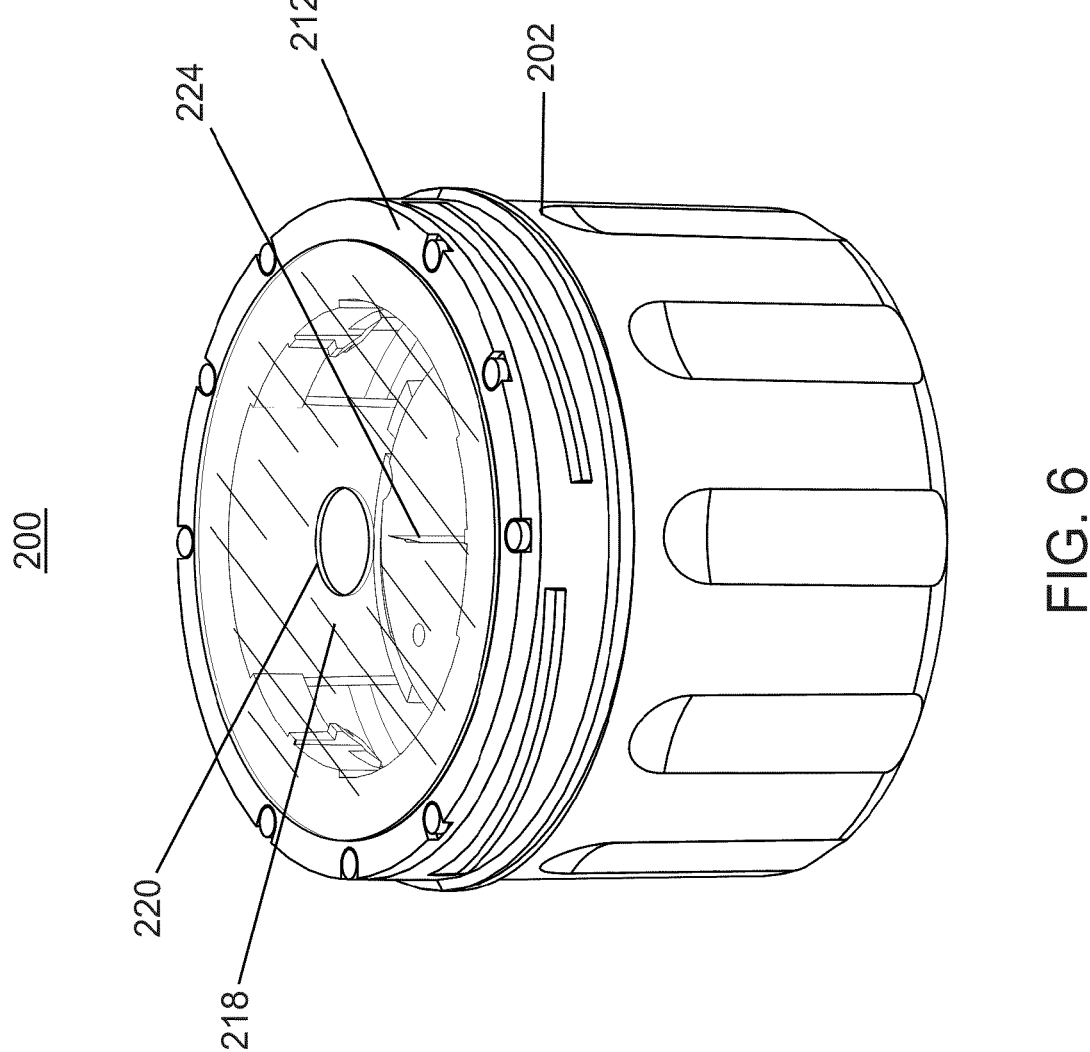

The distal portion of inserter 200 is illustrated in FIG. 6. In some embodiments, an adhesive pad 218, having adhesive material 218 on both faces, is provided across the distal portion 212 of the housing 202. A central aperture 220 may be provided in adhesive pad 218. As will be described in greater detail herein, inserter 200 supports a medical device, such as on body housing 122 (not shown) and a sharp 224. In some embodiments, on body housing 122, includes an analyte sensor 14. During insertion, sharp 224 passes through aperture 220 and into the skin of the subject carrying at least the sensor 14 with it.

Figure 7:
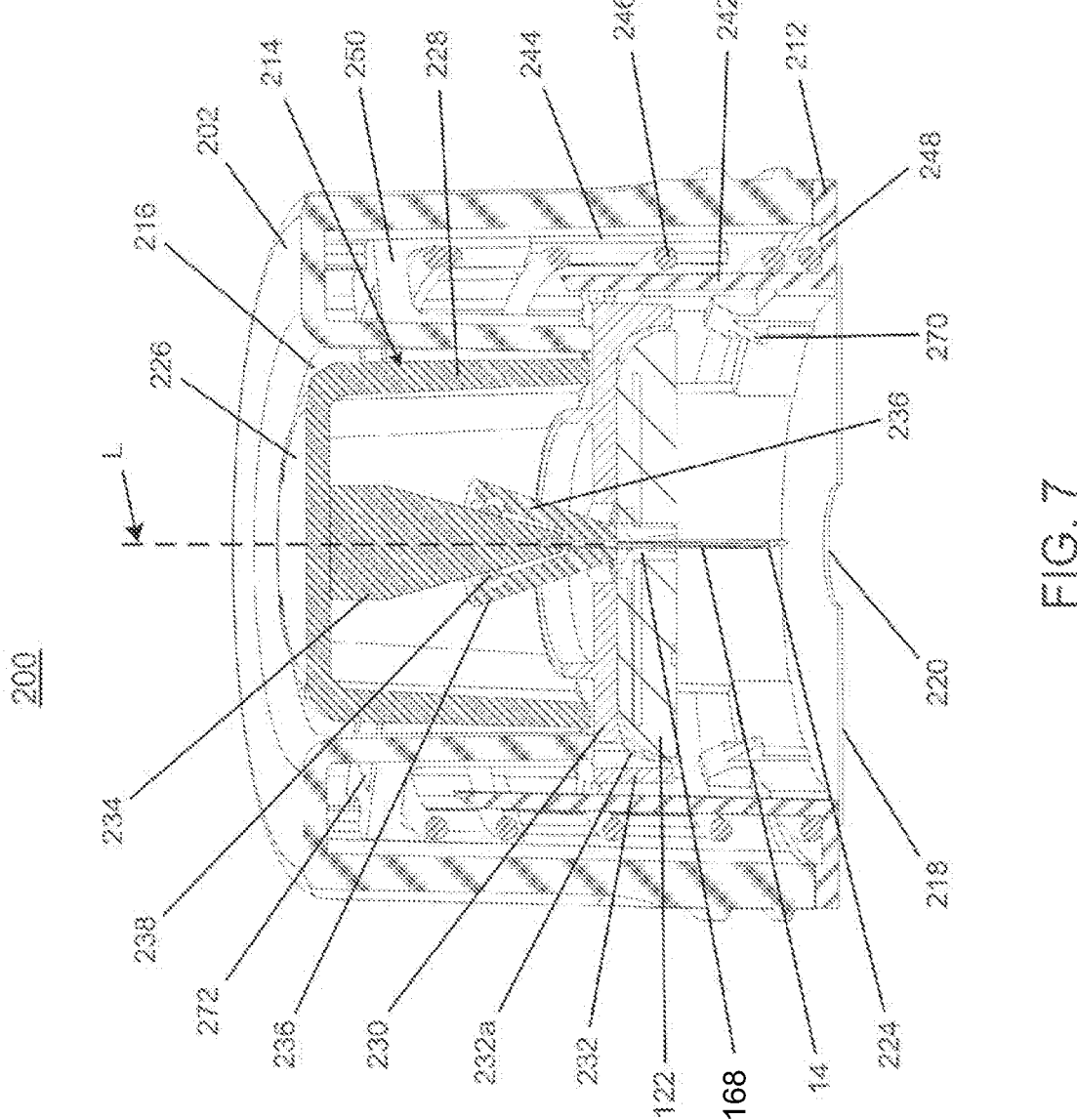
FIGS. 7-8 are sectional, perspective views of the inserter of FIG. 4 in accordance with the disclosed subject matter.

FIG. 7 illustrates inserter 200 in cross-section, in an initial configuration prior to use, after removal of the distal cap 204. Actuator 214 may be cylindrical in shape (or other shape as appropriate) and, including an upper contact surface 226, capable of being depressed by a user and/or a mechanism, as described herein. Actuator 214 may further include side walls 228 extending downwardly from upper surface 226, and which engage or otherwise contact the upper surface of carriage 230. Carriage 230 provides a support for holding the medical device, such as on body housing 122, prior to and during installation. In some embodiments, carriage 230 includes a distal portion 232, which may be configured to form a substantially concave recess 232a as shown in this embodiment, for supporting the medical device therein. In some embodiments, the on body housing 122 is supported within the recess 232a of carriage 230 in a snap-fit or other relationship. In some embodiments, carriage 230 does not include a recess. In such embodiments, carriage may include one or more projections which contact and/or advance the on body housing 122. (See, e.g., FIGS. 122, 135-136 herein.)

Figure 8:
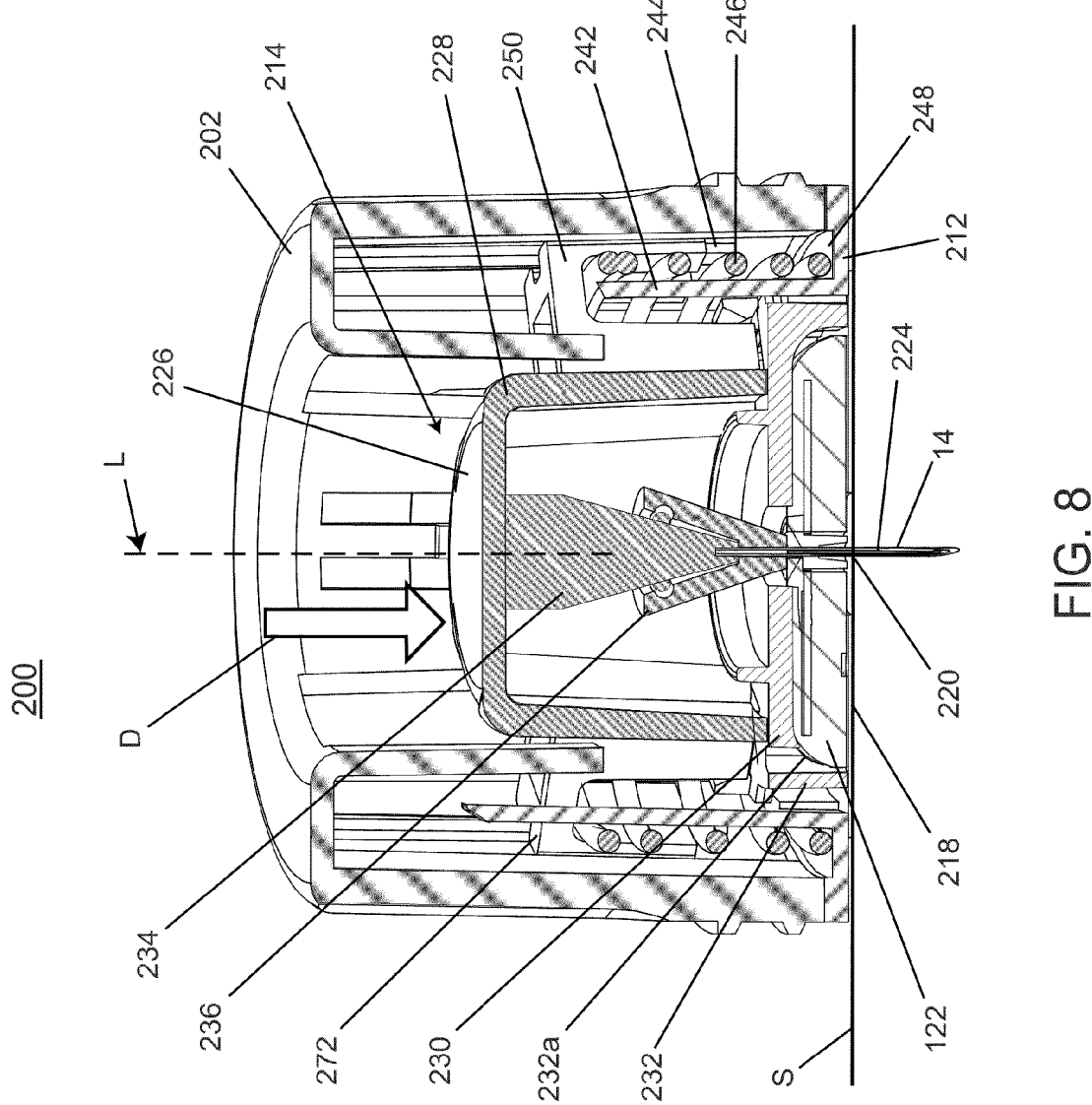

In FIG. 8 the longitudinal axis L of the inserter 200 is illustrated. Extending distally from the upper surface 226 of actuator 214 and substantially parallel to the longitudinal axis is a support member 234, which may have an elongated configuration. Support member 234 supports needle hub 236, from which sharp 224 extends longitudinally within the inserter 200. In some embodiments, the sharp 224 is supported at an oblique angle, e.g., between about 0° and 90° with respect to the skin surface. Needle hub 236 can be secured to support member 234 via an interlocking O-ring configuration, adhesive, or other techniques known in the art. Support member 234 can be omitted and needle hub 236 can be secured to the actuator 214 directly in some embodiments, e.g., by manufacturing needle hub 236 as a single component with actuator 214 or by otherwise adhering needle hub 236 to actuator 214.

In some embodiments, sharp 224 is a solid needle, for example, if inserter 200 is used to insert a cannula. In some embodiments, sharp 224 is provided with a substantially cylindrical configuration defining an interior bore, e.g., a rigid cylindrical member or a hypodermic-style needle. Sharp 224 may also be provided with an elongated longitudinal opening or gap in the wall of the sharp 224 (see, sharp 224 in FIGS. 11-18). In some embodiments, sharp 224 is fabricated from a sheet of metal, and folded into a substantially "V" or "U" or "C" configuration in cross-section to define the longitudinal recess.

Figures 9, 10:
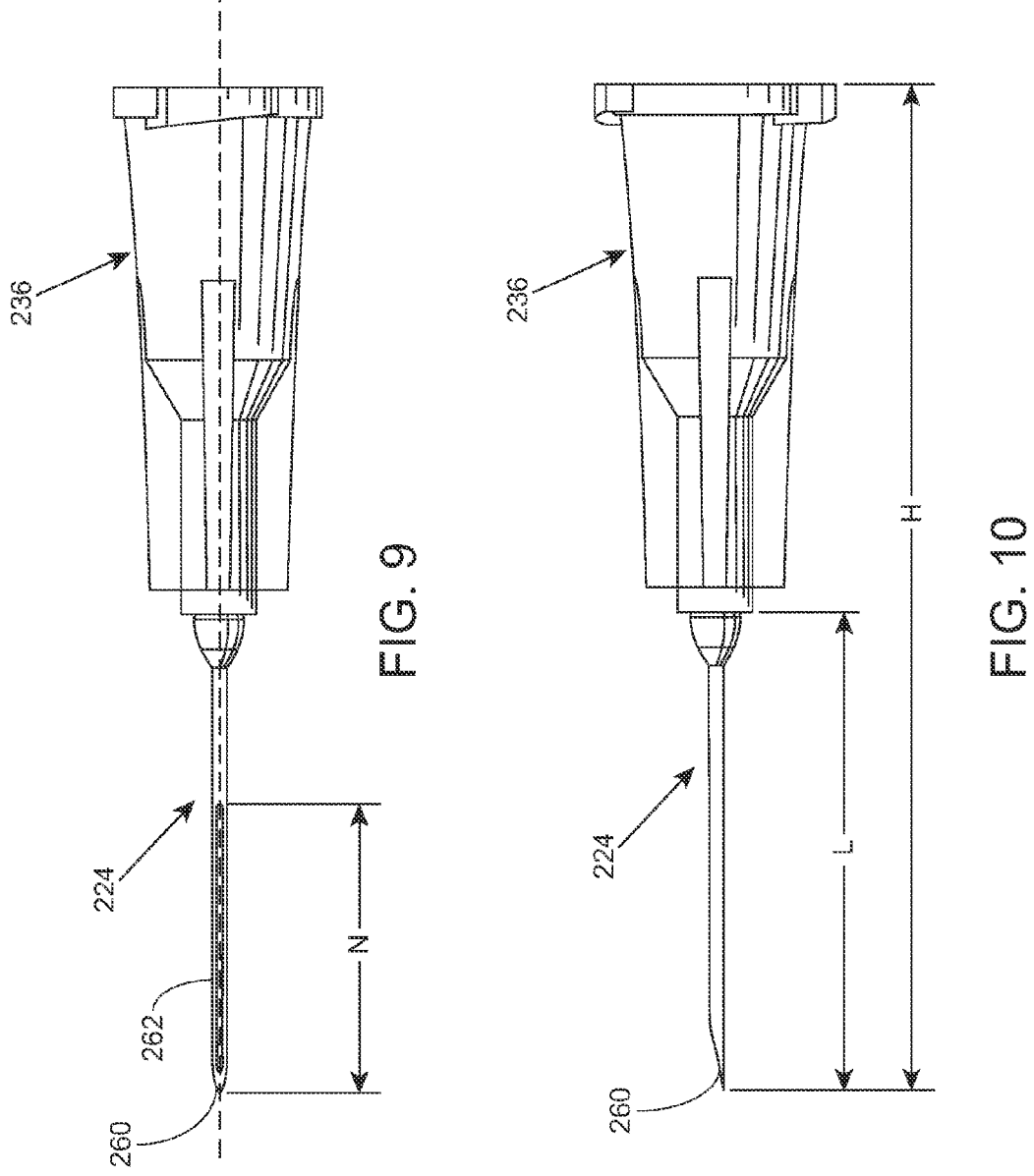
FIGS. 9-10 are schematic views of a needle hub in accordance with one embodiment of the disclosed subject matter.

Needle hub 236 is further illustrated in FIGS. 9-10. Needle hub 236 supports sharp 224, having a sharpened distal portion 260. In some embodiments, as discussed herein, a longitudinal wall opening or gap 262 is provided in at least a portion of the wall of the sharp 224. The length N of the gap 262 is selected to be commensurate with the length of the insertion portion 30 through to the proximal retention portion 48 of the sensor 14 where the bend at line B occurs (See FIGS. 2-3), and in certain embodiments may be about 3 mm to about 50 mm, e.g., about 5 mm, or about 10 mm, or about 15 mm, or about 20 mm. The length L of the sharp 224 may be about 3 mm to about 50 mm, e.g., 5 mm or more, or about 10 mm, or about 20 mm, or about 30 mm, or about 50 mm, and is selected based upon the length of the insertion portion 30 of a sensor and the desired depth of the insertion portion 30 of the sensor 14. In some embodiments, the distance or spacing between the two edges of the gap is about 0.2 mm to about 0.5 mm, e.g., about 0.22 mm, about 0.25 mm, etc. (See, spacing 257 in FIG. 11).

The distal portion 260 of sharp 224 is illustrated in greater detail in FIGS. 11-13. As illustrated in FIG. 11, sharp 224 has a substantially "C"- or "U"-shaped profile in this embodiment, but may have other configurations, e.g., substantially "V"-shaped. A longitudinal gap 262 is provided in the wall of the sharp 224. FIG. 12 illustrates distal portion 260 is provided with an angled tip. In some embodiments, the angled tip may be provided with a first angled tip portion 264 and a second steep-angled tip portion 266. The exemplary configuration, which includes multiple edges and faces, provides a sharp point to reduce penetration force, trauma, and bleeding for the subject. The distal section of the sensor body has a width sized to fit within the gap 262 of the insertion sharp 224 having a diameter less than about 20 to about 26 gauge, e.g., 21 gauge to about 25 gauge, where in certain embodiments the sharp is 21 gauge or 23 gauge or 25 gauge. Such sharp may be used with a sensor having a width or diameter—at least the portion that is carried by the sharp—of about 0.20 mm to about 0.80 mm, e.g., about 0.25 mm to about 0.60 mm, where in some embodiments the width or diameter of at least a portion of a sensor is 0.27 mm or 0.33 mm or 0.58 mm. In some embodiments, sharp 224 is fabricated from a sheet of metal and folded into a substantially "V" or "U" or "C" configuration in cross-section.

Figure 14:
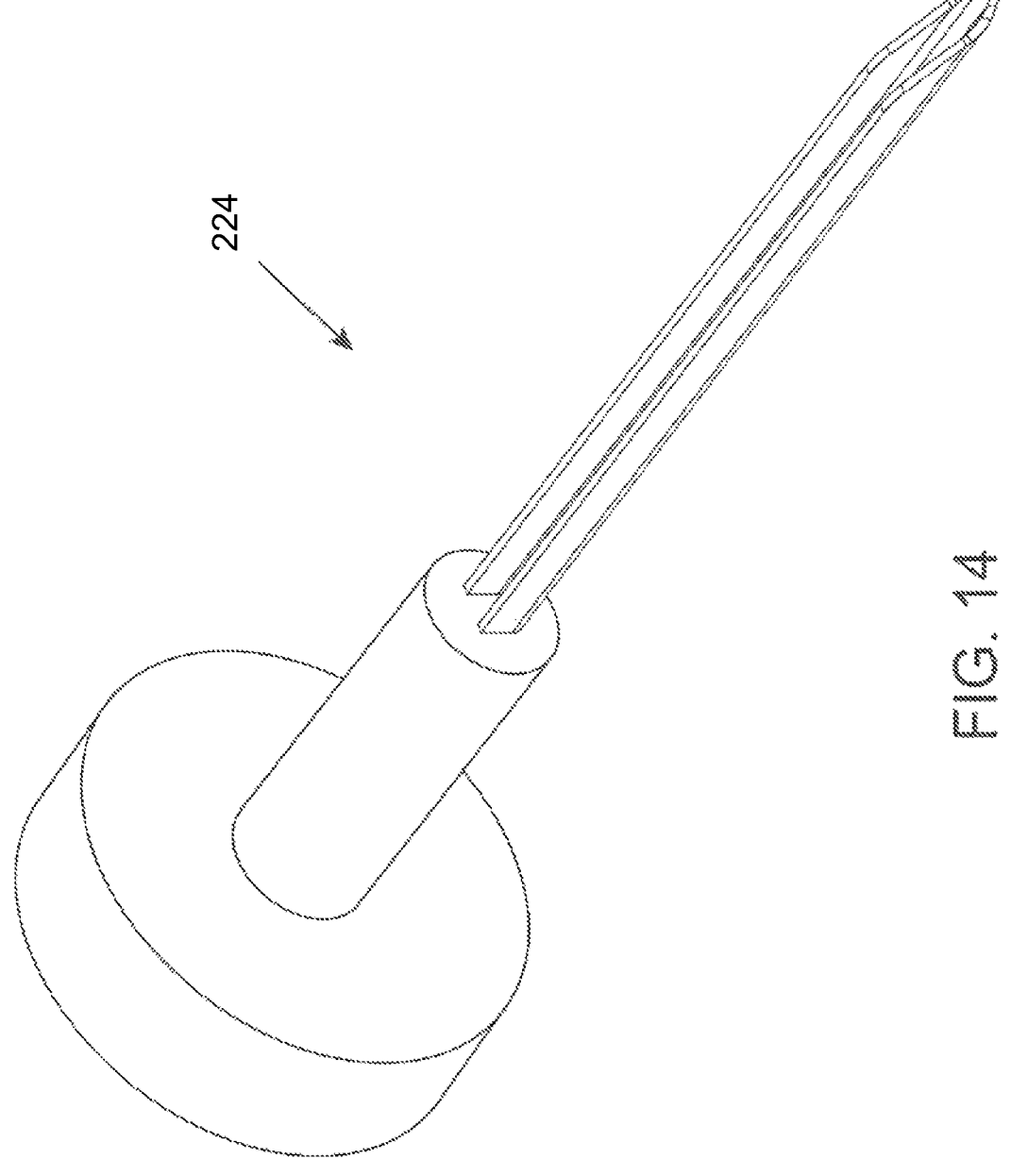
FIG. 14 is a perspective view of a sharp in accordance with one embodiment of the disclosed subject matter.

Various technologies can be used to manufacture a folded sheet of metal to form sharp 224. For example, etched-sheet metal technology can be used to form the sharp 224. In this manner, the sharp can be formed having a very sharp edge so that penetration through the skin during insertion is less painful. In other embodiments, a progressive die technology may be utilized to form a complex sheet-metal shape that has a sharp edge as depicted in FIG. 14. In some embodiments, the sharp 224 can be molded with a plastic cap so that the sharp can be handled during the inserter assembly process. Further, the die cut sharp may be molded with plastic to reinforce the "V," "U," or "C" shaped sheet metal configuration. In some embodiments, a "U" shaped cross-section can be provided with having flat, rather than curved walls. The "U" shaped configuration provides the advantage that they can more securely and closely hold the sensor. Also, the "U" shaped configuration provides the advantage that it has a reduced cross-section when compared with a comparable circular cross section. Further details of the tip of sharp 224 are illustrated in FIGS. 14A-C. As illustrated in FIGS. 14A-B, a top view of the sharp 224 is shown. This represents a flat portion of the sharp, e.g., the bottom of the "U" configuration. A tip is formed by first distal edges 263 closest to the distal tip and second distal edges 265 between the first distal edges 263 and the substantially parallel side walls 269. In some embodiments, the first distal edges 263 form an "included tip" angle of about 15 degrees, about 30 degrees, or about 60 degrees. Such angle is symmetrical, that is, equal angles from the longitudinal axis of the sharp 224. The second distal edges 265 provide a somewhat less acute angle than the first distal edges 263. In some embodiments, the "lead in" angle may be about 20 degrees, about 45 degrees, or about 65 degrees. By having a tip defined by two angles, a first, smaller "included angle" and a second, larger "lead in angle," allows the tip to meet several objectives. First, the small included angle allows the tip to pierce the skin with less trauma. Second, by broadening out to a larger angle, the overall length of the tip is reduced, and strength of the tip is increased. FIG. 14C illustrates a side view of the sharp 224 and illustrates the side walls 269. An additional angle, i.e., the "lead-out" angle is provided by the rising edge 267 of the sharp. The edge 267 provides the ability to separate the tissue to allow placement of the sensor 14. In other embodiments, a laser-cut sharp can be formed. In this manner, the laser can be used to form the wall opening or gap 262 and first-angled tip portion 264 and a second, steep-angled tip portion 266.

Figure 15:
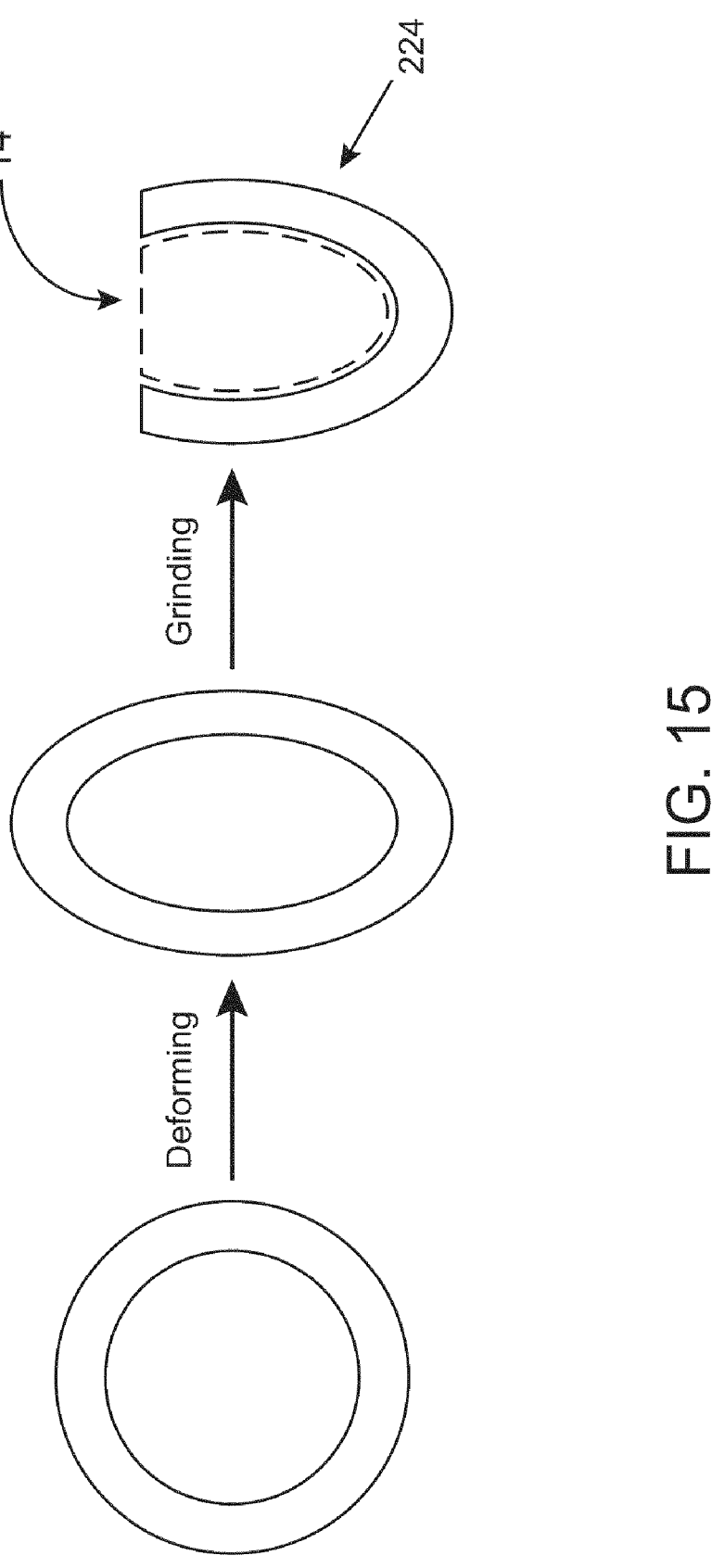
FIG. 15 is a schematic view of an alternate embodiment for forming a sharp to be used in an inserter in accordance with one embodiment of the disclosed subject matter.

In another embodiment, sharp 224 may be formed from a standard hypodermic needle utilizing the method depicted in FIG. 15. First, the hypodermic needle (having a circular cross-section) is cut to the desired length for sharp 224. Next, the hypodermic needle is compressed so that its cross-section is permanently deformed from a circular shape to an oval shape. The tip of the hypodermic needle is then ground to a bevel to produce a sharp point to reduce the required penetration force, as previously discussed. Finally, the top section of the needle is removed by appropriate techniques (e.g., grinding, electropolish, etc.). The resulting sharp 224 has a "U"-shaped configuration and provides ample space for the insertion of sensor 14. In some embodiments, the tip-grinding step and the compression step may be carried out in reversed order.

Due to the compression step, a user may initially start with a larger diameter hypodermic needle so that the finished sharp 224 will have similar dimensions to the previously described sharps.

Figure 16:
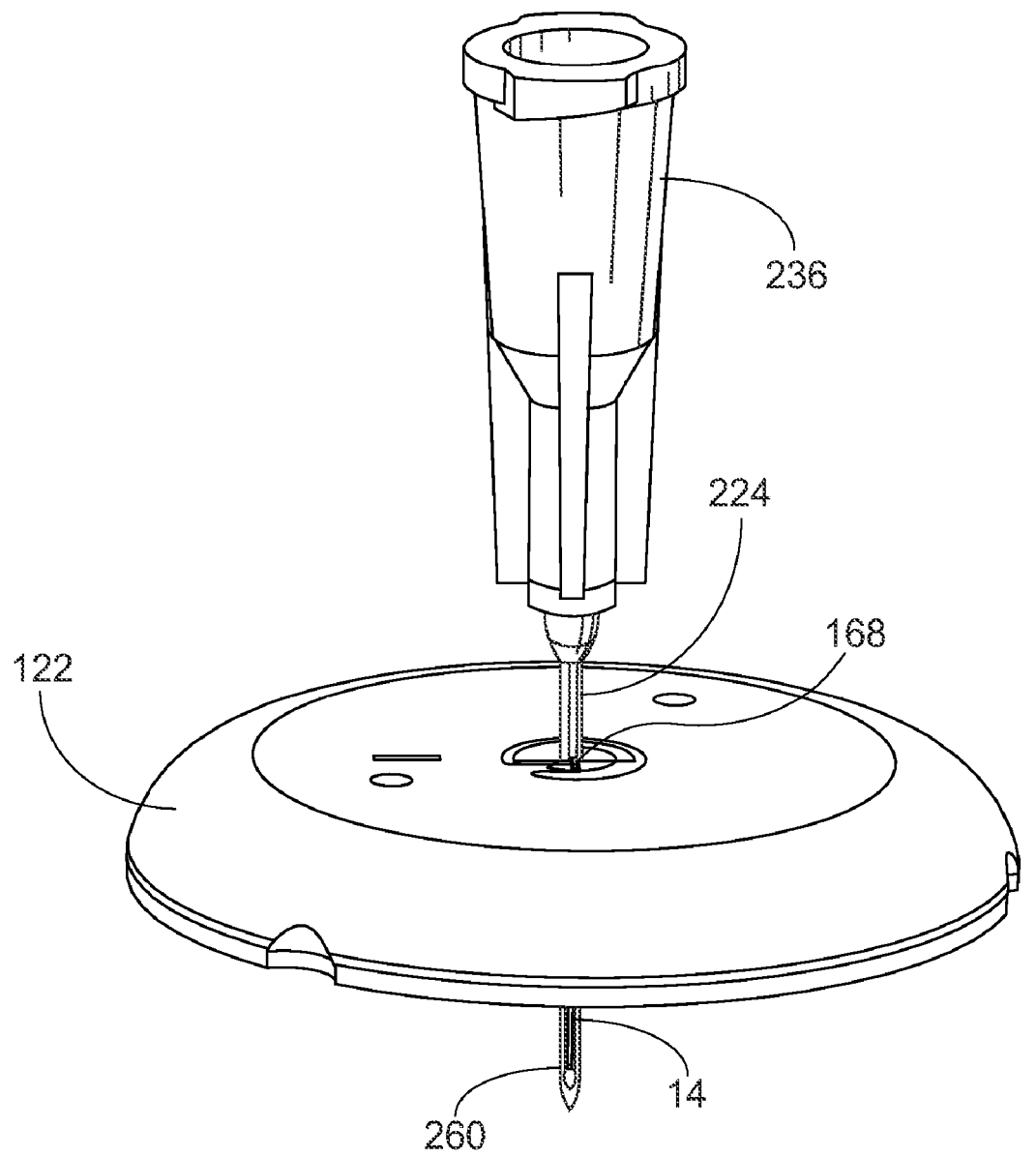
FIG. 16 is a perspective view of an inserter in accordance with one embodiment of the disclosed subject matter.
Figure 17:
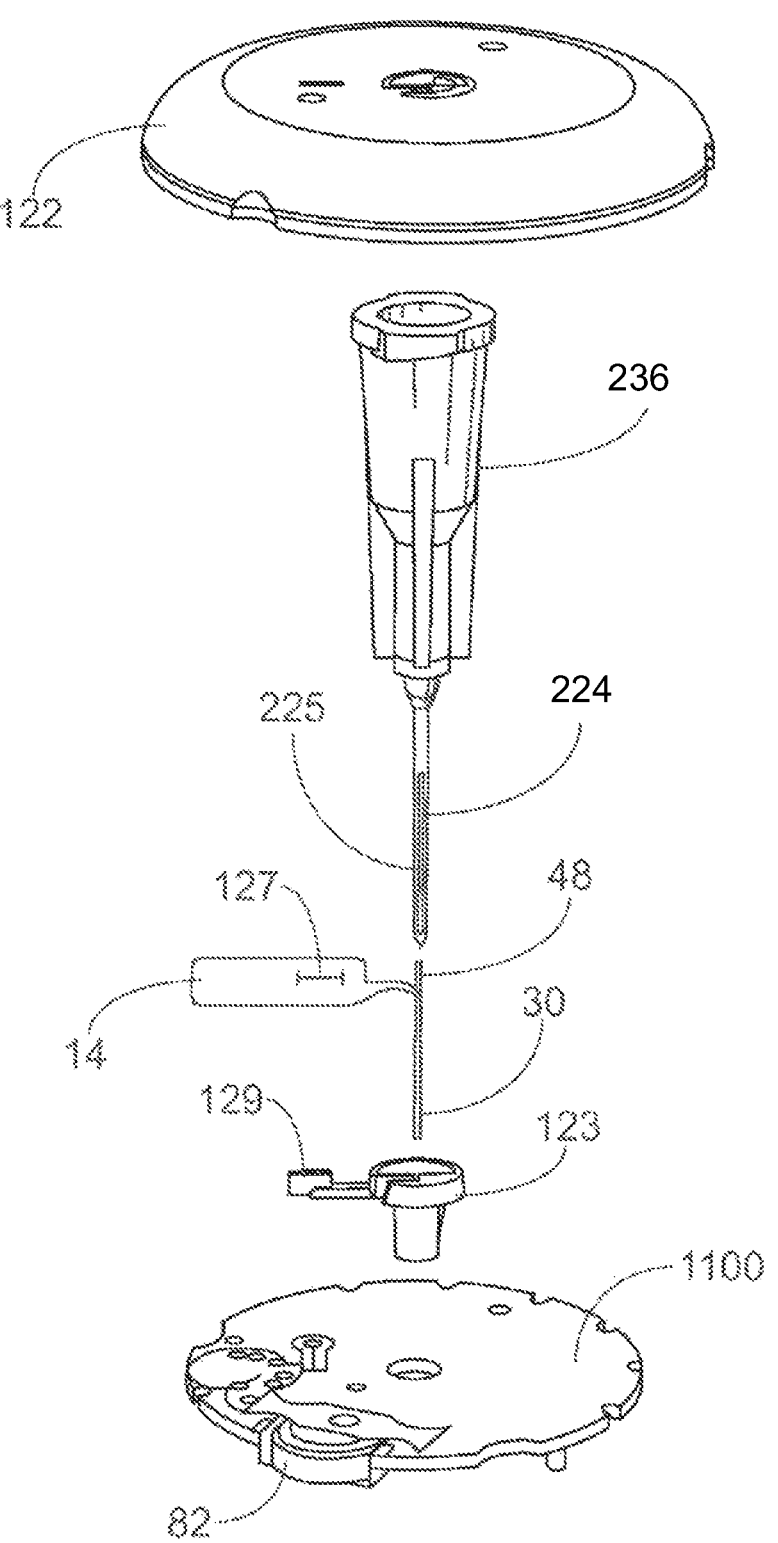
FIG. 17 is a perspective view with parts separated of an inserter in accordance with one embodiment of the disclosed subject matter.
Figure 18:
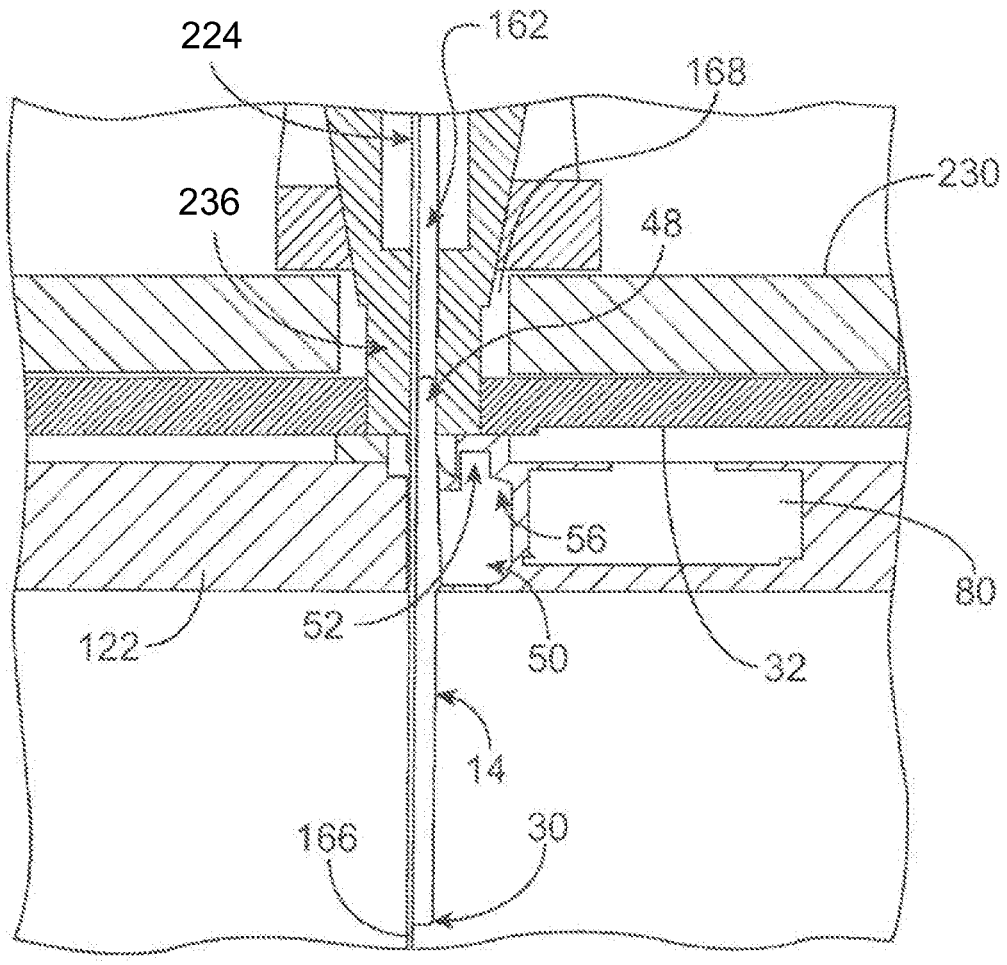
FIG. 18 is an enlarged sectional view with parts separated of an inserter in accordance with one embodiment of the disclosed subject matter.

FIGS. 16-18 illustrate the position of on body housing 122 with respect to the needle hub 236 and sharp 224. The on body housing 122 can be configured to hold at least a portion of sensor 14 and on body electronics 1100 (also referred to herein as electronics 80). As illustrated in FIG. 16, the sharp 224 extends through an aperture 168 in the on body housing 122. Thus, in some embodiments, the sharp 224 is uncoupled to on body housing 122. The distal portion of sensor 14 is positioned within the sharp 224. As further illustrated in FIG. 17, on body electronics 1100 and sensor hub 123 are positioned within on body housing 122. Sensor 14 may include an optional positioning structure, or slit 127, which receives a positioning member, such as tab 129 of sensor hub 123. A power supply 82, such as a battery, e.g., a single use disposable battery, or rechargeable battery, is optionally provided.

Figure 17A:
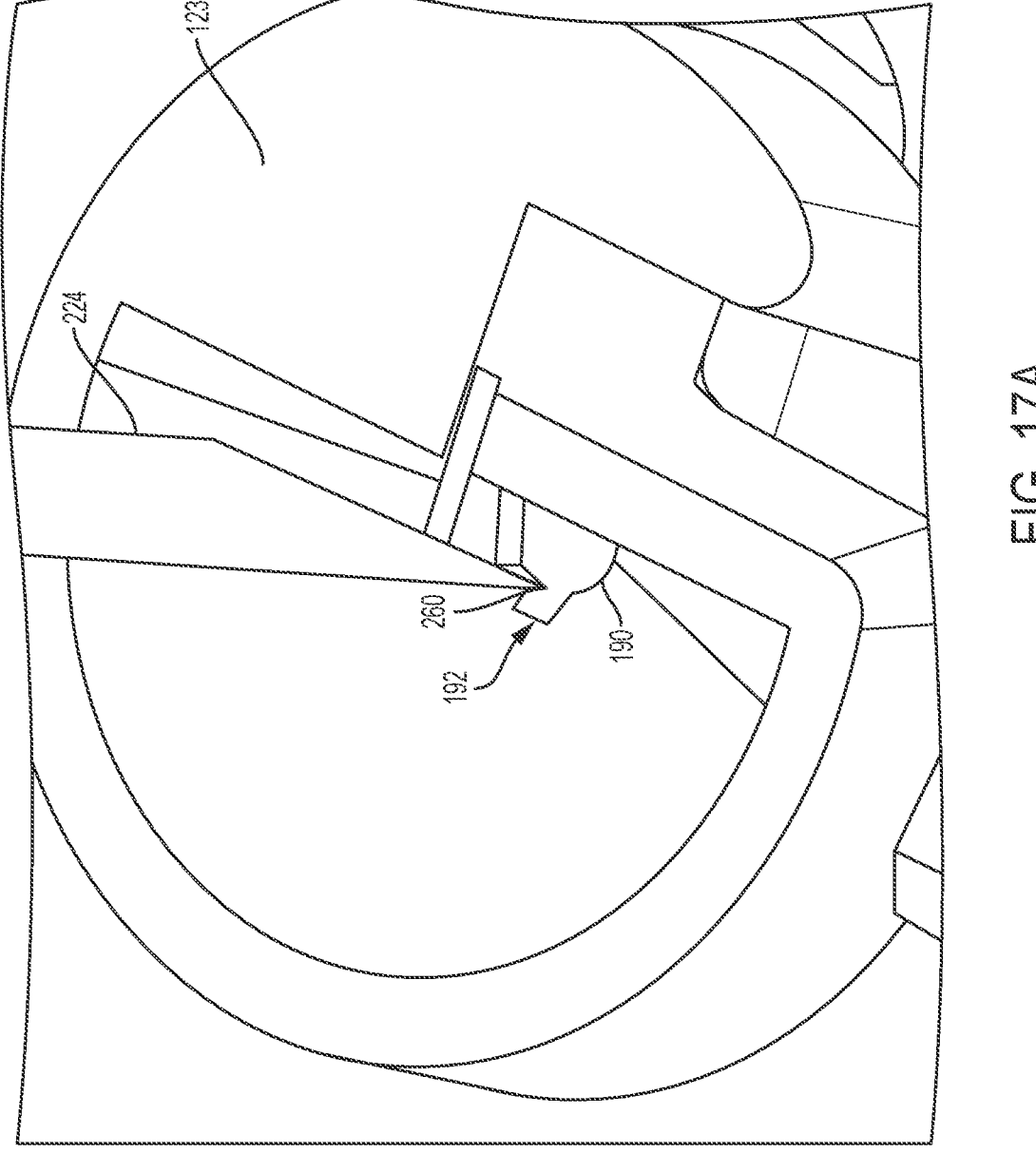
FIG. 17A is an enlarged perspective view of a portion of an inserter in accordance with one embodiment of the disclosed subject matter.

FIG. 17A illustrates a detail of sensor hub 123, which includes an aperture 190 through which sharp 224 and sensor 14 are configured to pass through. In some embodiments, aperture 190 is provided with an additional side channel 192 continuous with the aperture 190. Side channel 192 is positioned in the location in which the pointed tip 260 of the sharp 224 would first pass through the aperture. Ideally, the tip 260 passes through the aperture without contacting the sensor hub 123. However, if there is any misalignment, the tip 260 makes contact with the sensor hub 123 and may be damaged and/or it may become jammed or otherwise unable to pass through the aperture. The side channel 192 provides additional clearance for the tip 260 to pass through the aperture undamaged.

FIG. 18 illustrates in cross-section the orientation of the on body housing 122 with respect to the sharp 224 of inserter 200. As discussed herein, sensor 14 is disposed in a substantially bent configuration in some embodiments, such that a portion of the sensor, e.g., the insertion portion 30 and the proximal retention portion 48, are substantially vertical (e.g., substantially aligned with the longitudinal axis of the inserter 200 and substantially perpendicular to the skin surface) and the contact portion 32 (shown in profile) is oriented in a substantially horizontal configuration, and in electrical contact with on body electronics 1100. The sensor tab 50 can be encapsulated in the plastic of the on body housing 122 and secured in place. The notch 56 provides further stability to the sensor 14, e.g., by allowing the sensor tab 50 to be encased by the material of the on body housing 122, and further provides a means for vertically orienting the sensor 14 during mounting, e.g., by allowing vertical positioning of the notch 56 with respect the on body housing 122.

The sensor 14, mounted with the on body housing 122, can be disposed within a recess of the carriage 230 such as a concave recess in the carriage 230. Alternatively, the sensor 14, mounted with the on body housing 122 can be disposed between the support structure and one or more projections extending from the wall of the sheath 242 (not shown). In yet another alternative, the sensor 14 mounted with the on body housing 122 can be held in position by a releasable friction fit coupling to the sharp 224. In this manner, the carriage need not have a recess within which the sensor mounted with the on body housing is disposed. In the initial configuration of the inserter 200 (see, e.g., FIG. 7) the sharp 224 extends through a longitudinal aperture 168 formed in a carriage 230. In some embodiments, the aperture 168 is appropriately sized, such that neither the sharp 224 nor needle hub 236 is in contact with the carriage 230. Accordingly, the needle hub 236 (and sharp 224) on the one hand, and the carriage 230 and the on body housing 122, on the other hand, move simultaneously but independently from one another. In other embodiments, a friction fit may be provided between the aperture and the sharp.

The insertion portion 30 and proximal retention portion 48 of the sensor 14 are disposed within a longitudinal bore 162 within the sharp 224 (See, e.g., FIG. 7). The proximal retention portion 48 is disposed within the longitudinal bore of the sharp 224 and provides additional stability to the mounting of the sensor 14 within the sharp 224. The longitudinal wall gap or opening 262 of sharp 224 is aligned with the sensor 14, such that the tab 50 and the contact portion 32 extend laterally outward from the sharp 224.

In some embodiments, a resilient member 70 may be included to provide frictional contact with the sharp 224 and/or the sensor 14. Such frictional contact provides additional stability between the on body housing 122 and sharp 224, as depicted in FIGS. 19-21. In some embodiments, resilient member 70 may be formed as a spherical, ovoid, cylindrical, cube-shaped member, etc. Resilient member 70 may be formed from any elastomeric material, e.g., molded plastic components, rubber, nitrile, viton, urethane, etc.

In some embodiments, resilient member 70 is press-fit into a recess, such as an eccentric bore 72 located in on body housing 122 (FIG. 21). When sharp 224 is inserted within an aperture in the on body housing 122, the resilient member 70 exerts a pressure on sharp 224 and sensor 14 to hold them firmly in groove 74. In some embodiments, groove 74 is a V-shape. Alternatively, groove 74 may be U-shaped depending on the configuration of sensor 14 and sharp 224. In some embodiments, resilient member 70 is provided with a flattened or recessed surface which abuts sharp 224.

The sensor 14, mounted with the on body housing 122, is carried by the carriage, e.g., disposed within the concave recess 232a in the carriage 230, as described hereinabove (see, e.g., FIGS. 16-21). In the initial configuration of the inserter 200 (see, e.g., FIG. 7), the sharp 224 extends through a longitudinal aperture formed in the carriage 230. In some embodiments, the aperture is appropriately sized, such that neither the sharp 224 nor needle hub 236 is in contact with the carriage 230. In other words, in some embodiments a clearance may be provided between the surfaces of the carriage and the sharp and needle hub. In some cases, sharp 224 is capable of substantial lateral movement or "play" with respect to aperture. Accordingly, the needle hub 236 (and sharp 224) on the one hand, and the carriage 230 and the on body housing 122, on the other hand, can move simultaneously but independently from one another.

Referring back to FIG. 17, the insertion portion 30 and proximal retention portion 48 of the sensor 14 are disposed within a longitudinal bore of the sharp 224. The proximal retention portion 48 is disposed within the longitudinal bore 225 of the sharp 224 and provides additional stability to the disposition of the sensor 14 within longitudinal bore 225 of the sharp 224. The longitudinal wall gap of sharp 224 is aligned with the sensor 14, such that the tab 50 and the contact portion 32 extend laterally outward from the sharp 224.

With continued reference to FIG. 7, an optional sheath 242 is positioned within housing 202, having an annular configuration and including a circumferential recess 244 in which a retraction spring 246 is positioned. The distal portion of spring 246 contacts a spring retention portion 248 in sheath 242. The proximal portion of spring 246 contacts one or more tabs 250 extending laterally outwardly from actuator 214. In the initial configuration, the spring 246 may be in a semi-compressed state, i.e., not fully compressed, nor fully extended. It is understood that sheath 242 may be omitted from inserter 200, and a recess, such as recess 244, provided within housing 202. Similarly, recess 244 may be omitted entirely, and spring 246 or other actuator may be disposed between stops in housing 202.

Depression of the actuator 214 causes distal longitudinal movement of the carriage 230 and sharp 224, from a proximal position (spaced apart from the skin of the subject) to a distal position (closer to the skin of the subject). During such downward, distal movement, spring 246 is further compressed between spring retention portion 248 and flanges 270.

As illustrated in FIG. 8, depression of the contact surface 226 moves the actuator side walls 228 and the tabs 250 downwardly distally against the bias of spring 246. Contact of the side wall 228 of the actuator 214 with the upper surface of the carriage 230 during depression of the actuator 214 imposes a downward force and consequential distal movement of the carriage 230. As the sharp 224 is urged distally, it carries the sensor insertion portion 30 into the subcutaneous portion of the subject's skin S.

Figure 24:
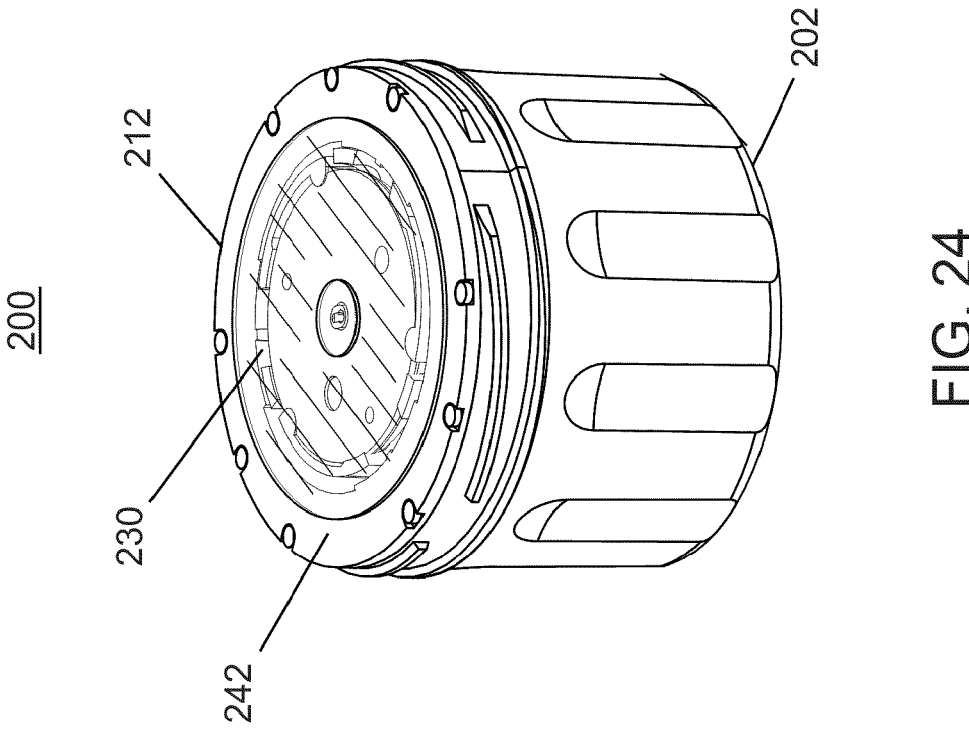
FIGS. 23-24 are perspective views of the inserter of FIG. 4 in accordance with the disclosed subject matter.

As illustrated in FIG. 7, flanges 270 are disposed in the inner wall of sheath 242. When carriage 230 reaches a distal position, as shown in FIG. 8, the flanges 270 engage the proximal (upper) surface of the carriage 230, and thereby inhibit proximal movement of the carriage 230 (see also FIG. 24). The distal (lower) surface of the on body housing 122 engages the upper surface of adhesive pad 218, thereby becoming adhered to the skin surface S of the subject. As the flanges 270 engage the carriage 230, the flanges 270 also engage fingers 274 disposed on the proximal face of the carriage 230. Fingers 274 are pivoted inwards by flanges 270. Such pivoting of fingers 274 causes fingers 274 to become disengaged from retention tab 250 on actuator 214. Spring 246 is thereby permitted to decompress and expand, and thereby provide an upward force on actuator 214. If the user or some apparatus provides no downward force, or minimal downward force to overcome the bias of spring 246, the actuator 214, along with needle hub 236 and sharp 224 move proximally, withdrawing the sharp 224 from the skin S of the subject.

Figure 22:
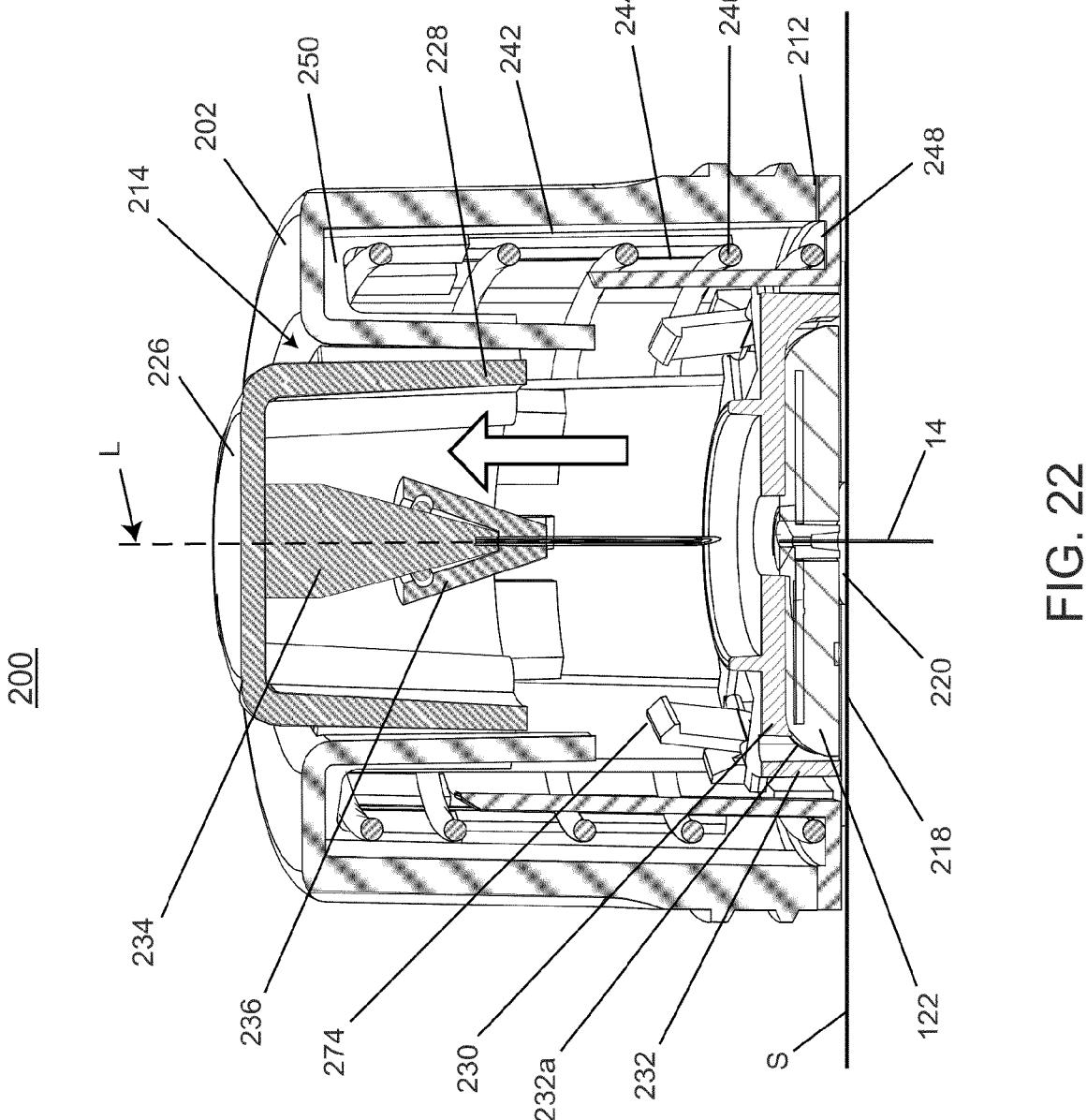
FIG. 22 is a sectional, perspective views of the inserter of FIG. 4 in accordance with the disclosed subject matter.
Figure 23:
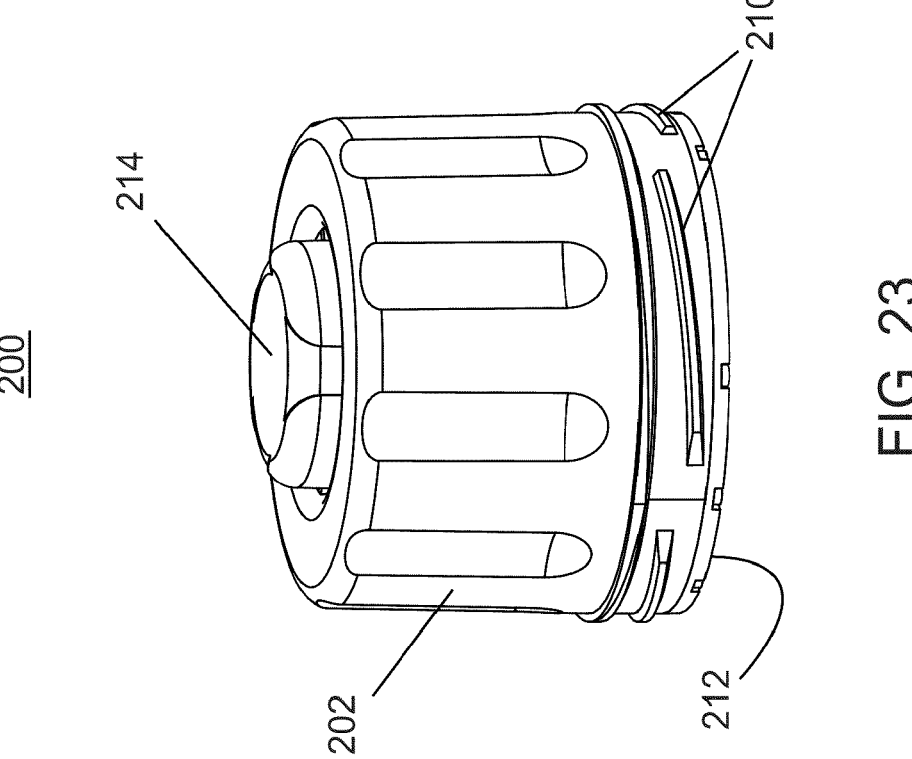

As shown in FIGS. 22 and 23, the actuator 214 and coupled sharp 224 advances to a more proximal position than at the initial configuration illustrated in FIGS. 5 and 7 due to the decoupling of actuator 214 from carrier 30. Thus, the sharp 224 retracts from a distal position to a proximal position after installation of the on body housing 122 and insertion of at least a portion of the sensor.

A further embodiment of an inserter is illustrated in FIGS. 25-39 and designated inserter 300. In some embodiments, inserter 300 has a maximum diameter of about 30 mm to about 60 mm, e.g., about 40 mm, about 43 mm, about 43.5 mm, about 50.5 mm, about 54.5 mm, etc. In some embodiments, inserter 300 has a maximum height of about 40 mm to about 80 mm, e.g., about 44 mm, about 46 mm, about 50 mm, about 53 mm, about 67 mm, about 71 mm, etc. Such height is defined by the total length of the housing 302 and the sheath 342. In some embodiments, inserter 300 has a volume of about 35 cm$^3$ to about 110 cm$^3$, e.g., about 40 cm$^3$, about 41 cm$^3$, about 50 cm$^3$, about 60 cm$^3$, about 61 cm$^3$, about 62 cm$^3$, about 69 cm$^3$, about 70 cm$^3$, about 79 cm$^3$, about 90 cm$^3$, about 106 cm$^3$, etc. Such dimensions are defined by the total length of the housing 302 and the sheath 342.

Figure 26:
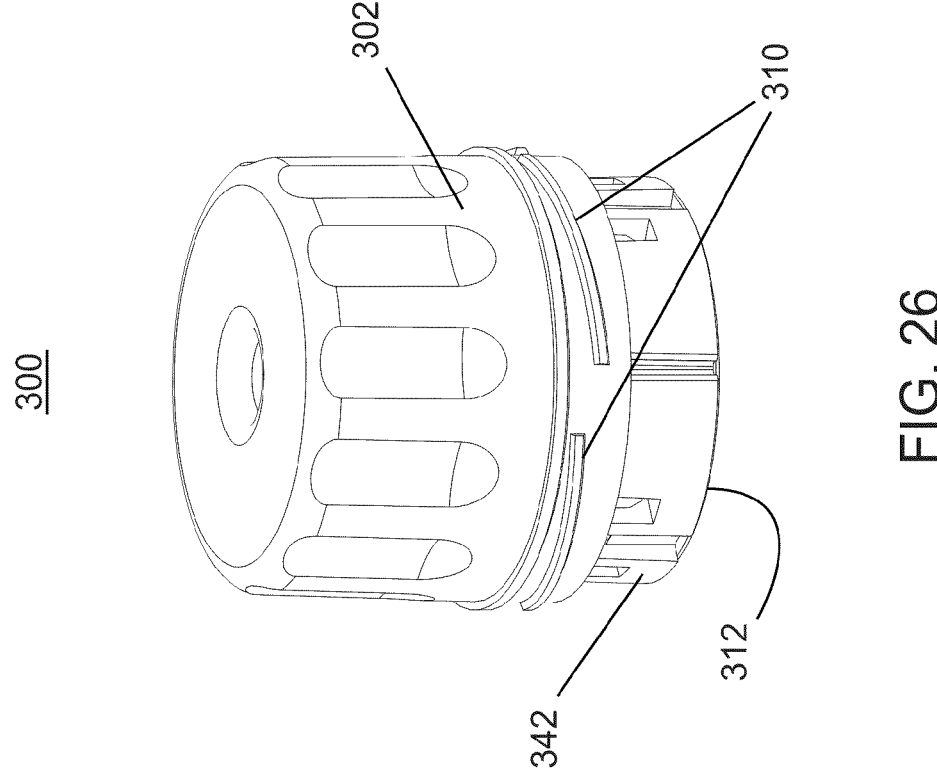
FIGS. 25-26 are perspective views of another embodiment of an inserter in accordance with the disclosed subject matter.
Figure 25:
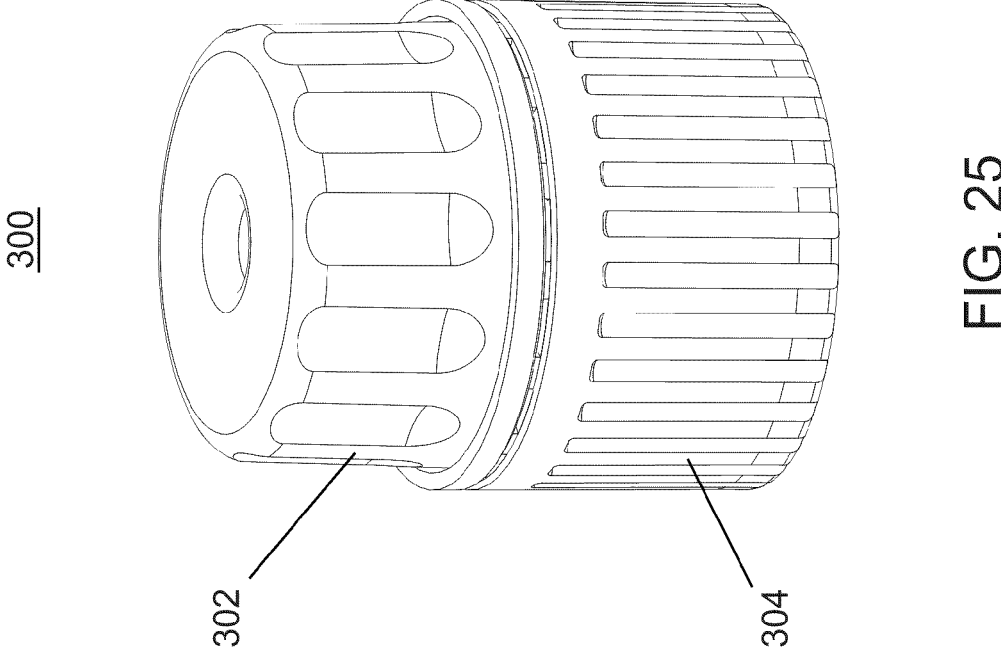

As illustrated in FIGS. 25-26, inserter 300 in certain embodiments includes, e.g., a handle 302, a sheath 342, and a removable distal cap 304 for maintaining a sterile environment for the medical device and sharp housed therein. FIG. 26 illustrates that distal cap 304 is removed from handle 302. Distal cap 304 is secured to handle 302 by one of a number of securement means, e.g., by use of threads 310. Sheath 342 defines a distal surface 312 for placement on the skin of a subject. Inserter 300 may be utilized to advance a medical device into the skin of the subject. In some embodiments, handle 302 is advanced relative to sheath 342 in order to advance the medical device into the skin of the patient.

Figures 27, 28, 29:
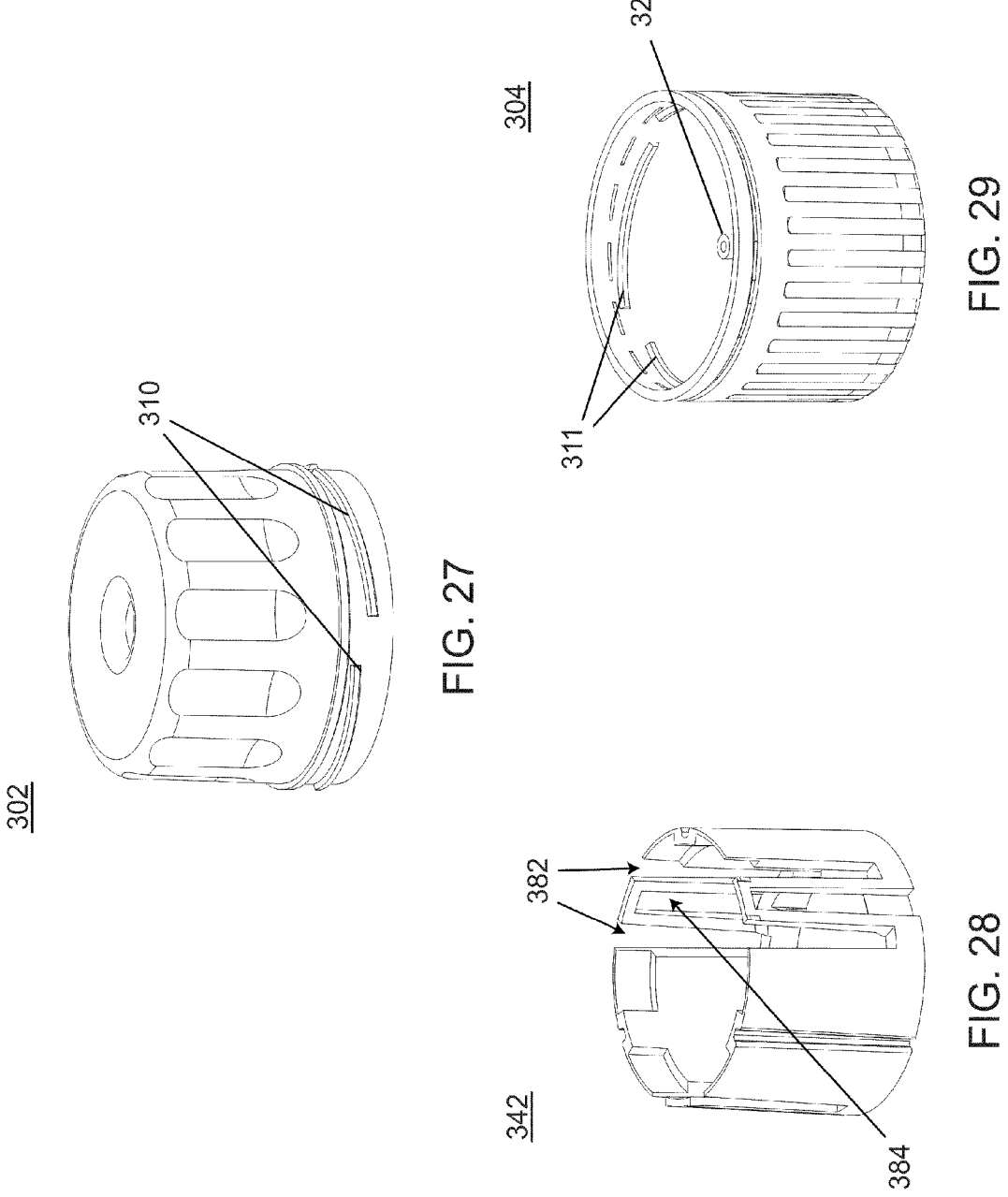
FIGS. 27-32 are perspective views of components of the inserter of FIG. 25 in accordance with the disclosed subject matter.

The components of inserter 300 in certain embodiments are illustrated in FIGS. 27-32. As illustrated in FIG. 27, handle 302 may include threads 310 for attachment of cap 304 via threads 311 (as illustrated in FIG. 29). It is understood that other securement techniques, such as a snap-fit or friction-fit may be used to secure cap 304. Cap 304 may include a receptacle 325 for positioning of the sharp 324. Sheath 342, as illustrated in FIG. 28, includes longitudinal notches 382.

Figures 30, 31, 32:
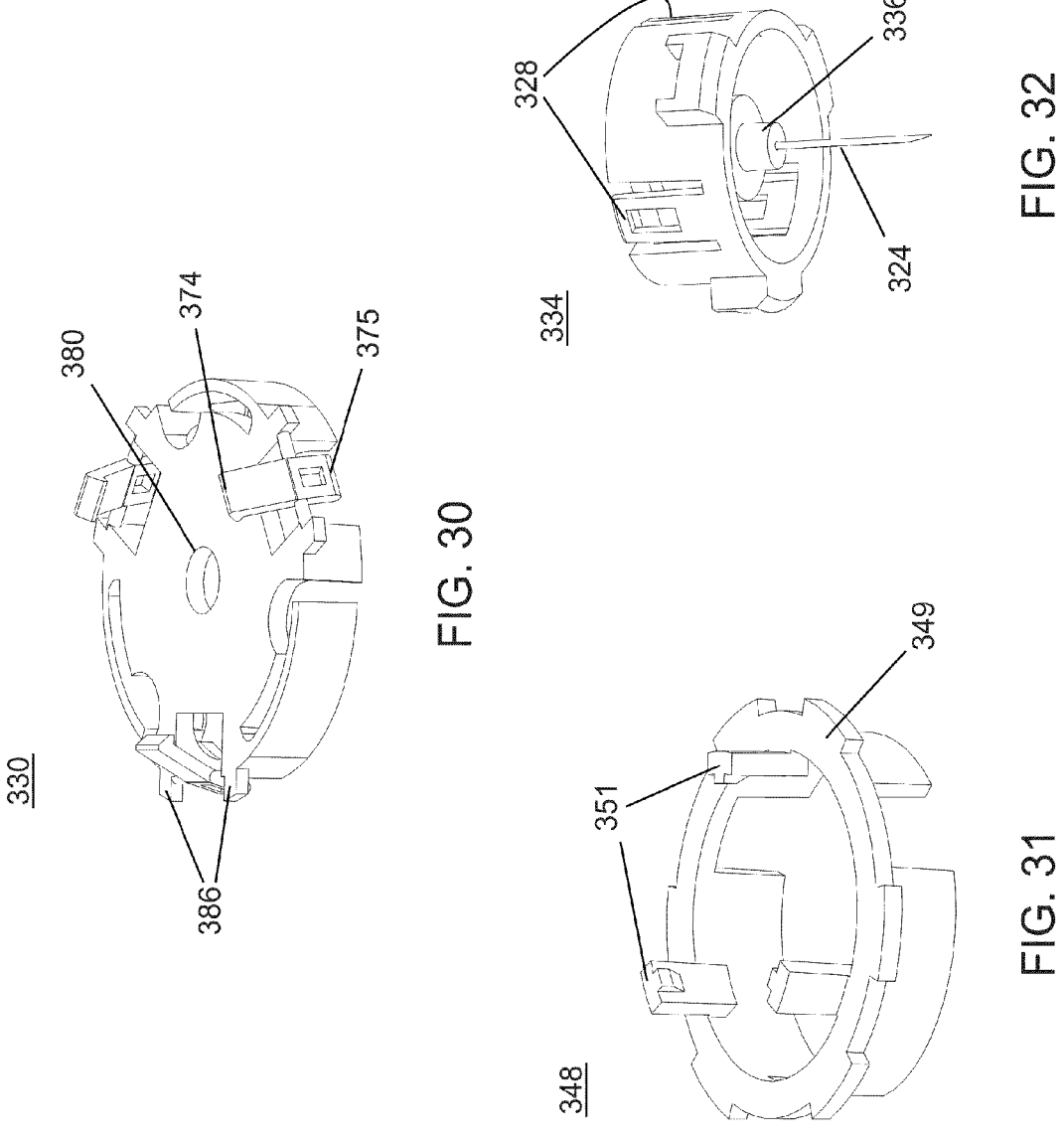
Figure 36:
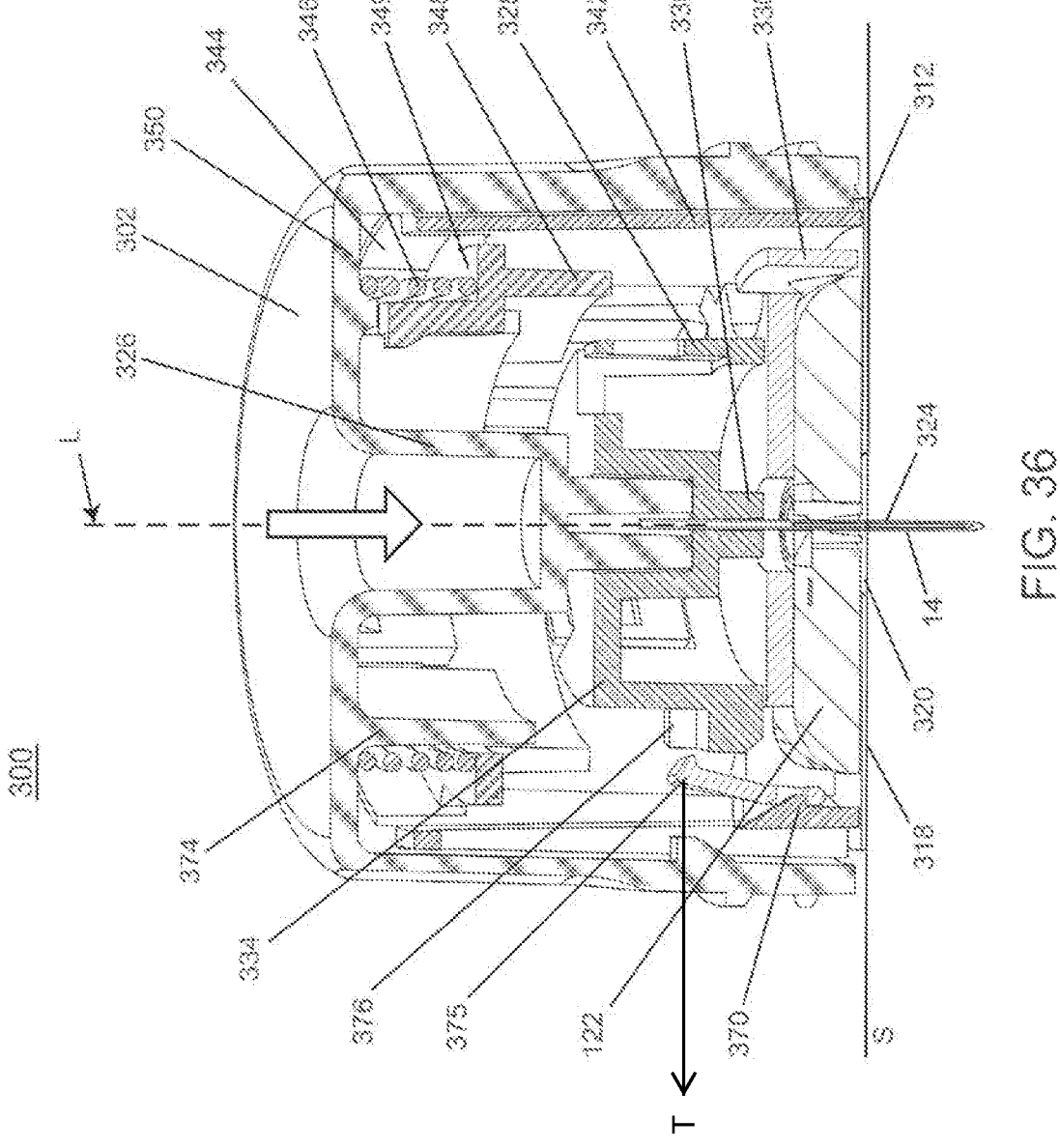
FIGS. 36-37 are sectional, perspective views of the inserter of FIG. 25 in accordance with the disclosed subject matter.

Projections 386 on carriage 330, as illustrated in FIG. 30, are configured to engage sheath to secure carriage 330 within the inserter 300, thereby preventing release of the carriage 330 from the inserter 300. When the projections 386 of carrier reach the bottom of the notches 382, such bottom surface acts as the retention portion that prevents the carriage 330 from falling out of the inserter 300. Projections 375 engage with the triangular latch features 370 of the sheath 342 as illustrated in FIGS. 34 and 36.

Figure 34:
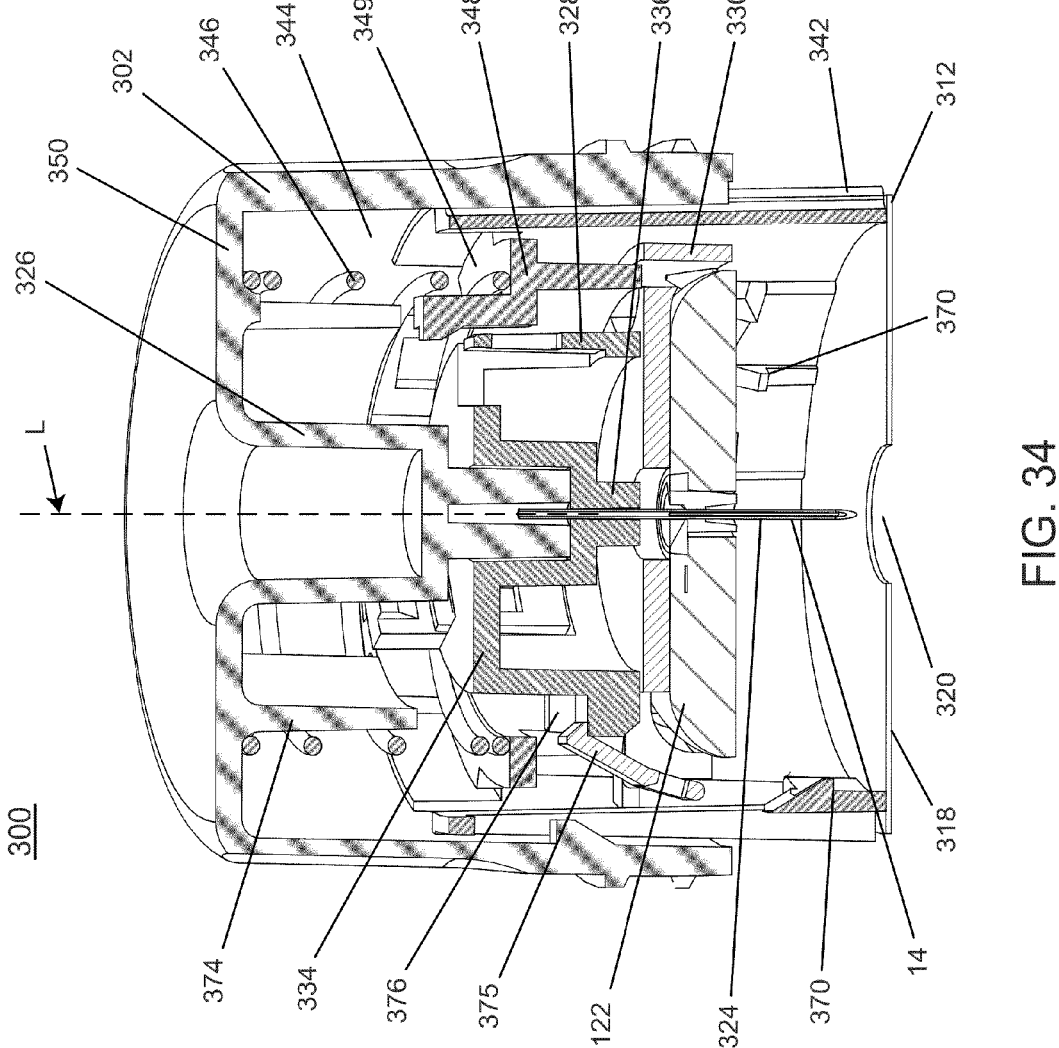
FIG. 34 is a sectional, perspective view of the inserter of FIG. 25 in accordance with the disclosed subject matter.

Carriage 330 also is provided with fingers 375 which engage a shoulder wall 376 of sharp 324 (as illustrated in FIG. 34), as will be described in greater detail herein.

In certain embodiments, inserter 300 also includes a spring retention component 348, as illustrated in FIG. 31. Spring retention component 348 defines an upper surface 349, which engages spring 346 (as illustrated in FIG. 34). Spring retention component 348 also includes locking towers 351 including projections, which engage apertures 328 of needle carrier 334 to prevent accidental deployment of the sharp 324 after use of the inserter 300 is completed.

Figure 33:
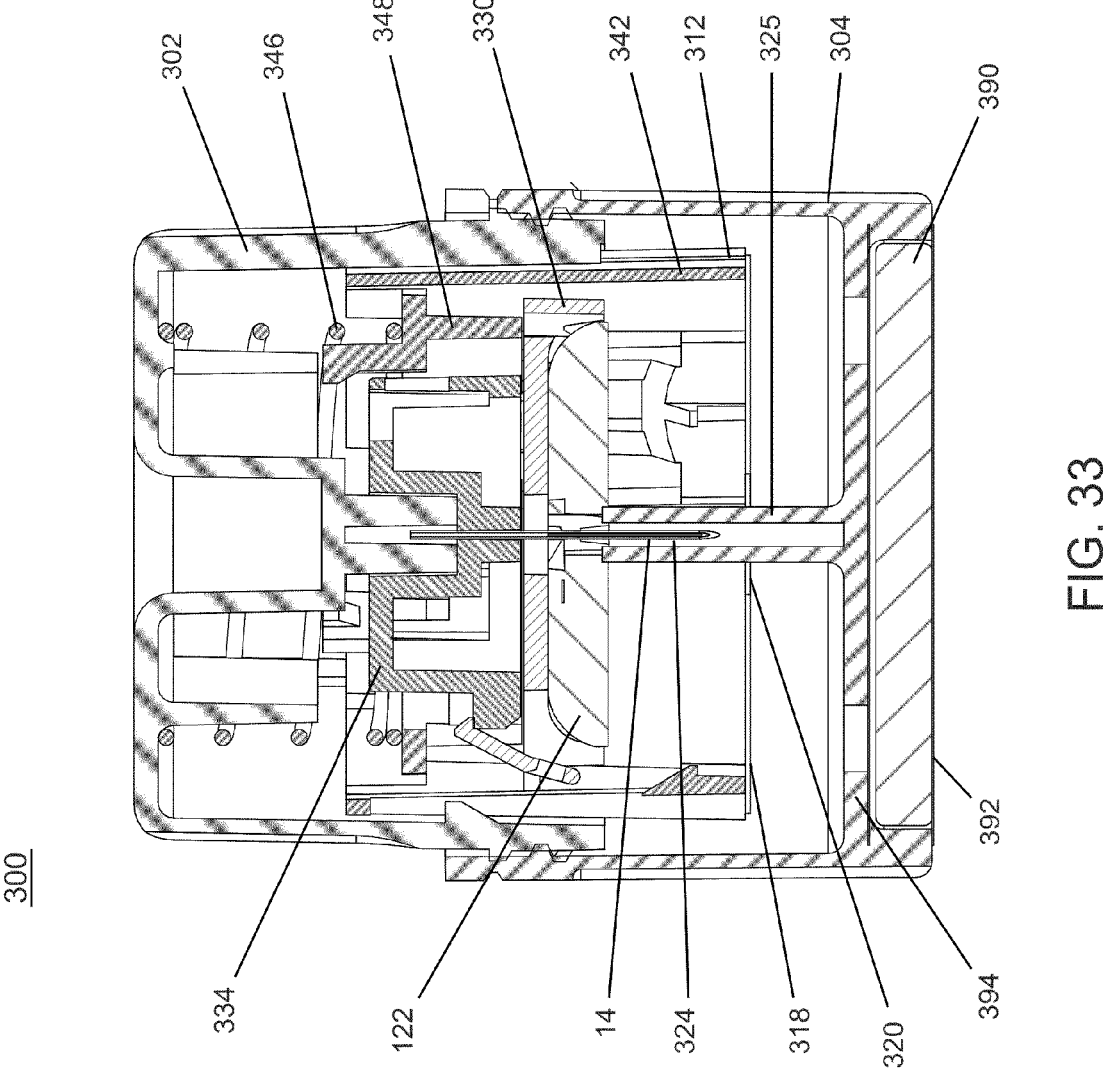
FIG. 33 is a sectional view of the inserter of FIG. 25 in accordance with the disclosed subject matter.

Inserter 300 is illustrated in cross-section in FIG. 33 prior to use. Cap 304 is attached to the distal portion of inserter 300, via securement means, such as inter-engagement of threads 310 and 311. Cap 304 includes a desiccant tablet 390; a seal, such as a foil seal 392; and a Tyvek® layer 394, which allows breathability between the desiccant tablet 390 and the interior of the inserter 300.

Figure 35:
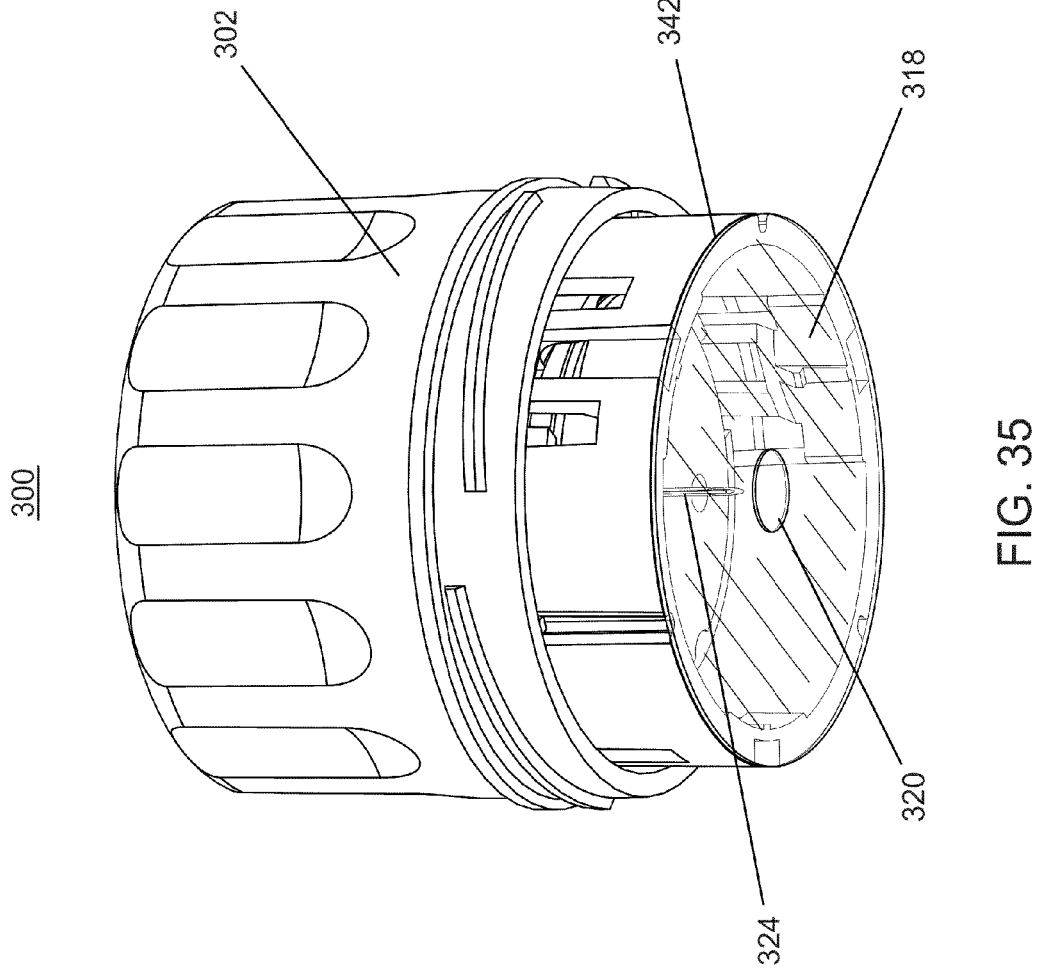
FIG. 35 is a perspective view of the inserter of FIG. 25 in accordance with the disclosed subject matter.

As illustrated in FIG. 34, the inserter 300 includes an initial configuration in which the handle 302 is disposed in a proximal position with respect to the sheath 342. In such configuration, the sharp 324 is disposed in a configuration spaced apart from the aperture 320 of the adhesive layer 318. The distal portion of inserter 300 is illustrated in FIG. 35.

With continued reference to FIG. 34, the longitudinal axis L of the inserter 300 is illustrated. Extending distally from the upper surface of handle 302 is an inner wall portion 326 and intermediate wall portion 374. Support member 334 extends from wall portion 326 and supports needle hub 336, from which sharp 324 extends longitudinally within the inserter 300. In some embodiments, the sharp is supported at an oblique angle, e.g., between 0° and 90° with respect to the skin surface.

Sheath 342 is positioned within handle 302, having an annular configuration in which a retraction spring 346 is positioned. The distal portion of spring 346 contacts a surface 349 of spring retention component 348. The proximal portion of spring 346 contacts the inner surface 350 of handle 302. In the initial configuration, the spring 346 is in an extended or semi-extended configuration.

FIG. 36 illustrates inserter 300 in cross-section, during insertion. Depression of handle 302 with respect to sheath 342 against the bias of spring 346 causes distal longitudinal movement of the carriage 330 and sharp 324, from a proximal position towards a distal position. During such downward, distal movement, spring 346 is compressed between surface 349 of spring retention component 348 and surface 350 of handle 302. As the sharp 324 is urged distally by housing 302, it carries the sensor insertion portion 30 of sensor 14 into the subject's skin S.

As carriage 330 reaches a distal position, the distal surface of the on body housing 122 engages the upper surface of adhesive pad 318, thereby becoming adhered to the skin surface S of the subject. Also, flange 370 engages fingers 375 disposed on the carriage 330. Fingers 375 are pivoted outwards by flanges 370 in direction T. Such pivoting of fingers 375 causes fingers 375 to become disengaged from slots 376 in intermediate housing walls 374. Carriage 330 is thereby disengaged from handle 302 and needle carrier 334.

Figure 37:
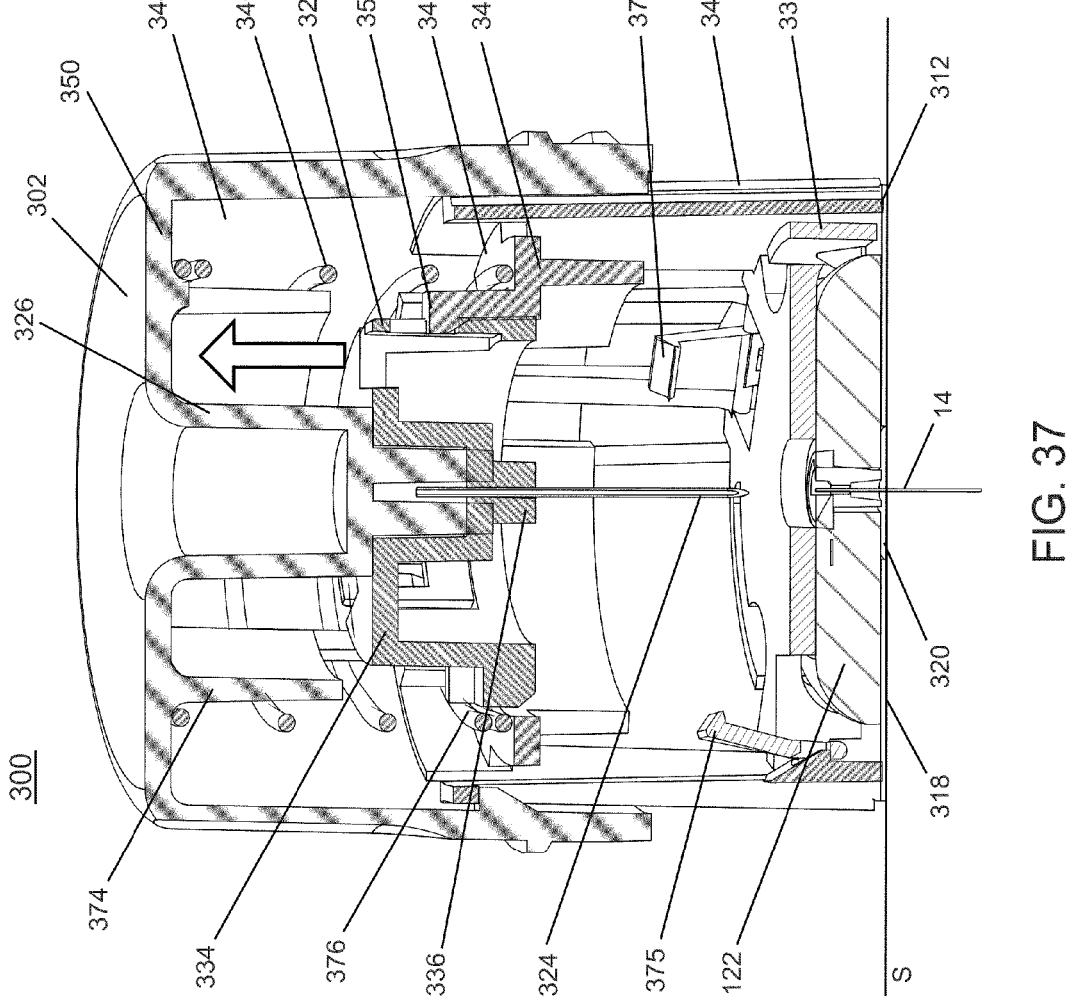
Figure 39:
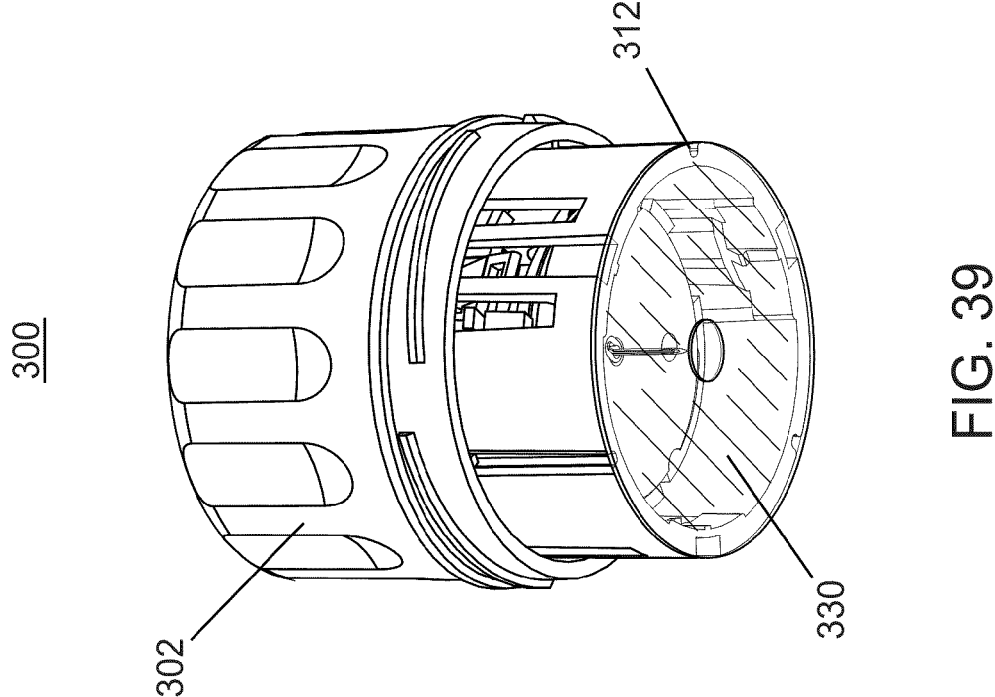
FIGS. 38-39 are perspective views of the inserter of FIG. 25 in accordance with the disclosed subject matter.
Figure 38:
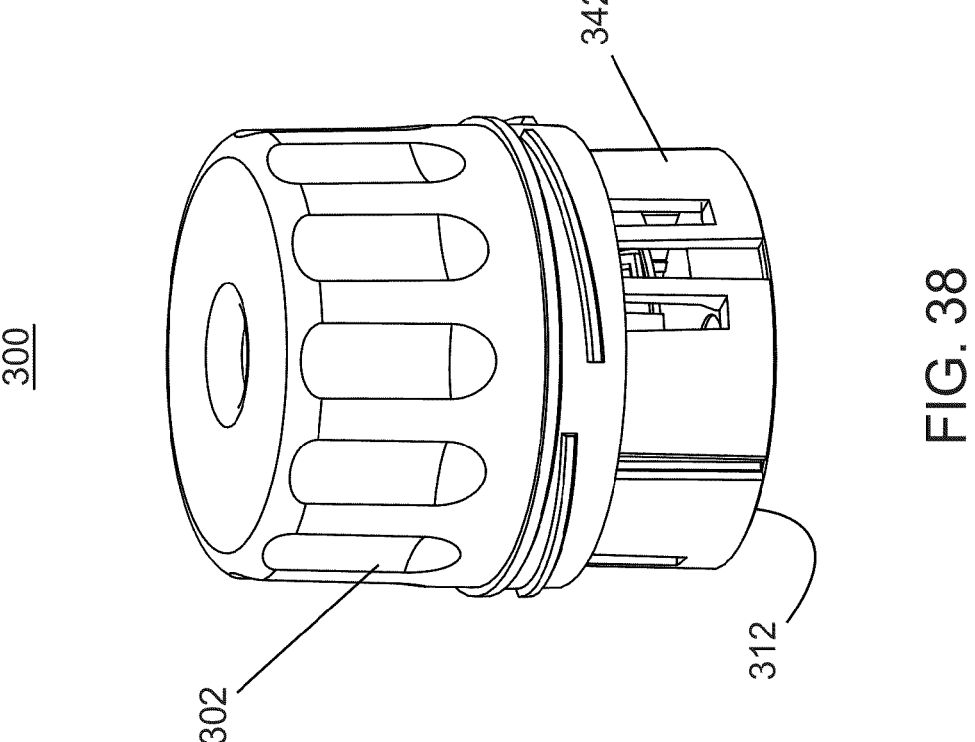

As illustrated in FIG. 37, handle 302, along with needle hub 336 and sharp 324 are permitted to move proximally, while the sheath 342 and on body housing 122 remain adjacent to the skin of the subject. If the user or some apparatus provides no downward force, or minimal downward force to the handle 302 to overcome the bias of spring 346, spring 346 is permitted to expand, thereby withdrawing the sharp 324 from the skin S of the subject.

Upon reaching the proximal position, flanges 328 on needle carrier 334 engage locking towers 351 of needle floor component 348. The inter-engagement of flanges 328 and locking towers 351 prevents inadvertent deployment of sharp 324 after installation of the medical device.

A further embodiment of an inserter is illustrated in FIGS. 40-50, and designated inserter 400. In some embodiments, inserter 400 has a maximum diameter of about 30 mm to about 60 mm, e.g., about 40 mm, about 43 mm, about 43.5 mm, about 50.5 mm, about 54.5 mm, etc. In some embodiments, inserter 400 has a maximum height of about 40 mm to about 80 mm, e.g., about 44 mm, about 46 mm, about 50 mm, about 53 mm, about 67 mm, about 71 mm, etc. In some embodiments, inserter 400 has a volume of about 35 cm$^3$ to about 110 cm$^3$, e.g., about 40 cm$^3$, about 41 cm$^3$, about 50 cm$^3$, about 60 cm$^3$, about 61 cm$^3$, about 62 cm$^3$, about 69 cm$^3$, about 70 cm$^3$, about 79 cm$^3$, about 90 cm$^3$, about 106 cm$^3$, etc. The maximum height is measured from the top of the housing 402 to the distal surface 412. The volume is measured as the combined volume of the housing 402 and the sheath 442 in an expanded position.

Figure 41:
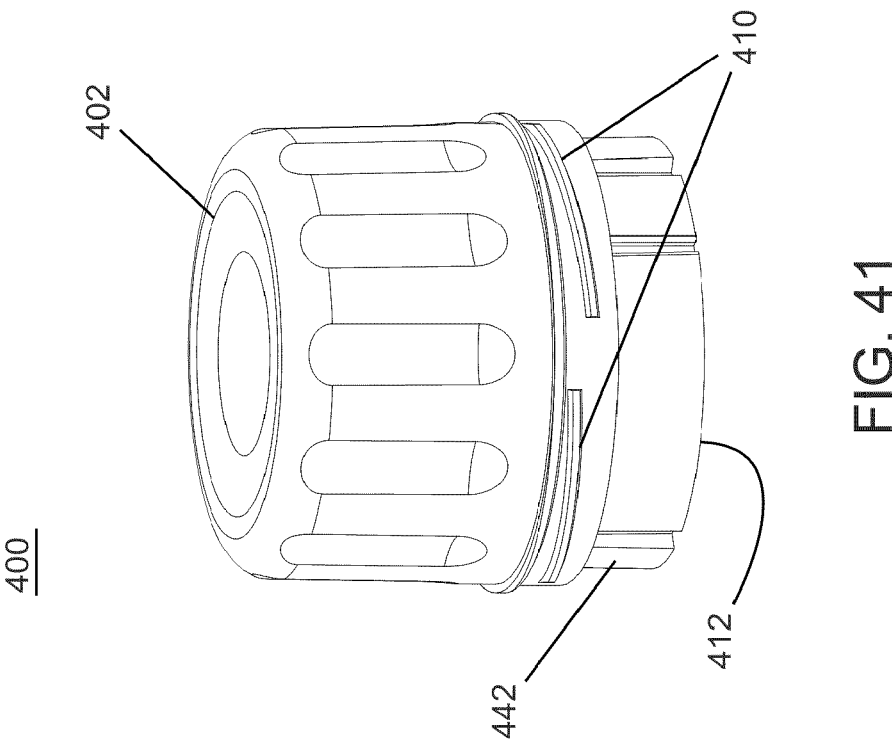
FIGS. 40-41 are perspective views of another embodiment of an inserter in accordance with the disclosed subject matter.
Figure 40:
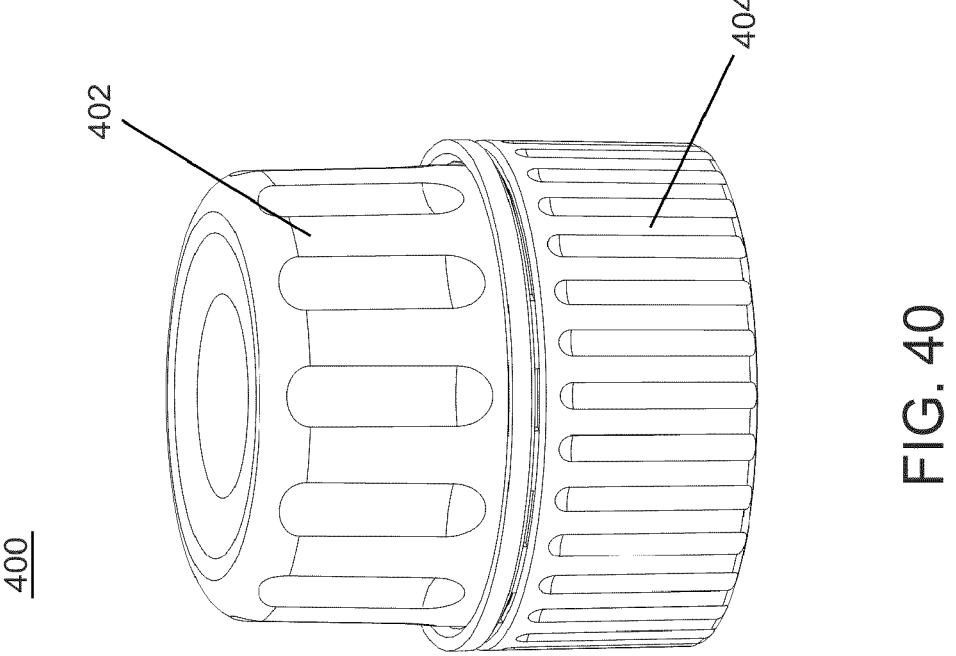

Inserter 400 generally includes, e.g., a handle 402, sheath 442, and a removable distal cap 404 for maintaining a sterile environment for the medical device and sharp housed therein. As illustrated in FIG. 41, distal cap 404 is shown removed from handle 402. Distal cap 404 is detachably secured to handle 402, e.g., by use of threads 410. Sheath 442 includes a distal surface 412 for placement on the skin of a subject. Inserter 400 may be utilized to advance a medical device into the skin of the subject. In some embodiments, handle 402 is advanced relative to sheath 442 in order to advance the medical device distally and into the skin of the patient.

Figures 42, 43, 44:
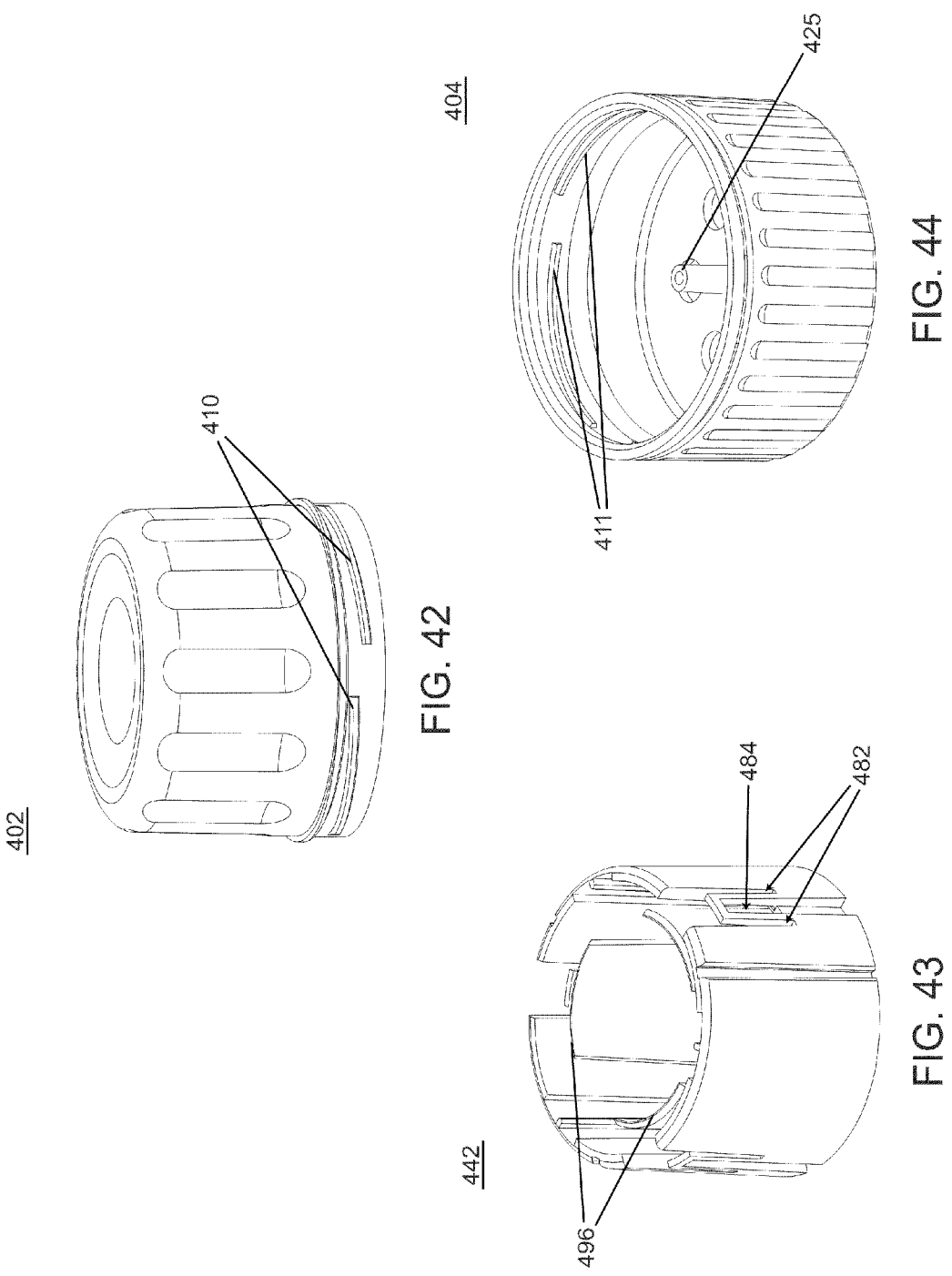
FIGS. 42-46 are perspective views of components of the inserter of FIG. 40 in accordance with the disclosed subject matter.
Figure 45:
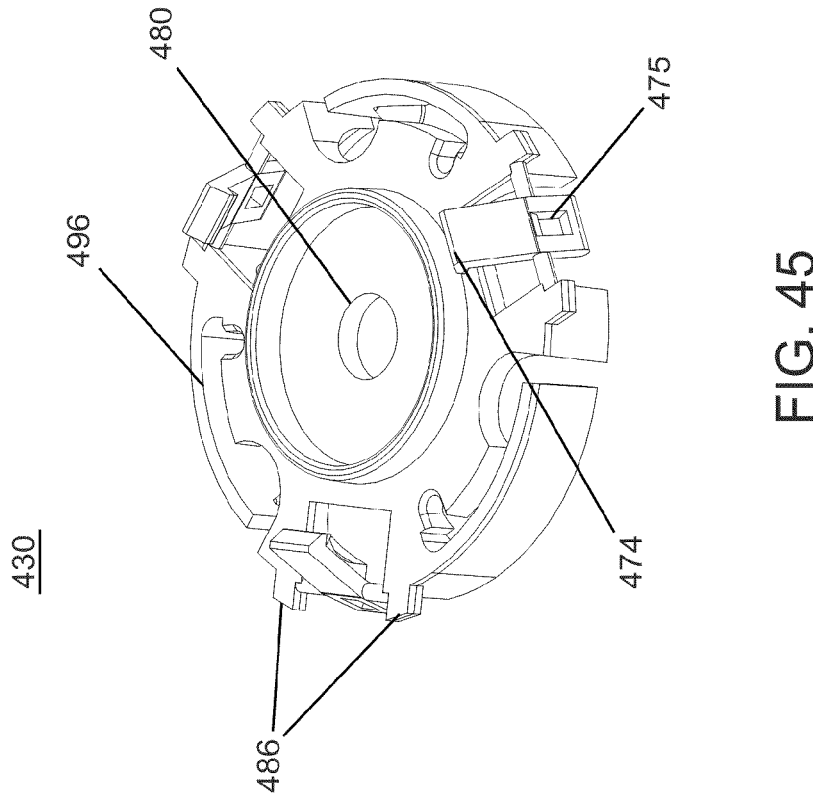
Figure 49:
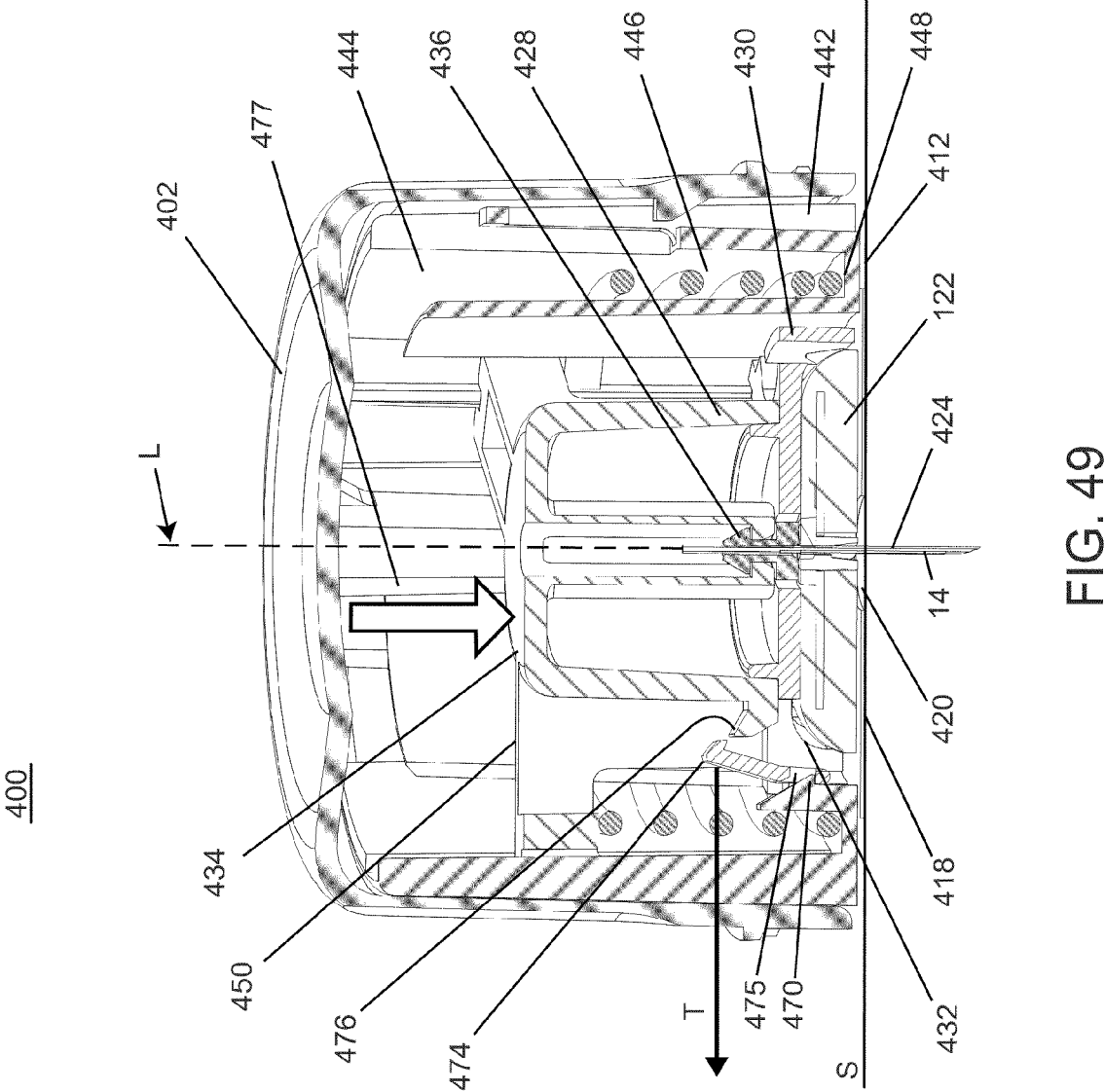
Figure 50:
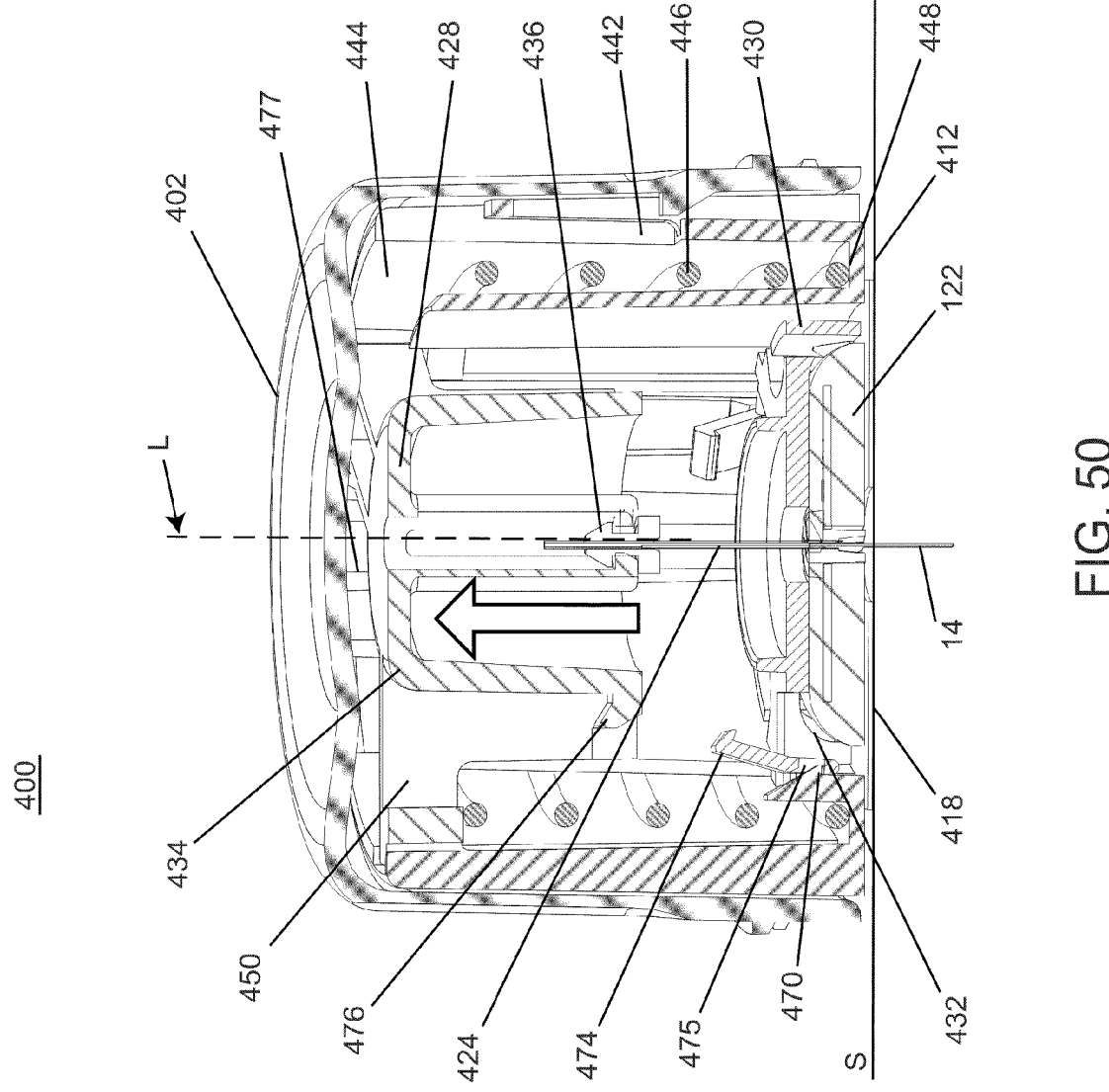

The components of inserter 400 are illustrated in FIGS. 42-46. As illustrated in FIG. 42, handle 402 includes threads 410 for attachment of cap 404 via threads 411 (as illustrated in FIG. 44). Cap 404 may include a receptacle 425 for positioning of the sharp 424. Sheath 442, as illustrated in FIG. 43, includes longitudinal notches 482. Projections 486 on carriage 430, as illustrated in FIG. 45, are configured to engage sheath 442 to secure carriage 430 within inserter 400, thereby preventing release of the carriage from the inserter. Sheath 442 also includes notches 484 which receive projection 475 of carriage 430. The bottom of the notches acts as the retention portion that prevents the carriage 430 from falling out of the inserter 400. Projections 475 engage with the latch features 470 of the sheath 442 as illustrated in FIGS. 49 and 50. Carriage 430 also is provided with fingers 474 which engage a shoulder wall 476 of needle carrier 436, as illustrated in FIGS. 48-49, and as will be described in greater detail herein.

Figure 46:
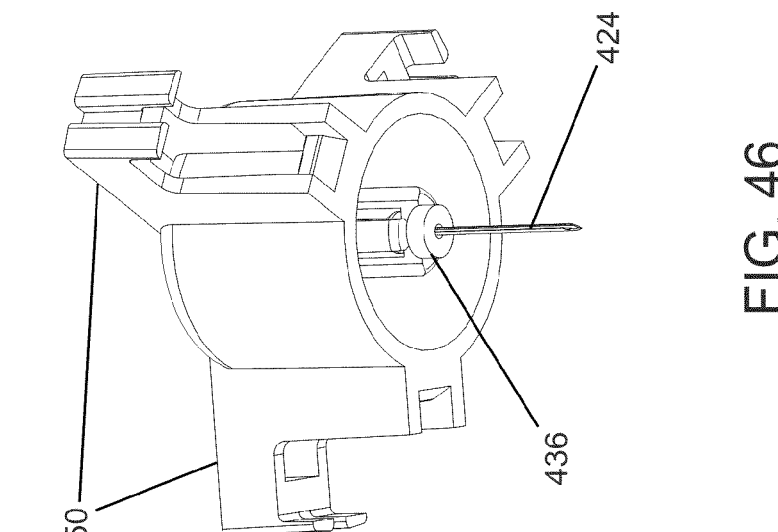
Figure 48:
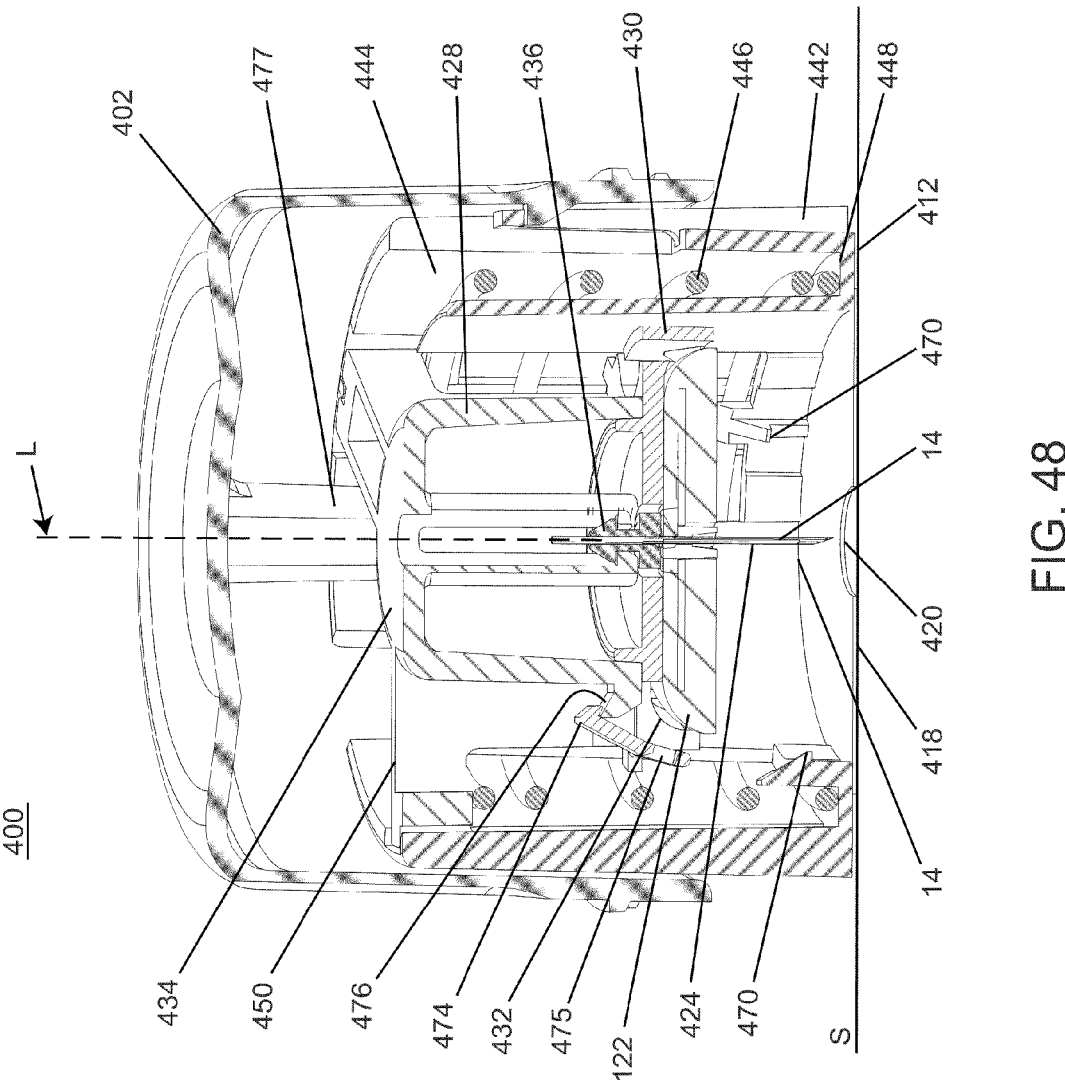
FIGS. 48-50 are sectional, perspective views of the inserter of FIG. 40 in accordance with the disclosed subject matter.

Sheath 442 also includes a spring retention portion 448, provided at the distal end of circumferential notch 496, as illustrated in FIG. 48. Needle carrier 434, as illustrated in FIG. 46, includes wings 450, which provide an upper engagement surface for spring 446. Wings 450 also include a shoulder 476 for engagement with fingers 474 of carriage 430.

Figure 47:
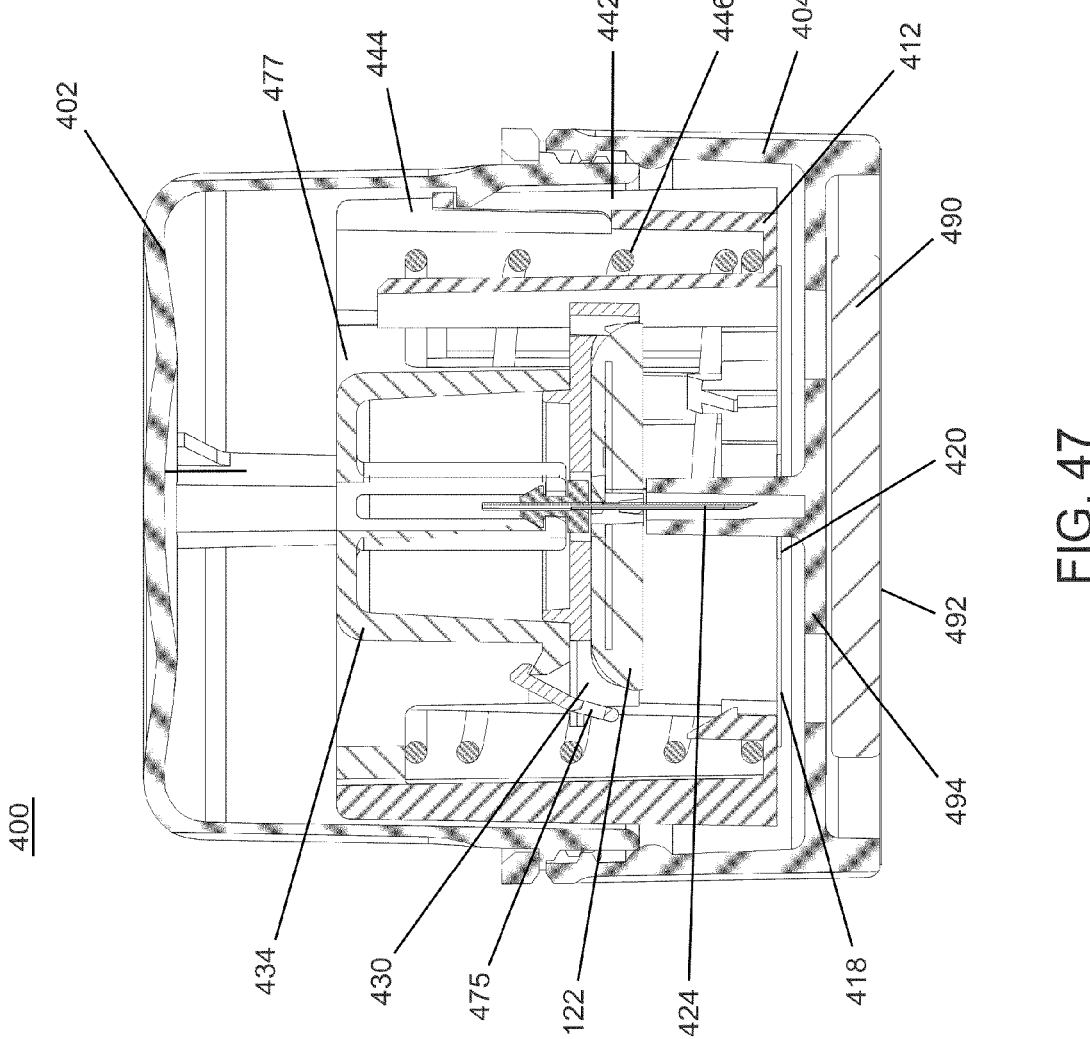
FIG. 47 is a sectional views of the inserter of FIG. 40 in accordance with the disclosed subject matter.

Inserter 400 is illustrated in cross-section in FIG. 47 in a state prior to use and prior to removal of cap 404, which is shown attached to the distal portion of handle 402, via inter-engagement of threads 410 and 411. Cap 404 includes a desiccant tablet 490, a seal such as a foil seal 492, and a Tyvek® layer 494, which allows breathability between the desiccant tablet 490 and the interior of the inserter 400.

As illustrated in FIG. 48, the inserter 400 is shown in an initial configuration in which handle 402 is disposed in a proximal position with respect to the sheath 442. In such configuration, the sharp 424 is disposed in a configuration spaced apart from the aperture 420 of the adhesive layer 418. The longitudinal axis L of the inserter 400 is illustrated. Extending distally from the upper surface of handle 402 is inner wall 475. The distal end portions of wall 475 provide a downward force on the carriage 430 upon depression of the handle 402 by a user. Alternatively, instead of handle having a distally extending inner wall, the carriage can include one or more upwardly extending walls or projections (not shown). The one or more upwardly extending inner walls or projections can have a length sufficient to either contact the upper surface of 402 or, alternatively, contact corresponding downwardly extending inner walls of the handle 402. In this manner, depression of handle 402 by a user provides a downward force on the one or more upwardly extending walls or projections of the carriage to advance the carriage (and on-body unit) distally to an installation and insertion position. (See FIGS. 49-50.) In one embodiment a downwardly extending wall of the handle 402 and a corresponding upwardly extending wall of the carriage are aligned such that depression of the handle 402 by a user allows the upwardly extending wall and the downwardly extending wall to make direct contact, thereby permitting the carriage 430 and on-body unit to advance distally. In such embodiment, the downwardly extending inner wall of the handle has a distal end that is disposed proximally of the proximal most end of sheath 442.

Needle carrier 434 can be axially moveable within handle 402. Needle carrier 434 supports needle hub 436, from which sharp 424 extends longitudinally within inserter 400. In some embodiments, sharp 424 is supported at an oblique angle, e.g., between and including about 0° and 90° with respect to the skin surface. Initially, needle carrier 434 is coupled to carriage 430 via inter-engagement of fingers 474 of carriage 430 with shoulder 476 of needle carrier 434. Spring 446 is disposed between spring retention portion 448 of sheath 442 and wings 450 (FIG. 46) of needle carrier 434. Initially, spring 446 is in an expanded or semi-expanded state while handle 402 is disposed proximally from sheath 442. In another exemplary embodiment, needle carrier 434 can be secured to handle 402, for example, secured to downwardly extending inner wall 475. In this manner, needle carrier and carriage 430 are longitudinally moveable along the line defined by L shown in FIG. 48 with respect to sheath 442. In this regard, needle carrier 434 includes one or more apertures to receive one or more downwardly extending inner walls 475 of handle 402. In some embodiments, neither the needle carrier 434 nor the carriage 430 are in slidable contact with sheath 442, e.g., spaced apart from sheath 442, during longitudinal movement of the needle carrier 434 and/or carriage 430.

FIG. 49 illustrates inserter 400 in cross-section, during insertion. Depression of handle 402 with respect to sheath 442, against the bias of spring 446, causes distal longitudinal movement of the carriage 430 and needle carrier 434, from a proximal position towards a distal position. During such downward proximal movement, spring 446 is compressed between spring retention portion 448 and wings 450 (FIG. 46) of needle carrier 434. As the sharp 424 is urged distally, it carries the sensor insertion portion 30 of sensor 14 (FIG. 17) into the subcutaneous portion of the subject's skin S.

As carriage 430 reaches a distal position (close to the skin of the subject), the distal surface of the on body housing 122 engages the upper surface of adhesive pad 418, thereby becoming adhered to the skin surface S of the subject. Flange 470 engages fingers 474 disposed on the carriage 430. Fingers 474 are pivoted outwards by flanges 470 in direction T. Such pivoting of fingers 474 causes fingers 474 to become disengaged from shoulder 476 of needle carrier 434. Needle carrier 434 is thereby disengaged from carriage 430. Such pivoting of fingers 474 also engages opening in 474 with flange 470, thus locking carriage 430 in the distal position.

As illustrated in FIG. 50, disengagement of the needle carrier 434 from the carriage 430 permits the spring 446 to expand, thereby advancing the needle carrier 434 to a proximal position (away from the skin of the subject) and withdrawing the sharp 424 from under the skin surface S of the subject while leaving the sensor 14 in the skin. Once the sharp 424 has been withdrawn from the subject, it is no longer accessible from the distal portion of the inserter 400 and unable to make contact by accident with the subject's skin because it is positioned at a proximal position within the carrier handle 402.

Figure 51:
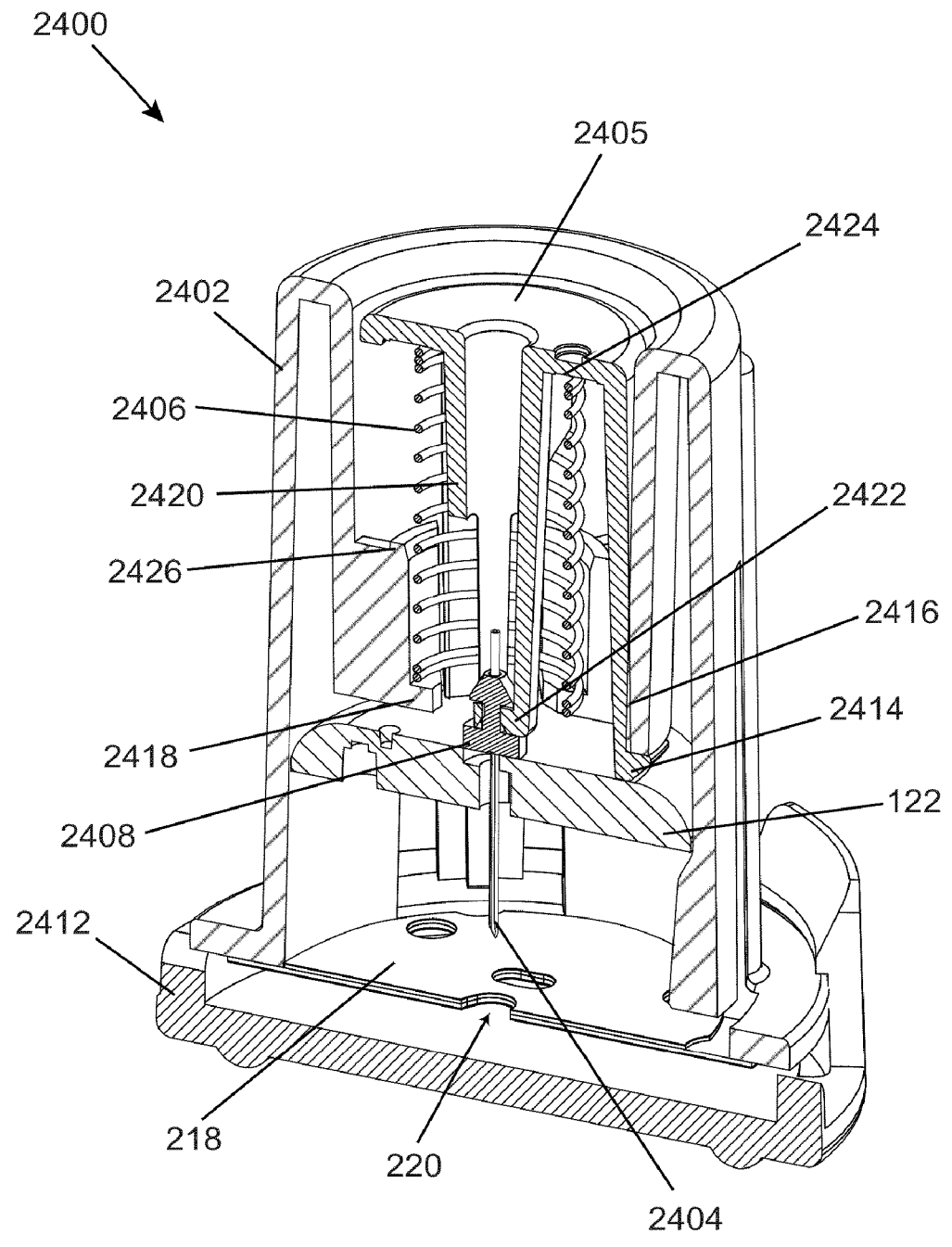
FIG. 51 is a cross-sectional view of another inserter in accordance with the disclosed subject matter.

An inserter 2400 in accordance with another exemplary embodiment is illustrated in FIG. 51. In some embodiments, inserter 2400 has a maximum diameter, of about 30 mm to about 60 mm, e.g., about 40 mm, about 43 mm, about 43.5 mm, about 50.5 mm, about 54.5 mm, etc. In some embodiments, inserter 2400 has a maximum height of about 40 mm to about 80 mm, e.g., about 44 mm, about 46 mm, about 50 mm, about 53 mm, about 67 mm, about 71 mm, etc. In some embodiments, inserter 2400 has a volume of about 35 cm$^3$ to about 110 cm$^3$, e.g., about 40 cm$^3$, about 41 cm$^3$, about 50 cm$^3$, about 60 cm$^3$, about 61 cm$^3$, about 62 cm$^3$, about 69 cm$^3$, about 70 cm$^3$, about 79 cm$^3$, about 90 cm$^3$, about 106 cm$^3$, etc. The height is measured from the distal surface of the housing 2402 (adjacent to adhesive 218) to the top surface. The volume is measure by the volume of the housing 2402.

With reference to FIG. 51, inserter 2400 includes a housing 2402 and a removable distal cap 2412 for protecting the medical device and sharp housed therein. Housing 2402 and distal cap 2412 may be fabricated from any suitable materials such as metal, plastic, etc. In some embodiments, cap 2412 may be fabricated from a polymer or plastic material.

Figure 52:
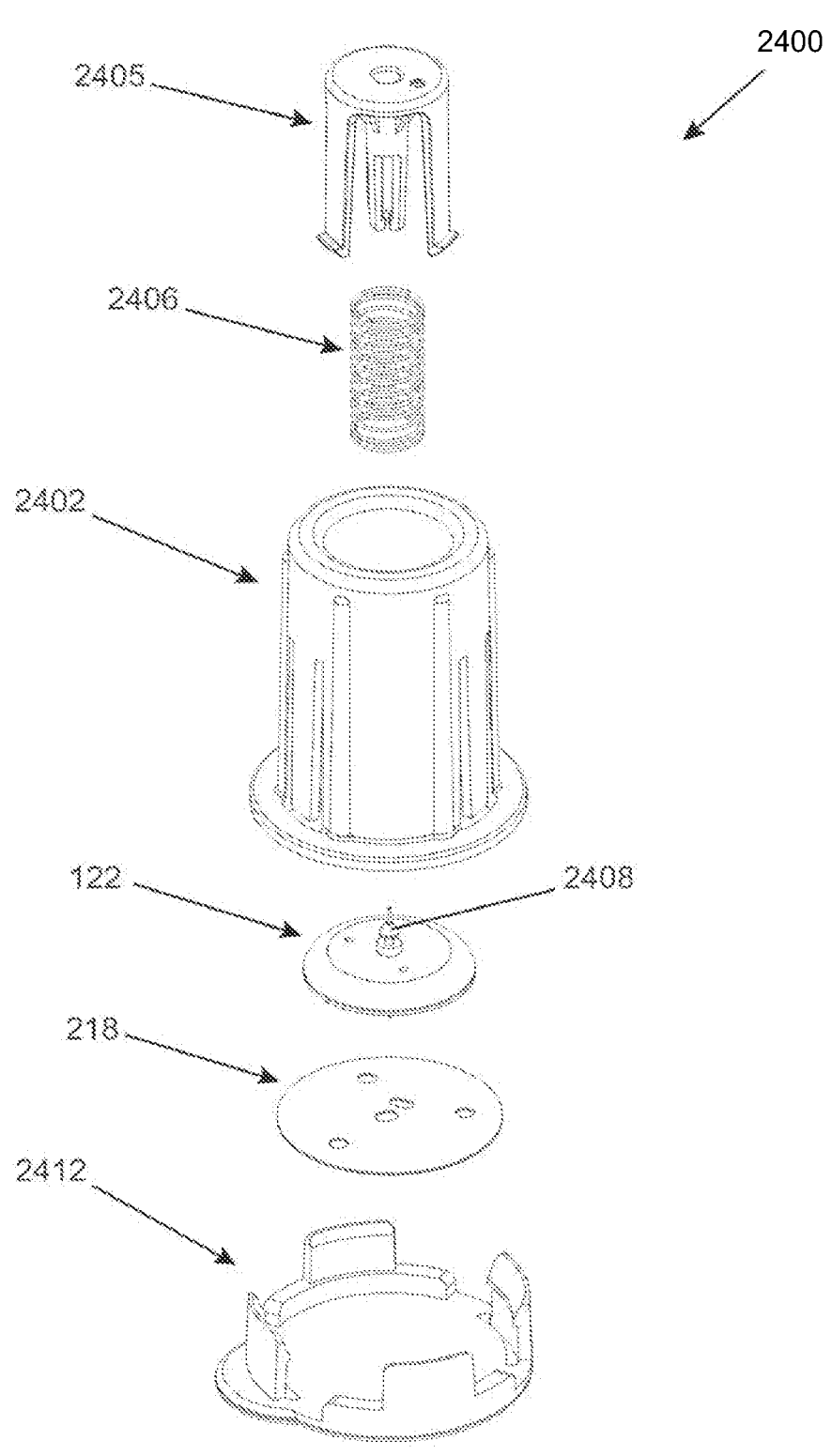
FIG. 52 is an exploded perspective view of the inserter of FIG. 51 in accordance with the disclosed subject matter.

An exploded view of the components of inserter 2400 is illustrated in FIG. 52. As shown, inserter 2400 generally comprises plunger 2405, spring 2406, housing 2402, sharp 2404 (not shown in FIG. 52), on body housing 122, sharp holder 2408, adhesive patch 218, and cap 2412 when fully assembled.

Figure 53:
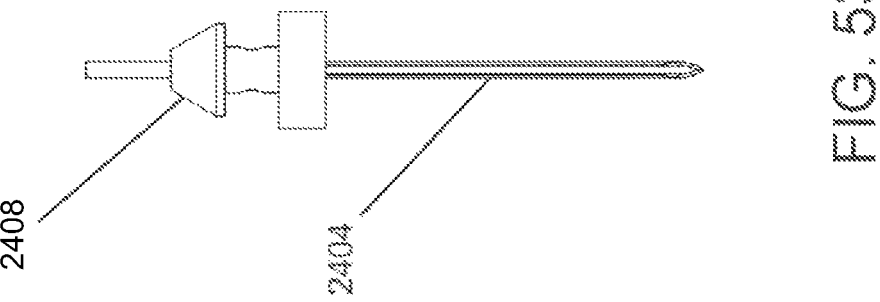

A more detailed view of sharp holder 2408 is shown in FIG. 53. Needle holder 2408 retains sharp 2404 in a fixed position with respect to itself within inserter 2400, thereby allowing it to safely penetrate a subject's skin during later use.

Figure 54:
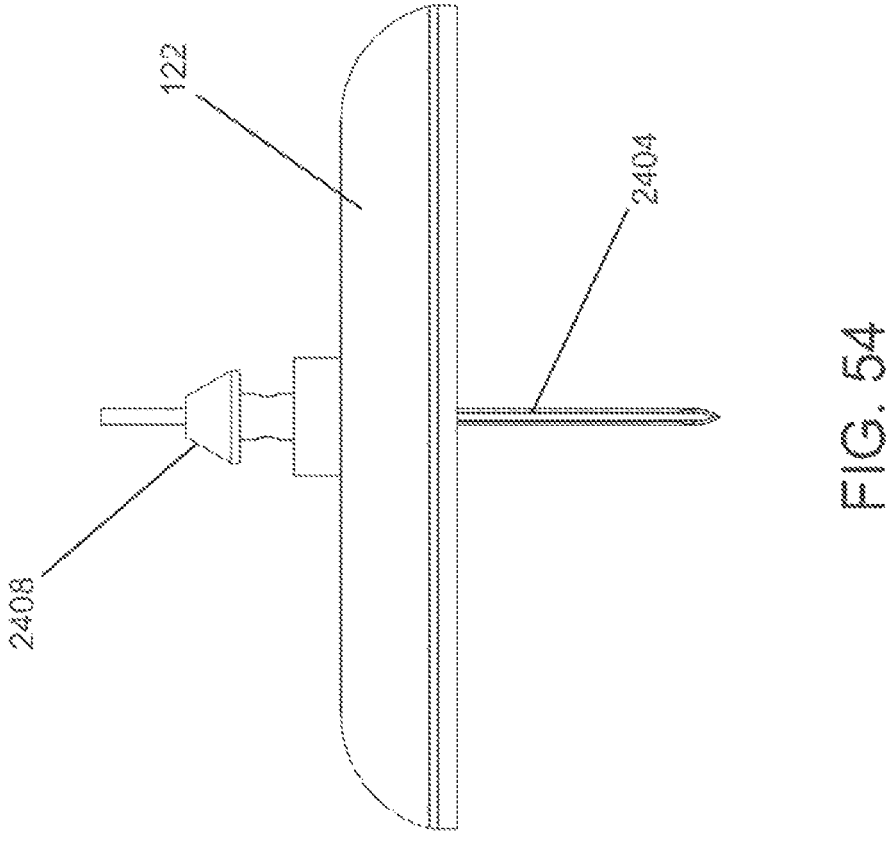
FIGS. 53 and 54 are side views of the inserter of FIG. 51 showing the assembly of various components in accordance with the disclosed subject matter.

To assemble inserter 2400, sharp 2404 and hub 2408 are inserted through an opening in on body housing 122 as shown in FIG. 54. Needle holder 2408 prevents sharp 2404 from being fully inserted through on body housing 122. In some embodiments, on body housing 122 includes an analyte sensor 14 and on body electronics 1100.

Figure 56:
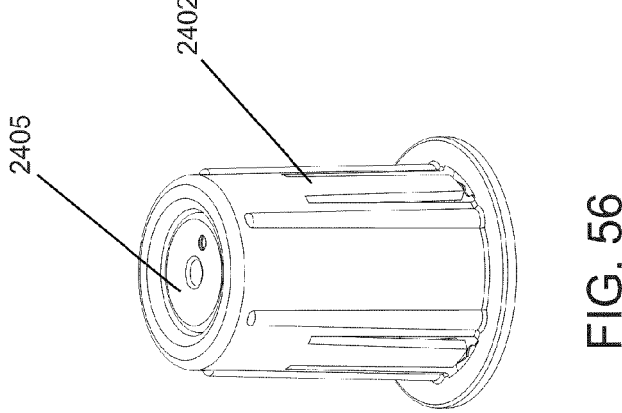
FIGS. 55-60 are perspective views of the inserter of FIG. 51 showing the assembly of various components in accordance with the disclosed subject matter.
Figure 55:
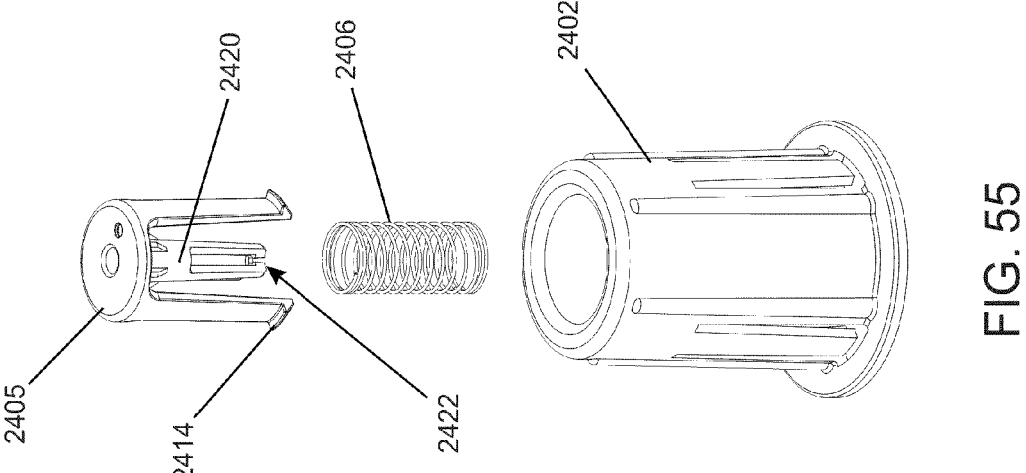
Figure 57:
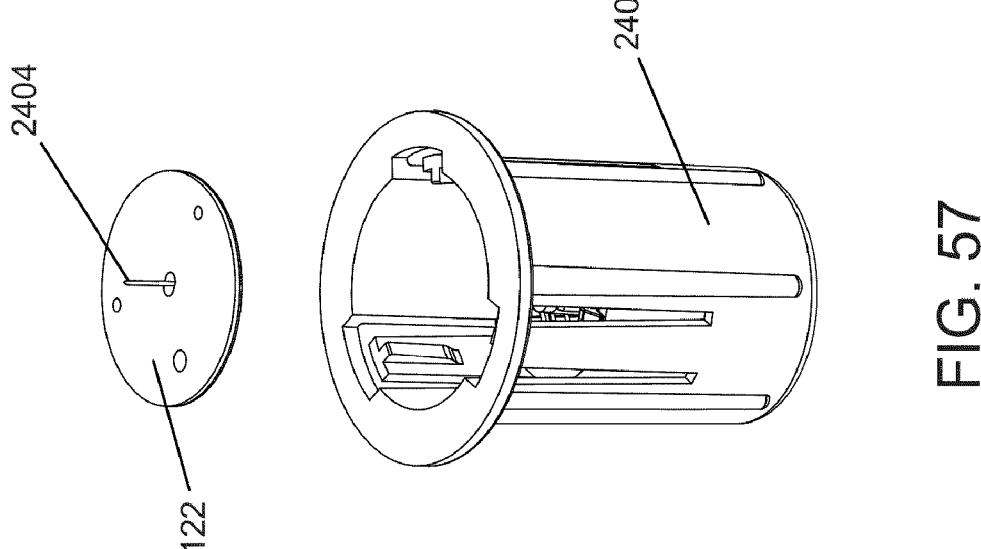

Next, plunger 2405, spring 2406, and housing 2402 are assembled as shown in FIGS. 55-57. Plunger 2405 contains a spring retention member which is inserted through the center of spring 2406. Lip 2414 of plunger 2405 engages inner wall 2416 of housing 2402 when assembled (FIG. 51). This causes spring 2406 to be contained between lip 2418 of housing member 2402 and the bottom surface 2424 of plunger 2405. The resulting sub-assembly of inserter 2400 shown in allows plunger 2405 to move between a proximal position, with spring 2406 in a preloaded condition, and a distal position, wherein bottom surface 2424 engages wall 2426 of housing 2402.

Figure 58:
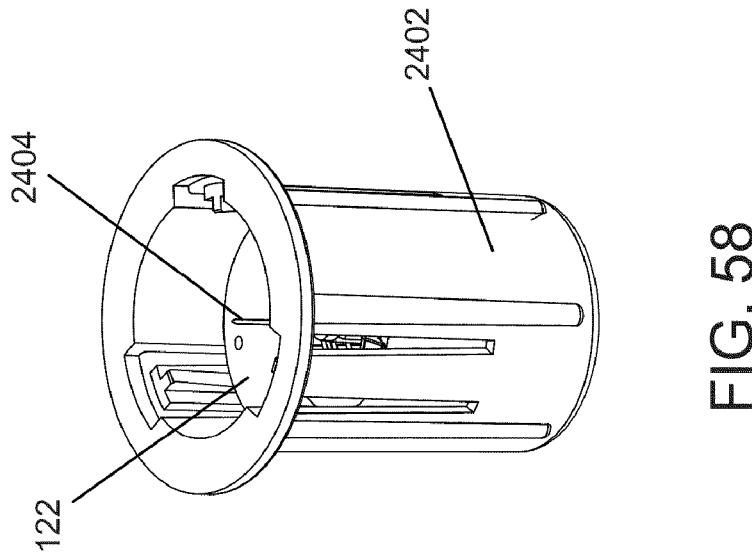

The on body housing assembly shown in FIG. 54 is then inserted into the inserter sub-assembly shown in FIGS. 55-57. As shown in FIG. 57, on body housing 122 is inserted into housing 2402 with the tip of sharp 2404 pointing away from plunger 2405. The resulting assembly is depicted in FIG. 58. As shown in FIG. 51, grooves on sharp holder 2408 engage tabs 2422 on plunger 2405. The on body housing 122 is axially retained in the housing 2402 by the housing arms detent features 2440.

Figure 60:
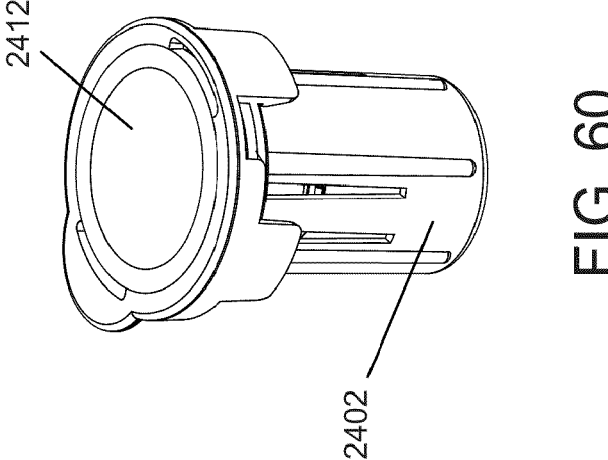
Figure 59:
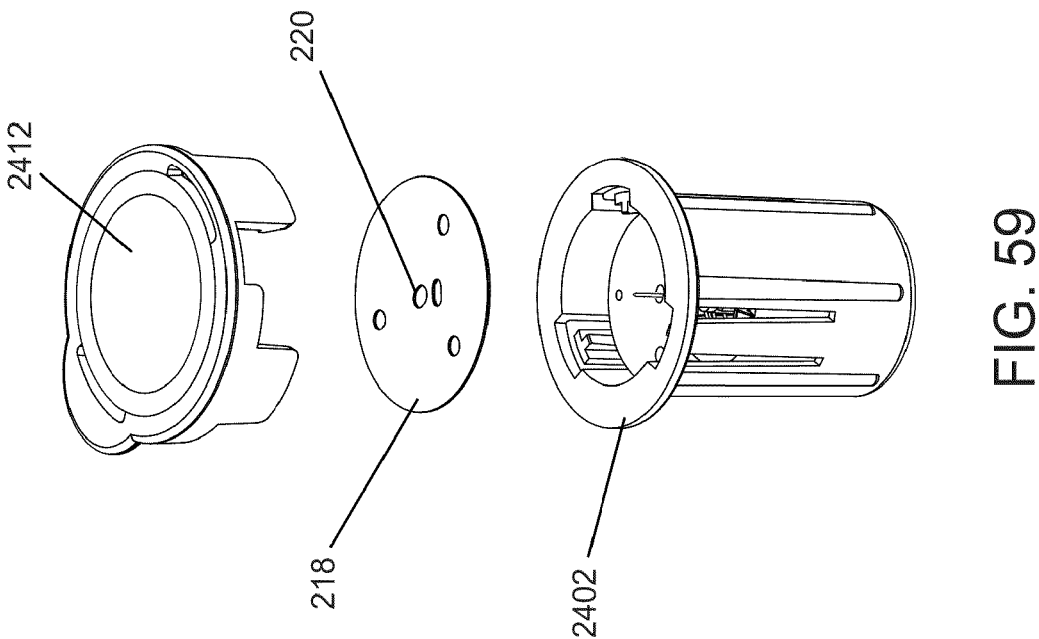

Finally, adhesive patch 218 is placed over the opening of housing 2402 and cap 2412 is friction fit over housing 2402 as shown in FIG. 59. The fully assembled inserter 2400 is depicted in FIG. 60. In some embodiments, adhesive pad 218 has an adhesive material on both faces. A central aperture 220 may be provided in adhesive pad 218 to allow sharp 2404 to be deployed into the skin of a subject. During insertion, sharp 2404 passes through aperture 220 and into the skin of the subject carrying at least the sensor with it.

FIG. 61 illustrates inserter 2400 in cross-section, in an initial configuration prior to use, after removal of the distal cap 2412. As shown, sharp 2404 extends longitudinally within the inserter 2400. In some embodiments, sharp 2404 is supported at an oblique angle, e.g., between and including about 0° and 90° with respect to the skin surface.

In some embodiments, sharp 2404 is provided with a substantially cylindrical configuration defining an interior bore, e.g., a rigid cylindrical member or a hypodermic-style needle. Sharp 2404 may also be provided with an elongated longitudinal opening or gap in the wall of the sharp 2404. In some embodiments, sharp 2404 is fabricated from a sheet of metal, and folded into a substantially "V" or "U" or "C" configuration in cross-section to define the longitudinal recess.

Depression of plunger 2405 causes distal longitudinal movement of on body housing 122 and sharp 2404, from a proximal position to a distal position. During such downward, distal movement, spring 246 is further compressed between lip 2418 and bottom surface 2424. Detent 2440 provides a minimum force threshold to overcome before on body housing 122 can continue on its downward distal movement. Beyond a minimum force threshold, detent 2440 is pushed outward by on body housing 122, and on body housing 122 then translates onto ramp 2442. The friction between on body housing 122 and ramp 2442 of the housing hold the on body housing 122 up against plunger 2405.

Figure 62:
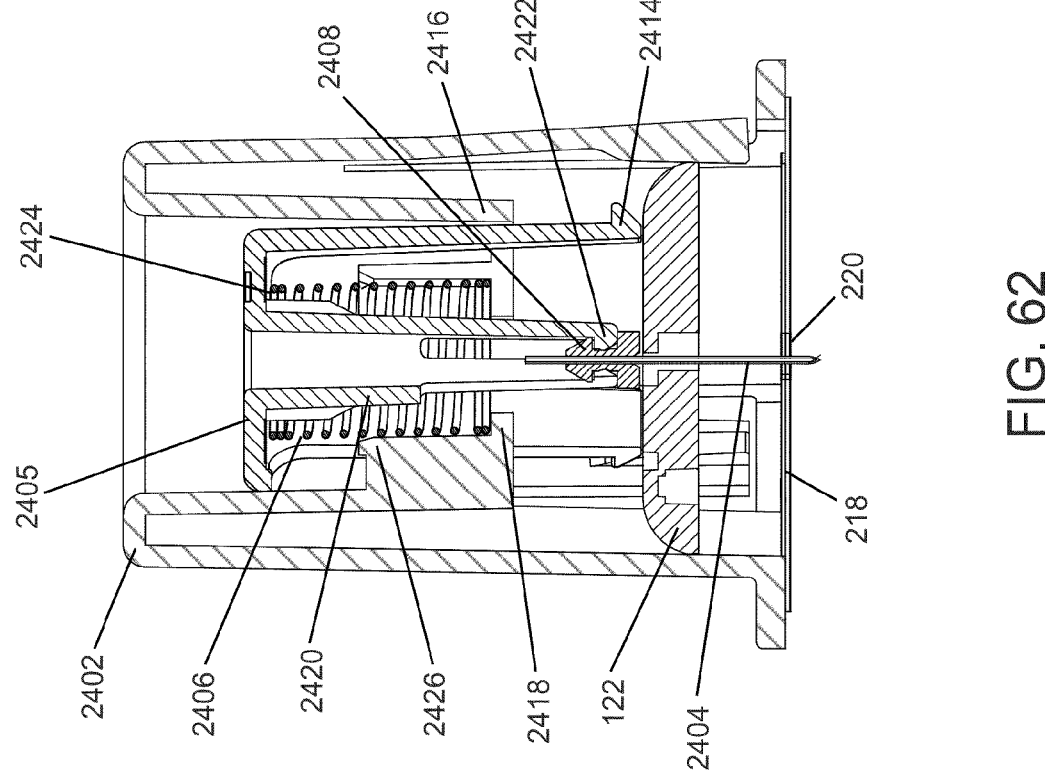

As illustrated in FIG. 62, depression of plunger 2405 advances the inserter 2400 from an initial configuration to a deployed configuration. Contact of plunger 2405 and hub 2408 during depression of plunger 2405 imposes a downward force and consequential distal movement of sharp 2404. As the sharp 2404 is urged distally, it carries the sensor insertion portion 30 into the subcutaneous portion of the subject's skin S. Contact of plunger 2405 and sensor housing 122 during depression of plunger 2405 imposes a downward force and consequential distal movement of sensor housing 122. Lip features 2414 of plunger 2405 maintain parallelism of sensor housing 122 to subject skin S during distal movement.

When plunger 2405 reaches a distal position, as shown in FIG. 63, bottom surface 2424 engages wall 2426 and prevents further downward movement. The distal (lower) surface of on body housing 122 engages the upper surface of adhesive pad 218, thereby becoming adhered to the skin surface S of the subject.

Figure 64:
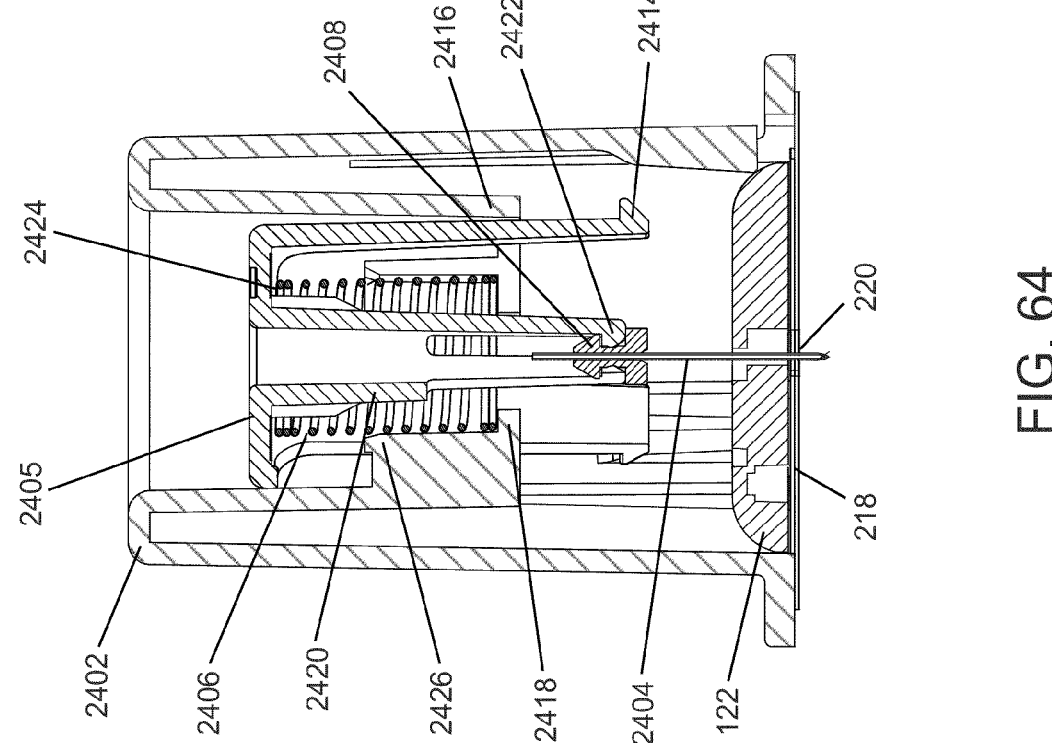
Figure 65:
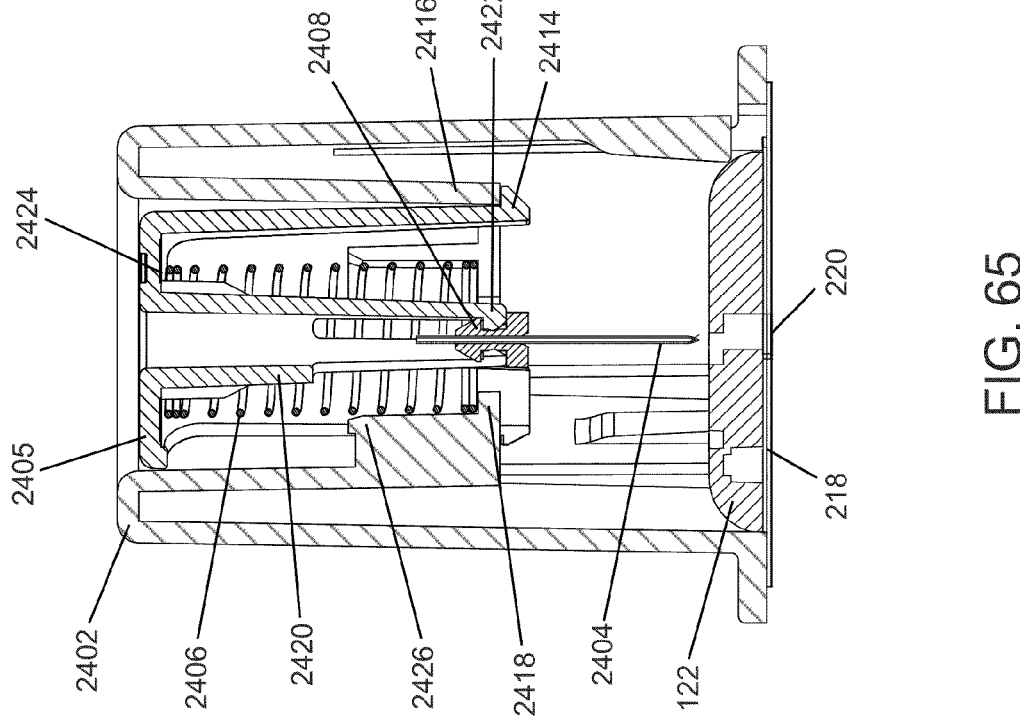

As the subject or some apparatus removes force from plunger 2405, spring 2406 urges plunger 2405 toward its proximal position (away from the skin surface) as shown in FIG. 64, leaving on body housing 122 adhered to the skin surface S of the subject. Tabs 2427 provide additional downward force to the on body housing 122 to assist holding it to adhesive patch 218 while the sharp 2404 is withdrawn through on body housing 122. Eventually, the upward force exerted by spring 2406 returns inserter 2400 to its initial configuration as illustrated in FIG. 65.

Figure 66:
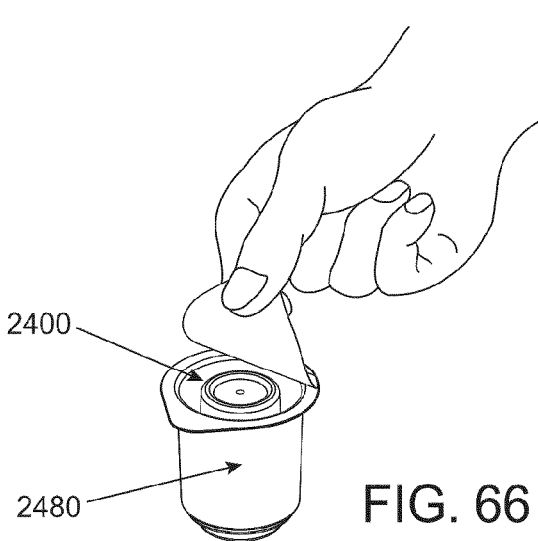
FIGS. 66-68 illustrate a process for utilizing a sterilized versions of the inserter of FIG. 51 in accordance with the disclosed subject matter.
Figure 67:
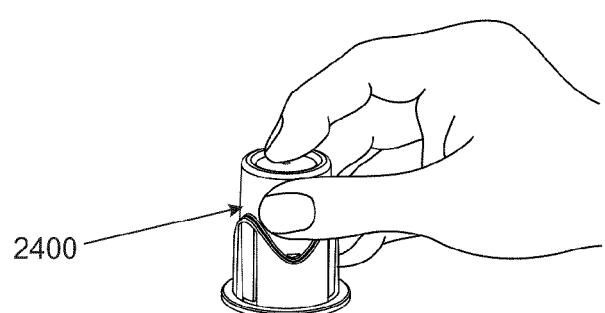
Figure 68:
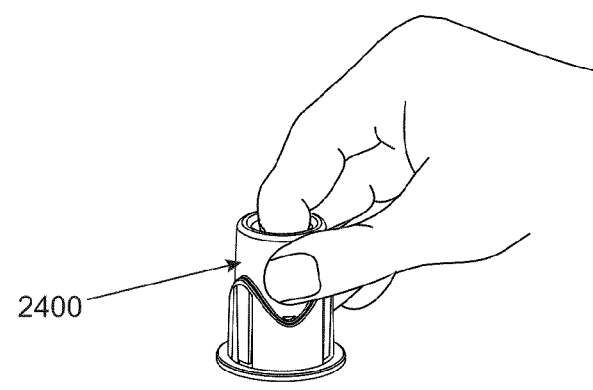
Figure 69:
FIG. 69-72 illustrates an alternate process for utilizing a sterilized versions of the inserter of FIG. 51 in accordance with the disclosed subject matter.
Figure 70:
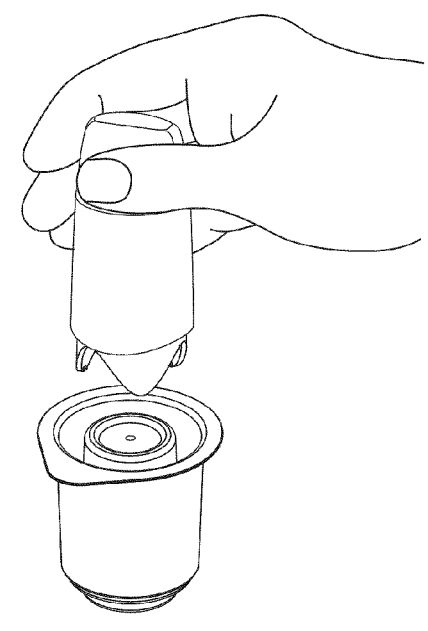
Figure 71:
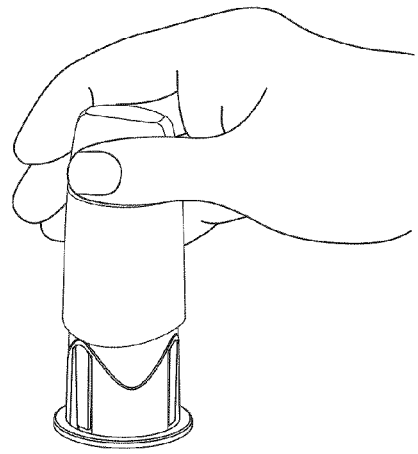
Figure 72:
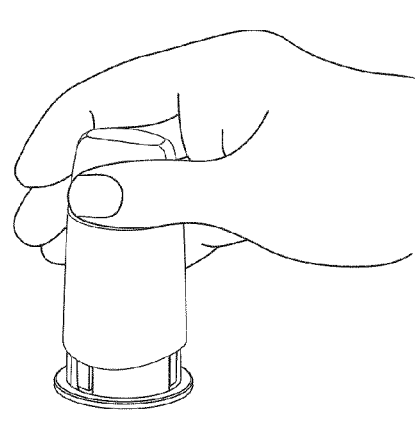

In some embodiments, inserter 2400 may be distributed in a sterilized package 2480 as depicted in FIG. 66. To use inserter 2400 in this configuration, a user would first clean the insertion site on the skin with alcohol. The user would then remove inserter 2400 from sterilized package 2480 as shown in FIG. 66. Next a user would place the inserter on the insertion site and push down on plunger 2405 until on body housing 122 is adhered to the subject's skin as shown in FIGS. 67-68. The user would then release the plunger 2405. Finally, the user would remove inserter 2400 from the insertion site and dispose of the inserter.

A further embodiment of an inserter is illustrated in FIGS. 73-87, and designated inserter 2500. In some embodiments, inserter 2500 has a maximum diameter of about 30 mm to about 60 mm, e.g., about 40 mm, about 43 mm, about 43.5 mm, about 50.25 mm, about 52 mm, etc. In some embodiments, inserter 2500 has a maximum height of about 40 mm to about 80 mm, e.g., about 44 mm, about 46 mm, about 50.25 mm, about 53 mm, about 67 mm, about 71 mm, etc. In some embodiments, inserter 2500 has a volume of about 35 cm³ to about 110 cm³, e.g., about 40 cm³, about 41 cm³, about 50 cm³, about 60 cm³, about 61 cm³, about 62 cm³, about 69 cm³, about 70 cm³, about 79 cm³, about 90 cm³, about 106 cm³, etc. The height of the inserter is measured from the top of housing 2502 to the distal surface of the sheath 2512 that is intended to contact the skin of the subject. The volume of the inserter may be measured as the volume of the housing and the portion of the sheath 2512 that may extend from the housing 2502.

Inserter 2500 generally includes, e.g., a handle 2502, sheath 2512, and a removable distal cap 2504 for maintaining a sterile environment for the medical device and sharp housed therein (FIG. 73). As illustrated in FIGS. 74-75, handle 2502 is shown removed from distal cap 2504. Distal cap 2504 is detachably secured to handle 2502, e.g., by use of threads 2506. It is understood that cap may be secured using snap-fit or press-fit configuration. Inserter 2500 may be utilized to advance a medical device into the skin of the subject. In some embodiments, handle 2502 is advanced relative to sheath 2512 in order to advance the medical device distally and into the skin of the patient.

Handle 2502 further includes needle carrier guides 2508 which allow the needle carrier 2514 to slidingly move relative to distal cap 2504. In an alternate embodiment, a detent prevents sheath 2512 from moving towards a "firing position" until a minimum force is applied. Location feature 2510 allows for the proper positioning of carriage 2516 when engaged.

Figure 87:
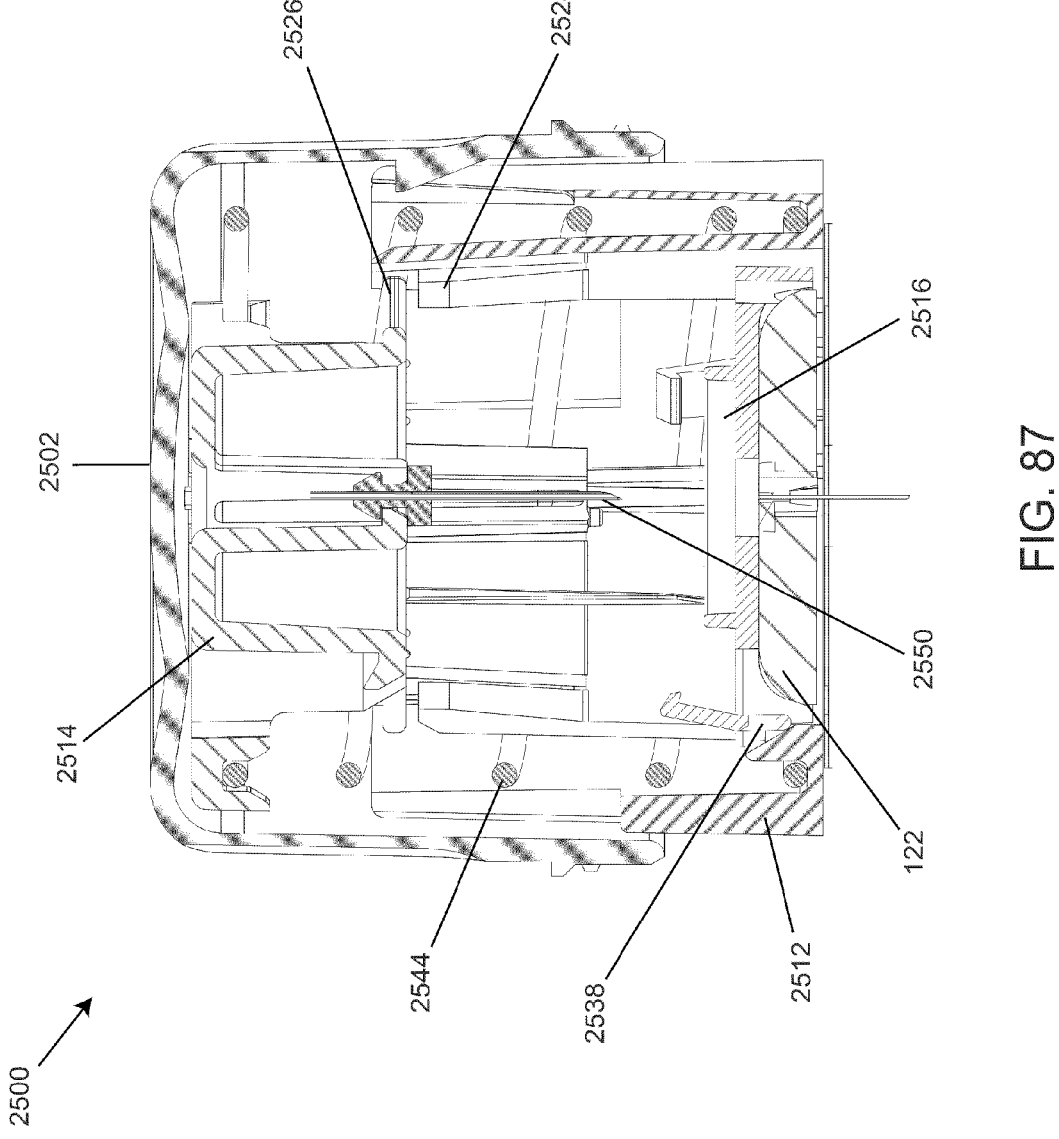

Further components of inserter 2500 are illustrated in FIGS. 76-80. Sheath 2512, as illustrated in FIG. 76, may include longitudinal notches 2518 which snap into detents 2507. Retention members, such as ribs 2520, pinch spring arms 2522 located on carriage 2516 to prevent on body housing 122 from falling out of inserter 2500. Ribs 2520 do not extend to the bottom of sheath 2512, thus allowing carriage 2516 to release on body housing 122 when it has traveled to the bottom of sheath 2512 during insertion. Interfering structure, such as locking beam 2524, prevents inserter 2500 from being used again once needle carrier 2514 passes the locking beam (FIG. 87). Specifically, locking feature 2526 of needle carrier 2514 engages with locking beam 2524 to prevent further use of inserter 2500.

Needle carrier 2514 is illustrated in greater detail in FIGS. 77-78. In some embodiments, needle carrier 2514 includes guides, such as rail guides 2528, which interface with rail guides 2508, thereby allowing needle carrier 2514 to slidingly move relative to handle 2502. Notches 2527 are provided in sheath 2512 which has a larger dimension than the wings of needle carrier 2514, such that the needle carrier 2514 does not contact sheath 2512 during longitudinal movement of needle carrier 2514. Needle carrier 2514 also comprises detents/notches 2530 which interface with the upper edge of the spring when inserter 2500 is fully assembled (see FIGS. 81-87). In some embodiments, needle carrier 2514 comprises an attachment feature 2532 capable of accommodating a custom needle hub or attachment.

Figure 79:
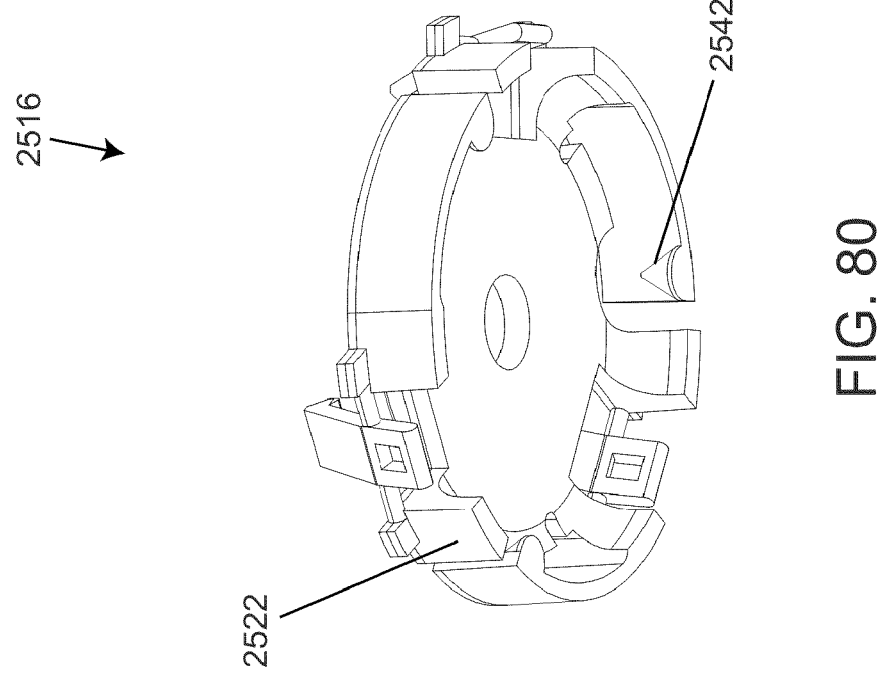
Figure 80:
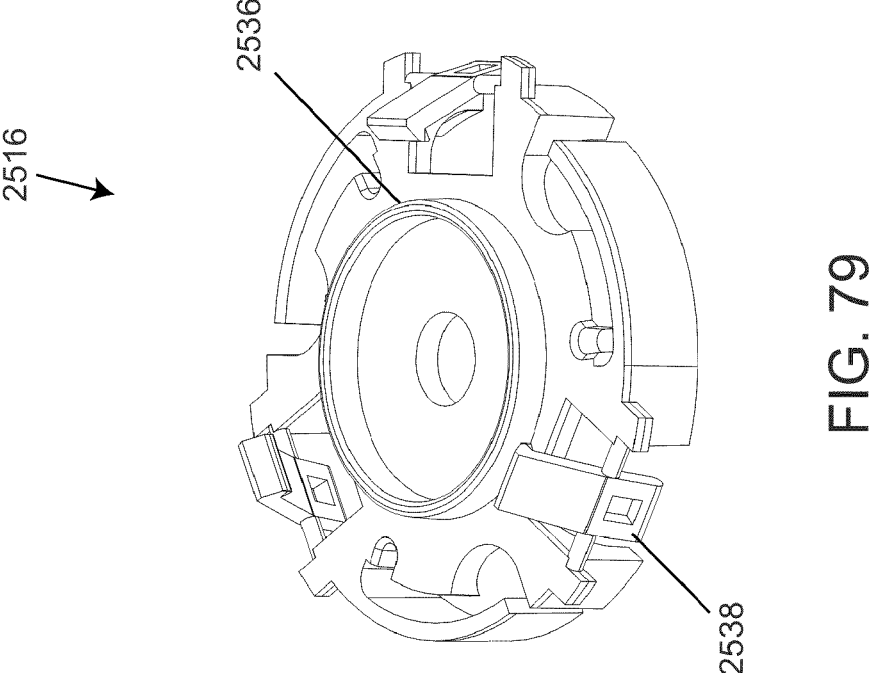

Carriage 2516 is illustrated in greater detail in FIGS. 79-80. As shown, carriage 2516 may comprise latches 2538 which connect it to needle carrier 2514 by locking with latches 2540. Spring hook 2542 allows for support for retaining on body housing 122 when the inserter has not been fired and allows for release of on body housing 122 when it has been attached to the skin of the user. (See, FIGS. 122, 125, 135-140.)

Figure 81:
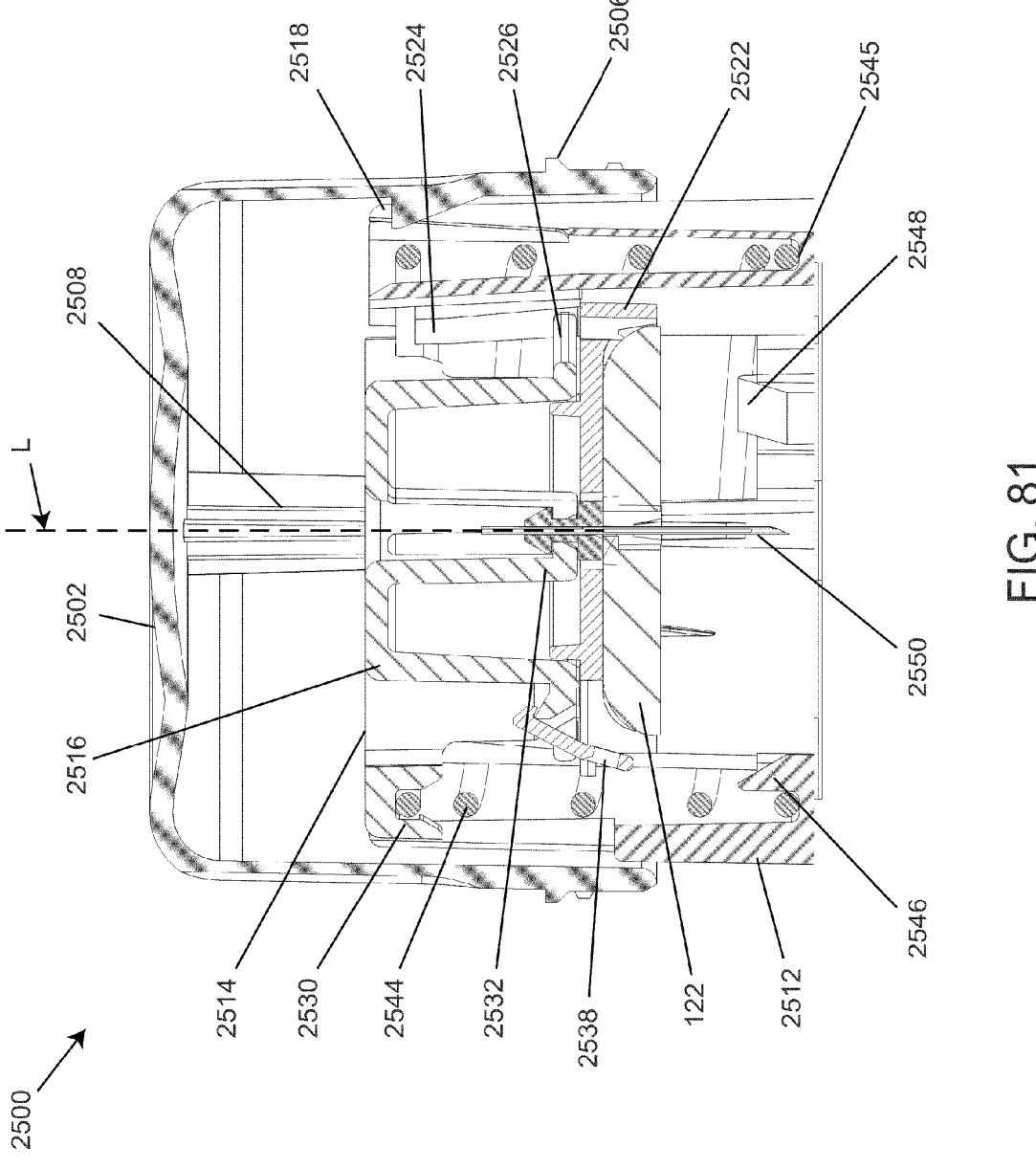
FIGS. 81-87 are cross-sectional views of the inserter of FIG. 73 in accordance with the disclosed subject matter.

Inserter 2500 is illustrated in cross-section in FIG. 81 in a state prior to use in which handle 2502 is disposed in a proximal position with respect to the sheath 2512. In such configuration, the sharp 2550 is disposed in a configuration spaced apart from the aperture 420 of the adhesive layer (not shown). The longitudinal axis L of the inserter 2500 is illustrated. The upper surface of spring 2544 is retained in inserter 2500 by detents/notches 2530 located on needle carrier 2514. The bottom surface of spring 2544 is retained by spring floor 2545 located on sheath 2512. Initially, spring 2544 is in an expanded or semi-expanded state while handle 2502 is disposed proximally from sheath 2512.

Figure 84:
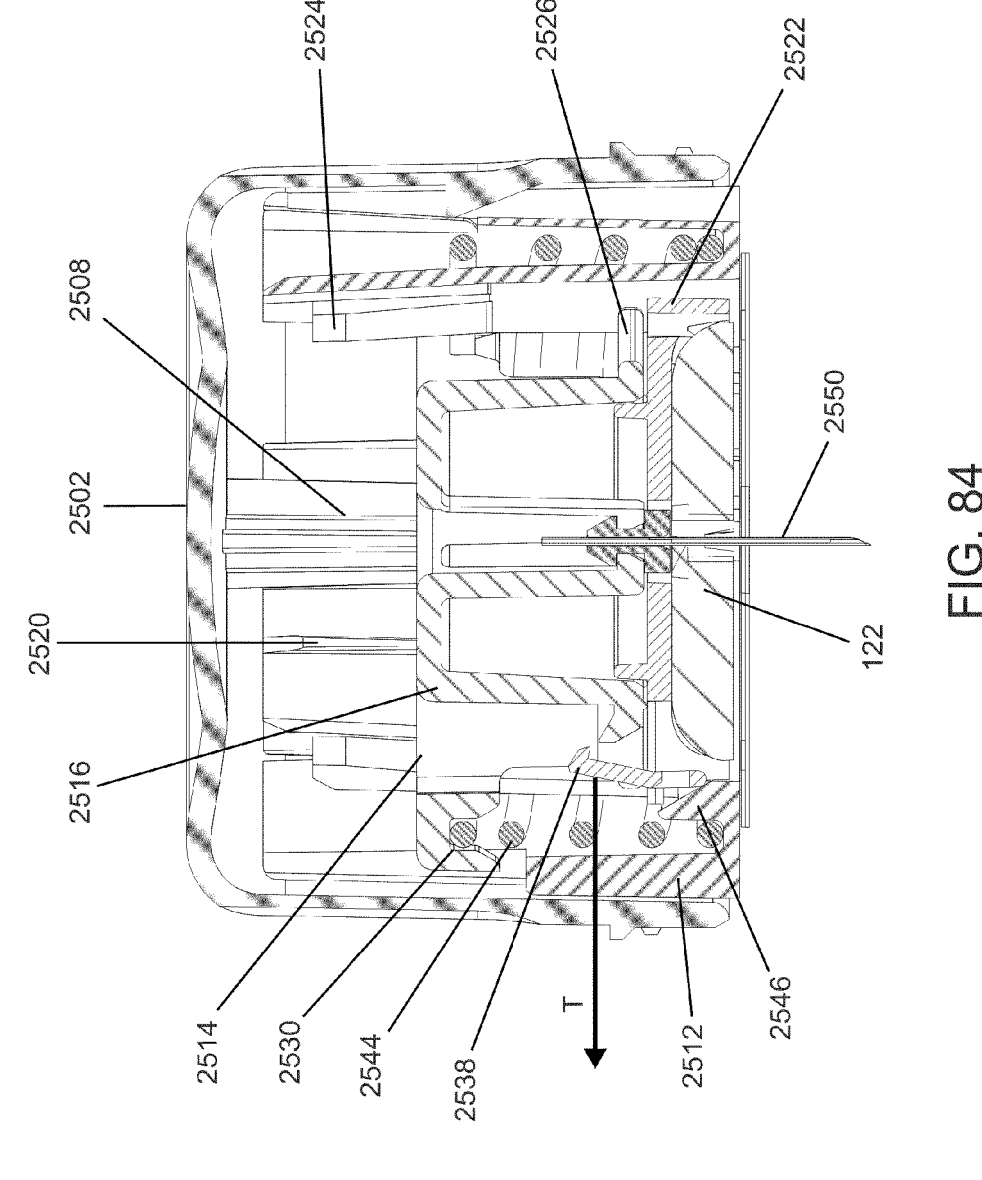

Extending distally from the upper surface of handle 2502 is inner wall 2508. In some embodiments, the distal end portions of wall 2508 provide a downward force on carriage 2516 upon depression of handle 2502 by a user. Alternatively, instead of handle 2502 having a distally extending inner wall 2508, carriage 2516 can include one or more upwardly extending walls or projections (not shown). The one or more upwardly extending inner walls or projections of the carriage 2516 can have a length sufficient to either contact the inside of the upper surface of handle 2502 or, alternatively, contact corresponding downwardly extending inner walls of handle 2502. In this manner, depression of handle 2502 by a user provides a downward force on the one or more upwardly extending walls or projections of carriage 2516 to advance carriage 2516 (and on body housing 122) distally to an installation and insertion position (FIG. 84). In such embodiment, the downwardly extending inner wall of the handle has a distal end that is disposed proximally of the proximal most end of sheath 2512.

Sharp 2550 extends longitudinally from needle carrier 2514 within inserter 2500. In some embodiments, sharp 2550 is supported at an oblique angle, e.g., between about 0° and 90° with respect to the skin surface.

Figure 82:
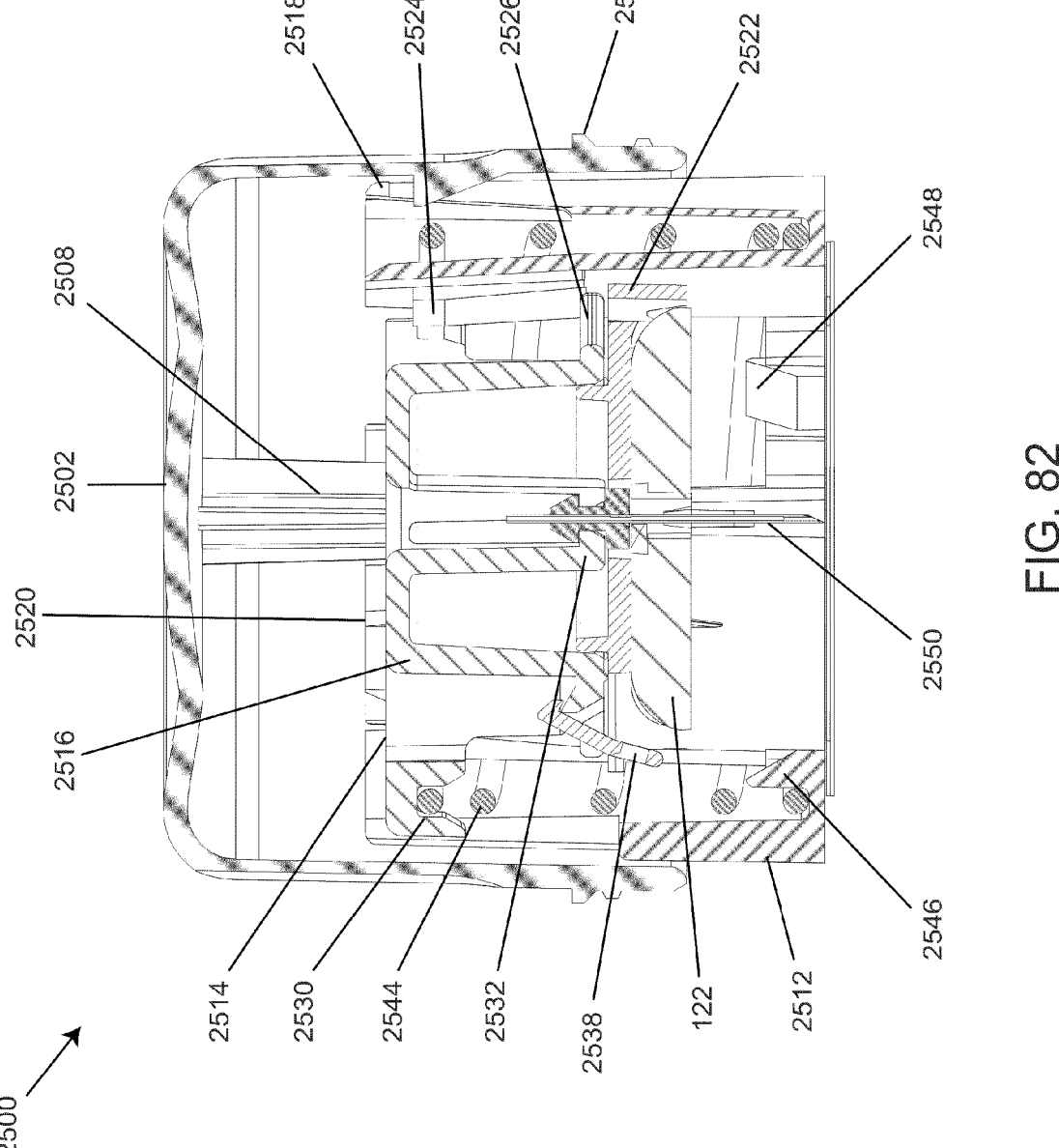
Figure 83:
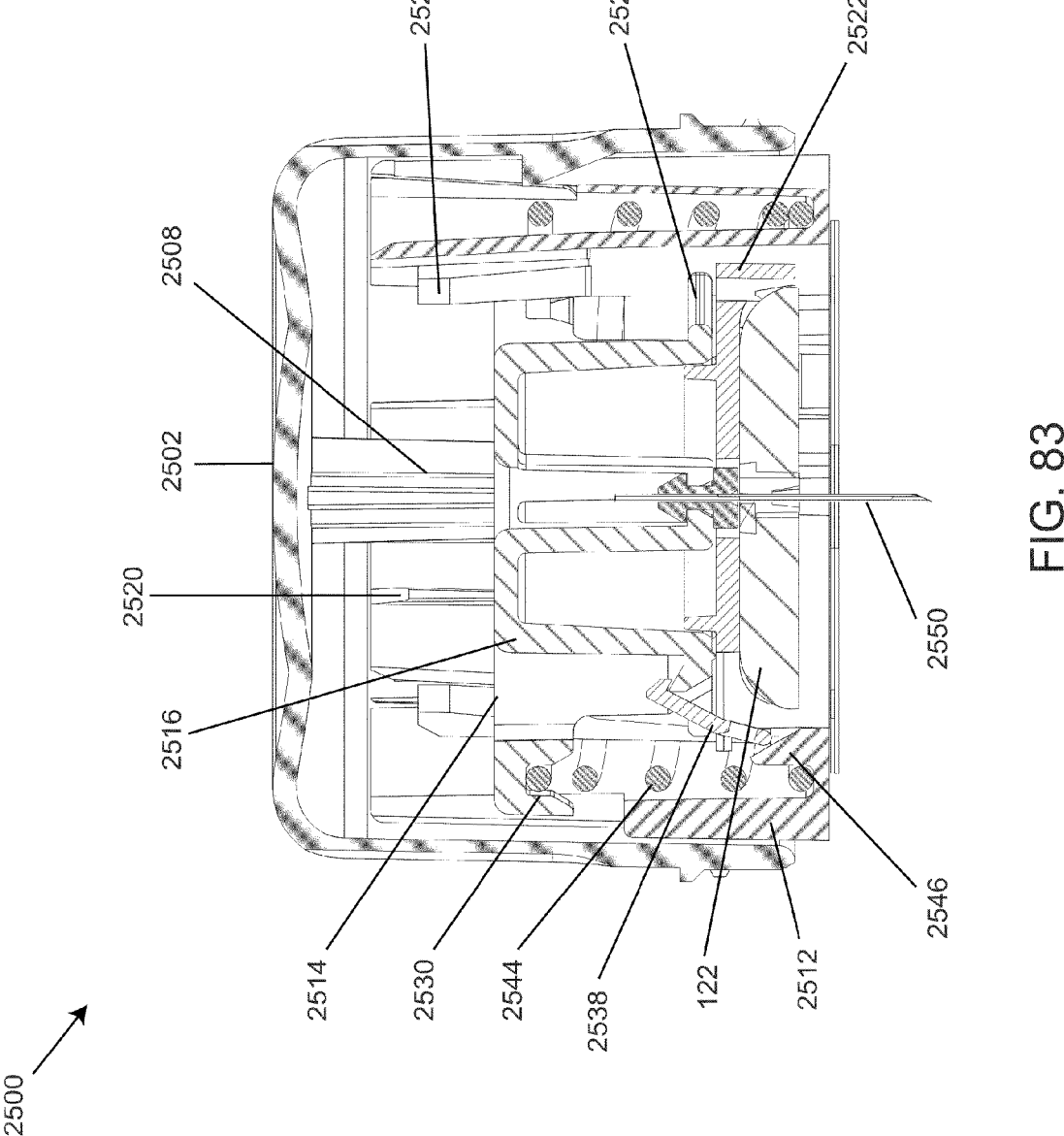

FIG. 82 illustrates inserter 2500 in cross-section after a user applies an initial downward force to button 2502. Further depression of handle 2502 with respect to sheath 2512, against the bias of spring 2544, causes distal longitudinal movement of the carriage 2516 and needle carrier 2514, from a proximal position towards a distal position as shown in FIG. 83. During such downward proximal movement, spring 2544 is compressed between detents/notches 2530 and retention tab 2546. As sharp 2550 is further urged distally, it carries the sensor insertion portion 30 of sensor 14 (FIG. 17) into the subject's skin S.

As carriage 2516 reaches a distal position (near the subject's skin) as shown in FIG. 83, the distal surface of the on body housing 122 engages the upper surface of adhesive pad (not shown), thereby becoming adhered to the skin surface S of the subject. Latch 2538 engages the upper surface of retention tab 2546 as shown in FIG. 84. As a result, the top portion of latch 2538 is pivoted outward in direction T. Such pivoting of latch 2538 causes needle carrier to become disengaged from carriage 2516.

Figure 85:
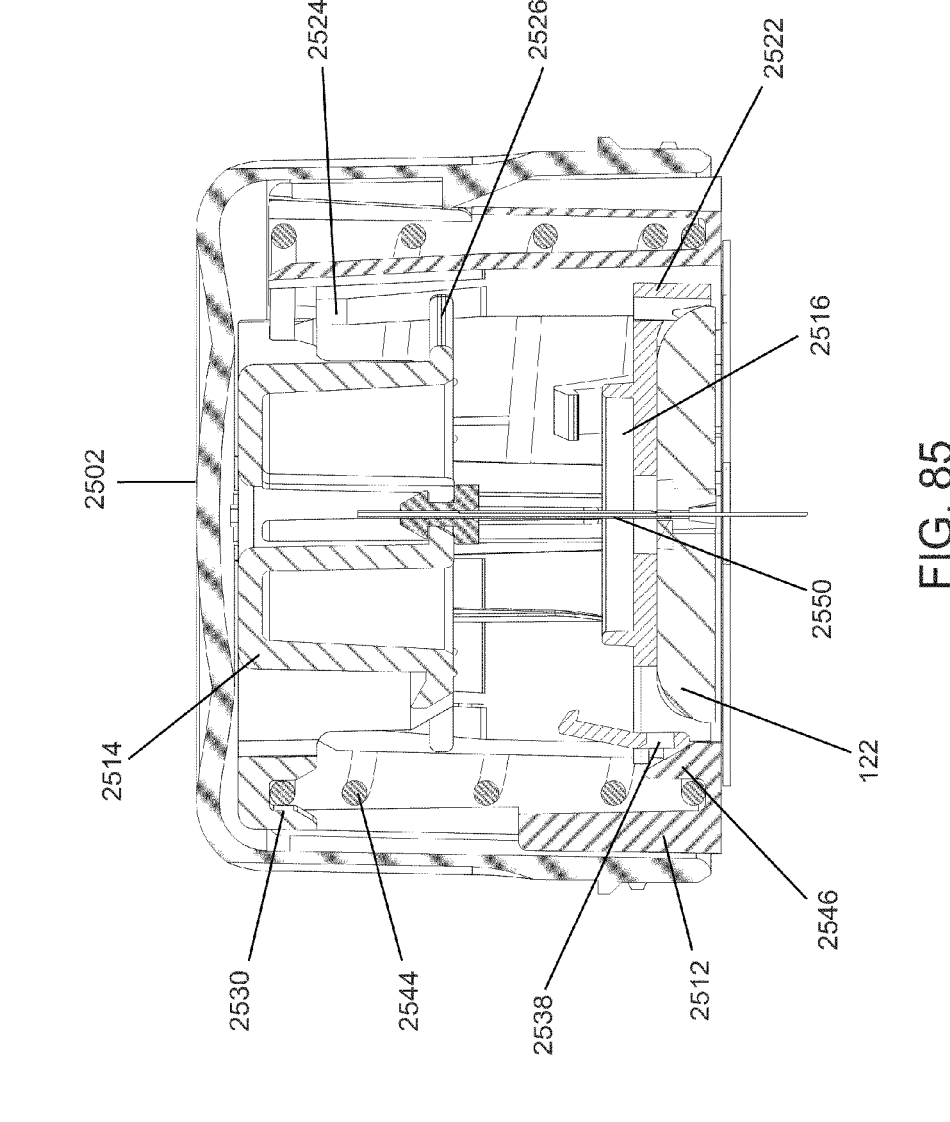
Figure 86:
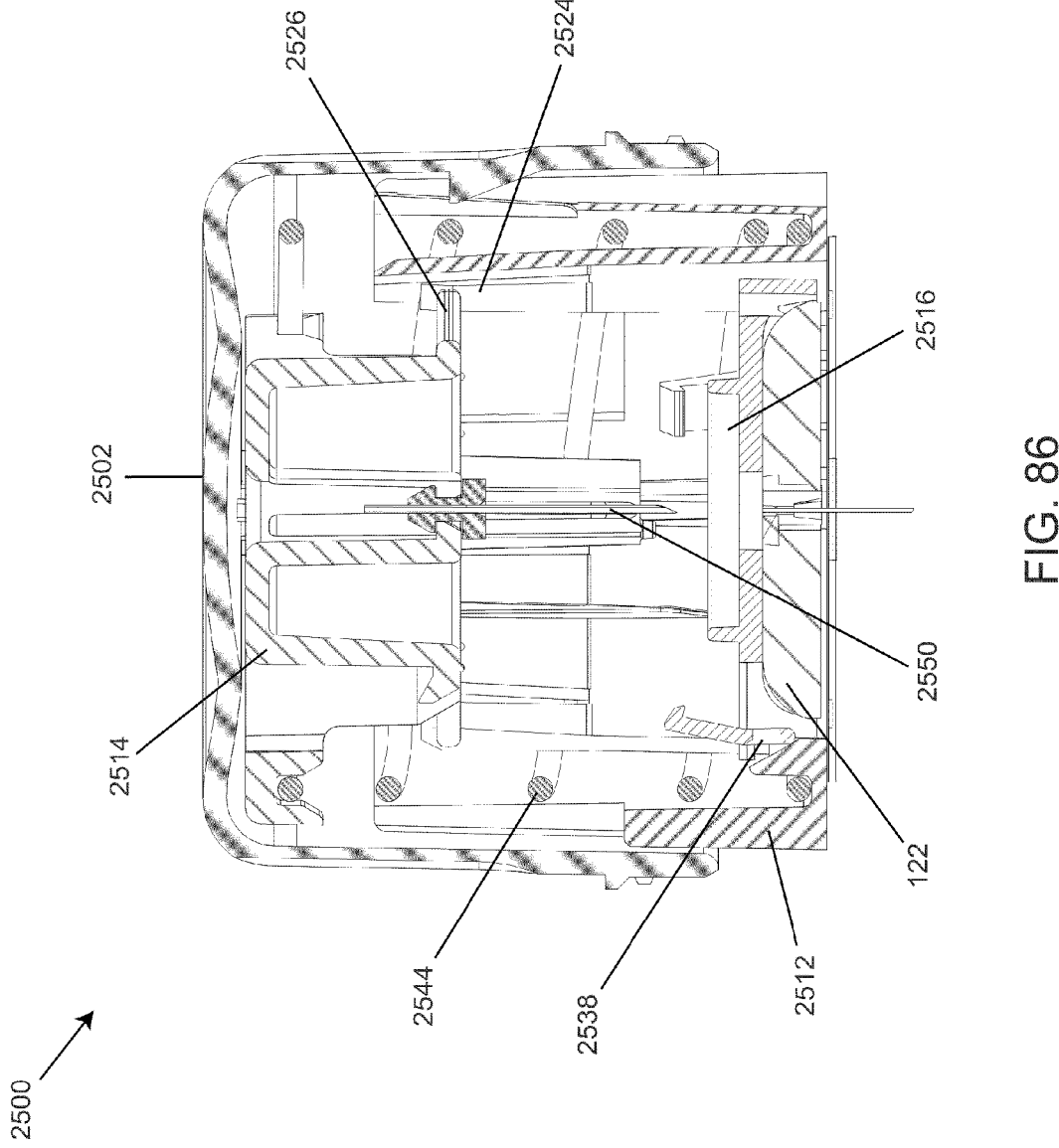

As illustrated in FIG. 85, disengagement of the needle carrier 2514 from the carriage 2516 permits spring 2544 to expand, thereby advancing the needle carrier 2514 to a proximal position and withdrawing the sharp 2550 from the skin S of the subject while leaving the on body housing 122 attached to the skin. As the sharp is withdrawn (FIG. 86), locking feature 2526 advances past locking beam 2524 because of the upward force exerted on needle carrier 2514 by spring 2544.

Referring now to FIG. 87, once the sharp 2550 has been withdrawn from the subject, button 2502 cannot be pressed again because any downward movement will be blocked by the interaction of locking beam 2524 and locking feature 2526.

Figure 88:
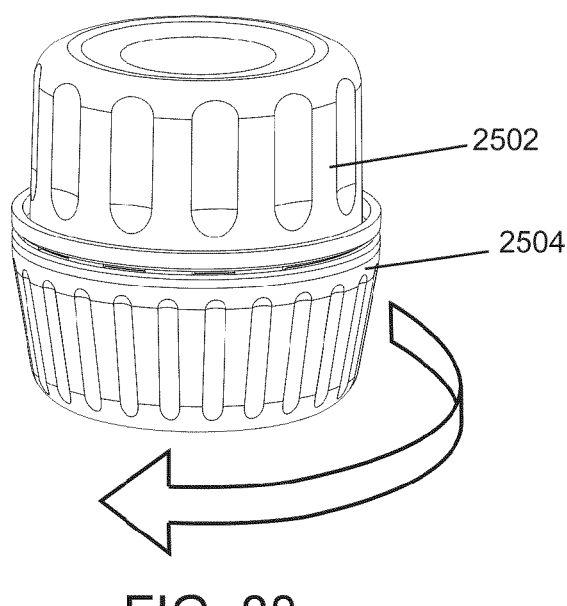
FIGS. 88-90 illustrate a process for utilizing a sterilized version of the inserter of FIG. 73 in accordance with the disclosed subject matter.
Figure 89:
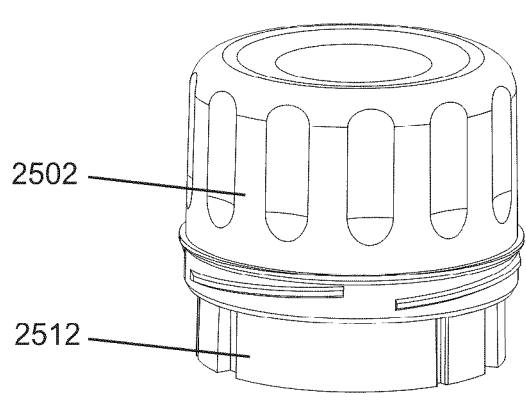
Figure 90:
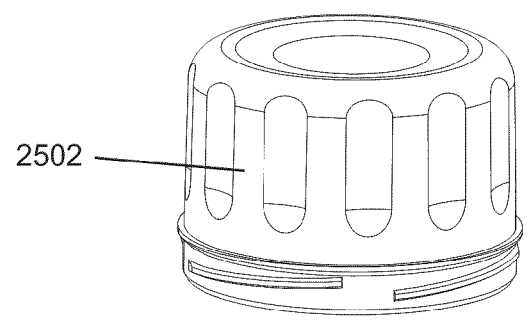

In some embodiments, inserter 2500 may come in a sterilized package which is capable of a one-time use as shown in FIGS. 88-90. To use inserter 2500 in this manner, a user would first sterilize the insertion site on the skin with alcohol. The subject would then twist off cap 2504 as shown in FIG. 88. Next a subject would place the inserter on the sterilized insertion site and push down on inserter 2500 until on body housing 122 is adhered to the subject's skin as shown in FIGS. 89-90. Finally, the subject would remove inserter 2500 from the insertion site and dispose of the inserter. In this manner, the inserter 2500 itself serves as its own sterilized packaging. This procedure applies also to the other inserters described herein.

A further embodiment of an inserter is illustrated in FIGS. 91-108, and designated inserter 2700. In some embodiments, inserter 2700 has a maximum diameter of about 30 mm to about 60 mm, e.g., about 40 mm, about 43 mm, about 43.5 mm, about 46 mm, about 50 mm, etc. In some embodiments, inserter 2700 has a maximum height of about 40 mm to about 80 mm, e.g., about 44 mm, about 46 mm, about 49.5 mm, about 55 mm, about 67 mm, about 71 mm, etc. In some embodiments, inserter 2700 has a volume of about 35 cm$^3$ to about 110 cm$^3$, e.g., about 40 cm$^3$, about 41 cm$^3$, about 50 cm$^3$, about 60 cm$^3$, about 61 cm$^3$, about 62 cm$^3$, about 69 cm$^3$, about 70 cm$^3$, about 79 cm$^3$, about 90 cm$^3$, about 106 cm$^3$, etc. The maximum height refers to the height defined from the top of the housing 2702 to the portion of the sheath 2708 that contacts the subject's skin. The volume is measured as the volume of the housing 2702 and the portion of the sheath 2708 extending from the housing.

Inserter 2700 generally includes, e.g., a housing 2702 (FIGS. 92-93), sheath 2708 (FIGS. 94-95), and a removable distal cap 2704 for maintaining a sterile environment for the medical device and sharp housed therein (FIG. 91). As illustrated in FIGS. 92-93, housing 2702 is shown removed from distal cap 2704. Distal cap 2704 is detachably secured to housing 2702, e.g., by use of threads 2706. It is understood that cap may be secured using snap-fit or press-fit configuration. Inserter 2700 may be utilized to advance a medical device into the skin of the subject. Sheath 2708 generally defines a cavity or open space, within which sharp carrier 2716 and medical device carrier 2730 are moveable. In some embodiments, housing 2702 is advanced relative to sheath 2708 in order to advance the medical device distally and into the skin of the patient.

Housing 2702 includes sheath guide rail 2710 which interfaces with rail guides 2712 located on sheath 2708 (FIG. 94), thereby allowing housing 2702 to slidingly move longitudinally relative to sheath 2708. Housing 2702 may further include sharp carrier guide rail 2714 which interfaces with rail guides 2718 located on sharp carrier 2716 (FIG.

97). Sheath 2708, sharp carrier 2716, and housing 2702 may alternatively move relative to one another without the use of guide rails.

Ledge 2720 and/or ledge 2722 are provided on an interior portion of housing 2702. Ledge 2720 engages sheath 2708 to hold sheath 2708 in a pre-use position prior to insertion of the medical device. Ledge 2722 engages sheath 2708 to secure sheath 2708 in a post-use position after insertion of the medical device. Housing 2702 further includes detent 2724 which prevents housing 2702 from moving relative to sheath 2708 until a minimum force has been applied, e.g., distally by user to housing 2702. The sheath 2708 is secured to the housing 2702 via snap 2726. Snap 2726 snaps into the housing detent 2724. (In some embodiments, it is pinched between ledge 2720 and detent 2724, thus controlling its longitudinal position relative to the housing 2702). The needle carrier 2716 is located and secured to the medical device carrier 2730 (located via interaction of locating features 2748 and 2750 and secured via interaction of carrier arms 2732 and angled top surface of 2716). The ledge 2720 is a controlled surface onto which the top of sheath surface 2728 will engage at the end of the insertion stroke to prevent further relative movement in some embodiments.

Figure 95:
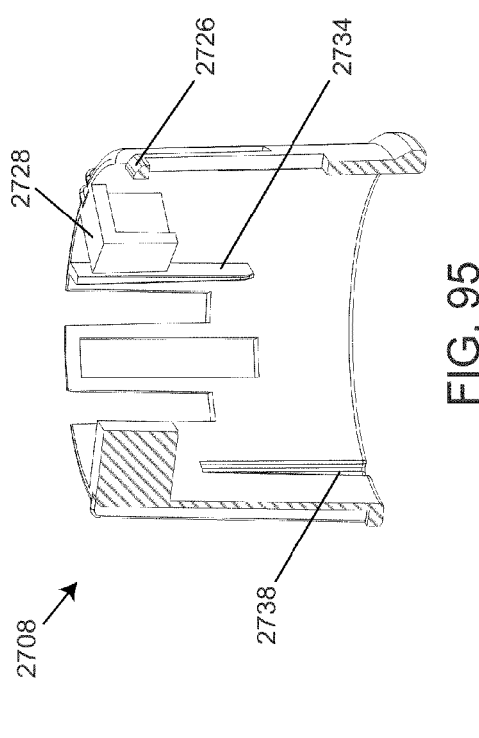
Figure 94:
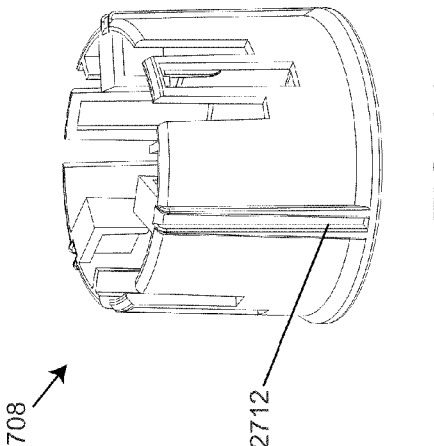

Further components of inserter 2700 are illustrated in FIGS. 94-99. Sheath 2708 is a generally cylindrical component. As illustrated in FIGS. 94-95, sheath 2708 may include attachment snaps 2726 which are biased into detent 2724 of housing 2702 to create a minimum force that must be overcome in order to advance sharp 224 into the subject's skin and install the on body housing 122. The interaction of the snap 2726 with the detent 2724 and ledge 2720 holds the assembly in a slop/rattle free position. In some embodiments, the force to be overcome can be about 0.5 lbf to about 5 lbf, e.g., about 1 lbf, about 2 lbf, about 3 lbf, about 4 lbf, etc. Support wall 2728 prevents carrier arms 2732 on carrier 2730 from bending outwardly, clear of sharp carrier 2716. Ribs 2734 pinch carrier arms 2732 on carrier 2730, thus preventing on body housing 122 from falling out of inserter 2700 when sheath 2708 is in the extended position. Ribs 2734 are not present at the bottom of sheath 2708, thus allowing room for spring arms 2736 on carrier 2730 to release on body housing 122 when carrier 2730 has traveled to the bottom of sheath 2708. Slot 2738, located on sheath 2708, interfaces with locating feature 2740 on carrier 2730, thus orienting carrier 2730 to sheath 2708 during assembly. Once force is overcome to allow carrier 2730 to move distally towards the subject's skin, no further force is required to retract the sharp 324 from the subject's skin.

Figure 97:
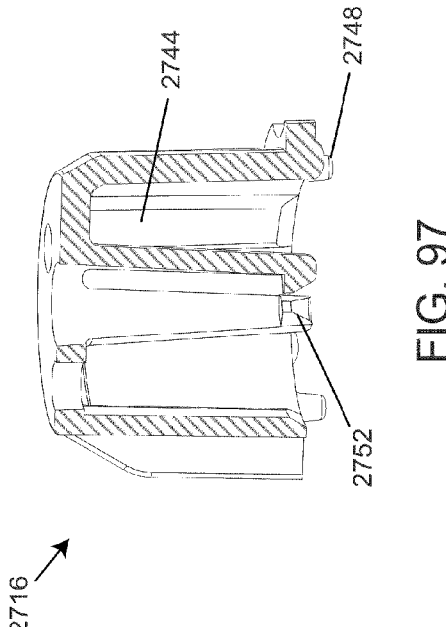
Figure 96:
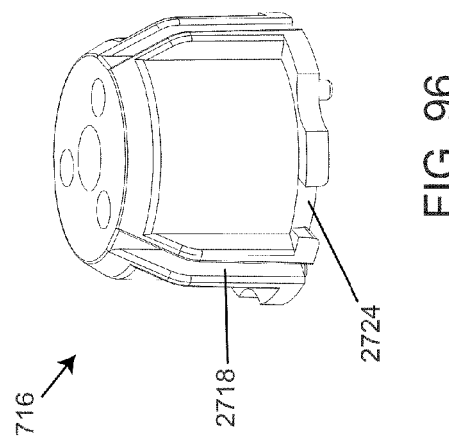
Figure 100:
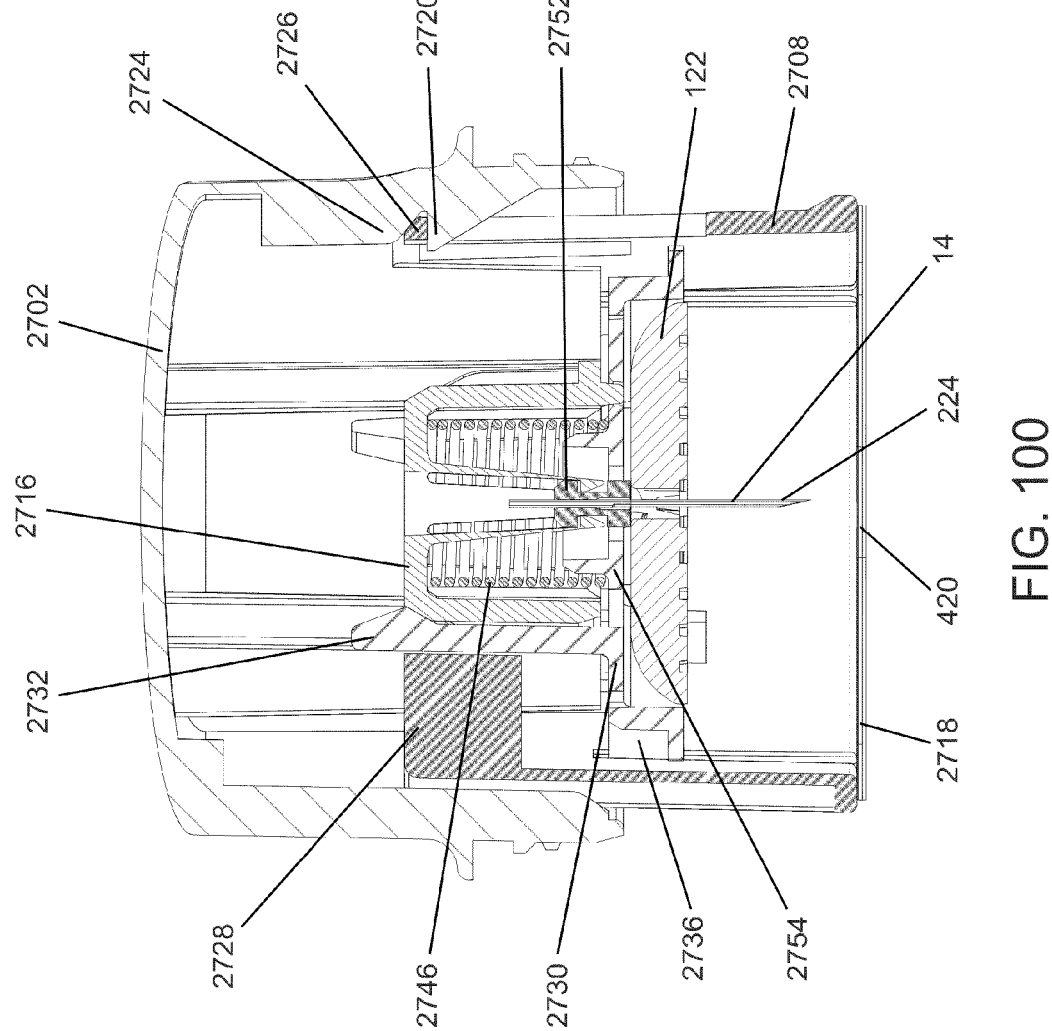
FIGS. 100-106 are cross-sectional views of the inserter of FIG. 91 in accordance with the disclosed subject matter.

Referring next to FIGS. 96-97, depicted is sharp carrier 2716 in a perspective and cross-sectional view, respectively. Sharp carrier 2716 contains notches 2724 which allow clearance for the passage of carrier arms 2732 located on medical device carrier 2730. Guidance walls 2744 securely hold spring 2746 in place (FIG. 100). Locating features 2748, e.g., bosses or tabs, align with locating features 2750, e.g., recesses or apertures, on carrier 2730. Snap features 2752 secure sharp 224 securely within inserter 2700. It is contemplated that sharp 224 may be secured to sharp carrier 2716 by other techniques, e.g., friction fit, adhesive, welding, etc.

Figure 99:
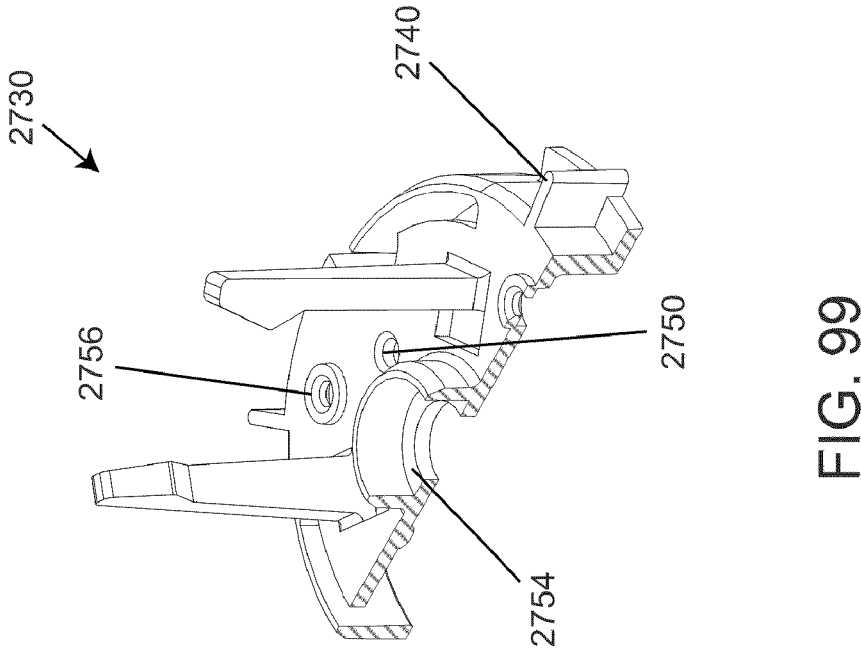
Figure 98:
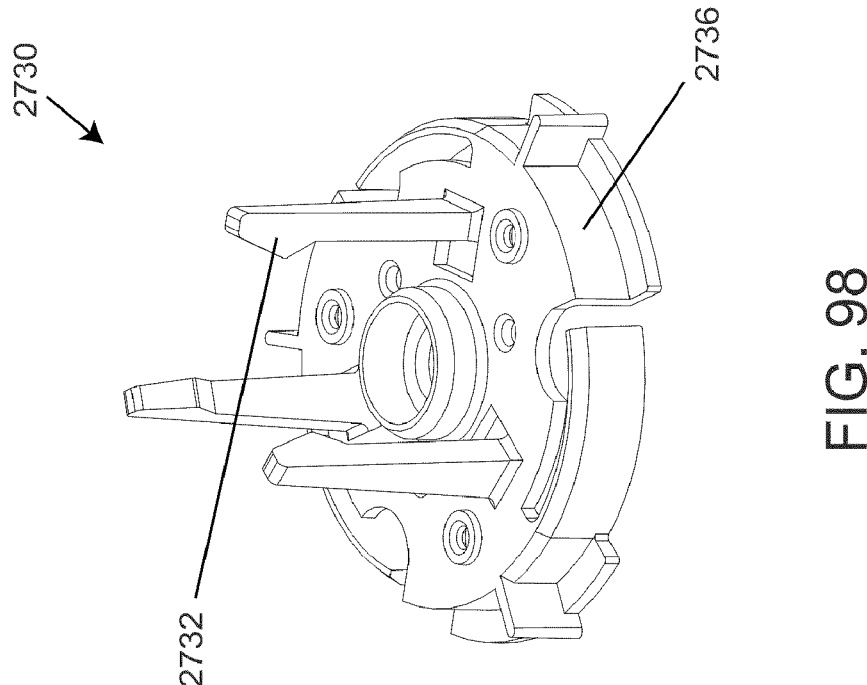

Medical device carrier 2730 is depicted in more detail in FIGS. 98-99. As shown, carrier 2730 contains spring locating ring 2754 which receives one end of spring 2746. In some embodiments, spring 2746 surrounds spring locating ring 2754. In some embodiments, the inner area remains clear to leave room for the deflection of sharp carrier feature snaps 2752 that move outwardly when the sharp is inserted.

Carrier 2730 further comprises locating features 2756 which interface with locating features on housing 2702. (See FIGS. 135-136).

Inserter 2700 is illustrated in cross-section in FIG. 100 in a state prior to use in which housing 2702 is disposed in a proximal position with respect to the sheath 2708. In such orientation, sharp 224 is disposed in a configuration spaced apart from the aperture 420 of the adhesive layer 118. The upper surface of spring 2746 is retained in inserter 2700 by sharp carrier 2716. The bottom surface of spring 2746 is retained by spring location ring 2754. Initially, spring 2746 is in a compressed or semi-compressed state while housing 2702 is disposed proximally from sheath 2708.

Sharp 224 extends longitudinally from sharp carrier 2716 within inserter 2700. In some embodiments, sharp 224 is supported at an oblique angle, e.g., between and including about 0° and 90° with respect to the skin surface.

Figure 101:
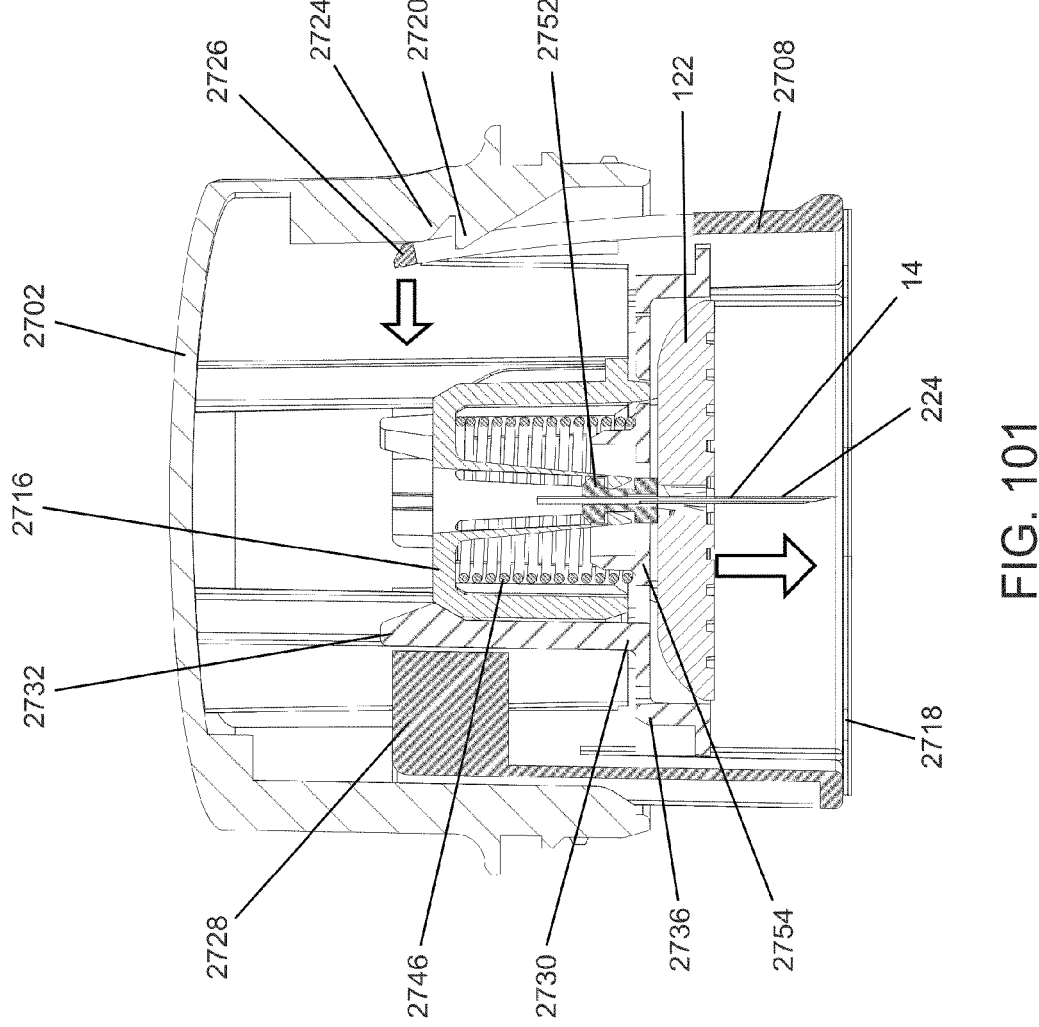
Figure 102:
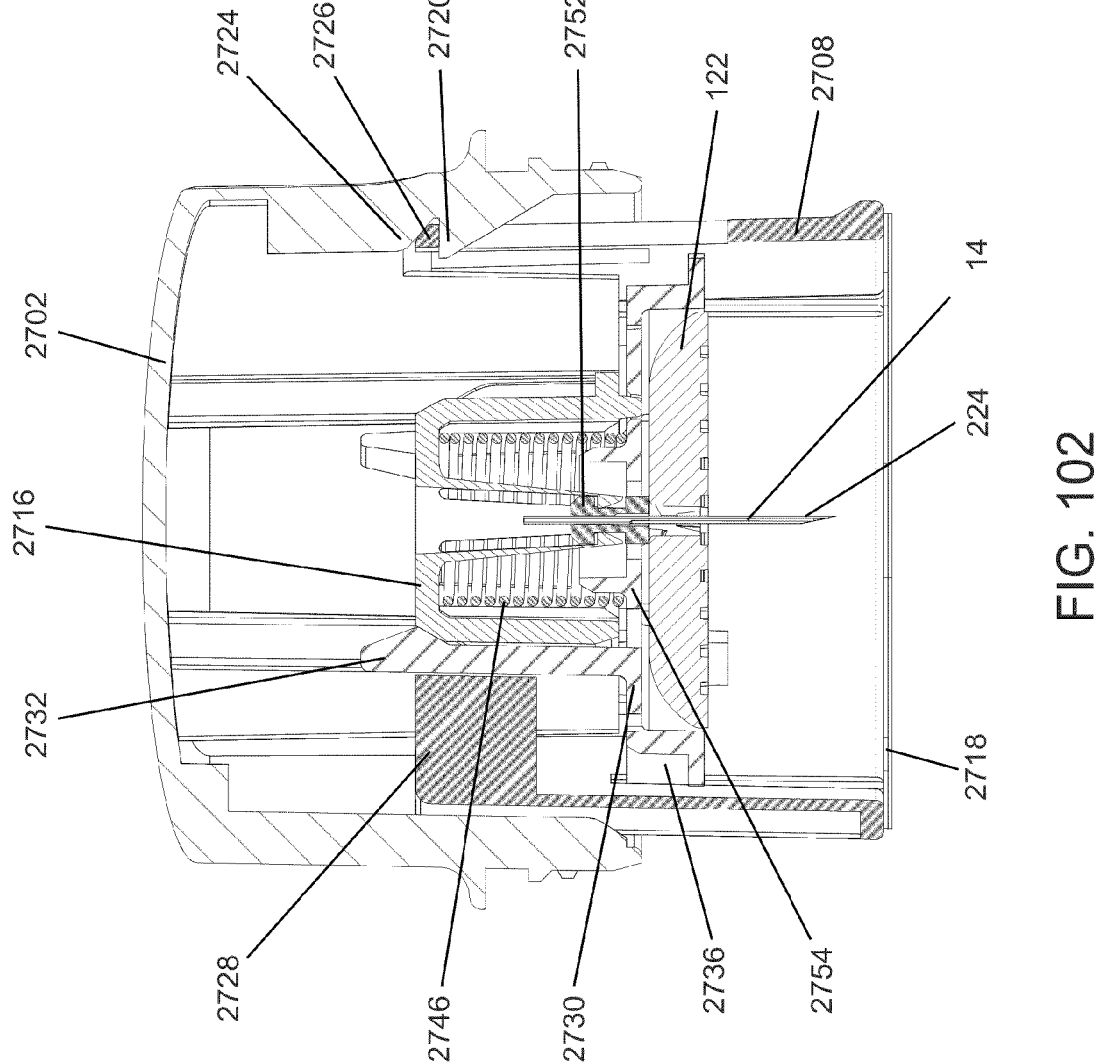

FIG. 101 illustrates inserter 2700 in cross-section after a user applies an initial downward force to housing 2702. In some embodiments, a predetermined minimum force must be used so that attachment snaps 2726 advance past detent 2724.

Figure 103:
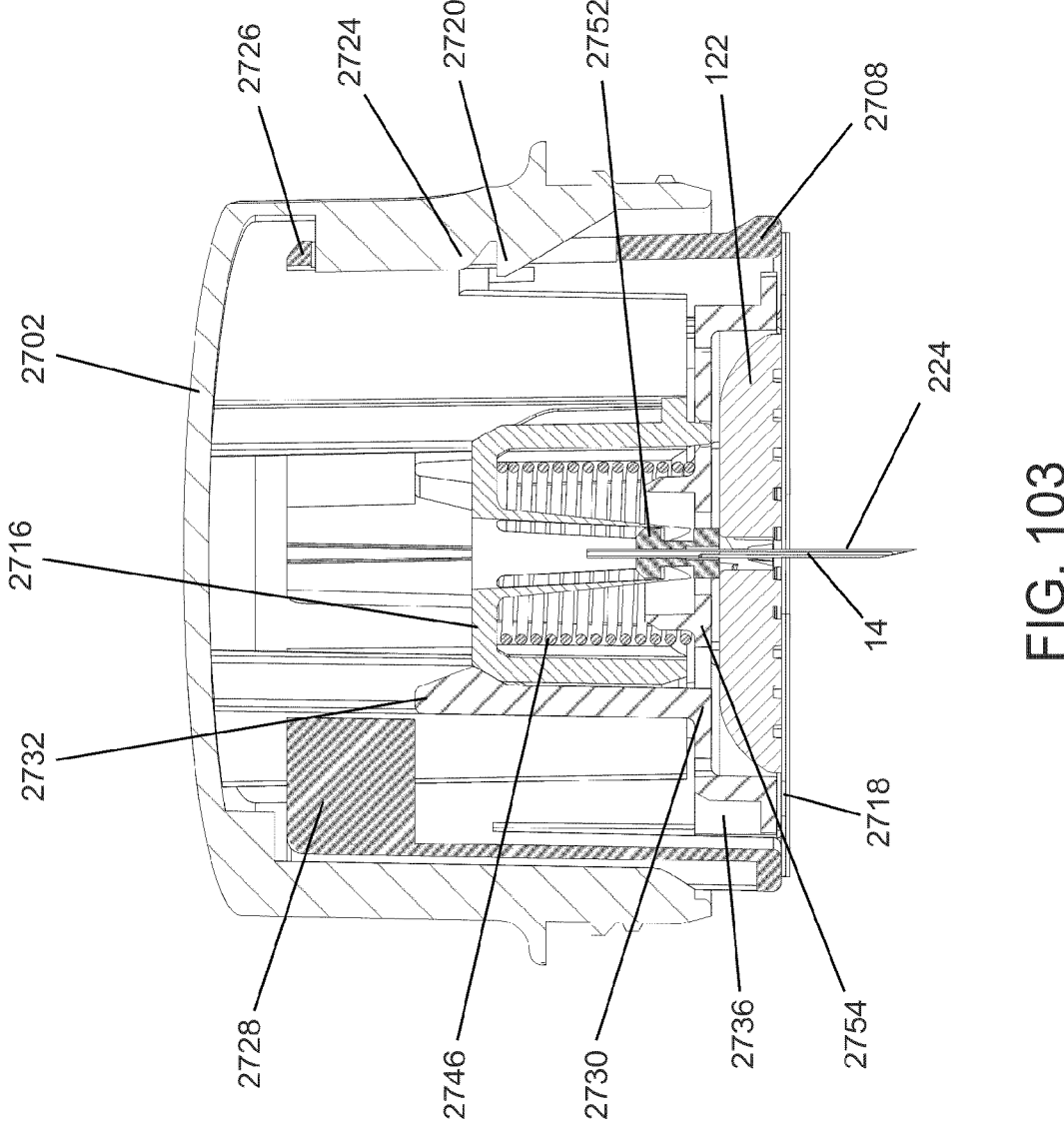
Figure 104:
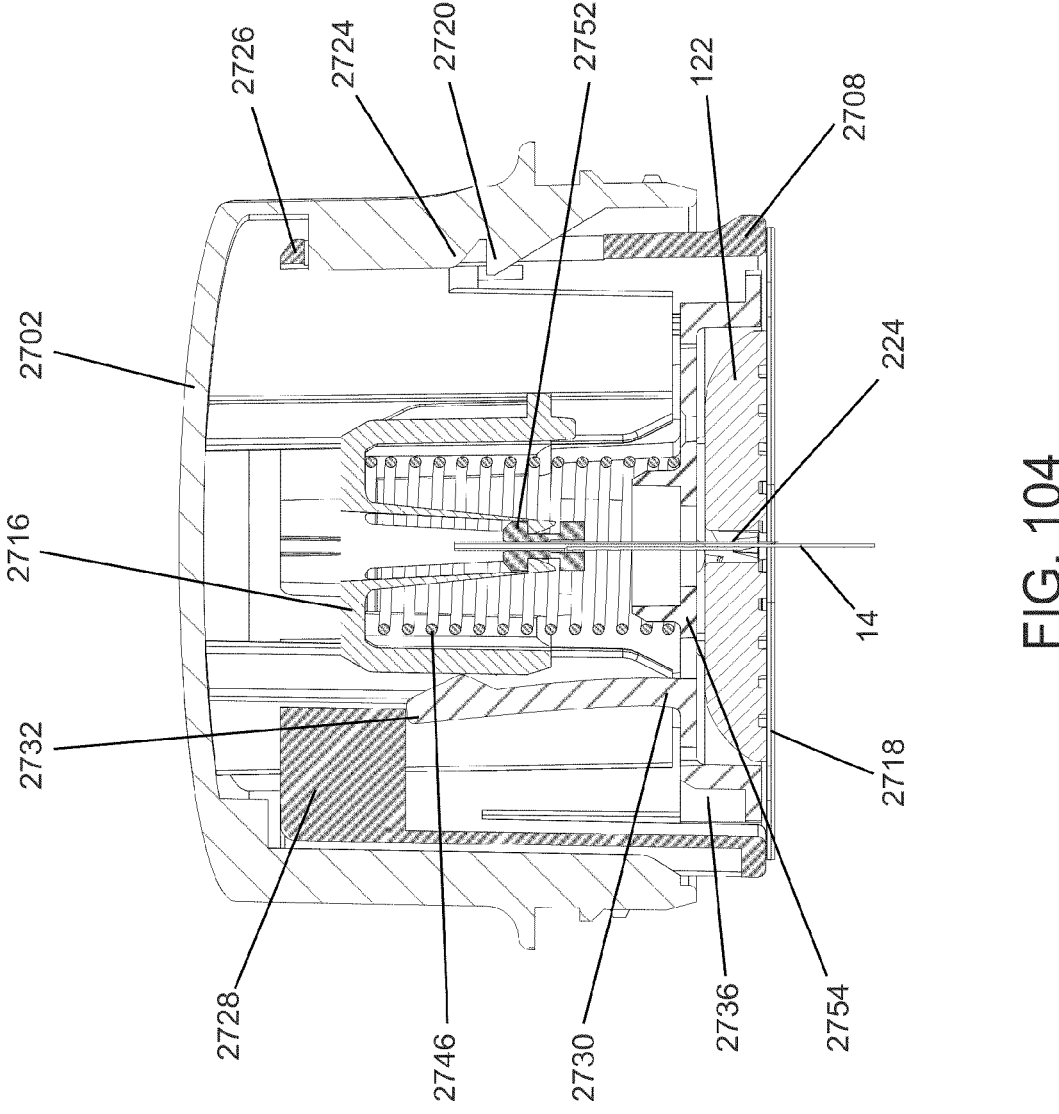

After detent 2724 has been overcome, e.g., snap 2726 is radially displaced, further depression of housing 2702 with respect to sheath 2708 causes distal longitudinal movement of the carrier 2730 and sharp carrier 2716, from a proximal position towards a distal position as shown in FIG. 103. As sharp 224 is further urged distally, it carries the sensor insertion portion 30 of sensor 14 (FIG. 17) into the subcutaneous portion of the subject's skin S.

Figure 105:
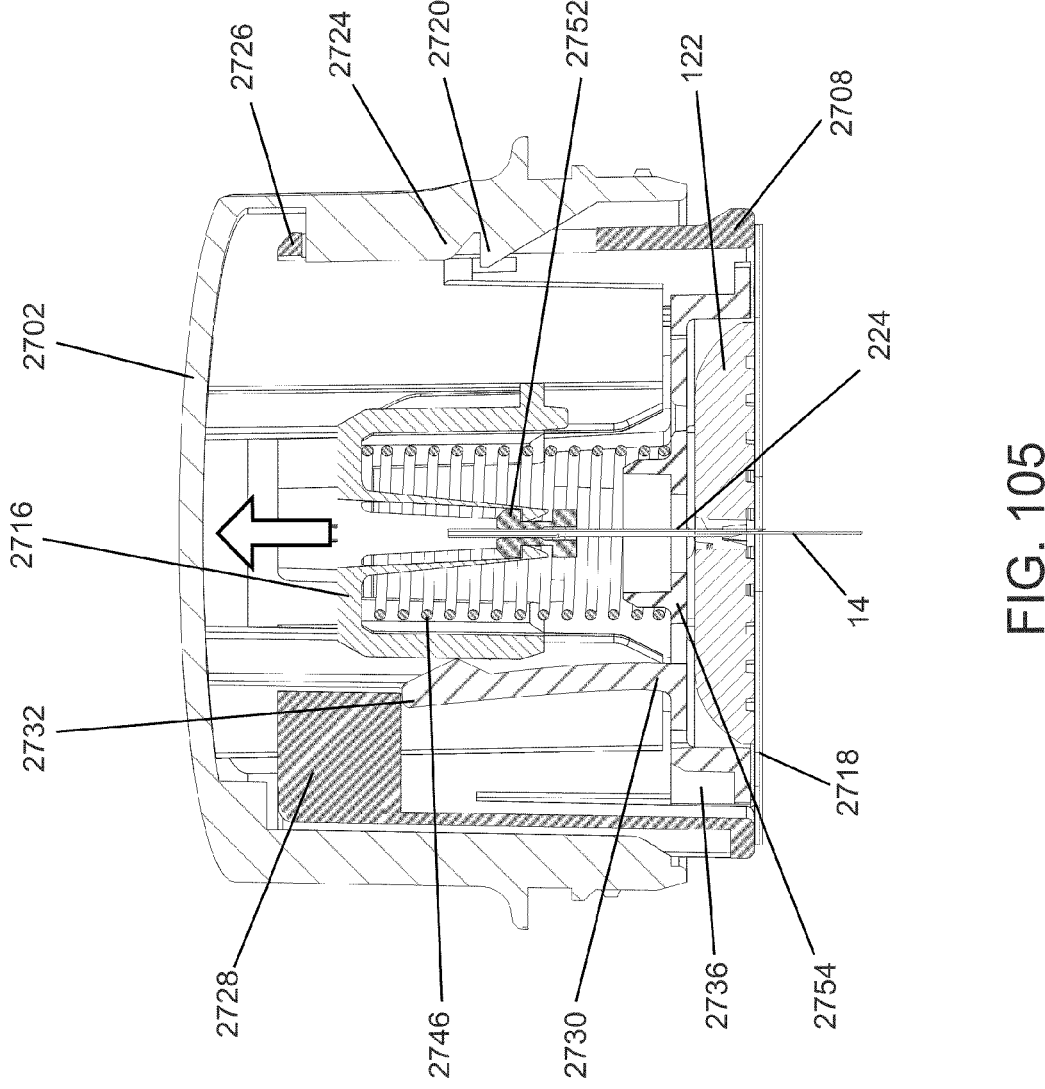
Figure 106:
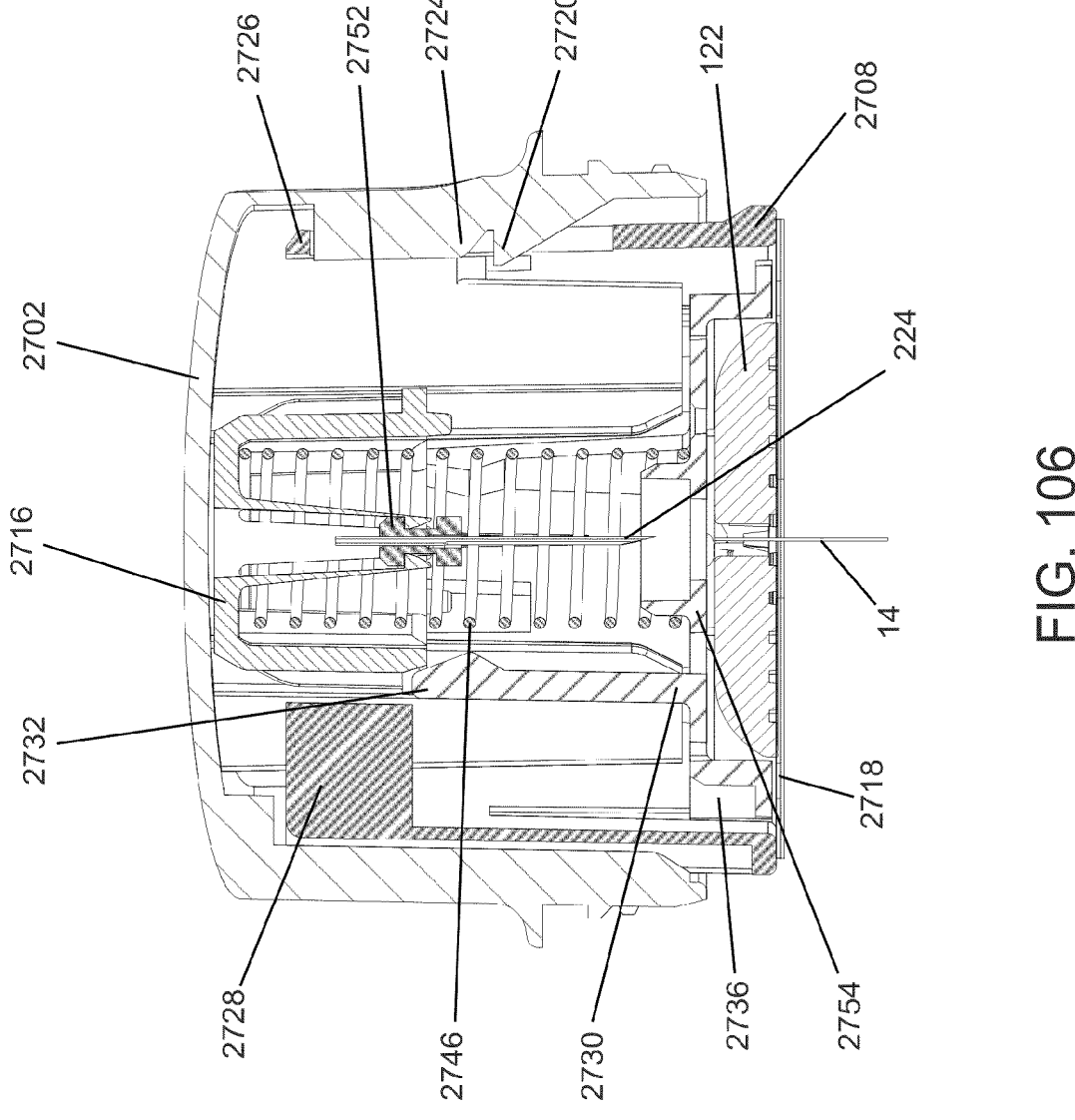
Figure 109:
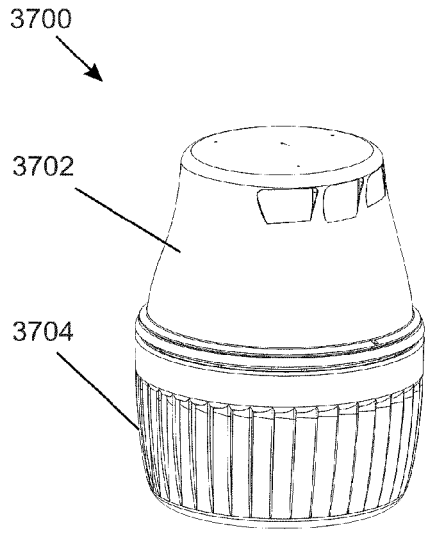
Figure 110:
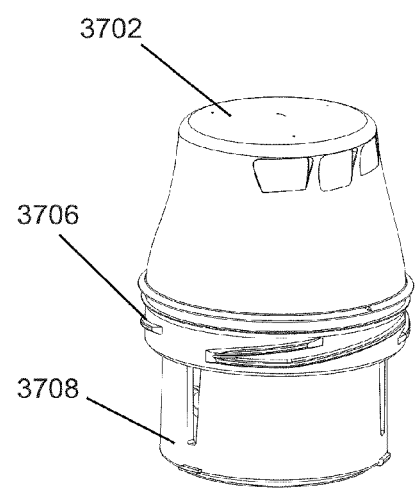
Figure 111:
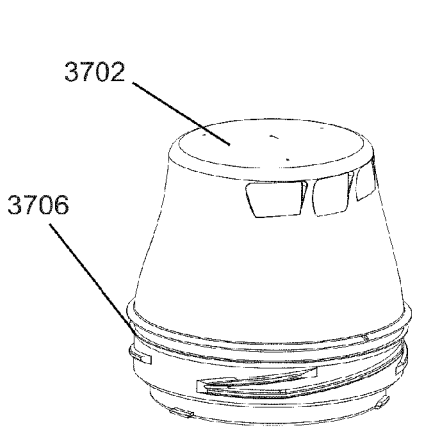

As carrier 2716 reaches a distal position (FIG. 103), the distal surface of the on body housing 122 engages the upper surface of adhesive pad 2718, thereby becoming adhered to the skin surface S of the subject. Concurrently, carrier arms 2732 are advanced distally and clear the support wall 2728. This allows carrier arms 2732 to deflect radially outwardly. (See, FIG. 104). When carrier arms 2732 deflect radially outwardly, shoulder portions of carrier arms 2732 are no longer in an interference relationship with the sharp carrier 2716. Thus spring 2746 is permitted to expand as shown in FIG. 105, thereby advancing the sharp carrier 2716 to a proximal position and withdrawing the sharp 224 from the skin S of the subject while leaving the on body housing 122 attached to the skin. Handle 2702 is maintained in the distal position. Sheath snap 2726 of the sheath 2708 have now moved up to lock over feature 2722 of the housing 2702. Now the housing 2702 and the sheath 2708 can no longer move longitudinally with respect to each other, and provides an indication to a user that the inserter has been used. In FIG. 106, the medical device carrier 2730 acts as a needle guard to prevent a user for touching the needle.

In some embodiments, the changing interaction of sheath snap 2726 with the housing detent/ledges 2720, 2724, and 2722 determine whether the sheath 2708 is locked. When snap 2726 is in the pre-fire position, ledge 2720 prevents sheath 2708 from being pulled out of the housing 2702. In this position, detent 2724 may also impede the movement of pushing the sheath 2708 into the housing 2702. When the detent is overcome by at least a minimum force, the sheath 2704 moves longitudinally with respect to the housing 2702 until the snap 2726 snaps over housing ledge 2722. At this point, ledge 2722 prevents the sheath 2708 from being pulled out of the housing again, but from a new position (this position may be referred to as the used/post-fire position). Sharp carrier snap 2752 function is to hold onto the sharp 224. In some embodiments, the sharp carrier 2716 is held in the post-fire position relative to the housing 2702 by, e.g., an interference between the rails of the housing 2714 and the guide rails of the sharp carrier 2718 (this interference is only present once the sharp carrier is fully retracted) and/or by medical device carrier projections interfering with the bottom/floor of the sharp carrier (See, e.g., FIG. 106). In another embodiment of inserter 2700, adhesive pad 118 may be attached directly to on body housing 122. This necessitates a different shape of inserter 2700 as depicted in FIG. 107. Additionally, carrier 2730 is slightly wider to accommodate adhesive pad 118 attached to on body housing 122 (FIG. 108).

A further embodiment of an inserter is illustrated in FIGS. 109-134. In some embodiments, inserter 3700 has a maximum diameter of about 30 mm to about 60 mm, e.g., about 40 mm, about 43 mm, about 43.5 mm, about 46 mm, about 50 mm, etc. In some embodiments, inserter 3700 has a maximum height of about 40 mm to about 80 mm, e.g., about 44 mm, about 46 mm, about 49.5 mm, about 55 mm, about 67 mm, about 71 mm, etc. In some embodiments, inserter 3700 has a volume of about 35 $cm^3$ to about 110 $cm^3$, e.g., about 40 $cm^3$, about 41 $cm^3$, about 50 $cm^3$, about 60 $cm^3$, about 61 $cm^3$, about 62 $cm^3$, about 69 $cm^3$, about 70 $cm^3$, about 79 $cm^3$, about 90 $cm^3$, about 106 $cm^3$, etc. The maximum height refers to the height defined from the top of the housing 3702 to the portion of the sheath 3708 that contacts the subject's skin. The volume is measured as the volume of the housing 3702 and the portion of the sheath 3708 extending from the housing.

Figure 112:
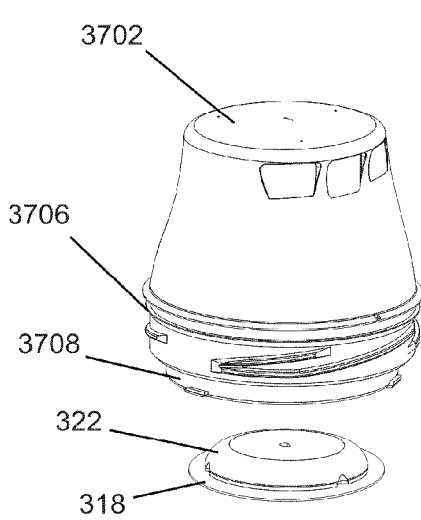

FIGS. 109-112 depict the various stages of insertion from an initial stage in which the cap is attached (FIG. 109), to removal of the cap (FIG. 110), deployment of the sharp and on body housing unit (FIG. 111) and removal of the inserter from the subject's skin (FIG. 112).

Inserter 3700 generally includes, e.g., a housing 3702 (FIGS. 109, 113-114), sheath 3708 (FIGS. 115-116), and a removable distal cap 3704 (FIGS. 117-119) for maintaining a sterile environment for the medical device and sharp housed therein. As illustrated in FIGS. 109 and 117-119, housing 3702 is shown removed from distal cap 3704. Distal cap 3704 is detachably secured to housing 3702, e.g., by use of threads 3706. It is understood that in some embodiments, the cap may be secured using snap-fit or press-fit configuration.

Inserter 3700 may be utilized to advance a medical device into the skin of the subject. Sheath 3708 generally encloses or defines a cavity, within which sharp carrier 3716 (FIGS. 120-121) and medical device carrier 3730 (FIG. 122) are moveable. In some embodiments, housing 3702 is advanced relative to sheath 3708 in order to advance the medical device distally and into the skin of the patient.

Figure 114:
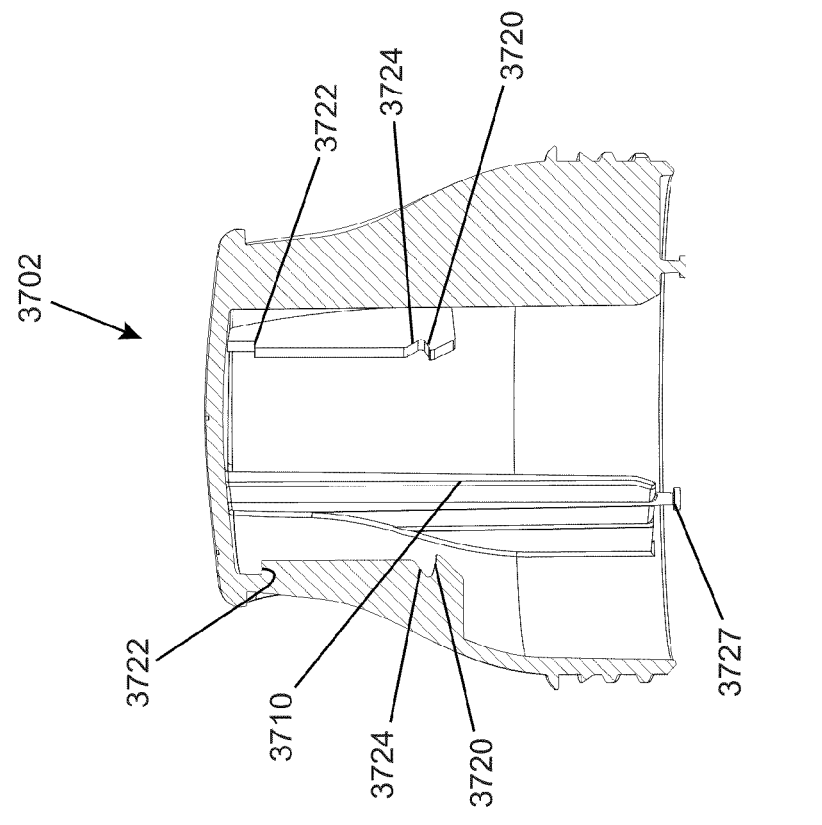
Figure 113:
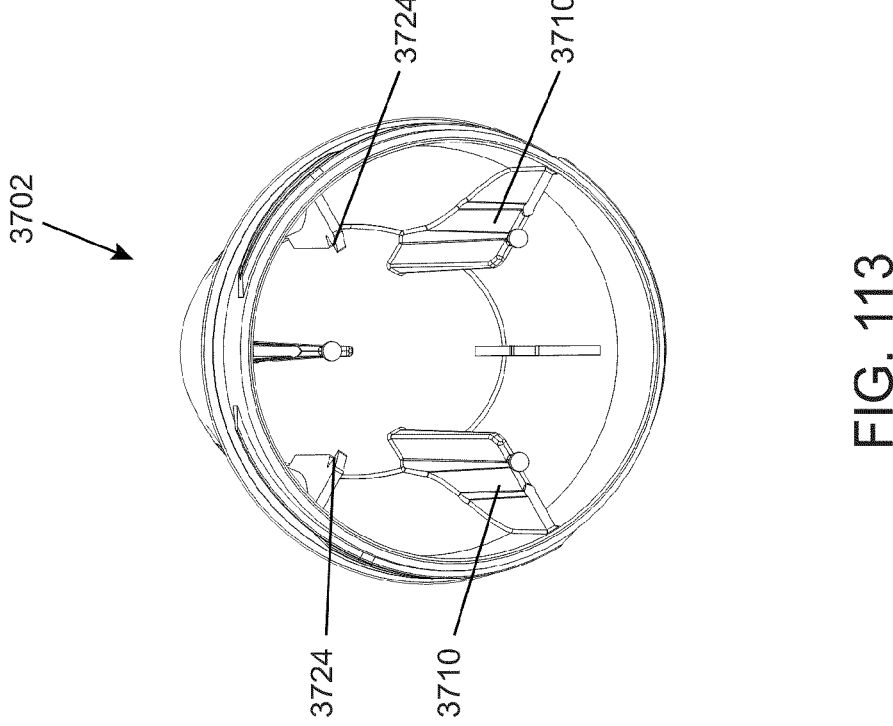

Housing 3702 includes sheath guide rail 3710 which interfaces with rail guides 3712 located on sheath 3708, thereby allowing housing 3702 to slidingly move relative to sheath 3708. Sheath 3708, sharp carrier 3716, and housing 3702 may alternatively move relative to one another without the use of guide rails. The housing can include a distally extending sidewall having a non-linear or arcuate shape. In the embodiment illustrated in FIGS. 109-134 the housing is configured with an undulating sidewall which transitions from a concave portion (upper portion of housing 3702) to a convex portion (lower portion of housing 3702). (FIG. 114). This contour enhances the user's tactile recognition and provides a more ergonomic gripping surface which reduces accidental slippage by the user's hand. Further, the housing is configured with a cavity sized to receive the sheath 3708, as described in further detail below.

Housing ledge 3720 and/or ledge 3722 are provided on an interior portion of housing 3702. Ledge 3720 engages sheath 3708 to hold sheath 3708 in a pre-use position prior to insertion of the medical device. Ledge 3722 engages sheath 3708 to secure sheath 3708 in a post-use position after insertion of the medical device. Housing 3702 further includes detent 3724 which prevents housing 3702 from moving relative to sheath 3708 until a minimum force has been applied, e.g., distally by user to housing 3702. The sheath 3708 is secured to the housing 3702 via retention features 3726, which can be configured, e.g., as a snap. Retention feature 3726 snaps into the housing detent 3724 (In some embodiments, it is pinched between ledge 3720 and detent 3724, thus controlling its height relative to the housing 3702). In some embodiments, the surfaces of the housing ledges 3720, 3722, 3724 and retention features 3726 are configured to engage in a single point of contact or a plurality of discrete points of contact, e.g., line. Such discrete points of contact are advantageous over conformal surface-to-surface contact in that a more thorough sterilization process can be performed. A variety of sterilization mediums can be employed, e.g., Ethylene Oxide (EtO), wherein the gaseous medium is delivered over the various inserter components. Accordingly, the discrete points of contact allow for a greater surface area of each inserter component to be exposed to the gaseous medium, thereby providing for a more thorough and rapid sterilization process. The housing includes distally extending protrusions 3727 which are received in apertures 3756 of the medical device carrier 3730 to couple the housing and medical device carrier, by such techniques as, e.g., heat staking, ultrasonic bonding, adhesive bonding, snap fit, etc. Coupling the housing and the medical device is performed, in some embodiments, by e.g., heat staking, ultrasonic bonding, adhesive bonding, snap fit, etc. Consequently, there is no relative movement between the housing 3702 and the medical device carrier 3730.

Figures 115, 116:
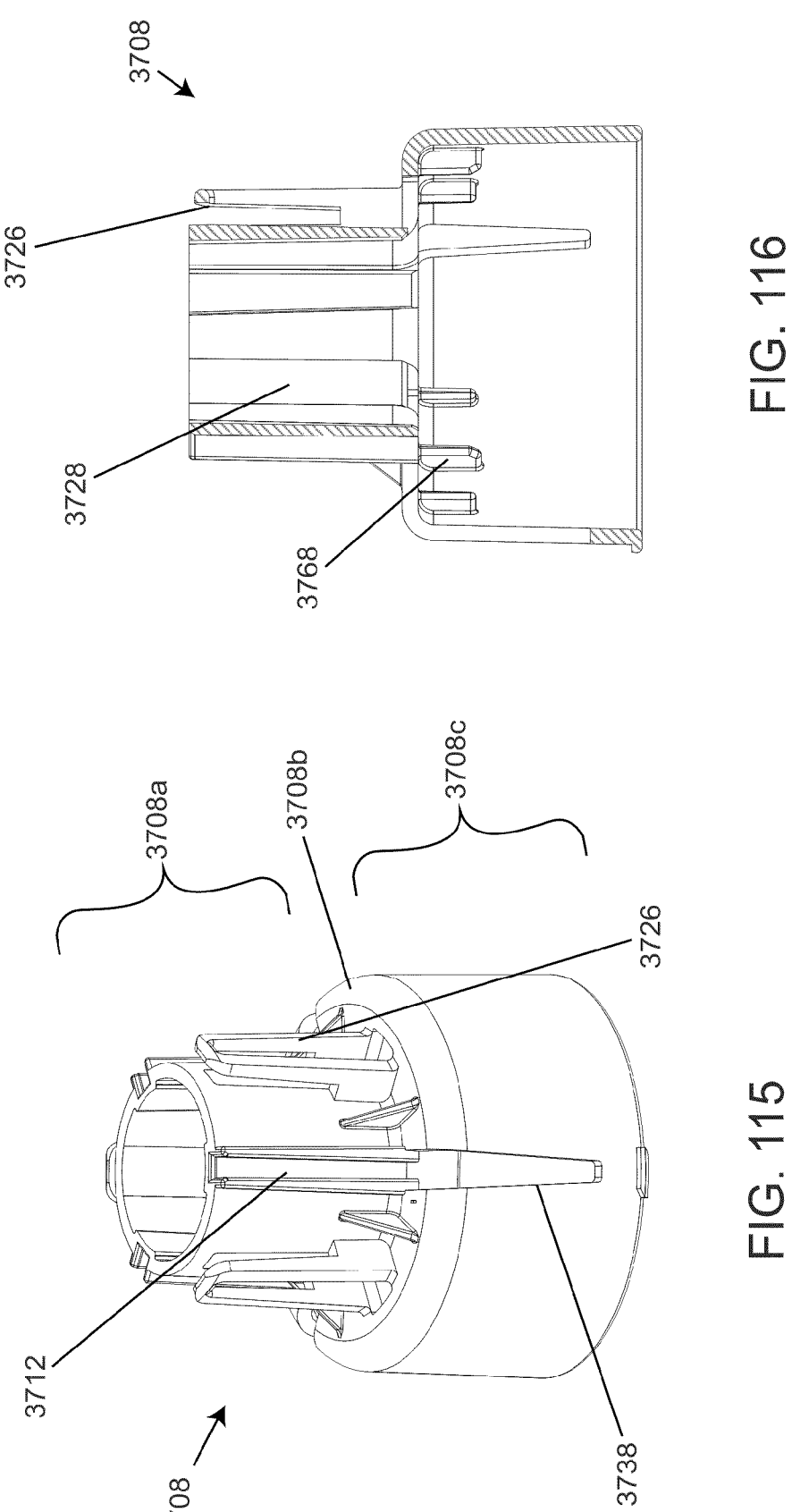

Sheath 3708 is generally formed as a unitary tubular member having proximal 3708a and distal 3708c cylindrical portions. In some embodiments, the portions 3708a and 3708c have an elliptical, square, hexagonal, or other cross-section. As illustrated in FIGS. 115-116, the distal cylindrical portion 3708c (i.e., the lower portion) can be formed with a greater diameter than the proximal portion 3708a, with the proximal and distal portions integrally connected via a shelf 3708b. Accordingly, the sheath 3708 can be formed as a single-piece and generally cylindrical member with the proximal portion having sufficient rigidity to prevent displacement of the carrier arms 3732, as described in further detail below. Sheath 3708 can include retention members 3726, e.g., detent snaps, which are biased into detent 3724 of housing 3702 to create a minimum force that must be overcome in order to advance sharp 324 into the subject's skin and install the on body housing 322. The retention members 3726 can extend proximally from the shelf 3708b of the sheath and be formed as a separate member such that the retention members are spaced or offset from the cylindrical wall of the sheath. The actuation force of the inserter is determined by the stiffness of retention members 3726 (which is a function of length, thickness, and cross section) as well as the steepness of the angle of detent 3724 of the housing. In some embodiments, the force to be overcome can be about 0.5 lbf to about 5 lbf., e.g., about 1 lbf, about 2 lbf, about 3 lbf, about 4 lbf, etc.

As described above, the proximal portion 3708a of the sheath is sized such that an interior support wall surface 3728 prevents carrier arms 3732 on medical device carrier 3730 from displacement or bending outwardly, clear of sharp carrier 3716. Maintaining the carrier arms 3732 in a fixed or constrained position within the sheath allows a user to accurately know the relative positioning of the needle within the inserter. Conversely, the distal portion 3708c of the sheath is sized such that the diameter of the interior wall surface is greater than the carrier arms 3732, thus allowing room for spring arms 3732 on carrier 3730 to expand or displace radially outward thereby releasing the sharp carrier 3716 to retract to the proximal position. Guide rails 3712 are included on the exterior surface of the proximal portion of the sheath 3708a. The guide rails 3712 remain engaged with the housing guide rail 3710 of the housing throughout the insertion operation, i.e., from advancement of the housing from the proximal position to the distal position. Thus even prior to insertion, rotational position of the housing and sheath is controlled, and "rocking" is minimized. In general, rocking is minimized by increasing the length of engagement with respect to the diameter of engagement. In the embodiment disclosed herein, the length of engagement between the sheath and housing, i.e. along the longitudinal axis, is relatively large while the diameter at which the engagement occurs is relatively small, i.e. at proximal portion of sheath 3708a. Additionally, sheath 3708 includes a slot 3738 extending distally from the shelf 3708b and configured to receive the guide rail 3710 of the housing upon delivery of the medical device and insertion of the sharp into the subject.

Figure 121:
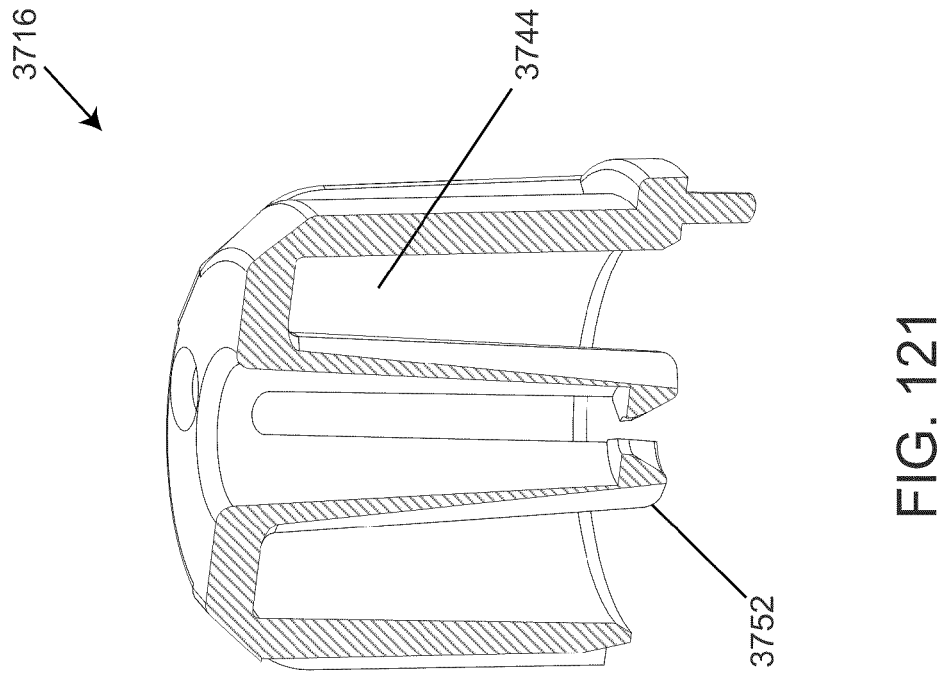
Figure 120:
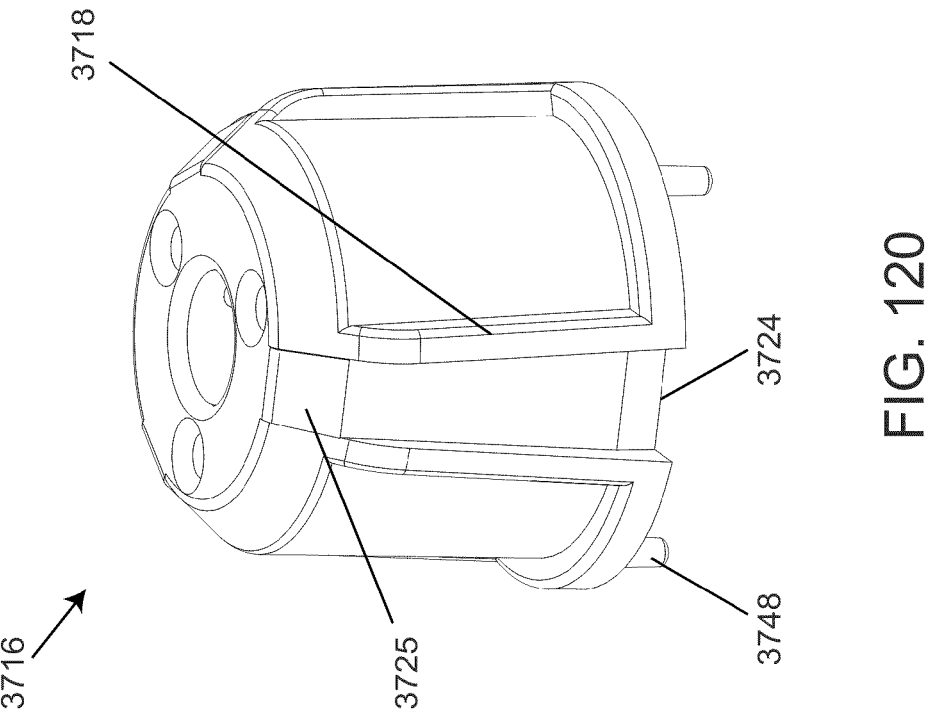
Figure 128:
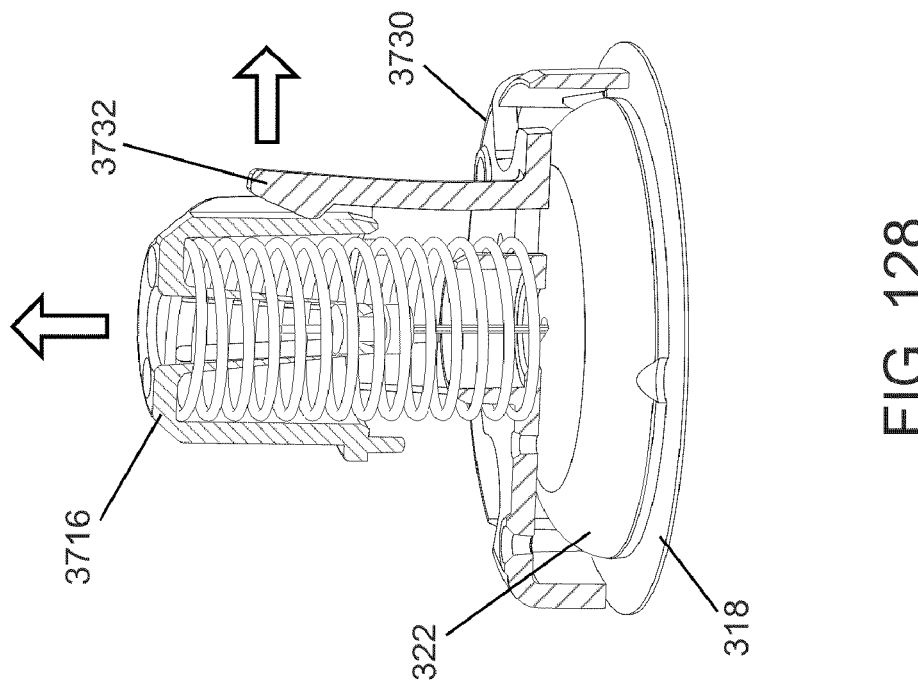
Figure 127:
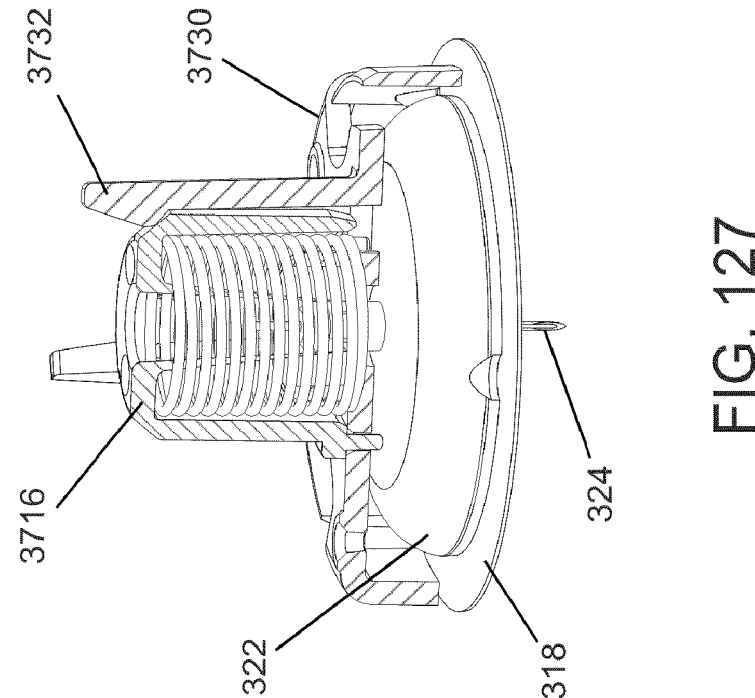

Referring next to FIGS. 120-121, depicted is sharp carrier 3716 in a perspective and cross-sectional view, respectively. Sharp carrier 3716 contains notches 3724 which allow clearance for the passage of carrier arms 3732 located on medical device carrier 3730. Guidance walls 3744 securely hold spring 3746 in place (FIGS. 127-128). The top or proximal edge of the sharp carrier includes a chamfered or sloped edge 3725. Locating features 3748, e.g., standoffs or distally extending protrusions, aligned with locating features 3750, e.g., recesses or apertures, on carrier 3730. Accordingly, the sharp carrier 3716 is located and secured to the medical device carrier 3730 (located via interaction of locating features 3748 and 3750 and secured via interaction of carrier arms 3732 and angled edge surface of 3725. These locating features can extend through the medical device carrier 3730 and directly engage the on body housing 322. Accordingly, when a user actuates the inserter, the sharp carrier drives the on body housing 322 and sharp 324 towards the subject via the protrusions 3748. The direct coupling of the sharp carrier enhances the control of the positioning of on body housing 322, and prevents skewing of the on body housing 322 or sharp 324. Additionally, snap features 3752 secure sharp 324 securely within inserter 3700. It is contemplated that sharp 324 may be secured to sharp carrier 3716 by other techniques, e.g., friction fit, adhesive, welding, etc.

Figure 122:
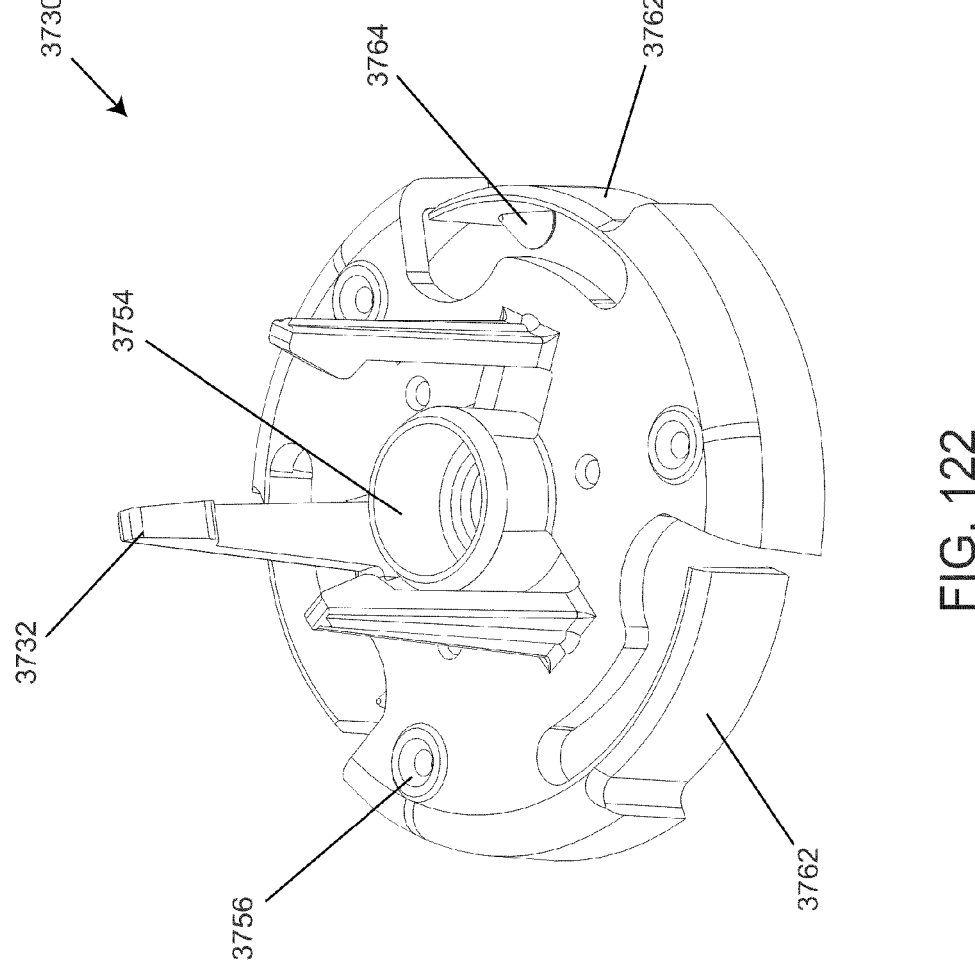

Medical device carrier 3730 is depicted in more detail in FIG. 122. As shown, carrier 3730 contains spring locating ring 3754 that receives one end of spring 3746. In some embodiments, spring 3746 surrounds spring locating ring 3754. In some embodiments, the inner area remains clear to leave room for the deflection of sharp carrier feature snaps 3752 that deflect out when the sharp is inserted. As described above, carrier 3730 further comprises locating features 3756 which interface with locating features on housing 3702. Furthermore, detents can be formed at the end of carrier arms 3732 of the medical device carrier to abut or otherwise the sloped edge 3725 of the sharp carrier. As described above, the detents on carrier arms 3732 are configured to engage the edge 3725 of the sharp carrier in a discrete point of contact fashion in order to realize the aforementioned sterilization advantages. Additionally, these surfaces can be configured with rounded surfaces that ensure that there is no surface to "snag" during the release of the sharp carrier. The medical device carrier 3700 further includes one or more housing gripping arms 3762 (e.g., three are depicted in FIG. 122) which hold the on body housing 322 in place. In some embodiments, gripping arms 3762 are provided with engagement boss 3764 which are configured to engage with corresponding recesses 3766 provided on the side walls of the on body housing 322. Such engagement of the recesses 3766 with the gripping arms 3762 maintains the proper height location of the on body housing 322. Ribs 3768 or other projections on the interior surface of the distal portion 3708c of the sheath 3708 hold these gripping arms 3762 securely in place against the on body housing 322 while the sheath is fully extended. When the medical device carrier 3730 advances along the sheath 3708 to reach the proximal position during use, the gripping arms 3762 are no longer supported by the sheath 3708 and the force of the adhesive skin patch 318 overcomes the retention force of the gripping arms 3762.

Figure 125:
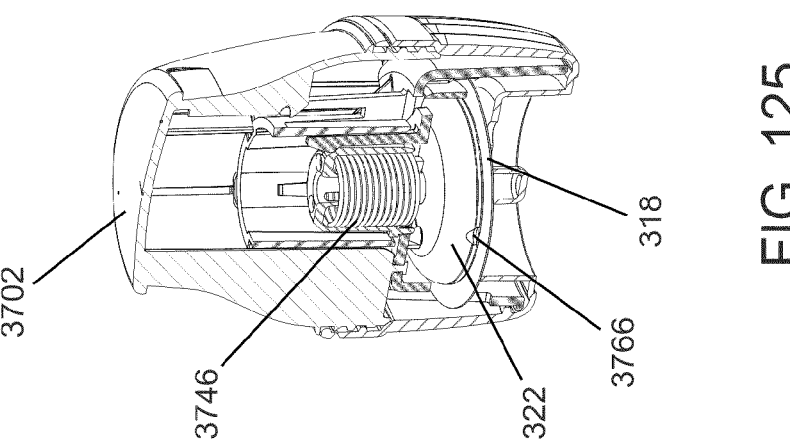
Figure 124:
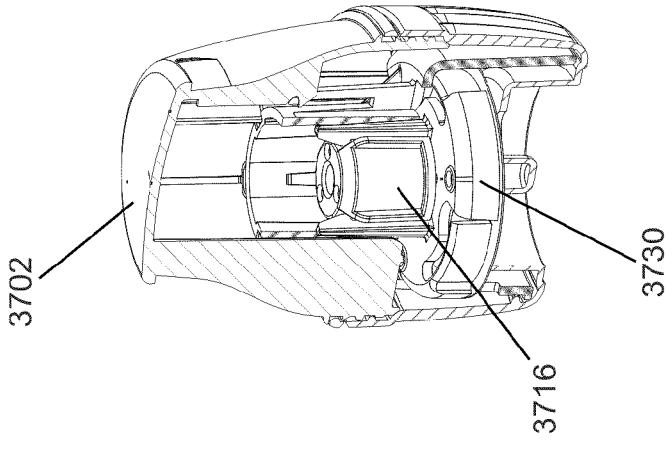
Figure 123:
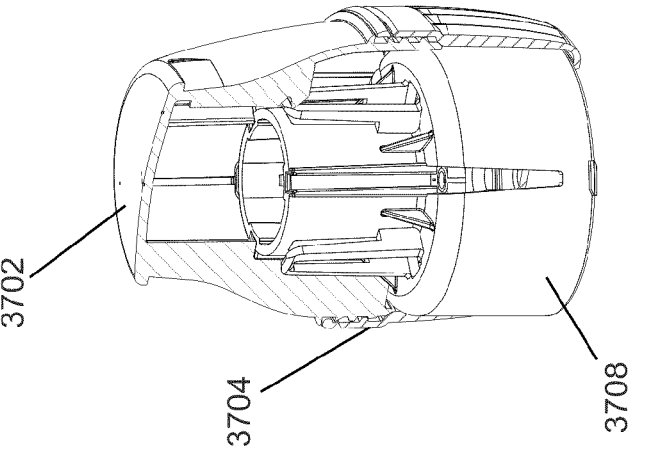
Figure 126:
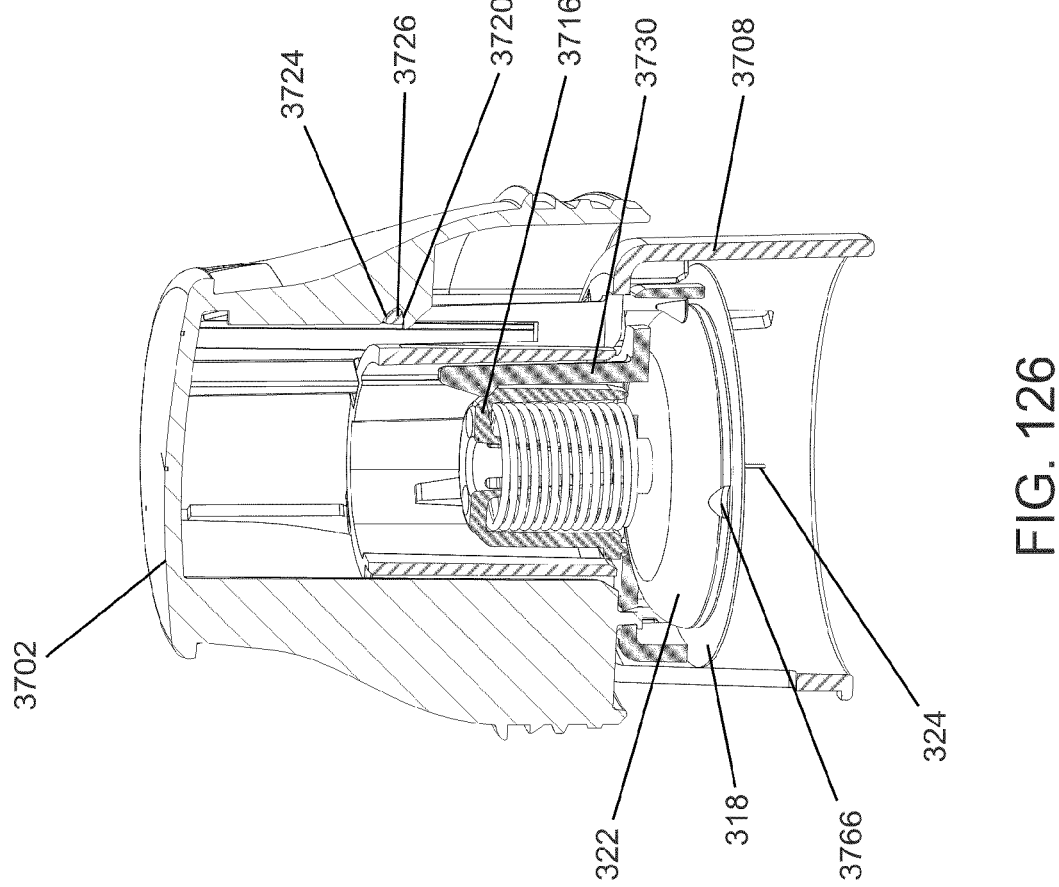

Inserter 3700 is illustrated in cross-section in FIGS. 123-125 in a state prior to use in which housing 3702 is disposed in a proximal position with respect to the sheath 3708 and the cap 3704 secured to the housing. FIG. 126 illustrates a cross-sectional view of the inserter in a state prior to use after the cap 3704 has been removed. The upper surface of spring 3746 is retained in inserter 3700 by sharp carrier 3716. The bottom surface of spring 3746 is retained by spring location ring 3754 of the medical device carrier 3730. Initially, spring 3746 is in a compressed or semi-compressed state while housing 3702 is disposed proximally from sheath 3708.

Sharp 324 extends longitudinally from sharp carrier 3716 within inserter 3700. In some embodiments, sharp 324 is supported at an oblique angle, e.g., between and including about 0° and 90° with respect to the skin surface.

Figure 129:
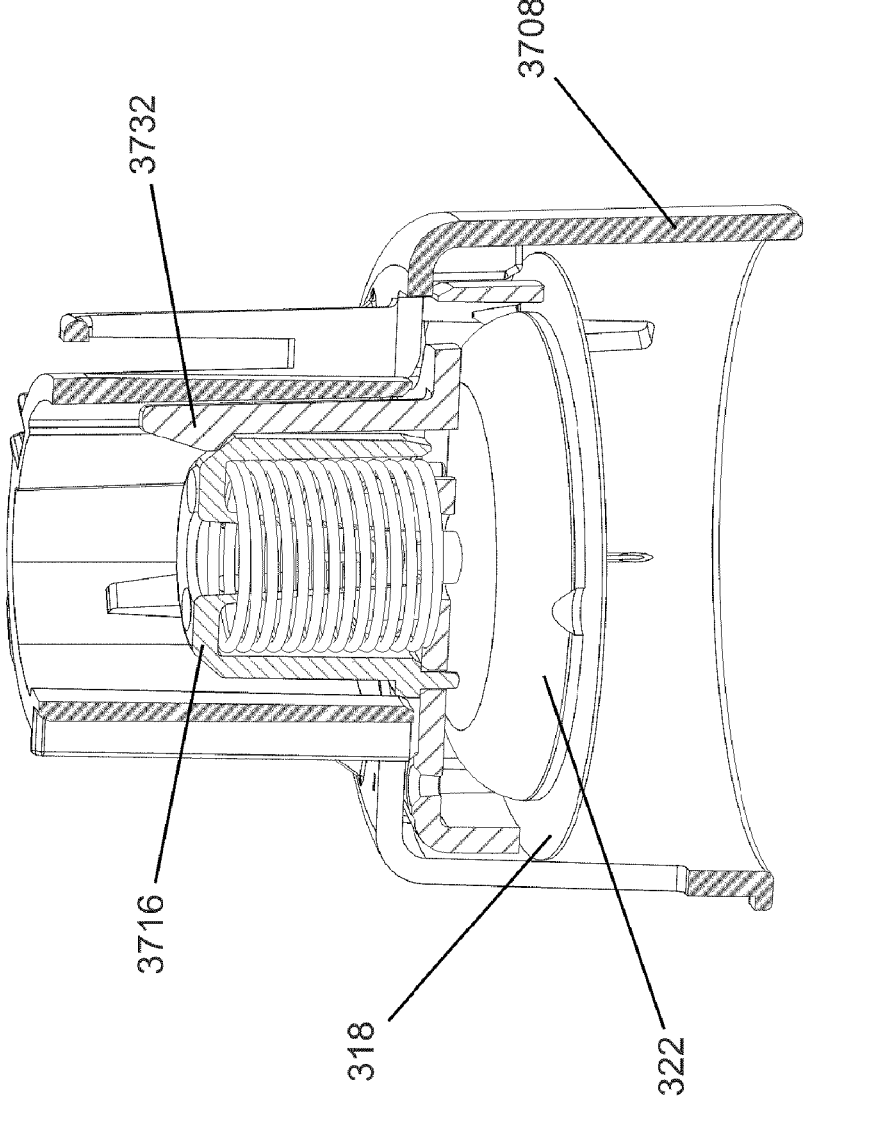

FIGS. 127-128 depict the relationship between the medical device carrier 3730 and the sharp carrier 3716 (with the housing 3702 and sheath 3708 omitted for sake of clarity). FIG. 127 depicts the initial position of the medical device carrier 3730 and the sharp carrier 3716 with the carrier arms 3732 engaged with the sloped edge 3725 of the sharp carrier. In this position there is no relative movement between the medical device carrier 3730 and the sharp carrier 3716. However, the carrier arms 3732 are not of sufficient rigidity or bias to counteract the bias of the spring 3746 in order to maintain the sharp carrier in the position shown in FIG. 127 without support from the sheath, as shown in FIG. 129. Accordingly, the spring 3746 urges the sharp carrier 3716 in the proximal direction thereby displacing the carrier arms 3732 radially outward as shown in FIG. 128.

Figure 130:
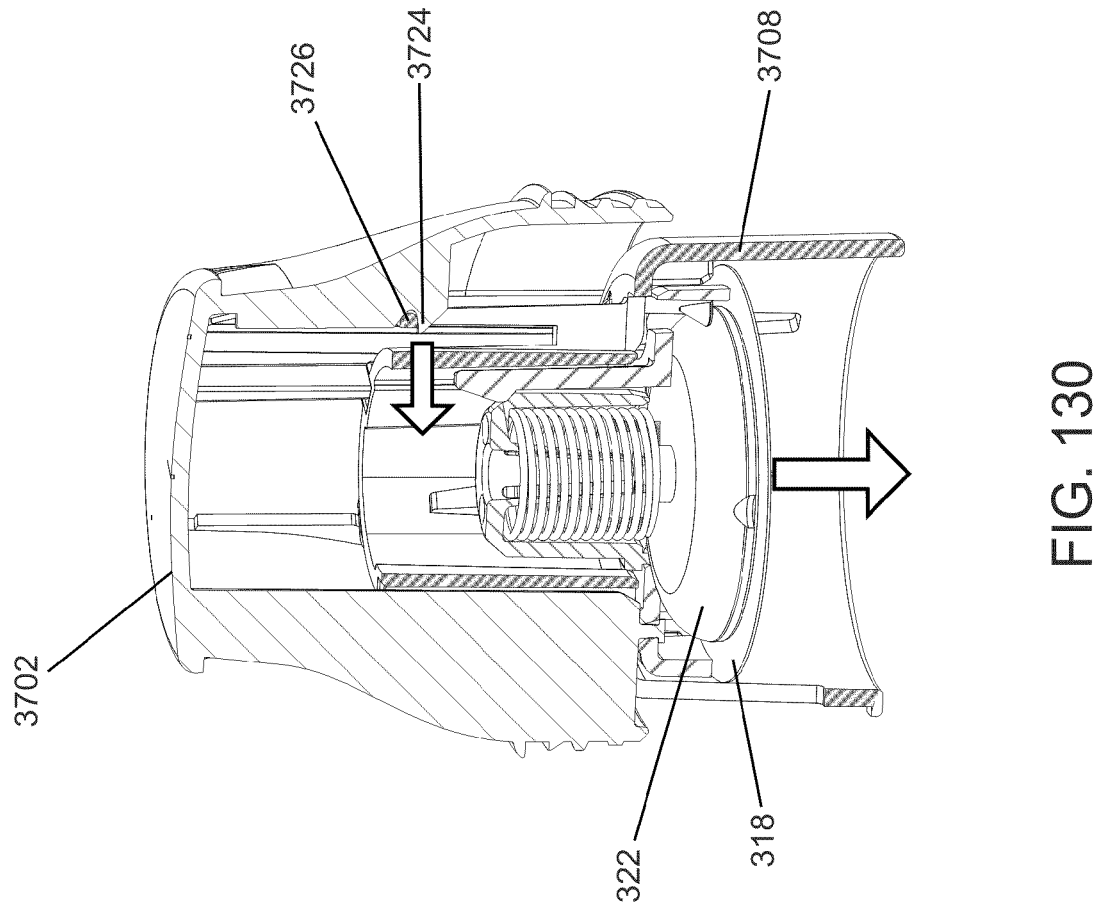

FIG. 130 illustrates inserter 3700 in cross-section after a user applies an initial downward force to housing 3702. In some embodiments, a predetermined minimum force must be used so that attachment snaps 3726 advance past detent 3724.

Figure 132:
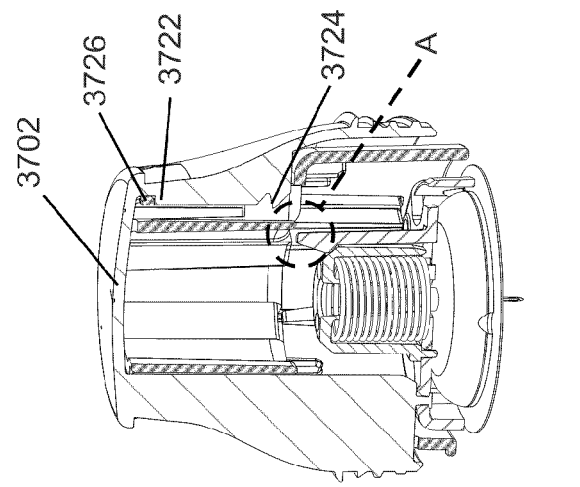
Figure 131:
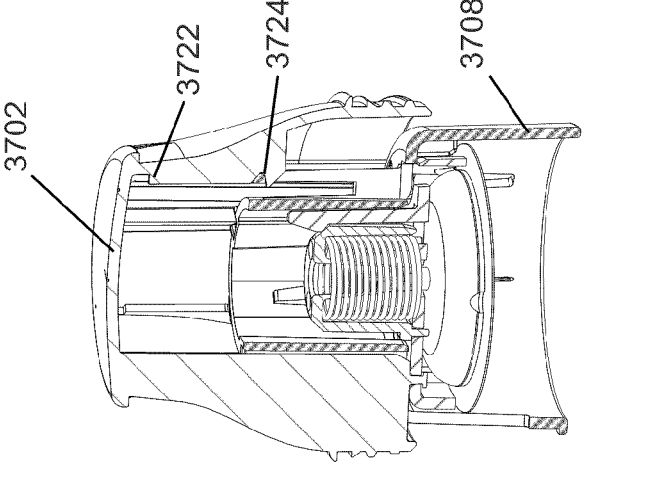
Figure 134:
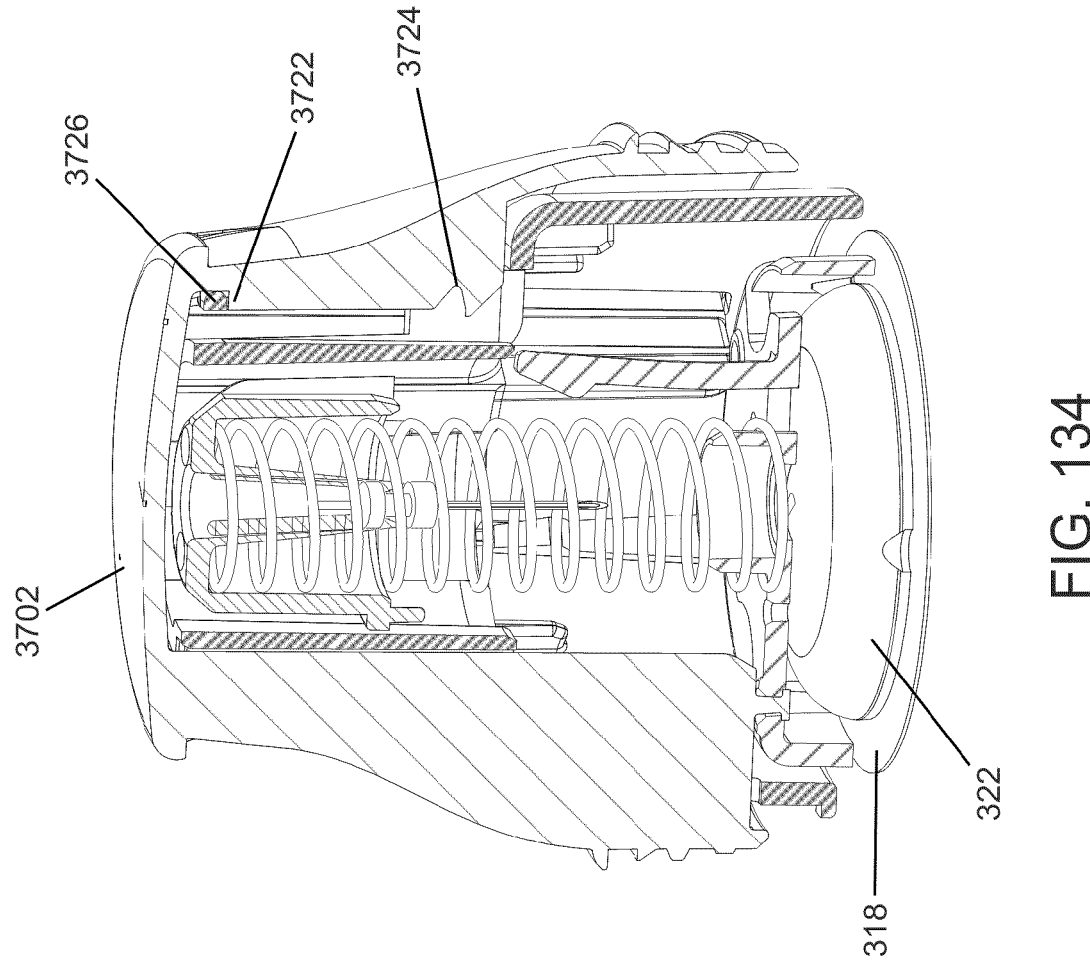

After detent 3724 has been overcome, e.g., snap 3726 of the sheath is displaced radially inward, further depression of housing 3702 with respect to sheath 3708 causes distal longitudinal movement of the medical device carrier 3730 and sharp carrier 3716, from a proximal position towards a distal position as shown in FIGS. 131-132. During this phase of insertion, the interior surface of proximal portion 3708a of the sheath remains engaged with the carrier arms 3732 to prevent radial displacement of the arms 3732, and thus maintains the coupling of the medical device carrier 3730, on body housing 322, sharp 324 and sharp carrier 3716. As sharp 324 is further urged distally, it carries the sensor insertion portion 30 of sensor 14 (FIG. 17) into the subcutaneous portion of the subject's skin S.

Figure 133:
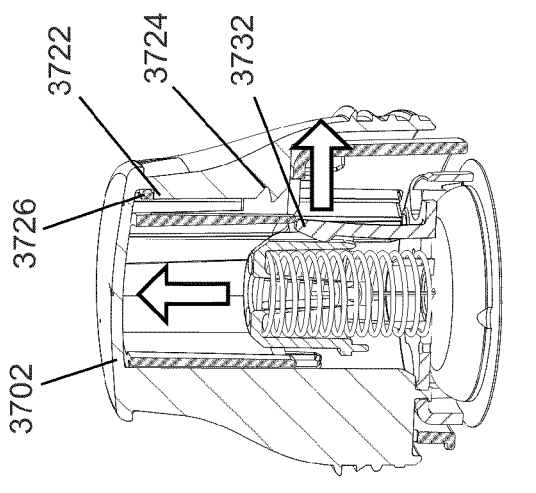

As carrier 3716 reaches a distal position, the on body housing 322 along with the adhesive pad 318 engage the skin surface S of the subject, thereby becoming adhered. Concurrently, carrier arms 3732 are advanced distally beyond shelf 3708b of the sheath and clear the support wall 3708a (as highlighted by focus point "A" in FIG. 132). This allows carrier arms 3732 to deflect radially outwardly into the larger diameter distal portion 3708c of the sheath as shown in FIG. 133. When carrier arms 3732 deflect outwardly, shoulder portions of carrier arms 3732 are no longer in an interference relationship with the sharp carrier 3716. Thus spring 3746 is permitted to expand as shown in FIG. 133, thereby retracting the sharp carrier 3716 to a proximal position and withdrawing the sharp 324 from the skin S of the subject while leaving the on body housing 322 attached to the skin. Housing (or handle) 3702 is maintained in the distal position and extends over the sheath in a telescoping manner. Sheath detent or snap 3726 of the sheath 3708 can then lock over feature 3722 of the housing 3702. Accordingly, the housing 3702 and the sheath 3708 can no longer move longitudinally with respect to each other.

In some embodiments, the changing interaction of sheath detent or snap 3726 with the housing detent/ledges 3720, 3724, and 3722 determine whether the sheath 3708 is locked. When snap 3726 is in the pre-fire position, ledge 3720 prevents sheath 3708 from being pulled out of the housing 3702. In this position, detent 3724 may also impede the movement of pushing the sheath 3708 into the housing 3702. When the detent is overcome by at least a minimum force, the sheath 3708 moves longitudinally with respect to the housing 3702 until the snap 3726 snaps over housing ledge 3722. At this point, ledge 3722 prevents the sheath 3708 from being pulled out of the housing again, but from a new position (this position may be referred to as the used/post-fire position). Sharp carrier snap 3752 function is to hold onto the sharp/needle. In some embodiments, the sharp/needle carrier 3716 is held in the post-fire position relative to the housing 3702 by, e.g., an interference between the rails of the housing 3710 and the guide rails of the sharp carrier 3718 (this interference is only present once the sharp carrier is fully retracted) and/or by medical device carrier projections 3732 interfering with the bottom/floor of the sharp carrier (See, e.g., FIG. 134). In another embodiment of inserter 3700, adhesive pad 318 may be attached to sheath 3708 prior to use. Upon reaching the distal position, the distal surface of on body housing 322 engages the upper surface of adhesive pad 318, thereby becoming adhered to the skin surface S of the subject.

Figures 135, 136:
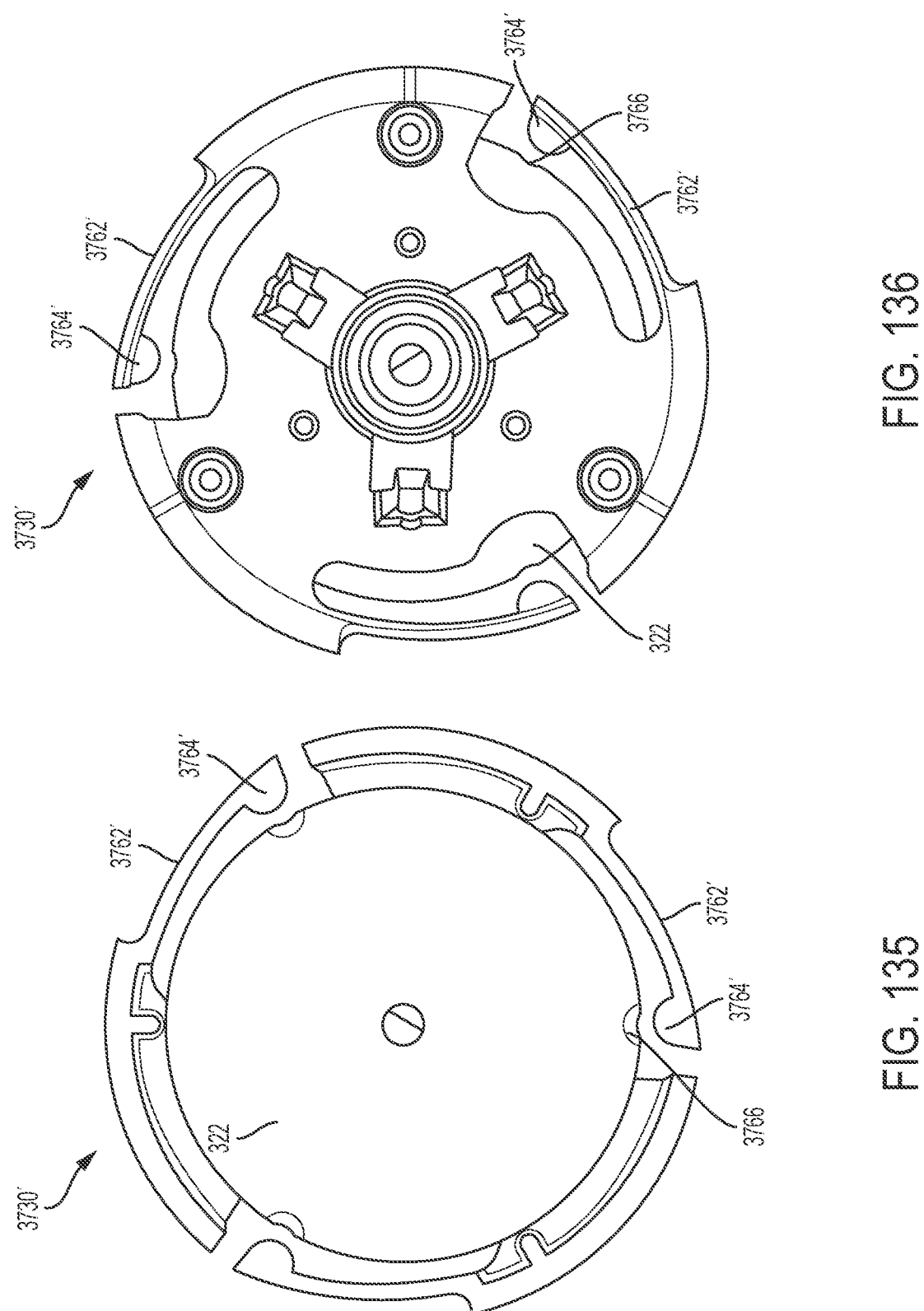
FIGS. 135-136 illustrate bottom and top views, respectively, of the medical device carrier in accordance with the disclosed subject matter.

Another embodiment of the inserter 3700' is substantially identical to the inserter 3700 discussed hereinabove with the differences noted herein. As illustrated in FIGS. 135-136, the medical device carrier 3730' is substantially identical to carrier 3730. However, carrier 3730' includes one or more gripping arms 3762' including an engagement boss 3764' which is configured to engage with corresponding recesses 3766 provided on the side walls of the on body housing 322. In some embodiments, the gripping arms 3762' are configured to be spaced radially apart from the on body housing 322 in the relaxed, unstressed configuration. When an inwardly directed force is applied to the gripping arms 3762', they may be directed into contact with the on body housing 322.

Figure 138:
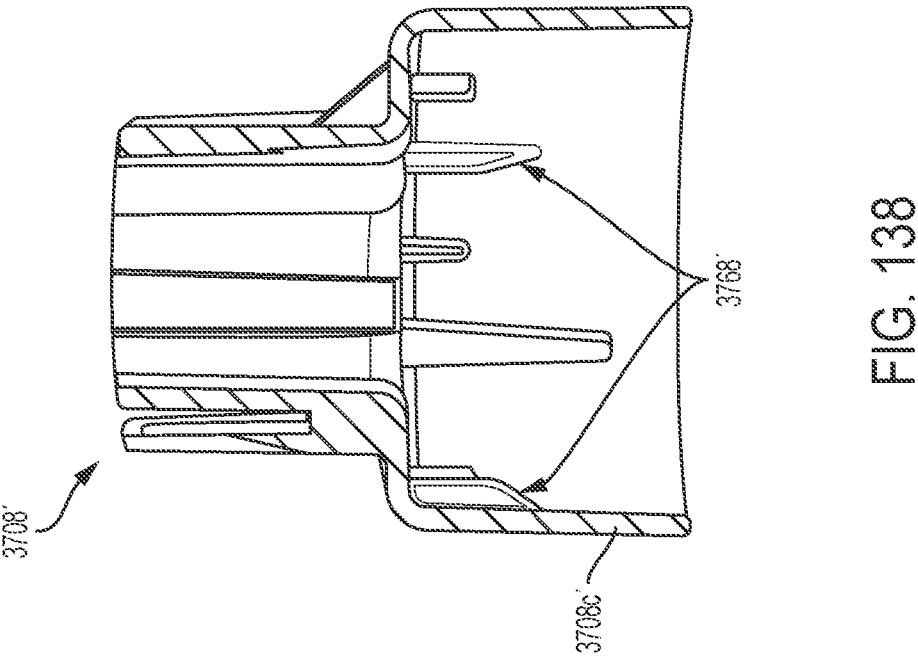
FIGS. 137-138 illustrate the sheath component of an inserter in accordance with the disclosed subject matter.
Figure 137:
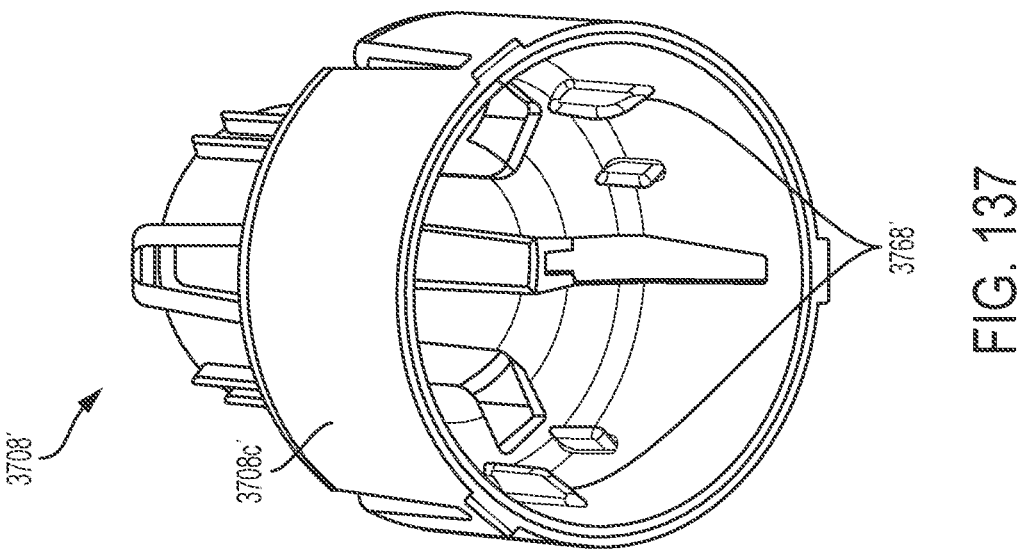
Figures 139, 140:
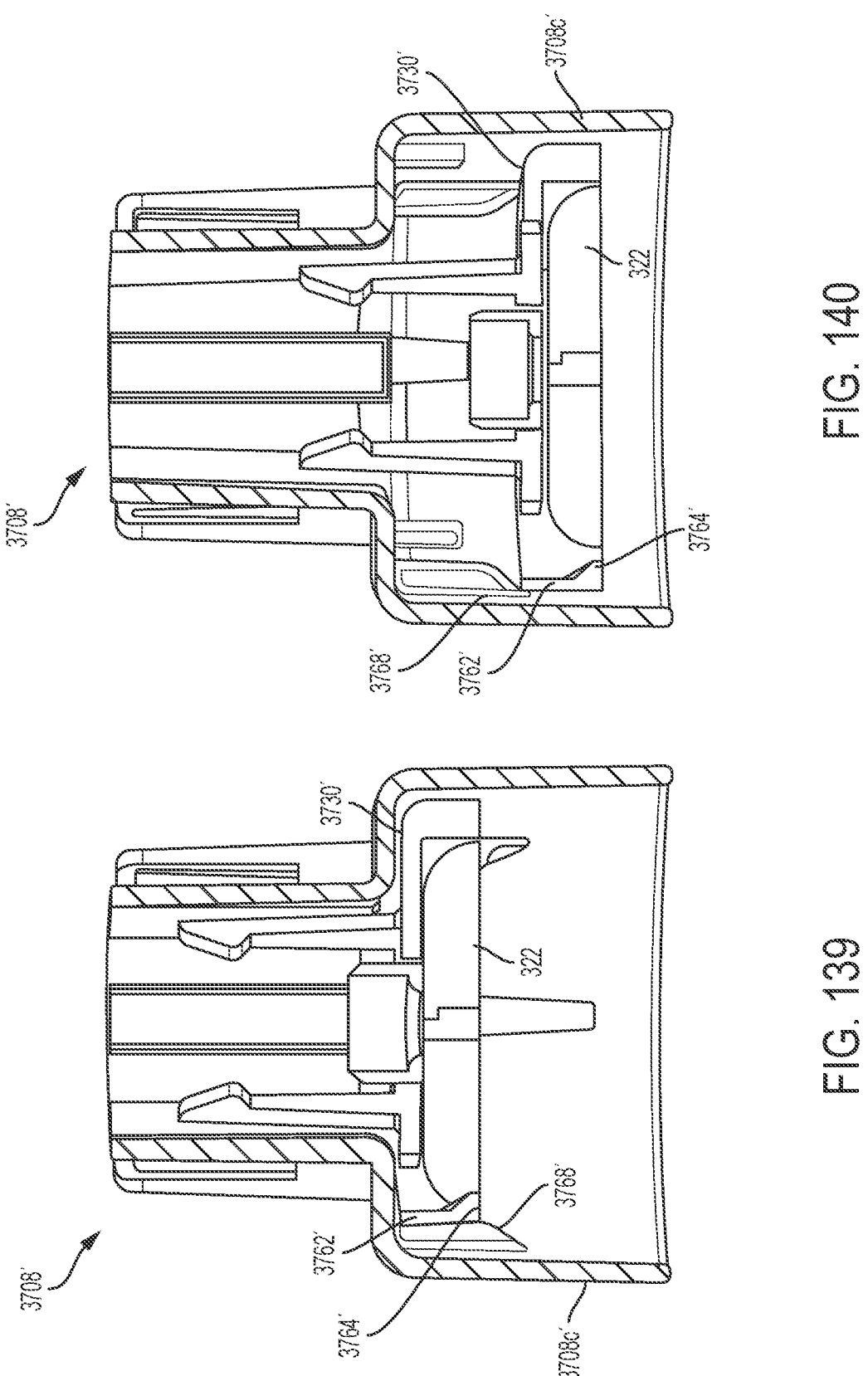
FIGS. 139-140 illustrate, in cross section, the progressive advancement of the on body housing in accordance with the disclosed subject matter.

Perspective and sectional views of sheath 3708' are illustrated, respectively, in FIGS. 137-138. The inside of distal portion 3708c' includes one or more ramp members 3768', which are positioned to engage the gripping arms 3762' and provide a radially inwardly directed force. As illustrated in FIG. 139, in the initial configuration, the medical device carrier 3730' is positioned in a proximal position with respect to the sheath 3708'. In this configuration, the gripping arms 3762' are deflected radially inwardly by the ramp member 3768' such that the engagement boss 3764' is in contact with the recesses 3766 of the on body housing 322. This configuration provides support for the on body housing 322. As illustrated in FIG. 140, as the carrier 3730' is advanced distally, the gripping arms 3762' clear the ramp member 3768', the gripping arms 3762' begin to deflect radially outwardly according to their normal bias, thereby releasing the engagement boss 3764' from the recesses 3768' of on body housing 322. Release of the gripping arms 3762' facilitates the separation of the on body housing 322 form the inserter 3700'.

In some embodiments, the on body housing is assembled on the body of the user. For example, the on body housing may be comprised of a mounting unit 3780 and an electronics housing 3782. The mounting unit 3780 may include a mount and a sensor. In some embodiments, the sensor is at least partially positioned within the mount and the distal insertion portion extends out of the mount. An inserter, such as inserter 3700 described herein, is used to advance the distal portion of the sensor into the skin of the subject and to adhere the mount to the skin of the user. Subsequently, the electronics housing 3782 is mounted onto the mounting unit 3780. Electrical contact is made between the electronics housing 3782 and the sensor in order to transfer the analyte readings from the sensor to the electronics housing 3782.

Figures 141, 142, 143, 144:
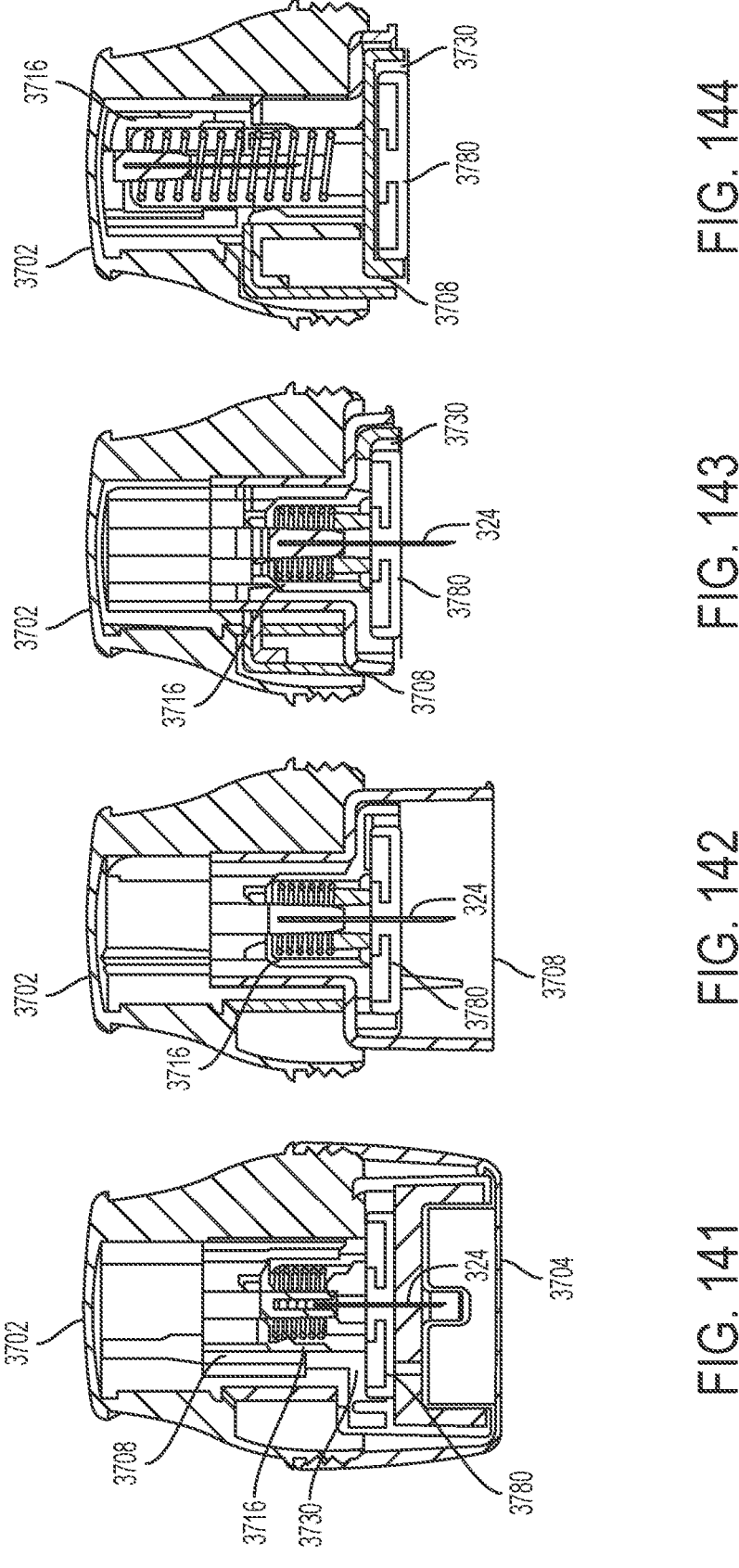
FIGS. 141-144 illustrate the advancement of the on body housing within an inserter in accordance with the disclosed subject matter.

As illustrated in FIG. 141, the inserter 3700 is initially arranged with the cap 3704 attached to the housing 3702. The mounting unit 3780 is positioned in the medical device carrier 3730, with the sharp 324 extending distally in a surrounding position about the sensor. FIGS. 142-144 illustrate the sequence of inserting the sensor into the skin of the user and the attachment of the mounting unit 3780 to the skin of the user. In FIG. 142, the sheath 3708 is placed on the skin. In FIG. 143, the housing 3702 is advanced distally towards the skin of the user, thereby advancing the medical device carrier, the mounting unit 3780 and the sharp 324 towards the skin of the patient. In FIG. 144, upon reaching the distal position of the housing 3702, the sharp carrier 3716 is released, thereby moving to the proximal position.

Figures 145A, 145B, 146A, 146B, 147A, 147B:
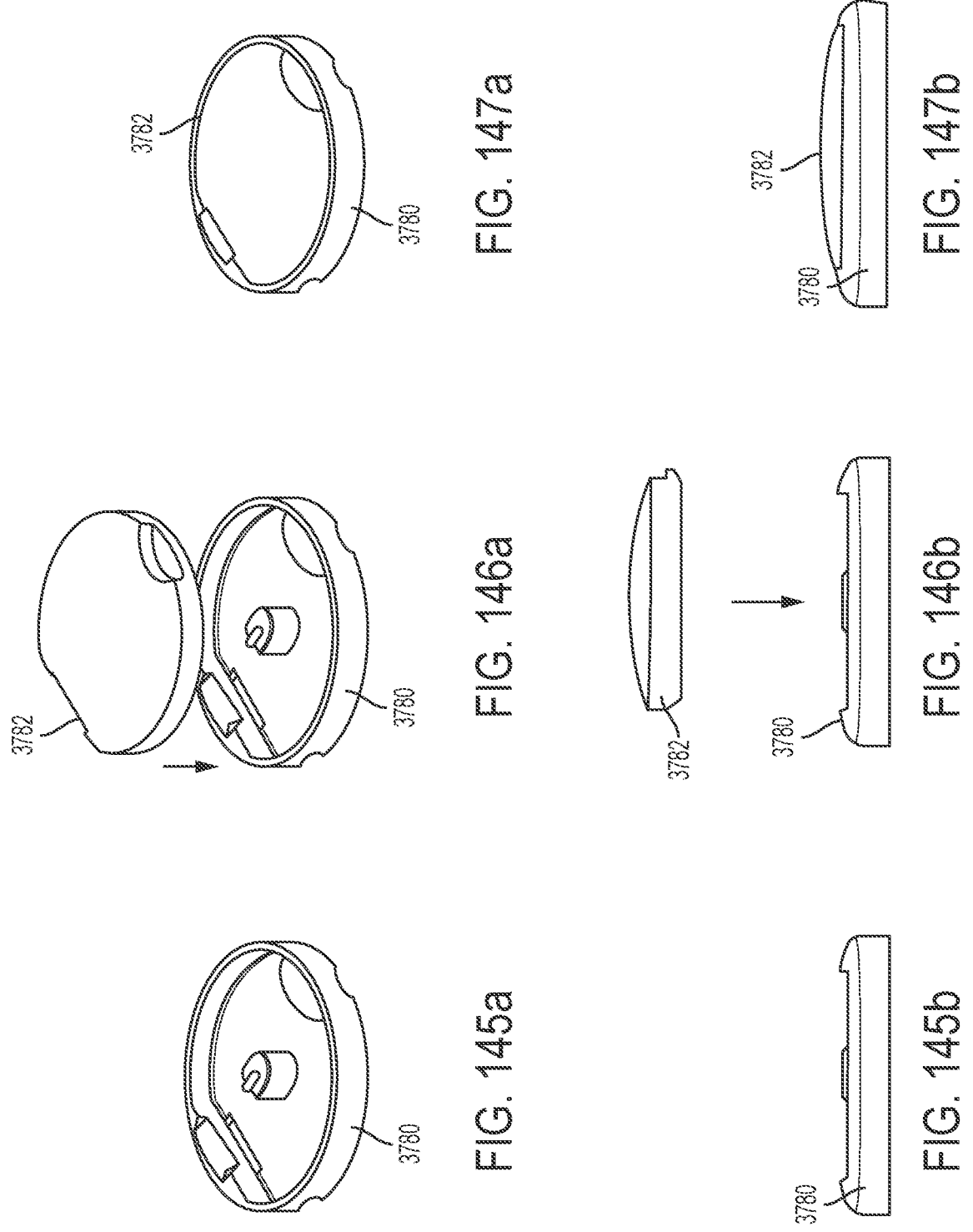

As illustrated in FIGS. 145a and 145b, the mounting unit 3780 is positioned on the skin with the distal portion of the sensor inserted into the skin. As illustrated in FIGS. 146a and 146b, the electronics housing 3782 is inserted into the mounting unit 3780, and shown in the final configuration in FIGS. 147a and 147b.

Figure 148:
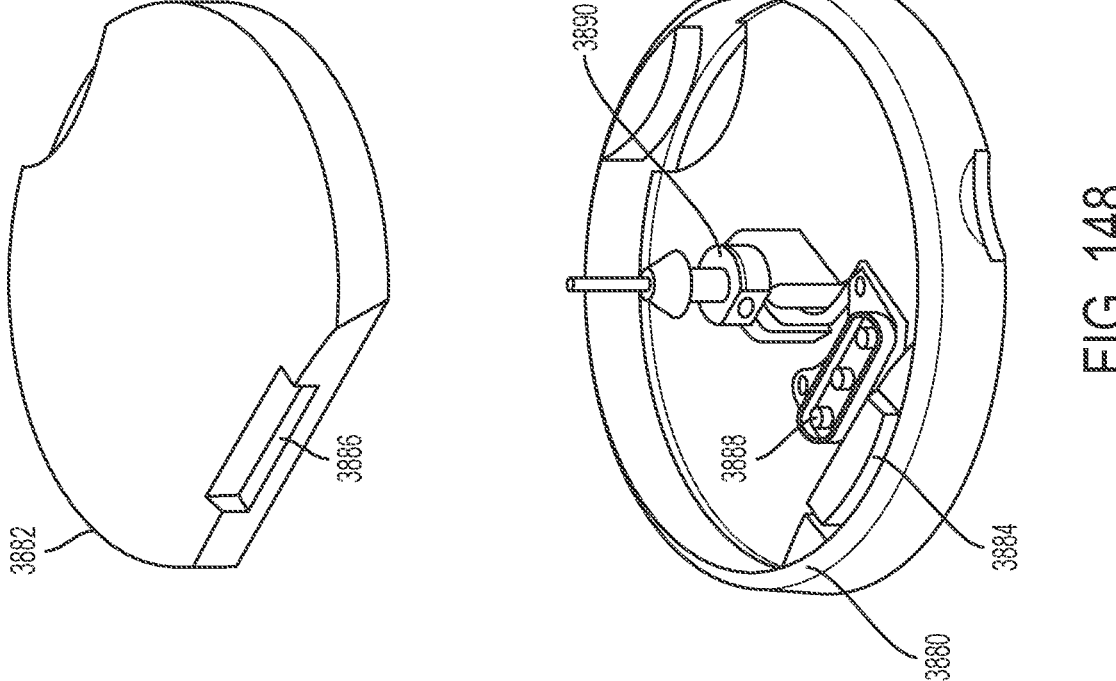
FIG. 148 illustrates a two-piece on body housing in accordance with the disclosed subject matter.

In an exemplary embodiment of on body housing 3800 illustrated in FIG. 148, electronics housing 3882 is mounted on mounting unit 3880. Mounting unit 3880 includes a detent 3884 for coupling with a recess 3886 on the electronics housing 3882 in, e.g., a toe-in snap configuration. It is understood that the detent and recess configuration may be reversed such that the recess is on the mounting unit and the detent is on the electronics housing. The electronics housing 3882 electrically couples with the mounting unit 3880 by the electrical contacts 3888 on the mounting unit 3880 which are coupled to electrical contacts (not shown) on the electronics housing 3882. The sensor hub 3890 stores at least a portion of the sensor which is electrically coupled to the contacts 3888.

In another exemplary embodiment illustrated in FIG. 149, the on body housing 3900 is attached by first attaching the mounting unit 3980 to the skin of the user. Subsequently, sensor 14 is positioned at least partially beneath the skin of the user. Electronics housing 3982 is coupled to the mounting unit 3980 by inserting the flanges 3986 under a corresponding flange of the mounting unit 3980. Contacts 3988 of the electronics housing 3982 are then coupled to contacts on the sensor 14 in order to provide the sensor readings from the sensor to the electronics housing 3982.

In some embodiments, the on body housing is assembled on a surface (such as a tabletop) prior to insertion into the user. For example, as illustrated in FIGS. 150-156, the on body housing may be comprised of a housing unit 4020 and a sensor hub 4022. The housing unit 4020 may include a mount and on body electronics. In some embodiments, the sensor is at least partially positioned within the sensor hub 4022 and the distal insertion portion extends out of the sensor hub 4022. The sensor hub 4022 is contained in the inserter, and the housing unit 4020 is positioned in the inserter 3700. Electrical contact is made between the housing unit 4020 and the sensor in order to transfer the analyte readings from the sensor to the housing unit 4020. The inserter, similar to inserter 3700 described herein, is used to advance the distal portion of the sensor into the skin of the subject and to adhere the housing unit 4020 to the skin of the user.

Figures 150, 151, 152, 153:
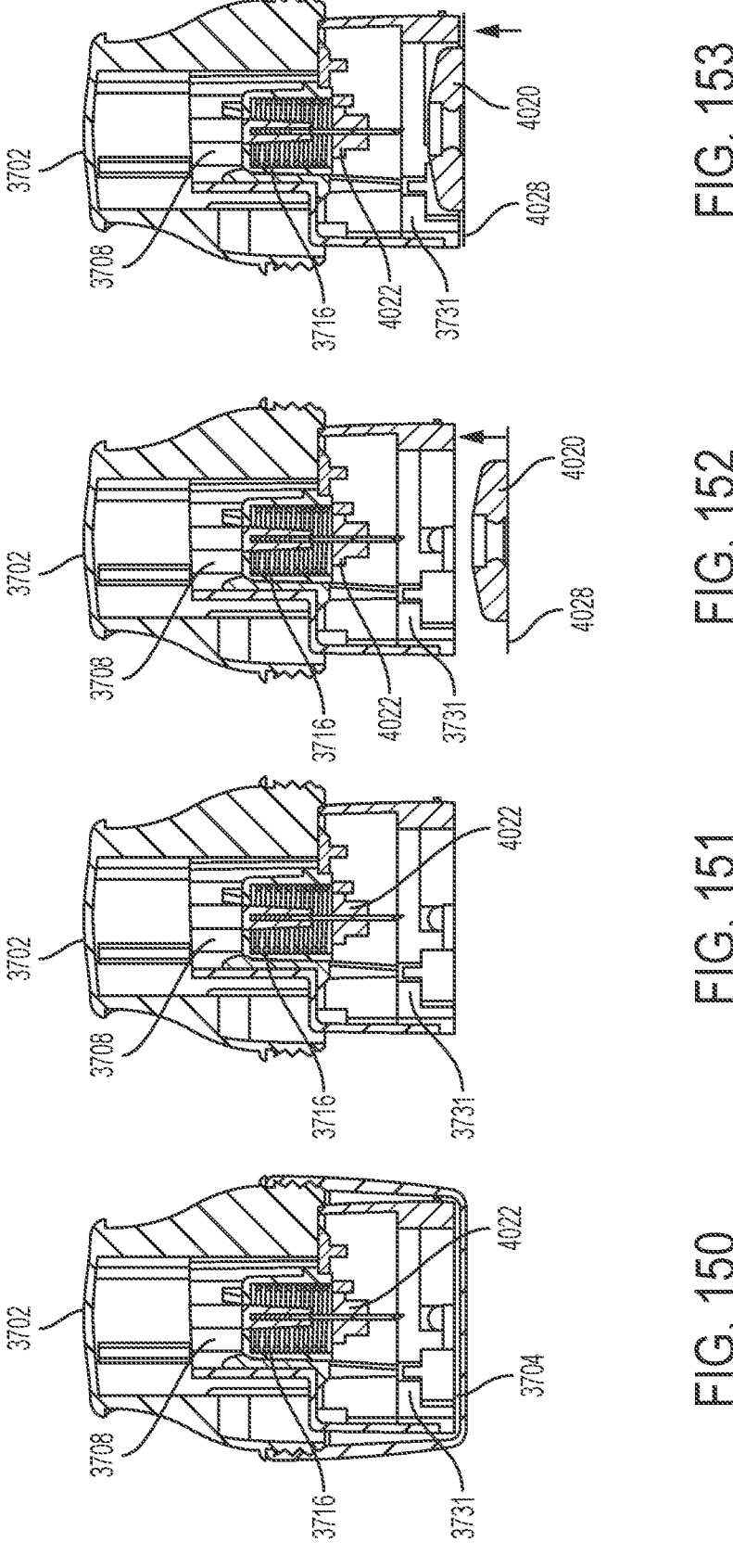
FIGS. 150-156 illustrate the advancement of a two piece on body housing in accordance with the disclosed subject matter.
Figure 156:
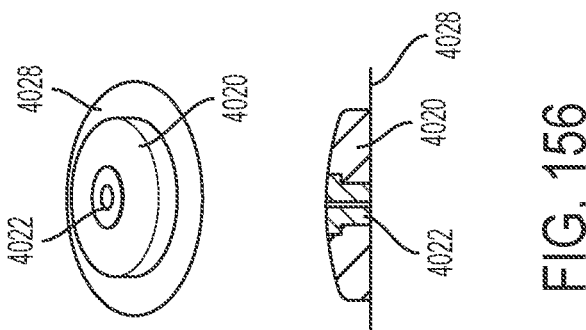
Figure 155:
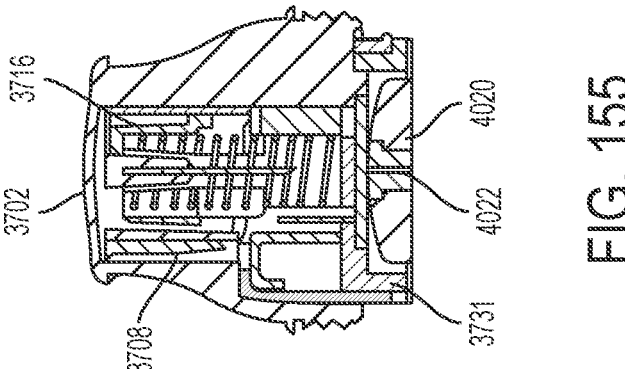
Figure 154:
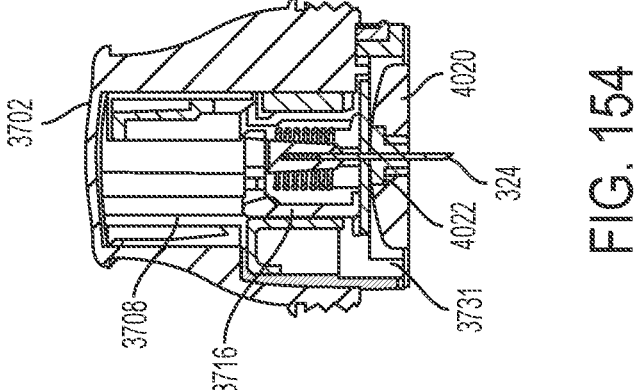

As illustrated in FIG. 150, the inserter 3700 is initially arranged with the cap 3704 attached to the housing 3702. The sensor hub 4022 is supported by the sharp carrier 3716, with the sharp 324 extending distally in a surrounding position about the sensor. FIGS. 151-155 illustrate the sequence of inserting the sensor into the skin of the user and the attachment of the housing unit 4020 to the skin of the user. In FIG. 151, the cap 3704 is removed. In FIGS. 152-153, the housing unit 4020 is positioned in the housing support 3731, for example, by use of adhesive patch 4028. In FIG. 154, the sharp carrier 3716 is advanced distally, thereby advancing the sensor hub 4022 distally and into engagement with the housing unit 4020. In FIG. 155, the sharp carrier 3716 is released, thereby allowing the sharp carrier 3716 to move proximally. The inserter 3700 is removed, leaving the sensor hub 4022 coupled to the housing unit 4020, as illustrated in FIG. 156.

Figure 158:
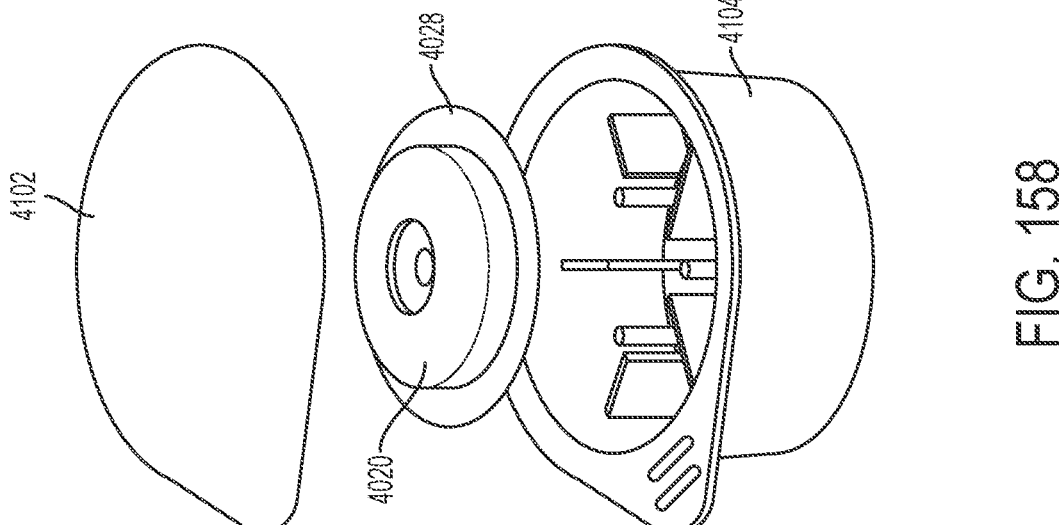
FIGS. 157-158 illustrate the assembly of the two piece on body housing in accordance with the disclosed subject matter.
Figure 157:
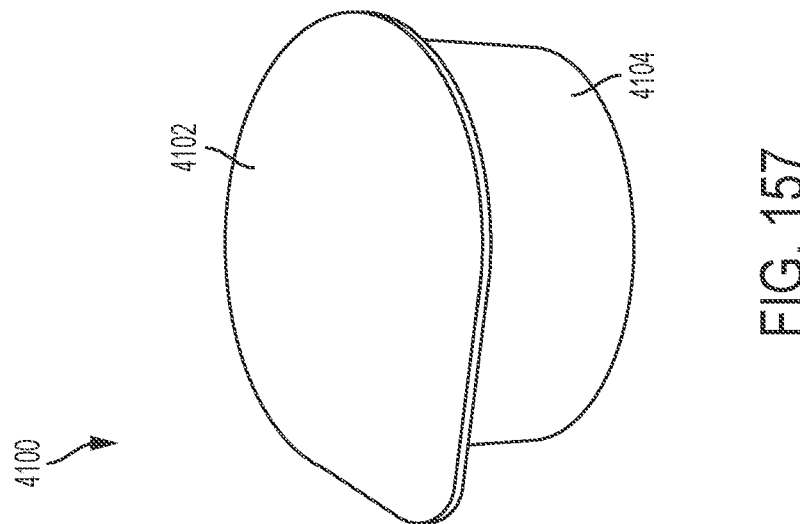

In some embodiments, the housing unit 4020 and the adhesive patch 4028 are stored in a sealed compartment 4100 as shown in FIG. 157. The compartment 4100 includes a lower cap portion 4104 and a cover portion 4102, manufactured from a flexible material such as metal foil or plastic. As shown in FIG. 158, the lower cap portion 4104 stores the sterilized housing unit 4020 and adhesive patch 4028 therein until ready for use. In some embodiments, the adhesive patch 4028 includes adhesive on both sides.

Figure 159:
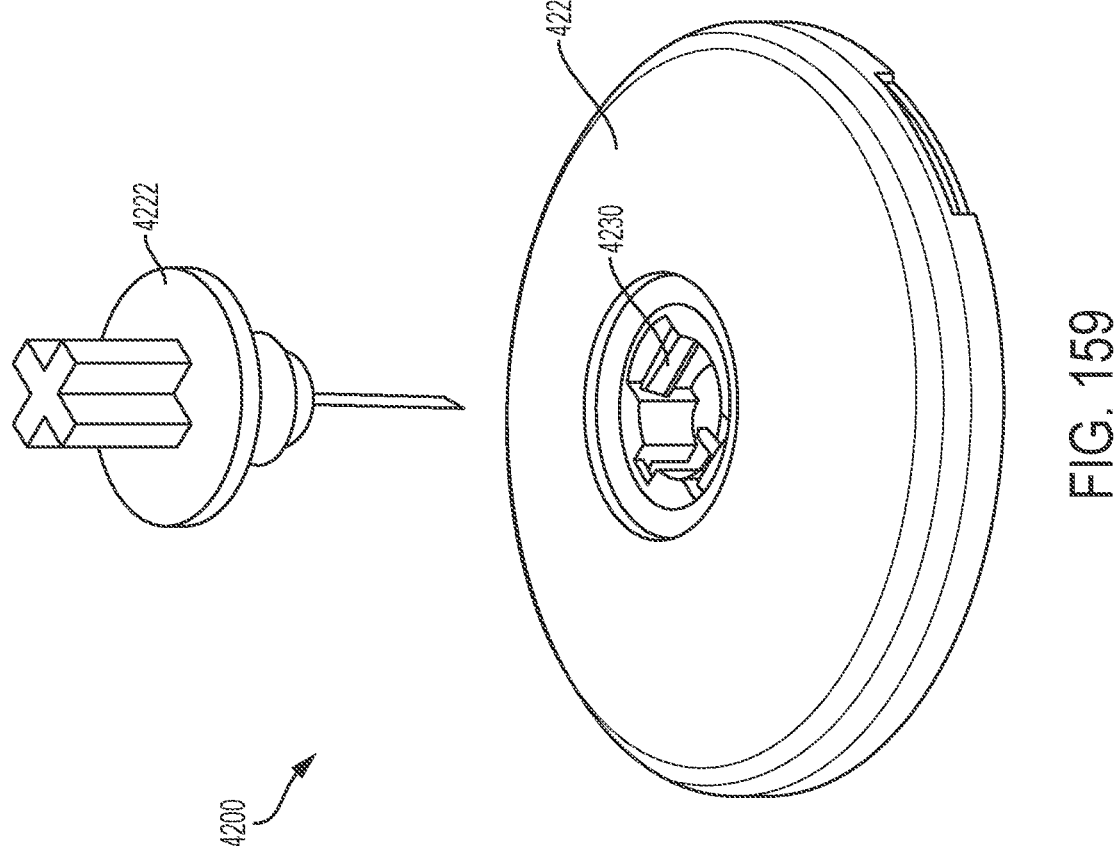
FIGS. 159-164 illustrate two piece on body housings in accordance with the disclosed subject matter.

In some embodiments, on body housing 4200 includes housing unit 4220 and sensor hub 4222 as illustrated in FIG. 159. The sensor may be insert molded with mechanical contacts. The PCB in the housing unit 4220 may include leaf spring contacts 4230. The sensor hub 4222 may be mechanically attached to the housing unit 4220, e.g., the electrical contacts may function as mechanical snaps. Sealing may be provided by an elastomeric gasket. The housing unit 4220 may be macromelt or injection molded.

Figure 160:
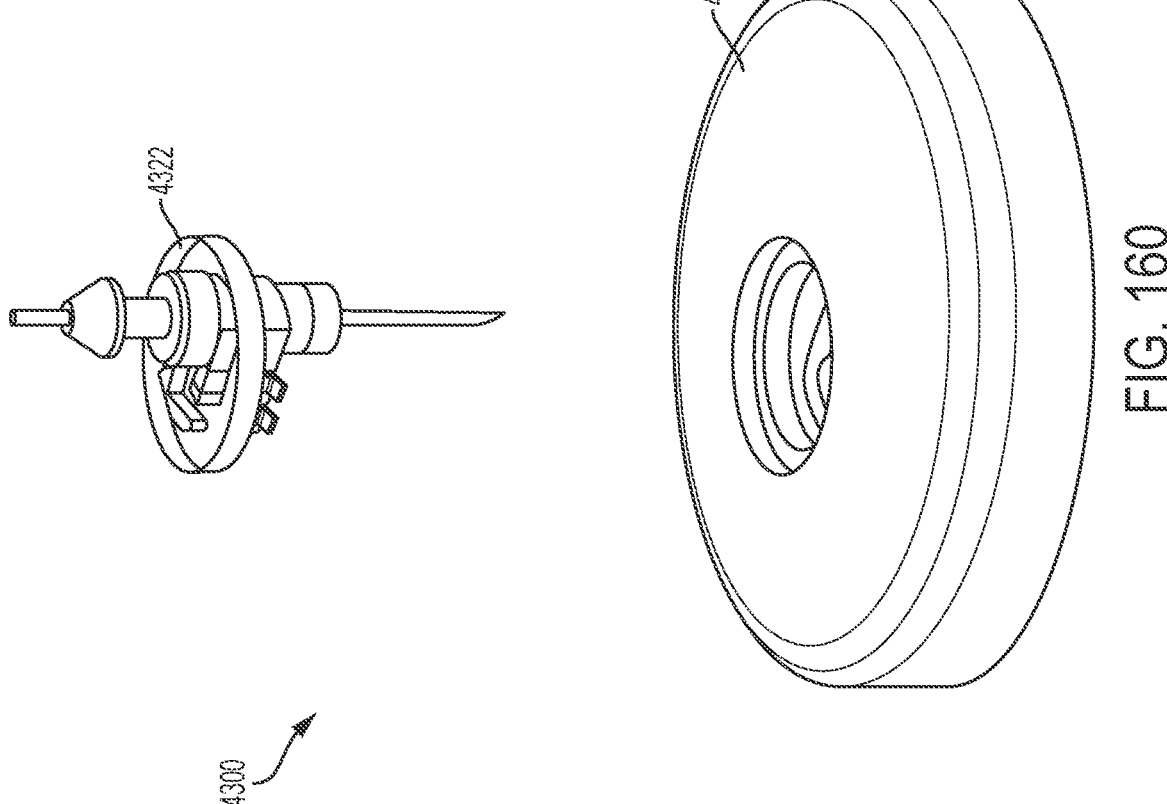

In some embodiments, on body housing 4300 includes housing unit 4320 and sensor hub 4322 as illustrated in FIG. 160. The sensor may have insert molded contacts. The PCB in housing unit 4320 may include exposed pads. Mechanical attachment of the housing unit and sensor hub may be accomplished by molded snaps. The needle guide may be injection molded or overmolded macromelt of TPE (thermoplastic elastomer). The housing unit 4320 may be macromelt or injection molded.

Figure 161:
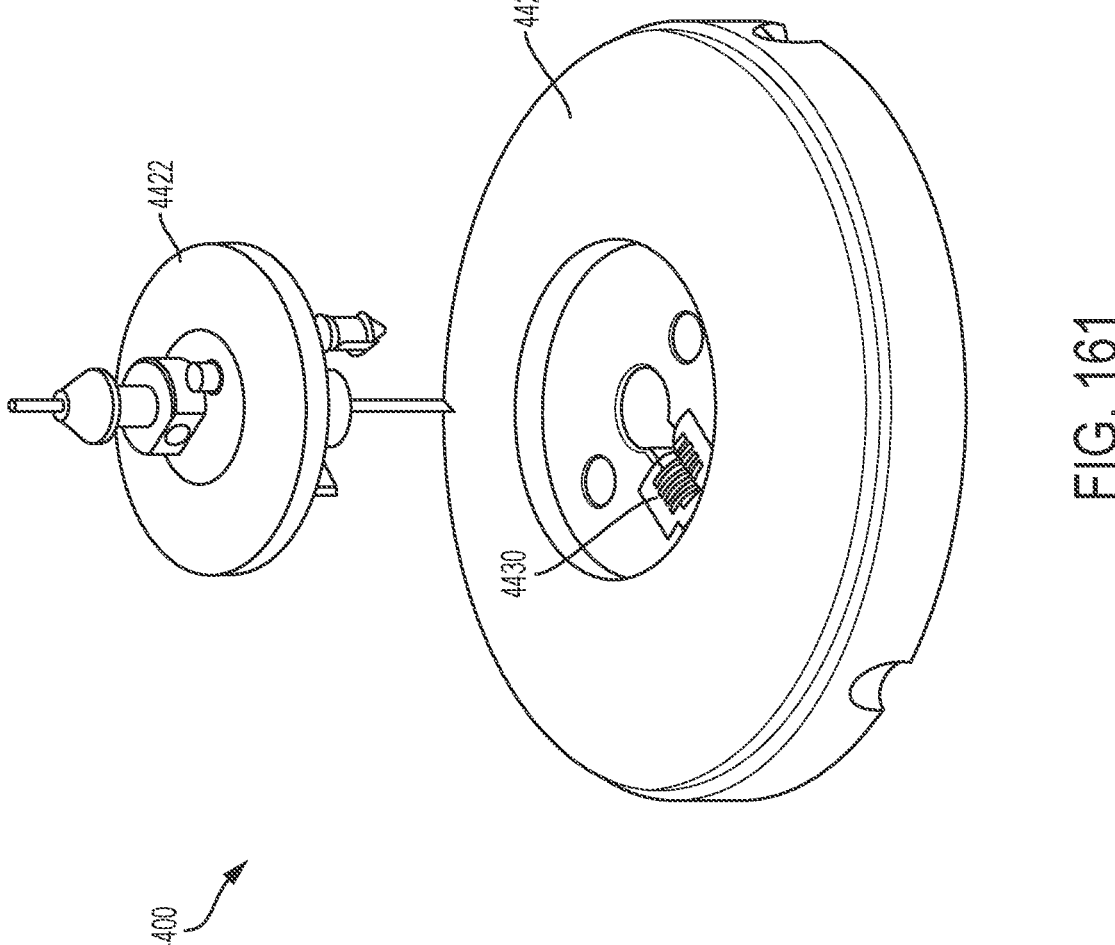
Figure 162:
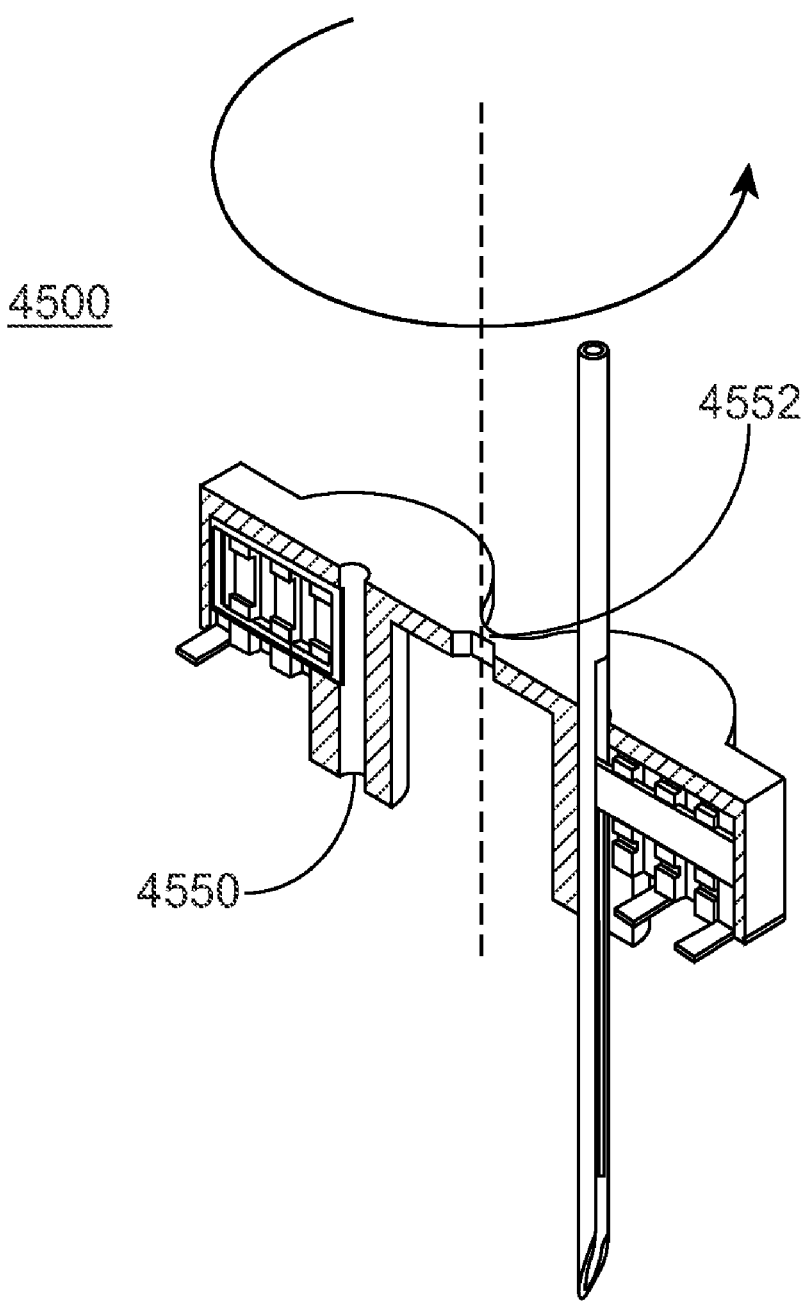

In some embodiments, on body housing 4400 includes housing unit 4420 and sensor hub 4422 as illustrated in FIG. 161. The sensor may have exposed pads on the flag or contact portion of the sensor. The PCB in housing unit 4420 may include a SMT ZIF connector, or similar 4430. Mechanical attachment of the housing unit and sensor hub may be accomplished by molded snaps. The needle guide may be injection molded plastic with elastomer overmold. The housing unit 4320 may be macromelt overmold.

In some embodiments, a clamshell type arrangement 4500 is provided which includes a needle guide 4550 having a living hinge arrangement 4552. The sensor may include bent metal contacts that are inserted after molding. The PCB may include PCB pads. The mechanical attachment is performed by adhesive of mechanical snap to PCB. The transponder housing, not shown, may be injection molded, UV or ultrasonic bonded.

Figure 163:
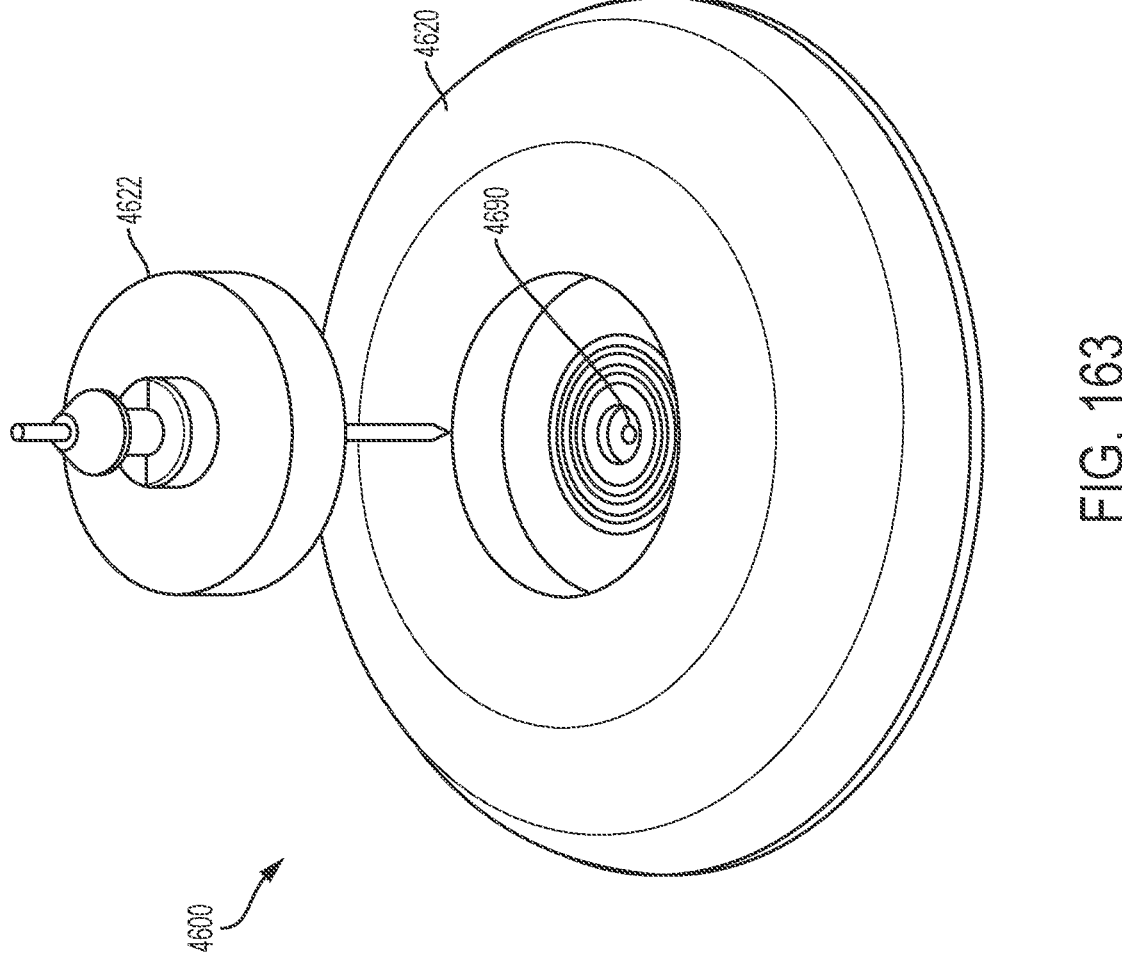

In some embodiments, on body housing 4600 includes housing unit 4620 and sensor hub 4622 as illustrated in FIG. 163. The sensor 14 may have exposed pads on the flag or contact portion of the sensor. The PCB in housing unit 4620 may include concentric exposed pads 4690. Mechanical attachment of the housing unit and sensor hub may be accomplished by molded snaps or PSA. The needle guide may be injection molded plastic with elastomer overmold. The housing unit 4620 may be macromelt overmold.

Figure 164:
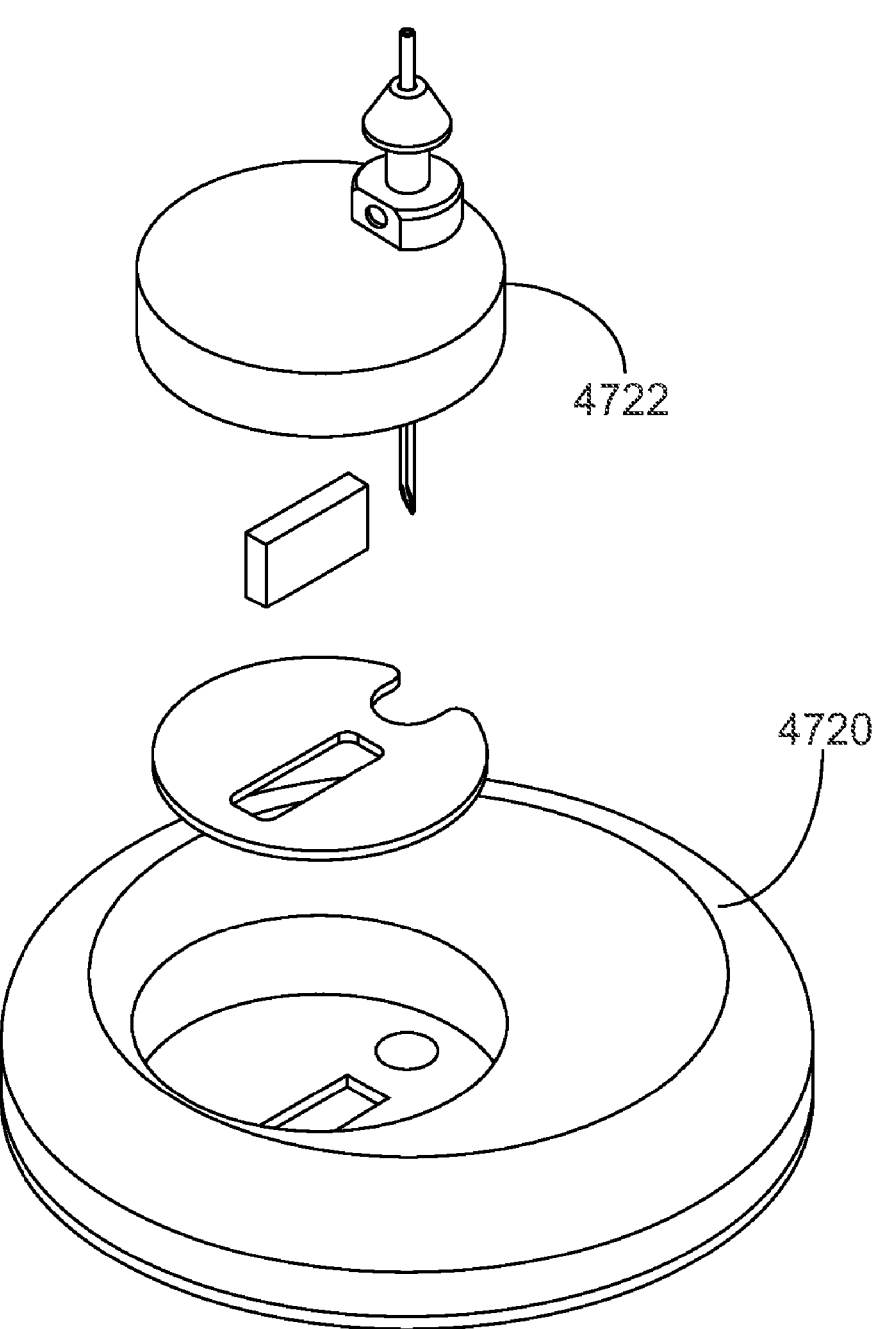

In some embodiments, on body housing 4700 includes housing unit 4720 and sensor hub 4722 as illustrated in FIG. 164. The sensor may have exposed pads on the flag and may also include a compressed anisotropic zebra, conductive elastomeric or similar. The PCB in housing unit 4720 may include exposed pads. Mechanical attachment of the housing unit and sensor hub may be accomplished by snaps. The needle guide may overmold macromelt or TPE. The housing unit 4720 may be macromelt overmold.

It is understood that the subject matter described herein is not limited to particular embodiments described, as such may, of course, vary. It is also understood that the terminology used herein is for the purpose of describing particular embodiments only, and is not intended to be limiting, since the scope of the present subject matter is limited only by the appended claims.

The invention claimed is:

1. An insertion apparatus comprising:
   a sheath having a distal surface for placement on a subject;
   a device support adapted to releasably couple with a medical device comprising a sensor;
   a sharp support adapted to support a sharp;
   a detent and a ledge; and
   a housing movable from a proximal position to a distal position relative to the sheath and adapted to urge the device support and the sharp support distally to insert the sharp and the sensor into the subject;
   wherein at least a portion of the sheath is disposed within a cavity of the housing;
   wherein the insertion apparatus has an interlock configuration that prevents movement of the housing from the proximal position until overcome by a force applied distally to the housing; and wherein the detent is held in contact with the ledge when the insertion apparatus is in the interlock configuration.

2. The apparatus of claim 1, wherein the detent and the ledge form a snap.

3. The apparatus of claim 1, wherein the detent extends from a surface of the insertion apparatus.

4. The apparatus of claim 3, wherein the detent extends from a surface of the sheath, and wherein the ledge is in the housing.

5. The apparatus of claim 1, wherein the interlock configuration is a first interlock configuration, and wherein the insertion apparatus has a second interlock configuration that prevents movement of the housing from the distal position.

6. The apparatus of claim 5, wherein the ledge is a first ledge, wherein the insertion apparatus comprises a second ledge, and wherein the detent is held in contact with the second ledge when the insertion apparatus is in the second interlock configuration.

7. The apparatus of claim 6, wherein the detent and the second ledge form a snap.

8. The apparatus of claim 6, wherein the detent extends from a surface of the insertion apparatus.

9. The apparatus of claim 8, wherein the detent extends from a surface of the sheath, and wherein the second ledge is in the housing.

10. The apparatus of claim 6, wherein the first ledge is positioned proximal to the second ledge.

11. The apparatus of claim 10, wherein the detent extends from a surface of the sheath, and wherein the first ledge and the second ledge are in the housing.

12. The apparatus of claim 1, wherein the interlock configuration is a first interlock configuration and wherein the insertion apparatus has a second interlock configuration that prevents relative movement of the housing from the distal position.

13. An insertion apparatus comprising:

a sheath having a distal surface for placement on a subject;

a device support adapted to releasably couple with a medical device comprising a sensor;

a sharp support adapted to support a sharp;

a detent and a ledge; and a housing movable from a proximal position to a distal position relative to the sheath and adapted to urge the device support and the sharp support distally to insert the sharp and the sensor into the subject;

wherein at least a portion of the sheath is disposed within a cavity of the housing;

wherein the insertion apparatus has an interlock configuration that prevents movement of the housing from the distal position, and wherein the detent is held in contact with the ledge when the insertion apparatus is in the interlock configuration.

14. The apparatus of claim 13, wherein the detent and the ledge form a snap.

15. The apparatus of claim 13, wherein the detent extends from a surface of the insertion apparatus.

16. The apparatus of claim 15, wherein the detent extends from a surface of the sheath, and wherein the ledge is in the housing.

17. The apparatus of claim 1, wherein the medical device further comprises on body electronics coupled with the sensor.

18. The apparatus of claim 17, wherein the on body electronics are configured to communicate glucose information to a monitor unit in response to a request from the monitor unit.

19. The apparatus of claim 13, wherein the medical device further comprises on body electronics coupled with the sensor.

20. The apparatus of claim 19, wherein the on body electronics are configured to communicate glucose information to a monitor unit in response to a request from the monitor unit.

* * * * *